(12) United States Patent
Walker et al.

(10) Patent No.: US 6,921,653 B2
(45) Date of Patent: Jul. 26, 2005

(54) CRYSTALLINE UDP-GLYCOSYL TRANSFERASE (MURG) AND METHODS OF USE THEREOF

(75) Inventors: Suzanne Walker, Princeton, NJ (US); Sha Ha, Princeton, NJ (US)

(73) Assignee: Princeton University, Princeton, NJ (US)

( * ) Notice: Subject to any disclaimer, the term of this patent is extended or adjusted under 35 U.S.C. 154(b) by 716 days.

(21) Appl. No.: 09/829,275

(22) Filed: Apr. 9, 2001

(65) Prior Publication Data

US 2003/0077803 A1 Apr. 24, 2003

Related U.S. Application Data

(60) Provisional application No. 60/204,930, filed on May 17, 2000.

(51) Int. Cl.$^7$ .................................................. C12N 9/10
(52) U.S. Cl. ...................................................... 435/193
(58) Field of Search ...................... 435/15, 193; 702/19

(56) References Cited

U.S. PATENT DOCUMENTS 5,068,191 A    11/1991   Clausen et al. ............. 435/193

FOREIGN PATENT DOCUMENTS

WO    WO 99/38958    8/1999

*Primary Examiner*—Nashaat T. Nashed
(74) *Attorney, Agent, or Firm*—Mathews, Collins, Shepherd & McKay, P.A.

(57) ABSTRACT

The present invention relates to crystals of the *Escherichia coli* MurG, a membrane-associated UDP-glycosyltransferase involved in peptidoglycan biosynthesis. The present invention also relates to three-dimensional atomic coordinates of the MurG protein, three-dimensional structures of the protein, and images thereof. The present invention relates to methods of crystallizing MurG proteins.

3 Claims, 5 Drawing Sheets

(4 of 5 Drawing Sheet(s) Filed in Color)

ial support under NIH grant AI44854-01. The U.S. government has certain rights in the invention.

CRYSTALLINE UDP-GLYCOSYL TRANSFERASE (MURG) AND METHODS OF USE THEREOF

This application claims the benefit of provisional application No. 60/204,930, filed May 17, 2000.

This invention was made, in part, with U.S. governmental support under NIH grant A144854-01. The U.S. government has certain rights in the invention.

FIELD OF THE INVENTION

The present invention relates to crystals of the *Escherichia coli* MurG, a membrane-associated UDP-glycosyltransferase involved in peptidoglycan biosynthesis. The present invention also relates to three-dimensional atomic coordinates of the MurG protein, three-dimensional structures of the protein, and images thereof. The present invention also relates to the atomic coordinates and three-dimensional structures of the α-carbon backbone of the MurG protein and images thereof. The present invention further relates to the atomic coordinates and three-dimensional structures of the α-carbon backbone and conserved amino acid residue sidechains of the MurG protein and images thereof. The present invention further relates to three-dimensional atomic coordinates of the donor nucleotide binding site, the acceptor binding site, and the membrane association site of the MurG protein, three-dimensional structures of the binding domains, and images thereof. The present invention also relates to computer readable media encoded with sets of the three-dimensional coordinates of the *E. coli* MurG protein, the α-carbon backbone of the MurG protein, the α-carbon backbone and the conserved amino acid residue sidechains of the MurG protein, the donor nucleotide binding site, the acceptor binding site, and the membfane association site. The present invention relates to methods of crystallizing MurG proteins.

The present invention relates to models of three-dimensional structures of UDP-glycosyltransferases and, in particular, MurG proteins, based on the three-dimensional structure of crystals of the *Escherichia coli* MurG. The present invention also relates to models of the three-dimensional structures of the α-carbon backbone of UDP-glycosyltransferases and MurG proteins. The present invention further relates to models of the three-dimensional structure of the α-carbon backbone and conserved amino acid residue sidechains of UDP-glycosyltransferases, in particular, MurG proteins. The present invention further relates to models of the three-dimensional structures of donor nucleotide binding sites, acceptor binding sites, and membrane association sites of UDP-glycosyltransferases, in particular, MurG proteins. The present invention also relates to methods of drug design using models of this invention. The present invention further relates to compounds identified using models of the present invention that bind, inhibit or stimulate UDP-glycosyltransferases or MurG proteins. The present invention relates to compositions comprising compounds identified using the models of this invention for therapeutic or diagnositic uses. Also, the present invention relates to methods of making models of the present invention.

BACKGROUND OF THE INVENTION

The increasing frequency of resistance to existing antibiotics represents a serious public health threat. Structural and mechanistic information on essential bacterial enzymes could lead to the development of antibiotics that are active against resistant microorganisms. Both gram positive and gram negative bacterial cells are surrounded by a cross-linked carbohydrate polymer, peptidoglycan, which protects them from rupturing under high osmotic pressures. Many of the best antibiotics function by inhibiting peptidoglycan synthesis, which ultimately causes cell lysis. In recent years, intense effort has been focused on determining the structures of the enzymes that synthesize peptidoglycan. Structures of several of the early enzymes in the biosynthetic pathway have been reported (Benson et al., 1995; Bertrand et al., 1997; Fan et al., 1994; Skarzynski et al., 1996); however, the later enzymes have proven more difficult to study because both they and their substrates are membrane-associated.

MurG is the last enzyme involved in the intracellular phase of peptidoglycan synthesis (Bugg & Walsh, 1993). It catalyzes the transfer of N-acetyl glucosamine (NAG) from UDP to the C4 hydroxyl of a lipid-linked N-acetylmuramoyl pentapeptide (NAM) to form a β-linked NAG-NAM disaccharide that is transported across the cell membrane where it is polymerized and cross-linked (FIG. 1). In bacterial cells MurG associates with the cytoplasmic surface of the membrane (Bupp & van Heijenoort, 1993). However, we have found that *E. coli* MurG can be solubilized at high concentrations in active form (Ha et al., 1999).

The elucidation of the protein structure of a MurG protein is of importance in the identification and formulation of anti-bacterial agents. Until the discovery of the present invention, the structure and resulting mechanism by which MurG functions was not known. Thus, despite the important role of MurG in peptidoglycan synthesis, development of useful agents for treatment or diagnosis of disease was hindered by lack of structural information of the protein.

In order to obtain structural information on a MurG protein, it is important to have purified, active enzyme. The demonstration of activity requires a suitable assay, which in turn requires access to the natural substrates or analogues thereof. The study of MurG was hampered by difficulties obtaining and handling the lipid-linked NAM substrate (commonly known as Lipid I). This problem was overcome by Walker and coworkers, who developed a synthetic route to a set of substrate analogues of Lipid I that were shown to function as glycosyl acceptors in a glycosyl transfer reaction catalyzed by MurG. Some of these substrate analogues are freely water soluble, making it possible to monitor the activity of purified *E. coli* MurG in buffer in the absence of natural or artificial membranes or detergents.

The linear nucleic acid and amino acid sequences of *E. coli* MurG were reported in 1992. Subsequently, the nucleic acid and amino acid sequence of *B. subtilus* MurG was reported. Since then, many bacterial genomes have been sequenced and the information has been deposited in databases. Information based only on linear sequences, however, cannot accurately predict the three-dimensional structure of the protein and its functional domains.

Therefore, there is a need in the art to elucidate the three-dimensional structure of a MurG protein. One three-dimensional structure of a MurG protein can be used to construct models of other MurG proteins and to facilitate the structure determination of crystalline forms of other MurG proteins., Structures and models of MurG proteins can also be used to design proteins containing only the donor binding site or the acceptor binding site. These proteins can be used in assays, including NMR-based assays, to identify—or characterize the mode of binding of—ligands that bind in or near the vicinity of the substrates. These ligands or compounds can then be used as leads for the design of inhibitors that have therapeutic activity. Structures and models of MurG proteins can also be used in computer-based drug design.

SUMMARY OF THE INVENTION

The present invention relates to crystalline *Escherichia coli* MurG protein. Obtaining such crystals is an unexpected result. It is well known in the protein crystallographic art that obtaining crystals of quality sufficient for determining the structure of a protein is unpredictable. In particular, obtaining crystals of quality sufficient for determining the three-dimensional (3-D) structure of MurG has not been achievable until the crystallization of MurG as disclosed in the present application. As such, determination of the three-dimensional structure of MurG has not been possible until the discovery of the present invention. Additionally, until the discovery of the present invention, derivation of the three-dimensional structure and models of other MurG proteins has not been possible. The present inventors are also the first to define the three-dimensional structure and provide three-dimensional models for drug design for MurG proteins.

Accordingly, one object of the present invention is to provide crystals of sufficient quality to obtain a determination of the three-dimensional atomic coordinates and structures of MurG to high resolution, preferably to the resolution of less than 2.0 angstroms (A). The present invention also provides methods for producing crystalline MurG protein.

The value of the crystals of *E. coli* MurG protein extends beyond merely being able to obtain such crystals. The knowledge obtained concerning the MurG crystal structure, for example, has been used by the present inventors to define the heretofore unknown tertiary structure of the MurG protein and to identify the location of the glycosyl donor and glycosyl acceptor binding domains, as well as the location of the amino acid residues that are invariant in all MurG proteins. This information can be used to design inhibitors of MurG that have therapeutic utility. The atomic coordinates of *E. coli* MurG also are used to model the heretofore unknown tertiary structures of other MurG proteins having substantially related linear amino acid sequences, such as for MurG proteins from other microorganisms. It is anticipated that homology models can be constructed even from amino acid sequences with relatively low homology because the present inventors have identified the location of the invariant amino acid residues in MurG. The relative spatial orientations of such residues is expected to be conserved in all MurG proteins.

Comparison of nucleic acid and amino acid sequences of MurG proteins indicates that the linear amino acid sequences can vary significantly. Homology between MurG proteins from different microorganisms varies from less than 30% to greater than 90%, reflecting the evolutionary relationship between the organisms. The low homology between distantly related MurG homologues is not believed to reflect significantly different folded structures. It is well known that many amino acid sequences are capable of adopting the same general fold. *E. coli* MurG contains an alpha/beta folding pattern, one of the most common folds known in proteins. It is likely that all MurG homologues contain a similar alphabeta fold despite the differences in the linear amino acid sequences. What gives these proteins their identity is not the general fold, but the specific details—i.e., the presentation of certain amino acids on the folded structure. The present inventors have identified the location in *E. coli* MurG of a set of residues that are invariant in all MurG homologues. It is to be expected that these residues would adopt a similar spatial location with respect to the folded structure in all MurG homologues. Therefore, these invariant residues, which have been selected by evolution as the critical residues for the binding and catalytic function of the protein, provide essential information on the location of the active site and on critical contacts to the substrates/products. They also serve as constraints that make it possible to, predict the three-dimensional structures even of distantly related MurG homologues. Thus, knowledge of the three-dimensional structure of the *E. coli* MurG protein has provided a starting point for investigation into the structure of all MurG proteins.

Accordingly, a object of the present invention is to provide information regarding the atomic coordinates and three-dimensional structures of (1) the MurG protein, (2) the α-carbon backbone of the MurG protein, (3) the α-carbon backbone and conserved amino acid residues of the MurG protein, (4) the donor nucleotide binding site, (5) the acceptor binding site, and (6) the membrane association site MurG proteins.

It is also an object of this invention to solve the three-dimensional structure of UDP-glycosyltransferases, in particular target NTURG proteins, and to determine their structure and/or atomic coordinates. Further, it is an object of this invention to use the structure or atomic coordinates of the *E. coli* MurG crystal to solve the structure of different MurG protein crystals, or a crystal of a mutant protein, homolog or co-complex of MurG.

The present invention relates to models of three-dimensional structures of UDP-glycosyltransferases, in particular MurG proteins, based on the atomic coordinates of crystalline *E. coli* MurG protein.

It is a further object of this invention to provide, UDP-glycosyltransferase enzyme mutants characterized by one or more different properties as compared with wild-type MurG. These properties include altered surface charge, increased stability to subunit dissociation, altered substrate specificity or higher specific activity. MurG mutants are useful to identify those amino acids that are most important for the enzymatic activity of MurG. This information, in turn, allows the design of improved inhibitors of MurG as compared with peptidic MurG inhibitors.

Another object of the present invention is to provide computer readable mediums encoded with a set of three-dimensional coordinates of the *E. coli* MurG protein, the c-carbon backbone of the MurG protein, the c-carbon backbone and conserved amino acid residues of the MurG protein, and the nucleotide donor binding site, the acceptor binding site, the membrane association site of the MurG protein.

Another embodiment of the present invention provides three-dimensional and two-dimensional computer images of the three-dimensional structure of MurG protein, the α-carbon backbone of the MurG protein, the α-carbon backbone and conserved amino acid residues of the MurG protein, and the nucleotide donor binding site, the acceptor binding site, the membrane association site of the MurG protein.

The knowledge of the three-dimensional structure of MurG also provides a means for designing proteins that have altered beneficial functions by analyzing the structure and interactions between individual amino acids of the protein. For example, the present inventors have shown that *E. coli* MurG consists of two domains separated by a cleft.

Noncovalent interactions between the two domains are not extensive. The present inventors have shown that the domains fold independently and can, therefore, be expressed independently either alone or as part of a recombinant protein containing the acceptor binding site from one MurG homologue and the donor binding site from another MurG homologue. It would be expected that the domains of other MurG proteins could also be expressed independently, either alone or as chimaeras with other MurG domains. Independently expressed domains of the protein are useful for discovering ligands that bind to the individual domains.

The knowledge of the three-dimensional structure of *E. coli* MurG protein and models of other MurG proteins also provides a means for designing and producing compounds that regulate, inhibit or antagonize functions of the MurG protein (i.e., structure based drug design). For example, chemical compounds can be designed to block binding of UDP-GlcNAc to a MurG protein using various computer programs and models.

It is also an object of this invention to use the structure coordinates and atomic details of MurG, or its mutants or homologues or co-complexes, to design, evaluate computationally, synthesize and use inhibitors of MurG that avoid the undesirable physical and pharmacologic properties of peptidic MurG inhibitors.

Another embodiment of the present invention is a composition comprising MurG protein in a crystalline form.

Yet another embodiment of the present invention is a method for producing crystals of MurG, comprising combining MurG protein in a suitable buffer with a suitable amount of a reservoir buffer containing a detergent, and inducing crystal formation to produce said MurG crystals.

BRIEF DESCRIPTION OF THE DRAWINGS

The patent or application file contains at least one drawing executed in color. Copies of this patent or patent application publication with color drawings will be provided by the Office upon request and payment of the necessary fees.

DEFINITIONS

Figure 1:
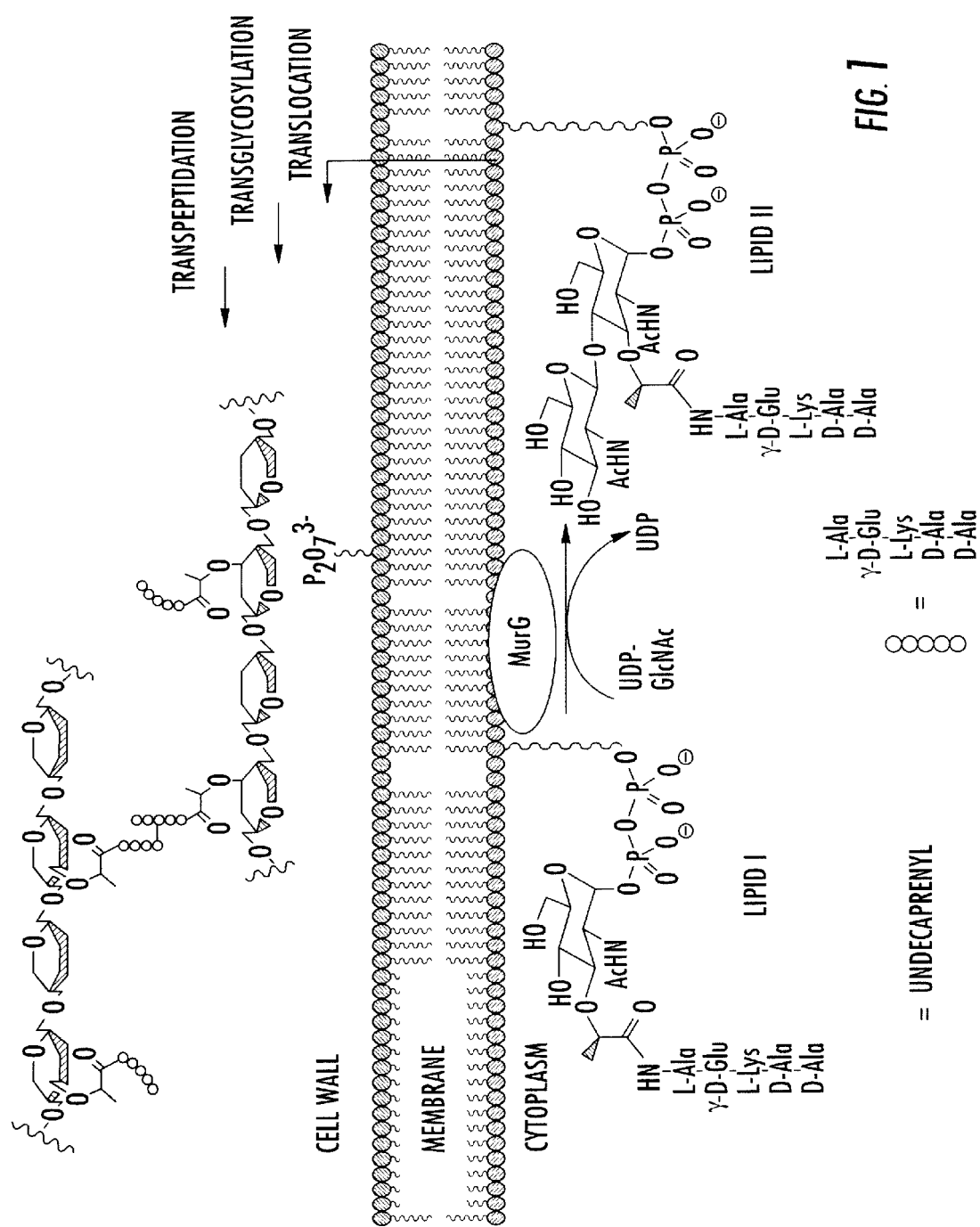
FIG. 1. Pathway for peptidoglycan biosynthesis.

It is to be noted that the term "a" or "an" entity refers to one or more of that entity; for example, a compound refers to one or more compounds or at least one compound. As such, the terms "a" (or "an"), "one or more", and "at least one" can be used interchangeably herein.

It is also to be noted that the terms "comprising", "including" and "having" can be used interchangeably. Furthermore, a compound "selected from the group consisting of" refers to one or more of the compounds in the list that follows, including mixtures (i.e., combinations) of two or more of the compounds.

According to the present invention, an isolated, or pure, protein, is a protein that has been removed form its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

It is also to be noted that the terms "tertiary" and "three-dimensional" can be used interchangeably.

It is also to be noted that reference to a "MurG protein" can also be recited as "MurG" and such terms can be used to refer to the complete MurG protein, a portion of the MurG protein, such as a polypeptide.

The following terms are also used herein:

The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, gamma-carboxyglutamic acid, arginine, omithine and lysine. Unless specifically indicated, all amino acids referred to in this application are in the L-form.

The terin "unnatural amino acids" means amino acids that are not naturally found in proteins. Examples of unnatural amino acids used herein, include racemic mixtures of selenocysteine and selenomethionine. In addition, unnatural amino acids include the D or L forms of nor-leucine, para-nitrophenylalanine, homophenylalanine, parafluorophenylalanine, 3-amino-p2-benzylpropionic acid, homoarginine, and D-phenylalanine.

The term "positively charged amino acid" includes any naturally occurring or unnatural amino acid having a positively charged side chain under normal physiological conditions. Examples of positively charged naturally occurring amino acids are arginine, lysine and histidine.

The term "negatively charged amino acid" includes any naturally occurring or unnatural amino acid having a negatively charged side chain under normal physiological conditions. Examples of negatively charged naturally occurring amino acids are aspartic acid and glutamic acid.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

Figure 3A:
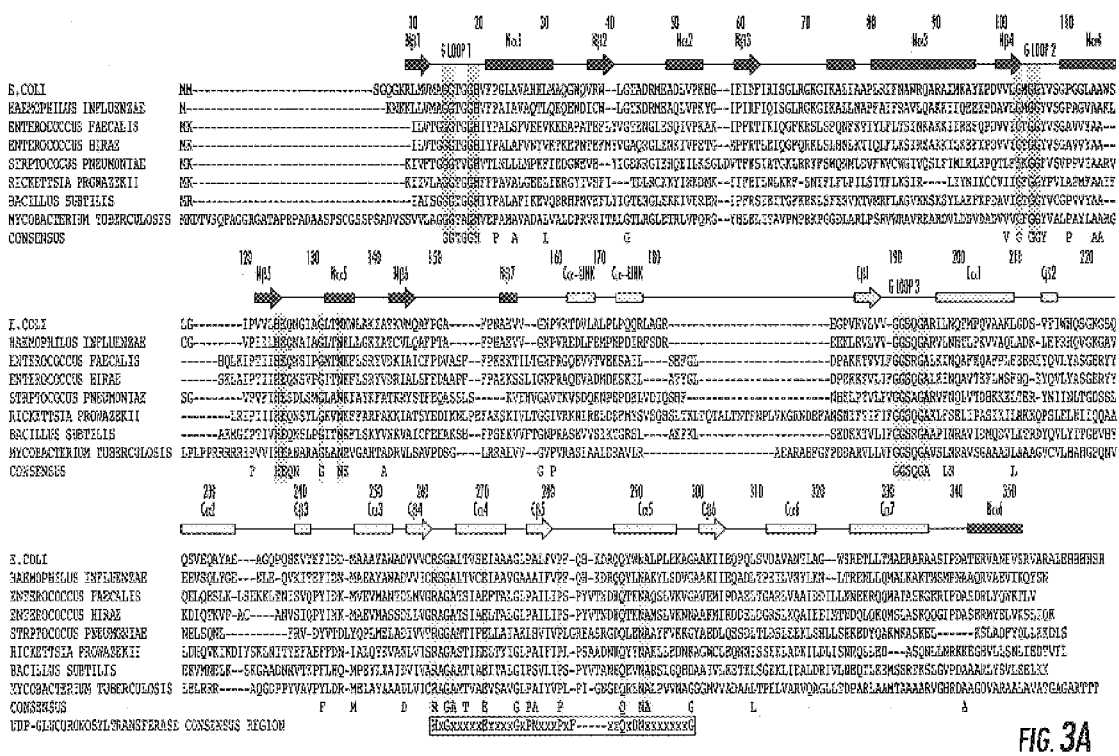
FIG. 3. Identification of critical residues in MurG and related glycosyltransferases. A. Sequence alignment of *E. coli* MurG with homologs from seven other bacterial strains, deliberately chosen to represent a disparate group of organisms. The secondary structure of *E. coli* MurG is shown above the sequences. Gaps mapping to the loop regions of *E. coli* MurG suggest that some sequences include other structural elements. Residues highlighted in blue are invariant among the eighteen MurG sequences available. Residues highlighted in yellow are identical in 85% of the eighteen homologs, while in the remaining 15%, only closely related amino acid substitutions are found. Highly conserved residues that do not meet the stringent criteria established for highlighting are shown in the consensus sequence. A consensus motif for UDP-glucuronosyltransferases is also shown. Numbering is with respect to the overexpressed *E. coli* MurG construct, which contains an additional N-terininal methionine. B. Mapping of the G loops and other highlighted residues from FIG. 3a in red on the MurG structure. Side chains for highly conserved residues are also shown. C. Model for the proposed UDP-binding subdomain found in many UDP-glycosyltransferases based on the *E. coli* MurG structure. Conserved residues in UDP-glucuronosyltransferases are highlighted in red. Side chains are shown for residues that are located near the cleft and may be involved in substrate binding. The glutamate residue is proposed to interact with the ribose sugar. The dotted loop varies in length within the MurG family and in other UDP-sugar transferases, but the N and Q on the following helix are invariant. Note that the UDPglucuronosyltransferases contain a conserved D preceding the Q, which is not shown on this model.

The term "MurG" refers to a UDP-glycosyltransferase that has a two domain strucuture, where each domain contains a set of invariant residues as shown in FIG. 3a, including any mutant, homologue or co-complex or any similar enzyme that catalyzes the transfer of N-acetylglucosamine (GlcNAc) from UDP to the C4 hydroxyl of the lipidlinked MurNAc pentapeptide.

The term "mutant" refers to a MurG polypeptide, i.e., a polypeptide displaying the biological activity of a wild-type MurG, characterized by the replacement of at least one amino acid from the wild-type, E. coli MurG sequence according to Ikeda, et al., Nucleic Acids Res. 1990, and Mengin-LeCreuix et al., Nucleic Acids Res. 1990. Such a mutant may be prepared, for example, by expression of MurG cDNA previously altered in its coding sequence by PCR-based mutagenesis method.

MurG mutants may also be generated by site-specific incorporation of unnatural amino acids into MurG proteins using the general biosynthetic method of Noren, C. J., et al., Science, 244, pp. 182–188 (1989). In this method, the codon encoding the amino acid of interest in wild-type MurG is replaced by a "blank" nonsense codon, TAG, using oligonucleotide-directed mutagenesis (described in detail, infra). A suppressor tRNA directed against this codon is then chemically aminoacylated in vitro with the desired unnatural amino acid. The aminoacylated tRNA is then added to an in vitro translation system to yield a mutant MurG enzyme with the site-specific incorporated unnatural amino acid.

Selenocysteine or selenomethionine may be incorporated into wild-type or mutant MurG by expression of MurG-encoding cDNAs in auxotrophic E. coli strains. Hendrickson, W. A. et al., EMBO J., 9(5), pp. 1665–1672 (1990). In this method, the wild-type or mutagenized MurG cDNA may be expressed in a host organism on a growth medium depleted of either natural cysteine or methionine (or both) but enriched in selenocysteine or selenomethionine (or both).

The term "altered surface charge" means a change in one or more of the charge units of a mutant polypeptide, at physiological pH, as compared to wild-type MurG. This is preferably achieved by mutation of at least one amino acid of wild-type MurG to an amino acid comprising a side chain with a different charge at physiological pH than the original wild-type side chain.

The change in surface charge is determined by measuring the isoelectric point (pI) of the polypeptide molecule containing the substituted amino acid and comparing it to the isoelectric point of the wild-type MurG molecule.

The term "altered substrate specificity" refers to a change in the ability of a mutant MurG to cleave a substrate as compared to wild-type MurG.

The "kinetic form" of MurG refers to the condition of the enzyme in its free or unbound form or bound to a chemical entity at either its active site or accessory binding site.

A "competitive" inhibitor is one that inhibits MurG activity by binding to the same kinetic form of MurG as its substrate binds-thus directly competing with the substrate for the active site of MurG. Competitive inhibition can be reversed completely by increasing the substrate concentration.

An "uncompetitive" inhibitor is one that inhibits MurG by binding to a different kinetic form of the enzyme than does the substrate. Such inhibitors bind to MurG already bound with the substrate and not to the free enzyme. Uncompetitive inhibition cannot be reversed completely by increasing the substrate concentration.

A "non-competitive" inhibitor is one that can bind to either the free or substrate bound form of MurG.

Those of skill in the art may identify inhibitors as competitive, uncompetitive or non-competitive, by computer fitting enzyme kinetic data using standard equations according to Segel, I. H., Enzyme Kinetics, J. Wiley & Sons, (1975). It should also be understood that uncompetitive or non-competitive inhibitors apcording to this invention may bind to the accessory binding site.

The term "homolog" means a protein having at least 25% amino acid sequence identity with MurG or any functional part of MurG, and including certain invariant amino acid residues corresponding to G14, G15, G18, H19, G104, H124, E125, G190, G191, S192, G194, A195, R261, G263, A264, E269, P281, Q289, N292 and A293 (as numbered in the E. coli MurG sequence set forth in FIG. 3a) and also including three glycine rich loops. A homolog may contain some or all of the invariant residues.

The term "co-complex" means MurG or a mutant or homologue of MurG in covalent or non-covalent association with a chemical entity or compound.

The term "associating with" refers to a condition of proximity between a chemical entity or compound, or portions thereof, and a MurG molecule or portions thereof. The association may be non-covalent—wherein the juxtaposition is energetically favored by hydrogen bonding or van der Waals or electrostatic interactions—or it may be covalent.

The term ".beta.-sheet" refers to the conformation of a polypeptide chain stretched into an extended zig-zig conformation. Portions of polypeptide chains that run "parallel" all run in the same direction. Polypeptide chains that arc "antiparallel" run in the opposite direction from the parallel chains.

The terms "atomic coordinates" or "structure coordinates" refer to mathematical coordinates derived from mathematical equations related to the patterns obtained on diffraction of a monochromatic beam of X-rays by the atoms (scattering centers) of a MurG molecule in crystal form. The diffraction data are used to calculate an electron density map of the repeating unit of the crystal. The electron density maps are used to establish the positions of the individual atoms within the unit cell of the crystal.

The term "heavy atom derivatization" refers to the method of producing a chemically modified form of a crystal of MurG. In practice, a MurG crystal is soaked in a solution containing heavy metal atom salts, or organometallic compounds, e.g., lead chloride, gold thiomalate, thimerosal, uranyl acetate or mercuric chloride, which can diffuse through the crystal and bind to the surface of the protein. The location(s) of the bound heavy metal atom(s) can be deetermined by X-ray diffraction analysis of the soaked crystal. This information, in turn, is used to generate the phase information used to construct three-dimensional structure of the enzyme. Blundel, T. L. and N. L. Johnson, Protein Crystallography, Academic Press (1976).

Those of skill in the art understand that a set of structure coordinates determined by X-ray crystallography is not without standard error. For the purpose of this invention, any set of structure coordinates for MurG or MurG homologues or MurG mutants that have a root mean square deviation of protein backbone atoms (N, C.alpha., C and 0) of less than 0.75 Å when superimposed—using backbone atoms—on the structure coordinates listed in Table 1, Table 2 or Table 3 shall be considered identical.

The term "unit cell" refers to a basic parallelepiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal.

The term "molecular replacement" refers to a method that involves generating a preliminary model of a MurG crystal whose structure coordinates are unknown, by orienting and positioning a molecule whose structure coordinates are known (e.g., MurG coordinates from Table 1, 2, or 3) within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. Lattman, K., "Use of the Rotation and Translation Functions", in Methods in Enzymology, 115, pp. 55–77 (1985); M. G. Rossmann, ed., "The Molecular Replacement Method", Int. Sci. Rev. Ser., No. 13, Gordon & Breach, New York, (1972). Using the structure coordinates of MurG provided by this invention, molecular replacement may be used to determine the structure coordinates of a crystalline mutant or homologue of MurG or of a different crystal form of MurG.

DETAILED DESCRIPTION OF THE INVENTION

The present invention relates to the discovery of the three-dimensional structure of the crystalline form of the *E. coli* MurG protein, models of such three-dimensional structures, a method of structure based drug design using such structures, methods to identify ligands or compounds that interact or bind with such structures, the compounds identified by such methods, and the use of such compounds in therapeutic compositions.

More particularly, the present invention relates to novel crystals of *E. coli* MurG protein, methods of production of such crystals, three-dimensional coordinates of MurG protein, MurG structures and models derived from the *E. coli* MurG structure, and uses of such structures and models to derive other MurG structures and in ligand discovery and drug design strategies.

The present invention also relates to three-dimensional structures and coordinates of the donor nucleotide binding site, the acceptor binding site, and the membrane association site of the MurG protein, structures and models of the binding sites, and uses of such structures and models to derive the binding sites of other MurG proteins and in drug design strategies.

Solely for ease of explanation, the description of the invention is divided into the following sections: (1) crystals of MurG protein; (2) methods of crystallization; (3) three-dimensional crystal coordinates and structure of *E. coli* MurG; (4) three-dimensional coordinates and structure of the donor nucleotide binding site of MurG; (5) coordinates and structure of the acceptor binding site of MurG; (5) three-dimensional coordinates and structure of the membrane association site; (6) two-dimensional and three-dimensional images of the protein, α-carbon backbone, α-carbon backbone with conserved amino acid residues, and binding sites; and (7) computer readable mediums comprising the three-dimensional coordinates of the MurG protein, α-carbon backbone, α-carbon backbone with conserved amino acid residues, and binding sites; (8) images of structures of MurG protiensand binding sites; (9) models of MurG proteins and binding sites thereof and methods of using the structure of MurG to determine the structures of other MurG proteins and binding sites; (10) structure based drug design using models of MurG protein and binding site structures; (11) compounds derived from structure based drug design; and (12) therapeutic compositions using drugs designed from structure based drug design.

Crystals

One embodiment of the present invention includes a pomposition comprising a MurG protein in a crystalline form (i.e., MurG crystals). As used herein, the terms (crystalline MurG" and "MurG crystal" both refer to crystallized MurG protein and are intended to be used interchangeably. More particularly, an embodiment of the present invention includes a composition comprising an *E. coli* MurG protein in a crystalline form. Preferably, a crystalline MurG is produced using the crystal formation method described herein, in particular according to the method disclosed in Example 1. A MurG crystal of the present invention comprises any crystal structure and preferably precipitates as a triclinic crystal. Preferably, a composition of the present invention includes MurG crystal molecules arranged in a crystalline manner in a P1 space group with two molecules per assymmetric unit so as to form a unit cell of dimensions a-60.613 Å, b=66.356 Å, c=67.902 Å, α=64.294, β=83.520, γ=65.448. A preferred crystal of the present invention provides X-ray diffraction data for determination of atomic coordinates to a resolution of about 3.0 Å, preferably to about 2.4 Å, and more preferably to about 1.8 Å.

Another embodiment of the present invention includes crystalline MurG protein co-crystallized with a donor nucleotide or substrate or substrate analog. Preferably, a donor nucleotide is UDP or UDP-GlcNAc (UDP-N-acetylglucosamine) or an analog thereof. The substrate or substrate analog is preferably Lipid I or Lipid II or analogs of Lipid I or Lipid II. More specifically, Lipid I and II analogs are as described in PCT/US99/02187, published as WO99/38958 and U.S. Provisional Application No. 60/122,966 filed Mar. 3, 1999 and 60/137,696 filed Jun. 4, 1999, and International Application No. PCT/US00/05554 entitled "Bacterial transglycosylases: Assays for monitoring the activity using Lipid II substrate analogs and methods for discovering antibiotics," all incorporated herein by reference in their entirety.

Included in the present invention, a variety of MurG proteins from numerous organisms can be used to prepare MurG crystals, including but not limited to, microorganisms such as bacteria, higher-order bacteria, thermal stable bacteria, spirochetes, small pathogenic organisms, fungi, protozoa, cyanobacteria, and trypanosomes. More particularly, bacteria such as but not limited to, *Escherichia coli, Bacillus subtilis, Aquefe-x aeolicus, Borrelia burgdorferi, Chlamydia pneumoniae, Chlamydia trachomatis, Enterococcus jaecais, Enterococcus hirae, Haemophilus influenzae, Helicobacter pylori* J99, *Helicobacter pylori, Mjrobacterium tuberculosis, Porphyromonas gingivalis, Rickettsia prowazekii, Streptomyces coelicolor, Streptomyces collinus, Streptococcus pneumoniae, Synechocystis* sp. (strain PCC6803), *Thermotoga maritime*, and *Treponemapallidum.*

In another embodiment of the present invention, the MurG proteins or fragments thereof, mutants or homologs are expressed in, for example, an *E. coli* host cell for use expressing sufficient quantities of sufficiently purified protein to form crystals. The present inventors have demonstrated that it is possible to express *Enterococcus. jaecalis* MurG in *E. coli* cells—so the MurG proteins from many organisms can be cloned into expression vectors suitable for expression in *E. coli* cells. This would facilitate obtaining sufficient quanitites of isolated or purified MurG proteins. The expression of *E. jaecalis* MurG protein in *E. coli* host cells is performed, for example, by expressing the *E. jaecalis* MurG gene cloned into a pET21b expression vector and transformed into an *E. coli* host cell. The MurG protein is over-expressed with a C-terminal his tag (LEHHHHHH) which allows the protein to be purified using a His-tag affinity column. The protein is then crystallized and the atomic coordinates are determined using X-ray diffraction and methods known to those skilled in the art.

It is another embodiment of the present invention to provide for the construction and expression of chimaeric MurG proteins to enable the crystallization and determination of the three-dimensional coordinates of such chimeras. For example, if there are problems obtaining or crystallizing MurGs from other organisms, the present invention provides information that makes it possible to make chimaeric proteins containing the donor or acceptor binding site from *E. coli* MurG and the corresponding acceptor or donor binding site from another organism. Chimaeric proteins could be easier to express, handle, or crystallize. For example, we have found that *E. faecalis* MurG is more difficult to solubilize that *E. coli* MurG (requiring more detergent). It is believed that the problems are related to the acceptor binding domain having a stronger affinity for the bacterial membranes. To overcome this problem, one can attach the donor binding domain of *E. faecalis* to the *E. coli* acceptor binding site and determine structure to see details of *E. faecalis* donor binding domain.

According to the present invention, crystalline MurG can be used to determine the ability of a chemical compound to bind to a MurG protein in a manner predicted by a structure based drug design method of the present invention. Preferably, a MurG crystal is soaked in a solution containing a chemical compound of the present invention. Binding of the chemical compound to the crystal is then determined by methods standard in the art. Thereby, the co-crystal of MurG and a compound of interest is determined.

Methods of Crystallization

The present invention includes a method for producing crystals of MurG proteins, comprising: combining MurG protein with a reservoir solution and inducing crystal formation to produce MurG crystals. Another embodiment of the present invention, a method for producing crystals of MurG protein comprises combining MurG protein with UDP-GlcNAc in a 1:3 ratio and with a reservoir solution and inducing crystal formation to produce MurG crystals.

Preferably, crystals of MurG are formed using a solution containing a range of MurG protein from about 1 mg/ml to about 20 mg/ml, more preferably above 5 mg/ml, limited only by the solubility of the protein, which may vary depending on the specific amino acid sequence.

A reservoir solution contains the buffer, the precipitant, and additives if necessary. A suitable reservoir buffer of the present invention comprises NaMES (2-[N-morpho]inolethanesulfonic acid, sodium salt) buffer, NaHEPES (N-[2-hydroxyethyl]piperazine-N'-[2-ethanesulfonic acid, sodium salt) buffer, Tris (tris[hydroxymethyl]aminomethane) buffer, and any buffer which has the PKa between 5.5 and 8.0. A suitable NaMES buffer solution has a pH range from about 5.6–6.5. Most preferably, the NaMES buffer has a pH of about 6.5. The precipitant comprises ammonium sulfate, saturated sodium and potassium tartrate and polyethylene glycol. A suitable concentration of ammonium sulfate can range from 0.8 M to 1.5 M. Most preferably, the ammonium sulfate concentration is about 0.96 M. A suitable additive comprises detergents like Triton X-100 and n-octyl-beta-glucoside. The concentration of Triton X-100 can range from 0.1% to 1%. Most preferably, the concentration of Triton X-100 is 0.4%.

In a preferred embodiment, MurG crystals are produced by a method comprising concentrating MurG protein in a buffer solution, mixing the protein concentrate with UDP-GlcNAc in a 1:3 molar ratio, mixing equal volumes of protein solution with a reservoir solution, and inducing crystal formation to produce MurG crystals.

In a particular embodiment of the invention, MurG crystals are produced by a method comprising concentrating MurG protein to 10 mg/ml in a buffer of 20 mM Tris-HCl, pH 7.9/150 mM NaCl and 50 mM EDTA; mixing the protein concentrate with UDP-GlcNAc in a 1:3 molar ratio; mixing equal volumes of protein solution with a reservoir solution comprising (0.1 M NaMES, pH 6.5, 0.96 M $(NH_4)_3SO_4$, 0.4% TRITON® X-100, and 10 mM dithiolthreitol (DTT)), and inducing crystal formation using hanging drop vapor-diffusion. This preferred method is described in greater detail in Example 1.

Supersaturated solutions of MurG protein can be induced to crystallize by several methods including, but not limited to, vapor diffusion, liquid diffusion, batch crystallization, constant temperature and temperature induction or a combination thereof. Preferably, supersaturated solutions of MurG protein are induced to crystallize by vapor diffusion (i.e., hanging drop method). In a vapor diffusion method, a MurG protein solution is combined with a reservoir solution of the present invention that will cause the MurG protein solution to become supersaturated and form MurG crystals at a constant temperature. Vapor diffusion is preferably performed under a controlled temperature in the range of from about 15° C. to about 30° C., more preferably from about 20° C. to about 25° C., and most preferably at a constant temperature of about 22° C.

In another preferred embodiment, the present invention includes a method to produce crystals of MurG protein comprising the steps of: (a) preparing an about 10 mg/ml solution of MurG protein in a Tris-HCl buffer, (mixing UDP-GlcNAc with the Mur-G protein solution in a 3:1 molar ratio, (c) dropping 2 µl droplet of this protein sample onto a coverslip, (d) adding an equal volume of reservoir solution to this droplet and inverting this over a well containing about 1 ml of the reservoir solution; and (e) incubating until crystals of MurG form.

Any isolated MurG protein can be used with the present method. An isolated MurG protein can be isolated from its natural milieu or produced using recombinant DNA technology (e.g., polymerase chain reaction (PCR) amplification, cloning) or chemical synthesis. To produce recombinant MurG protein, a nucleic acid molecule encoding a MurG protein can be inserted into any vector capable of expressing the nucleic acid in a host clell. Suitable and preferred nucleic acid molecules to include in recombinant vectors of the present invention are as disclosed herein. Such suitable and preferred nucleic acid molecules include numerous MurG encoding genes that have been isolated to date, and that will be isolated in the future. A preferred nucleic acid molecule of the present invention encodes a homologue of MurG. Homologues of MurG can be recognized by the presence of certain conserved amino acid residues or sequences.

A sequence alignment for six MurG sequences is shown in FIG. 3A. Highlighted residues include those that are invariant or almost invariant across all MurG proteins. A nucleic acid molecule of the present invention can encode any portion of a MurG protein, preferably a full-length MurG protein or either of the two domains. A more preferred nucleic acid molecule to include in a recombinant vector, and particularly in a recombinant molecule, includes a nucleic acid molecule encoding a protein having the amino acid sequence represented by amino acid sequences of MurG proteins as deposited in the NCBI database and are identified with Accession Nos. CAB51993, A71316, E70579, C71699, F70195, A43727, JC1275, BVECMG, CEECAM, O83535, Q9ZK59, CAB85280, AAF39020, BAA18775, AAD26629, CAB73295, P37585, Q9ZHA9, Q9ZHDC0, Q9ZBA5, Q9X4H4, Q9WY74, P74657, O06224, Q9Z702, O84766, O69552, O67238, O51708, O25770, O07670, O07109, P45065, CAB66324, AAC68356, AAF06830, P18579, P17443, P17952, P16457, P07862, AAE23178, AAD53936, CAA18668, CAA38869, CAA38868, CAA38867, CAA38866, AAD08196, BAA01453, BAA01455, BAA01454, AAD19042, CAA45558, CAA74235, AAD10537, AAD06652, AAC95450, CAA14869, AAC73201, AAC65509, AAC67113, AAC45636, CAB08640, AAC22793, AAC07193, BAA24357, CAB13395, BAA01355, AAB35538, 1904153C, 1808265B, 1808265A, CAA36866, CAA36869, CAA36868, CAA36867, CAA36776, and AAA99436. Further, examples of nucleic acid molecules encoding MurG proteins have been deposited in NCBI, Genbank, and have Accession Nos. AL162758, AE002281, D90917, AF110367, AL139077, AJ242646, AE000520, AE000511, LA2023, U00096, NC-000922, AE000783, AE000657, AE001348, AF099188, AR048673, AR048672, AF179611, AL022602, AL109663, X55034, AE000621, D10602, AE001670, X64259, Y13922, U10879, AE001535, AF068902, AJ235271, AE000118, AE001227, AE001176, U94707, Z95388, U32793, AE000727, D84504, Z99111, D10483, X52644, X52540, and L24773. These sequences are known and are publicly available. Further, as additional genomes and genes are sequenced, more MurG encoding nucleotide sequences will become available, and can be used in the present invention.

In specific embodiments of the invention, the protein sequence of $E.\ coli$ MurG was reported in 1990 (Ikeda et al. Nucleic Acids Res. 1990, 19:4014; and Mengin-Lecreuix, D. et al., Nucleic Acids Res. 1990, 18:2810.). $E.\ coli$ genomic DNA can be purified from $E.\ coli$ or purchased from ATCC, or the gene for $E.\ coli$ MurG is cloned into a plasmid can be obtained from numerous sources. Primers were designed to the portions of the gene corresponding to the N and C termini of the protein. The primers also encoded restriction enzyme sites outside the protein coding region. The gene sequence was amplified; the corresponding double stranded nucleic acid molecule was cut with appropriate restriction enzymes for cloning into a commercially available expression vector (pET expression vectors available from Novagen provide for numerous variations of MurG protein—wild-type or fusion proteins or proteins with affinity tags at N or C terminus. We have worked with several constructs but found that MurG with a His-tag at C-terminus crystallized best; the protein sequence contained an extra methionine at N-terminus and eight extra residues at C terminus, six of which were histidines. The vector used was pET21b. (as described in Ha et al. J. Am. Chem. Soc. 121, (1999) 8415–8426 hereby incorporated by reference in its entirety).

A recombinant vector of the present invention can be either RNA (probably not) or DNA, and typically includes, but is not limited to, a virus or plasmid. Any recombinant vector and host cell that provides for expression of a MurG protein encoding mucleic acid sequence can be used in the present invention to express MurG protein for crystallization. Preferred vectors are engineered for high level expression in $E.\ coli$ such as, but not limited to, pET vectors. We have found that over-expression of MurG from either $E.\ coli$ or $E.\ faecalis$ in $E.\ coli$ cells is not toxic and, thus, this approach will work for other MurG proteins.

As used herein, an expression vector is a DNA vector that is capable of transforming a host cell and of affecting expression of a specified nucleic acid molecule. Expression vectors of the present invention include any vectors that function (i.e., direct gene expression) in recombinant cells of the present invention, including bacterial, fungal, and other microorganisms cells. Preferred expression vectors of the present invention direct expression in bacterial cells from a plasmid. A preferred recombinant molecule of the present invention comprises pET21b with $E.\ coli$ MurG gene cloned into the Nde 1 and Xho 1 sites.

An expression vector of the present invention can be transformed into any suitable host cell to form a recombinant cell. A suitable host cell includes any cell capable of expressing a nucleic acid molecule inserted into the expression vector. For example, a procaryotic expression vector can be transformed into a bacterial host cell. If the expression vector contains a T7 promoter then a source of T7 RNA polymerase must be provided to induce expression. Some host cells contain the T7 RNA polymerase gene in a repressed state. Expression of T7 RNA polymerase can be induced with a chemical signal such as IPTG or heat. Alternatively, a source of T7 RNA polymerase can be introduced at the appropriate time by infection with a phage containing a copy of T7 RNA polymerase. A wide range of hosts strains can be infected with a suitable phage. Some host strains have been engineered to contain inducible copies of T7 RNA polymerase gene. Such host strains include BL21(DE3) and derivatives thereof. A preferred host strain of the present invention is BL21(DE3)pLysS or BL21 (DE3)pLysE, which are commercially available from Novagen and can be readily transformed with a DNA plasmid vector containing a MurG gene under the control of the 17 promoter. As already stated above, a preferred vector is a pET vector, preferably containing a restriction enzyme site permitting cloning of the gene as a fusion containing a C-terminal his tag.

In a preferred embodiment, one method to isolate MurG protein useful for producing MurG crystals includes recovery of MurG protein having a C-terminal LEHHHHHH (His tag) sequence purified as described in Ha et al. (1999, J. Amer. Chem. Soc. 121:8415–8426). One of skill in the art is able to modify this procedure in order to purify other proteins can be produced as C-terminal histadine (his) tags. The purification conditions for specific MurG proteins will vary depending upon the particular characteristics of the proteins such as their isoelectric point, molecular weight, etc. It is known that the isoelectric points of different MurG homologues vary a bit, although they are generally relatively high. Also, some MurG homologues may be more hydrophobic than others, which will mean differences in amount of detergent necessary for purification. It is likely that all the MurG homologues can be purified over nickel affinity columns using the C-terminal his-tag as a handle. Those skilled in the art of protein purification will know how to modify purification parameters depending upon the protein characteristics, in order to purify the protein for crystallization.

Structure of MurG Protein

One embodiment of the present invention includes a model of a MurG protein, in which the model represents a three-dimensional structure of a MurG protein. Another embodiment of the present invention includes the three-dimensional structure of a MurG protein. A three-dimensional structure of a MurG protein encompassed by the present invention substantially conforms with the atomic coordinates represented in Table 1. According to the present invention, the use of the term "substantially conforms" refers to at least a portion of a three-dimensional structure of a MurG protein which is sufficiently spatially similar to at least a portion of a specified three-dimensional configuration of a particular set of atomic coordinates (e.g., those represented by Table 1) to allow the three-dimensional structure of another MurG protein to be modeled or calculated using the particular set of atomic coordinates defining the three-dimensional configuration of the MurG protein. For example, but not meant to be a limitation, homology modeling can be done using the linear sequence of a different MurG and $E.$ $coli$ coordinates; molecular replacement can allow the solution of a different MurG structure using the $E.$ $coli$ MurG coordinates and experimental data such as x-ray diffraction pattern from a different MurG crystal. According to the present invention, a three-dimensional structure of a given portion or chain of a first MurG protein can substantially conform to at least a portion of the atomic coordinates which represent a three-dimensional configuration of a second MurG.

More particularly, a structure that substantially conforms to a given set of atomic coordinates is a structure wherein at least about 50% of such structure has an average root-mean-square deviation (RMSD) of less than about 2.5 Å for the α-carbon or C-alpha backbone atoms in secondary structure elements in each domain, and more preferably, less than about 2.0 Å for the C-alpha backbone atoms in secondary structure elements in each domain, and, in increasing preference, less than about 1.5 Å, less than about 1.0 Å, less than about 0.7 Å, and more preferably, less than about 0.5 Å for the C-alpha backbone atoms in secondary structure elements in each domain. In a more preferred embodiment, a structure that substantially conforms to a given set of atomic coordinates is a structure wherein at least about 75% of such structure has the recited average root-mean-square deviation (RMSD) value, and more preferably, at least about 90% of such structure has the recited average RMSD value, and most preferably, about 100% of such structure has the recited average RMSD value.

In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates. Preferably, a three-dimensional structure that substantially conforms to a given set of atomic coordinates is a structure wherein at least about 50% of the common amino acid side chains have an average RMSD value of less than about 1.5 Å, and more preferably, less than about 1.3 Å, and in increasing preference, less than about 1.0 Å, less than about 0.7 Å, and most preferably, less than about 0.3 Å.

In a more preferred embodiment, a structure that substantially conforms to a given set of atomic coordinates is a structure wherein at least about 75% of the common amino acid side chains have the recited average RMSD value, and more preferably, at least about 90% of the common amino acid side chains have the recited average RMSD value, and most preferably, about 100% of the common amino acid side chains have the recited average RMSD value.

In more preferred embodiments of the present invention, a large number of different "rotamers" or "rotational isomers" of the MurG protein are encompassed by three-dimensional structures of the invention in which the amino acid side chains are at a variety of positions in crystalline forms of the protein or for the protein in solution. Different rotamers refer to molecules of identical configuration may be distinguished as having different conformations after rotation about the various molecular bonds. Therefore, while the same or similar amino acids may be present, the exact location will vary depending upon the freedom of rotation of the bonds due to hydrogen bonding, and other molecular forces.

Structure of the α-Carbon Backbone OF MurG and the α-Carbon Backbone and Conserved Amino Acid Residues The present invention includes the three-dimensional structure of the α-carbon or C-alpha backbone of a MurG protein, in particular the $E.$ $Coli$ MurG protein. A three-dimensional structure of the C-alpha backbone of the MurG protein encompassed by the present invention substantially conforms with the atomic coordinates represented in Table 2.

More particularly, a structure that substantially conforms to a given set of atomic coordinates is a structure wherein at least about 50% of such structure has an average root-mean-square deviation (RMSD) of less than about 2.5 Å for the C-alpha backbone atoms in secondary structure elements in each domain, and more preferably, less than about 2.0 Å for the C-alpha backbone atoms in secondary structure elements in each domain, and, in increasing preference, less than about 1.5 Å, less than about 1.0 Å, less than about 0.7 Å, and more preferably, less than about 0.5 Å for the C-alpha backbone atoms in secondary structure elements in each domain. In a more preferred embodiment, a structure that substantially conforms to a given set of atomic coordinates is a structure wherein at least about 75% of such structure has the recited average root-mean-square deviation (RMSD) value, and more preferably, at least about 90% of such structure has the recited average RMSD value, and most preferably, about 100% of such structure has the recited average RMSD value. The C-alpha backbone of MurG proteins is expected to be more conserved than the location of the particular amino acid residue side chains.

The present invention also includes the three-dimensional structure of the α-carbon or C-alpha backbone and conserved or invariant amino acid residue side chains of a MurG protein, in particular the *E. coli* MurG protein. A three-dimensional structure of the C-alpha backbone and conserved amino acid residues of the MurG protein encompassed by the present invention substantially conforms with the atomic coordinates represented in Table 3. The conserved amino acids are highlighted in blue in FIG. 3a and include G14, G15, G18, H19, G104, H124, E125, G190, G191, S192, G194, A195, R261, G263, A264, E269, P281, Q289, N292 and A293 (as numbered in the *E. Coli* MurG sequence set forth in FIG. 3a).

More particularly, a structure that substantially conforms to a given set of atomic coordinates is a structure wherein at least about 50% of such structure has an average root-mean-square deviation (RMSD) of less than about 2.5 Å, for the C-alpha backbone and conserved amino acid residue atoms in secondary structure elements in each domain, and more preferably, less than about 2.0 Å for the backbone atoms in secondary structure elements in each domain, and, in increasing preference, less than about 1.5 Å, less than about 1.0 Å, less than about 0.7 Å, and more preferably, less than about 0.5 Å for the backbone atoms in secondary structure elements in each domain. In a more preferred embodiment, a structure that substantially conforms to a given set of atomic coordinates is a structure wherein at least about 75% of such structure has the recited average rootmean-square deviation (RMSD) value, and more preferably, at least about 90% of such structure has the recited average RMSD value, and most preferably, about 100% of such structure has the recited average RMSD value.

Structure of the Donor Nucleotide Binding Site of MurG Proteins

An embodiment of the present invention includes the three-dimensional structure of a donor nucleotide binding site of a MurG protein, in particular an *E. coli* MurG protein. A more preferred embodiment of the present invention includes a three-dimensional structure of a donor nucleotide binding site of a MurG protein wherein the three-dimensional structure of the donor nucleotide binding site substantially conforms to the atomic coordinates in Table 4. In a preferred embodiment, the donor nucleotide binding site is a UDP-GlcNAc binding site of a MurG protein.

Figure 4A:
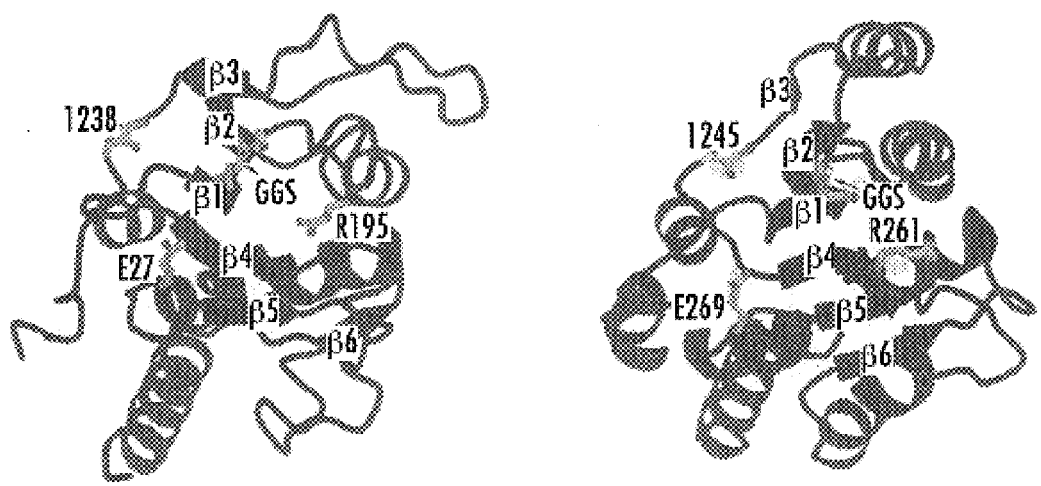
FIG. 4. Structural analysis of the substrate binding pockets in MurG. A. Structural comparison between the C-terminal domain of phage T4 β-glucosyltransferase (left) and the C-terminal domain of *E. coli* MurG (right). The aligned six β-strands are magenta, the aligned α-helices are orange, and the other structural elements are blue. In β-glucosyltransferase, key residues involved in UDP binding are highlighted in yellow. The analogous residues in MurG are also highlighted in yellow. B. A close-up view of the proposed donor binding pocket in the MurG C domain with the docked UDP-GlcNAc. Conserved residues in MurG are colored magenta. The carbonyl oxygen of residue 1245 is shown in red, and its backbone nitrogen is shown in blue. C. The surface of *E. coli* MurG. The G loops and other conserved residues in MurG are colored magenta. The proposed membrane binding interface is also highlighted with hydrophobic residues in yellow and positively charged residues in blue.

As described in Example 1, the donor nucleotide binding site is located in the C-terminal domain (see FIG. 4a). This binding site is based on the comparison of β-glucosyltransferase (BGT) and *E. coli* MurG and based on experiments done in our laboratory showing that the isolated C domain binds to a UDP-hexose column (See Example 1).

The atomic coordinates of Table 4 set forth the donor nucleotide binding site three-dimensional structure without a donor nucleotide such as UDP-GlcNAc bound to the MurG protein.

According to the present invention, the use of the term "substantially conforms" refers to at least a portion of a three-dimensional structure of a donor nucleotide binding site of a MurG protein which is sufficiently spatially similar to at least a portion of a specified three-dimensional configuration of a particular set of atomic coordinates (e.g., those represented by Table 4) to allow the three-dimensional structure of the donor nucleotide binding domain to be modeled or calculated (i.e., by molecular replacement) using the particular set of atomic coordinates defining the three-dimensional configuration of the donor nucleotide binding site of a MurG protein. According to the present invention, a three-dimensional structure of a given donor nucleotide binding site of a first MurG protein can substantially conform to at least a portion of the atomic coordinates which represent a three-dimensional configuration of a second MurG. Since the atomic coordinates of Table 4 were obtained from the *E. coli* MurG crystal protein without a donor nucleotide bound, there will be some variation from the atomic coordinates of the donor nucleotide binding site when a nucleotide is bound vs. unbound. Therefore, a structure "substantially conforming" to that represented by the atomic coordinates in Table 4, will include a structure obtained from co-crytallization of the protein with a donor nucleotide.

More particularly, a structure that substantially conforms to a given set of atomic coordinates is a structure wherein at least about 50% of such structure has an average root-mean-square deviation (RMSD) of less than about 1.5 Å for the C-alpha backbone atoms in secondary structure elements in each domain, and more preferably, less than about 1.3 Å for the C-alpha backbone atoms in secondary structure elements in each domain, and, in increasing preference, less than about 1.0 Å, less than about 0.7 Å, and more preferably less than about 0.5 Å for the C-alpha backbone atoms in secondary structure elements in each domain. In a more preferred embodiment, a structure that substantially conforms to a given set of atomic coordinates is a structure wherein at least about 75% of such structure has the recited average root-mean-square deviation (RMSD) value, and more preferably, at least about 90% of such structure has the recited average RMSD value.

In an even more preferred embodiment, the above definition of "substantially conforms" can be extended to include atoms of the conserved or invariant amino acid side chains located within the binding site. As used herein, the phrase "conserved amino acid side chains" refers to amino acid side chains that are conserved between MurG proteins within the donor nucleotide binding site. The conserved amino acid residues of the donor nucleotide binding site have been identified as I125, R261, G263, A264, E269, P281, Q289, N292 and A293 (as numbered in the *E. coli* MurG sequence set forth in FIG. 3a) and the G loop found between residues numbered 190–195 having residues G190, G191, S192, G194, and A195. Some or all of these conserved residues are necessary for binding the nucleotide donor.

Preferably, a three-dimensional structure that substantially conforms to a given set of atomic coordinates is a structure wherein at least about 50% of the conserved amino acid side chains have an average RMSD value of less than about 1.5 Å, and more preferably, less than about 1.3 Å, and in increasing preference, less than about 1.0 Å, less than about 0.7 Å, and most preferably, less than about 0.3 Å. In a more preferred embodiment, a structure that substantially conforms to a given set of atomic coordinates is a structure wherein at least about 75% of the conserved amino acid side chains have the recited average RMSD value, and more preferably, at least about 90% of the conserved amino acid side chains have the recited average RMSD value, and most preferably, about 100% of the conserved amino acid side chains have the recited average RMSD value.

Structure of the Acceptor Binding Site of MurG Protein

An embodiment of the present invention includes the three-dimensional structure of an acceptor binding site of a MurG protein. A three-dimensional structure of a acceptor binding site of a MurG protein encompassed by the present invention substantially conforms with the atomic coordinates represented in Table 5. A more preferred embodiment of the present invention includes a three-dimensional structure of an acceptor binding site of a MurG protein wherein the three dimensional structure of the acceptor binding site substantially conforms to the atomic coordinates Table 5.

According to the present invention, the use of the term "acceptors" refers to Lipid I and analogues thereof. For the purposes of obtaining co-crystals containing acceptor analogues bound to the acceptor binding site better, the analogues need not be functional acceptors in a MurG assay. In particular embodiments of the present invention, the acceptor is selected from the group consisting of, but not limited to Lipid I, and analogs of Lipid I (see compounds described in Ha et al., J. Amer. Chem. Soc. 1999, vol. 121:8415–26, incorporated by herein by reference in its entirety).

Figure 4B:
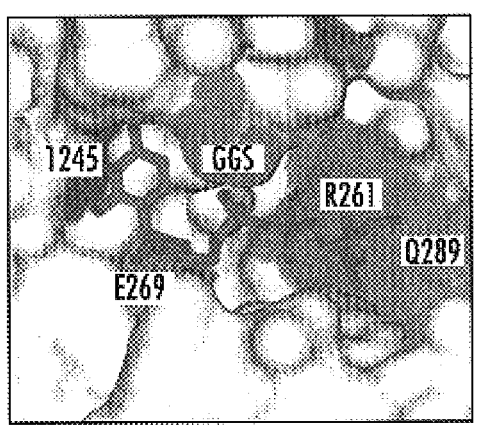
Figure 4C:
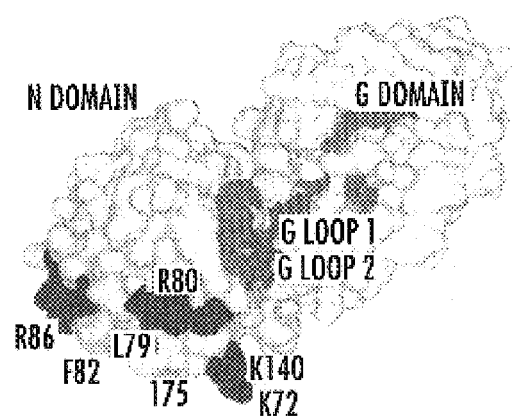

As described in Example 1, the acceptor binding site is located in the N-terminal domain of a MurG protein (see FIGS. 3a and 4c). The acceptor binding site or domain is characterized by three highly conserved regions, twp of which are glycine-rich loops (also referred to as "G loops") that face the cleft between the C-terminal and N-terminal domains. The conserved residues of the acceptor binding site comprise G14, G15, G18, H19, G104, H124, and E125 (as numbered in the E. coli MurG sequence set forth in FIG. 3a) and two conserved G loop structures.

According to the present invention, the use of the term "substantially conforms" refers to at least a portion of a three-dimensional structure of an acceptor binding site of a MurG protein which is sufficiently spatially similar to at least a portion of a specified three-dimensional configuration of a particular set of atomic coordinates (e.g., those represented by Table 5) to allow the three-dimensional structure of the acceptor binding site to be modeled or calculated (i.e., by homology modeling) using the particular set of atomic coordinates defining the three-dimensional configuration of the acceptor binding site of a MurG protein. According to the present invention, a three-dimensional structure of a given acceptor binding site of a first MurG protein can substantially conform to at least a portion of the atomic coordinates which represent a three-dimensional configuration of a second MurG.

In an even more preferred embodiment, the above definition of "substantially conforms" can be extended to include atoms of the conserved amino acid side chains. As used herein, the phrase "conserved amino acid side chains" refers to the conserved or invariant amino acid side chains that are common to MurG proteins. Preferably, a three-dimensional structure that substantially conforms to a given set of atomic coordinates is a structure wherein at least about 50% of the conserved amino acid side chains have an average RMSD value of less than about 1.5 Å, and more preferably, less than about 1.3 Å, and in increasing preference, less than about 1.0 Å, less than about 0.7 Å, and most preferably, less than about 0.3 Å. In a more preferred embodiment, a structure that substantially conforms to a given set of atomic coordinates is a structure wherein at least about 75% of the conserved amino acid side chains have the recited average RMSD value, and more preferably, at least about 90% of the conserved amino acid side chains have the recited average RMSD value, and most preferably, about 100% of the conserved amino acid side chains have the recited average RMSD value.

Structure of a Membrane Association Site of MurG Protein

An embodiment of the present invention includes the three-dimensional structure of a membrane association site of a MurG protein. A three-dimensional structure of a membrane association site of a MurG protein encompassed by the present invention substantially conforms with the atomic coordinates represented in Table 6. A more preferred embodiment of the present invention includes a three-dimensional structure of an acceptor binding site of a MurG protein wherein the three-dimensional structure of the acceptor binding site substantially conforms to the atomic coordinates in Table 6.

According to the present invention, the use of the term "membrane association site" refers to the region of a MurG protein that associates with cytoplasmic surface of bacterial membranes where it performs the reaction of coupling a soluble donor sugar to the membrane anchored acceptor sugar, Lipid I. Analysis of the E. coli MurG protein structure shows a hydrophobic patch consisting of residues I75, L79, F82, W85, and W116 in the N-domain. The membrane association site is where the MurG protein associates with the bacterial membranes, and that it is target for inhibitors if we find that a) we can bind to it with another molecule; b) we can disrupt membrane association by binding to it; or c) disrupting membrane association inhibits activity.

As described in Example 1, the membrane association site is located in the N-terminal domain of a Mur protein (see FIG. 4c). The location of the membrane association site is in close proximity to the acceptor binding site and membrane association in this patch would bring the two M-terminal G-loops close to the membrane surface where the diphosphate portion of the acceptor is located.

According to the present invention, the use of the term "substantially conforms" refers to at least a portion of a three-dimensional structure of a membrane association site of a MurG protein which is sufficiently spatially similar to at least a portion of a specified three-dimensional configuration of a particular set of atomic coordinates (e.g., those represented by Table 6) to allow the three-dimensional structure of the membrane association site to be modeled or calculated (i.e., by molecular replacement) using the particular set of atomic coordinates defining the three-dimensional configuration of the membrane association site of a MurG protein. According to the present invention, a three-dimensional structure of a given membrane association site of a first MurG protein can substantially conform to at least a portion of the atomic coordinates which represent a three-dimensional configuration of a second Mur).

More particularly, a structure that substantially conforms to a given set of atomic coordinates is a structure wherein at least about 50% of such structure has an average root-mean-square deviation (RMSD) of less than about 1.5 Å for the structural elements in the site, and more preferably, less than about 1.3 Å for the structure elements in each site, and, in increasing preference, less than about 1.0 Å, less than about 0.7 Å, less than about 0.5 Å, and more preferably, less than about 0.3 Å for the structural elements in each site. In a more preferred embodiment, a structure that substantially conforms to a given set of atomic coordinates is a structure wherein at least about 75% of such structure has the recited average root-mean-square deviation (RMSD) value, and more preferably, at least about 90% of such structure has the recited average RMSD value, and most preferably, about 100% of such structure has the recited average RMSD value.

In an even more preferred embodiment, the above definition of "substantially conforms" can be extended to include atoms of α-carbon backbone and conserved amino acid side chains. As used herein, the phrase "conserved amino acid side chains" refers to amino acid side chains that are conserved between MurG proteins. Preferably, a three-dimensional structure that substantially conforms to a given set of atomic coordinates is a structure wherein at least about 50% of the conserved α-carbon backbone and conserved amino acid side chains have an average RMSD value of less than about 1.5 Å, and more preferably, less than about 1.3 Å, and in increasing preference, less than about 1.0 Å, less than about 0.7 Å, and most preferably, less than about. 0.3 Å. In a more preferred embodiment, a structure that substantially conforms to a given set of atomic coordinates is a structure wherein at least about 75% of the α-carbon backbone and conserved amino acid side chains have the recited average RMSD value, and more preferably, at least about 90% of the α-carbon backbone and conserved acid side chains have the recited average RMSD value, and most preferably, about 100% of the α-carbon and conserved amino acid side chains have the recited average RMSD value.

Computer Readable Medium

Another embodiment of the present invention relates to a computer-readable medium encoded with a set three-dimensional coordinates selected from the group consisting of the three-dimensional coordinates represented in Table 1, the three-dimensional coordinates represented in Table 2, the three-dimensional coordinates represented in Table 3, the three-dimensional coordinates represented in Table 4, the three-dimensional coordinates represented in Table 5, or the three-dimensional coordinates represented in Table 6, wherein using a graphical display software program, the three-dimensional coordinates create an electronic file that can be visualized on a computer capable of representing said electronic file as a three-dimensional image. Preferably, the three-dimensional image is of a MurG protein, the α-carbon backbone of MurG, the α-carbon backbone and conserved amino acid residue sidechains of MurG, the donor nucleotide binding site of MurG, the acceptor binding site of MurG, or the membrane association site of MurG.

Yet another embodiment of the present invention relates to a computer-readable medium encoded with a set of three-dimensional coordinates of a three-dimensional structure which substantially conforms to the three-dimensional coordinates represented in Table 1, wherein using a graphical display software program, the three-dimensional coordinates create an electronic file that can be visualized on a computer capable of representing said electronic file as a three-dimensional image. In other embodiments, the present invention relates to a computer-readable medium encoded with a set of three-dimensional coordinates of a three-dimensional structure which substantially conforms to the three-dimensional coordinates represented in Table 2, Table 3, Table 4, Table 5 or Table 6, wherein using a graphical display software program, the three-dimensional coordinates create an electronic file that can be visualized on a computer capable of representing said electronic file as a three-dimensional image. Preferably, the three-dimensional image is of a MurG protein, the α-carbon backbone of MurG, the α-carbon backbone and conserved amino acid residue sidechains of MurG, the donor nucleotide binding site of MurG, the acceptor binding site of MurG, or the membrane association site of MurG.

Images

One embodiment of the present invention relates to a two dimensional image of an E. coli MurG protein including those illustrated in FIGS. 3–4. Most of these figures were drawn with the MOLSCRIPT program. Preferably, the two dimensional image is of a MurG protein, the α-carbon backbone of MurG, the α-carbon backbone and conserved amino acid residue sidechains of MurG, the donor nucleotide binding site of MurG, the acceptor binding site of MurG, or the membrane association site of MurG.

Another embodiment of the present invention includes a three-dimensional computer image of the three-dimensional structure of a MurG protein, preferably the E. coli MurG protein. Suitable structures of which to produce three-dimensional computer images are disclosed herein. Preferably, a computer image is created to a structure substantially conforming with the three-dimensional coordinates represented in Table 1.

Another embodiment of the present invention includes an image of an MurG protein that is generated when a set of three-dimensional coordinates comprising the three-dimensional coordinates represented in Table I are analyzed on a computer using a graphical display software program to create an electronic file of the image and visualizing the electronic file as a three-dimensional image. Suitable structures to image are disclosed herein. Preferably, the three-dimensional structures are of a MurG protein, the α-carbon backbone of MurG, the α-carbon backbone and conserved amino acid residue sidechains of MurG, the donor nucleotide binding site of MurG, the acceptor binding site of MurG, or the membrane association site of MurG. Most preferably, the MurG protein is the E. coli MurG protein described herein. A computer image of the present invention can. be produced using any suitable software program, including, but not limited to, MOLSCRIPT 2.0 (Avatar Software AB, Helenebrgsgatan 21 C, SE-11713, Stockholm, Sweden), the graphical display program 0 (Jones et al., Acta Crystallography, vol. A47, p. 110, 1991), or the graphical display program GRASP. Suitable computer hardware useful for producing an image of the present invention are known to those of skill in the art. Preferred computer hardware includes a Silicon Graphics Workstation.

Models of MurG Proteins and Binding Sites

According to the present invention, a three-dimensional structure of the E. coli MurG protein and its binding sites of the present invention can be used to derive a model of the three-dimensional structure of another MurG protein and its binding sites (i.e., a structure to be modeled). As used herein, a "structure" of a protein refers to the components and the manner of arrangement of the components to constitute a protein or binding site. Also, as used herein, the term "model" refers to a representation of a tangible medium of the three-dimensional structure of a protein, polypeptide or peptide, or binding site of a protein. For example, a model can be a representation of the three-dimensional structure in a electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Computer screen images and pictures of the model can be visualized in a number of formats including space-filling representations, α-carbon traces, ribbon diagrams and electron density maps.

Suitable target MurG proteins and their associated binding sites to model using a method of the present invention include any MurG protein and binding sites that are at least in part structurally related to the *E. coli* MurG protein or its binding sites. A preferred target MurG structure that is at least in part structurally related includes a target MurG structure having an amino acid sequence that is at least about 25%, preferably at least about 30%, more preferably at least about 36%, more preferably at least about 40%, even more preferably at least about 50%, more preferably at least about 60%, more preferably at least about 70%, more preferably at least about 80%, and more preferably at least about 90% identical to an amino acid sequence of the *E. coli* MurG protein, across the full-length of the target MurG structure sequence when using, for example, a sequence alignment program such as DNAsiS™ program (available from Hitachi Software, San Bruno, Calif.) or the MacVector™ program (available from the Eastman Kodak Company, New Haven, Conn.) or the GCγ™ program (available from the "GCγ", University of Wisconsin, Madison, Wis.), such alignment being performed for example, using the standard default values accompanying such alignment programs.

Preferred MurG proteins and their binding sites are set forth in the amino acid sequences of MurG proteins as deposited in the NCBI database and are identified with Accession Nos. CAB51993, A71316, E70579, C71699, F70195, A43727, JC1275, BVECMG, CEECAM, O83535, Q9ZK59, CAB85280, AAF39020, BAA18775, AAD26629, CAB73295, P37585, Q9ZHA9, Q9ZHDC0, Q9ZBA5, Q9X4H4, Q9WY74, P74657, O06224, Q9Z702, O84766, O69552, O67238, O51708, O25770, O07670, O07109, P45065, CAB66324, AAC68356, AAF06830, P18579, P17443, P17952, P16457, P07862, AAE23178, AAD53936, CAA18668, CAA38869, CAA38868, CAA38867, CAA38866, AAD08196, BAA01453, BAA01455, BAA01454, AAD19042, CAA45558, CAA74235, AAD10537, AAD06652, AAC95450, CAA14869, AAC73201, AAC65509, AAC67113, AAC45636, CAB08640, AAC22793, AAC07193, BAA24357, CAB13395, BAA01355, AAB35538, 1904153C, 1808265B, 1808265A, CAA36866, CAA36869, CAA36868, CAA36867, CAA36776, and AAA99436. The amino acid sequences are publicly available.

A variety of MurG proteins from numerous organisms can be used to prepare models of MurG proteins and binding sites, including but not limited to, microorganisms such as bacteria, higher-order bacteria, thermal stable bacteria, spirochetes, small pathogenic organisms, fungi, protozoa, cyanobacteria, and trypanosomes. More particularly, bacteria such as but not limited to, *Escherichia coli, Bacillus subtilis, Aquefex aeolicus, Borrelia burgdorferi, Chlamydia pneumoniae, Chlamydia trachomatis, Enterococcus faecais, Enterococcus hirae, Haemophilus influenzae, Helicobacter pyloir J99, Helicobacter pylori, Mycobacterium tuberculosis, Porphyromonas gingivalis, Rickettsia prowazekii, Streptomyces coelicolor, Streptomyces collinus, Streptococcus pneumoniae, Synechocystis* sp. (strain PCC6803), *Thermotoga maritime*, and *Treponema pallidum*. It is noted that nucleotide and amino acid sequences for many of the above identified organisms are known and publicly available.

Preferred target MurG proteins and binding site structures to model also include, but are not limited to, derivatives of MurG proteins, such as a MurG protein having one or more amino acid residues substituted, deleted or added (referred to herein as MurG mutants), or proteins encoded by natural variants of a nucleic acid molecule encoding a MurG.

In another embodiment of the invention, the process of building a homology model for a protein is divided into the following steps:
(1) Determine which proteins are related to the model protein;
(2) Determine structurally conserved regions (SCRs);
(3) Align the amino acid sequence of the unknown protein with those of the reference protein(s) within the SCRs;
(4) Assign coordinates in the conserved regions;
(5) Predict conformations for the rest of the peptide chain, including loops between the SCRs and possibly the N- and C-termini;
(6) Search for the optimum side chain conformations for residues that differ from those in the reference proteins; and
(7) Use energy minimization and molecular dynamics to refine the molecular structure so that steric strain introduced during the model-building process can be relieved.

Published sequences are readily available through on-line databases on the Internet, such as SwissProt (http://www.expasy.ch/sprot/sprot-top.html). MurG specific and related sequences are obtained for use for building homology models by text-based or sequence similarity searching. SCRs for MurG is the entire protein, considering the *E. coli* MurG crystal structure is the only similar sequence with structural data. Alignment of the sequences using an appropriate alignment program and algorithm, such as Clustal W, allows appropriate assignment of the *E. coli* protein coordinates to a MurG sequence of unknown structure. The Modeler program performs the conformational predictions for the peptide chain and side chains. Dynamics and minimization using an appropriate program and algorithm, such as Discover.

Modeler Description:

Modeler is an automated homology-modeling scheme designed to find the most probable three-dimensional structure of a protein, given its amino acid sequence and its alignment with related structures. It derives 3D protein models without the time consuming separate stages of core region identification and loop region building or searching that is inherent to manual homology modeling schemes. The related or reference protein structures are used to derive spatial restraints expressed as probability density functions (PDFs) for each of the restrained features of the model. As an example, the main chain conformation of a given residue in the model will be described by restraints that depend upon the residue type, the main chain conformation of equivalent residues in the reference proteins and the local sequence similarity. The probability distribution functions that are used in restraining the model structure are derived from correlations between structural features in a database of families of homologous proteins aligned on the basis of their 3D structure. These functions are used to restrain C—C distances, main chain N—O distances, main chain and side chain dihedral angles, etc. The individual restraints are assembled into a single molecular probability density function (MPDF). The three-dimensional protein model is then obtained by an optimization of this MPDF. The optimization procedure itself consists of a variable target function method (Braun and Go, 1985) with conjugate gradient minimization scheme followed by an optional restrained simulated annealing molecular dynamics scheme.

While several reference structures are used in the traditional homology model building process, only one set of coordinates can be used in any one peptide segment. Modeler is able to simultaneously incorporate structural data from one or more reference proteins. Structural features in the reference proteins are used to derive spatial restraints which in turn are used to generate model protein structures using conjugate gradient and simulated annealing optimization procedures.

Clustal W description:

Clustal W aligns multiple sequences using a progressive pairwise alignment algorithm. It first generates all possible pairwise alignments for a list of sequences and then builds the guide tree based on their pairwise sequence identity, aligning the sequences following the order of the guide tree.

Several unique features in Clustal W improve the sensitivity of the alignment of divergent protein sequences (Thompson et al, 1994a).

(1) Individual weights are assigned to each sequence in a partial alignment in order to downweight near-duplicate sequences and upweight the most divergent ones.

(2) Amino acid substitution matrices are varied at different alignment stages according to the divergence of the sequences to be aligned.

(3) Residue-specific gap penalties and locally reduced gap penalties in hydrophilic regions encourage new gaps in potential loop regions rather than regular secondary structure.

(4) Positions in early alignments, where gaps have been opened, receive locally reduced gap penalties to encourage the opening of new gaps at these positions.

Discover Description:

The Discover program performs energy minimization, template forcing, torsion forcing, and dynamic trajectories and calculates properties such as interaction energies, derivatives, mean square displacements, and vibrational frequencies. It provides tools for performing simulations under various conditions including constant temperature, constant pressure, constant stress, periodic boundaries, and fixed and restrained atoms.

Homology modeling methods are known to those skilled in the art and are described in the following homology references:

Bacon, D. J.; Anderson, W. F. "Multiple sequence alignment," J. Mol. Biol., 191, 153–161 (1990).

Barker, W. C.; George, D. G.; Hunt, L. T. "Protein Sequence Database," in Methods in Enzymology, 183, 49, Academic Press:San Diego (1990).

Barton, G. J. "Protein multiple sequence alignment and flexible pattern matching," Meth Enzyrnol, 183, 403–428 (1990).

Benedetti, E.; Morelli, G.; Nemethy, G; Scheraga H. A. "Statistical and Energetic Analysis of Side-chain Conformations in Oligopeptides," Int. J. Peptide Protein Res. 22, 1–15 (1983).

Berger, M. P.; Munson, P. J. "A novel randomized iterative strategy for aligning multiple protein sequences," Comput Appl Biosci, 7, 479–484 (1991).

Blundell, T. L.; Sibanda, B. L.; Sternberg, M. J. E.; Thornton, J. M. "Knowledge-based prediction of protein structures and the design of novel molecules," Nature, 326, 347 (1987).

Blundell, T. L.; Carney, D.; Gardner, S.; Hayes, F.; Howlin, B.; Hubbard, T.; Overington, J.; Singh, D. A.; Sibanda, B. L.; Sutcliff, M. "Knowledge-based protein modelling and design," Eur. J. Biochem., 172, 513 (1988).

Browne, W. J.; North, A. C. T.; Phillips, D. C.; Brew, K.; Vanaman, T. C.; Hill, R. L. "A Possible Three-dimensional Structure of Bovine-Lactalbumin based on that of Hen's Egg-White Lysozyme," J. Mol. Biol., 42, 65 (1969).

Burks, C. et al. "GenBank: Current Status and Future Directions," in Methods in Enzymology, 183, 3–4, Academic Press: San Diego (1990).

Chothia, C. "Hydrophobic Bonding and Accessible Surface Area in Proteins", Nature, 248, 338–339 (1974).

Chothia, C. "The Nature of the Accessible and Buried Surfaces in Proteins," J. Mol. Biol., 105, 1–14 (1976).

Connolly, M. L. "Solvent-Accessible Surfaces of Proteins and Nucleic Acids", Science, 221, 709–713 (1983).

Dayhoff, M. O,; Barker, W. C.; Hunt, L. T. "Establishing Homologies in Protein Sequences," Methods in Enzymology, 91, 524 (1983).

Dayhoff, M. O.; Schwartz, R. M.; Orcutt, B. C. "A model of evolutionary change in proteins," In: Atlas of protein sequence and structure, Dayhoff M. O., Ed., Washington: Natl. Biomed. Res. Found., Vol.5, Suppl. 3, 345–352 (1978).

Depiereux, E.; Feytmans, E. "Simultaneous and multivariate alignment of protein sequences: correspondence between physicochemical profiles and structurally conserved regions (SCR)," Protein Engng, 4, 603–613 (1991).

Dill, K. "Dominant Forces in Protein Folding", Biochem., 29, 7133–7155 (1990).

Eisenberg, D.; Weiss, R. M.; Terwilliger, T. C.; Wilcox, W. "Hydrophobic Moments and Protein Structure," Faraday Symp. Chem. Soc., 17, 109–120 (1982).

Eisenberg, D.; McLachlan, A. D. "Solvation Energy in Protein Folding and Binding", Nature, 319, 199–203 (1986).

EMBL Data Library; European Molecular Biology Laboratory, Postfach 10.2209, 6900, Heidelberg, Germany Engelman, D. M.; Steitz, T. A. "The spontaneous insertion of proteins into and across membranes: the helical hairpin hypothesis," Cell, 23, 411 (1981).

Engelman, D. M.; Steitz, T. A.; Goldman, A. "Identifying Nonpolar Transbilayer Helices in Amino Acid Sequences of Membrane Proteins," Ann. Rev. Biophys. Chem., 15, 321 (1986).

Gamier, J.; Robson, B. in Prediction of Protein Structure and the Principles of Protein Conformation, Fasman, G., Ed., Plenum: New York, Ch. 10, 417–465 (1989)

GenBank database; IntelliGenetics, Inc., 700 El Camino Real East, Mountain View, Calif. 94040

Gonnet, G. H. Cohen, M. A. Brenner, S. A. Science, 256, 1433 (1992).

Greer, J. "Model for haptoglobin heavy chain based upon structural homology," Proc. Nat. Acad. Sci. U.S.A., 77, 3393 (1980). 1

Greer, J. "Comparative Model-building of the Mammalian Serine Proteases," J. Mol. Biol., 153, 1027 (1981).

Greer, J. "Model Structure for the Inflammatory Protein C5a," Science, 228, 1055 (1985).

Henikoff, S. and Henikoff, J. G. Proc. Natl. Acad. Sci. USA 89, 10915–10919 (1992).

Hopp, T. P.; Woods, K. "Prediction of protein antigenic determinants from amino acid sequences," Proc. Natl. Acad. Sci. USA, 78, 3824–3828 (1981).

Jackson, R. M.; Sternberg, M. J. "Protein Surface Area Defined", Nature, 366, 638 (1993). Janin, J. "Surface and inside volumes in globular proteins," Nature, 277, 491–492 (1979). Johnson, M. S.; Doolittle, R. F. "A method for the simultaneous alignment of three or more amino acid sequence," J. Mol. Evol., 23, 267–278 (1986).

Kabsch, W.; Sander, C. "Dictionary of protein secondary structure: Pattern recognition of hydrogen-bonded and geometrical features," Biopolymers, 22, 2577–2637 (1983).

Kahn, P.; Cameron, G. "EMBL Data Library," in Methods in Enzymology, 183, 26, 31, Academic Press: San Diego (1990).

Karlin, S.; Altschul, S. F. "Methods for assessing the statistical significance of molecular sequence features by using general scoring schemes," Proc. Natl. Acad. Sci. USA, 87, 22642268 (1990).

Karlin, S.; Dembo, A.; Kawabata, T. "Statistical composition of high-scoring segments from molecular sequences," Ann. Stat., 18, 571–581 (1990).

Karlin, S.; Brendel, V. "Chance and statistical significance in protein and DNA sequence analysis," Science, 257, 39–49 (1992).

Kyte, J.; Doolittle, R. F. "A Simple Method for Displaying the Hydrophobic Character of a Protein," J. Mol. Biol., 157, 105–132 (1982).

Lee, B.; Richards, F. M. "The Interpretation of Protein Structures: Estimation of Static Accessibility", J. Mol. Biol., 55, 379–400 (1971).

Lipman, D. J.; Pearson, W. R. "Rapid and Sensitive Protein Similarity Searches," Science, 227, 1435–1441 (1985).

Lipman, D. J.; Altschul, S. F.; Kececioglu, J. D. "A tool for multiple sequence alignment," Proc. Natl. Acad. Sci. USA, 86, 4412–4415 (1989).

Mas, M. T.; Smith, K. C.; Yarmush, D. L.; Aisaka, K.; Fine, R. M. "Modeling the anti-CEA antibody combining site by homology and conformational search," Proteins: Struct., Func., and Genet., 14, 483–498 (1992).

McGregor, M. J.; Islam, S. A.; Sternberg, M. J. "Analysis of the Relationship between Side-chain Conformation and Secondary Structure in Globular Proteins," J. Mol. Biol. 198, 195–210 (1987).

Murata, M.; Richardson, J. S.; Sussman, J. L. "Simultaneous comparison of three protein sequences," Proc. Natl. Acad. Sci. USA, 82, 3073–3077 (1985).

Needleman, S. B.; Wunsch, C. D. "A General Method Applicable to the Search for Similarities in the Amino Acid Sequence of Two Proteins," J. Mol. Biol., 48, 443–453 (1970).

Novotny, J.; Bruccoleri, R.; Karplus, M. "An Analysis of Incorrectly Folded Protein Models", J. Mol. Biol., 177, 787–818 (1984).

Ooi, T.; Oobatake, M.; Nemethy, G.; Scheraga, H. "Accessible Surface Areas as a Measure of the Thermodynamic Parameters of Hydration of Peptides", Proc. Natl. Acad. Sci., 84, 3086–3090 (1987).

Pascarella, S. and Argos, P. "Analysis of insertions/deletions in protein structures", J. Mol. Biol. 224, 461–471 (1992).

Pearson, W. R.; Lipman, D. J. "Improved tools for biological sequence comparison," Proc. Natl. Acad. Sci. USA, 85, 2444–2448 (1988).

Pearson, W. R. "Rapid and sensitive sequence comparison with FASTP and FASTA," Methods in Enzymology, 183, 63–98 (1990).

PIR/NBRF database, National Biomedical Research Foundation, Georgetown University Medical Center, 3900 Reservoir Rd., NW, Washington, D.C. 20007

Ponder, J. W.; Richards, F. M. "Tertiary Templates in Proteins. Use of Packing Criteria in the Enumeration of Allowed Sequences for Different Structural Classes," J. Mol. Biol., 193, 775–791 (1987).

Press, W. H.; Flannery, B. P.; Teukolsky, S. A.; Vetterling, W. T. Numerical Recipes in C, Cambridge University Press: Cambridge (1988).

Prevelige, Jr., P.; Fasman, G. in Prediction of Protein Structure and the Principles of Protein Conformation; Fasman, G., Ed.; Plenum: New York, Ch. 9, 391–416 (1989).

Saitou, N. and Nei, M. "The neighbor-joining method: a new method for reconstructing phylogenetic trees" Mol. Biol. Evol. 4, 406–425 (1987). 1

Schuler, G. D.; Altschul, S. F.; Lipman, D. J. "A workbench for multiple alignment construction and analysis," Proteins Struct. Func. Gen., 9, 180–190 (1991).

Shenkin, P. S., Private communication (1992).

Shenkin, P. S.; Yarmush, D. L.; Fine, R. M.; Wang, H.; Levinthal, C. "Predicting Antibody Hypervariable Loop Conformation. I. Ensembles of Random Conformations for Ringlike Structures," Biopolymers, 26, 2053–2085 (1987).

Shotton, D. M.; Watson, H. C. "Three-dimensional Structure of Tosyl-elastase," Nature, 225, 811 (1970).

Shrake, A.; Rupley, J. A. "Environment and Exposure to Solvent of Protein Atoms. Lysozyme and Insulin", J. Mol. Biol., 79, 351–371 (1973).

Still, W. C.; Tempczyk, A.; Hawley, R. C.; Hendrickson, T. "Semianalytical Treatment of Solvation for Molecular Mechanics and Dynamics", J. Am. Chem. Soc., 112, 6127–6129 (1990).

Summers, N. L.; Carlson, W. D.; Karplus, M. "Analysis of Side-chain Orientations in Homologous Proteins," J. Mol. Biol. 196, 175–198 (1987).

Thompson, J. D. Higgins, D. G. and Gibson, T. J. "CLUSTAL W: improving the sensitivity of progressive multiple sequence alignment through sequence weighting, position-specific gap penalties and weight matrix choice" Nucl. Acids Res. 22, 4673–4680(1994a).

Thompson, J. D. Higgins, D. G. and Gibson, T. J. "Improved sensitivity of profile searches through the use of sequence weights and gap excision" CABIOS, 10, 19–29 (1994b).

Vila, J.; Williams, R. L.; Vasquez, M.; Scheraga, H. A. "Empirical Solvation Models Can be Used to Differentiate Native From Near-native Conformations of Bovine Pancreatic Trypsin Inhibitor", Proteins, 10, 199–218 (1991).

Vingron, M; Argos, P. "A fast and sensitive multiple sequence alignment algorithm," Comput. Appl. Biosci., 5, 115–121 (1989).

von Freyberg, B.; Richmond, T. J.; Braun, W. "Surface Area Included in Energy Refinement of Proteins: A Comparative Study on Atomic Solvation Parameters", J. Mol. Biol., 233, 275–292 (1993).

Wesson, L.; Eisenberg, D. "Atomic Solvation Parameters Applied to Molecular Dynamics of Proteins in Solution", Protein Science, 1, 227–235 (1992).

Allen, F. H.; Kennard, O. "3D Search and Research Using the Cambridge Structural Database", Chemical Design Automation News, 8, 31–37 (1993).

Engh, R. A.; Huber, R. "Accurate Bond and Angle Parameters for X-ray Protein Structure Refinement", Acta Cryst., A47, 292–300 (1991).

Laskowski, R. A.; MacArthur, M. W.; Moss, D. S.; Thornton, J. M. "PROCHECK: A Program to Check the Stereochemical Quality of Protein Structures, J. Appl. Cryst., 26: 283(1993).

MacArthur, M. W.; Thornton, J. M. "Conformational Analysis of Protein Structures Derived From NMR Data", Proteins, 17, 232–251 (1993).

Mardia, K. V. Statistics of Directional Data, Academic Press, New York, p. 133 (1972).

Morris, A. L.; MacArthur, M. W.; Hutchinson, E. G.; Thornton, J. M. "Stereochemical Quality of Protein Structure Coordinates", Proteins, 12, 345–364 (1992).

The Modeler Program is known to those skilled in the art and is discussed in the following references:

Bernstein, F. C.; T. F. Koetzle, G. J. B. Williams, E. F. Meyer Jr, M. D. Brice, J. R. Rodgers, O. Kennard, T. Schimanouchi, M. Tasumi, "The protein data bank: A computer based archival file for macromolecular structures," J. Mol. Biol. 112, 535–542 (1977).

Blundell, T. L.; B. L. Sibanda; M. J. E. Sternberg; J. M. Thornton "Knowledge-based prediction of protein structures and the design of novel molecules" Nature (London) 326 347–352 (1987).

Blundell, T. L.; D. Carney; S. Gardner; F. Hayes; B. Howlin: T. Hubbard; J. Overinton; D. A. Singh; B. L. Sibanda; M. Sutcliff "Knowledge-based protein modelling and design" Eur. J. Biochem. 172–513 (1988)

Browne, W. J.; A. C. T. North; D. C. Phillips; K. Brew; T. C. Vanaman; R. C. Hill "A possible three-dimensional structure of bovine-lactalbumin based on that of hen's eggwhite lysozyme" J. Mol. Biol. 42 65–86 (1969).

Braun, W. and N. Go "Calculation of protein conformations by proton-proton distance constraints: A new efficient algorithm" J. Mol. Biol. 186, 611–626 (1985).

Brooks, B. R.; R. E. Bruccoleri, B. D. Olafson, D. J. States, S. Swarninathan, M. Karplus, J. Comp. Chem. 4, 187 (1983)

Greer, J. "Model for haptoglobin heavy chain based upon structural homology" Proc. Nat. Acad. Se. U.S.A. 77 3393 (1980).

Greer, J. "Comparative model-building of the mammalian serine proteases" J. Mol. Biol. 153 1027–1042 (1981).

Greer, J. "Model structure for the Inflammatory Protein C5a" Science 228 1055 (1985).

Matsumoto, R., A. ali, N. Ghildyal, M. Karplus, R. L. Stevens "Packaging of proteases and proteoglycans in the granules of mast cells and other hematopoietic cells" J. Biol. Chem, 270, 19524–19531 (1995).

Melo, F. & Feytnans, E. "Novel knowledge-based mean force potential at the atomic level" J. Mol. Biol. 267, 207–222 (1997)

Nilsson, L.; M. Karplus, J. Comp. Chem., 7, 591 (1986).

Ponder, Richards, J. Mol. Biol. 194 775–791 (1987).

Sali, A. "Modeling mutations and homologous proteins," Curr. Opin. Biotech., 6 437–451 (1995a).

Sali, A. "Protein modeling by satisfaction of spatial restraints" Molecular Medicine Today, 1 270–277 (1995b).

Sali, A.; T. L. Blundell, "Definition of general topological equivalence in protein structures: A procedure involving comparison of properties and relationships through simulated annealing and dynamic programming," J. Mol. Biol., 212 403–428 (1990).

Sali, A.; T. L. Blundell, "Comparative protein modeling by satisfaction of spatial restraints," Mol. Biol., 234 779–815 (1993a).

Sali, A.; R. Matsumoto, H. P. McNeil, M. Karplus, R. L. Stevens, "Three-dimensional models of four mouse mast cell chymases. Identification of proteoglycan-binding regions and protease-specific antigenic epitopes," J. Biol. Chem., 268 9023–9034 (1993b).

Sali, A.; J. P. Overington, "Derivation of rules for comparative protein modeling from a database of protein structure alignments,"Protein Sci., 31, 582–1596 (1994).

Sali, A.; L. Pottertone, F. Yuan, H. van Vlijmen and M. Karplus "Evaluation of comparative protein modeling by MODELLER" Proteins 23, 318–326 (1995).

Shotton, D. M.; H. C. Watson "Three-dimensional STructure of Tosyl-elastase" Nature 225 811 (1970).

The CFF Force Field is known to those skilled in the art and is discussed in the following references:

Baldridge, K.; Fine, R.; Hagler, A. J. Comp. Chem. 15, 1217–1227 (1994).

Dinur, U.; Hagler, A. T. J. Amer. Chem. Soc. 111, 5149–5151 (1989).

Dinur, U.; Hagler, A. T. In Reviews in Computational Chemistry, Vol. 2, K. B. Lipkowitz; D. B. Boyd, Eds., VCH Publishers: New York, 99–164 (1991).

Francl, M. M.; Pietro, W. J.; Hehre, W. J.; Binkley, J. S.; Gordon, M. S.; DeFrees, D. J.; Pople, J. A. J. Chem. Phys. 77, 3654–3665 (1982).

Hagler, A. T.; Huler, E.; Lifson, S. J. Amer. Chem. Soc. 96, 5319–5327(1974).

Hagler, A. T.; Lifson, S.; Dauber, P. J. Amer. Chem. Soc. 101, 5122–5130 (1979a).

Hagler, A. T.; Dauber, P.; Lifson, S. J. Amer. Chem. Soc.— 101, 5131–5141 (1979b).

Hariharan, P. C.; Pople, J. A. Theor. Chim. Acta 28, 213–222 (1973).

Hassan, M.; Nguyen, D. T.; Li, Z.; Hwang, M.-J.; Kitson, D. H.; Hagler, A. T. (in preparation).

Hwang, M.-J.; Stockfisch, T. P.; Hagler, A. T. J. Amer. Chem. Soc. 116, 2515–2525 (1994).

Kurihara, H.; Nguyen, D. T.; Hassan, M.; Hagler, A. T. (in preparation).

Maple, J. R.; Hwang, M-J.; Stockfisch, T. P.; Dinur, U.; Waldman, M.; Ewig, C. S.; Hagler, A. T. J. Comp. Chem. 15, 162–182 (1994).

Michalska, D.; Schaad, L. J.; Carsky, P.; Hess, Jr., B. A.; Ewig, C. S. J. Comp. Chem., 9, 495(1988).

Waldman, M.; Hagler, A. T. J. Comp. Chem. 14, 1077–1084 (1993).

All the references cited above are incorporated by reference in the entireties.

Structure Based Drug Design

The present invention relates to the use of the crystal structure of the *E. coli* MurG protein represented by the atomic coordinates in Table 1 to make models of MurG proteins and binding sites thereof. The present invention also relates to the use of the crystal structure, α-carbon backbone, α-carbon backbone plus conserved amino acid residue side chains or binding sites of the *E. coli* MurG protein to construct models of these structures in other MurG proteins.

For the first time, the present invention permits the use of molecular design techniques to design, select and synthesize chemical entities and compounds, including inhibitory compounds, capable of binding to the active site or accessory binding site of MurG, in whole or in part.

On approach enabled by this invention, is to use the structure coordinates of MurG to design compounds that bind to the enzyme and alter the physical properties of the compounds in different ways, e.g., solubility. For example, this invention enables the design of compounds that act as inhibitors of the MurG enzyme by binding to, all or a portion of, the active site of MurG.

A second design approach is to probe a MurG crystal with molecules composed of a variety of different chemical entities to determine optimal sites for interaction between candidate MurG inhibitors and the enzyme. For example, high resolution X-ray diffraction data collected from crystals saturated with solvent allows the determination of where each type of solvent molecule sticks. Small molecules that bind tightly to those sites can then be designed and synthesized and tested for their MurG inhibitor activity. Travis, J., Science, 262, p. 1374 (1993).

This invention also enables the development of compounds that can isomerize to short-lived reaction intermediates in the chemical reaction of a substrate or other compound that binds to MurG, with MurG. Thus, the time-dependent analysis of structural changes in MurG during its interaction with other molecules is enabled. The reaction intermediates of MurG can also be deduced from the reaction product in co-complex with MurG. Such information is useful to design improved analogues of known MurG inhibitors or to design novel classes of inhibitors based on the reaction intermediates of the MurG enzyme and MurG-inhibitor co-complex. This provides a novel route for designing MurG inhibitors with both high specificity and stability.

Another approach made possible and enabled by this invention, is to screen computationally small molecule data bases for chemical entities or compounds that can bind in whole, or in part, to the MurG enzyme. In this screening, the quality of fit of such entities or compounds to the binding site may be judged either by shape complementarity or by estimated interaction energy. Meng, E. C. et al., J. Coma. Chem., 13, pp. 505–524 (1992).

Because MurG may crystallize in more than one crystal form, the structure coordinates of MurG, or portions thereof, as provided by this invention are particularly useful to solve the structure of those other crystal forms of MurG. They may also be used to solve the structure of MurG mutants, MurG co-complexes, or of the crystalline form of any other protein with significant amino acid sequence homology to any functional domain of MurG.

One method that may be employed for this purpose is molecular replacement. In this method, the unknown crystal structure, whether it is another crystal form of MurG a MurG mutant, or a MurG co-complex, or the crystal of some other protein with significant amino acid sequence homology to any functional domain of MurG, may be determined using the MurG structure coordinates of this invention as provided in Tables 1–6. This method will provide an accurate structural form for the unknown crystal more quickly and efficiently than attempting to determine such information ab initio.

In addition, in accordance with this invention, MurG mutants may be crystallized in co-complex with known MurG inhibitors. The crystal structures of a series of such complexes may then be solved by molecular replacement and compared with that of wild-type MurG. Potential sites for modification within the various binding sites of the enzyme may thus be identified. This information/provides an additional tool for determining the most efficient binding interactions, for example, increased hydrophobic interactions, between MurG and a chemical entity or compound.

All of the complexes referred to above may be studied using well-known X-ray diffraction techniques and may be refined versus 2–3 .ANG. resolution X-ray date to an R value of about 0.20 or less using computer software, such as X-PLOR (Yale University, .COPYRGT.1992, distributed by Molecular Simulations, Inc.). See, e.g., Blundel & Johnson, supra; Methods in Enzvmoloav, vol. 114 & 115, H. W. Wyckoff et al., eds., Academic Press (1985). This information may thus be used to design, synthezie and optimize novel classes of MurG inhibitors.

The structure coordinates of MurG mutants provided in this invention also facilitate the identification of related proteins or enzymes analogous to MurG in function, structure or both, thereby further leading to novel therapeutic modes for treating or preventing UDP-glycosyltaansferase mediated diseases.

The design of compounds that bind to or inhibit MurG according to this invention generally involves consideration of two factors. First, the compound must be capable of physically and structurally associating with MurG. Non-covalent molecular interactions important in the association of MurG with its substrate include hydrogen bonding, van der Waals and hydrophobic interactions.

Second, the compound must be able to assume a conformation that allows it to associate with MurG. Although certain portions of the compound will not directly participate in this association with MurG, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of MurG, or the spacing between functional groups of a compound comprising several chemical entities that directly interact with MurG.

The potential inhibitory or binding effect of a chemical compound on MurG may be analyzed prior to its actual synthesis and testing by the use of computer modelling techniques. If the theoretical structure of the given compound suggests insufficient interaction and association between it and MurG, synthesis and testing of the compound is obviated. However, if computer modelling indicates a strong interaction, the molecule may then be synthesized and tested for its ability to bind to MurG and inhibit using the assay of Walker et al. patents (cited supra). In this manner, synthesis of inoperative compounds may be avoided.

An inhibitory or other binding compound of MurG may be computationally evaluated and designed by means of a series of steps in which chemical entities or fragments are screened and selected for their ability to associate with the individual binding pockets or other areas of MurG.

One skilled in the art may use one of several methods to screen chemical entities or fragments for their ability to associate with MurG and more particularly with the individual binding pockets of the MurG donor nucleotide binding site, acceptor binding site or membrane association site. This process may begin by visual inspection of, for example, the binding sites on the computer screen based on the MurG coordinates in Tables 1–6. Selected fragments or chemical entities may then be positioned in a variety of orientations, or docked, within an individual binding pocket of MurG as defined supra. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities, including but not limited to:

1. GRID (Goodford, P. J., "A Computational Procedure for Determining Energetically Favorable Binding Sites on Biologically Important Macromolecules" J. Med. Chem., 28, pp. 849–857 (1985)). GRID is available &orn Oxford University, Oxford, UK.
2. MCSS (Miranker, A. and M. Karplus, "Functionality Maps of Binding Sites: A Multiple Copy Simultaneous Search Method." Proteins: Structure, Function and Genetics, 11, pp. 29–34 (1991)). MCSS is available from Molecular Simulations, Burlington, Mass.
3. AUTODOCK (Goodsell, D. S. and A. J. Olsen, "Automated Docking of Substrates to Proteins by Simulated Annealing" Proteins: Structure. Function, and Genetics, 8, pp. 195–202 (1990)) (AUTODOCK is available from Scripps Research Institute, La Jolla, Calif.).
4. DOCK (Kuntz, I. D. et al., "A Geometric Approach to Macromolecule-Ligand Interactions" J. Mol. Biol., 161, pp. 269–288 (1982)). DOCK is available from University of California, San Francisco, Calif.

Once suitable chemical entities or fragments have been selected, they can be assembled into a single compound or inhibitor. Assembly may be proceeded by visual inspection of the relationship of the fragments to each other on the three-dimensional image displayed on a computer screen in relation to the structure coordinates of MurG. This would be followed by manual model building using software such as Quanta or Sybyl.

Useful programs to aid one of skill in the art in connecting the individual chemical entities or fragments include, but are not limited to:
1. CAVEAT (Bartlett, P. A. et al, "CAVEAT: A Program to Facilitate the Structure-Derived Design of Biologically Active Molecules". In Molecular Recognition in Chemical and Biological Problems", Special Pub., Royal Chem. Soc., 78, pp. 182–196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", J. Med. Chem., 35, pp. 2145–2154 (1992)).
3. HOOK (available from Molecular Simulations, Burlington, Mass.).

Instead of proceeding to build a MurG inhibitor in a step-wise fashion one fragment or chemical entity at a time as described above, inhibitory or other MurG binding compounds may be designed as a whole or "de novo" using either an empty active site or optionally including some portion(s) of a known inhibitor(s). These methods include, but are not limited to:
1. LUDI (Bohm, H.-J., "The Computer Program LUDI: A New Method for the De Novo Design of Enzyme Inhibitors", J. ComR. Aid. Molec. Design, 6, pp. 61–78 (1992)). LUDI is available from Biosym Technologies, San Diego, Calif.
2. LEGEND (Nishibata, Y. and A. Itai, Tetrahedron, 47, p. 8985 (1991)). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883–894 (1990). See also, Navia, M. A. and M. A. Mureko, "The Use of Structural Information in Drug Design", Current Opinions in Structural Biology, 2, pp. 202–210 (1992).

Once a compound has been designed or selected by the above methods, the efficiency with which that compound may bind to MurG may be tested and optimized by computational evaluation. For example, a compound that has been designed or selected to function as a MurG-inhibitor must also preferably traverse a volume not overlapping that occupied by the active site when it is bound to the native substrate. An effective MurG inhibitor must preferably demonstrate a relatively small difference in energy between its bound and free states (i.e., a small deformation energy of binding). Thus, the most efficient MurG inhibitors should preferably be designed with a deformation energy of binding of not greater than about 10 kcal/mole, preferably, not greater than 7 kcal/mole. MurG inhibitors may interact with the enzyme in more than one conformation that is similar in overall binding energy. In those cases, the deformation energy of binding is taken to be the difference between the energy of the free compound and the average energy of the conformations observed when the inhibitor binds to the enzyme.

A compound designed or selected as binding to MurG may be further computationally optimized so that in its bound state it would preferably lack repulsive electrostatic interaction with the target enzyme. Such non-complementary (e.g., electrostatic) interactions include repulsive charge-charge, dipole-dipole and charge-dipole interactions. Specifically, the sum of all electrostatic interactions between the inhibitor and the enzyme when the inhibitor is bound to MurG, preferably make a neutral or favorable contribution to the enthalpy of binding.

Specific computer software is available in the art to evaluate compound deformation energy and electrostatic interaction. Examples of programs designed for such uses include, but are not limited to: Gaussian 92, revision C [M. J. Frisch, Gaussian, Inc., Pittsburgh, Pa. COPYRIGHT. 1992]; AMBER, version 4.0 [P. A. Kollman, University of California at San Francisco, COPYRIGHT. 1994]; QUANTA/CHARMM [Molecular Simulations, Inc., Burlington, Mass. COPYRIGHT. 1994]; and Insight II/Discover (Biosysm Technologies Inc., San Diego, Calif. COPYRIGHT. 1994). These programs may be implemented, for instance, using a Silicon Graphics workstation, IRIS Octane or IBM RISC/6000 workstation. Other hardware systems and software packages will be known to those skilled in the art.

Once a MurG-binding compound has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to MurG by the same computer methods described in detail, above.

Compounds and Compositions Comprising Compounds Derived from Structure Based Drug Design One embodiment of the present invention is a compound that is capable of binding to a MurG protein, inhibiting the activity of a MurG protein, or stimulating the activity of a MurG protein. Suitable inhibitory compounds of the present invention can: (1) inhibit (i.e., prevent or block) the activity of MurG enzyme by binding to a MurG donor nucleotide binding site and interfering with the binding of the donor nucleotide molecule; (2) inhibit the activity of MurG enzyme by binding to the MurG acceptor binding site and interfering with the binding of the acceptor molecule; (3) inhibit the activity of a MurG enzyme by binding to the membrane association site and interfering with the association of the protein with the bacterial membrane and/or acceptor molecule.

Another embodiment of the present invention is a compound that is capable of stimulating MurG activity. Suitable stimulatory compounds of the present invention can stimulate the activity of a MurG enzyme by binding to the protein at a binding site and causing an increase in enzymatic activity, for example, by increasing the enzymes affinity to bind a donor nucleotide, an acceptor molecule or improve the enzymes stability or increasing the binding affinity of a molecule to MurG.

Such compounds that bind to, inhibit or stimulate activity of a MurG protein include, for example, compounds that mimic donor nucleotide molecules. In preferred embodiments, the compound includes, for example, pyrimidine nucleoside analogues. In yet another preferred embodiment, the compounds include compounds comprising a pyrimidine nucleoside with a substituent containing at least one heteroatom attached to the C5 hydroxyl. In more particular embodiments, pyrimidine derivatives make complementary hydrogen bonding contacts to the amide backbone segment containing Ile 245 and also contact glutamate 269.

Another embodiment of the present invention is a compound that binds to the acceptor binding site of the MurG protein, hereinafter referred to a acceptor analogs. An acceptor analog refers to a compound that interacts with (e.g., binds to, associates with, modifies) the acceptor binding site of a MurG protein. An acceptor analog, for example, is a compound that mimics the natural acceptor molecule, Lipid I. Examples of such acceptor analogs are set forth in Ha et al., J. Amer. Chem. Soc. 1999, and PCT/US99/02187, U.S. Provisional Application No. 60/073,376 filed Feb. 2, 1998, incorporated herein by reference.

Another embodiment of the present invention is a compound that binds to the MurG protein, that are enzyme product analogs, hereinafter referred to as Lipid I analogs. A Lipid II analog refers to a compound that interacts with (i.e., binds to, associates with, modifies) the acceptor binding site of a Mur G protein which mimics the product of the transglycosylase reaction.

Inhibitory and stimulatory compounds of the present invention can be identified by various means known to those of skill in the art. For example, binding of an inhibitory compound to, or otherwise interaction with, a MurG protein, can be determined with MurG in solution, for example, using assays described in PCT/US99/02187, U.S. Provisional Application No. 60/073,376 filed Feb. 2, 1998, and PCT/US00/05554, U.S. Provisional Application Nos. 60/122,966 and 60/137,696, incorporated herein by reference.

According to the present invention, suitable compounds of the present invention include peptides or other organic molecules, and inorganic molecules. Suitable organic molecules include small organic molecules. Preferably, a compound of the present invention is not harmful (i.e., toxic) to an animal when administered to an animal.

Compounds of the present invention also can be identified using structure based drug design techniques known to those skilled in the art and described herein above.

Also according to the present invention, compounds are suitable for use in the inhibition of bacterial or microbial growth in an animal, and for example, function as an antibiotic for treatment of bacterial infections in animals.

The present invention also includes compositions comprising compounds of the present invention that inhibit or stimulate MurG activity which function as antibiotics or antimicrobial agents in animals. Compositions of the present invention can be used therapeutically or diagnostically in an animal. Compositions of the present invention comprises at least one compound of the present invention. In a preferred embodiment, compositions of the present invention further comprise a carrier. More particularly, a suitable carrier is a pharmaceutically acceptable carrier known to those skilled in the art.

TABLE 1

ATOMIC COORDINATES OF *E. COLI* MURG PROTEIN

REMARK coordinates from minimization refinementREMARK refinement resolution: 40.0–1.9 AREMARK starting r = 0.2200 free__r = 0.2466REMARK final r = 0.2200 free__r = 0.2466REMARK rmsd bonds = 0.005558 rmsd angles = 1.29505REMARK wa = 1.08391REMARK target = mlf cycles = 1 steps = 30REMARK sg = P1 a = 60.613 b = 66.356 c = 67.902 alpha = 64.294 beta = 83.520 gamma = 65.448REMARK parameter file 1: CNS__TOPPAR: protein__rep.paramREMARK parameter file 2: CNS__TOPPAR: water__rep.paramREMARK parameter file 3: CNS__TOPPAR: ion__paramREMARK molecular structure file: gen.mtfREMARK input coordinates: gen.pdbREMARK reflection file = native.cvREMARK ncs = noneREMARK B-correction resolution: 6.0–1.9REMARK initial B-factor correction applied to fobs: REMARK B11 = 0.747 B22 = 2.098 B33 = 2.845REMARK B12 = −1.847 B13 = −3.752 B23 = 6.401REMARK B-factor correction applied to coordinate array B: 0.038REMARK bulk solvent: density level = 0.351665 e/A^3, B-factor = 43.8282 A^2REMARK reflections with |Fobs|/sigma__F < 2.0 rejectedREMARK reflections with |Fobs| > 10000 * rms(Fobs) rejectedREMARK theoretical total number of refl. in resol. range: 68102 (100.0%)REMARK number of unobserved reflections (no entry or |F| = 0): 2825 (4.1%) REMARK number of reflections rejected: 3288 (4.8%)REMARK total number of reflections used: 61989 91.0%)REMARK number of reflections in working set:

TABLE 1-continued

ATOMIC COORDINATES OF E. COLI MURG PROTEIN 55765 (81.9%)REMARK number of reflections in test set:
6224 (9.1%)CRYST1 60.613 66.356 67.902 64.29 83.52 65.45 P 1
REMARK FILENAME = "minimize5.pdb" REMARK DATE: Jan. 14, 2000 15:25:36
created by user: shaREMARK VERSION:
0.5

| ATOM | 1 | CB | LYS | A | 7 | 0.142 | 3.434 | 35.023 | 1.00 | 43.02 | AAAA |
|------|---|----|-----|---|---|-------|-------|--------|------|-------|------|
| ATOM | 2 | CG | LYS | A | 7 | 1.076 | 4.457 | 35.641 | 1.00 | 46.34 | AAAA |
| ATOM | 3 | CD | LYS | A | 7 | 0.452 | 5.841 | 35.634 | 1.00 | 47.39 | AAAA |
| ATOM | 4 | CE | LYS | A | 7 | 1.345 | 6.846 | 36.332 | 1.00 | 48.65 | AAAA |
| ATOM | 5 | NZ | LYS | A | 7 | 0.780 | 8.221 | 36.276 | 1.00 | 51.04 | AAAA |
| ATOM | 6 | C | LYS | A | 7 | −2.239 | 2.733 | 34.833 | 1.00 | 39.64 | AAAA |
| ATOM | 7 | O | LYS | A | 7 | −2.050 | 1.717 | 34.160 | 1.00 | 39.64 | AAAA |
| ATOM | 8 | N | LYS | A | 7 | −0.974 | 2.320 | 36.947 | 1.00 | 42.05 | AAAA |
| ATOM | 9 | CA | LYS | A | 7 | −1.170 | 3.245 | 35.788 | 1.00 | 41.31 | AAAA |
| ATOM | 10 | N | ARG | A | 8 | −3.357 | 3.451 | 34.773 | 1.00 | 37.24 | AAAA |
| ATOM | 11 | CA | ARG | A | 8 | −4.469 | 3.076 | 33.906 | 1.00 | 34.91 | AAAA |
| ATOM | 12 | CB | ARG | A | 8 | −5.782 | 3.109 | 34.686 | 1.00 | 36.65 | AAAA |
| ATOM | 13 | CG | ARG | A | 8 | −5.950 | 2.017 | 35.721 | 1.00 | 39.89 | AAAA |
| ATOM | 14 | CD | ARG | A | 8 | −7.323 | 2.124 | 36.356 | 1.00 | 42.12 | AAAA |
| ATOM | 15 | NE | ARG | A | 8 | −7.663 | 0.960 | 37.163 | 1.00 | 45.03 | AAAA |
| ATOM | 16 | CZ | ARG | A | 8 | −7.031 | 0.610 | 38.279 | 1.00 | 46.29 | AAAA |
| ATOM | 17 | NH1 | ARG | A | 8 | −6.015 | 1.337 | 38.725 | 1.00 | 46.88 | AAAA |
| ATOM | 18 | NH2 | ARG | A | 8 | −7.420 | −0.466 | 38.952 | 1.00 | 47.41 | AAAA |
| ATOM | 19 | C | ARG | A | 8 | −4.584 | 3.999 | 32.696 | 1.00 | 32.27 | AAAA |
| ATOM | 20 | O | ARG | A | 8 | −4.602 | 5.224 | 32.832 | 1.00 | 31.60 | AAAA |
| ATOM | 21 | N | LEU | A | 9 | −4.663 | 3.403 | 31.512 | 1.00 | 29.57 | AAAA |
| ATOM | 22 | CA | LEU | A | 9 | −4.792 | 4.171 | 30.283 | 1.00 | 27.45 | AAAA |
| ATOM | 23 | CB | LEU | A | 9 | −3.581 | 3.954 | 29.362 | 1.00 | 26.31 | AAAA |
| ATOM | 24 | CG | LEU | A | 9 | −3.752 | 4.466 | 27.916 | 1.00 | 25.77 | AAAA |
| ATOM | 25 | CD1 | LEU | A | 9 | −3.670 | 5.985 | 27.895 | 1.00 | 24.31 | AAAA |
| ATOM | 26 | CD2 | LEU | A | 9 | −2.679 | 3.870 | 26.993 | 1.00 | 26.22 | AAAA |
| ATOM | 27 | C | LEU | A | 9 | −6.038 | 3.762 | 29.523 | 1.00 | 25.97 | AAAA |
| ATOM | 28 | O | LEU | A | 9 | −6.397 | 2.587 | 29.485 | 1.00 | 25.57 | AAAA |
| ATOM | 29 | N | MET | A | 10 | −6.713 | 4.738 | 28.928 | 1.00 | 25.37 | AAAA |
| ATOM | 30 | CA | MET | A | 10 | −7.866 | 4.429 | 28.101 | 1.00 | 24.70 | AAAA |
| ATOM | 31 | CB | MET | A | 10 | −9.142 | 5.101 | 28.612 | 1.00 | 25.60 | AAAA |
| ATOM | 32 | CG | MET | A | 10 | −10.323 | 4.873 | 27.675 | 1.00 | 25.77 | AAAA |
| ATOM | 33 | SD | MET | A | 10 | −11.916 | 4.958 | 28.492 | 1.00 | 26.63 | AAAA |
| ATOM | 34 | CE | MET | A | 10 | −12.197 | 3.222 | 28.862 | 1.00 | 25.72 | AAAA |
| ATOM | 35 | C | MET | A | 10 | −7.528 | 4.943 | 26.715 | 1.00 | 23.31 | AAAA |
| ATOM | 36 | O | MET | A | 10 | −7.198 | 6.116 | 26.544 | 1.00 | 24.02 | AAAA |
| ATOM | 37 | N | VAL | A | 11 | −7.574 | 4.059 | 25.727 | 1.00 | 22.25 | AAAA |
| ATOM | 38 | CA | VAL | A | 11 | −7.278 | 4.461 | 24.359 | 1.00 | 22.34 | AAAA |
| ATOM | 39 | CB | VAL | A | 11 | −6.444 | 3.386 | 23.624 | 1.00 | 22.75 | AAAA |
| ATOM | 40 | CG1 | VAL | A | 11 | −6.256 | 3.768 | 22.158 | 1.00 | 20.51 | AAAA |
| ATOM | 41 | CG2 | VAL | A | 11 | −5.082 | 3.239 | 24.310 | 1.00 | 21.75 | AAAA |
| ATOM | 42 | C | VAL | A | 11 | −8.612 | 4.654 | 23.646 | 1.00 | 22.94 | AAAA |
| ATOM | 43 | O | VAL | A | 11 | −9.525 | 3.843 | 23.804 | 1.00 | 23.37 | AAAA |
| ATOM | 44 | N | MET | A | 12 | −8.722 | 5.734 | 22.878 | 1.00 | 22.18 | AAAA |
| ATOM | 45 | CA | MET | A | 12 | −9.949 | 6.034 | 22.146 | 1.00 | 23.10 | AAAA |
| ATOM | 46 | CB | MET | A | 12 | −10.496 | 7.399 | 22.589 | 1.00 | 22.78 | AAAA |
| ATOM | 47 | CG | MET | A | 12 | −10.359 | 7.655 | 24.096 | 1.00 | 23.92 | AAAA |
| ATOM | 48 | SD | MET | A | 12 | −10.955 | 9.279 | 24.657 | 1.00 | 25.51 | AAAA |
| ATOM | 49 | CE | MET | A | 12 | −9.641 | 10.349 | 24.162 | 1.00 | 22.79 | AAAA |
| ATOM | 50 | C | MET | A | 12 | −9.582 | 6.072 | 20.673 | 1.00 | 22.97 | AAAA |
| ATOM | 51 | O | MET | A | 12 | −8.917 | 6.997 | 20.226 | 1.00 | 21.16 | AAAA |
| ATOM | 52 | N | ALA | A | 13 | −9.992 | 5.057 | 19.921 | 1.00 | 26.97 | AAAA |
| ATOM | 53 | CA | ALA | A | 13 | −9.665 | 5.008 | 18.498 | 1.00 | 30.88 | AAAA |
| ATOM | 54 | CB | ALA | A | 13 | −8.381 | 4.212 | 18.288 | 1.00 | 31.18 | AAAA |
| ATOM | 55 | C | ALA | A | 13 | −10.813 | 4.412 | 17.685 | 1.00 | 34.35 | AAAA |
| ATOM | 56 | O | ALA | A | 13 | −11.328 | 3.335 | 18.006 | 1.00 | 35.86 | AAAA |
| ATOM | 57 | N | GLY | A | 14 | −11.176 | 5.127 | 16.622 | 1.00 | 37.37 | AAAA |
| ATOM | 58 | CA | GLY | A | 14 | −12.287 | 4.762 | 15.757 | 1.00 | 40.54 | AAAA |
| ATOM | 59 | C | GLY | A | 14 | −12.239 | 3.583 | 14.808 | 1.00 | 41.52 | AAAA |
| ATOM | 60 | O | GLY | A | 14 | −11.267 | 2.831 | 14.755 | 1.00 | 43.26 | AAAA |
| ATOM | 61 | N | GLY | A | 15 | −13.322 | 3.451 | 14.042 | 1.00 | 42.70 | AAAA |
| ATOM | 62 | CA | GLY | A | 15 | −13.491 | 2.363 | 13.094 | 1.00 | 43.13 | AAAA |
| ATOM | 63 | C | GLY | A | 15 | −12.660 | 2.286 | 11.825 | 1.00 | 43.41 | AAAA |
| ATOM | 64 | O | GLY | A | 15 | −13.212 | 2.187 | 10.730 | 1.00 | 44.39 | AAAA |
| ATOM | 65 | N | THR | A | 16 | −11.340 | 2.333 | 11.966 | 1.00 | 43.38 | AAAA |
| ATOM | 66 | CA | THR | A | 16 | −10.426 | 2.204 | 10.833 | 1.00 | 43.22 | AAAA |
| ATOM | 67 | CB | THR | A | 16 | −10.120 | 3.551 | 10.110 | 1.00 | 44.23 | AAAA |
| ATOM | 68 | OG1 | THR | A | 16 | −9.302 | 4.375 | 10.949 | 1.00 | 44.41 | AAAA |
| ATOM | 69 | CG2 | THR | A | 16 | −11.404 | 4.286 | 9.754 | 1.00 | 43.74 | AAAA |
| ATOM | 70 | C | THR | A | 16 | −9.118 | 1.679 | 11.402 | 1.00 | 43.06 | AAAA |
| ATOM | 71 | O | THR | A | 16 | −8.728 | 2.042 | 12.517 | 1.00 | 42.99 | AAAA |
| ATOM | 72 | N | GLY | A | 17 | −8.453 | 0.810 | 10.649 | 1.00 | 41.81 | AAAA |

TABLE 1-continued

ATOMIC COORDINATES OF E. COLI MURG PROTEIN

| ATOM | 73 | CA | GLY | A | 17 | −7.190 | 0.268 | 11.109 | 1.00 | 40.71 | AAAA |
|---|---|---|---|---|---|---|---|---|---|---|---|
| ATOM | 74 | C | GLY | A | 17 | −6.202 | 1.401 | 11.275 | 1.00 | 39.54 | AAAA |
| ATOM | 75 | O | GLY | A | 17 | −5.275 | 1.330 | 12.085 | 1.00 | 39.73 | AAAA |
| ATOM | 76 | N | GLY | A | 18 | −6.413 | 2.460 | 10.500 | 1.00 | 37.79 | AAAA |
| ATOM | 77 | CA | GLY | A | 18 | −5.539 | 3.611 | 10.572 | 1.00 | 35.68 | AAAA |
| ATOM | 78 | C | GLY | A | 18 | −5.394 | 4.116 | 11.994 | 1.00 | 34.88 | AAAA |
| ATOM | 79 | O | GLY | A | 18 | −4.285 | 4.441 | 12.427 | 1.00 | 35.21 | AAAA |
| ATOM | 80 | N | HIS | A | 19 | −6.503 | 4.186 | 12.728 | 1.00 | 32.89 | AAAA |
| ATOM | 81 | CA | HIS | A | 19 | −6.454 | 4.664 | 14.110 | 1.00 | 32.14 | AAAA |
| ATOM | 82 | CB | HIS | A | 19 | −7.759 | 5.371 | 14.504 | 1.00 | 30.28 | AAAA |
| ATOM | 83 | CG | HIS | A | 19 | −8.150 | 6.504 | 13.605 | 1.00 | 28.85 | AAAA |
| ATOM | 84 | CD2 | HIS | A | 19 | −9.336 | 6.808 | 13.027 | 1.00 | 27.83 | AAAA |
| ATOM | 85 | ND1 | HIS | A | 19 | −7.288 | 7.524 | 13.265 | 1.00 | 28.68 | AAAA |
| ATOM | 86 | CE1 | HIS | A | 19 | −7.926 | 8.407 | 12.517 | 1.00 | 28.09 | AAAA |
| ATOM | 87 | NE2 | HIS | A | 19 | −9.170 | 7.996 | 12.358 | 1.00 | 27.45 | AAAA |
| ATOM | 88 | C | HIS | A | 19 | −6.229 | 3.533 | 15.108 | 1.00 | 31.91 | AAAA |
| ATOM | 89 | O | HIS | A | 19 | −5.480 | 3.684 | 16.072 | 1.00 | 31.76 | AAAA |
| ATOM | 90 | N | VAL | A | 20 | −6.895 | 2.407 | 14.881 | 1.00 | 31.82 | AAAA |
| ATOM | 91 | CA | VAL | A | 20 | −6.813 | 1.271 | 15.788 | 1.00 | 33.08 | AAAA |
| ATOM | 92 | CB | VAL | A | 20 | −7.875 | 0.215 | 15.430 | 1.00 | 33.31 | AAAA |
| ATOM | 93 | CG1 | VAL | A | 20 | −7.766 | −0.982 | 16.361 | 1.00 | 33.91 | AAAA |
| ATOM | 94 | CG2 | VAL | A | 20 | −9.260 | 0.830 | 15.540 | 1.00 | 34.25 | AAAA |
| ATOM | 95 | C | VAL | A | 20 | −5.452 | 0.587 | 15.898 | 1.00 | 33.31 | AAAA |
| ATOM | 96 | O | VAL | A | 20 | −4.977 | 0.337 | 17.008 | 1.00 | 32.99 | AAAA |
| ATOM | 97 | N | PHE | A | 21 | −4.823 | 0.288 | 14.765 | 1.00 | 33.64 | AAAA |
| ATOM | 98 | CA | PHE | A | 21 | −3.526 | −0.385 | 14.794 | 1.00 | 33.68 | AAAA |
| ATOM | 99 | CB | PHE | A | 21 | −3.020 | −0.648 | 13.368 | 1.00 | 35.58 | AAAA |
| ATOM | 100 | CG | PHE | A | 21 | −3.900 | −1.578 | 12.577 | 1.00 | 39.10 | AAAA |
| ATOM | 101 | CD1 | PHE | A | 21 | −4.463 | −2.701 | 13.174 | 1.00 | 40.50 | AAAA |
| ATOM | 102 | CD2 | PHE | A | 21 | −4.157 | −1.338 | 11.232 | 1.00 | 41.05 | AAAA |
| ATOM | 103 | CE1 | PHE | A | 21 | −5.271 | −3.572 | 12.446 | 1.00 | 41.55 | AAAA |
| ATOM | 104 | CE2 | PHE | A | 21 | −4.964 | −2.205 | 10.492 | 1.00 | 41.86 | AAAA |
| ATOM | 105 | CZ | PHE | A | 21 | −5.521 | −3.323 | 11.103 | 1.00 | 42.12 | AAAA |
| ATOM | 106 | C | PHE | A | 21 | −2.456 | 0.350 | 15.605 | 1.00 | 32.04 | AAAA |
| ATOM | 107 | O | PHE | A | 21 | −1.789 | −0.257 | 16.443 | 1.00 | 31.30 | AAAA |
| ATOM | 108 | N | PRO | A | 22 | −2.277 | 1.662 | 15.375 | 1.00 | 31.37 | AAAA |
| ATOM | 109 | CD | PRO | A | 22 | −2.939 | 2.544 | 14.400 | 1.00 | 31.41 | AAAA |
| ATOM | 110 | CA | PRO | A | 22 | −1.259 | 2.396 | 16.139 | 1.00 | 30.01 | AAAA |
| ATOM | 111 | CB | PRO | A | 22 | −1.301 | 3.799 | 15.536 | 1.00 | 30.97 | AAAA |
| ATOM | 112 | CG | PRO | A | 22 | −1.892 | 3.592 | 14.175 | 1.00 | 31.19 | AAAA |
| ATOM | 113 | C | PRO | A | 22 | −1.620 | 2.411 | 17.624 | 1.00 | 29.31 | AAAA |
| ATOM | 114 | O | PRO | A | 22 | −0.749 | 2.366 | 18.489 | 1.00 | 27.42 | AAAA |
| ATOM | 115 | N | GLY | A | 23 | −2.918 | 2.483 | 17.903 | 1.00 | 28.99 | AAAA |
| ATOM | 116 | CA | GLY | A | 23 | −3.380 | 2.492 | 19.277 | 1.00 | 28.59 | AAAA |
| ATOM | 117 | C | GLY | A | 23 | −3.035 | 1.196 | 19.990 | 1.00 | 29.00 | AAAA |
| ATOM | 118 | O | GLY | A | 23 | −2.649 | 1.205 | 21.160 | 1.00 | 28.48 | AAAA |
| ATOM | 119 | N | LEU | A | 24 | −3.168 | 0.078 | 19.282 | 1.00 | 28.08 | AAAA |
| ATOM | 120 | CA | LEU | A | 24 | −2.863 | −1.227 | 19.859 | 1.00 | 28.39 | AAAA |
| ATOM | 121 | CB | LEU | A | 24 | −3.306 | −2.347 | 18.913 | 1.00 | 28.16 | AAAA |
| ATOM | 122 | CG | LEU | A | 24 | −4.811 | −2.605 | 18.843 | 1.00 | 28.45 | AAAA |
| ATOM | 123 | CD1 | LEU | A | 24 | −5.117 | −3.583 | 17.714 | 1.00 | 29.25 | AAAA |
| ATOM | 124 | CD2 | LEU | A | 24 | −5.291 | −3.158 | 20.181 | 1.00 | 29.35 | AAAA |
| ATOM | 125 | C | LEU | A | 24 | −1.373 | −1.350 | 20.147 | 1.00 | 28.37 | AAAA |
| ATOM | 126 | O | LEU | A | 24 | −0.966 | −1.986 | 21.126 | 1.00 | 28.60 | AAAA |
| ATOM | 127 | N | ALA | A | 25 | −0.555 | −0.743 | 19.296 | 1.00 | 27.77 | AAAA |
| ATOM | 128 | CA | ALA | A | 25 | 0.887 | −0.795 | 19.497 | 1.00 | 28.98 | AAAA |
| ATOM | 129 | CB | ALA | A | 25 | 1.616 | −0.142 | 18.321 | 1.00 | 27.53 | AAAA |
| ATOM | 130 | C | ALA | A | 25 | 1.256 | −0.093 | 20.800 | 1.00 | 29.10 | AAAA |
| ATOM | 131 | O | ALA | A | 25 | 2.035 | −0.618 | 21.595 | 1.00 | 29.49 | AAAA |
| ATOM | 132 | N | VAL | A | 26 | 0.694 | 1.094 | 21.020 | 1.00 | 28.82 | AAAA |
| ATOM | 133 | CA | VAL | A | 26 | 0.982 | 1.853 | 22.233 | 1.00 | 28.94 | AAAA |
| ATOM | 134 | CB | VAL | A | 26 | 0.400 | 3.290 | 22.157 | 1.00 | 29.74 | AAAA |
| ATOM | 135 | CG1 | VAL | A | 26 | 0.691 | 4.049 | 23.454 | 1.00 | 29.76 | AAAA |
| ATOM | 136 | CG2 | VAL | A | 26 | 1.009 | 4.026 | 20.981 | 1.00 | 29.14 | AAAA |
| ATOM | 137 | C | VAL | A | 26 | 0.409 | 1.131 | 23.450 | 1.00 | 29.18 | AAAA |
| ATOM | 138 | O | VAL | A | 26 | 1.020 | 1.118 | 24.518 | 1.00 | 29.62 | AAAA |
| ATOM | 139 | N | ALA | A | 27 | −0.757 | 0.518 | 23.286 | 1.00 | 27.98 | AAAA |
| ATOM | 140 | CA | ALA | A | 27 | −1.371 | −0.215 | 24.382 | 1.00 | 29.32 | AAAA |
| ATOM | 141 | CB | ALA | A | 27 | −2.719 | −0.755 | 23.950 | 1.00 | 28.32 | AAAA |
| ATOM | 142 | C | ALA | A | 27 | −0.462 | −1.372 | 24.840 | 1.00 | 30.04 | AAAA |
| ATOM | 143 | O | ALA | A | 27 | −0.084 | −1.454 | 26.015 | 1.00 | 29.89 | AAAA |
| ATOM | 144 | N | HIS | A | 28 | −0.120 | −2.259 | 23.907 | 1.00 | 30.92 | AAAA |
| ATOM | 145 | CA | HIS | A | 28 | 0.734 | −3.413 | 24.201 | 1.00 | 30.62 | AAAA |
| ATOM | 146 | CB | HIS | A | 28 | 1.024 | −4.214 | 22.924 | 1.00 | 30.20 | AAAA |
| ATOM | 147 | CG | HIS | A | 28 | −0.112 | −5.080 | 22.483 | 1.00 | 31.65 | AAAA |
| ATOM | 148 | CD2 | HIS | A | 28 | −0.764 | −5.162 | 21.299 | 1.00 | 31.33 | AAAA |
| ATOM | 149 | ND1 | HIS | A | 28 | −0.717 | −5.996 | 23.319 | 1.00 | 31.81 | AAAA |

TABLE 1-continued

ATOMIC COORDINATES OF E. COLI MURG PROTEIN

| ATOM | 150 | CE1 | HIS | A | 28 | -1.696 | -6.600 | 22.670 | 1.00 | 32.38 | AAAA |
|---|---|---|---|---|---|---|---|---|---|---|---|
| ATOM | 151 | NE2 | HIS | A | 28 | -1.747 | -6.112 | 21.443 | 1.00 | 32.85 | AAAA |
| ATOM | 152 | C | HIS | A | 28 | 2.054 | -2.989 | 24.823 | 1.00 | 30.90 | AAAA |
| ATOM | 153 | O | HIS | A | 28 | 2.537 | -3.601 | 25.779 | 1.00 | 30.92 | AAAA |
| ATOM | 154 | N | HIS | A | 29 | 2.636 | -1.939 | 24.263 | 1.00 | 30.28 | AAAA |
| ATOM | 155 | CA | HIS | A | 29 | 3.899 | -1.415 | 24.742 | 1.00 | 30.76 | AAAA |
| ATOM | 156 | CB | HIS | A | 29 | 4.276 | -0.195 | 23.911 | 1.00 | 31.40 | AAAA |
| ATOM | 157 | CG | HIS | A | 29 | 5.679 | 0.274 | 24.122 | 1.00 | 33.14 | AAAA |
| ATOM | 158 | CD2 | HIS | A | 29 | 6.188 | 1.226 | 24.939 | 1.00 | 33.77 | AAAA |
| ATOM | 159 | ND1 | HIS | A | 29 | 6.748 | -0.240 | 23.420 | 1.00 | 34.47 | AAAA |
| ATOM | 160 | CE1 | HIS | A | 29 | 7.855 | 0.381 | 23.791 | 1.00 | 34.76 | AAAA |
| ATOM | 161 | NE2 | HIS | A | 29 | 7.542 | 1.275 | 24.711 | 1.00 | 34.09 | AAAA |
| ATOM | 162 | C | HIS | A | 29 | 3.835 | -1.032 | 26.227 | 1.00 | 31.63 | AAAA |
| ATOM | 163 | O | HIS | A | 29 | 4.763 | -1.315 | 26.990 | 1.00 | 30.76 | AAAA |
| ATOM | 164 | N | LEU | A | 30 | 2.744 | -0.388 | 26.638 | 1.00 | 29.72 | AAAA |
| ATOM | 165 | CA | LEU | A | 30 | 2.603 | 0.035 | 28.028 | 1.00 | 30.08 | AAAA |
| ATOM | 166 | CB | LEU | A | 30 | 1.631 | 1.225 | 28.126 | 1.00 | 29.45 | AAAA |
| ATOM | 167 | CG | LEU | A | 30 | 2.107 | 2.503 | 27.420 | 1.00 | 28.69 | AAAA |
| ATOM | 168 | CD1 | LEU | A | 30 | 1.026 | 3.587 | 27.477 | 1.00 | 27.76 | AAAA |
| ATOM | 169 | CD2 | LEU | A | 30 | 3.383 | 2.998 | 28.075 | 1.00 | 28.99 | AAAA |
| ATOM | 170 | C | LEU | A | 30 | 2.153 | -1.096 | 28.950 | 1.00 | 30.55 | AAAA |
| ATOM | 171 | O | LEU | A | 30 | 2.538 | -1.136 | 30.120 | 1.00 | 31.28 | AAAA |
| ATOM | 172 | N | MET | A | 31 | 1.340 | -2.012 | 28.438 | 1.00 | 31.26 | AAAA |
| ATOM | 173 | CA | MET | A | 31 | 0.884 | -3.130 | 29.256 | 1.00 | 33.71 | AAAA |
| ATOM | 174 | CB | MET | A | 31 | -0.118 | -3.999 | 28.494 | 1.00 | 34.12 | AAAA |
| ATOM | 175 | CG | MET | A | 31 | -1.452 | -3.341 | 28.249 | 1.00 | 34.98 | AAAA |
| ATOM | 176 | SD | MET | A | 31 | -2.618 | -4.475 | 27.485 | 1.00 | 38.51 | AAAA |
| ATOM | 177 | CE | MET | A | 31 | -2.086 | -4.401 | 25.803 | 1.00 | 37.49 | AAAA |
| ATOM | 178 | C | MET | A | 31 | 2.078 | -3.987 | 29.664 | 1.00 | 35.03 | AAAA |
| ATOM | 179 | O | MET | A | 31 | 2.101 | -4.548 | 30.758 | 1.00 | 36.09 | AAAA |
| ATOM | 180 | N | ALA | A | 32 | 3.062 | -4.085 | 28.776 | 1.00 | 35.62 | AAAA |
| ATOM | 181 | CA | ALA | A | 32 | 4.262 | -4.871 | 29.044 | 1.00 | 37.61 | AAAA |
| ATOM | 182 | CB | ALA | A | 32 | 5.049 | -5.087 | 27.755 | 1.00 | 37.79 | AAAA |
| ATOM | 183 | C | ALA | A | 32 | 5.133 | -4.158 | 30.070 | 1.00 | 38.72 | AAAA |
| ATOM | 184 | O | ALA | A | 32 | 6.223 | -4.621 | 30.409 | 1.00 | 39.48 | AAAA |
| ATOM | 185 | N | GLN | A | 33 | 4.654 | -3.022 | 30.560 | 1.00 | 38.28 | AAAA |
| ATOM | 186 | CA | GLN | A | 33 | 5.408 | -2.275 | 31.548 | 1.00 | 38.14 | AAAA |
| ATOM | 187 | CB | GLN | A | 33 | 5.903 | -0.969 | 30.941 | 1.00 | 39.68 | AAAA |
| ATOM | 188 | CG | GLN | A | 33 | 6.856 | -1.210 | 29.791 | 1.00 | 42.76 | AAAA |
| ATOM | 189 | CD | GLN | A | 33 | 7.262 | 0.061 | 29.096 | 1.00 | 44.20 | AAAA |
| ATOM | 190 | OE1 | GLN | A | 33 | 7.803 | 0.975 | 29.717 | 1.00 | 46.28 | AAAA |
| ATOM | 191 | NE2 | GLN | A | 33 | 7.002 | 0.131 | 27.795 | 1.00 | 44.60 | AAAA |
| ATOM | 192 | C | GLN | A | 33 | 4.576 | -2.020 | 32.787 | 1.00 | 36.68 | AAAA |
| ATOM | 193 | O | GLN | A | 33 | 4.822 | -1.075 | 33.532 | 1.00 | 37.34 | AAAA |
| ATOM | 194 | N | GLY | A | 34 | 3.585 | -2.877 | 33.000 | 1.00 | 35.86 | AAAA |
| ATOM | 195 | CA | GLY | A | 34 | 2.738 | -2.755 | 34.170 | 1.00 | 35.52 | AAAA |
| ATOM | 196 | C | GLY | A | 34 | 1.461 | -1.951 | 34.008 | 1.00 | 34.34 | AAAA |
| ATOM | 197 | O | GLY | A | 34 | 0.611 | -1.974 | 34.897 | 1.00 | 33.67 | AAAA |
| ATOM | 198 | N | TRP | A | 35 | 1.314 | -1.248 | 32.890 | 1.00 | 34.23 | AAAA |
| ATOM | 199 | CA | TRP | A | 35 | 0.121 | -0.435 | 32.661 | 1.00 | 33.63 | AAAA |
| ATOM | 200 | CB | TRP | A | 35 | 0.324 | 0.509 | 31.474 | 1.00 | 34.84 | AAAA |
| ATOM | 201 | CG | TRP | A | 35 | 1.150 | 1.722 | 31.753 | 1.00 | 35.09 | AAAA |
| ATOM | 202 | CD2 | TRP | A | 35 | 0.722 | 3.087 | 31.659 | 1.00 | 36.11 | AAAA |
| ATOM | 203 | CE2 | TRP | A | 35 | 1.840 | 3.897 | 31.957 | 1.00 | 36.13 | AAAA |
| ATOM | 204 | CE3 | TRP | A | 35 | -0.499 | 3.705 | 31.350 | 1.00 | 37.33 | AAAA |
| ATOM | 205 | CD1 | TRP | A | 35 | 2.469 | 1.759 | 32.099 | 1.00 | 35.78 | AAAA |
| ATOM | 206 | NE1 | TRP | A | 35 | 2.893 | 3.062 | 32.221 | 1.00 | 34.49 | AAAA |
| ATOM | 207 | CZ2 | TRP | A | 35 | 1.776 | 5.293 | 31.955 | 1.00 | 37.71 | AAAA |
| ATOM | 208 | CZ3 | TRP | A | 35 | -0.563 | 5.095 | 31.348 | 1.00 | 37.99 | AAAA |
| ATOM | 209 | CH2 | TRP | A | 35 | 0.570 | 5.874 | 31.650 | 1.00 | 38.17 | AAAA |
| ATOM | 210 | C | TRP | A | 35 | -1.153 | -1.228 | 32.402 | 1.00 | 33.77 | AAAA |
| ATOM | 211 | O | TRP | A | 35 | -1.136 | -2.282 | 31.763 | 1.00 | 32.95 | AAAA |
| ATOM | 212 | N | GLN | A | 36 | -2.261 | -0.704 | 32.912 | 1.00 | 32.90 | AAAA |
| ATOM | 213 | CA | GLN | A | 36 | -3.567 | -1.301 | 32.696 | 1.00 | 33.08 | AAAA |
| ATOM | 214 | CB | GLN | A | 36 | -4.448 | -1.160 | 33.937 | 1.00 | 34.93 | AAAA |
| ATOM | 215 | CG | GLN | A | 36 | -4.240 | -2.228 | 34.992 | 1.00 | 38.58 | AAAA |
| ATOM | 216 | CD | GLN | A | 36 | -5.272 | -2.143 | 36.103 | 1.00 | 40.36 | AAAA |
| ATOM | 217 | OE1 | GLN | A | 36 | -5.295 | -1.186 | 36.874 | 1.00 | 42.12 | AAAA |
| ATOM | 218 | NE2 | GLN | A | 36 | -6.140 | -3.146 | 36.181 | 1.00 | 42.80 | AAAA |
| ATOM | 219 | C | GLN | A | 36 | -4.160 | -0.482 | 31.552 | 1.00 | 32.42 | AAAA |
| ATOM | 220 | O | GLN | A | 36 | -4.114 | 0.748 | 31.583 | 1.00 | 31.42 | AAAA |
| ATOM | 221 | N | VAL | A | 37 | -4.697 | -1.157 | 30.541 | 1.00 | 32.07 | AAAA |
| ATOM | 222 | CA | VAL | A | 37 | -5.276 | -0.456 | 29.403 | 1.00 | 31.91 | AAAA |
| ATOM | 223 | CB | VAL | A | 37 | -4.436 | -0.656 | 28.123 | 1.00 | 32.46 | AAAA |
| ATOM | 224 | CG1 | VAL | A | 37 | -5.010 | 0.179 | 26.983 | 1.00 | 32.66 | AAAA |
| ATOM | 225 | CG2 | VAL | A | 37 | -2.994 | -0.269 | 28.379 | 1.00 | 31.40 | AAAA |
| ATOM | 226 | C | VAL | A | 37 | -6.693 | -0.917 | 29.118 | 1.00 | 32.15 | AAAA |

TABLE 1-continued

ATOMIC COORDINATES OF E. COLI MURG PROTEIN

| ATOM | 227 | O | VAL | A | 37 | -7.017 | -2.104 | 29.225 | 1.00 | 31.04 | AAAA |
|---|---|---|---|---|---|---|---|---|---|---|---|
| ATOM | 228 | N | ARG | A | 38 | -7.532 | 0.046 | 28.752 | 1.00 | 30.74 | AAAA |
| ATOM | 229 | CA | ARG | A | 38 | -8.925 | -0.202 | 28.433 | 1.00 | 31.08 | AAAA |
| ATOM | 230 | CB | ARG | A | 38 | -9.807 | 0.325 | 29.562 | 1.00 | 33.01 | AAAA |
| ATOM | 231 | CG | ARG | A | 38 | -11.251 | -0.116 | 29.499 | 1.00 | 37.13 | AAAA |
| ATOM | 232 | CD | ARG | A | 38 | -11.532 | -1.185 | 30.529 | 1.00 | 39.30 | AAAA |
| ATOM | 233 | NE | ARG | A | 38 | -12.937 | -1.567 | 30.519 | 1.00 | 41.65 | AAAA |
| ATOM | 234 | CZ | ARG | A | 38 | -13.464 | -2.495 | 31.308 | 1.00 | 43.12 | AAAA |
| ATOM | 235 | NH1 | ARG | A | 38 | -12.697 | -3.142 | 32.176 | 1.00 | 43.84 | AAAA |
| ATOM | 236 | NH2 | ARG | A | 38 | -14.758 | -2.773 | 31.227 | 1.00 | 43.90 | AAAA |
| ATOM | 237 | C | ARG | A | 38 | -9.196 | 0.568 | 27.143 | 1.00 | 29.87 | AAAA |
| ATOM | 238 | O | ARG | A | 38 | -8.574 | 1.601 | 26.883 | 1.00 | 28.94 | AAAA |
| ATOM | 239 | N | TRP | A | 39 | -10.119 | 0.072 | 26.332 | 1.00 | 28.69 | AAAA |
| ATOM | 240 | CA | TRP | A | 39 | -10.414 | 0.729 | 25.071 | 1.00 | 28.19 | AAAA |
| ATOM | 241 | CB | TRP | A | 39 | -10.321 | -0.305 | 23.939 | 1.00 | 29.84 | AAAA |
| ATOM | 242 | CG | TRP | A | 39 | -10.046 | 0.269 | 22.583 | 1.00 | 33.23 | AAAA |
| ATOM | 243 | CD2 | TRP | A | 39 | -8.774 | 0.339 | 21.919 | 1.00 | 33.62 | AAAA |
| ATOM | 244 | CE2 | TRP | A | 39 | -8.995 | 0.945 | 20.661 | 1.00 | 34.00 | AAAA |
| ATOM | 245 | CE3 | TRP | A | 39 | -7.470 | -0.052 | 22.261 | 1.00 | 33.80 | AAAA |
| ATOM | 246 | CD1 | TRP | A | 39 | -10.955 | 0.823 | 21.729 | 1.00 | 34.36 | AAAA |
| ATOM | 247 | NE1 | TRP | A | 39 | -10.332 | 1.230 | 20.573 | 1.00 | 33.43 | AAAA |
| ATOM | 248 | CZ2 | TRP | A | 39 | -7.960 | 1.171 | 19.743 | 1.00 | 34.56 | AAAA |
| ATOM | 249 | CZ3 | TRP | A | 39 | -6.442 | 0.171 | 21.350 | 1.00 | 35.28 | AAAA |
| ATOM | 250 | CH2 | TRP | A | 39 | -6.695 | 0.779 | 20.102 | 1.00 | 34.47 | AAAA |
| ATOM | 251 | C | TRP | A | 39 | -11.790 | 1.395 | 25.081 | 1.00 | 26.35 | AAAA |
| ATOM | 252 | O | TRP | A | 39 | -12.683 | 0.994 | 25.826 | 1.00 | 26.68 | AAAA |
| ATOM | 253 | N | LEU | A | 40 | -11.935 | 2.438 | 24.269 | 1.00 | 25.04 | AAAA |
| ATOM | 254 | CA | LEU | A | 40 | -13.197 | 3.159 | 24.130 | 1.00 | 23.18 | AAAA |
| ATOM | 255 | CB | LEU | A | 40 | -13.074 | 4.602 | 24.637 | 1.00 | 22.55 | AAAA |
| ATOM | 256 | CG | LEU | A | 40 | -14.395 | 5.381 | 24.623 | 1.00 | 20.79 | AAAA |
| ATOM | 257 | CD1 | LEU | A | 40 | -15.314 | 4.801 | 25.675 | 1.00 | 21.21 | AAAA |
| ATOM | 258 | CD2 | LEU | A | 40 | -14.149 | 6.868 | 24.905 | 1.00 | 21.72 | AAAA |
| ATOM | 259 | C | LEU | A | 40 | -13.495 | 3.179 | 22.634 | 1.00 | 22.87 | AAAA |
| ATOM | 260 | O | LEU | A | 40 | -12.718 | 3.721 | 21.854 | 1.00 | 22.99 | AAAA |
| ATOM | 261 | N | GLY | A | 41 | -14.608 | 2.580 | 22.232 | 1.00 | 25.02 | AAAA |
| ATOM | 262 | CA | GLY | A | 41 | -14.946 | 2.553 | 20.821 | 1.00 | 25.95 | AAAA |
| ATOM | 263 | C | GLY | A | 41 | -16.426 | 2.332 | 20.594 | 1.00 | 28.01 | AAAA |
| ATOM | 264 | O | GLY | A | 41 | -17.234 | 2.555 | 21.494 | 1.00 | 28.82 | AAAA |
| ATOM | 265 | N | THR | A | 42 | -16.783 | 1.884 | 19.395 | 1.00 | 29.77 | AAAA |
| ATOM | 266 | CA | THR | A | 42 | -18.185 | 1.641 | 19.059 | 1.00 | 31.41 | AAAA |
| ATOM | 267 | CB | THR | A | 42 | -18.603 | 2.497 | 17.855 | 1.00 | 32.12 | AAAA |
| ATOM | 268 | OG1 | THR | A | 42 | -18.293 | 3.871 | 18.119 | 1.00 | 34.95 | AAAA |
| ATOM | 269 | CG2 | THR | A | 42 | -20.098 | 2.367 | 17.611 | 1.00 | 34.55 | AAAA |
| ATOM | 270 | C | THR | A | 42 | -18.458 | 0.168 | 18.741 | 1.00 | 32.23 | AAAA |
| ATOM | 271 | O | THR | A | 42 | -17.721 | -0.463 | 17.986 | 1.00 | 29.57 | AAAA |
| ATOM | 272 | N | ALA | A | 43 | -19.541 | -0.360 | 19.306 | 1.00 | 34.77 | AAAA |
| ATOM | 273 | CA | ALA | A | 43 | -19.920 | -1.760 | 19.127 | 1.00 | 37.23 | AAAA |
| ATOM | 274 | CB | ALA | A | 43 | -21.173 | -2.060 | 19.948 | 1.00 | 37.66 | AAAA |
| ATOM | 275 | C | ALA | A | 43 | -20.126 | -2.232 | 17.686 | 1.00 | 39.10 | AAAA |
| ATOM | 276 | O | ALA | A | 43 | -20.088 | -3.434 | 17.422 | 1.00 | 39.09 | AAAA |
| ATOM | 277 | N | ASP | A | 44 | -20.333 | -1.304 | 16.757 | 1.00 | 40.78 | AAAA |
| ATOM | 278 | CA | ASP | A | 44 | -20.557 | -1.671 | 15.361 | 1.00 | 42.78 | AAAA |
| ATOM | 279 | CB | ASP | A | 44 | -21.678 | -0.812 | 14.774 | 1.00 | 44.80 | AAAA |
| ATOM | 280 | CG | ASP | A | 44 | -21.438 | 0.670 | 14.973 | 1.00 | 46.37 | AAAA |
| ATOM | 281 | OD1 | ASP | A | 44 | -20.464 | 1.206 | 14.400 | 1.00 | 48.22 | AAAA |
| ATOM | 282 | OD2 | ASP | A | 44 | -22.220 | 1.302 | 15.712 | 1.00 | 49.14 | AAAA |
| ATOM | 283 | C | ASP | A | 44 | -19.324 | -1.559 | 14.472 | 1.00 | 43.14 | AAAA |
| ATOM | 284 | O | ASP | A | 44 | -19.320 | -2.061 | 13.349 | 1.00 | 44.14 | AAAA |
| ATOM | 285 | N | ARG | A | 45 | -18.281 | -0.904 | 14.970 | 1.00 | 42.77 | AAAA |
| ATOM | 286 | CA | ARG | A | 45 | -17.056 | -0.730 | 14.199 | 1.00 | 42.34 | AAAA |
| ATOM | 287 | CB | ARG | A | 45 | -16.415 | 0.614 | 14.550 | 1.00 | 44.43 | AAAA |
| ATOM | 288 | CG | ARG | A | 45 | -17.206 | 1.822 | 14.056 | 1.00 | 48.23 | AAAA |
| ATOM | 289 | CD | ARG | A | 45 | -17.272 | 1.845 | 12.533 | 1.00 | 51.20 | AAAA |
| ATOM | 290 | NE | ARG | A | 45 | -17.950 | 3.029 | 12.014 | 1.00 | 54.35 | AAAA |
| ATOM | 291 | CZ | ARG | A | 45 | -17.526 | 4.279 | 12.191 | 1.00 | 56.26 | AAAA |
| ATOM | 292 | NH1 | ARG | A | 45 | -16.417 | 4.522 | 12.881 | 1.00 | 56.45 | AAAA |
| ATOM | 293 | NH2 | ARG | A | 45 | -18.212 | 5.290 | 11.670 | 1.00 | 57.50 | AAAA |
| ATOM | 294 | C | ARG | A | 45 | -16.054 | -1.872 | 14.401 | 1.00 | 41.11 | AAAA |
| ATOM | 295 | O | ARG | A | 45 | -16.194 | -2.679 | 15.320 | 1.00 | 40.45 | AAAA |
| ATOM | 296 | N | MET | A | 46 | -15.041 | -1.928 | 13.543 | 1.00 | 39.55 | AAAA |
| ATOM | 297 | CA | MET | A | 46 | -14.038 | -2.990 | 13.604 | 1.00 | 39.67 | AAAA |
| ATOM | 298 | CB | MET | A | 46 | -13.041 | -2.839 | 12.444 | 1.00 | 39.68 | AAAA |
| ATOM | 299 | CG | MET | A | 46 | -12.239 | -1.544 | 12.423 | 1.00 | 42.15 | AAAA |
| ATOM | 300 | SD | MET | A | 46 | -10.690 | -1.620 | 13.352 | 1.00 | 44.74 | AAAA |
| ATOM | 301 | CE | MET | A | 46 | -9.559 | -2.332 | 12.128 | 1.00 | 41.92 | AAAA |
| ATOM | 302 | C | MET | A | 46 | -13.279 | -3.148 | 14.926 | 1.00 | 38.68 | AAAA |
| ATOM | 303 | O | MET | A | 46 | -12.772 | -4.232 | 15.219 | 1.00 | 38.02 | AAAA |

TABLE 1-continued

ATOMIC COORDINATES OF E. COLI MURG PROTEIN

| ATOM | 304 | N   | GLU | A | 47 | −13.198 | −2.092  | 15.730 | 1.00 | 37.48 | AAAA |
|------|-----|-----|-----|---|----|---------|---------|--------|------|-------|------|
| ATOM | 305 | CA  | GLU | A | 47 | −12.486 | −2.198  | 17.002 | 1.00 | 36.91 | AAAA |
| ATOM | 306 | CB  | GLU | A | 47 | −12.309 | −0.820  | 17.650 | 1.00 | 35.19 | AAAA |
| ATOM | 307 | CG  | GLU | A | 47 | −13.615 | −0.150  | 18.058 | 1.00 | 34.12 | AAAA |
| ATOM | 308 | CD  | GLU | A | 47 | −14.142 | 0.807   | 17.003 | 1.00 | 34.06 | AAAA |
| ATOM | 309 | OE1 | GLU | A | 47 | −13.712 | 0.707   | 15.832 | 1.00 | 33.13 | AAAA |
| ATOM | 310 | OE2 | GLU | A | 47 | −14.995 | 1.652   | 17.350 | 1.00 | 32.08 | AAAA |
| ATOM | 311 | C   | GLU | A | 47 | −13.225 | −3.123  | 17.972 | 1.00 | 36.96 | AAAA |
| ATOM | 312 | O   | GLU | A | 47 | −12.612 | −3.744  | 18.842 | 1.00 | 37.00 | AAAA |
| ATOM | 313 | N   | ALA | A | 48 | −14.541 | −3.222  | 17.818 | 1.00 | 36.76 | AAAA |
| ATOM | 314 | CA  | ALA | A | 48 | −15.342 | −4.066  | 18.700 | 1.00 | 36.98 | AAAA |
| ATOM | 315 | CB  | ALA | A | 48 | −16.823 | −3.917  | 18.365 | 1.00 | 37.33 | AAAA |
| ATOM | 316 | C   | ALA | A | 48 | −14.943 | −5.533  | 18.623 | 1.00 | 38.23 | AAAA |
| ATOM | 317 | O   | ALA | A | 48 | −15.100 | −6.281  | 19.590 | 1.00 | 37.91 | AAAA |
| ATOM | 318 | N   | ASP | A | 49 | −14.430 | −5.947  | 17.470 | 1.00 | 39.31 | AAAA |
| ATOM | 319 | CA  | ASP | A | 49 | −14.027 | −7.332  | 17.286 | 1.00 | 40.97 | AAAA |
| ATOM | 320 | CB  | ASP | A | 49 | −14.477 | −7.832  | 15.909 | 1.00 | 42.68 | AAAA |
| ATOM | 321 | CG  | ASP | A | 49 | −15.988 | −7.912  | 15.783 | 1.00 | 44.91 | AAAA |
| ATOM | 322 | OD1 | ASP | A | 49 | −16.612 | −8.681  | 16.549 | 1.00 | 45.64 | AAAA |
| ATOM | 323 | OD2 | ASP | A | 49 | −16.552 | −7.205  | 14.918 | 1.00 | 46.44 | AAAA |
| ATOM | 324 | C   | ASP | A | 49 | −12.524 | −7.519  | 17.426 | 1.00 | 40.10 | AAAA |
| ATOM | 325 | O   | ASP | A | 49 | −12.069 | −8.518  | 17.974 | 1.00 | 40.92 | AAAA |
| ATOM | 326 | N   | LEU | A | 50 | −11.761 | −6.549  | 16.940 | 1.00 | 39.40 | AAAA |
| ATOM | 327 | CA  | LEU | A | 50 | −10.306 | −6.623  | 16.982 | 1.00 | 39.05 | AAAA |
| ATOM | 328 | CB  | LEU | A | 50 | −9.710  | −5.578  | 16.036 | 1.00 | 38.17 | AAAA |
| ATOM | 329 | CG  | LEU | A | 50 | −8.183  | −5.562  | 15.942 | 1.00 | 38.18 | AAAA |
| ATOM | 330 | CD1 | LEU | A | 50 | −7.685  | −6.916  | 15.462 | 1.00 | 37.91 | AAAA |
| ATOM | 331 | CD2 | LEU | A | 50 | −7.740  | −4.460  | 14.999 | 1.00 | 37.50 | AAAA |
| ATOM | 332 | C   | LEU | A | 50 | −9.666  | −6.486  | 18.365 | 1.00 | 39.12 | AAAA |
| ATOM | 333 | O   | LEU | A | 50 | −8.805  | −7.286  | 18.732 | 1.00 | 38.56 | AAAA |
| ATOM | 334 | N   | VAL | A | 51 | −10.084 | −5.483  | 19.132 | 1.00 | 38.79 | AAAA |
| ATOM | 335 | CA  | VAL | A | 51 | −9.516  | −5.257  | 20.459 | 1.00 | 37.64 | AAAA |
| ATOM | 336 | CB  | VAL | A | 51 | −10.127 | −3.989  | 21.111 | 1.00 | 36.87 | AAAA |
| ATOM | 337 | CG1 | VAL | A | 51 | −9.571  | −3.795  | 22.523 | 1.00 | 35.15 | AAAA |
| ATOM | 338 | CG2 | VAL | A | 51 | −9.810  | −2.777  | 20.256 | 1.00 | 34.42 | AAAA |
| ATOM | 339 | C   | VAL | A | 51 | −9.647  | −6.449  | 21.415 | 1.00 | 37.87 | AAAA |
| ATOM | 340 | O   | VAL | A | 51 | −8.695  | −6.790  | 22.115 | 1.00 | 37.54 | AAAA |
| ATOM | 341 | N   | PRO | A | 52 | −10.825 | −7.093  | 21.465 | 1.00 | 38.44 | AAAA |
| ATOM | 342 | CD  | PRO | A | 52 | −12.141 | −6.700  | 20.932 | 1.00 | 38.92 | AAAA |
| ATOM | 343 | CA  | PRO | A | 52 | −10.959 | −8.237  | 22.373 | 1.00 | 39.32 | AAAA |
| ATOM | 344 | CB  | PRO | A | 52 | −12.436 | −8.602  | 22.253 | 1.00 | 39.97 | AAAA |
| ATOM | 345 | CG  | PRO | A | 52 | −13.080 | −7.277  | 21.962 | 1.00 | 38.98 | AAAA |
| ATOM | 346 | C   | PRO | A | 52 | −10.035 | −9.392  | 21.974 | 1.00 | 40.07 | AAAA |
| ATOM | 347 | O   | PRO | A | 52 | −9.685  | −10.232 | 22.805 | 1.00 | 40.30 | AAAA |
| ATOM | 348 | N   | LYS | A | 53 | −9.649  | −9.427  | 20.699 | 1.00 | 40.35 | AAAA |
| ATOM | 349 | CA  | LYS | A | 53 | −8.752  | −10.463 | 20.193 | 1.00 | 40.58 | AAAA |
| ATOM | 350 | CB  | LYS | A | 53 | −8.812  | −10.541 | 18.661 | 1.00 | 41.25 | AAAA |
| ATOM | 351 | CG  | LYS | A | 53 | −10.093 | −11.169 | 18.129 | 1.00 | 43.24 | AAAA |
| ATOM | 352 | CD  | LYS | A | 53 | −10.033 | −11.383 | 16.627 | 1.00 | 44.40 | AAAA |
| ATOM | 353 | CE  | LYS | A | 53 | −11.280 | −12.102 | 16.133 | 1.00 | 45.87 | AAAA |
| ATOM | 354 | NZ  | LYS | A | 53 | −11.250 | −12.342 | 14.659 | 1.00 | 47.88 | AAAA |
| ATOM | 355 | C   | LYS | A | 53 | −7.323  | −10.184 | 20.636 | 1.00 | 39.99 | AAAA |
| ATOM | 356 | O   | LYS | A | 53 | −6.426  | −11.006 | 20.432 | 1.00 | 39.70 | AAAA |
| ATOM | 357 | N   | HIS | A | 54 | −7.112  | −9.014  | 21.231 | 1.00 | 38.65 | AAAA |
| ATOM | 358 | CA  | HIS | A | 54 | −5.790  | −8.642  | 21.727 | 1.00 | 37.71 | AAAA |
| ATOM | 359 | CB  | HIS | A | 54 | −5.408  | −7.233  | 21.272 | 1.00 | 37.50 | AAAA |
| ATOM | 360 | CG  | HIS | A | 54 | −4.903  | −7.164  | 19.864 | 1.00 | 37.59 | AAAA |
| ATOM | 361 | CD2 | HIS | A | 54 | −5.483  | −7.502  | 18.687 | 1.00 | 37.67 | AAAA |
| ATOM | 362 | ND1 | HIS | A | 54 | −3.658  | −6.666  | 19.546 | 1.00 | 37.90 | AAAA |
| ATOM | 363 | CE1 | HIS | A | 54 | −3.492  | −6.698  | 18.235 | 1.00 | 37.11 | AAAA |
| ATOM | 364 | NE2 | HIS | A | 54 | −4.586  | −7.202  | 17.691 | 1.00 | 36.75 | AAAA |
| ATOM | 365 | C   | HIS | A | 54 | −5.788  | −8.711  | 23.248 | 1.00 | 37.10 | AAAA |
| ATOM | 366 | O   | HIS | A | 54 | −4.871  | −8.214  | 23.899 | 1.00 | 37.35 | AAAA |
| ATOM | 367 | N   | GLY | A | 55 | −6.828  | −9.331  | 23.800 | 1.00 | 36.15 | AAAA |
| ATOM | 368 | CA  | GLY | A | 55 | −6.948  | −9.477  | 25.240 | 1.00 | 36.70 | AAAA |
| ATOM | 369 | C   | GLY | A | 55 | −7.266  | −8.200  | 25.997 | 1.00 | 36.66 | AAAA |
| ATOM | 370 | O   | GLY | A | 55 | −7.145  | −8.157  | 27.222 | 1.00 | 36.89 | AAAA |
| ATOM | 371 | N   | ILE | A | 56 | −7.686  | −7.163  | 25.277 | 1.00 | 35.61 | AAAA |
| ATOM | 372 | CA  | ILE | A | 56 | −8.009  | −5.885  | 25.900 | 1.00 | 34.03 | AAAA |
| ATOM | 373 | CB  | ILE | A | 56 | −7.389  | −4.723  | 25.100 | 1.00 | 32.39 | AAAA |
| ATOM | 374 | CG2 | ILE | A | 56 | −7.748  | −3.386  | 25.750 | 1.00 | 31.80 | AAAA |
| ATOM | 375 | CG1 | ILE | A | 56 | −5.869  | −4.904  | 25.031 | 1.00 | 31.50 | AAAA |
| ATOM | 376 | CD1 | ILE | A | 56 | −5.149  | −3.900  | 24.144 | 1.00 | 30.46 | AAAA |
| ATOM | 377 | C   | ILE | A | 56 | −9.516  | −5.668  | 26.017 | 1.00 | 34.37 | AAAA |
| ATOM | 378 | O   | ILE | A | 56 | −10.263 | −5.908  | 25.067 | 1.00 | 34.29 | AAAA |
| ATOM | 379 | N   | GLU | A | 57 | −9.955  | −5.224  | 27.193 | 1.00 | 34.18 | AAAA |
| ATOM | 380 | CA  | GLU | A | 57 | −11.370 | −4.969  | 27.432 | 1.00 | 34.19 | AAAA |

TABLE 1-continued

ATOMIC COORDINATES OF E. COLI MURG PROTEIN

| ATOM | 381 | CB | GLU | A | 57 | −11.638 | −4.733 | 28.922 | 1.00 | 37.08 | AAAA |
|---|---|---|---|---|---|---|---|---|---|---|---|
| ATOM | 382 | CG | GLU | A | 57 | −11.301 | −5.913 | 29.837 | 1.00 | 41.06 | AAAA |
| ATOM | 383 | CD | GLU | A | 57 | −12.180 | −7.127 | 29.591 | 1.00 | 44.07 | AAAA |
| ATOM | 384 | OE1 | GLU | A | 57 | −12.011 | −8.135 | 30.313 | 1.00 | 45.83 | AAAA |
| ATOM | 385 | OE2 | GLU | A | 57 | −13.040 | −7.078 | 28.682 | 1.00 | 46.00 | AAAA |
| ATOM | 386 | C | GLU | A | 57 | −11.751 | −3.723 | 26.645 | 1.00 | 32.88 | AAAA |
| ATOM | 387 | O | GLU | A | 57 | −10.905 | −2.870 | 26.368 | 1.00 | 31.69 | AAAA |
| ATOM | 388 | N | ILE | A | 58 | −13.022 | −3.611 | 26.285 | 1.00 | 31.36 | AAAA |
| ATOM | 389 | CA | ILE | A | 58 | −13.454 | −2.454 | 25.529 | 1.00 | 29.92 | AAAA |
| ATOM | 390 | CB | ILE | A | 58 | −13.390 | −2.749 | 24.009 | 1.00 | 29.51 | AAAA |
| ATOM | 391 | CG2 | ILE | A | 58 | −14.175 | −4.015 | 23.689 | 1.00 | 28.67 | AAAA |
| ATOM | 392 | CG1 | ILE | A | 58 | −13.895 | −1.543 | 23.216 | 1.00 | 29.61 | AAAA |
| ATOM | 393 | CD1 | ILE | A | 58 | −13.578 | −1.623 | 21.734 | 1.00 | 29.09 | AAAA |
| ATOM | 394 | C | ILE | A | 58 | −14.843 | −1.984 | 25.927 | 1.00 | 29.49 | AAAA |
| ATOM | 395 | O | ILE | A | 58 | −15.791 | −2.764 | 25.968 | 1.00 | 27.83 | AAAA |
| ATOM | 396 | N | ASP | A | 59 | −14.939 | −0.700 | 26.252 | 1.00 | 29.28 | AAAA |
| ATOM | 397 | CA | ASP | A | 59 | −16.202 | −0.091 | 26.626 | 1.00 | 29.70 | AAAA |
| ATOM | 398 | CB | ASP | A | 59 | −15.999 | 0.916 | 27.759 | 1.00 | 30.90 | AAAA |
| ATOM | 399 | CG | ASP | A | 59 | −15.676 | 0.245 | 29.083 | 1.00 | 32.17 | AAAA |
| ATOM | 400 | OD1 | ASP | A | 59 | −16.485 | −0.591 | 29.540 | 1.00 | 33.00 | AAAA |
| ATOM | 401 | OD2 | ASP | A | 59 | −14.615 | 0.554 | 29.664 | 1.00 | 33.03 | AAAA |
| ATOM | 402 | C | ASP | A | 59 | −16.723 | 0.608 | 25.378 | 1.00 | 30.39 | AAAA |
| ATOM | 403 | O | ASP | A | 59 | −15.947 | 1.165 | 24.600 | 1.00 | 30.45 | AAAA |
| ATOM | 404 | N | PHE | A | 60 | −18.033 | 0.570 | 25.180 | 1.00 | 31.29 | AAAA |
| ATOM | 405 | CA | PHE | A | 60 | −18.612 | 1.183 | 24.000 | 1.00 | 32.36 | AAAA |
| ATOM | 406 | CB | PHE | A | 60 | −19.469 | 0.166 | 23.239 | 1.00 | 33.01 | AAAA |
| ATOM | 407 | CG | PHE | A | 60 | −18.720 | −1.056 | 22.793 | 1.00 | 33.55 | AAAA |
| ATOM | 408 | CD1 | PHE | A | 60 | −19.033 | −2.307 | 23.318 | 1.00 | 34.07 | AAAA |
| ATOM | 409 | CD2 | PHE | A | 60 | −17.720 | −0.964 | 21.832 | 1.00 | 34.02 | AAAA |
| ATOM | 410 | CE1 | PHE | A | 60 | −18.362 | −3.451 | 22.890 | 1.00 | 33.73 | AAAA |
| ATOM | 411 | CE2 | PHE | A | 60 | −17.042 | −2.104 | 21.397 | 1.00 | 34.93 | AAAA |
| ATOM | 412 | CZ | PHE | A | 60 | −17.366 | −3.348 | 21.928 | 1.00 | 34.12 | AAAA |
| ATOM | 413 | C | PHE | A | 60 | −19.469 | 2.395 | 24.300 | 1.00 | 32.89 | AAAA |
| ATOM | 414 | O | PHE | A | 60 | −20.062 | 2.508 | 25.372 | 1.00 | 33.13 | AAAA |
| ATOM | 415 | N | ILE | A | 61 | −19.502 | 3.309 | 23.338 | 1.00 | 34.43 | AAAA |
| ATOM | 416 | CA | ILE | A | 61 | −20.326 | 4.500 | 23.421 | 1.00 | 36.08 | AAAA |
| ATOM | 417 | CB | ILE | A | 61 | −19.545 | 5.785 | 23.056 | 1.00 | 36.15 | AAAA |
| ATOM | 418 | CG2 | ILE | A | 61 | −20.511 | 6.957 | 22.913 | 1.00 | 36.47 | AAAA |
| ATOM | 419 | CG1 | ILE | A | 61 | −18.504 | 6.092 | 24.136 | 1.00 | 37.27 | AAAA |
| ATOM | 420 | CD1 | ILE | A | 61 | −17.711 | 7.360 | 23.875 | 1.00 | 38.32 | AAAA |
| ATOM | 421 | C | ILE | A | 61 | −21.380 | 4.230 | 22.353 | 1.00 | 37.27 | AAAA |
| ATOM | 422 | O | ILE | A | 61 | −21.050 | 3.901 | 21.215 | 1.00 | 36.29 | AAAA |
| ATOM | 423 | N | ARG | A | 62 | −22.644 | 4.337 | 22.728 | 1.00 | 39.91 | AAAA |
| ATOM | 424 | CA | ARG | A | 62 | −23.732 | 4.087 | 21.797 | 1.00 | 43.16 | AAAA |
| ATOM | 425 | CB | ARG | A | 62 | −24.818 | 3.268 | 22.494 | 1.00 | 44.19 | AAAA |
| ATOM | 426 | CG | ARG | A | 62 | −26.183 | 3.312 | 21.825 | 1.00 | 48.33 | AAAA |
| ATOM | 427 | CD | ARG | A | 62 | −27.207 | 2.581 | 22.680 | 1.00 | 50.28 | AAAA |
| ATOM | 428 | NE | ARG | A | 62 | −28.584 | 2.906 | 22.319 | 1.00 | 52.71 | AAAA |
| ATOM | 429 | CZ | ARG | A | 62 | −29.646 | 2.419 | 22.951 | 1.00 | 53.14 | AAAA |
| ATOM | 430 | NH1 | ARG | A | 62 | −29.482 | 1.586 | 23.968 | 1.00 | 54.03 | AAAA |
| ATOM | 431 | NH2 | ARG | A | 62 | −30.870 | 2.767 | 22.573 | 1.00 | 53.49 | AAAA |
| ATOM | 432 | C | ARG | A | 62 | −24.302 | 5.400 | 21.280 | 1.00 | 44.33 | AAAA |
| ATOM | 433 | O | ARG | A | 62 | −24.942 | 6.140 | 22.021 | 1.00 | 43.98 | AAAA |
| ATOM | 434 | N | ILE | A | 63 | −24.053 | 5.686 | 20.005 | 1.00 | 46.60 | AAAA |
| ATOM | 435 | CA | ILE | A | 63 | −24.537 | 6.912 | 19.378 | 1.00 | 49.26 | AAAA |
| ATOM | 436 | CB | ILE | A | 63 | −23.369 | 7.834 | 18.965 | 1.00 | 49.17 | AAAA |
| ATOM | 437 | CG2 | ILE | A | 63 | −23.903 | 9.208 | 18.593 | 1.00 | 50.31 | AAAA |
| ATOM | 438 | CG1 | ILE | A | 63 | −22.368 | 7.967 | 20.113 | 1.00 | 49.48 | AAAA |
| ATOM | 439 | CD1 | ILE | A | 63 | −21.158 | 8.822 | 19.775 | 1.00 | 49.03 | AAAA |
| ATOM | 440 | C | ILE | A | 63 | −25.316 | 6.540 | 18.123 | 1.00 | 50.72 | AAAA |
| ATOM | 441 | O | ILE | A | 63 | −24.724 | 6.219 | 17.093 | 1.00 | 50.90 | AAAA |
| ATOM | 442 | N | SER | A | 64 | −26.639 | 6.591 | 18.209 | 1.00 | 52.58 | AAAA |
| ATOM | 443 | CA | SER | A | 64 | −27.488 | 6.235 | 17.078 | 1.00 | 54.45 | AAAA |
| ATOM | 444 | CB | SER | A | 64 | −28.731 | 5.491 | 17.574 | 1.00 | 54.65 | AAAA |
| ATOM | 445 | OG | SER | A | 64 | −29.528 | 6.329 | 18.391 | 1.00 | 55.29 | AAAA |
| ATOM | 446 | C | SER | A | 64 | −27.927 | 7.433 | 16.242 | 1.00 | 55.33 | AAAA |
| ATOM | 447 | O | SER | A | 64 | −27.919 | 8.571 | 16.713 | 1.00 | 55.34 | AAAA |
| ATOM | 448 | N | GLY | A | 65 | −28.301 | 7.158 | 14.993 | 1.00 | 56.31 | AAAA |
| ATOM | 449 | CA | GLY | A | 65 | −28.774 | 8.196 | 14.090 | 1.00 | 57.42 | AAAA |
| ATOM | 450 | C | GLY | A | 65 | −27.751 | 9.156 | 13.508 | 1.00 | 58.34 | AAAA |
| ATOM | 451 | O | GLY | A | 65 | −28.052 | 10.333 | 13.315 | 1.00 | 58.53 | AAAA |
| ATOM | 452 | N | LEU | A | 66 | −26.552 | 8.668 | 13.207 | 1.00 | 59.08 | AAAA |
| ATOM | 453 | CA | LEU | A | 66 | −25.514 | 9.530 | 12.648 | 1.00 | 59.80 | AAAA |
| ATOM | 454 | CB | LEU | A | 66 | −24.147 | 9.153 | 13.229 | 1.00 | 59.99 | AAAA |
| ATOM | 455 | CG | LEU | A | 66 | −23.927 | 9.513 | 14.704 | 1.00 | 60.38 | AAAA |
| ATOM | 456 | CD1 | LEU | A | 66 | −23.983 | 11.026 | 14.877 | 1.00 | 60.37 | AAAA |
| ATOM | 457 | CD2 | LEU | A | 66 | −24.983 | 8.840 | 15.565 | 1.00 | 60.47 | AAAA |

TABLE 1-continued

ATOMIC COORDINATES OF E. COLI MURG PROTEIN

| | | | | | | | | | | | |
|---|---|---|---|---|---|---|---|---|---|---|---|
| ATOM | 458 | C | LEU | A | 66 | −25.467 | 9.497 | 11.121 | 1.00 | 60.04 | AAAA |
| ATOM | 459 | O | LEU | A | 66 | −25.049 | 10.466 | 10.484 | 1.00 | 59.29 | AAAA |
| ATOM | 460 | N | ARG | A | 67 | −25.892 | 8.378 | 10.541 | 1.00 | 60.97 | AAAA |
| ATOM | 461 | CA | ARG | A | 67 | −25.923 | 8.224 | 9.089 | 1.00 | 61.57 | AAAA |
| ATOM | 462 | CB | ARG | A | 67 | −26.860 | 9.273 | 8.484 | 1.00 | 62.96 | AAAA |
| ATOM | 463 | CG | ARG | A | 67 | −28.340 | 8.984 | 8.698 | 1.00 | 65.29 | AAAA |
| ATOM | 464 | CD | ARG | A | 67 | −29.138 | 10.270 | 8.842 | 1.00 | 66.93 | AAAA |
| ATOM | 465 | NE | ARG | A | 67 | −30.566 | 10.067 | 8.611 | 1.00 | 68.58 | AAAA |
| ATOM | 466 | CZ | ARG | A | 67 | −31.514 | 10.924 | 8.980 | 1.00 | 69.56 | AAAA |
| ATOM | 467 | NH1 | ARG | A | 67 | −31.192 | 12.048 | 9.607 | 1.00 | 69.39 | AAAA |
| ATOM | 468 | NH2 | ARG | A | 67 | −32.788 | 10.665 | 8.709 | 1.00 | 69.97 | AAAA |
| ATOM | 469 | C | ARG | A | 67 | −24.558 | 8.301 | 8.409 | 1.00 | 61.08 | AAAA |
| ATOM | 470 | O | ARG | A | 67 | −24.474 | 8.448 | 7.191 | 1.00 | 61.57 | AAAA |
| ATOM | 471 | N | GLY | A | 68 | −23.489 | 8.204 | 9.189 | 1.00 | 60.22 | AAAA |
| ATOM | 472 | CA | GLY | A | 68 | −22.161 | 8.249 | 8.605 | 1.00 | 58.95 | AAAA |
| ATOM | 473 | C | GLY | A | 68 | −21.531 | 9.627 | 8.541 | 1.00 | 58.19 | AAAA |
| ATOM | 474 | O | GLY | A | 68 | −20.373 | 9.763 | 8.140 | 1.00 | 58.31 | AAAA |
| ATOM | 475 | N | LYS | A | 69 | −22.282 | 10.655 | 8.921 | 1.00 | 57.03 | AAAA |
| ATOM | 476 | CA | LYS | A | 69 | −21.746 | 12.009 | 8.904 | 1.00 | 55.91 | AAAA |
| ATOM | 477 | CB | LYS | A | 69 | −22.812 | 13.015 | 9.349 | 1.00 | 56.90 | AAAA |
| ATOM | 478 | CG | LYS | A | 69 | −23.827 | 13.368 | 8.264 | 1.00 | 57.91 | AAAA |
| ATOM | 479 | CD | LYS | A | 69 | −23.167 | 14.147 | 7.133 | 1.00 | 58.56 | AAAA |
| ATOM | 480 | CE | LYS | A | 69 | −24.163 | 14.517 | 6.044 | 1.00 | 59.37 | AAAA |
| ATOM | 481 | NZ | LYS | A | 69 | −23.522 | 15.327 | 4.965 | 1.00 | 59.41 | AAAA |
| ATOM | 482 | C | LYS | A | 69 | −20.527 | 12.078 | 9.818 | 1.00 | 54.19 | AAAA |
| ATOM | 483 | O | LYS | A | 69 | −19.447 | 12.480 | 9.392 | 1.00 | 54.69 | AAAA |
| ATOM | 484 | N | GLY | A | 70 | −20.697 | 11.676 | 11.072 | 1.00 | 51.77 | AAAA |
| ATOM | 485 | CA | GLY | A | 70 | −19.575 | 11.692 | 11.991 | 1.00 | 48.95 | AAAA |
| ATOM | 486 | C | GLY | A | 70 | −19.668 | 12.687 | 13.129 | 1.00 | 46.84 | AAAA |
| ATOM | 487 | O | GLY | A | 70 | −20.754 | 12.975 | 13.629 | 1.00 | 46.29 | AAAA |
| ATOM | 488 | N | ILE | A | 71 | −18.515 | 13.221 | 13.523 | 1.00 | 45.26 | AAAA |
| ATOM | 489 | CA | ILE | A | 71 | −18.415 | 14.174 | 14.623 | 1.00 | 43.82 | AAAA |
| ATOM | 490 | CB | ILE | A | 71 | −16.936 | 14.463 | 14.959 | 1.00 | 42.91 | AAAA |
| ATOM | 491 | CG2 | ILE | A | 71 | −16.262 | 15.142 | 13.786 | 1.00 | 42.86 | AAAA |
| ATOM | 492 | CG1 | ILE | A | 71 | −16.839 | 15.325 | 16.217 | 1.00 | 41.89 | AAAA |
| ATOM | 493 | CD1 | ILE | A | 71 | −17.324 | 14.619 | 17.471 | 1.00 | 42.12 | AAAA |
| ATOM | 494 | C | ILE | A | 71 | −19.127 | 15.501 | 14.367 | 1.00 | 43.91 | AAAA |
| ATOM | 495 | O | ILE | A | 71 | −19.635 | 16.125 | 15.296 | 1.00 | 43.71 | AAAA |
| ATOM | 496 | N | LYS | A | 72 | −19.154 | 15.935 | 13.112 | 1.00 | 43.92 | AAAA |
| ATOM | 497 | CA | LYS | A | 72 | −19.815 | 17.188 | 12.757 | 1.00 | 43.85 | AAAA |
| ATOM | 498 | CB | LYS | A | 72 | −19.559 | 17.526 | 11.284 | 1.00 | 45.17 | AAAA |
| ATOM | 499 | CG | LYS | A | 72 | −20.140 | 16.517 | 10.297 | 1.00 | 46.64 | AAAA |
| ATOM | 500 | CD | LYS | A | 72 | −19.590 | 15.112 | 10.516 | 1.00 | 47.65 | AAAA |
| ATOM | 501 | CE | LYS | A | 72 | −18.070 | 15.074 | 10.388 | 1.00 | 47.12 | AAAA |
| ATOM | 502 | NZ | LYS | A | 72 | −17.533 | 13.692 | 10.506 | 1.00 | 46.69 | AAAA |
| ATOM | 503 | C | LYS | A | 72 | −21.318 | 17.073 | 13.003 | 1.00 | 42.82 | AAAA |
| ATOM | 504 | O | LYS | A | 72 | −21.969 | 18.035 | 13.414 | 1.00 | 43.31 | AAAA |
| ATOM | 505 | N | ALA | A | 73 | −21.862 | 15.889 | 12.752 | 1.00 | 41.38 | AAAA |
| ATOM | 506 | CA | ALA | A | 73 | −23.282 | 15.650 | 12.954 | 1.00 | 39.79 | AAAA |
| ATOM | 507 | CB | ALA | A | 73 | −23.700 | 14.379 | 12.238 | 1.00 | 39.55 | AAAA |
| ATOM | 508 | C | ALA | A | 73 | −23.575 | 15.524 | 14.438 | 1.00 | 39.28 | AAAA |
| ATOM | 509 | O | ALA | A | 73 | −24.509 | 16.132 | 14.959 | 1.00 | 37.60 | AAAA |
| ATOM | 510 | N | LEU | A | 74 | −22.760 | 14.725 | 15.116 | 1.00 | 38.96 | AAAA |
| ATOM | 511 | CA | LEU | A | 74 | −22.933 | 14.498 | 16.541 | 1.00 | 38.75 | AAAA |
| ATOM | 512 | CB | LEU | A | 74 | −21.817 | 13.575 | 17.055 | 1.00 | 39.47 | AAAA |
| ATOM | 513 | CG | LEU | A | 74 | −21.826 | 13.192 | 18.536 | 1.00 | 39.30 | AAAA |
| ATOM | 514 | CD1 | LEU | A | 74 | −21.439 | 14.383 | 19.366 | 1.00 | 40.12 | AAAA |
| ATOM | 515 | CD2 | LEU | A | 74 | −23.199 | 12.673 | 18.936 | 1.00 | 39.66 | AAAA |
| ATOM | 516 | C | LEU | A | 74 | −22.938 | 15.808 | 17.317 | 1.00 | 38.15 | AAAA |
| ATOM | 517 | O | LEU | A | 74 | −23.768 | 16.012 | 18.206 | 1.00 | 37.74 | AAAA |
| ATOM | 518 | N | ILE | A | 75 | −22.014 | 16.699 | 16.982 | 1.00 | 38.08 | AAAA |
| ATOM | 519 | CA | ILE | A | 75 | −21.923 | 17.975 | 17.678 | 1.00 | 39.02 | AAAA |
| ATOM | 520 | CB | ILE | A | 75 | −20.605 | 18.707 | 17.319 | 1.00 | 40.76 | AAAA |
| ATOM | 521 | CG2 | ILE | A | 75 | −20.616 | 19.109 | 15.856 | 1.00 | 41.16 | AAAA |
| ATOM | 522 | CD1 | ILE | A | 75 | −20.426 | 19.938 | 18.209 | 1.00 | 42.50 | AAAA |
| ATOM | 523 | CD1 | ILE | A | 75 | −20.302 | 19.616 | 19.690 | 1.00 | 44.15 | AAAA |
| ATOM | 524 | C | ILE | A | 75 | −23.114 | 18.886 | 17.377 | 1.00 | 38.41 | AAAA |
| ATOM | 525 | O | ILE | A | 75 | −23.396 | 19.818 | 18.130 | 1.00 | 38.12 | AAAA |
| ATOM | 526 | N | ALA | A | 76 | −23.816 | 18.602 | 16.283 | 1.00 | 38.04 | AAAA |
| ATOM | 527 | CA | ALA | A | 76 | −24.971 | 19.399 | 15.878 | 1.00 | 37.19 | AAAA |
| ATOM | 528 | CB | ALA | A | 76 | −25.060 | 19.454 | 14.350 | 1.00 | 37.36 | AAAA |
| ATOM | 529 | C | ALA | A | 76 | −26.268 | 18.847 | 16.455 | 1.00 | 36.15 | AAAA |
| ATOM | 530 | O | ALA | A | 76 | −27.352 | 19.323 | 16.124 | 1.00 | 35.97 | AAAA |
| ATOM | 531 | N | ALA | A | 77 | −26.156 | 17.834 | 17.309 | 1.00 | 34.42 | AAAA |
| ATOM | 532 | CA | ALA | A | 77 | −27.326 | 17.225 | 17.935 | 1.00 | 33.14 | AAAA |
| ATOM | 533 | CB | ALA | A | 77 | −27.460 | 15.780 | 17.499 | 1.00 | 33.13 | AAAA |
| ATOM | 534 | C | ALA | A | 77 | −27.125 | 17.311 | 19.443 | 1.00 | 32.59 | AAAA |

TABLE 1-continued

ATOMIC COORDINATES OF E. COLI MURG PROTEIN

| ATOM | 535 | O   | ALA | A | 77 | −26.502 | 16.436 | 20.042 | 1.00 | 31.09 | AAAA |
|------|-----|-----|-----|---|----|---------|--------|--------|------|-------|------|
| ATOM | 536 | N   | PRO | A | 78 | −27.664 | 18.372 | 20.073 | 1.00 | 32.06 | AAAA |
| ATOM | 537 | CD  | PRO | A | 78 | −28.619 | 19.290 | 19.423 | 1.00 | 31.98 | AAAA |
| ATOM | 538 | CA  | PRO | A | 78 | −27.577 | 18.653 | 21.514 | 1.00 | 31.07 | AAAA |
| ATOM | 539 | CB  | PRO | A | 78 | −28.671 | 19.701 | 21.727 | 1.00 | 32.32 | AAAA |
| ATOM | 540 | CG  | PRO | A | 78 | −28.703 | 20.427 | 20.414 | 1.00 | 32.04 | AAAA |
| ATOM | 541 | C   | PRO | A | 78 | −27.748 | 17.450 | 22.443 | 1.00 | 30.50 | AAAA |
| ATOM | 542 | O   | PRO | A | 78 | −26.874 | 17.155 | 23.257 | 1.00 | 29.52 | AAAA |
| ATOM | 543 | N   | LEU | A | 79 | −28.878 | 16.766 | 22.334 | 1.00 | 28.95 | AAAA |
| ATOM | 544 | CA  | LEU | A | 79 | −29.130 | 15.619 | 23.194 | 1.00 | 29.33 | AAAA |
| ATOM | 545 | CB  | LEU | A | 79 | −30.573 | 15.137 | 23.023 | 1.00 | 29.48 | AAAA |
| ATOM | 546 | CG  | LEU | A | 79 | −31.644 | 16.154 | 23.435 | 1.00 | 30.82 | AAAA |
| ATOM | 547 | CD1 | LEU | A | 79 | −33.025 | 15.542 | 23.234 | 1.00 | 31.23 | AAAA |
| ATOM | 548 | CD2 | LEU | A | 79 | −31.450 | 16.558 | 24.901 | 1.00 | 30.46 | AAAA |
| ATOM | 549 | C   | LEU | A | 79 | −28.160 | 14.465 | 22.950 | 1.00 | 28.58 | AAAA |
| ATOM | 550 | O   | LEU | A | 79 | −27.745 | 13.795 | 23.898 | 1.00 | 27.00 | AAAA |
| ATOM | 551 | N   | ARG | A | 80 | −27.794 | 14.240 | 21.689 | 1.00 | 27.70 | AAAA |
| ATOM | 552 | CA  | ARG | A | 80 | −26.877 | 13.156 | 21.348 | 1.00 | 28.33 | AAAA |
| ATOM | 553 | CB  | ARG | A | 80 | −26.813 | 12.941 | 19.836 | 1.00 | 30.44 | AAAA |
| ATOM | 554 | CG  | ARG | A | 80 | −28.037 | 12.294 | 19.222 | 1.00 | 36.59 | AAAA |
| ATOM | 555 | CD  | ARG | A | 80 | −27.657 | 11.616 | 17.915 | 1.00 | 38.91 | AAAA |
| ATOM | 556 | NE  | ARG | A | 80 | −28.821 | 11.189 | 17.151 | 1.00 | 43.51 | AAAA |
| ATOM | 557 | CZ  | ARG | A | 80 | −29.537 | 11.991 | 16.370 | 1.00 | 44.36 | AAAA |
| ATOM | 558 | NH1 | ARG | A | 80 | −29.207 | 13.270 | 16.244 | 1.00 | 45.19 | AAAA |
| ATOM | 559 | NH2 | ARG | A | 80 | −30.589 | 11.513 | 15.721 | 1.00 | 45.91 | AAAA |
| ATOM | 560 | C   | ARG | A | 80 | −25.464 | 13.384 | 21.871 | 1.00 | 27.39 | AAAA |
| ATOM | 561 | O   | ARG | A | 80 | −24.835 | 12.455 | 22.392 | 1.00 | 26.07 | AAAA |
| ATOM | 562 | N   | ILE | A | 81 | −24.950 | 14.603 | 21.719 | 1.00 | 26.19 | AAAA |
| ATOM | 563 | CA  | ILE | A | 81 | −23.608 | 14.886 | 22.217 | 1.00 | 24.89 | AAAA |
| ATOM | 564 | CB  | ILE | A | 81 | −23.081 | 16.269 | 21.702 | 1.00 | 25.72 | AAAA |
| ATOM | 565 | CG2 | ILE | A | 81 | −24.069 | 17.373 | 22.021 | 1.00 | 26.90 | AAAA |
| ATOM | 566 | CG1 | ILE | A | 81 | −21.722 | 16.584 | 22.332 | 1.00 | 25.98 | AAAA |
| ATOM | 567 | CD1 | ILE | A | 81 | −20.696 | 15.474 | 22.169 | 1.00 | 26.39 | AAAA |
| ATOM | 568 | C   | ILE | A | 81 | −23.609 | 14.832 | 23.752 | 1.00 | 24.30 | AAAA |
| ATOM | 569 | O   | ILE | A | 81 | −22.669 | 14.315 | 24.365 | 1.00 | 22.57 | AAAA |
| ATOM | 570 | N   | ILE | A | 82 | −24.672 | 15.344 | 24.367 | 1.00 | 22.71 | AAAA |
| ATOM | 571 | CA  | PHE | A | 82 | −24.800 | 15.333 | 25.827 | 1.00 | 22.28 | AAAA |
| ATOM | 572 | CB  | PHE | A | 82 | −26.099 | 16.029 | 26.236 | 1.00 | 21.54 | AAAA |
| ATOM | 573 | CG  | PHE | A | 82 | −26.281 | 16.184 | 27.730 | 1.00 | 20.67 | AAAA |
| ATOM | 574 | CD1 | PHE | A | 82 | −25.244 | 16.644 | 28.538 | 1.00 | 21.08 | AAAA |
| ATOM | 575 | CD2 | PHE | A | 82 | −27.512 | 15.907 | 28.318 | 1.00 | 21.44 | AAAA |
| ATOM | 576 | CE1 | PHE | A | 82 | −25.430 | 16.831 | 29.916 | 1.00 | 20.18 | AAAA |
| ATOM | 577 | CH2 | PHE | A | 82 | −27.719 | 16.093 | 29.700 | 1.00 | 19.77 | AAAA |
| ATOM | 578 | CZ  | PHE | A | 82 | −26.678 | 16.555 | 30.497 | 1.00 | 20.80 | AAAA |
| ATOM | 579 | C   | PHE | A | 82 | −24.797 | 13.887 | 26.330 | 1.00 | 21.61 | AAAA |
| ATOM | 580 | O   | PHE | A | 82 | −24.091 | 13.536 | 27.285 | 1.00 | 21.05 | AAAA |
| ATOM | 581 | N   | ASN | A | 83 | −25.577 | 13.042 | 25.669 | 1.00 | 21.80 | AAAA |
| ATOM | 582 | CA  | ASN | A | 83 | −25.648 | 11.640 | 26.045 | 1.00 | 22.62 | AAAA |
| ATOM | 583 | CB  | ASN | A | 83 | −26.806 | 10.969 | 25.296 | 1.00 | 22.62 | AAAA |
| ATOM | 584 | CG  | ASN | A | 83 | −26.921 | 9.495  | 25.612 | 1.00 | 25.00 | AAAA |
| ATOM | 585 | OD1 | ASN | A | 83 | −26.227 | 8.677  | 25.031 | 1.00 | 26.80 | AAAA |
| ATOM | 586 | ND2 | ASN | A | 83 | −27.791 | 9.153  | 26.548 | 1.00 | 28.27 | AAAA |
| ATOM | 587 | C   | ASN | A | 83 | −24.324 | 10.888 | 25.805 | 1.00 | 21.61 | AAAA |
| ATOM | 588 | O   | ASN | A | 83 | −23.903 | 10.080 | 26.639 | 1.00 | 22.04 | AAAA |
| ATOM | 589 | N   | ALA | A | 84 | −23.658 | 11.150 | 24.686 | 1.00 | 19.98 | AAAA |
| ATOM | 590 | CA  | ALA | A | 84 | −22.383 | 10.480 | 24.401 | 1.00 | 19.25 | AAAA |
| ATOM | 591 | CB  | ALA | A | 84 | −21.912 | 10.817 | 22.981 | 1.00 | 20.79 | AAAA |
| ATOM | 592 | C   | ALA | A | 84 | −21.318 | 10.906 | 25.424 | 1.00 | 19.48 | AAAA |
| ATOM | 593 | O   | ALA | A | 84 | −20.509 | 10.095 | 25.880 | 1.00 | 18.26 | AAAA |
| ATOM | 594 | N   | TRP | A | 85 | −21.322 | 12.188 | 25.769 | 1.00 | 17.57 | AAAA |
| ATOM | 595 | CA  | TRP | A | 85 | −20.390 | 12.736 | 26.749 | 1.00 | 18.15 | AAAA |
| ATOM | 596 | CB  | TRP | A | 85 | −20.561 | 14.260 | 26.781 | 1.00 | 17.16 | AAAA |
| ATOM | 597 | CG  | TRP | A | 85 | −19.863 | 15.007 | 27.892 | 1.00 | 16.32 | AAAA |
| ATOM | 598 | CD2 | TRP | A | 85 | −20.300 | 16.233 | 28.472 | 1.00 | 16.29 | AAAA |
| ATOM | 599 | CE2 | TRP | A | 85 | −19.340 | 16.605 | 29.445 | 1.00 | 15.39 | AAAA |
| ATOM | 600 | CE3 | TRP | A | 85 | −21.413 | 17.062 | 28.266 | 1.00 | 16.28 | AAAA |
| ATOM | 601 | CD1 | TRP | A | 85 | −18.677 | 14.682 | 28.519 | 1.00 | 15.58 | AAAA |
| ATOM | 602 | NE1 | TRP | A | 85 | −18.364 | 15.639 | 29.454 | 1.00 | 14.76 | AAAA |
| ATOM | 603 | CZ2 | TRP | A | 85 | −19.458 | 17.762 | 30.204 | 1.00 | 14.50 | AAAA |
| ATOM | 604 | CZ3 | TRP | A | 85 | −21.530 | 18.218 | 29.027 | 1.00 | 16.55 | AAAA |
| ATOM | 605 | CH2 | TRP | A | 85 | −20.553 | 18.558 | 29.988 | 1.00 | 15.65 | AAAA |
| ATOM | 606 | C   | TRP | A | 85 | −20.639 | 12.099 | 28.125 | 1.00 | 19.04 | AAAA |
| ATOM | 607 | O   | TRP | A | 85 | −19.696 | 11.691 | 28.820 | 1.00 | 17.64 | AAAA |
| ATOM | 608 | N   | ARG | A | 86 | −21.903 | 11.986 | 28.516 | 1.00 | 18.52 | AAAA |
| ATOM | 609 | CA  | ARG | A | 86 | −22.216 | 11.375 | 29.803 | 1.00 | 19.34 | AAAA |
| ATOM | 610 | CB  | ARG | A | 86 | −23.675 | 11.654 | 30.181 | 1.00 | 19.24 | AAAA |
| ATOM | 611 | CG  | ARG | A | 86 | −23.892 | 13.104 | 30.660 | 1.00 | 18.36 | AAAA |

TABLE 1-continued

ATOMIC COORDINATES OF E. COLI MURG PROTEIN

| ATOM | 612 | CD | ARG | A | 86 | −25.318 | 13.357 | 31.154 | 1.00 | 19.61 | AAAA |
|---|---|---|---|---|---|---|---|---|---|---|---|
| ATOM | 613 | NE | ARG | A | 86 | −26.303 | 13.245 | 30.072 | 1.00 | 19.64 | AAAA |
| ATOM | 614 | CZ | ARG | A | 86 | −27.021 | 12.156 | 29.807 | 1.00 | 21.06 | AAAA |
| ATOM | 615 | NH1 | ARG | A | 86 | −26.880 | 11.063 | 30.548 | 1.00 | 19.09 | AAAA |
| ATOM | 616 | NH2 | ARG | A | 86 | −27.879 | 12.156 | 28.787 | 1.00 | 18.59 | AAAA |
| ATOM | 627 | O | GLN | A | 87 | −19.846 | 6.687 | 29.576 | 1.00 | 18.93 | AAAA |
| ATOM | 628 | N | ALA | A | 88 | −19.471 | 8.479 | 28.255 | 1.00 | 20.24 | AAAA |
| ATOM | 629 | CA | ALA | A | 88 | −18.023 | 8.436 | 28.412 | 1.00 | 20.23 | AAAA |
| ATOM | 630 | CB | ALA | A | 88 | −17.355 | 9.386 | 27.419 | 1.00 | 18.84 | AAAA |
| ATOM | 631 | C | ALA | A | 88 | −17.622 | 8.787 | 29.841 | 1.00 | 20.11 | AAAA |
| ATOM | 632 | O | ALA | A | 88 | −16.687 | 8.202 | 30.388 | 1.00 | 20.39 | AAAA |
| ATOM | 633 | N | ARG | A | 89 | −18.309 | 9.745 | 30.454 | 1.00 | 18.15 | AAAA |
| ATOM | 634 | CA | ARG | A | 89 | −17.985 | 10.091 | 31.836 | 1.00 | 19.16 | AAAA |
| ATOM | 635 | CB | ARG | A | 89 | −18.797 | 11.302 | 32.313 | 1.00 | 16.58 | AAAA |
| ATOM | 636 | CG | ARG | A | 89 | −18.225 | 12.657 | 31.896 | 1.00 | 17.41 | AAAA |
| ATOM | 637 | CD | ARG | A | 89 | −19.196 | 13.769 | 32.284 | 1.00 | 15.10 | AAAA |
| ATOM | 638 | NE | ARG | A | 89 | −19.437 | 13.835 | 33.729 | 1.00 | 16.60 | AAAA |
| ATOM | 639 | CZ | ARG | A | 89 | −18.675 | 14.506 | 34.587 | 1.00 | 16.76 | AAAA |
| ATOM | 640 | NH1 | ARG | A | 89 | −17.609 | 15.173 | 34.157 | 1.00 | 16.02 | AAAA |
| ATOM | 641 | NH2 | ARG | A | 89 | −18.990 | 14.531 | 35.877 | 1.00 | 15.64 | AAAA |
| ATOM | 642 | C | ARG | A | 89 | −18.258 | 8.902 | 32.764 | 1.00 | 19.91 | AAAA |
| ATOM | 643 | O | ARG | A | 89 | −17.469 | 8.618 | 33.674 | 1.00 | 18.92 | AAAA |
| ATOM | 644 | N | ALA | A | 90 | −19.371 | 8.213 | 32.544 | 1.00 | 21.12 | AAAA |
| ATOM | 645 | CA | ALA | A | 90 | −19.719 | 7.063 | 33.386 | 1.00 | 23.31 | AAAA |
| ATOM | 646 | CB | ALA | A | 90 | −21.080 | 6.502 | 32.976 | 1.00 | 24.02 | AAAA |
| ATOM | 647 | C | ALA | A | 90 | −18.640 | 5.990 | 33.257 | 1.00 | 24.57 | AAAA |
| ATOM | 648 | O | ALA | A | 90 | −18.236 | 5.367 | 34.243 | 1.00 | 24.35 | AAAA |
| ATOM | 649 | N | ILE | A | 91 | −18.173 | 5.790 | 32.031 | 1.00 | 24.03 | AAAA |
| ATOM | 650 | CA | ILE | A | 91 | −17.135 | 4.816 | 31.746 | 1.00 | 24.73 | AAAA |
| ATOM | 651 | CB | ILE | A | 91 | −16.922 | 4.699 | 30.209 | 1.00 | 25.99 | AAAA |
| ATOM | 652 | CG2 | ILE | A | 91 | −15.547 | 4.086 | 29.890 | 1.00 | 25.27 | AAAA |
| ATOM | 653 | CG1 | ILE | A | 91 | −18.061 | 3.875 | 29.601 | 1.00 | 25.74 | AAAA |
| ATOM | 654 | CD1 | ILE | A | 91 | −18.123 | 3.931 | 28.085 | 1.00 | 25.37 | AAAA |
| ATOM | 655 | C | ILE | A | 91 | −15.823 | 5.196 | 32.436 | 1.00 | 25.69 | AAAA |
| ATOM | 656 | O | ILE | A | 91 | −15.133 | 4.339 | 32.991 | 1.00 | 25.17 | AAAA |
| ATOM | 657 | N | MET | A | 92 | −15.482 | 6.481 | 32.410 | 1.00 | 24.39 | AAAA |
| ATOM | 658 | CA | MET | A | 92 | −14.243 | 6.933 | 33.024 | 1.00 | 24.61 | AAAA |
| ATOM | 659 | CB | MET | A | 92 | −13.798 | 8.258 | 32.391 | 1.00 | 23.19 | AAAA |
| ATOM | 660 | CG | MET | A | 92 | −13.480 | 8.088 | 30.908 | 1.00 | 21.54 | AAAA |
| ATOM | 661 | SD | MET | A | 92 | −12.816 | 9.554 | 30.108 | 1.00 | 21.51 | AAAA |
| ATOM | 662 | CE | MET | A | 92 | −12.756 | 9.008 | 28.463 | 1.00 | 17.14 | AAAA |
| ATOM | 663 | C | MET | A | 92 | −14.325 | 7.041 | 34.545 | 1.00 | 24.72 | AAAA |
| ATOM | 664 | O | MET | A | 92 | −13.311 | 6.918 | 35.236 | 1.00 | 24.71 | AAAA |
| ATOM | 665 | N | LYS | A | 93 | −15.524 | 7.262 | 35.070 | 1.00 | 24.64 | AAAA |
| ATOM | 666 | CA | LYS | A | 93 | −15.700 | 7.337 | 36.517 | 1.00 | 26.89 | AAAA |
| ATOM | 667 | CB | LYS | A | 93 | −17.102 | 7.840 | 36.864 | 1.00 | 27.06 | AAAA |
| ATOM | 668 | CG | LYS | A | 93 | −17.269 | 9.345 | 36.831 | 1.00 | 26.10 | AAAA |
| ATOM | 669 | CD | LYS | A | 93 | −18.641 | 9.742 | 37.366 | 1.00 | 28.56 | AAAA |
| ATOM | 670 | CE | LYS | A | 93 | −18.762 | 11.251 | 37.483 | 1.00 | 28.03 | AAAA |
| ATOM | 671 | NZ | LYS | A | 93 | −20.068 | 11.663 | 38.060 | 1.00 | 29.77 | AAAA |
| ATOM | 672 | C | LYS | A | 93 | −15.495 | 5.938 | 37.119 | 1.00 | 28.19 | AAAA |
| ATOM | 673 | O | LYS | A | 93 | −14.994 | 5.792 | 38.238 | 1.00 | 28.43 | AAAA |
| ATOM | 674 | N | ALA | A | 94 | −15.880 | 4.912 | 36.367 | 1.00 | 29.30 | AAAA |
| ATOM | 675 | CA | ALA | A | 94 | −15.736 | 3.532 | 36.831 | 1.00 | 30.63 | AAAA |
| ATOM | 676 | CB | ALA | A | 94 | −16.750 | 2.635 | 36.131 | 1.00 | 30.03 | AAAA |
| ATOM | 677 | C | ALA | A | 94 | −14.325 | 2.981 | 36.622 | 1.00 | 30.40 | AAAA |
| ATOM | 678 | O | ALA | A | 94 | −13.778 | 2.322 | 37.507 | 1.00 | 30.67 | AAAA |
| ATOM | 679 | N | TYR | A | 95 | −13.735 | 3.255 | 35.462 | 1.00 | 29.39 | AAAA |
| ATOM | 680 | CA | TYR | A | 95 | −12.394 | 2.764 | 35.163 | 1.00 | 29.94 | AAAA |
| ATOM | 681 | CB | TYR | A | 95 | −12.189 | 2.685 | 33.648 | 1.00 | 29.85 | AAAA |
| ATOM | 682 | CG | TYR | A | 95 | −10.838 | 2.151 | 33.224 | 1.00 | 31.64 | AAAA |
| ATOM | 683 | CD1 | TYR | A | 95 | −10.382 | 0.907 | 33.669 | 1.00 | 31.90 | AAAA |
| ATOM | 684 | CE1 | TYR | A | 95 | −9.139 | 0.414 | 33.270 | 1.00 | 32.14 | AAAA |
| ATOM | 685 | CD2 | TYR | A | 95 | −10.015 | 2.886 | 32.370 | 1.00 | 30.90 | AAAA |
| ATOM | 686 | CE2 | TYR | A | 95 | −8.779 | 2.405 | 31.969 | 1.00 | 31.95 | AAAA |
| ATOM | 687 | CZ | TYR | A | 95 | −8.345 | 1.167 | 32.423 | 1.00 | 32.95 | AAAA |
| ATOM | 688 | OH | TYR | A | 95 | −7.120 | 0.687 | 32.019 | 1.00 | 33.09 | AAAA |
| ATOM | 689 | C | TYR | A | 95 | −11.312 | 3.633 | 35.791 | 1.00 | 29.90 | AAAA |
| ATOM | 690 | O | TYR | A | 95 | −10.253 | 3.137 | 36.190 | 1.00 | 28.99 | AAAA |
| ATOM | 691 | N | LYS | A | 96 | −11.584 | 4.930 | 35.871 | 1.00 | 28.94 | AAAA |
| ATOM | 692 | CA | LYS | A | 96 | −10.658 | 5.893 | 36.452 | 1.00 | 29.17 | AAAA |
| ATOM | 693 | CB | LYS | A | 96 | −10.543 | 5.658 | 37.966 | 1.00 | 32.14 | AAAA |
| ATOM | 694 | CG | LYS | A | 96 | −11.871 | 5.829 | 38.690 | 1.00 | 35.57 | AAAA |
| ATOM | 695 | CD | LYS | A | 96 | −11.784 | 5.541 | 40.183 | 1.00 | 38.37 | AAAA |
| ATOM | 696 | CE | LYS | A | 96 | −13.158 | 5.718 | 40.828 | 1.00 | 39.96 | AAAA |
| ATOM | 697 | NZ | LYS | A | 96 | −13.170 | 5.428 | 42.295 | 1.00 | 42.96 | AAAA |
| ATOM | 698 | C | LYS | A | 96 | −9.274 | 5.884 | 35.817 | 1.00 | 27.78 | AAAA |

TABLE 1-continued

ATOMIC COORDINATES OF E. COLI MURG PROTEIN

| ATOM | 699 | O | LYS | A | 96 | −8.281 | 5.608 | 36.482 | 1.00 | 28.12 | AAAA |
|---|---|---|---|---|---|---|---|---|---|---|---|
| ATOM | 700 | N | PRO | A | 97 | −9.187 | 6.185 | 34.509 | 1.00 | 26.15 | AAAA |
| ATOM | 701 | CD | PRO | A | 97 | −10.258 | 6.519 | 33.547 | 1.00 | 24.76 | AAAA |
| ATOM | 702 | CA | PRO | A | 97 | −7.867 | 6.191 | 33.868 | 1.00 | 24.70 | AAAA |
| ATOM | 703 | CB | PRO | A | 97 | −8.202 | 6.241 | 32.381 | 1.00 | 23.96 | AAAA |
| ATOM | 704 | CG | PRO | A | 97 | −9.477 | 7.078 | 32.362 | 1.00 | 24.55 | AAAA |
| ATOM | 705 | C | PRO | A | 97 | −7.060 | 7.408 | 34.320 | 1.00 | 24.77 | AAAA |
| ATOM | 706 | O | PRO | A | 97 | −7.628 | 8.438 | 34.684 | 1.00 | 23.93 | AAAA |
| ATOM | 707 | N | ASP | A | 98 | −5.737 | 7.288 | 34.314 | 1.00 | 24.94 | AAAA |
| ATOM | 708 | CA | ASP | A | 98 | −4.890 | 8.404 | 34.717 | 1.00 | 24.75 | AAAA |
| ATOM | 709 | CB | ASP | A | 98 | −3.554 | 7.891 | 35.261 | 1.00 | 26.69 | AAAA |
| ATOM | 710 | CG | ASP | A | 98 | −3.725 | 7.040 | 36.509 | 1.00 | 28.25 | AAAA |
| ATOM | 711 | OD1 | ASP | A | 98 | −3.546 | 5.808 | 36.426 | 1.00 | 28.34 | AAAA |
| ATOM | 712 | OD2 | ASP | A | 98 | −4.053 | 7.603 | 37.569 | 1.00 | 29.50 | AAAA |
| ATOM | 713 | C | ASP | A | 98 | −4.654 | 9.328 | 33.529 | 1.00 | 23.89 | AAAA |
| ATOM | 714 | O | ASP | A | 98 | −4.267 | 10.486 | 33.681 | 1.00 | 22.57 | AAAA |
| ATOM | 715 | N | VAL | A | 99 | −4.918 | 8.807 | 32.339 | 1.00 | 24.10 | AAAA |
| ATOM | 716 | CA | VAL | A | 99 | −4.740 | 9.569 | 31.111 | 1.00 | 23.85 | AAAA |
| ATOM | 717 | CB | VAL | A | 99 | −3.237 | 9.633 | 30.730 | 1.00 | 25.11 | AAAA |
| ATOM | 718 | CG1 | VAL | A | 99 | −2.684 | 8.220 | 30.614 | 1.00 | 25.72 | AAAA |
| ATOM | 719 | CG2 | VAL | A | 99 | −3.044 | 10.372 | 29.420 | 1.00 | 24.76 | AAAA |
| ATOM | 720 | C | VAL | A | 99 | −5.498 | 8.865 | 29.989 | 1.00 | 22.90 | AAAA |
| ATOM | 721 | O | VAL | A | 99 | −5.767 | 7.667 | 30.073 | 1.00 | 22.05 | AAAA |
| ATOM | 722 | N | VAL | A | 100 | −5.869 | 9.613 | 28.951 | 1.00 | 22.07 | AAAA |
| ATOM | 723 | CA | VAL | A | 100 | −6.544 | 9.008 | 27.808 | 1.00 | 21.38 | AAAA |
| ATOM | 724 | CB | VAL | A | 100 | −8.038 | 9.451 | 27.663 | 1.00 | 21.17 | AAAA |
| ATOM | 725 | CG1 | VAL | A | 100 | −8.804 | 9.095 | 28.914 | 1.00 | 21.06 | AAAA |
| ATOM | 726 | CG2 | VAL | A | 100 | −8.139 | 10.942 | 27.354 | 1.00 | 22.14 | AAAA |
| ATOM | 727 | C | VAL | A | 100 | −5.777 | 9.398 | 26.559 | 1.00 | 21.31 | AAAA |
| ATOM | 728 | O | VAL | A | 100 | −5.244 | 10.505 | 26.464 | 1.00 | 21.01 | AAAA |
| ATOM | 729 | N | LEU | A | 101 | −5.701 | 8.468 | 25.612 | 1.00 | 21.54 | AAAA |
| ATOM | 730 | CA | LEU | A | 101 | −4.994 | 8.697 | 24.362 | 1.00 | 22.01 | AAAA |
| ATOM | 731 | CB | LEU | A | 101 | −3.944 | 7.599 | 24.139 | 1.00 | 23.42 | AAAA |
| ATOM | 732 | CG | LEU | A | 101 | −2.691 | 7.856 | 23.288 | 1.00 | 25.21 | AAAA |
| ATOM | 733 | CD1 | LEU | A | 101 | −2.230 | 6.515 | 22.696 | 1.00 | 25.87 | AAAA |
| ATOM | 734 | CD2 | LEU | A | 101 | −2.930 | 8.854 | 22.187 | 1.00 | 26.43 | AAAA |
| ATOM | 735 | C | LEU | A | 101 | −6.006 | 8.644 | 23.222 | 1.00 | 21.51 | AAAA |
| ATOM | 736 | O | LEU | A | 101 | −6.667 | 7.625 | 23.029 | 1.00 | 21.94 | AAAA |
| ATOM | 737 | N | GLY | A | 102 | −6.127 | 9.742 | 22.484 | 1.00 | 21.18 | AAAA |
| ATOM | 738 | CA | GLY | A | 102 | −7.043 | 9.780 | 21.358 | 1.00 | 21.84 | AAAA |
| ATOM | 739 | C | GLY | A | 102 | −6.246 | 9.586 | 20.079 | 1.00 | 21.20 | AAAA |
| ATOM | 740 | O | GLY | A | 102 | −5.294 | 10.324 | 19.837 | 1.00 | 22.62 | AAAA |
| ATOM | 741 | N | MET | A | 103 | −6.627 | 8.599 | 19.270 | 1.00 | 21.18 | AAAA |
| ATOM | 742 | CA | MET | A | 103 | −5.933 | 8.312 | 18.015 | 1.00 | 22.83 | AAAA |
| ATOM | 743 | CB | MET | A | 103 | −5.715 | 6.805 | 17.865 | 1.00 | 23.16 | AAAA |
| ATOM | 744 | CG | MET | A | 103 | −4.978 | 6.140 | 19.030 | 1.00 | 24.31 | AAAA |
| ATOM | 745 | SD | MET | A | 103 | −3.333 | 6.804 | 19.308 | 1.00 | 27.62 | AAAA |
| ATOM | 746 | CE | MET | A | 103 | −2.455 | 6.156 | 17.873 | 1.00 | 26.43 | AAAA |
| ATOM | 747 | C | MET | A | 103 | −6.709 | 8.823 | 16.795 | 1.00 | 23.47 | AAAA |
| ATOM | 748 | O | MET | A | 103 | −6.351 | 8.532 | 15.653 | 1.00 | 23.75 | AAAA |
| ATOM | 749 | N | GLY | A | 104 | −7.767 | 9.590 | 17.043 | 1.00 | 25.38 | AAAA |
| ATOM | 750 | CA | GLY | A | 104 | −8.585 | 10.114 | 15.959 | 1.00 | 25.56 | AAAA |
| ATOM | 751 | C | GLY | A | 104 | −9.878 | 9.326 | 15.833 | 1.00 | 25.55 | AAAA |
| ATOM | 752 | O | GLY | A | 104 | −10.004 | 8.241 | 16.404 | 1.00 | 26.58 | AAAA |
| ATOM | 753 | N | GLY | A | 105 | −10.840 | 9.854 | 15.082 | 1.00 | 26.06 | AAAA |
| ATOM | 754 | CA | GLY | A | 105 | −12.107 | 9.159 | 14.930 | 1.00 | 26.21 | AAAA |
| ATOM | 755 | C | GLY | A | 105 | −13.140 | 9.819 | 15.823 | 1.00 | 26.96 | AAAA |
| ATOM | 756 | O | GLY | A | 105 | −12.810 | 10.258 | 16.926 | 1.00 | 25.49 | AAAA |
| ATOM | 757 | N | TYR | A | 106 | −14.393 | 9.863 | 15.376 | 1.00 | 27.65 | AAAA |
| ATOM | 758 | CA | TYR | A | 106 | −15.434 | 10.534 | 16.145 | 1.00 | 28.10 | AAAA |
| ATOM | 759 | CB | TYR | A | 106 | −16.759 | 10.556 | 15.362 | 1.00 | 31.05 | AAAA |
| ATOM | 760 | CG | TYR | A | 106 | −17.536 | 9.257 | 15.303 | 1.00 | 33.49 | AAAA |
| ATOM | 761 | CD1 | TYR | A | 106 | −18.269 | 8.802 | 16.400 | 1.00 | 34.81 | AAAA |
| ATOM | 762 | CE1 | TYR | A | 106 | −19.038 | 7.634 | 16.323 | 1.00 | 36.18 | AAAA |
| ATOM | 763 | CD2 | TYR | A | 106 | −17.581 | 8.509 | 14.123 | 1.00 | 35.64 | AAAA |
| ATOM | 764 | CE2 | TYR | A | 106 | −18.343 | 7.344 | 14.032 | 1.00 | 36.47 | AAAA |
| ATOM | 765 | CZ | TYR | A | 106 | −19.069 | 6.912 | 15.133 | 1.00 | 37.27 | AAAA |
| ATOM | 766 | OH | TYR | A | 106 | −19.829 | 5.766 | 15.027 | 1.00 | 38.99 | AAAA |
| ATOM | 767 | C | TYR | A | 106 | −15.678 | 10.072 | 17.576 | 1.00 | 26.46 | AAAA |
| ATOM | 768 | O | TYR | A | 106 | −15.976 | 10.897 | 18.430 | 1.00 | 26.55 | AAAA |
| ATOM | 769 | N | VAL | A | 107 | −15.549 | 8.780 | 17.858 | 1.00 | 25.31 | AAAA |
| ATOM | 770 | CA | VAL | A | 107 | −15.783 | 8.318 | 19.223 | 1.00 | 23.91 | AAAA |
| ATOM | 771 | CB | VAL | A | 107 | −15.659 | 6.772 | 19.335 | 1.00 | 25.47 | AAAA |
| ATOM | 772 | CG1 | VAL | A | 107 | −14.224 | 6.327 | 19.076 | 1.00 | 26.57 | AAAA |
| ATOM | 773 | CG2 | VAL | A | 107 | −16.126 | 6.315 | 20.711 | 1.00 | 24.96 | AAAA |
| ATOM | 774 | C | VAL | A | 107 | −14.836 | 8.993 | 20.223 | 1.00 | 23.22 | AAAA |
| ATOM | 775 | O | VAL | A | 107 | −15.190 | 9.190 | 21.389 | 1.00 | 23.17 | AAAA |

TABLE 1-continued

ATOMIC COORDINATES OF E. COLI MURG PROTEIN

| ATOM | 776 | N | SER | A | 108 | −13.650 | 9.381 | 19.765 | 1.00 | 23.13 | AAAA |
|---|---|---|---|---|---|---|---|---|---|---|---|
| ATOM | 777 | CA | SER | A | 108 | −12.676 | 10.029 | 20.643 | 1.00 | 23.40 | AAAA |
| ATOM | 778 | CB | SER | A | 108 | −11.301 | 10.108 | 19.967 | 1.00 | 23.85 | AAAA |
| ATOM | 779 | OG | SER | A | 108 | −11.292 | 11.038 | 18.899 | 1.00 | 25.04 | AAAA |
| ATOM | 780 | C | SER | A | 108 | −13.121 | 11.430 | 21.044 | 1.00 | 23.03 | AAAA |
| ATOM | 781 | O | SER | A | 108 | −12.592 | 12.009 | 21.993 | 1.00 | 22.32 | AAAA |
| ATOM | 782 | N | GLY | A | 109 | −14.089 | 11.979 | 20.310 | 1.00 | 21.84 | AAAA |
| ATOM | 783 | CA | GLY | A | 109 | −14.583 | 13.307 | 20.627 | 1.00 | 21.98 | AAAA |
| ATOM | 784 | C | GLY | A | 109 | −15.297 | 13.342 | 21.972 | 1.00 | 20.30 | AAAA |
| ATOM | 785 | O | GLY | A | 109 | −14.898 | 14.088 | 22.856 | 1.00 | 21.37 | AAAA |
| ATOM | 786 | N | PRO | A | 110 | −16.369 | 12.557 | 22.155 | 1.00 | 20.07 | AAAA |
| ATOM | 787 | CD | PRO | A | 110 | −16.992 | 11.637 | 21.191 | 1.00 | 20.80 | AAAA |
| ATOM | 788 | CA | PRO | A | 110 | −17.085 | 12.550 | 23.436 | 1.00 | 19.58 | AAAA |
| ATOM | 789 | CB | PRO | A | 110 | −18.232 | 11.569 | 23.199 | 1.00 | 20.85 | AAAA |
| ATOM | 790 | CG | PRO | A | 110 | −18.398 | 11.548 | 21.702 | 1.00 | 22.43 | AAAA |
| ATOM | 791 | C | PRO | A | 110 | −16.136 | 12.031 | 24.524 | 1.00 | 18.52 | AAAA |
| ATOM | 792 | O | PRO | A | 110 | −16.184 | 12.462 | 25.675 | 1.00 | 19.12 | AAAA |
| ATOM | 793 | N | GLY | A | 111 | −15.286 | 11.086 | 24.140 | 1.00 | 19.12 | AAAA |
| ATOM | 794 | CA | GLY | A | 111 | −14.332 | 10.525 | 25.087 | 1.00 | 18.87 | AAAA |
| ATOM | 795 | C | GLY | A | 111 | −13.402 | 11.601 | 25.612 | 1.00 | 17.97 | AAAA |
| ATOM | 796 | O | GLY | A | 111 | −13.208 | 11.730 | 26.813 | 1.00 | 19.32 | AAAA |
| ATOM | 797 | N | GLY | A | 112 | −12.822 | 12.380 | 24.704 | 1.00 | 18.62 | AAAA |
| ATOM | 798 | CA | GLY | A | 112 | −11.925 | 13.451 | 25.105 | 1.00 | 17.38 | AAAA |
| ATOM | 799 | C | GLY | A | 112 | −12.610 | 14.509 | 25.957 | 1.00 | 17.36 | AAAA |
| ATOM | 800 | O | GLY | A | 112 | −12.035 | 14.997 | 26.936 | 1.00 | 16.49 | AAAA |
| ATOM | 801 | N | LEU | A | 113 | −13.837 | 14.864 | 25.583 | 1.00 | 16.45 | AAAA |
| ATOM | 802 | CA | LEU | A | 113 | −14.611 | 15.866 | 26.314 | 1.00 | 17.35 | AAAA |
| ATOM | 803 | CB | LEU | A | 113 | −15.974 | 16.079 | 25.640 | 1.00 | 17.68 | AAAA |
| ATOM | 804 | CG | LEU | A | 113 | −16.735 | 17.409 | 25.805 | 1.00 | 21.99 | AAAA |
| ATOM | 805 | CD1 | LEU | A | 113 | −18.205 | 17.154 | 25.511 | 1.00 | 20.80 | AAAA |
| ATOM | 806 | CD2 | LEU | A | 113 | −16.570 | 18.007 | 27.178 | 1.00 | 22.94 | AAAA |
| ATOM | 807 | C | LEU | A | 113 | −14.836 | 15.329 | 27.725 | 1.00 | 16.05 | AAAA |
| ATOM | 808 | O | LEU | A | 113 | −14.695 | 16.045 | 28.711 | 1.00 | 16.63 | AAAA |
| ATOM | 809 | N | ALA | A | 114 | −15.199 | 14.056 | 27.801 | 1.00 | 16.59 | AAAA |
| ATOM | 810 | CA | ALA | A | 114 | −15.442 | 13.416 | 29.087 | 1.00 | 15.95 | AAAA |
| ATOM | 811 | CB | ALA | A | 114 | −15.859 | 11.963 | 28.868 | 1.00 | 17.72 | AAAA |
| ATOM | 812 | C | ALA | A | 114 | −14.194 | 13.492 | 29.968 | 1.00 | 15.37 | AAAA |
| ATOM | 813 | O | ALA | A | 114 | −14.260 | 13.952 | 31.105 | 1.00 | 15.94 | AAAA |
| ATOM | 814 | N | ALA | A | 115 | −13.053 | 13.050 | 29.452 | 1.00 | 16.63 | AAAA |
| ATOM | 815 | CA | ALA | A | 115 | −11.820 | 13.098 | 30.251 | 1.00 | 15.65 | AAAA |
| ATOM | 816 | CB | ALA | A | 115 | −10.641 | 12.518 | 29.450 | 1.00 | 15.52 | AAAA |
| ATOM | 817 | C | ALA | A | 115 | −11.506 | 14.530 | 30.693 | 1.00 | 16.10 | AAAA |
| ATOM | 818 | O | ALA | A | 115 | −11.141 | 14.777 | 31.841 | 1.00 | 15.67 | AAAA |
| ATOM | 819 | N | TRP | A | 116 | −11.650 | 15.480 | 29.778 | 1.00 | 16.71 | AAAA |
| ATOM | 820 | CA | TRP | A | 116 | −11.380 | 16.873 | 30.100 | 1.00 | 17.31 | AAAA |
| ATOM | 821 | CB | TRP | A | 116 | −11.542 | 17.723 | 28.835 | 1.00 | 18.91 | AAAA |
| ATOM | 822 | CG | TRP | A | 116 | −11.172 | 19.155 | 29.003 | 1.00 | 21.69 | AAAA |
| ATOM | 823 | CD2 | TRP | A | 116 | −12.008 | 20.277 | 28.740 | 1.00 | 23.65 | AAAA |
| ATOM | 824 | CE2 | TRP | A | 116 | −11.262 | 21.438 | 29.048 | 1.00 | 25.14 | AAAA |
| ATOM | 825 | CE3 | TRP | A | 116 | −13.321 | 20.418 | 28.268 | 1.00 | 26.49 | AAAA |
| ATOM | 826 | CD1 | TRP | A | 116 | −9.979 | 19.658 | 29.447 | 1.00 | 23.00 | AAAA |
| ATOM | 827 | NE1 | TRP | A | 116 | −10.025 | 21.032 | 29.479 | 1.00 | 24.96 | AAAA |
| ATOM | 828 | CZ2 | TRP | A | 116 | −11.785 | 22.724 | 28.902 | 1.00 | 26.16 | AAAA |
| ATOM | 829 | CZ3 | TRP | A | 116 | −13.842 | 21.702 | 28.122 | 1.00 | 26.44 | AAAA |
| ATOM | 830 | CH2 | TRP | A | 116 | −13.072 | 22.834 | 28.439 | 1.00 | 25.35 | AAAA |
| ATOM | 831 | C | TRP | A | 116 | −12.292 | 17.377 | 31.233 | 1.00 | 16.50 | AAAA |
| ATOM | 832 | O | TRP | A | 116 | −11.835 | 18.080 | 32.137 | 1.00 | 16.03 | AAAA |
| ATOM | 833 | N | SER | A | 117 | −13.565 | 16.990 | 31.200 | 1.00 | 16.73 | AAAA |
| ATOM | 834 | CA | SER | A | 117 | −14.528 | 17.399 | 32.229 | 1.00 | 17.06 | AAAA |
| ATOM | 835 | CB | SER | A | 117 | −15.961 | 17.116 | 31.762 | 1.00 | 16.18 | AAAA |
| ATOM | 836 | OG | SER | A | 117 | −16.270 | 15.731 | 31.743 | 1.00 | 18.31 | AAAA |
| ATOM | 837 | C | SER | A | 117 | −14.289 | 16.720 | 33.586 | 1.00 | 18.05 | AAAA |
| ATOM | 838 | O | SER | A | 117 | −14.837 | 17.147 | 34.605 | 1.00 | 17.79 | AAAA |
| ATOM | 839 | N | LEU | A | 118 | −13.466 | 15.678 | 33.594 | 1.00 | 18.13 | AAAA |
| ATOM | 840 | CA | LEU | A | 118 | −13.146 | 14.950 | 34.827 | 1.00 | 19.26 | AAAA |
| ATOM | 841 | CB | LEU | A | 118 | −13.262 | 13.441 | 34.587 | 1.00 | 18.09 | AAAA |
| ATOM | 842 | CG | LEU | A | 118 | −14.686 | 12.932 | 34.353 | 1.00 | 20.04 | AAAA |
| ATOM | 843 | CD1 | LEU | A | 118 | −14.659 | 11.484 | 33.869 | 1.00 | 20.30 | AAAA |
| ATOM | 844 | CD2 | LEU | A | 118 | −15.480 | 13.064 | 35.646 | 1.00 | 20.40 | AAAA |
| ATOM | 845 | C | LEU | A | 118 | −11.736 | 15.283 | 35.305 | 1.00 | 20.78 | AAAA |
| ATOM | 846 | O | LEU | A | 118 | −11.267 | 14.763 | 36.321 | 1.00 | 20.64 | AAAA |
| ATOM | 847 | N | GLY | A | 119 | −11.057 | 16.152 | 34.566 | 1.00 | 21.27 | AAAA |
| ATOM | 848 | CA | GLY | A | 119 | −9.706 | 16.537 | 34.943 | 1.00 | 21.97 | AAAA |
| ATOM | 849 | C | GLY | A | 119 | −8.648 | 15.519 | 34.550 | 1.00 | 21.55 | AAAA |
| ATOM | 850 | O | GLY | A | 119 | −7.515 | 15.582 | 35.034 | 1.00 | 21.92 | AAAA |
| ATOM | 851 | N | ILE | A | 120 | −9.009 | 14.584 | 33.678 | 1.00 | 20.43 | AAAA |
| ATOM | 852 | CA | ILE | A | 120 | −8.082 | 13.548 | 33.214 | 1.00 | 21.09 | AAAA |

TABLE 1-continued

ATOMIC COORDINATES OF E. COLI MURG PROTEIN

| ATOM | 853 | CB | ILE | A | 120 | −8.853 | 12.270 | 32.836 | 1.00 | 20.95 | AAAA |
|------|-----|-----|-----|---|-----|--------|--------|--------|------|-------|------|
| ATOM | 854 | CG2 | ILE | A | 120 | −7.902 | 11.226 | 32.275 | 1.00 | 22.20 | AAAA |
| ATOM | 855 | CG1 | ILE | A | 120 | −9.624 | 11.748 | 34.051 | 1.00 | 22.05 | AAAA |
| ATOM | 856 | CD1 | ILE | A | 120 | −10.688 | 10.709 | 33.689 | 1.00 | 21.95 | AAAA |
| ATOM | 857 | C | ILE | A | 120 | −7.358 | 14.088 | 31.978 | 1.00 | 20.81 | AAAA |
| ATOM | 858 | O | ILE | A | 120 | −8.001 | 14.465 | 31.004 | 1.00 | 21.35 | AAAA |
| ATOM | 859 | N | PRO | A | 121 | −6.013 | 14.131 | 31.999 | 1.00 | 20.67 | AAAA |
| ATOM | 860 | CD | PRO | A | 121 | −5.052 | 13.722 | 33.040 | 1.00 | 20.88 | AAAA |
| ATOM | 861 | CA | PRO | A | 121 | −5.320 | 14.658 | 30.819 | 1.00 | 20.52 | AAAA |
| ATOM | 862 | CB | PRO | A | 121 | −3.842 | 14.649 | 31.237 | 1.00 | 21.37 | AAAA |
| ATOM | 863 | CG | PRO | A | 121 | −3.777 | 13.532 | 32.240 | 1.00 | 22.04 | AAAA |
| ATOM | 864 | C | PRO | A | 121 | −5.580 | 13.893 | 29.536 | 1.00 | 19.38 | AAAA |
| ATOM | 865 | O | PRO | A | 121 | −5.717 | 12.671 | 29.538 | 1.00 | 18.17 | AAAA |
| ATOM | 866 | N | VAL | A | 122 | −5.647 | 14.645 | 28.442 | 1.00 | 20.01 | AAAA |
| ATOM | 867 | CA | VAL | A | 122 | −5.903 | 14.102 | 27.120 | 1.00 | 19.76 | AAAA |
| ATOM | 868 | CB | VAL | A | 122 | −7.047 | 14.866 | 26.421 | 1.00 | 18.63 | AAAA |
| ATOM | 869 | CG1 | VAL | A | 122 | −7.286 | 14.281 | 25.033 | 1.00 | 20.46 | AAAA |
| ATOM | 870 | CG2 | VAL | A | 122 | −8.320 | 14.790 | 27.264 | 1.00 | 20.31 | AAAA |
| ATOM | 871 | C | VAL | A | 122 | −4.672 | 14.205 | 26.223 | 1.00 | 19.39 | AAAA |
| ATOM | 872 | O | VAL | A | 122 | −4.096 | 15.282 | 26.069 | 1.00 | 19.66 | AAAA |
| ATOM | 873 | N | VAL | A | 123 | −4.284 | 13.079 | 25.634 | 1.00 | 19.86 | AAAA |
| ATOM | 874 | CA | VAL | A | 123 | −3.134 | 13.029 | 24.734 | 1.00 | 20.22 | AAAA |
| ATOM | 875 | CB | VAL | A | 123 | −2.086 | 11.982 | 25.200 | 1.00 | 20.59 | AAAA |
| ATOM | 876 | CG1 | VAL | A | 123 | −0.898 | 11.957 | 24.226 | 1.00 | 20.51 | AAAA |
| ATOM | 877 | CG2 | VAL | A | 123 | −1.602 | 12.317 | 26.606 | 1.00 | 17.21 | AAAA |
| ATOM | 878 | C | VAL | A | 123 | −3.684 | 12.600 | 23.381 | 1.00 | 21.06 | AAAA |
| ATOM | 879 | O | VAL | A | 123 | −4.482 | 11.666 | 23.300 | 1.00 | 22.10 | AAAA |
| ATOM | 880 | N | LEU | A | 124 | −3.269 | 13.284 | 22.325 | 1.00 | 21.08 | AAAA |
| ATOM | 881 | CA | LEU | A | 124 | −3.746 | 12.952 | 20.989 | 1.00 | 21.68 | AAAA |
| ATOM | 882 | CB | LEU | A | 124 | −4.463 | 14.149 | 20.366 | 1.00 | 21.81 | AAAA |
| ATOM | 883 | CG | LEU | A | 124 | −5.629 | 14.805 | 21.105 | 1.00 | 21.93 | AAAA |
| ATOM | 884 | CD1 | LEU | A | 124 | −6.133 | 15.980 | 20.268 | 1.00 | 22.15 | AAAA |
| ATOM | 885 | CD2 | LEU | A | 124 | −6.737 | 13.787 | 21.337 | 1.00 | 21.49 | AAAA |
| ATOM | 886 | C | LEU | A | 124 | −2.628 | 12.558 | 20.038 | 1.00 | 21.67 | AAAA |
| ATOM | 887 | O | LEU | A | 124 | −1.493 | 13.011 | 20.170 | 1.00 | 22.39 | AAAA |
| ATOM | 888 | N | HIS | A | 125 | −2.964 | 11.713 | 19.075 | 1.00 | 22.63 | AAAA |
| ATOM | 889 | CA | HIS | A | 125 | −2.014 | 11.336 | 18.036 | 1.00 | 24.74 | AAAA |
| ATOM | 890 | CB | HIS | A | 125 | −1.429 | 9.939 | 18.244 | 1.00 | 24.62 | AAAA |
| ATOM | 891 | CG | HIS | A | 125 | −0.471 | 9.540 | 17.162 | 1.00 | 27.30 | AAAA |
| ATOM | 892 | CD2 | HIS | A | 125 | −0.629 | 8.744 | 16.079 | 1.00 | 27.23 | AAAA |
| ATOM | 893 | ND1 | HIS | A | 125 | 0.806 | 10.057 | 17.072 | 1.00 | 29.96 | AAAA |
| ATOM | 894 | CE1 | HIS | A | 125 | 1.391 | 9.597 | 15.979 | 1.00 | 27.40 | AAAA |
| ATOM | 895 | NE2 | HIS | A | 125 | 0.541 | 8.799 | 15.358 | 1.00 | 28.94 | AAAA |
| ATOM | 896 | C | HIS | A | 125 | −2.763 | 11.364 | 16.705 | 1.00 | 24.38 | AAAA |
| ATOM | 897 | O | HIS | A | 125 | −3.813 | 10.741 | 16.565 | 1.00 | 23.93 | AAAA |
| ATOM | 898 | N | GLU | A | 126 | −2.233 | 12.111 | 15.744 | 1.00 | 24.36 | AAAA |
| ATOM | 899 | CA | GLU | A | 126 | −2.836 | 12.199 | 14.420 | 1.00 | 26.31 | AAAA |
| ATOM | 900 | CB | GLU | A | 126 | −2.992 | 13.664 | 14.005 | 1.00 | 25.81 | AAAA |
| ATOM | 901 | CG | GLU | A | 126 | −3.465 | 13.861 | 12.567 | 1.00 | 26.62 | AAAA |
| ATOM | 902 | CD | GLU | A | 126 | −4.795 | 13.196 | 12.288 | 1.00 | 27.69 | AAAA |
| ATOM | 903 | OE1 | GLU | A | 126 | −5.785 | 13.544 | 12.965 | 1.00 | 27.90 | AAAA |
| ATOM | 904 | OE2 | GLU | A | 126 | −4.855 | 12.326 | 11.391 | 1.00 | 27.53 | AAAA |
| ATOM | 905 | C | GLU | A | 126 | −1.901 | 11.472 | 13.456 | 1.00 | 27.49 | AAAA |
| ATOM | 906 | O | GLU | A | 126 | −0.727 | 11.819 | 13.349 | 1.00 | 27.87 | AAAA |
| ATOM | 907 | N | GLN | A | 127 | −2.423 | 10.463 | 12.765 | 1.00 | 28.80 | AAAA |
| ATOM | 908 | CA | GLN | A | 127 | −1.617 | 9.682 | 11.834 | 1.00 | 30.09 | AAAA |
| ATOM | 909 | CB | GLN | A | 127 | −2.192 | 8.264 | 11.688 | 1.00 | 28.89 | AAAA |
| ATOM | 910 | CG | GLN | A | 127 | −2.184 | 7.421 | 12.958 | 1.00 | 28.94 | AAAA |
| ATOM | 911 | CD | GLN | A | 127 | −3.456 | 7.578 | 13.775 | 1.00 | 29.34 | AAAA |
| ATOM | 912 | OE1 | GLN | A | 127 | −4.543 | 7.207 | 13.329 | 1.00 | 29.36 | AAAA |
| ATOM | 913 | NE2 | GLN | A | 127 | −3.326 | 8.131 | 14.973 | 1.00 | 28.70 | AAAA |
| ATOM | 914 | C | GLN | A | 127 | −1.455 | 10.277 | 10.438 | 1.00 | 30.92 | AAAA |
| ATOM | 915 | O | GLN | A | 127 | −0.428 | 10.068 | 9.794 | 1.00 | 31.21 | AAAA |
| ATOM | 916 | N | ASN | A | 128 | −2.448 | 11.038 | 9.986 | 1.00 | 32.48 | AAAA |
| ATOM | 917 | CA | ASN | A | 128 | −2.434 | 11.596 | 8.634 | 1.00 | 33.12 | AAAA |
| ATOM | 918 | CB | ASN | A | 128 | −3.864 | 11.589 | 8.083 | 1.00 | 32.20 | AAAA |
| ATOM | 919 | CG | ASN | A | 128 | −4.606 | 10.312 | 8.424 | 1.00 | 33.05 | AAAA |
| ATOM | 920 | OD1 | ASN | A | 128 | −5.296 | 10.236 | 9.445 | 1.00 | 33.34 | AAAA |
| ATOM | 921 | ND2 | ASN | A | 128 | −4.454 | 9.292 | 7.584 | 1.00 | 31.22 | AAAA |
| ATOM | 922 | C | ASN | A | 128 | −1.809 | 12.971 | 8.394 | 1.00 | 33.60 | AAAA |
| ATOM | 923 | O | ASN | A | 128 | −1.571 | 13.744 | 9.327 | 1.00 | 34.03 | AAAA |
| ATOM | 924 | N | GLY | A | 129 | −1.550 | 13.256 | 7.117 | 1.00 | 33.69 | AAAA |
| ATOM | 925 | CA | GLY | A | 129 | −0.959 | 14.524 | 6.718 | 1.00 | 33.68 | AAAA |
| ATOM | 926 | C | GLY | A | 129 | −1.903 | 15.682 | 6.972 | 1.00 | 33.41 | AAAA |
| ATOM | 927 | O | GLY | A | 129 | −1.482 | 16.834 | 7.057 | 1.00 | 32.92 | AAAA |
| ATOM | 928 | N | ILE | A | 130 | −3.192 | 15.374 | 7.070 | 1.00 | 33.49 | AAAA |
| ATOM | 929 | CA | ILE | A | 130 | −4.205 | 16.383 | 7.361 | 1.00 | 33.06 | AAAA |

TABLE 1-continued

ATOMIC COORDINATES OF E. COLI MURG PROTEIN

| ATOM | 930 | CB | ILE | A | 130 | −5.204 | 16.570 | 6.206 | 1.00 | 33.49 | AAAA |
|---|---|---|---|---|---|---|---|---|---|---|---|
| ATOM | 931 | CG2 | ILE | A | 130 | −4.548 | 17.358 | 5.083 | 1.00 | 35.66 | AAAA |
| ATOM | 932 | CG1 | ILE | A | 130 | −5.736 | 15.209 | 5.751 | 1.00 | 34.45 | AAAA |
| ATOM | 933 | CD1 | ILE | A | 130 | −6.775 | 15.279 | 4.665 | 1.00 | 35.68 | AAAA |
| ATOM | 934 | C | ILE | A | 130 | −4.964 | 15.892 | 8.584 | 1.00 | 32.19 | AAAA |
| ATOM | 935 | O | ILE | A | 130 | −5.379 | 14.733 | 8.644 | 1.00 | 32.07 | AAAA |
| ATOM | 936 | N | ALA | A | 131 | −5.135 | 16.771 | 9.561 | 1.00 | 31.26 | AAAA |
| ATOM | 937 | CA | ALA | A | 131 | −5.832 | 16.404 | 10.788 | 1.00 | 30.63 | AAAA |
| ATOM | 938 | CB | ALA | A | 131 | −5.735 | 17.547 | 11.800 | 1.00 | 30.70 | AAAA |
| ATOM | 939 | C | ALA | A | 131 | −7.292 | 16.038 | 10.556 | 1.00 | 30.27 | AAAA |
| ATOM | 940 | O | ALA | A | 131 | −7.992 | 16.682 | 9.774 | 1.00 | 30.54 | AAAA |
| ATOM | 941 | N | GLY | A | 132 | −7.743 | 14.987 | 11.232 | 1.00 | 29.03 | AAAA |
| ATOM | 942 | CA | GLY | A | 132 | −9.131 | 14.587 | 11.119 | 1.00 | 27.98 | AAAA |
| ATOM | 943 | C | GLY | A | 132 | −9.902 | 15.678 | 11.837 | 1.00 | 26.80 | AAAA |
| ATOM | 944 | O | GLY | A | 132 | −9.326 | 16.387 | 12.660 | 1.00 | 25.68 | AAAA |
| ATOM | 945 | N | LEU | A | 133 | −11.188 | 15.827 | 11.543 | 1.00 | 26.51 | AAAA |
| ATOM | 946 | CA | LEU | A | 133 | −11.973 | 16.882 | 12.186 | 1.00 | 26.70 | AAAA |
| ATOM | 947 | CB | LEU | A | 133 | −13.363 | 16.967 | 11.538 | 1.00 | 28.16 | AAAA |
| ATOM | 948 | CG | LEU | A | 133 | −14.275 | 18.138 | 11.936 | 1.00 | 28.52 | AAAA |
| ATOM | 949 | CD1 | LEU | A | 133 | −14.889 | 17.874 | 13.280 | 1.00 | 32.18 | AAAA |
| ATOM | 950 | CD2 | LEU | A | 133 | −13.486 | 19.436 | 11.960 | 1.00 | 30.27 | AAAA |
| ATOM | 951 | C | LEU | A | 133 | −12.097 | 16.713 | 13.703 | 1.00 | 25.88 | AAAA |
| ATOM | 952 | O | LEU | A | 133 | −12.063 | 17.700 | 14.444 | 1.00 | 26.12 | AAAA |
| ATOM | 953 | N | THR | A | 134 | −12.240 | 15.475 | 14.169 | 1.00 | 24.18 | AAAA |
| ATOM | 954 | CA | THR | A | 134 | −12.353 | 15.230 | 15.608 | 1.00 | 23.78 | AAAA |
| ATOM | 955 | CB | THR | A | 134 | −12.605 | 13.729 | 15.922 | 1.00 | 23.18 | AAAA |
| ATOM | 956 | OG1 | THR | A | 134 | −13.814 | 13.300 | 15.285 | 1.00 | 23.74 | AAAA |
| ATOM | 957 | CG2 | THR | A | 134 | −12.751 | 13.511 | 17.433 | 1.00 | 23.66 | AAAA |
| ATOM | 958 | C | THR | A | 134 | −11.071 | 15.671 | 16.315 | 1.00 | 22.68 | AAAA |
| ATOM | 959 | O | THR | A | 134 | −11.116 | 16.368 | 17.328 | 1.00 | 21.38 | AAAA |
| ATOM | 960 | N | ASN | A | 135 | −9.927 | 15.267 | 15.771 | 1.00 | 23.98 | AAAA |
| ATOM | 961 | CA | ASN | A | 135 | −8.636 | 15.623 | 16.358 | 1.00 | 24.64 | AAAA |
| ATOM | 962 | CB | ASN | A | 135 | −7.488 | 14.936 | 15.597 | 1.00 | 24.49 | AAAA |
| ATOM | 963 | CG | ASN | A | 135 | −7.020 | 13.638 | 16.264 | 1.00 | 25.25 | AAAA |
| ATOM | 964 | OD1 | ASN | A | 135 | −6.267 | 12.856 | 15.668 | 1.00 | 25.70 | AAAA |
| ATOM | 965 | ND2 | ASN | A | 135 | −7.445 | 13.415 | 17.504 | 1.00 | 22.51 | AAAA |
| ATOM | 966 | C | ASN | A | 135 | −8.421 | 17.135 | 16.349 | 1.00 | 25.19 | AAAA |
| ATOM | 967 | O | ASN | A | 135 | −7.890 | 17.702 | 17.301 | 1.00 | 24.79 | AAAA |
| ATOM | 968 | N | LYS | A | 136 | −8.839 | 17.792 | 15.274 | 1.00 | 26.78 | AAAA |
| ATOM | 969 | CA | LYS | A | 136 | −8.661 | 19.234 | 15.177 | 1.00 | 28.71 | AAAA |
| ATOM | 970 | CB | LYS | A | 136 | −9.165 | 19.743 | 13.828 | 1.00 | 30.84 | AAAA |
| ATOM | 971 | CG | LYS | A | 136 | −8.816 | 21.195 | 13.563 | 1.00 | 34.68 | AAAA |
| ATOM | 972 | CD | LYS | A | 136 | −9.206 | 21.596 | 12.148 | 1.00 | 36.19 | AAAA |
| ATOM | 973 | CE | LYS | A | 136 | −8.810 | 23.033 | 11.846 | 1.00 | 37.78 | AAAA |
| ATOM | 974 | NZ | LYS | A | 136 | −9.124 | 23.414 | 10.432 | 1.00 | 40.33 | AAAA |
| ATOM | 975 | C | LYS | A | 136 | −9.370 | 19.981 | 16.304 | 1.00 | 28.66 | AAAA |
| ATOM | 976 | O | LYS | A | 136 | −8.803 | 20.900 | 16.902 | 1.00 | 28.47 | AAAA |
| ATOM | 977 | N | TRP | A | 137 | −10.606 | 19.589 | 16.596 | 1.00 | 28.05 | AAAA |
| ATOM | 978 | CA | TRP | A | 137 | −11.363 | 20.243 | 17.656 | 1.00 | 28.85 | AAAA |
| ATOM | 979 | CB | TRP | A | 137 | −12.855 | 19.921 | 17.516 | 1.00 | 31.86 | AAAA |
| ATOM | 980 | CG | TRP | A | 137 | −13.485 | 20.502 | 16.282 | 1.00 | 34.71 | AAAA |
| ATOM | 981 | CD2 | TRP | A | 137 | −14.788 | 20.206 | 15.755 | 1.00 | 36.70 | AAAA |
| ATOM | 982 | CE2 | TRP | A | 137 | −14.982 | 21.036 | 14.630 | 1.00 | 37.21 | AAAA |
| ATOM | 983 | CE3 | TRP | A | 137 | −15.811 | 19.321 | 16.130 | 1.00 | 38.46 | AAAA |
| ATOM | 984 | CD1 | TRP | A | 137 | −12.959 | 21.466 | 15.471 | 1.00 | 36.22 | AAAA |
| ATOM | 985 | NE1 | TRP | A | 137 | −13.851 | 21.794 | 14.480 | 1.00 | 36.96 | AAAA |
| ATOM | 986 | CZ2 | TRP | A | 137 | −16.160 | 21.010 | 13.869 | 1.00 | 38.57 | AAAA |
| ATOM | 987 | CZ3 | TRP | A | 137 | −16.986 | 19.295 | 15.373 | 1.00 | 39.12 | AAAA |
| ATOM | 988 | CH2 | TRP | A | 137 | −17.148 | 20.136 | 14.255 | 1.00 | 39.31 | AAAA |
| ATOM | 989 | C | TRP | A | 137 | −10.868 | 19.803 | 19.029 | 1.00 | 28.01 | AAAA |
| ATOM | 990 | O | TRP | A | 137 | −10.763 | 20.605 | 19.955 | 1.00 | 27.04 | AAAA |
| ATOM | 991 | N | LEU | A | 138 | −10.548 | 18.520 | 19.143 | 1.00 | 27.31 | AAAA |
| ATOM | 992 | CA | LEU | A | 138 | −10.072 | 17.943 | 20.393 | 1.00 | 26.35 | AAAA |
| ATOM | 993 | CB | LEU | A | 138 | −9.879 | 16.444 | 20.174 | 1.00 | 27.79 | AAAA |
| ATOM | 994 | CG | LEU | A | 138 | −10.054 | 15.384 | 21.262 | 1.00 | 30.24 | AAAA |
| ATOM | 995 | CD1 | LEU | A | 138 | −11.263 | 15.650 | 22.142 | 1.00 | 29.67 | AAAA |
| ATOM | 996 | CD2 | LEU | A | 138 | −10.178 | 14.036 | 20.562 | 1.00 | 30.06 | AAAA |
| ATOM | 997 | C | LEU | A | 138 | −8.772 | 18.609 | 20.834 | 1.00 | 25.34 | AAAA |
| ATOM | 998 | O | LEU | A | 138 | −8.532 | 18.814 | 22.030 | 1.00 | 23.81 | AAAA |
| ATOM | 999 | N | ALA | A | 139 | −7.931 | 18.953 | 19.865 | 1.00 | 26.03 | AAAA |
| ATOM | 1000 | CA | ALA | A | 139 | −6.657 | 19.595 | 20.160 | 1.00 | 26.05 | AAAA |
| ATOM | 1001 | CB | ALA | A | 139 | −5.918 | 19.934 | 18.858 | 1.00 | 26.98 | AAAA |
| ATOM | 1002 | C | ALA | A | 139 | −6.847 | 20.858 | 21.002 | 1.00 | 26.86 | AAAA |
| ATOM | 1003 | O | ALA | A | 139 | −5.929 | 21.286 | 21.697 | 1.00 | 26.11 | AAAA |
| ATOM | 1004 | N | LYS | A | 140 | −8.044 | 21.439 | 20.952 | 1.00 | 26.32 | AAAA |
| ATOM | 1005 | CA | LYS | A | 140 | −8.329 | 22.649 | 21.716 | 1.00 | 26.90 | AAAA |
| ATOM | 1006 | CB | LYS | A | 140 | −9.644 | 23.276 | 21.238 | 1.00 | 29.14 | AAAA |

TABLE 1-continued

ATOMIC COORDINATES OF E. COLI MURG PROTEIN

| ATOM | 1007 | CG  | LYS | A | 140 | −9.665  | 23.595 | 19.749 | 1.00 | 31.62 | AAAA |
|------|------|-----|-----|---|-----|---------|--------|--------|------|-------|------|
| ATOM | 1008 | CD  | LYS | A | 140 | −8.523  | 24.513 | 19.364 | 1.00 | 35.02 | AAAA |
| ATOM | 1009 | CE  | LYS | A | 140 | −8.811  | 25.975 | 19.704 | 1.00 | 37.44 | AAAA |
| ATOM | 1010 | NZ  | LYS | A | 140 | −9.865  | 26.555 | 18.812 | 1.00 | 40.43 | AAAA |
| ATOM | 1011 | C   | LYS | A | 140 | −8.395  | 22.414 | 23.230 | 1.00 | 25.59 | AAAA |
| ATOM | 1012 | O   | LYS | A | 140 | −8.333  | 23.361 | 24.004 | 1.00 | 24.94 | AAAA |
| ATOM | 1013 | N   | ILE | A | 141 | −8.526  | 21.159 | 23.649 | 1.00 | 24.13 | AAAA |
| ATOM | 1014 | CA  | ILE | A | 141 | −8.587  | 20.844 | 25.075 | 1.00 | 23.31 | AAAA |
| ATOM | 1015 | CB  | ILE | A | 141 | −9.971  | 20.270 | 25.477 | 1.00 | 22.85 | AAAA |
| ATOM | 1016 | CG2 | ILE | A | 141 | −11.046 | 21.355 | 25.372 | 1.00 | 23.88 | AAAA |
| ATOM | 1017 | CG1 | ILE | A | 141 | −10.313 | 19.071 | 24.595 | 1.00 | 23.34 | AAAA |
| ATOM | 1018 | CD1 | ILE | A | 141 | −11.574 | 18.339 | 25.012 | 1.00 | 25.61 | AAAA |
| ATOM | 1019 | C   | ILE | A | 141 | −7.524  | 19.822 | 25.482 | 1.00 | 23.06 | AAAA |
| ATOM | 1020 | O   | ILE | A | 141 | −7.427  | 19.450 | 26.655 | 1.00 | 22.52 | AAAA |
| ATOM | 1021 | N   | ALA | A | 142 | −6.724  | 19.375 | 24.520 | 1.00 | 21.80 | AAAA |
| ATOM | 1022 | CA  | ALA | A | 142 | −5.695  | 18.379 | 24.803 | 1.00 | 21.97 | AAAA |
| ATOM | 1023 | CB  | ALA | A | 142 | −5.231  | 17.739 | 23.495 | 1.00 | 20.41 | AAAA |
| ATOM | 1024 | C   | ALA | A | 142 | −4.491  | 18.924 | 25.580 | 1.00 | 21.11 | AAAA |
| ATOM | 1025 | O   | ALA | A | 142 | −4.132  | 20.094 | 25.465 | 1.00 | 22.76 | AAAA |
| ATOM | 1026 | N   | THR | A | 143 | −3.887  | 18.056 | 26.384 | 1.00 | 21.92 | AAAA |
| ATOM | 1027 | CA  | THR | A | 143 | −2.707  | 18.391 | 27.178 | 1.00 | 22.64 | AAAA |
| ATOM | 1028 | CB  | THR | A | 143 | −2.598  | 17.450 | 28.400 | 1.00 | 23.91 | AAAA |
| ATOM | 1029 | OG1 | THR | A | 143 | −3.751  | 17.635 | 29.232 | 1.00 | 25.42 | AAAA |
| ATOM | 1030 | CG2 | THR | A | 143 | −1.329  | 17.735 | 29.209 | 1.00 | 24.48 | AAAA |
| ATOM | 1031 | C   | THR | A | 143 | −1.454  | 18.235 | 26.312 | 1.00 | 22.79 | AAAA |
| ATOM | 1032 | O   | THR | A | 143 | −0.444  | 18.910 | 26.517 | 1.00 | 23.30 | AAAA |
| ATOM | 1033 | N   | LYS | A | 144 | −1.525  | 17.341 | 25.335 | 1.00 | 23.20 | AAAA |
| ATOM | 1034 | CA  | LYS | A | 144 | −0.398  | 17.106 | 24.440 | 1.00 | 25.09 | AAAA |
| ATOM | 1035 | CB  | LYS | A | 144 | 0.565   | 16.083 | 25.049 | 1.00 | 25.01 | AAAA |
| ATOM | 1036 | CG  | LYS | A | 144 | 1.706   | 15.658 | 24.129 | 1.00 | 28.28 | AAAA |
| ATOM | 1037 | CD  | LYS | A | 144 | 2.604   | 16.838 | 23.747 | 1.00 | 27.48 | AAAA |
| ATOM | 1038 | CE  | LYS | A | 144 | 3.818   | 16.373 | 22.946 | 1.00 | 29.11 | AAAA |
| ATOM | 1039 | NZ  | LYS | A | 144 | 4.722   | 17.507 | 22.587 | 1.00 | 28.97 | AAAA |
| ATOM | 1040 | C   | LYS | A | 144 | −0.896  | 16.595 | 23.102 | 1.00 | 24.77 | AAAA |
| ATOM | 1041 | O   | LYS | A | 144 | −1.688  | 15.660 | 23.039 | 1.00 | 24.45 | AAAA |
| ATOM | 1042 | N   | VAL | A | 145 | −0.432  | 17.218 | 22.030 | 1.00 | 24.92 | AAAA |
| ATOM | 1043 | CA  | VAL | A | 145 | −0.830  | 16.793 | 20.701 | 1.00 | 25.14 | AAAA |
| ATOM | 1044 | CB  | VAL | A | 145 | −1.510  | 17.938 | 19.919 | 1.00 | 24.18 | AAAA |
| ATOM | 1045 | CG1 | VAL | A | 145 | −2.023  | 17.418 | 18.591 | 1.00 | 24.71 | AAAA |
| ATOM | 1046 | CG2 | VAL | A | 145 | −2.658  | 18.528 | 20.740 | 1.00 | 25.82 | AAAA |
| ATOM | 1047 | C   | VAL | A | 145 | 0.420   | 16.356 | 19.950 | 1.00 | 25.49 | AAAA |
| ATOM | 1048 | O   | VAL | A | 145 | 1.449   | 17.034 | 19.995 | 1.00 | 25.76 | AAAA |
| ATOM | 1049 | N   | MET | A | 146 | 0.324   | 15.208 | 19.289 | 1.00 | 26.18 | AAAA |
| ATOM | 1050 | CA  | MET | A | 146 | 1.421   | 14.654 | 18.503 | 1.00 | 26.41 | AAAA |
| ATOM | 1051 | CB  | MET | A | 146 | 2.000   | 13.396 | 19.172 | 1.00 | 26.85 | AAAA |
| ATOM | 1052 | CG  | MET | A | 146 | 2.826   | 13.653 | 20.430 | 1.00 | 25.85 | AAAA |
| ATOM | 1053 | SD  | MET | A | 146 | 3.306   | 12.116 | 21.269 | 1.00 | 28.45 | AAAA |
| ATOM | 1054 | CE  | MET | A | 146 | 1.827   | 11.741 | 22.217 | 1.00 | 26.47 | AAAA |
| ATOM | 1055 | C   | MET | A | 146 | 0.860   | 14.293 | 17.131 | 1.00 | 27.20 | AAAA |
| ATOM | 1056 | O   | MET | A | 146 | −0.311  | 13.934 | 16.998 | 1.00 | 25.68 | AAAA |
| ATOM | 1057 | N   | GLN | A | 147 | 1.701   | 14.395 | 16.111 | 1.00 | 28.03 | AAAA |
| ATOM | 1058 | CA  | GLN | A | 147 | 1.294   | 14.091 | 14.748 | 1.00 | 28.39 | AAAA |
| ATOM | 1059 | CB  | GLN | A | 147 | 1.067   | 15.388 | 13.979 | 1.00 | 28.65 | AAAA |
| ATOM | 1060 | CG  | GLN | A | 147 | 2.203   | 16.371 | 14.142 | 1.00 | 30.13 | AAAA |
| ATOM | 1061 | CD  | GLN | A | 147 | 2.006   | 17.653 | 13.360 | 1.00 | 29.84 | AAAA |
| ATOM | 1062 | OE1 | GLN | A | 147 | 2.730   | 18.629 | 13.565 | 1.00 | 32.18 | AAAA |
| ATOM | 1063 | NE2 | GLN | A | 147 | 1.036   | 17.657 | 12.453 | 1.00 | 29.40 | AAAA |
| ATOM | 1064 | C   | GLN | A | 147 | 2.394   | 13.274 | 14.085 | 1.00 | 29.45 | AAAA |
| ATOM | 1065 | O   | GLN | A | 147 | 3.570   | 13.420 | 14.424 | 1.00 | 29.21 | AAAA |
| ATOM | 1066 | N   | ALA | A | 148 | 2.010   | 12.412 | 13.150 | 1.00 | 29.90 | AAAA |
| ATOM | 1067 | CA  | ALA | A | 148 | 2.975   | 11.563 | 12.461 | 1.00 | 31.39 | AAAA |
| ATOM | 1068 | CB  | ALA | A | 148 | 2.254   | 10.468 | 11.690 | 1.00 | 30.97 | AAAA |
| ATOM | 1069 | C   | ALA | A | 148 | 3.846   | 12.373 | 11.514 | 1.00 | 32.66 | AAAA |
| ATOM | 1070 | O   | ALA | A | 148 | 5.071   | 12.231 | 11.517 | 1.00 | 32.76 | AAAA |
| ATOM | 1071 | N   | PHE | A | 149 | 3.205   | 13.220 | 10.712 | 1.00 | 33.44 | AAAA |
| ATOM | 1072 | CA  | PHE | A | 149 | 3.903   | 14.059 | 9.744  | 1.00 | 35.09 | AAAA |
| ATOM | 1073 | CB  | PHE | A | 149 | 3.367   | 13.814 | 8.332  | 1.00 | 34.59 | AAAA |
| ATOM | 1074 | CG  | PHE | A | 149 | 3.200   | 12.367 | 7.985  | 1.00 | 35.35 | AAAA |
| ATOM | 1075 | CD1 | PHE | A | 149 | 1.935   | 11.789 | 7.958  | 1.00 | 34.17 | AAAA |
| ATOM | 1076 | CD2 | PHE | A | 149 | 4.304   | 11.579 | 7.685  | 1.00 | 34.88 | AAAA |
| ATOM | 1077 | CE1 | PHE | A | 149 | 1.771   | 10.448 | 7.637  | 1.00 | 34.20 | AAAA |
| ATOM | 1078 | CE2 | PHE | A | 149 | 4.148   | 10.236 | 7.364  | 1.00 | 36.09 | AAAA |
| ATOM | 1079 | CZ  | PHE | A | 149 | 2.878   | 9.670  | 7.340  | 1.00 | 35.09 | AAAA |
| ATOM | 1080 | C   | PHE | A | 149 | 3.719   | 15.536 | 10.056 | 1.00 | 36.17 | AAAA |
| ATOM | 1081 | O   | PHE | A | 149 | 2.697   | 15.939 | 10.606 | 1.00 | 37.06 | AAAA |
| ATOM | 1082 | N   | PRO | A | 150 | 4.709   | 16.370 | 9.704  | 1.00 | 37.23 | AAAA |
| ATOM | 1083 | CD  | PRO | A | 150 | 6.002   | 16.078 | 9.056  | 1.00 | 37.75 | AAAA |

TABLE 1-continued

ATOMIC COORDINATES OF E. COLI MURG PROTEIN

| ATOM | 1084 | CA | PRO | A | 150 | 4.569 | 17.803 | 9.975 | 1.00 | 38.03 | AAAA |
|---|---|---|---|---|---|---|---|---|---|---|---|
| ATOM | 1085 | CB | PRO | A | 150 | 5.967 | 18.341 | 9.682 | 1.00 | 38.69 | AAAA |
| ATOM | 1086 | CG | PRO | A | 150 | 6.432 | 17.448 | 8.569 | 1.00 | 38.52 | AAAA |
| ATOM | 1087 | C | PRO | A | 150 | 3.510 | 18.369 | 9.028 | 1.00 | 38.18 | AAAA |
| ATOM | 1088 | O | PRO | A | 150 | 3.355 | 17.878 | 7.912 | 1.00 | 38.42 | AAAA |
| ATOM | 1089 | N | GLY | A | 151 | 2.763 | 19.374 | 9.475 | 1.00 | 38.74 | AAAA |
| ATOM | 1090 | CA | GLY | A | 151 | 1.749 | 19.952 | 8.609 | 1.00 | 38.66 | AAAA |
| ATOM | 1091 | C | GLY | A | 151 | 0.300 | 19.705 | 8.996 | 1.00 | 38.69 | AAAA |
| ATOM | 1092 | O | GLY | A | 151 | −0.571 | 20.502 | 8.645 | 1.00 | 38.08 | AAAA |
| ATOM | 1093 | N | ALA | A | 152 | 0.024 | 18.602 | 9.689 | 1.00 | 38.70 | AAAA |
| ATOM | 1094 | CA | ALA | A | 152 | −1.343 | 18.311 | 10.112 | 1.00 | 38.90 | AAAA |
| ATOM | 1095 | CB | ALA | A | 152 | −1.402 | 16.980 | 10.859 | 1.00 | 38.46 | AAAA |
| ATOM | 1096 | C | ALA | A | 152 | −1.729 | 19.461 | 11.032 | 1.00 | 39.30 | AAAA |
| ATOM | 1097 | O | ALA | A | 152 | −2.753 | 20.114 | 10.838 | 1.00 | 40.05 | AAAA |
| ATOM | 1098 | N | PHE | A | 153 | −0.887 | 19.700 | 12.031 | 1.00 | 39.42 | AAAA |
| ATOM | 1099 | CA | PHE | A | 153 | −1.084 | 20.795 | 12.971 | 1.00 | 39.90 | AAAA |
| ATOM | 1100 | CB | PHE | A | 153 | −1.209 | 20.286 | 14.409 | 1.00 | 39.04 | AAAA |
| ATOM | 1101 | CG | PHE | A | 153 | −2.478 | 19.535 | 14.685 | 1.00 | 38.06 | AAAA |
| ATOM | 1102 | CD1 | PHE | A | 153 | −2.571 | 18.175 | 14.419 | 1.00 | 36.71 | AAAA |
| ATOM | 1103 | CD2 | PHE | A | 153 | −3.582 | 20.190 | 15.228 | 1.00 | 37.52 | AAAA |
| ATOM | 1104 | CE1 | PHE | A | 153 | −3.747 | 17.475 | 14.692 | 1.00 | 36.39 | AAAA |
| ATOM | 1105 | CE2 | PHE | A | 153 | −4.761 | 19.500 | 15.502 | 1.00 | 36.08 | AAAA |
| ATOM | 1106 | CZ | PHE | A | 153 | −4.842 | 18.140 | 15.235 | 1.00 | 36.20 | AAAA |
| ATOM | 1107 | C | PHE | A | 153 | 0.143 | 21.696 | 12.865 | 1.00 | 40.75 | AAAA |
| ATOM | 1108 | O | PHE | A | 153 | 1.238 | 21.228 | 12.543 | 1.00 | 41.03 | AAAA |
| ATOM | 1109 | N | PRO | A | 154 | −0.026 | 23.001 | 13.128 | 1.00 | 41.05 | AAAA |
| ATOM | 1110 | CD | PRO | A | 154 | −1.328 | 23.667 | 13.304 | 1.00 | 41.17 | AAAA |
| ATOM | 1111 | CA | PRO | A | 154 | 1.052 | 23.992 | 13.068 | 1.00 | 41.57 | AAAA |
| ATOM | 1112 | CB | PRO | A | 154 | 0.339 | 25.292 | 13.428 | 1.00 | 41.69 | AAAA |
| ATOM | 1113 | CG | PRO | A | 154 | −1.024 | 25.081 | 12.876 | 1.00 | 41.76 | AAAA |
| ATOM | 1114 | C | PRO | A | 154 | 2.260 | 23.744 | 13.975 | 1.00 | 42.12 | AAAA |
| ATOM | 1115 | O | PRO | A | 154 | 3.400 | 23.833 | 13.515 | 1.00 | 43.15 | AAAA |
| ATOM | 1116 | N | ASN | A | 155 | 2.023 | 23.432 | 15.249 | 1.00 | 41.75 | AAAA |
| ATOM | 1117 | CA | ASN | A | 155 | 3.135 | 23.230 | 16.180 | 1.00 | 41.57 | AAAA |
| ATOM | 1118 | CB | ASN | A | 155 | 3.180 | 24.389 | 17.179 | 1.00 | 44.02 | AAAA |
| ATOM | 1119 | CG | ASN | A | 155 | 2.961 | 25.736 | 16.522 | 1.00 | 45.69 | AAAA |
| ATOM | 1120 | OD1 | ASN | A | 155 | 1.862 | 26.045 | 16.058 | 1.00 | 47.64 | AAAA |
| ATOM | 1121 | ND2 | ASN | A | 155 | 4.010 | 26.545 | 16.475 | 1.00 | 47.43 | AAAA |
| ATOM | 1122 | C | ASN | A | 155 | 3.193 | 21.921 | 16.970 | 1.00 | 40.83 | AAAA |
| ATOM | 1123 | O | ASN | A | 155 | 3.973 | 21.814 | 17.917 | 1.00 | 41.17 | AAAA |
| ATOM | 1124 | N | ALA | A | 156 | 2.390 | 20.929 | 16.601 | 1.00 | 38.83 | AAAA |
| ATOM | 1125 | CA | ALA | A | 156 | 2.400 | 19.658 | 17.326 | 1.00 | 37.19 | AAAA |
| ATOM | 1126 | CB | ALA | A | 156 | 1.203 | 18.811 | 16.909 | 1.00 | 36.03 | AAAA |
| ATOM | 1127 | C | ALA | A | 156 | 3.698 | 18.882 | 17.090 | 1.00 | 35.95 | AAAA |
| ATOM | 1128 | O | ALA | A | 156 | 4.206 | 18.834 | 15.971 | 1.00 | 35.55 | AAAA |
| ATOM | 1129 | N | GLU | A | 157 | 4.233 | 18.275 | 18.146 | 1.00 | 35.08 | AAAA |
| ATOM | 1130 | CA | GLU | A | 157 | 5.464 | 17.505 | 18.022 | 1.00 | 33.77 | AAAA |
| ATOM | 1131 | CB | GLU | A | 157 | 5.848 | 16.881 | 19.373 | 1.00 | 34.33 | AAAA |
| ATOM | 1132 | CG | GLU | A | 157 | 7.175 | 16.124 | 19.352 | 1.00 | 34.59 | AAAA |
| ATOM | 1133 | CD | GLU | A | 157 | 7.487 | 15.430 | 20.670 | 1.00 | 35.45 | AAAA |
| ATOM | 1134 | OE1 | GLU | A | 157 | 8.517 | 14.729 | 20.746 | 1.00 | 34.09 | AAAA |
| ATOM | 1135 | OE2 | GLU | A | 157 | 6.705 | 15.582 | 21.631 | 1.00 | 36.21 | AAAA |
| ATOM | 1136 | C | GLU | A | 157 | 5.282 | 16.405 | 16.970 | 1.00 | 32.70 | AAAA |
| ATOM | 1137 | O | GLU | A | 157 | 4.262 | 15.709 | 16.952 | 1.00 | 31.88 | AAAA |
| ATOM | 1138 | N | VAL | A | 158 | 6.268 | 16.265 | 16.088 | 1.00 | 31.00 | AAAA |
| ATOM | 1139 | CA | VAL | A | 158 | 6.230 | 15.255 | 15.032 | 1.00 | 30.25 | AAAA |
| ATOM | 1140 | CB | VAL | A | 158 | 6.926 | 15.768 | 13.751 | 1.00 | 30.33 | AAAA |
| ATOM | 1141 | CG1 | VAL | A | 158 | 7.013 | 14.653 | 12.719 | 1.00 | 29.98 | AAAA |
| ATOM | 1142 | CG2 | VAL | A | 158 | 6.147 | 16.953 | 13.181 | 1.00 | 30.15 | AAAA |
| ATOM | 1143 | C | VAL | A | 158 | 6.937 | 13.998 | 15.529 | 1.00 | 29.69 | AAAA |
| ATOM | 1144 | O | VAL | A | 158 | 8.142 | 14.020 | 15.798 | 1.00 | 29.80 | AAAA |
| ATOM | 1145 | N | VAL | A | 159 | 6.182 | 12.909 | 15.645 | 1.00 | 28.61 | AAAA |
| ATOM | 1146 | CA | VAL | A | 159 | 6.715 | 11.647 | 16.149 | 1.00 | 29.00 | AAAA |
| ATOM | 1147 | CB | VAL | A | 159 | 6.019 | 11.250 | 17.469 | 1.00 | 28.75 | AAAA |
| ATOM | 1148 | CG1 | VAL | A | 159 | 6.129 | 12.384 | 18.482 | 1.00 | 28.06 | AAAA |
| ATOM | 1149 | CG2 | VAL | A | 159 | 4.552 | 10.921 | 17.197 | 1.00 | 28.06 | AAAA |
| ATOM | 1150 | C | VAL | A | 159 | 6.581 | 10.469 | 15.186 | 1.00 | 29.32 | AAAA |
| ATOM | 1151 | O | VAL | A | 159 | 7.066 | 9.376 | 15.479 | 1.00 | 29.89 | AAAA |
| ATOM | 1152 | N | GLY | A | 160 | 5.915 | 10.688 | 14.054 | 1.00 | 30.03 | AAAA |
| ATOM | 1153 | CA | GLY | A | 160 | 5.727 | 9.628 | 13.075 | 1.00 | 29.63 | AAAA |
| ATOM | 1154 | C | GLY | A | 160 | 4.678 | 8.608 | 13.483 | 1.00 | 29.61 | AAAA |
| ATOM | 1155 | O | GLY | A | 160 | 3.917 | 8.849 | 14.416 | 1.00 | 29.30 | AAAA |
| ATOM | 1156 | N | ASN | A | 161 | 4.635 | 7.475 | 12.782 | 1.00 | 29.30 | AAAA |
| ATOM | 1157 | CA | ASN | A | 161 | 3.677 | 6.401 | 13.074 | 1.00 | 29.78 | AAAA |
| ATOM | 1158 | CB | ASN | A | 161 | 2.800 | 6.097 | 11.858 | 1.00 | 30.70 | AAAA |
| ATOM | 1159 | CG | ASN | A | 161 | 1.755 | 7.154 | 11.609 | 1.00 | 32.16 | AAAA |
| ATOM | 1160 | OD1 | ASN | A | 161 | 0.951 | 7.461 | 12.492 | 1.00 | 31.78 | AAAA |

TABLE 1-continued

ATOMIC COORDINATES OF E. COLI MURG PROTEIN

| ATOM | 1161 | ND2 | ASN | A | 161 | 1.750 | 7.711 | 10.400 | 1.00 | 30.88 | AAAA |
|------|------|-----|-----|---|-----|-------|-------|--------|------|-------|------|
| ATOM | 1162 | C | ASN | A | 161 | 4.344 | 5.089 | 13.462 | 1.00 | 29.50 | AAAA |
| ATOM | 1163 | O | ASN | A | 161 | 5.471 | 4.810 | 13.058 | 1.00 | 29.61 | AAAA |
| ATOM | 1164 | N | PRO | A | 162 | 3.648 | 4.263 | 14.251 | 1.00 | 29.59 | AAAA |
| ATOM | 1165 | CD | PRO | A | 162 | 2.441 | 4.571 | 15.039 | 1.00 | 29.95 | AAAA |
| ATOM | 1166 | CA | PRO | A | 162 | 4.219 | 2.977 | 14.650 | 1.00 | 29.65 | AAAA |
| ATOM | 1167 | CB | PRO | A | 162 | 3.143 | 2.389 | 15.553 | 1.00 | 29.79 | AAAA |
| ATOM | 1168 | CG | PRO | A | 162 | 2.559 | 3.608 | 16.200 | 1.00 | 30.38 | AAAA |
| ATOM | 1169 | C | PRO | A | 162 | 4.423 | 2.135 | 13.389 | 1.00 | 30.13 | AAAA |
| ATOM | 1170 | O | PRO | A | 162 | 3.535 | 2.063 | 12.531 | 1.00 | 28.48 | AAAA |
| ATOM | 1171 | N | VAL | A | 163 | 5.590 | 1.508 | 13.287 | 1.00 | 29.92 | AAAA |
| ATOM | 1172 | CA | VAL | A | 163 | 5.935 | 0.664 | 12.149 | 1.00 | 29.89 | AAAA |
| ATOM | 1173 | CB | VAL | A | 163 | 7.182 | 1.224 | 11.417 | 1.00 | 31.04 | AAAA |
| ATOM | 1174 | CG1 | VAL | A | 163 | 7.571 | 0.308 | 10.260 | 1.00 | 30.44 | AAAA |
| ATOM | 1175 | CG2 | VAL | A | 163 | 6.902 | 2.631 | 10.914 | 1.00 | 29.10 | AAAA |
| ATOM | 1176 | C | VAL | A | 163 | 6.258 | −0.744 | 12.652 | 1.00 | 31.06 | AAAA |
| ATOM | 1177 | O | VAL | A | 163 | 6.884 | −0.892 | 13.706 | 1.00 | 29.66 | AAAA |
| ATOM | 1178 | N | ARG | A | 164 | 5.820 | −1.773 | 11.927 | 1.00 | 31.83 | AAAA |
| ATOM | 1179 | CA | ARG | A | 164 | 6.124 | −3.142 | 12.339 | 1.00 | 34.34 | AAAA |
| ATOM | 1180 | CB | ARG | A | 164 | 5.533 | −4.167 | 11.354 | 1.00 | 36.31 | AAAA |
| ATOM | 1181 | CG | ARG | A | 164 | 5.704 | −3.841 | 9.876 | 1.00 | 39.86 | AAAA |
| ATOM | 1182 | CD | ARG | A | 164 | 4.855 | −4.770 | 8.997 | 1.00 | 41.13 | AAAA |
| ATOM | 1183 | NE | ARG | A | 164 | 5.368 | −6.140 | 8.946 | 1.00 | 43.44 | AAAA |
| ATOM | 1184 | CZ | ARG | A | 164 | 4.765 | −7.145 | 8.311 | 1.00 | 44.08 | AAAA |
| ATOM | 1185 | NH1 | ARG | A | 164 | 3.619 | −6.940 | 7.671 | 1.00 | 44.91 | AAAA |
| ATOM | 1186 | NH2 | ARG | A | 164 | 5.308 | −8.355 | 8.308 | 1.00 | 44.44 | AAAA |
| ATOM | 1187 | C | ARG | A | 164 | 7.649 | −3.248 | 12.419 | 1.00 | 34.72 | AAAA |
| ATOM | 1188 | O | ARG | A | 164 | 8.364 | −2.769 | 11.537 | 1.00 | 33.63 | AAAA |
| ATOM | 1189 | N | THR | A | 165 | 8.138 | −3.855 | 13.496 | 1.00 | 34.72 | AAAA |
| ATOM | 1190 | CA | THR | A | 165 | 9.567 | −3.969 | 13.730 | 1.00 | 34.94 | AAAA |
| ATOM | 1191 | CB | THR | A | 165 | 9.839 | −4.437 | 15.177 | 1.00 | 35.90 | AAAA |
| ATOM | 1192 | OG1 | THR | A | 165 | 9.008 | −5.563 | 15.488 | 1.00 | 36.96 | AAAA |
| ATOM | 1193 | CG2 | THR | A | 165 | 9.530 | −3.313 | 16.149 | 1.00 | 35.88 | AAAA |
| ATOM | 1194 | C | THR | A | 165 | 10.373 | −4.814 | 12.749 | 1.00 | 34.61 | AAAA |
| ATOM | 1195 | O | THR | A | 165 | 11.577 | −4.603 | 12.608 | 1.00 | 34.56 | AAAA |
| ATOM | 1196 | N | ASP | A | 166 | 9.739 | −5.765 | 12.068 | 1.00 | 34.66 | AAAA |
| ATOM | 1197 | CA | ASP | A | 166 | 10.492 | −6.558 | 11.103 | 1.00 | 34.85 | AAAA |
| ATOM | 1198 | CB | ASP | A | 166 | 9.697 | −7.784 | 10.642 | 1.00 | 36.47 | AAAA |
| ATOM | 1199 | CG | ASP | A | 166 | 8.341 | −7.430 | 10.089 | 1.00 | 37.65 | AAAA |
| ATOM | 1200 | OD1 | ASP | A | 166 | 7.566 | −8.365 | 9.804 | 1.00 | 41.03 | AAAA |
| ATOM | 1201 | OD2 | ASP | A | 166 | 8.048 | −6.227 | 9.937 | 1.00 | 39.97 | AAAA |
| ATOM | 1202 | C | ASP | A | 166 | 10.862 | −5.667 | 9.917 | 1.00 | 33.70 | AAAA |
| ATOM | 1203 | O | ASP | A | 166 | 11.846 | −5.925 | 9.224 | 1.00 | 34.04 | AAAA |
| ATOM | 1204 | N | VAL | A | 167 | 10.081 | −4.610 | 9.694 | 1.00 | 31.98 | AAAA |
| ATOM | 1205 | CA | VAL | A | 167 | 10.366 | −3.667 | 8.611 | 1.00 | 31.43 | AAAA |
| ATOM | 1206 | CB | VAL | A | 167 | 9.096 | −2.888 | 8.170 | 1.00 | 31.53 | AAAA |
| ATOM | 1207 | CG1 | VAL | A | 167 | 9.485 | −1.738 | 7.248 | 1.00 | 30.83 | AAAA |
| ATOM | 1208 | CG2 | VAL | A | 167 | 8.120 | −3.825 | 7.458 | 1.00 | 31.61 | AAAA |
| ATOM | 1209 | C | VAL | A | 167 | 11.400 | −2.657 | 9.108 | 1.00 | 31.23 | AAAA |
| ATOM | 1210 | O | VAL | A | 167 | 12.320 | −2.268 | 8.380 | 1.00 | 30.04 | AAAA |
| ATOM | 1211 | N | LEU | A | 168 | 11.243 | −2.238 | 10.359 | 1.00 | 31.72 | AAAA |
| ATOM | 1212 | CA | LEU | A | 168 | 12.159 | −1.277 | 10.959 | 1.00 | 32.61 | AAAA |
| ATOM | 1213 | CB | LEU | A | 168 | 11.714 | −0.942 | 12.387 | 1.00 | 33.77 | AAAA |
| ATOM | 1214 | CG | LEU | A | 168 | 10.490 | −0.040 | 12.562 | 1.00 | 34.46 | AAAA |
| ATOM | 1215 | CD1 | LEU | A | 168 | 10.141 | 0.076 | 14.041 | 1.00 | 35.50 | AAAA |
| ATOM | 1216 | CD2 | LEU | A | 168 | 10.790 | 1.338 | 11.974 | 1.00 | 34.18 | AAAA |
| ATOM | 1217 | C | LEU | A | 168 | 13.594 | −1.790 | 10.986 | 1.00 | 32.72 | AAAA |
| ATOM | 1218 | O | LEU | A | 168 | 14.538 | −1.002 | 10.923 | 1.00 | 32.67 | AAAA |
| ATOM | 1219 | N | ALA | A | 169 | 13.752 | −3.109 | 11.076 | 1.00 | 33.35 | AAAA |
| ATOM | 1220 | CA | ALA | A | 169 | 15.077 | −3.725 | 11.138 | 1.00 | 34.36 | AAAA |
| ATOM | 1221 | CB | ALA | A | 169 | 14.992 | −5.054 | 11.883 | 1.00 | 33.96 | AAAA |
| ATOM | 1222 | C | ALA | A | 169 | 15.746 | −3.939 | 9.777 | 1.00 | 35.45 | AAAA |
| ATOM | 1223 | O | ALA | A | 169 | 16.905 | −4.362 | 9.713 | 1.00 | 36.53 | AAAA |
| ATOM | 1224 | N | LEU | A | 170 | 15.030 | −3.651 | 8.695 | 1.00 | 34.52 | AAAA |
| ATOM | 1225 | CA | LEU | A | 170 | 15.590 | −3.833 | 7.358 | 1.00 | 34.60 | AAAA |
| ATOM | 1226 | CB | LEU | A | 170 | 14.577 | −3.423 | 6.281 | 1.00 | 34.25 | AAAA |
| ATOM | 1227 | CG | LEU | A | 170 | 13.363 | −4.333 | 6.071 | 1.00 | 33.98 | AAAA |
| ATOM | 1228 | CD1 | LEU | A | 170 | 12.393 | −3.675 | 5.101 | 1.00 | 34.11 | AAAA |
| ATOM | 1229 | CD2 | LEU | A | 170 | 13.820 | −5.688 | 5.543 | 1.00 | 33.52 | AAAA |
| ATOM | 1230 | C | LEU | A | 170 | 16.880 | −3.042 | 7.163 | 1.00 | 34.41 | AAAA |
| ATOM | 1231 | O | LEU | A | 170 | 17.001 | −1.902 | 7.616 | 1.00 | 33.45 | AAAA |
| ATOM | 1232 | N | PRO | A | 171 | 17.867 | −3.648 | 6.486 | 1.00 | 34.33 | AAAA |
| ATOM | 1233 | CD | PRO | A | 171 | 17.877 | −5.028 | 5.971 | 1.00 | 34.76 | AAAA |
| ATOM | 1234 | CA | PRO | A | 171 | 19.152 | −2.988 | 6.233 | 1.00 | 35.17 | AAAA |
| ATOM | 1235 | CB | PRO | A | 171 | 19.897 | −4.005 | 5.366 | 1.00 | 34.52 | AAAA |
| ATOM | 1236 | CG | PRO | A | 171 | 19.361 | −5.308 | 5.844 | 1.00 | 34.60 | AAAA |
| ATOM | 1237 | C | PRO | A | 171 | 18.938 | −1.665 | 5.503 | 1.00 | 35.39 | AAAA |

TABLE 1-continued

ATOMIC COORDINATES OF E. COLI MURG PROTEIN

| ATOM | 1238 | O   | PRO | A | 171 | 17.933 | -1.485 | 4.820   | 1.00 | 34.32 AAAA |
|------|------|-----|-----|---|-----|--------|--------|---------|------|------------|
| ATOM | 1239 | N   | LEU | A | 172 | 19.884 | -0.746 | 5.654   | 1.00 | 36.05 AAAA |
| ATOM | 1240 | CA  | LEU | A | 172 | 19.801 | 0.555  | 4.998   | 1.00 | 37.43 AAAA |
| ATOM | 1241 | CB  | LEU | A | 172 | 20.946 | 1.458  | 5.468   | 1.00 | 37.48 AAAA |
| ATOM | 1242 | CG  | LEU | A | 172 | 20.934 | 1.934  | 6.925   | 1.00 | 38.42 AAAA |
| ATOM | 1243 | CD1 | LEU | A | 172 | 19.751 | 2.863  | 7.158   | 1.00 | 37.89 AAAA |
| ATOM | 1244 | CD2 | LEU | A | 172 | 20.876 | 0.735  | 7.859   | 1.00 | 38.70 AAAA |
| ATOM | 1245 | C   | LEU | A | 172 | 19.865 | 0.400  | 3.479   | 1.00 | 38.03 AAAA |
| ATOM | 1246 | O   | LEU | A | 172 | 20.392 | -0.591 | 2.969   | 1.00 | 38.19 AAAA |
| ATOM | 1247 | N   | PRO | A | 173 | 19.329 | 1.383  | 2.737   | 1.00 | 38.41 AAAA |
| ATOM | 1248 | CD  | PRO | A | 173 | 18.647 | 2.586  | 3.248   | 1.00 | 38.12 AAAA |
| ATOM | 1249 | CA  | PRO | A | 173 | 19.319 | 1.367  | 1.271   | 1.00 | 39.54 AAAA |
| ATOM | 1250 | CB  | PRO | A | 173 | 18.853 | 2.778  | 0.923   | 1.00 | 38.97 AAAA |
| ATOM | 1251 | CG  | PRO | A | 173 | 17.898 | 3.076  | 2.029   | 1.00 | 38.41 AAAA |
| ATOM | 1252 | C   | PRO | A | 173 | 20.672 | 1.027  | 0.639   | 1.00 | 41.06 AAAA |
| ATOM | 1253 | O   | PRO | A | 173 | 20.751 | 0.205  | -0.276  | 1.00 | 41.26 AAAA |
| ATOM | 1254 | N   | GLN | A | 174 | 21.734 | 1.659  | 1.127   | 1.00 | 42.31 AAAA |
| ATOM | 1255 | CA  | GLN | A | 174 | 23.063 | 1.401  | 0.591   | 1.00 | 43.56 AAAA |
| ATOM | 1256 | CB  | GLN | A | 174 | 24.118 | 2.219  | 1.343   | 1.00 | 45.08 AAAA |
| ATOM | 1257 | CG  | GLN | A | 174 | 24.197 | 3.672  | 0.906   | 1.00 | 47.91 AAAA |
| ATOM | 1258 | CD  | GLN | A | 174 | 25.366 | 4.413  | 1.534   | 1.00 | 50.04 AAAA |
| ATOM | 1259 | OE1 | GLN | A | 174 | 25.665 | 5.552  | 1.164   | 1.00 | 50.92 AAAA |
| ATOM | 1260 | NE2 | GLN | A | 174 | 26.033 | 3.771  | 2.491   | 1.00 | 50.23 AAAA |
| ATOM | 1261 | C   | GLN | A | 174 | 23.415 | -0.076 | 0.667   | 1.00 | 43.25 AAAA |
| ATOM | 1262 | O   | GLN | A | 174 | 23.955 | -0.641 | -0.280  | 1.00 | 42.73 AAAA |
| ATOM | 1263 | N   | GLN | A | 175 | 23.098 | -0.702 | 1.794   | 1.00 | 43.02 AAAA |
| ATOM | 1264 | CA  | GLN | A | 175 | 23.398 | -2.115 | 1.981   | 1.00 | 43.41 AAAA |
| ATOM | 1265 | CB  | GLN | A | 175 | 23.206 | -2.505 | 3.449   | 1.00 | 44.88 AAAA |
| ATOM | 1266 | CG  | GLN | A | 175 | 23.844 | -1.544 | 4.444   | 1.00 | 47.91 AAAA |
| ATOM | 1267 | CD  | GLN | A | 175 | 25.331 | -1.344 | 4.211   | 1.00 | 49.82 AAAA |
| ATOM | 1268 | OE1 | GLN | A | 175 | 25.747 | -0.765 | 3.203   | 1.00 | 50.30 AAAA |
| ATOM | 1269 | NE2 | GLN | A | 175 | 26.145 | -1.826 | 5.148   | 1.00 | 51.04 AAAA |
| ATOM | 1270 | C   | GLN | A | 175 | 22.521 | -2.997 | 1.097   | 1.00 | 42.34 AAAA |
| ATOM | 1271 | O   | GLN | A | 175 | 22.996 | -3.961 | 0.500   | 1.00 | 41.64 AAAA |
| ATOM | 1272 | N   | ARG | A | 176 | 21.238 | -2.659 | 1.016   | 1.00 | 41.73 AAAA |
| ATOM | 1273 | CA  | ARG | A | 176 | 20.285 | -3.422 | 0.216   | 1.00 | 41.37 AAAA |
| ATOM | 1274 | CB  | ARG | A | 176 | 18.854 | -2.912 | 0.469   | 1.00 | 42.69 AAAA |
| ATOM | 1275 | CG  | ARG | A | 176 | 17.767 | -3.726 | -0.232  | 1.00 | 44.32 AAAA |
| ATOM | 1276 | CD  | ARG | A | 176 | 16.338 | -3.227 | 0.066   | 1.00 | 46.28 AAAA |
| ATOM | 1277 | NE  | ARG | A | 176 | 15.922 | -2.116 | -0.793  | 1.00 | 46.82 AAAA |
| ATOM | 1278 | CZ  | ARG | A | 176 | 16.043 | -0.829 | -0.479  | 1.00 | 47.07 AAAA |
| ATOM | 1279 | NH1 | ARG | A | 176 | 16.567 | -0.471 | 0.686   | 1.00 | 47.74 AAAA |
| ATOM | 1280 | NH2 | ARG | A | 176 | 15.645 | 0.102  | -1.337  | 1.00 | 46.75 AAAA |
| ATOM | 1281 | C   | ARG | A | 176 | 20.574 | -3.358 | -1.279  | 1.00 | 40.60 AAAA |
| ATOM | 1282 | O   | ARG | A | 176 | 20.485 | -4.366 | -1.981  | 1.00 | 39.33 AAAA |
| ATOM | 1283 | N   | LEU | A | 177 | 20.928 | -2.171 | -1.757  | 1.00 | 40.82 AAAA |
| ATOM | 1284 | CA  | LEU | A | 177 | 21.182 | -1.957 | -3.177  | 1.00 | 41.69 AAAA |
| ATOM | 1285 | CB  | LEU | A | 177 | 20.635 | -0.587 | -3.580  | 1.00 | 41.42 AAAA |
| ATOM | 1286 | CG  | LEU | A | 177 | 19.152 | -0.376 | -3.262  | 1.00 | 41.85 AAAA |
| ATOM | 1287 | CD1 | LEU | A | 177 | 18.756 | 1.059  | -3.578  | 1.00 | 41.44 AAAA |
| ATOM | 1288 | CD2 | LEU | A | 177 | 18.311 | -1.358 | -4.066  | 1.00 | 41.27 AAAA |
| ATOM | 1289 | C   | LEU | A | 177 | 22.632 | -2.080 | -3.636  | 1.00 | 42.12 AAAA |
| ATOM | 1290 | O   | LEU | A | 177 | 22.923 | -1.918 | -4.822  | 1.00 | 42.57 AAAA |
| ATOM | 1291 | N   | ALA | A | 178 | 23.536 | -2.374 | -2.709  | 1.00 | 42.36 AAAA |
| ATOM | 1292 | CA  | ALA | A | 178 | 24.951 | -2.505 | -3.047  | 1.00 | 41.77 AAAA |
| ATOM | 1293 | CB  | ALA | A | 178 | 25.774 | -2.711 | -1.778  | 1.00 | 42.52 AAAA |
| ATOM | 1294 | C   | ALA | A | 178 | 25.204 | -3.649 | -4.024  | 1.00 | 41.23 AAAA |
| ATOM | 1295 | O   | ALA | A | 178 | 24.981 | -4.818 | -3.701  | 1.00 | 41.31 AAAA |
| ATOM | 1296 | N   | GLY | A | 179 | 25.668 | -3.299 | -5.221  | 1.00 | 40.21 AAAA |
| ATOM | 1297 | CA  | GLY | A | 179 | 25.960 | -4.298 | -6.232  | 1.00 | 37.93 AAAA |
| ATOM | 1298 | C   | GLY | A | 179 | 24.747 | -4.873 | -6.938  | 1.00 | 36.85 AAAA |
| ATOM | 1299 | O   | GLY | A | 179 | 24.873 | -5.797 | -7.744  | 1.00 | 36.55 AAAA |
| ATOM | 1300 | N   | ARG | A | 180 | 23.566 | -4.333 | -6.654  | 1.00 | 35.52 AAAA |
| ATOM | 1301 | CA  | ARG | A | 180 | 22.362 | -4.844 | -7.289  | 1.00 | 34.04 AAAA |
| ATOM | 1302 | CB  | ARG | A | 180 | 21.114 | -4.428 | -6.504  | 1.00 | 31.99 AAAA |
| ATOM | 1303 | CG  | ARG | A | 180 | 19.840 | -5.038 | -7.055  | 1.00 | 29.72 AAAA |
| ATOM | 1304 | CD  | ARG | A | 180 | 18.608 | -4.609 | -6.268  | 1.00 | 27.51 AAAA |
| ATOM | 1305 | NE  | ARG | A | 180 | 18.531 | -5.233 | -4.948  | 1.00 | 25.67 AAAA |
| ATOM | 1306 | CZ  | ARG | A | 180 | 17.475 | -5.139 | -4.144  | 1.00 | 26.02 AAAA |
| ATOM | 1307 | NH1 | ARG | A | 180 | 16.414 | -4.441 | -4.533  | 1.00 | 24.19 AAAA |
| ATOM | 1308 | NH2 | ARG | A | 180 | 17.472 | -5.749 | -2.961  | 1.00 | 23.88 AAAA |
| ATOM | 1309 | C   | ARG | A | 180 | 22.251 | -4.353 | -8.726  | 1.00 | 34.92 AAAA |
| ATOM | 1310 | O   | ARG | A | 180 | 22.348 | -3.157 | -8.995  | 1.00 | 35.69 AAAA |
| ATOM | 1311 | N   | GLU | A | 181 | 22.055 | -5.290 | -9.646  | 1.00 | 34.98 AAAA |
| ATOM | 1312 | CA  | GLU | A | 181 | 21.917 | -4.969 | -11.059 | 1.00 | 35.58 AAAA |
| ATOM | 1313 | CB  | GLU | A | 181 | 23.188 | -5.354 | -11.822 | 1.00 | 37.16 AAAA |
| ATOM | 1314 | CG  | GLU | A | 181 | 24.411 | -4.540 | -11.436 | 1.00 | 40.11 AAAA |

TABLE 1-continued

ATOMIC COORDINATES OF E. COLI MURG PROTEIN

| ATOM | 1315 | CD | GLU | A | 181 | 25.666 | −4.983 | −12.169 | 1.00 | 42.11 | AAAA |
|---|---|---|---|---|---|---|---|---|---|---|---|
| ATOM | 1316 | OE1 | GLU | A | 181 | 26.698 | −4.284 | −12.056 | 1.00 | 42.94 | AAAA |
| ATOM | 1317 | OE2 | GLU | A | 181 | 25.623 | −6.033 | −12.848 | 1.00 | 43.38 | AAAA |
| ATOM | 1318 | C | GLU | A | 181 | 20.736 | −5.745 | −11.615 | 1.00 | 34.83 | AAAA |
| ATOM | 1319 | O | GLU | A | 181 | 20.148 | −6.577 | −10.919 | 1.00 | 35.81 | AAAA |
| ATOM | 1320 | N | GLY | A | 182 | 20.387 | −5.469 | −12.866 | 1.00 | 33.11 | AAAA |
| ATOM | 1321 | CA | GLY | A | 182 | 19.279 | −6.166 | −13.489 | 1.00 | 31.63 | AAAA |
| ATOM | 1322 | C | GLY | A | 182 | 17.989 | −5.368 | −13.523 | 1.00 | 30.40 | AAAA |
| ATOM | 1323 | O | GLY | A | 182 | 17.959 | −4.210 | −13.106 | 1.00 | 28.65 | AAAA |
| ATOM | 1324 | N | PRO | A | 183 | 16.898 | −5.974 | −14.015 | 1.00 | 29.29 | AAAA |
| ATOM | 1325 | CD | PRO | A | 183 | 16.829 | −7.363 | −14.498 | 1.00 | 30.43 | AAAA |
| ATOM | 1326 | CA | PRO | A | 183 | 15.589 | −5.327 | −14.109 | 1.00 | 29.46 | AAAA |
| ATOM | 1327 | CB | PRO | A | 183 | 14.675 | −6.463 | −14.560 | 1.00 | 29.59 | AAAA |
| ATOM | 1328 | CG | PRO | A | 183 | 15.597 | −7.333 | −15.362 | 1.00 | 30.17 | AAAA |
| ATOM | 1329 | C | PRO | A | 183 | 15.159 | −4.734 | −12.771 | 1.00 | 29.01 | AAAA |
| ATOM | 1330 | O | PRO | A | 183 | 15.455 | −5.289 | −11.708 | 1.00 | 27.87 | AAAA |
| ATOM | 1331 | N | VAL | A | 184 | 14.483 | −3.591 | −12.826 | 1.00 | 27.36 | AAAA |
| ATOM | 1332 | CA | VAL | A | 184 | 14.014 | −2.942 | −11.613 | 1.00 | 25.28 | AAAA |
| ATOM | 1333 | CB | VAL | A | 184 | 13.506 | −1.512 | −11.912 | 1.00 | 26.16 | AAAA |
| ATOM | 1334 | CG1 | VAL | A | 184 | 12.865 | −0.901 | −10.673 | 1.00 | 25.72 | AAAA |
| ATOM | 1335 | CG2 | VAL | A | 184 | 14.670 | −0.648 | −12.374 | 1.00 | 26.35 | AAAA |
| ATOM | 1336 | C | VAL | A | 184 | 12.896 | −3.799 | −11.032 | 1.00 | 23.68 | AAAA |
| ATOM | 1337 | O | VAL | A | 184 | 11.971 | −4.195 | −11.735 | 1.00 | 21.69 | AAAA |
| ATOM | 1338 | N | ARG | A | 185 | 13.003 | −4.102 | −9.744 | 1.00 | 23.12 | AAAA |
| ATOM | 1339 | CA | ARG | A | 185 | 12.015 | −4.931 | −9.065 | 1.00 | 22.35 | AAAA |
| ATOM | 1340 | CB | ARG | A | 185 | 12.687 | −5.649 | −7.897 | 1.00 | 23.23 | AAAA |
| ATOM | 1341 | CG | ARG | A | 185 | 13.910 | −6.440 | −8.323 | 1.00 | 25.75 | AAAA |
| ATOM | 1342 | CD | ARG | A | 185 | 14.729 | −6.847 | −7.120 | 1.00 | 27.07 | AAAA |
| ATOM | 1343 | NE | ARG | A | 185 | 15.976 | −7.502 | −7.495 | 1.00 | 28.67 | AAAA |
| ATOM | 1344 | CZ | ARG | A | 185 | 16.784 | −8.093 | −6.623 | 1.00 | 29.19 | AAAA |
| ATOM | 1345 | NH1 | ARG | A | 185 | 16.462 | −8.100 | −5.339 | 1.00 | 26.72 | AAAA |
| ATOM | 1346 | NH2 | ARG | A | 185 | 17.903 | −8.679 | −7.032 | 1.00 | 31.00 | AAAA |
| ATOM | 1347 | C | ARG | A | 185 | 10.860 | −4.066 | −8.574 | 1.00 | 21.55 | AAAA |
| ATOM | 1348 | O | ARG | A | 185 | 11.033 | −3.228 | −7.693 | 1.00 | 21.13 | AAAA |
| ATOM | 1349 | N | VAL | A | 186 | 9.687 | −4.263 | −9.166 | 1.00 | 21.59 | AAAA |
| ATOM | 1350 | CA | VAL | A | 186 | 8.515 | −3.480 | −8.805 | 1.00 | 21.51 | AAAA |
| ATOM | 1351 | CB | VAL | A | 186 | 7.745 | −3.005 | −10.064 | 1.00 | 21.61 | AAAA |
| ATOM | 1352 | CG1 | VAL | A | 186 | 6.574 | −2.124 | −9.656 | 1.00 | 21.27 | AAAA |
| ATOM | 1353 | CG2 | VAL | A | 186 | 8.689 | −2.252 | −11.001 | 1.00 | 22.25 | AAAA |
| ATOM | 1354 | C | VAL | A | 186 | 7.563 | −4.294 | −7.942 | 1.00 | 20.09 | AAAA |
| ATOM | 1355 | O | VAL | A | 186 | 7.064 | −5.330 | −8.361 | 1.00 | 20.16 | AAAA |
| ATOM | 1356 | N | LEU | A | 187 | 7.325 | −3.807 | −6.735 | 1.00 | 20.75 | AAAA |
| ATOM | 1357 | CA | LEU | A | 187 | 6.421 | −4.462 | −5.801 | 1.00 | 21.10 | AAAA |
| ATOM | 1358 | CB | LEU | A | 187 | 6.979 | −4.363 | −4.379 | 1.00 | 22.77 | AAAA |
| ATOM | 1359 | CG | LEU | A | 187 | 6.492 | −5.359 | −3.316 | 1.00 | 24.90 | AAAA |
| ATOM | 1360 | CD1 | LEU | A | 187 | 6.763 | −4.768 | −1.932 | 1.00 | 23.74 | AAAA |
| ATOM | 1361 | CD2 | LEU | A | 187 | 5.027 | −5.651 | −3.487 | 1.00 | 27.67 | AAAA |
| ATOM | 1362 | C | LEU | A | 187 | 5.104 | −3.691 | −5.871 | 1.00 | 21.37 | AAAA |
| ATOM | 1363 | O | LEU | A | 187 | 5.078 | −2.491 | −5.585 | 1.00 | 21.09 | AAAA |
| ATOM | 1364 | N | VAL | A | 188 | 4.034 | −4.377 | −6.262 | 1.00 | 21.43 | AAAA |
| ATOM | 1365 | CA | VAL | A | 188 | 2.706 | −3.774 | −6.355 | 1.00 | 22.58 | AAAA |
| ATOM | 1366 | CB | VAL | A | 188 | 1.988 | −4.190 | −7.657 | 1.00 | 22.95 | AAAA |
| ATOM | 1367 | CG1 | VAL | A | 188 | 0.643 | −3.488 | −7.765 | 1.00 | 22.98 | AAAA |
| ATOM | 1368 | CG2 | VAL | A | 188 | 2.853 | −3.842 | −8.855 | 1.00 | 23.03 | AAAA |
| ATOM | 1369 | C | VAL | A | 188 | 1.891 | −4.267 | −5.161 | 1.00 | 22.98 | AAAA |
| ATOM | 1370 | O | VAL | A | 188 | 1.603 | −5.456 | −5.051 | 1.00 | 22.38 | AAAA |
| ATOM | 1371 | N | VAL | A | 189 | 1.534 | −3.349 | −4.267 | 1.00 | 23.91 | AAAA |
| ATOM | 1372 | CA | VAL | A | 189 | 0.779 | −3.706 | −3.070 | 1.00 | 25.11 | AAAA |
| ATOM | 1373 | CB | VAL | A | 189 | 1.523 | −3.237 | −1.800 | 1.00 | 25.30 | AAAA |
| ATOM | 1374 | CG1 | VAL | A | 189 | 0.740 | −3.635 | −0.549 | 1.00 | 23.23 | AAAA |
| ATOM | 1375 | CG2 | VAL | A | 189 | 2.915 | −3.828 | −1.773 | 1.00 | 22.20 | AAAA |
| ATOM | 1376 | C | VAL | A | 189 | −0.619 | −3.096 | −3.080 | 1.00 | 26.20 | AAAA |
| ATOM | 1377 | O | VAL | A | 189 | −0.770 | −1.879 | −3.186 | 1.00 | 26.94 | AAAA |
| ATOM | 1378 | N | GLY | A | 190 | −1.629 | −3.955 | −2.975 | 1.00 | 27.50 | AAAA |
| ATOM | 1379 | CA | GLY | A | 190 | −3.007 | −3.505 | −2.966 | 1.00 | 30.27 | AAAA |
| ATOM | 1380 | C | GLY | A | 190 | −3.720 | −3.736 | −1.641 | 1.00 | 32.15 | AAAA |
| ATOM | 1381 | O | GLY | A | 190 | −4.896 | −3.403 | −1.499 | 1.00 | 32.00 | AAAA |
| ATOM | 1382 | N | GLY | A | 191 | −3.016 | −4.299 | −0.664 | 1.00 | 32.97 | AAAA |
| ATOM | 1383 | CA | GLY | A | 191 | −3.640 | −4.550 | 0.624 | 1.00 | 34.29 | AAAA |
| ATOM | 1384 | C | GLY | A | 191 | −4.507 | −5.794 | 0.607 | 1.00 | 34.92 | AAAA |
| ATOM | 1385 | O | GLY | A | 191 | −4.741 | −6.388 | −0.444 | 1.00 | 34.34 | AAAA |
| ATOM | 1386 | N | SER | A | 192 | −4.996 | −6.183 | 1.778 | 1.00 | 36.47 | AAAA |
| ATOM | 1387 | CA | SER | A | 192 | −5.827 | −7.377 | 1.910 | 1.00 | 38.39 | AAAA |
| ATOM | 1388 | CB | SER | A | 192 | −6.389 | −7.460 | 3.335 | 1.00 | 39.07 | AAAA |
| ATOM | 1389 | OG | SER | A | 192 | −7.124 | −6.291 | 3.658 | 1.00 | 41.25 | AAAA |
| ATOM | 1390 | C | SER | A | 192 | −6.974 | −7.472 | 0.903 | 1.00 | 38.69 | AAAA |
| ATOM | 1391 | O | SER | A | 192 | −7.293 | −8.557 | 0.410 | 1.00 | 38.58 | AAAA |

TABLE 1-continued

ATOMIC COORDINATES OF E. COLI MURG PROTEIN

| ATOM | 1392 | N | GLN | A | 193 | −7.599 | −6.344 | 0.595 | 1.00 | 38.60 | AAAA |
|---|---|---|---|---|---|---|---|---|---|---|---|
| ATOM | 1393 | CA | GLN | A | 193 | −8.715 | −6.367 | −0.339 | 1.00 | 39.91 | AAAA |
| ATOM | 1394 | CB | GLN | A | 193 | −9.787 | −5.367 | 0.110 | 1.00 | 41.97 | AAAA |
| ATOM | 1395 | CG | GLN | A | 193 | −10.354 | −5.679 | 1.497 | 1.00 | 43.94 | AAAA |
| ATOM | 1396 | CD | GLN | A | 193 | −10.790 | −7.135 | 1.640 | 1.00 | 45.71 | AAAA |
| ATOM | 1397 | OE1 | GLN | A | 193 | −11.677 | −7.607 | 0.922 | 1.00 | 46.93 | AAAA |
| ATOM | 1398 | NE2 | GLN | A | 193 | −10.162 | −7.853 | 2.567 | 1.00 | 45.80 | AAAA |
| ATOM | 1399 | C | GLN | A | 193 | −8.298 | −6.098 | −1.781 | 1.00 | 39.31 | AAAA |
| ATOM | 1400 | O | GLN | A | 193 | −9.076 | −6.320 | −2.708 | 1.00 | 39.52 | AAAA |
| ATOM | 1401 | N | GLY | A | 194 | −7.064 | −5.642 | −1.961 | 1.00 | 38.40 | AAAA |
| ATOM | 1402 | CA | GLY | A | 194 | −6.560 | −5.358 | −3.291 | 1.00 | 38.11 | AAAA |
| ATOM | 1403 | C | GLY | A | 194 | −6.961 | −3.987 | −3.797 | 1.00 | 37.62 | AAAA |
| ATOM | 1404 | O | GLY | A | 194 | −7.904 | −3.382 | −3.291 | 1.00 | 37.80 | AAAA |
| ATOM | 1405 | N | ALA | A | 195 | −6.228 | −3.489 | −4.787 | 1.00 | 36.62 | AAAA |
| ATOM | 1406 | CA | ALA | A | 195 | −6.513 | −2.191 | −5.387 | 1.00 | 36.35 | AAAA |
| ATOM | 1407 | CB | ALA | A | 195 | −5.290 | −1.291 | −5.305 | 1.00 | 35.75 | AAAA |
| ATOM | 1408 | C | ALA | A | 195 | −6.898 | −2.437 | −6.842 | 1.00 | 36.61 | AAAA |
| ATOM | 1409 | O | ALA | A | 195 | −6.038 | −2.519 | −7.717 | 1.00 | 35.93 | AAAA |
| ATOM | 1410 | N | ARG | A | 196 | −8.198 | −2.566 | −7.080 | 1.00 | 36.94 | AAAA |
| ATOM | 1411 | CA | ARG | A | 196 | −8.741 | −2.828 | −8.412 | 1.00 | 38.03 | AAAA |
| ATOM | 1412 | CB | ARG | A | 196 | −10.229 | −2.466 | −8.450 | 1.00 | 40.33 | AAAA |
| ATOM | 1413 | CG | ARG | A | 196 | −10.526 | −0.968 | −8.375 | 1.00 | 44.08 | AAAA |
| ATOM | 1414 | CD | ARG | A | 196 | −9.935 | −0.306 | −7.129 | 1.00 | 46.46 | AAAA |
| ATOM | 1415 | NE | ARG | A | 196 | −10.381 | −0.949 | −5.894 | 1.00 | 48.33 | AAAA |
| ATOM | 1416 | CZ | ARG | A | 196 | −10.199 | −0.439 | −4.682 | 1.00 | 48.85 | AAAA |
| ATOM | 1417 | NH1 | ARG | A | 196 | −9.581 | 0.725 | −4.538 | 1.00 | 49.51 | AAAA |
| ATOM | 1418 | NH2 | ARG | A | 196 | −10.636 | −1.093 | −3.615 | 1.00 | 49.95 | AAAA |
| ATOM | 1419 | C | ARG | A | 196 | −8.023 | −2.120 | −9.558 | 1.00 | 37.11 | AAAA |
| ATOM | 1420 | O | ARG | A | 196 | −7.729 | −2.736 | −10.583 | 1.00 | 36.96 | AAAA |
| ATOM | 1421 | N | ILE | A | 197 | −7.739 | −0.834 | −9.392 | 1.00 | 35.89 | AAAA |
| ATOM | 1422 | CA | ILE | A | 197 | −7.071 | −0.091 | −10.448 | 1.00 | 35.67 | AAAA |
| ATOM | 1423 | CB | ILE | A | 197 | −7.049 | 1.427 | −10.161 | 1.00 | 36.70 | AAAA |
| ATOM | 1424 | CG2 | ILE | A | 197 | −6.221 | 1.726 | −8.918 | 1.00 | 36.91 | AAAA |
| ATOM | 1425 | CG1 | ILE | A | 197 | −6.485 | 2.162 | −11.381 | 1.00 | 36.95 | AAAA |
| ATOM | 1426 | CD1 | ILE | A | 197 | −6.529 | 3.661 | −11.272 | 1.00 | 38.71 | AAAA |
| ATOM | 1427 | C | ILE | A | 197 | −5.644 | −0.580 | −10.694 | 1.00 | 34.73 | AAAA |
| ATOM | 1428 | O | ILE | A | 197 | −5.178 | −0.575 | −11.833 | 1.00 | 33.53 | AAAA |
| ATOM | 1429 | N | LEU | A | 198 | −4.948 | −0.992 | −9.638 | 1.00 | 32.35 | AAAA |
| ATOM | 1430 | CA | LEU | A | 198 | −3.588 | −1.494 | −9.813 | 1.00 | 31.48 | AAAA |
| ATOM | 1431 | CB | LEU | A | 198 | −2.862 | −1.633 | −8.467 | 1.00 | 31.03 | AAAA |
| ATOM | 1432 | CG | LEU | A | 198 | −2.548 | −0.342 | −7.704 | 1.00 | 32.00 | AAAA |
| ATOM | 1433 | CD1 | LEU | A | 198 | −1.773 | −0.688 | −6.442 | 1.00 | 30.82 | AAAA |
| ATOM | 1434 | CD2 | LEU | A | 198 | −1.734 | 0.607 | −8.566 | 1.00 | 30.86 | AAAA |
| ATOM | 1435 | C | LEU | A | 198 | −3.668 | −2.850 | −10.501 | 1.00 | 29.72 | AAAA |
| ATOM | 1436 | O | LEU | A | 198 | −2.837 | −3.173 | −11.344 | 1.00 | 29.46 | AAAA |
| ATOM | 1437 | N | ASN | A | 199 | −4.678 | −3.639 | −10.150 | 1.00 | 28.63 | AAAA |
| ATOM | 1438 | CA | ASN | A | 199 | −4.848 | −4.952 | −10.758 | 1.00 | 28.66 | AAAA |
| ATOM | 1439 | CB | ASN | A | 199 | −5.975 | −5.724 | −10.066 | 1.00 | 27.71 | AAAA |
| ATOM | 1440 | CG | ASN | A | 199 | −5.641 | −6.069 | −8.632 | 1.00 | 26.12 | AAAA |
| ATOM | 1441 | OD1 | ASN | A | 199 | −4.501 | −5.904 | −8.200 | 1.00 | 24.15 | AAAA |
| ATOM | 1442 | ND2 | ASN | A | 199 | −6.631 | −6.553 | −7.834 | 1.00 | 24.90 | AAAA |
| ATOM | 1443 | C | ASN | A | 199 | −5.144 | −4.841 | −12.248 | 1.00 | 29.87 | AAAA |
| ATOM | 1444 | O | ASN | A | 199 | −4.834 | −5.747 | −13.024 | 1.00 | 30.26 | AAAA |
| ATOM | 1445 | N | GLN | A | 200 | −5.746 | −3.725 | −12.644 | 1.00 | 31.15 | AAAA |
| ATOM | 1446 | CA | GLN | A | 200 | −6.085 | −3.498 | −14.044 | 1.00 | 33.06 | AAAA |
| ATOM | 1447 | CB | GLN | A | 200 | −7.396 | −2.706 | −14.145 | 1.00 | 34.24 | AAAA |
| ATOM | 1448 | CG | GLN | A | 200 | −8.590 | −3.368 | −13.471 | 1.00 | 38.64 | AAAA |
| ATOM | 1449 | CD | GLN | A | 200 | −8.923 | −4.734 | −14.050 | 1.00 | 41.05 | AAAA |
| ATOM | 1450 | OE1 | GLN | A | 200 | −9.131 | −4.879 | −15.256 | 1.00 | 43.10 | AAAA |
| ATOM | 1451 | NE2 | GLN | A | 200 | −8.983 | −5.745 | −13.185 | 1.00 | 43.12 | AAAA |
| ATOM | 1452 | C | GLN | A | 200 | −4.989 | −2.753 | −14.812 | 1.00 | 32.52 | AAAA |
| ATOM | 1453 | O | GLN | A | 200 | −4.809 | −2.970 | −16.008 | 1.00 | 34.23 | AAAA |
| ATOM | 1454 | N | THR | A | 201 | −4.247 | −1.895 | −14.120 | 1.00 | 31.87 | AAAA |
| ATOM | 1455 | CA | THR | A | 201 | −3.207 | −1.092 | −14.756 | 1.00 | 31.72 | AAAA |
| ATOM | 1456 | CB | THR | A | 201 | −3.046 | 0.245 | −13.999 | 1.00 | 32.41 | AAAA |
| ATOM | 1457 | OG1 | THR | A | 201 | −4.307 | 0.931 | −13.976 | 1.00 | 32.19 | AAAA |
| ATOM | 1458 | CG2 | THR | A | 201 | −2.003 | 1.131 | −14.668 | 1.00 | 32.29 | AAAA |
| ATOM | 1459 | C | THR | A | 201 | −1.817 | −1.728 | −14.925 | 1.00 | 32.02 | AAAA |
| ATOM | 1460 | O | THR | A | 201 | −1.206 | −1.626 | −15.991 | 1.00 | 31.47 | AAAA |
| ATOM | 1461 | N | MET | A | 202 | −1.320 | −2.394 | −13.892 | 1.00 | 30.61 | AAAA |
| ATOM | 1462 | CA | MET | A | 202 | 0.019 | −2.975 | −13.963 | 1.00 | 30.10 | AAAA |
| ATOM | 1463 | CB | MET | A | 202 | 0.430 | −3.507 | −12.592 | 1.00 | 29.71 | AAAA |
| ATOM | 1464 | CG | MET | A | 202 | 0.564 | −2.406 | −11.548 | 1.00 | 28.99 | AAAA |
| ATOM | 1465 | SD | MET | A | 202 | 1.518 | −0.961 | −12.098 | 1.00 | 31.46 | AAAA |
| ATOM | 1466 | CE | MET | A | 202 | 3.184 | −1.633 | −12.184 | 1.00 | 29.20 | AAAA |
| ATOM | 1467 | C | MET | A | 202 | 0.286 | −4.022 | −15.042 | 1.00 | 29.48 | AAAA |
| ATOM | 1468 | O | MET | A | 202 | 1.389 | −4.088 | −15.568 | 1.00 | 29.15 | AAAA |

TABLE 1-continued

ATOMIC COORDINATES OF E. COLI MURG PROTEIN

| ATOM | 1469 | N | PRO | A | 203 | -0.703 | -4.863 | -15.379 | 1.00 | 30.34 | AAAA |
|---|---|---|---|---|---|---|---|---|---|---|---|
| ATOM | 1470 | CD | PRO | A | 203 | -1.957 | -5.186 | -14.677 | 1.00 | 30.05 | AAAA |
| ATOM | 1471 | CA | PRO | A | 203 | -0.415 | -5.849 | -16.426 | 1.00 | 31.11 | AAAA |
| ATOM | 1472 | CB | PRO | A | 203 | -1.703 | -6.654 | -16.500 | 1.00 | 31.89 | AAAA |
| ATOM | 1473 | CG | PRO | A | 203 | -2.188 | -6.623 | -15.072 | 1.00 | 31.09 | AAAA |
| ATOM | 1474 | C | PRO | A | 203 | -0.103 | -5.139 | -17.746 | 1.00 | 33.02 | AAAA |
| ATOM | 1475 | O | PRO | A | 203 | 0.800 | -5.530 | -18.490 | 1.00 | 33.16 | AAAA |
| ATOM | 1476 | N | GLN | A | 204 | -0.855 | -4.081 | -18.020 | 1.00 | 33.88 | AAAA |
| ATOM | 1477 | CA | GLN | A | 204 | -0.666 | -3.314 | -19.242 | 1.00 | 34.99 | AAAA |
| ATOM | 1478 | CB | GLN | A | 204 | -1.836 | -2.347 | -19.431 | 1.00 | 37.12 | AAAA |
| ATOM | 1479 | CG | GLN | A | 204 | -3.177 | -3.067 | -19.538 | 1.00 | 40.86 | AAAA |
| ATOM | 1480 | CD | GLN | A | 204 | -4.354 | -2.121 | -19.700 | 1.00 | 43.77 | AAAA |
| ATOM | 1481 | OE1 | GLN | A | 204 | -4.406 | -1.330 | -20.647 | 1.00 | 45.55 | AAAA |
| ATOM | 1482 | NE2 | GLN | A | 204 | -5.310 | -2.198 | -18.776 | 1.00 | 44.11 | AAAA |
| ATOM | 1483 | C | GLN | A | 204 | 0.659 | -2.573 | -19.190 | 1.00 | 33.42 | AAAA |
| ATOM | 1484 | O | GLN | A | 204 | 1.331 | -2.431 | -20.206 | 1.00 | 34.40 | AAAA |
| ATOM | 1485 | N | VAL | A | 205 | 1.045 | -2.114 | -18.002 | 1.00 | 32.44 | AAAA |
| ATOM | 1486 | CA | VAL | A | 205 | 2.313 | -1.417 | -17.836 | 1.00 | 30.42 | AAAA |
| ATOM | 1487 | CB | VAL | A | 205 | 2.466 | -0.834 | -16.408 | 1.00 | 31.72 | AAAA |
| ATOM | 1488 | CG1 | VAL | A | 205 | 3.907 | -0.406 | -16.169 | 1.00 | 28.58 | AAAA |
| ATOM | 1489 | CG2 | VAL | A | 205 | 1.544 | 0.356 | -16.231 | 1.00 | 29.91 | AAAA |
| ATOM | 1490 | C | VAL | A | 205 | 3.446 | -2.407 | -18.086 | 1.00 | 30.65 | AAAA |
| ATOM | 1491 | O | VAL | A | 205 | 4.473 | -2.062 | -18.686 | 1.00 | 29.65 | AAAA |
| ATOM | 1492 | N | ALA | A | 206 | 3.255 | -3.638 | -17.616 | 1.00 | 29.08 | AAAA |
| ATOM | 1493 | CA | ALA | A | 206 | 4.253 | -4.688 | -17.796 | 1.00 | 30.43 | AAAA |
| ATOM | 1494 | CB | ALA | A | 206 | 3.763 | -6.002 | -17.169 | 1.00 | 27.77 | AAAA |
| ATOM | 1495 | C | ALA | A | 206 | 4.519 | -4.886 | -19.288 | 1.00 | 30.65 | AAAA |
| ATOM | 1496 | O | ALA | A | 206 | 5.668 | -5.040 | -19.709 | 1.00 | 30.70 | AAAA |
| ATOM | 1497 | N | ALA | A | 207 | 3.450 | -4.879 | -20.080 | 1.00 | 31.56 | AAAA |
| ATOM | 1498 | CA | ALA | A | 207 | 3.565 | -5.053 | -21.527 | 1.00 | 32.70 | AAAA |
| ATOM | 1499 | CB | ALA | A | 207 | 2.188 | -4.997 | -22.167 | 1.00 | 32.49 | AAAA |
| ATOM | 1500 | C | ALA | A | 207 | 4.470 | -3.990 | -22.145 | 1.00 | 32.72 | AAAA |
| ATOM | 1501 | O | ALA | A | 207 | 5.295 | -4.284 | -23.007 | 1.00 | 33.64 | AAAA |
| ATOM | 1502 | N | LYS | A | 208 | 4.321 | -2.754 | -21.692 | 1.00 | 33.07 | AAAA |
| ATOM | 1503 | CA | LYS | A | 208 | 5.112 | -1.651 | -22.216 | 1.00 | 33.20 | AAAA |
| ATOM | 1504 | CB | LYS | A | 208 | 4.477 | -0.313 | -21.814 | 1.00 | 35.14 | AAAA |
| ATOM | 1505 | CG | LYS | A | 208 | 3.199 | 0.044 | -22.578 | 1.00 | 38.07 | AAAA |
| ATOM | 1506 | CD | LYS | A | 208 | 2.166 | -1.062 | -22.482 | 1.00 | 40.27 | AAAA |
| ATOM | 1507 | CE | LYS | A | 208 | 0.892 | -0.731 | -23.233 | 1.00 | 41.02 | AAAA |
| ATOM | 1508 | NZ | LYS | A | 208 | -0.076 | -1.857 | -23.126 | 1.00 | 42.41 | AAAA |
| ATOM | 1509 | C | LYS | A | 208 | 6.571 | -1.668 | -21.779 | 1.00 | 32.58 | AAAA |
| ATOM | 1510 | O | LYS | A | 208 | 7.456 | -1.274 | -22.544 | 1.00 | 31.82 | AAAA |
| ATOM | 1511 | N | LEU | A | 209 | 6.829 | -2.121 | -20.556 | 1.00 | 30.72 | AAAA |
| ATOM | 1512 | CA | LEU | A | 209 | 8.193 | -2.143 | -20.042 | 1.00 | 30.48 | AAAA |
| ATOM | 1513 | CB | LEU | A | 209 | 8.191 | -1.848 | -18.535 | 1.00 | 29.34 | AAAA |
| ATOM | 1514 | CG | LEU | A | 209 | 7.596 | -0.498 | -18.107 | 1.00 | 31.02 | AAAA |
| ATOM | 1515 | CD1 | LEU | A | 209 | 7.779 | -0.318 | -16.605 | 1.00 | 29.42 | AAAA |
| ATOM | 1516 | CD2 | LEU | A | 209 | 8.273 | 0.641 | -18.859 | 1.00 | 31.39 | AAAA |
| ATOM | 1517 | C | LEU | A | 209 | 8.970 | -3.432 | -20.315 | 1.00 | 29.73 | AAAA |
| ATOM | 1518 | O | LEU | A | 209 | 10.191 | -3.455 | -20.174 | 1.00 | 31.33 | AAAA |
| ATOM | 1519 | N | GLY | A | 210 | 8.269 | -4.494 | -20.698 | 1.00 | 29.76 | AAAA |
| ATOM | 1520 | CA | GLY | A | 210 | 8.924 | -5.762 | -20.986 | 1.00 | 29.99 | AAAA |
| ATOM | 1521 | C | GLY | A | 210 | 10.007 | -6.188 | -20.003 | 1.00 | 30.99 | AAAA |
| ATOM | 1522 | O | GLY | A | 210 | 9.788 | -6.183 | -18.789 | 1.00 | 30.80 | AAAA |
| ATOM | 1523 | N | ASP | A | 211 | 11.181 | -6.536 | -20.535 | 1.00 | 30.05 | AAAA |
| ATOM | 1524 | CA | ASP | A | 211 | 12.332 | -6.999 | -19.749 | 1.00 | 29.42 | AAAA |
| ATOM | 1525 | CB | ASP | A | 211 | 13.466 | -7.479 | -20.676 | 1.00 | 30.83 | AAAA |
| ATOM | 1526 | CG | ASP | A | 211 | 13.119 | -8.735 | -21.449 | 1.00 | 32.09 | AAAA |
| ATOM | 1527 | OD1 | ASP | A | 211 | 13.977 | -9.193 | -22.235 | 1.00 | 34.13 | AAAA |
| ATOM | 1528 | OD2 | ASP | A | 211 | 12.005 | -9.269 | -21.283 | 1.00 | 32.72 | AAAA |
| ATOM | 1529 | C | ASP | A | 211 | 12.960 | -6.011 | -18.776 | 1.00 | 29.03 | AAAA |
| ATOM | 1530 | O | ASP | A | 211 | 13.781 | -6.417 | -17.945 | 1.00 | 27.69 | AAAA |
| ATOM | 1531 | N | SER | A | 212 | 12.613 | -4.730 | -18.876 | 1.00 | 28.54 | AAAA |
| ATOM | 1532 | CA | SER | A | 212 | 13.204 | -3.719 | -18.002 | 1.00 | 27.61 | AAAA |
| ATOM | 1533 | CB | SER | A | 212 | 12.927 | -2.308 | -18.538 | 1.00 | 28.62 | AAAA |
| ATOM | 1534 | OG | SER | A | 212 | 11.546 | -1.990 | -18.498 | 1.00 | 30.84 | AAAA |
| ATOM | 1535 | C | SER | A | 212 | 12.759 | -3.805 | -16.542 | 1.00 | 26.31 | AAAA |
| ATOM | 1536 | O | SER | A | 212 | 13.395 | -3.219 | -15.666 | 1.00 | 25.39 | AAAA |
| ATOM | 1537 | N | VAL | A | 213 | 11.675 | -4.528 | -16.284 | 1.00 | 25.65 | AAAA |
| ATOM | 1538 | CA | VAL | A | 213 | 11.187 | -4.671 | -14.914 | 1.00 | 24.52 | AAAA |
| ATOM | 1539 | CB | VAL | A | 213 | 9.967 | -3.747 | -14.621 | 1.00 | 25.58 | AAAA |
| ATOM | 1540 | CG1 | VAL | A | 213 | 10.296 | -2.298 | -14.953 | 1.00 | 26.31 | AAAA |
| ATOM | 1541 | CG2 | VAL | A | 213 | 8.758 | -4.225 | -15.394 | 1.00 | 25.15 | AAAA |
| ATOM | 1542 | C | VAL | A | 213 | 10.751 | -6.095 | -14.607 | 1.00 | 23.77 | AAAA |
| ATOM | 1543 | O | VAL | A | 213 | 10.427 | -6.874 | -15.506 | 1.00 | 23.79 | AAAA |
| ATOM | 1544 | N | THR | A | 214 | 10.770 | -6.432 | -13.323 | 1.00 | 23.49 | AAAA |
| ATOM | 1545 | CA | THR | A | 214 | 10.326 | -7.735 | -12.861 | 1.00 | 21.50 | AAAA |

TABLE 1-continued

ATOMIC COORDINATES OF *E. COLI* MURG PROTEIN

| ATOM | 1546 | CB  | THR | A | 214 | 11.499  | -8.600  | -12.325 | 1.00 | 21.99 AAAA |
|------|------|-----|-----|---|-----|---------|---------|---------|------|------------|
| ATOM | 1547 | OG1 | THR | A | 214 | 10.987  | -9.870  | -11.909 | 1.00 | 23.56 AAAA |
| ATOM | 1548 | CG2 | THR | A | 214 | 12.220  | -7.921  | -11.174 | 1.00 | 20.60 AAAA |
| ATOM | 1549 | C   | THR | A | 214 | 9.342   | -7.362  | -11.760 | 1.00 | 21.46 AAAA |
| ATOM | 1550 | O   | THR | A | 214 | 9.657   | -6.567  | -10.880 | 1.00 | 21.12 AAAA |
| ATOM | 1551 | N   | ILE | A | 215 | 8.150   | -7.938  | -11.827 | 1.00 | 21.73 AAAA |
| ATOM | 1552 | CA  | ILE | A | 215 | 7.083   | -7.601  | -10.894 | 1.00 | 22.01 AAAA |
| ATOM | 1553 | CB  | ILE | A | 215 | 5.831   | -7.139  | -11.688 | 1.00 | 22.41 AAAA |
| ATOM | 1554 | CG2 | ILE | A | 215 | 4.707   | -6.738  | -10.734 | 1.00 | 22.94 AAAA |
| ATOM | 1555 | CG1 | ILE | A | 215 | 6.198   | -5.964  | -12.599 | 1.00 | 22.71 AAAA |
| ATOM | 1556 | CD1 | ILE | A | 215 | 5.078   | -5.560  | -13.545 | 1.00 | 21.71 AAAA |
| ATOM | 1557 | C   | ILE | A | 215 | 6.617   | -8.685  | -9.929  | 1.00 | 21.67 AAAA |
| ATOM | 1558 | O   | ILE | A | 215 | 6.600   | -9.868  | -10.257 | 1.00 | 20.14 AAAA |
| ATOM | 1559 | N   | TRP | A | 216 | 6.248   | -8.247  | -8.728  | 1.00 | 21.03 AAAA |
| ATOM | 1560 | CA  | TRP | A | 216 | 5.677   | -9.121  | -7.708  | 1.00 | 21.08 AAAA |
| ATOM | 1561 | CB  | TRP | A | 216 | 6.541   | -9.186  | -6.455  | 1.00 | 21.14 AAAA |
| ATOM | 1562 | CG  | TRP | A | 216 | 5.941   | -10.063 | -5.370  | 1.00 | 21.49 AAAA |
| ATOM | 1563 | CD2 | TRP | A | 216 | 6.624   | -10.588 | -4.226  | 1.00 | 21.97 AAAA |
| ATOM | 1564 | CE2 | TRP | A | 216 | 5.674   | -11.309 | -3.461  | 1.00 | 22.67 AAAA |
| ATOM | 1565 | CE3 | TRP | A | 216 | 7.947   | -10.521 | -3.773  | 1.00 | 22.25 AAAA |
| ATOM | 1566 | CD1 | TRP | A | 216 | 4.639   | -10.478 | -5.262  | 1.00 | 21.72 AAAA |
| ATOM | 1567 | NE1 | TRP | A | 216 | 4.472   | -11.231 | -4.112  | 1.00 | 22.34 AAAA |
| ATOM | 1568 | CZ2 | TRP | A | 216 | 6.011   | -11.955 | -2.265  | 1.00 | 24.81 AAAA |
| ATOM | 1569 | CZ3 | TRP | A | 216 | 8.283   | -11.166 | -2.582  | 1.00 | 23.37 AAAA |
| ATOM | 1570 | CH2 | TRP | A | 216 | 7.316   | -11.872 | -1.843  | 1.00 | 23.19 AAAA |
| ATOM | 1571 | C   | TRP | A | 216 | 4.401   | -8.352  | -7.396  | 1.00 | 21.75 AAAA |
| ATOM | 1572 | O   | TRP | A | 216 | 4.442   | -7.330  | -6.719  | 1.00 | 22.71 AAAA |
| ATOM | 1573 | N   | HIS | A | 217 | 3.280   | -8.844  | -7.909  | 1.00 | 23.00 AAAA |
| ATOM | 1574 | CA  | HIS | A | 217 | 1.987   | -8.185  | -7.751  | 1.00 | 24.05 AAAA |
| ATOM | 1575 | CB  | HIS | A | 217 | 1.301   | -8.167  | -9.127  | 1.00 | 25.31 AAAA |
| ATOM | 1576 | CG  | HIS | A | 217 | 0.075   | -7.312  | -9.201  | 1.00 | 27.29 AAAA |
| ATOM | 1577 | CD2 | HIS | A | 217 | -1.008  | -7.226  | -8.391  | 1.00 | 27.56 AAAA |
| ATOM | 1578 | ND1 | HIS | A | 217 | -0.146  | -6.424  | -10.233 | 1.00 | 28.22 AAAA |
| ATOM | 1579 | CE1 | HIS | A | 217 | -1.311  | -5.828  | -10.057 | 1.00 | 28.76 AAAA |
| ATOM | 1580 | NE2 | HIS | A | 217 | -1.856  | -6.296  | -8.947  | 1.00 | 27.39 AAAA |
| ATOM | 1581 | C   | HIS | A | 217 | 1.095   | -8.880  | -6.714  | 1.00 | 22.49 AAAA |
| ATOM | 1582 | O   | HIS | A | 217 | 0.785   | -10.059 | -6.851  | 1.00 | 24.60 AAAA |
| ATOM | 1583 | N   | GLN | A | 218 | 0.696   | -8.144  | -5.679  | 1.00 | 24.33 AAAA |
| ATOM | 1584 | CA  | GLN | A | 218 | -0.184  | -8.676  | -4.629  | 1.00 | 24.84 AAAA |
| ATOM | 1585 | CB  | GLN | A | 218 | 0.271   | -8.181  | -3.250  | 1.00 | 25.16 AAAA |
| ATOM | 1586 | CG  | GLN | A | 218 | -0.572  | -8.709  | -2.084  | 1.00 | 26.40 AAAA |
| ATOM | 1587 | CD  | GLN | A | 218 | -1.629  | -7.722  | -1.608  | 1.00 | 27.63 AAAA |
| ATOM | 1588 | OE1 | GLN | A | 218 | -2.762  | -8.107  | -1.297  | 1.00 | 29.31 AAAA |
| ATOM | 1589 | NE2 | GLN | A | 218 | -1.260  | -6.455  | -1.525  | 1.00 | 24.88 AAAA |
| ATOM | 1590 | C   | GLN | A | 218 | -1.573  | -8.134  | -4.983  | 1.00 | 24.83 AAAA |
| ATOM | 1591 | O   | GLN | A | 218 | -1.859  | -6.960  | -4.767  | 1.00 | 24.21 AAAA |
| ATOM | 1592 | N   | SER | A | 219 | -2.413  | -9.008  | -5.531  | 1.00 | 25.76 AAAA |
| ATOM | 1593 | CA  | SER | A | 219 | -3.745  | -8.658  | -6.022  | 1.00 | 27.99 AAAA |
| ATOM | 1594 | CB  | SER | A | 219 | -4.189  | -9.704  | -7.035  | 1.00 | 28.46 AAAA |
| ATOM | 1595 | OG  | SER | A | 219 | -4.394  | -10.949 | -6.387  | 1.00 | 29.92 AAAA |
| ATOM | 1596 | C   | SER | A | 219 | -4.887  | -8.470  | -5.034  | 1.00 | 29.52 AAAA |
| ATOM | 1597 | O   | SER | A | 219 | -5.842  | -7.745  | -5.321  | 1.00 | 29.47 AAAA |
| ATOM | 1598 | N   | GLY | A | 220 | -4.806  | -9.135  | -3.890  | 1.00 | 30.25 AAAA |
| ATOM | 1599 | CA  | GLY | A | 220 | -5.874  | -9.031  | -2.919  | 1.00 | 31.33 AAAA |
| ATOM | 1600 | C   | GLY | A | 220 | -6.696  | -10.302 | -2.952  | 1.00 | 32.52 AAAA |
| ATOM | 1601 | O   | GLY | A | 220 | -6.554  | -11.126 | -3.862  | 1.00 | 31.13 AAAA |
| ATOM | 1602 | N   | LYS | A | 221 | -7.563  | -10.452 | -1.956  | 1.00 | 33.12 AAAA |
| ATOM | 1603 | CA  | LYS | A | 221 | -8.423  | -11.619 | -1.815  | 1.00 | 34.69 AAAA |
| ATOM | 1604 | CB  | LYS | A | 221 | -9.340  | -11.421 | -0.601  | 1.00 | 35.93 AAAA |
| ATOM | 1605 | CG  | LYS | A | 221 | -10.257 | -12.593 | -0.285  | 1.00 | 38.70 AAAA |
| ATOM | 1606 | CD  | LYS | A | 221 | -11.079 | -12.292 | 0.966   | 1.00 | 40.53 AAAA |
| ATOM | 1607 | CE  | LYS | A | 221 | -11.955 | -13.465 | 1.368   | 1.00 | 41.74 AAAA |
| ATOM | 1608 | NZ  | LYS | A | 221 | -12.724 | -13.160 | 2.614   | 1.00 | 43.70 AAAA |
| ATOM | 1609 | C   | LYS | A | 221 | -9.269  | -11.932 | -3.046  | 1.00 | 34.22 AAAA |
| ATOM | 1610 | O   | LYS | A | 221 | -9.979  | -11.070 | -3.561  | 1.00 | 34.62 AAAA |
| ATOM | 1611 | N   | GLY | A | 222 | -9.189  | -13.180 | -3.500  | 1.00 | 34.61 AAAA |
| ATOM | 1612 | CA  | GLY | A | 222 | -9.956  | -13.622 | -4.651  | 1.00 | 34.89 AAAA |
| ATOM | 1613 | C   | GLY | A | 222 | -9.598  | -13.027 | -6.000  | 1.00 | 35.07 AAAA |
| ATOM | 1614 | O   | GLY | A | 222 | -10.325 | -13.231 | -6.974  | 1.00 | 35.62 AAAA |
| ATOM | 1615 | N   | SER | A | 223 | -8.482  | -12.309 | -6.083  | 1.00 | 35.16 AAAA |
| ATOM | 1616 | CA  | SER | A | 223 | -8.083  | -11.691 | -7.349  | 1.00 | 35.04 AAAA |
| ATOM | 1617 | CB  | SER | A | 223 | -7.959  | -10.175 | -7.173  | 1.00 | 35.18 AAAA |
| ATOM | 1618 | OG  | SER | A | 223 | -9.222  | -9.593  | -6.913  | 1.00 | 36.67 AAAA |
| ATOM | 1619 | C   | SER | A | 223 | -6.783  | -12.226 | -7.949  | 1.00 | 34.73 AAAA |
| ATOM | 1620 | O   | SER | A | 223 | -6.343  | -11.758 | -9.002  | 1.00 | 33.65 AAAA |
| ATOM | 1621 | N   | GLN | A | 224 | -6.176  | -13.202 | -7.285  | 1.00 | 34.35 AAAA |
| ATOM | 1622 | CA  | GLN | A | 224 | -4.922  | -13.779 | -7.753  | 1.00 | 34.39 AAAA |

TABLE 1-continued

ATOMIC COORDINATES OF E. COLI MURG PROTEIN

| ATOM | 1623 | CB | GLN | A | 224 | −4.493 | −14.910 | −6.810 | 1.00 | 35.22 | AAAA |
|---|---|---|---|---|---|---|---|---|---|---|---|
| ATOM | 1624 | CG | GLN | A | 224 | −3.016 | −15.304 | −6.895 | 1.00 | 34.71 | AAAA |
| ATOM | 1625 | CD | GLN | A | 224 | −2.656 | −5.983 | −8.199 | 1.00 | 35.46 | AAAA |
| ATOM | 1626 | OE1 | GLN | A | 224 | −3.386 | −16.844 | −8.680 | 1.00 | 35.81 | AAAA |
| ATOM | 1627 | NE2 | GLN | A | 224 | −1.512 | −15.610 | −8.772 | 1.00 | 36.28 | AAAA |
| ATOM | 1628 | C | GLN | A | 224 | −5.033 | −14.301 | −9.188 | 1.00 | 35.00 | AAAA |
| ATOM | 1629 | O | GLN | A | 224 | −4.256 | −13.915 | −10.062 | 1.00 | 33.23 | AAAA |
| ATOM | 1630 | N | GLN | A | 225 | −6.018 | −15.160 | −9.432 | 1.00 | 35.33 | AAAA |
| ATOM | 1631 | CA | GLN | A | 225 | −6.208 | −15.747 | −10.752 | 1.00 | 36.18 | AAAA |
| ATOM | 1632 | CB | GLN | A | 225 | −7.251 | −16.871 | −10.675 | 1.00 | 38.35 | AAAA |
| ATOM | 1633 | CG | GLN | A | 225 | −6.692 | −18.174 | −10.103 | 1.00 | 40.67 | AAAA |
| ATOM | 1634 | CD | GLN | A | 225 | −7.732 | −19.274 | −9.983 | 1.00 | 43.02 | AAAA |
| ATOM | 1635 | OE1 | GLN | A | 225 | −8.418 | −19.609 | −10.952 | 1.00 | 44.03 | AAAA |
| ATOM | 1636 | NE2 | GLN | A | 225 | −7.846 | −19.850 | −8.789 | 1.00 | 43.72 | AAAA |
| ATOM | 1637 | C | GLN | A | 225 | −6.554 | −14.790 | −11.893 | 1.00 | 35.81 | AAAA |
| ATOM | 1638 | O | GLN | A | 225 | −6.113 | −15.001 | −13.023 | 1.00 | 35.91 | AAAA |
| ATOM | 1639 | N | SER | A | 226 | −7.325 | −13.741 | −11.619 | 1.00 | 34.00 | AAAA |
| ATOM | 1640 | CA | SER | A | 226 | −7.689 | −12.804 | −12.683 | 1.00 | 34.21 | AAAA |
| ATOM | 1641 | CB | SER | A | 226 | −8.865 | −11.920 | −12.251 | 1.00 | 34.12 | AAAA |
| ATOM | 1642 | OG | SER | A | 226 | −8.460 | −10.954 | −11.300 | 1.00 | 36.16 | AAAA |
| ATOM | 1643 | C | SER | A | 226 | −6.502 | −11.926 | −13.090 | 1.00 | 32.76 | AAAA |
| ATOM | 1644 | O | SER | A | 226 | −6.343 | −11.580 | −14.260 | 1.00 | 32.64 | AAAA |
| ATOM | 1645 | N | VAL | A | 227 | −5.669 | −11.566 | −12.121 | 1.00 | 31.82 | AAAA |
| ATOM | 1646 | CA | VAL | A | 227 | −4.498 | −10.737 | −12.400 | 1.00 | 30.69 | AAAA |
| ATOM | 1647 | CB | VAL | A | 227 | −3.942 | −10.117 | −11.102 | 1.00 | 29.27 | AAAA |
| ATOM | 1648 | CG1 | VAL | A | 227 | −2.619 | −9.413 | −11.370 | 1.00 | 29.04 | AAAA |
| ATOM | 1649 | CG2 | VAL | A | 227 | −4.951 | −9.117 | −10.546 | 1.00 | 29.09 | AAAA |
| ATOM | 1650 | C | VAL | A | 227 | −3.418 | −11.577 | −13.082 | 1.00 | 30.43 | AAAA |
| ATOM | 1651 | O | VAL | A | 227 | −2.716 | −11.103 | −13.973 | 1.00 | 29.50 | AAAA |
| ATOM | 1652 | N | GLU | A | 228 | −3.297 | −12.824 | −12.644 | 1.00 | 30.82 | AAAA |
| ATOM | 1653 | CA | GLU | A | 228 | −2.333 | −13.766 | −13.198 | 1.00 | 31.96 | AAAA |
| ATOM | 1654 | CB | GLU | A | 228 | −2.456 | −15.108 | −12.464 | 1.00 | 31.67 | AAAA |
| ATOM | 1655 | CG | GLU | A | 228 | −1.607 | −16.231 | −13.020 | 1.00 | 33.79 | AAAA |
| ATOM | 1656 | CD | GLU | A | 228 | −0.159 | −16.176 | −12.559 | 1.00 | 34.94 | AAAA |
| ATOM | 1657 | OE1 | GLU | A | 228 | 0.631 | −17.041 | −12.998 | 1.00 | 36.44 | AAAA |
| ATOM | 1658 | OE2 | GLU | A | 228 | 0.190 | −15.280 | −11.761 | 1.00 | 35.02 | AAAA |
| ATOM | 1659 | C | GLU | A | 228 | −2.658 | −13.944 | −14.685 | 1.00 | 32.05 | AAAA |
| ATOM | 1660 | O | GLU | A | 228 | −1.770 | −13.942 | −15.539 | 1.00 | 32.57 | AAAA |
| ATOM | 1661 | N | GLN | A | 229 | −3.945 | −14.082 | −14.981 | 1.00 | 31.94 | AAAA |
| ATOM | 1662 | CA | GLN | A | 229 | −4.405 | −14.255 | −16.351 | 1.00 | 32.98 | AAAA |
| ATOM | 1663 | CB | GLN | A | 229 | −5.896 | −14.616 | −16.359 | 1.00 | 35.59 | AAAA |
| ATOM | 1664 | CG | GLN | A | 229 | −6.375 | −15.211 | −17.674 | 1.00 | 39.28 | AAAA |
| ATOM | 1665 | CD | GLN | A | 229 | −7.825 | −15.665 | −17.623 | 1.00 | 41.31 | AAAA |
| ATOM | 1666 | OE1 | GLN | A | 229 | −8.317 | −16.307 | −18.553 | 1.00 | 43.67 | AAAA |
| ATOM | 1667 | NE2 | GLN | A | 229 | −8.516 | −15.332 | −16.538 | 1.00 | 43.19 | AAAA |
| ATOM | 1668 | C | GLN | A | 229 | −4.171 | −12.982 | −17.154 | 1.00 | 31.60 | AAAA |
| ATOM | 1669 | O | GLN | A | 229 | −3.878 | −13.037 | −18.348 | 1.00 | 32.04 | AAAA |
| ATOM | 1670 | N | ALA | A | 230 | −4.296 | −11.836 | −16.490 | 1.00 | 30.96 | AAAA |
| ATOM | 1671 | CA | ALA | A | 230 | −4.092 | −10.542 | −17.131 | 1.00 | 30.04 | AAAA |
| ATOM | 1672 | CB | ALA | A | 230 | −4.453 | −9.423 | −16.165 | 1.00 | 30.37 | AAAA |
| ATOM | 1673 | C | ALA | A | 230 | −2.649 | −10.379 | −17.598 | 1.00 | 29.65 | AAAA |
| ATOM | 1674 | O | ALA | A | 230 | −2.392 | −9.869 | −18.689 | 1.00 | 29.50 | AAAA |
| ATOM | 1675 | N | TYR | A | 231 | −1.706 | −10.802 | −16.762 | 1.00 | 27.99 | AAAA |
| ATOM | 1676 | CA | TYR | A | 231 | −0.295 | −10.707 | −17.111 | 1.00 | 27.27 | AAAA |
| ATOM | 1677 | CB | TYR | A | 231 | 0.571 | −11.065 | −15.898 | 1.00 | 26.63 | AAAA |
| ATOM | 1678 | CG | TYR | A | 231 | 0.829 | −9.898 | −14.975 | 1.00 | 24.33 | AAAA |
| ATOM | 1679 | CD1 | TYR | A | 231 | 1.687 | −8.866 | −15.354 | 1.00 | 22.96 | AAAA |
| ATOM | 1680 | CE1 | TYR | A | 231 | 1.926 | −7.786 | −14.520 | 1.00 | 22.17 | AAAA |
| ATOM | 1681 | CD2 | TYR | A | 231 | 0.210 | −9.817 | −13.725 | 1.00 | 24.32 | AAAA |
| ATOM | 1682 | CE2 | TYR | A | 231 | 0.442 | −8.737 | −12.879 | 1.00 | 21.70 | AAAA |
| ATOM | 1683 | CZ | TYR | A | 231 | 1.298 | −7.729 | −13.281 | 1.00 | 21.49 | AAAA |
| ATOM | 1684 | OH | TYR | A | 231 | 1.532 | −6.662 | −12.466 | 1.00 | 18.68 | AAAA |
| ATOM | 1685 | C | TYR | A | 231 | 0.047 | −11.618 | −18.285 | 1.00 | 28.10 | AAAA |
| ATOM | 1686 | O | TYR | A | 231 | 0.834 | −11.249 | −19.163 | 1.00 | 27.39 | AAAA |
| ATOM | 1687 | N | ALA | A | 232 | −0.547 | −12.808 | −18.297 | 1.00 | 28.86 | AAAA |
| ATOM | 1688 | CA | ALA | A | 232 | −0.310 | −13.775 | −19.364 | 1.00 | 29.80 | AAAA |
| ATOM | 1689 | CB | ALA | A | 232 | −1.013 | −15.091 | −19.046 | 1.00 | 30.32 | AAAA |
| ATOM | 1690 | C | ALA | A | 232 | −0.814 | −13.218 | −20.694 | 1.00 | 30.76 | AAAA |
| ATOM | 1691 | O | ALA | A | 232 | −0.147 | −13.336 | −21.725 | 1.00 | 30.92 | AAAA |
| ATOM | 1692 | N | GLU | A | 233 | −1.996 | −12.614 | −20.662 | 1.00 | 31.01 | AAAA |
| ATOM | 1693 | CA | GLU | A | 233 | −2.592 | −12.034 | −21.857 | 1.00 | 32.12 | AAAA |
| ATOM | 1694 | CB | GLU | A | 233 | −4.051 | −11.658 | −21.579 | 1.00 | 33.81 | AAAA |
| ATOM | 1695 | CG | GLU | A | 233 | −4.975 | −12.871 | −21.514 | 1.00 | 35.08 | AAAA |
| ATOM | 1696 | CD | GLU | A | 233 | −6.402 | −12.523 | −21.117 | 1.00 | 37.70 | AAAA |
| ATOM | 1697 | OE1 | GLU | A | 233 | −6.875 | −11.419 | −21.473 | 1.00 | 37.78 | AAAA |
| ATOM | 1698 | OE2 | GLU | A | 233 | −7.056 | −13.364 | −20.461 | 1.00 | 37.69 | AAAA |
| ATOM | 1699 | C | GLU | A | 233 | −1.800 | −10.820 | −22.325 | 1.00 | 32.01 | AAAA |

TABLE 1-continued

ATOMIC COORDINATES OF E. COLI MURG PROTEIN

| ATOM | 1700 | O | GLU | A | 233 | −1.825 | −10.463 | −23.508 | 1.00 | 32.48 | AAAA |
|---|---|---|---|---|---|---|---|---|---|---|---|
| ATOM | 1701 | N | ALA | A | 234 | −1.093 | −10.185 | −21.398 | 1.00 | 30.89 | AAAA |
| ATOM | 1702 | CA | ALA | A | 234 | −0.283 | −9.022 | −21.736 | 1.00 | 29.79 | AAAA |
| ATOM | 1703 | CB | ALA | A | 234 | −0.089 | −8.141 | −20.505 | 1.00 | 30.39 | AAAA |
| ATOM | 1704 | C | ALA | A | 234 | 1.070 | −9.501 | −22.265 | 1.00 | 28.79 | AAAA |
| ATOM | 1705 | O | ALA | A | 234 | 1.934 | −8.697 | −22.604 | 1.00 | 28.46 | AAAA |
| ATOM | 1706 | N | GLY | A | 235 | 1.243 | −10.818 | −22.314 | 1.00 | 27.19 | AAAA |
| ATOM | 1707 | CA | GLY | A | 235 | 2.484 | −11.388 | −22.807 | 1.00 | 26.98 | AAAA |
| ATOM | 1708 | C | GLY | A | 235 | 3.650 | −11.387 | −21.832 | 1.00 | 25.89 | AAAA |
| ATOM | 1709 | O | GLY | A | 235 | 4.798 | −11.527 | −22.253 | 1.00 | 25.26 | AAAA |
| ATOM | 1710 | N | GLN | A | 236 | 3.370 | −11.226 | −20.540 | 1.00 | 24.71 | AAAA |
| ATOM | 1711 | CA | GLN | A | 236 | 4.419 | −11.223 | −19.518 | 1.00 | 24.12 | AAAA |
| ATOM | 1712 | CB | GLN | A | 236 | 4.652 | −9.806 | −18.977 | 1.00 | 24.66 | AAAA |
| ATOM | 1713 | CG | GLN | A | 236 | 5.116 | −8.760 | −20.003 | 1.00 | 25.88 | AAAA |
| ATOM | 1714 | CD | GLN | A | 236 | 6.454 | −9.088 | −20.647 | 1.00 | 26.71 | AAAA |
| ATOM | 1715 | OE1 | GLN | A | 236 | 7.410 | −9.488 | −19.976 | 1.00 | 24.90 | AAAA |
| ATOM | 1716 | NE2 | GLN | A | 236 | 6.533 | −8.899 | −21.960 | 1.00 | 26.33 | AAAA |
| ATOM | 1717 | C | GLN | A | 236 | 3.959 | −12.132 | −18.379 | 1.00 | 22.79 | AAAA |
| ATOM | 1718 | O | GLN | A | 236 | 3.823 | −11.696 | −17.233 | 1.00 | 22.19 | AAAA |
| ATOM | 1719 | N | PRO | A | 237 | 3.740 | −13.419 | −18.679 | 1.00 | 22.50 | AAAA |
| ATOM | 1720 | CD | PRO | A | 237 | 4.087 | −14.093 | −19.945 | 1.00 | 21.90 | AAAA |
| ATOM | 1721 | CA | PRO | A | 237 | 3.282 | −14.395 | −17.684 | 1.00 | 22.78 | AAAA |
| ATOM | 1722 | CB | PRO | A | 237 | 2.998 | −15.626 | −18.531 | 1.00 | 22.52 | AAAA |
| ATOM | 1723 | CG | PRO | A | 237 | 4.105 | −15.558 | −19.543 | 1.00 | 23.54 | AAAA |
| ATOM | 1724 | C | PRO | A | 237 | 4.252 | −14.695 | −16.550 | 1.00 | 22.53 | AAAA |
| ATOM | 1725 | O | PRO | A | 237 | 3.845 | −15.217 | −15.512 | 1.00 | 23.09 | AAAA |
| ATOM | 1726 | N | GLN | A | 238 | 5.521 | −14.346 | −16.735 | 1.00 | 22.30 | AAAA |
| ATOM | 1727 | CA | GLN | A | 238 | 6.539 | −14.633 | −15.726 | 1.00 | 22.49 | AAAA |
| ATOM | 1728 | CB | GLN | A | 238 | 7.947 | −14.437 | −16.304 | 1.00 | 22.24 | AAAA |
| ATOM | 1729 | CG | GLN | A | 238 | 8.376 | −12.991 | −16.520 | 1.00 | 21.45 | AAAA |
| ATOM | 1730 | CD | GLN | A | 238 | 7.727 | −12.356 | −17.736 | 1.00 | 22.77 | AAAA |
| ATOM | 1731 | OE1 | GLN | A | 238 | 7.109 | −13.038 | −18.548 | 1.00 | 22.82 | AAAA |
| ATOM | 1732 | NE2 | GLN | A | 238 | 7.881 | −11.046 | −17.870 | 1.00 | 22.96 | AAAA |
| ATOM | 1733 | C | GLN | A | 238 | 6.453 | −13.856 | −14.426 | 1.00 | 21.84 | AAAA |
| ATOM | 1734 | O | GLN | A | 238 | 7.059 | −14.253 | −13.427 | 1.00 | 21.75 | AAAA |
| ATOM | 1735 | N | HIS | A | 239 | 5.724 | −12.748 | −14.420 | 1.00 | 22.21 | AAAA |
| ATOM | 1736 | CA | HIS | A | 239 | 5.632 | −11.963 | −13.202 | 1.00 | 22.02 | AAAA |
| ATOM | 1737 | CB | HIS | A | 239 | 4.919 | −10.638 | −13.479 | 1.00 | 22.03 | AAAA |
| ATOM | 1738 | CG | HIS | A | 239 | 5.688 | −9.734 | −14.392 | 1.00 | 22.30 | AAAA |
| ATOM | 1739 | CD2 | HIS | A | 239 | 5.315 | −9.057 | −15.505 | 1.00 | 22.95 | AAAA |
| ATOM | 1740 | ND1 | HIS | A | 239 | 7.021 | −9.445 | −14.197 | 1.00 | 21.95 | AAAA |
| ATOM | 1741 | CE1 | HIS | A | 239 | 7.437 | −8.628 | −15.149 | 1.00 | 23.56 | AAAA |
| ATOM | 1742 | NE2 | HIS | A | 239 | 6.421 | −8.378 | −15.956 | 1.00 | 21.89 | AAAA |
| ATOM | 1743 | C | HIS | A | 239 | 4.937 | −12.739 | −12.092 | 1.00 | 20.83 | AAAA |
| ATOM | 1744 | O | HIS | A | 239 | 4.036 | −13.538 | −12.352 | 1.00 | 21.43 | AAAA |
| ATOM | 1745 | N | LYS | A | 240 | 5.381 | −12.506 | −10.858 | 1.00 | 21.17 | AAAA |
| ATOM | 1746 | CA | LYS | A | 240 | 4.819 | −13.183 | −9.687 | 1.00 | 22.02 | AAAA |
| ATOM | 1747 | CB | LYS | A | 240 | 5.840 | −13.175 | −8.543 | 1.00 | 21.72 | AAAA |
| ATOM | 1748 | CG | LYS | A | 240 | 5.420 | −13.918 | −7.257 | 1.00 | 22.71 | AAAA |
| ATOM | 1749 | CD | LYS | A | 240 | 6.462 | −13.691 | −6.163 | 1.00 | 23.02 | AAAA |
| ATOM | 1750 | CE | LYS | A | 240 | 6.155 | −14.439 | −4.855 | 1.00 | 22.89 | AAAA |
| ATOM | 1751 | NZ | LYS | A | 240 | 6.359 | −15.920 | −4.960 | 1.00 | 23.41 | AAAA |
| ATOM | 1752 | C | LYS | A | 240 | 3.545 | −12.500 | −9.214 | 1.00 | 21.50 | AAAA |
| ATOM | 1753 | O | LYS | A | 240 | 3.527 | −11.288 | −9.022 | 1.00 | 22.79 | AAAA |
| ATOM | 1754 | N | VAL | A | 241 | 2.490 | −13.282 | −9.012 | 1.00 | 23.27 | AAAA |
| ATOM | 1755 | CA | VAL | A | 241 | 1.219 | −12.751 | −8.527 | 1.00 | 23.82 | AAAA |
| ATOM | 1756 | CB | VAL | A | 241 | 0.111 | −12.821 | −9.598 | 1.00 | 23.97 | AAAA |
| ATOM | 1757 | CG1 | VAL | A | 241 | −1.170 | −12.185 | −9.057 | 1.00 | 24.26 | AAAA |
| ATOM | 1758 | CG2 | VAL | A | 241 | 0.563 | −12.105 | −10.862 | 1.00 | 22.10 | AAAA |
| ATOM | 1759 | C | VAL | A | 241 | 0.751 | −13.565 | −7.323 | 1.00 | 23.52 | AAAA |
| ATOM | 1760 | O | VAL | A | 241 | 0.593 | −14.781 | −7.415 | 1.00 | 25.10 | AAAA |
| ATOM | 1761 | N | THR | A | 242 | 0.547 | −12.896 | −6.195 | 1.00 | 24.29 | AAAA |
| ATOM | 1762 | CA | THR | A | 242 | 0.083 | −13.578 | −4.991 | 1.00 | 25.34 | AAAA |
| ATOM | 1763 | CB | THR | A | 242 | 1.176 | −13.635 | −3.892 | 1.00 | 23.46 | AAAA |
| ATOM | 1764 | OG1 | THR | A | 242 | 1.633 | −12.312 | −3.590 | 1.00 | 24.62 | AAAA |
| ATOM | 1765 | CG2 | THR | A | 242 | 2.354 | −14.482 | −4.351 | 1.00 | 25.33 | AAAA |
| ATOM | 1766 | C | THR | A | 242 | −1.144 | −12.870 | −4.435 | 1.00 | 26.25 | AAAA |
| ATOM | 1767 | O | THR | A | 242 | −1.278 | −11.645 | −4.534 | 1.00 | 25.29 | AAAA |
| ATOM | 1768 | N | GLU | A | 243 | −2.051 | −13.647 | −3.860 | 1.00 | 26.45 | AAAA |
| ATOM | 1769 | CA | GLU | A | 243 | −3.256 | −13.070 | −3.293 | 1.00 | 28.18 | AAAA |
| ATOM | 1770 | CB | GLU | A | 243 | −4.152 | −14.184 | −2.746 | 1.00 | 28.90 | AAAA |
| ATOM | 1771 | CG | GLU | A | 243 | −5.463 | −13.705 | −2.156 | 1.00 | 32.51 | AAAA |
| ATOM | 1772 | CD | GLU | A | 243 | −6.448 | −14.845 | −1.957 | 1.00 | 33.27 | AAAA |
| ATOM | 1773 | OE1 | GLU | A | 243 | −6.002 | −15.969 | −1.646 | 1.00 | 33.05 | AAAA |
| ATOM | 1774 | OE2 | GLU | A | 243 | −7.665 | −14.612 | −2.107 | 1.00 | 34.89 | AAAA |
| ATOM | 1775 | C | GLU | A | 243 | −2.863 | −12.089 | −2.194 | 1.00 | 27.96 | AAAA |
| ATOM | 1776 | O | GLU | A | 243 | −3.331 | −10.951 | −2.164 | 1.00 | 28.25 | AAAA |

TABLE 1-continued

ATOMIC COORDINATES OF *E. COLI* MURG PROTEIN

| ATOM | 1777 | N   | PHE | A | 244 | -1.976 | -12.528 | -1.308 | 1.00 | 28.29 | AAAA |
|------|------|-----|-----|---|-----|--------|---------|--------|------|-------|------|
| ATOM | 1778 | CA  | PHE | A | 244 | -1.509 | -11.696 | -0.208 | 1.00 | 29.32 | AAAA |
| ATOM | 1779 | CB  | PHE | A | 244 | -2.079 | -12.202 | 1.122  | 1.00 | 31.34 | AAAA |
| ATOM | 1780 | CG  | PHE | A | 244 | -3.571 | -12.360 | 1.139  | 1.00 | 32.25 | AAAA |
| ATOM | 1781 | CD1 | PHE | A | 244 | -4.406 | -11.249 | 1.103  | 1.00 | 34.11 | AAAA |
| ATOM | 1782 | CD2 | PHE | A | 244 | -4.141 | -13.623 | 1.246  | 1.00 | 33.07 | AAAA |
| ATOM | 1783 | CE1 | PHE | A | 244 | -5.794 | -11.393 | 1.179  | 1.00 | 34.27 | AAAA |
| ATOM | 1784 | CE2 | PHE | A | 244 | -5.525 | -13.780 | 1.323  | 1.00 | 34.74 | AAAA |
| ATOM | 1785 | CZ  | PHE | A | 244 | -6.353 | -12.660 | 1.291  | 1.00 | 34.28 | AAAA |
| ATOM | 1786 | C   | PHE | A | 244 | 0.010  | -11.759 | -0.103 | 1.00 | 29.21 | AAAA |
| ATOM | 1787 | O   | PHE | A | 244 | 0.660  | -12.503 | -0.836 | 1.00 | 28.44 | AAAA |
| ATOM | 1788 | N   | ILE | A | 245 | 0.560  | -10.962 | 0.813  | 1.00 | 29.58 | AAAA |
| ATOM | 1789 | CA  | ILE | A | 245 | 1.993  | -10.956 | 1.116  | 1.00 | 30.22 | AAAA |
| ATOM | 1790 | CB  | ILE | A | 245 | 2.764  | -9.766  | 0.503  | 1.00 | 29.45 | AAAA |
| ATOM | 1791 | CG2 | ILE | A | 245 | 4.190  | -9.741  | 1.060  | 1.00 | 27.25 | AAAA |
| ATOM | 1792 | CG1 | ILE | A | 245 | 2.824  | -9.887  | -1.020 | 1.00 | 26.11 | AAAA |
| ATOM | 1793 | CD1 | ILE | A | 245 | 3.609  | -8.774  | -1.661 | 1.00 | 27.15 | AAAA |
| ATOM | 1794 | C   | ILE | A | 245 | 2.086  | -10.822 | 2.631  | 1.00 | 32.52 | AAAA |
| ATOM | 1795 | O   | ILE | A | 245 | 1.987  | -9.720  | 3.176  | 1.00 | 32.53 | AAAA |
| ATOM | 1796 | N   | ASP | A | 246 | 2.271  | -11.944 | 3.311  | 1.00 | 34.55 | AAAA |
| ATOM | 1797 | CA  | ASP | A | 246 | 2.357  | -11.926 | 4.763  | 1.00 | 36.92 | AAAA |
| ATOM | 1798 | CB  | ASP | A | 246 | 2.222  | -13.350 | 5.304  | 1.00 | 40.29 | AAAA |
| ATOM | 1799 | CG  | ASP | A | 246 | 0.831  | -13.926 | 5.075  | 1.00 | 43.98 | AAAA |
| ATOM | 1800 | OD1 | ASP | A | 246 | 0.659  | -15.159 | 5.218  | 1.00 | 46.68 | AAAA |
| ATOM | 1801 | OD2 | ASP | A | 246 | -0.093 | 13.143  | 4.760  | 1.00 | 45.65 | AAAA |
| ATOM | 1802 | C   | ASP | A | 246 | 3.650  | -11.286 | 5.247  | 1.00 | 36.42 | AAAA |
| ATOM | 1803 | O   | ASP | A | 246 | 3.631  | -10.384 | 6.092  | 1.00 | 37.48 | AAAA |
| ATOM | 1804 | N   | ASP | A | 247 | 4.771  | -11.733 | 4.694  | 1.00 | 35.16 | AAAA |
| ATOM | 1805 | CA  | ASP | A | 247 | 6.069  | -11.200 | 5.085  | 1.00 | 34.25 | AAAA |
| ATOM | 1806 | CB  | ASP | A | 247 | 7.145  | -12.268 | 4.887  | 1.00 | 33.07 | AAAA |
| ATOM | 1807 | CG  | ASP | A | 247 | 8.461  | -11.901 | 5.543  | 1.00 | 33.19 | AAAA |
| ATOM | 1808 | OD1 | ASP | A | 247 | 8.689  | -10.700 | 5.802  | 1.00 | 31.85 | AAAA |
| ATOM | 1809 | OD2 | ASP | A | 247 | 9.277  | -12.816 | 5.791  | 1.00 | 32.31 | AAAA |
| ATOM | 1810 | C   | ASP | A | 247 | 6.422  | -9.949  | 4.275  | 1.00 | 34.18 | AAAA |
| ATOM | 1811 | O   | ASP | A | 247 | 7.241  | -10.003 | 3.354  | 1.00 | 33.62 | AAAA |
| ATOM | 1812 | N   | MET | A | 248 | 5.801  | -8.825  | 4.617  | 1.00 | 33.66 | AAAA |
| ATOM | 1813 | CA  | MET | A | 248 | 6.069  | -7.577  | 3.916  | 1.00 | 33.29 | AAAA |
| ATOM | 1814 | CB  | MET | A | 248 | 5.192  | -6.448  | 4.461  | 1.00 | 34.30 | AAAA |
| ATOM | 1815 | CG  | MET | A | 248 | 3.852  | -6.314  | 3.757  | 1.00 | 36.70 | AAAA |
| ATOM | 1816 | SD  | MET | A | 248 | 4.042  | -5.940  | 1.987  | 1.00 | 40.22 | AAAA |
| ATOM | 1817 | CE  | MET | A | 248 | 2.590  | -6.667  | 1.361  | 1.00 | 39.66 | AAAA |
| ATOM | 1818 | C   | MET | A | 248 | 7.533  | -7.180  | 4.017  | 1.00 | 32.64 | AAAA |
| ATOM | 1819 | O   | MET | A | 248 | 8.082  | -6.587  | 3.088  | 1.00 | 32.59 | AAAA |
| ATOM | 1820 | N   | ALA | A | 249 | 8.166  | -7.500  | 5.142  | 1.00 | 30.31 | AAAA |
| ATOM | 1821 | CA  | ALA | A | 249 | 9.573  | -7.163  | 5.316  | 1.00 | 29.81 | AAAA |
| ATOM | 1822 | CB  | ALA | A | 249 | 10.061 | -7.597  | 6.706  | 1.00 | 28.83 | AAAA |
| ATOM | 1823 | C   | ALA | A | 249 | 10.406 | -7.837  | 4.223  | 1.00 | 27.72 | AAAA |
| ATOM | 1824 | O   | ALA | A | 249 | 11.277 | -7.208  | 3.622  | 1.00 | 27.98 | AAAA |
| ATOM | 1825 | N   | ALA | A | 250 | 10.127 | -9.112  | 3.960  | 1.00 | 27.22 | AAAA |
| ATOM | 1826 | CA  | ALA | A | 250 | 10.858 | -9.847  | 2.937  | 1.00 | 26.24 | AAAA |
| ATOM | 1827 | CB  | ALA | A | 250 | 10.449 | -11.305 | 2.946  | 1.00 | 26.77 | AAAA |
| ATOM | 1828 | C   | ALA | A | 250 | 10.624 | -9.250  | 1.553  | 1.00 | 26.35 | AAAA |
| ATOM | 1829 | O   | ALA | A | 250 | 11.543 | -9.192  | 0.739  | 1.00 | 26.73 | AAAA |
| ATOM | 1830 | N   | ALA | A | 251 | 9.400  | -8.807  | 1.279  | 1.00 | 25.03 | AAAA |
| ATOM | 1831 | CA  | ALA | A | 251 | 9.101  | -8.225  | -0.033 | 1.00 | 25.36 | AAAA |
| ATOM | 1832 | CB  | ALA | A | 251 | 7.597  | -8.044  | -0.205 | 1.00 | 24.69 | AAAA |
| ATOM | 1833 | C   | ALA | A | 251 | 9.816  | -6.891  | -0.209 | 1.00 | 24.97 | AAAA |
| ATOM | 1834 | O   | ALA | A | 251 | 10.342 | -6.586  | -1.287 | 1.00 | 24.32 | AAAA |
| ATOM | 1835 | N   | TYR | A | 252 | 9.832  | -6.097  | 0.855  | 1.00 | 24.41 | AAAA |
| ATOM | 1836 | CA  | TYR | A | 252 | 10.488 | -4.801  | 0.838  | 1.00 | 24.62 | AAAA |
| ATOM | 1837 | CB  | TYR | A | 252 | 10.191 | -4.033  | 2.131  | 1.00 | 26.30 | AAAA |
| ATOM | 1838 | CG  | TYR | A | 252 | 8.815  | -3.399  | 2.214  | 1.00 | 28.84 | AAAA |
| ATOM | 1839 | CD1 | TYR | A | 252 | 8.282  | -3.027  | 3.450  | 1.00 | 29.34 | AAAA |
| ATOM | 1840 | CE1 | TYR | A | 252 | 7.048  | -2.395  | 3.547  | 1.00 | 30.51 | AAAA |
| ATOM | 1841 | CD2 | TYR | A | 252 | 8.066  | -3.123  | 1.064  | 1.00 | 28.35 | AAAA |
| ATOM | 1842 | CE2 | TYR | A | 252 | 6.821  | -2.485  | 1.153  | 1.00 | 29.76 | AAAA |
| ATOM | 1843 | CZ  | TYR | A | 252 | 6.322  | -2.125  | 2.401  | 1.00 | 30.32 | AAAA |
| ATOM | 1844 | OH  | TYR | A | 252 | 5.103  | -1.492  | 2.515  | 1.00 | 29.75 | AAAA |
| ATOM | 1845 | C   | TYR | A | 252 | 11.998 | -4.972  | 0.694  | 1.00 | 25.22 | AAAA |
| ATOM | 1846 | O   | TYR | A | 252 | 12.668 | -4.106  | 0.139  | 1.00 | 24.57 | AAAA |
| ATOM | 1847 | N   | ALA | A | 253 | 12.527 | -6.084  | 1.204  | 1.00 | 23.97 | AAAA |
| ATOM | 1848 | CA  | ALA | A | 253 | 13.961 | -6.355  | 1.118  | 1.00 | 24.84 | AAAA |
| ATOM | 1849 | CB  | ALA | A | 253 | 14.311 | -7.606  | 1.906  | 1.00 | 23.83 | AAAA |
| ATOM | 1850 | C   | ALA | A | 253 | 14.319 | -6.560  | -0.347 | 1.00 | 24.16 | AAAA |
| ATOM | 1851 | O   | ALA | A | 253 | 15.325 | -6.045  | -0.831 | 1.00 | 26.29 | AAAA |
| ATOM | 1852 | N   | TRP | A | 254 | 13.469 | -7.315  | -1.032 | 1.00 | 23.19 | AAAA |
| ATOM | 1853 | CA  | TRP | A | 254 | 13.640 | -7.635  | -2.447 | 1.00 | 22.89 | AAAA |

TABLE 1-continued

ATOMIC COORDINATES OF E. COLI MURG PROTEIN

| ATOM | 1854 | CB  | TRP | A | 254 | 12.672 | -8.753 | -2.827 | 1.00 | 21.01 | AAAA |
|------|------|-----|-----|---|-----|--------|--------|--------|------|-------|------|
| ATOM | 1855 | CG  | TRP | A | 254 | 12.534 | -8.968 | -4.304 | 1.00 | 21.21 | AAAA |
| ATOM | 1856 | CD2 | TRP | A | 254 | 11.508 | -8.437 | -5.155 | 1.00 | 20.22 | AAAA |
| ATOM | 1857 | CE2 | TRP | A | 254 | 11.766 | -8.905 | -6.463 | 1.00 | 20.36 | AAAA |
| ATOM | 1858 | CE3 | TRP | A | 254 | 10.397 | -7.610 | -4.939 | 1.00 | 20.38 | AAAA |
| ATOM | 1859 | CD1 | TRP | A | 254 | 13.353 | -9.708 | -5.105 | 1.00 | 20.80 | AAAA |
| ATOM | 1860 | NE1 | TRP | A | 254 | 12.895 | -9.678 | -6.404 | 1.00 | 22.48 | AAAA |
| ATOM | 1861 | CZ2 | TRP | A | 254 | 10.948 | -8.573 | -7.559 | 1.00 | 21.36 | AAAA |
| ATOM | 1862 | CZ3 | TRP | A | 254 | 9.582  | -7.276 | -6.030 | 1.00 | 21.09 | AAAA |
| ATOM | 1863 | CH2 | TRP | A | 254 | 9.867  | -7.761 | -7.323 | 1.00 | 20.78 | AAAA |
| ATOM | 1864 | C   | TRP | A | 254 | 13.433 | -6.468 | -3.414 | 1.00 | 22.65 | AAAA |
| ATOM | 1865 | O   | TRP | A | 254 | 14.218 | -6.280 | -4.345 | 1.00 | 23.19 | AAAA |
| ATOM | 1866 | N   | ALA | A | 255 | 12.376 | -5.692 | -3.194 | 1.00 | 21.49 | AAAA |
| ATOM | 1867 | CA  | ALA | A | 255 | 12.024 | -4.586 | -4.086 | 1.00 | 21.80 | AAAA |
| ATOM | 1868 | CB  | ALA | A | 255 | 10.652 | -4.030 | -3.677 | 1.00 | 22.15 | AAAA |
| ATOM | 1869 | C   | ALA | A | 255 | 12.988 | -3.420 | -4.299 | 1.00 | 21.27 | AAAA |
| ATOM | 1870 | O   | ALA | A | 255 | 13.844 | -3.110 | -3.469 | 1.00 | 21.35 | AAAA |
| ATOM | 1871 | N   | ASP | A | 256 | 12.820 | -2.771 | -5.447 | 1.00 | 21.80 | AAAA |
| ATOM | 1872 | CA  | ASP | A | 256 | 13.600 | -1.590 | -5.807 | 1.00 | 21.58 | AAAA |
| ATOM | 1873 | CB  | ASP | A | 256 | 14.082 | -1.686 | -7.263 | 1.00 | 23.50 | AAAA |
| ATOM | 1874 | CG  | ASP | A | 256 | 15.329 | -2.542 | -7.415 | 1.00 | 23.21 | AAAA |
| ATOM | 1875 | OD1 | ASP | A | 256 | 15.354 | -3.417 | -8.306 | 1.00 | 24.63 | AAAA |
| ATOM | 1876 | OD2 | ASP | A | 256 | 16.289 | -2.328 | -6.648 | 1.00 | 25.60 | AAAA |
| ATOM | 1877 | C   | ASP | A | 256 | 12.651 | -0.397 | -5.670 | 1.00 | 22.26 | AAAA |
| ATOM | 1878 | O   | ASP | A | 256 | 13.053 | 0.703  | -5.300 | 1.00 | 22.77 | AAAA |
| ATOM | 1879 | N   | VAL | A | 257 | 11.379 | -0.637 | -5.968 | 1.00 | 23.20 | AAAA |
| ATOM | 1880 | CA  | VAL | A | 257 | 10.366 | 0.411  | -5.914 | 1.00 | 23.31 | AAAA |
| ATOM | 1881 | CB  | VAL | A | 257 | 10.313 | 1.167  | -7.267 | 1.00 | 23.63 | AAAA |
| ATOM | 1882 | CG1 | VAL | A | 257 | 9.950  | 0.206  | -8.373 | 1.00 | 21.70 | AAAA |
| ATOM | 1883 | CG2 | VAL | A | 257 | 9.312  | 2.315  | -7.205 | 1.00 | 23.86 | AAAA |
| ATOM | 1884 | C   | VAL | A | 257 | 8.997  | -0.197 | -5.607 | 1.00 | 23.39 | AAAA |
| ATOM | 1885 | O   | VAL | A | 257 | 8.735  | -1.351 | -5.933 | 1.00 | 22.20 | AAAA |
| ATOM | 1886 | N   | VAL | A | 258 | 8.127  | 0.587  | -4.978 | 1.00 | 24.57 | AAAA |
| ATOM | 1887 | CA  | VAL | A | 258 | 6.792  | 0.114  | -4.627 | 1.00 | 24.32 | AAAA |
| ATOM | 1888 | CB  | VAL | A | 258 | 6.590  | 0.100  | -3.085 | 1.00 | 25.07 | AAAA |
| ATOM | 1889 | CG1 | VAL | A | 258 | 5.275  | -0.596 | -2.731 | 1.00 | 25.09 | AAAA |
| ATOM | 1890 | CG2 | VAL | A | 258 | 7.755  | -0.599 | -2.406 | 1.00 | 25.19 | AAAA |
| ATOM | 1891 | C   | VAL | A | 258 | 5.695  | 0.993  | -5.228 | 1.00 | 24.77 | AAAA |
| ATOM | 1892 | O   | VAL | A | 258 | 5.806  | 2.220  | -5.241 | 1.00 | 25.72 | AAAA |
| ATOM | 1893 | N   | VAL | A | 259 | 4.650  | 0.352  | -5.738 | 1.00 | 24.90 | AAAA |
| ATOM | 1894 | CA  | VAL | A | 259 | 3.495  | 1.056  | -6.291 | 1.00 | 24.40 | AAAA |
| ATOM | 1895 | CB  | VAL | A | 259 | 3.152  | 0.593  | -7.713 | 1.00 | 24.26 | AAAA |
| ATOM | 1896 | CG1 | VAL | A | 259 | 1.928  | 1.371  | -8.226 | 1.00 | 22.17 | AAAA |
| ATOM | 1897 | CG2 | VAL | A | 259 | 4.344  | 0.801  | -8.628 | 1.00 | 21.85 | AAAA |
| ATOM | 1898 | C   | VAL | A | 259 | 2.351  | 0.653  | -5.368 | 1.00 | 25.42 | AAAA |
| ATOM | 1899 | O   | VAL | A | 259 | 2.018  | -0.528 | -5.274 | 1.00 | 25.59 | AAAA |
| ATOM | 1900 | N   | CYS | A | 260 | 1.752  | 1.623  | -4.685 | 1.00 | 25.57 | AAAA |
| ATOM | 1901 | CA  | CYS | A | 260 | 0.680  | 1.308  | -3.750 | 1.00 | 26.61 | AAAA |
| ATOM | 1902 | CB  | CYS | A | 260 | 1.286  | 0.675  | -2.495 | 1.00 | 25.90 | AAAA |
| ATOM | 1903 | SG  | CYS | A | 260 | 2.509  | 1.742  | -1.683 | 1.00 | 29.42 | AAAA |
| ATOM | 1904 | C   | CYS | A | 260 | -0.113 | 2.538  | -3.330 | 1.00 | 27.15 | AAAA |
| ATOM | 1905 | O   | CYS | A | 260 | 0.221  | 3.664  | -3.702 | 1.00 | 27.13 | AAAA |
| ATOM | 1906 | N   | ARG | A | 261 | -1.164 | 2.306  | -2.547 | 1.00 | 28.36 | AAAA |
| ATOM | 1907 | CA  | ARG | A | 261 | -1.986 | 3.391  | -2.023 | 1.00 | 29.99 | AAAA |
| ATOM | 1908 | CB  | ARG | A | 261 | -3.244 | 2.848  | -1.340 | 1.00 | 31.35 | AAAA |
| ATOM | 1909 | CG  | ARG | A | 261 | -4.237 | 2.168  | -2.258 | 1.00 | 33.82 | AAAA |
| ATOM | 1910 | CD  | ARG | A | 261 | -4.829 | 3.143  | -3.253 | 1.00 | 35.21 | AAAA |
| ATOM | 1911 | NE  | ARG | A | 261 | -5.949 | 2.547  | -3.975 | 1.00 | 36.21 | AAAA |
| ATOM | 1912 | CZ  | ARG | A | 261 | -6.550 | 3.107  | -5.017 | 1.00 | 36.46 | AAAA |
| ATOM | 1913 | NH1 | ARG | A | 261 | -6.138 | 4.283  | -5.470 | 1.00 | 36.95 | AAAA |
| ATOM | 1914 | NH2 | ARG | A | 261 | -7.571 | 2.493  | -5.599 | 1.00 | 37.72 | AAAA |
| ATOM | 1915 | C   | ARG | A | 261 | -1.118 | 4.076  | -0.979 | 1.00 | 30.75 | AAAA |
| ATOM | 1916 | O   | ARG | A | 261 | -0.041 | 3.575  | -0.641 | 1.00 | 29.94 | AAAA |
| ATOM | 1917 | N   | SER | A | 262 | -1.583 | 5.206  | -0.453 | 1.00 | 30.70 | AAAA |
| ATOM | 1918 | CA  | SER | A | 262 | -0.807 | 5.924  | 0.544  | 1.00 | 31.00 | AAAA |
| ATOM | 1919 | CB  | SER | A | 262 | -0.290 | 7.245  | -0.034 | 1.00 | 31.31 | AAAA |
| ATOM | 1920 | OG  | SER | A | 262 | -1.344 | 8.016  | -0.581 | 1.00 | 32.21 | AAAA |
| ATOM | 1921 | C   | SER | A | 262 | -1.526 | 6.182  | 1.868  | 1.00 | 30.92 | AAAA |
| ATOM | 1922 | O   | SER | A | 262 | -1.624 | 7.322  | 2.317  | 1.00 | 31.37 | AAAA |
| ATOM | 1923 | N   | GLY | A | 263 | -2.040 | 5.121  | 2.483  | 1.00 | 30.70 | AAAA |
| ATOM | 1924 | CA  | GLY | A | 263 | -2.669 | 5.277  | 3.779  | 1.00 | 29.85 | AAAA |
| ATOM | 1925 | C   | GLY | A | 263 | -1.510 | 5.663  | 4.680  | 1.00 | 29.40 | AAAA |
| ATOM | 1926 | O   | GLY | A | 263 | -0.367 | 5.287  | 4.394  | 1.00 | 28.65 | AAAA |
| ATOM | 1927 | N   | ALA | A | 264 | -1.787 | 6.404  | 5.751  | 1.00 | 28.11 | AAAA |
| ATOM | 1928 | CA  | ALA | A | 264 | -0.752 | 6.872  | 6.674  | 1.00 | 28.19 | AAAA |
| ATOM | 1929 | CB  | ALA | A | 264 | -1.399 | 7.563  | 7.879  | 1.00 | 27.89 | AAAA |
| ATOM | 1930 | C   | ALA | A | 264 | 0.249  | 5.826  | 7.166  | 1.00 | 27.95 | AAAA |

TABLE 1-continued

ATOMIC COORDINATES OF E. COLI MURG PROTEIN

| ATOM | 1931 | O | ALA | A | 264 | 1.454 | 6.056 | 7.117 | 1.00 | 28.65 | AAAA |
|------|------|-----|-----|---|-----|--------|--------|--------|------|-------|------|
| ATOM | 1932 | N | LEU | A | 265 | −0.239 | 4.693 | 7.656 | 1.00 | 27.93 | AAAA |
| ATOM | 1933 | CA | LEU | A | 265 | 0.662 | 3.659 | 8.158 | 1.00 | 27.76 | AAAA |
| ATOM | 1934 | CB | LEU | A | 265 | −0.141 | 2.524 | 8.798 | 1.00 | 28.60 | AAAA |
| ATOM | 1935 | CG | LEU | A | 265 | −1.049 | 2.984 | 9.947 | 1.00 | 29.56 | AAAA |
| ATOM | 1936 | CD1 | LEU | A | 265 | −1.680 | 1.775 | 10.615 | 1.00 | 28.94 | AAAA |
| ATOM | 1937 | CD2 | LEU | A | 265 | −0.245 | 3.797 | 10.957 | 1.00 | 29.94 | AAAA |
| ATOM | 1938 | C | LEU | A | 265 | 1.566 | 3.116 | 7.053 | 1.00 | 27.53 | AAAA |
| ATOM | 1939 | O | LEU | A | 265 | 2.731 | 2.779 | 7.297 | 1.00 | 25.35 | AAAA |
| ATOM | 1940 | N | THR | A | 266 | 1.026 | 3.043 | 5.841 | 1.00 | 27.19 | AAAA |
| ATOM | 1941 | CA | THR | A | 266 | 1.778 | 2.553 | 4.689 | 1.00 | 27.20 | AAAA |
| ATOM | 1942 | CB | THR | A | 266 | 0.859 | 2.383 | 3.455 | 1.00 | 27.48 | AAAA |
| ATOM | 1943 | OG1 | THR | A | 266 | −0.066 | 1.315 | 3.697 | 1.00 | 27.63 | AAAA |
| ATOM | 1944 | CG2 | THR | A | 266 | 1.683 | 2.059 | 2.202 | 1.00 | 27.00 | AAAA |
| ATOM | 1945 | C | THR | A | 266 | 2.916 | 3.507 | 4.341 | 1.00 | 27.11 | AAAA |
| ATOM | 1946 | O | THR | A | 266 | 4.036 | 3.072 | 4.070 | 1.00 | 26.97 | AAAA |
| ATOM | 1947 | N | VAL | A | 267 | 2.631 | 4.806 | 4.352 | 1.00 | 26.63 | AAAA |
| ATOM | 1948 | CA | VAL | A | 267 | 3.649 | 5.806 | 4.048 | 1.00 | 27.06 | AAAA |
| ATOM | 1949 | CB | VAL | A | 267 | 3.044 | 7.236 | 4.052 | 1.00 | 26.30 | AAAA |
| ATOM | 1950 | CG1 | VAL | A | 267 | 4.146 | 8.289 | 4.011 | 1.00 | 26.39 | AAAA |
| ATOM | 1951 | CG2 | VAL | A | 267 | 2.118 | 7.398 | 2.851 | 1.00 | 25.02 | AAAA |
| ATOM | 1952 | C | VAL | A | 267 | 4.809 | 5.730 | 5.044 | 1.00 | 28.55 | AAAA |
| ATOM | 1953 | O | VAL | A | 267 | 5.973 | 5.806 | 4.653 | 1.00 | 28.56 | AAAA |
| ATOM | 1954 | N | SER | A | 268 | 4.495 | 5.581 | 6.329 | 1.00 | 28.38 | AAAA |
| ATOM | 1955 | CA | SER | A | 268 | 5.537 | 5.492 | 7.351 | 1.00 | 29.48 | AAAA |
| ATOM | 1956 | CB | SER | A | 268 | 4.915 | 5.522 | 8.753 | 1.00 | 29.48 | AAAA |
| ATOM | 1957 | OG | SER | A | 268 | 4.291 | 6.768 | 9.003 | 1.00 | 30.64 | AAAA |
| ATOM | 1958 | C | SER | A | 268 | 6.348 | 4.208 | 7.179 | 1.00 | 28.97 | AAAA |
| ATOM | 1959 | O | SER | A | 268 | 7.557 | 4.181 | 7.399 | 1.00 | 30.06 | AAAA |
| ATOM | 1960 | N | GLU | A | 269 | 5.663 | 3.146 | 6.785 | 1.00 | 28.87 | AAAA |
| ATOM | 1961 | CA | GLU | A | 269 | 6.286 | 1.850 | 6.576 | 1.00 | 29.54 | AAAA |
| ATOM | 1962 | CB | GLU | A | 269 | 5.189 | 0.821 | 6.328 | 1.00 | 29.82 | AAAA |
| ATOM | 1963 | CG | GLU | A | 269 | 5.662 | −0.594 | 6.185 | 1.00 | 31.86 | AAAA |
| ATOM | 1964 | CD | GLU | A | 269 | 4.508 | −1.562 | 6.155 | 1.00 | 31.85 | AAAA |
| ATOM | 1965 | OE1 | GLU | A | 269 | 3.996 | −1.917 | 7.239 | 1.00 | 32.48 | AAAA |
| ATOM | 1966 | OE2 | GLU | A | 269 | 4.100 | −1.956 | 5.048 | 1.00 | 30.84 | AAAA |
| ATOM | 1967 | C | GLU | A | 269 | 7.263 | 1.910 | 5.394 | 1.00 | 29.59 | AAAA |
| ATOM | 1968 | O | GLU | A | 269 | 8.355 | 1.332 | 5.441 | 1.00 | 29.11 | AAAA |
| ATOM | 1969 | N | ILE | A | 270 | 6.867 | 2.616 | 4.340 | 1.00 | 27.88 | AAAA |
| ATOM | 1970 | CA | ILE | A | 270 | 7.711 | 2.763 | 3.158 | 1.00 | 28.64 | AAAA |
| ATOM | 1971 | CB | ILE | A | 270 | 6.968 | 3.520 | 2.028 | 1.00 | 28.20 | AAAA |
| ATOM | 1972 | CG2 | ILE | A | 270 | 7.948 | 3.931 | 0.940 | 1.00 | 28.68 | AAAA |
| ATOM | 1973 | CG1 | ILE | A | 270 | 5.845 | 2.646 | 1.461 | 1.00 | 28.04 | AAAA |
| ATOM | 1974 | CD1 | ILE | A | 270 | 6.318 | 1.366 | 0.805 | 1.00 | 30.11 | AAAA |
| ATOM | 1975 | C | ILE | A | 270 | 8.978 | 3.532 | 3.522 | 1.00 | 28.84 | AAAA |
| ATOM | 1976 | O | ILE | A | 270 | 10.076 | 3.194 | 3.075 | 1.00 | 28.96 | AAAA |
| ATOM | 1977 | N | ALA | A | 271 | 8.818 | 4.568 | 4.340 | 1.00 | 28.51 | AAAA |
| ATOM | 1978 | CA | ALA | A | 271 | 9.952 | 5.374 | 4.768 | 1.00 | 28.79 | AAAA |
| ATOM | 1979 | CB | ALA | A | 271 | 9.462 | 6.576 | 5.572 | 1.00 | 28.12 | AAAA |
| ATOM | 1980 | C | ALA | A | 271 | 10.918 | 4.530 | 5.603 | 1.00 | 29.26 | AAAA |
| ATOM | 1981 | O | ALA | A | 271 | 12.136 | 4.575 | 5.394 | 1.00 | 29.35 | AAAA |
| ATOM | 1982 | N | ALA | A | 272 | 10.370 | 3.755 | 6.534 | 1.00 | 28.79 | AAAA |
| ATOM | 1983 | CA | ALA | A | 272 | 11.187 | 2.904 | 7.397 | 1.00 | 29.79 | AAAA |
| ATOM | 1984 | CB | ALA | A | 272 | 10.301 | 2.207 | 8.430 | 1.00 | 29.28 | AAAA |
| ATOM | 1985 | C | ALA | A | 272 | 11.957 | 1.872 | 6.566 | 1.00 | 30.22 | AAAA |
| ATOM | 1986 | O | ALA | A | 272 | 13.102 | 1.539 | 6.876 | 1.00 | 29.36 | AAAA |
| ATOM | 1987 | N | ALA | A | 273 | 11.327 | 1.377 | 5.503 | 1.00 | 30.03 | AAAA |
| ATOM | 1988 | CA | ALA | A | 273 | 11.961 | 0.394 | 4.628 | 1.00 | 30.65 | AAAA |
| ATOM | 1989 | CB | ALA | A | 273 | 10.914 | −0.306 | 3.782 | 1.00 | 29.48 | AAAA |
| ATOM | 1990 | C | ALA | A | 273 | 13.005 | 1.041 | 3.720 | 1.00 | 31.45 | AAAA |
| ATOM | 1991 | O | ALA | A | 273 | 13.803 | 0.346 | 3.090 | 1.00 | 31.87 | AAAA |
| ATOM | 1992 | N | GLY | A | 274 | 12.998 | 2.368 | 3.662 | 1.00 | 31.20 | AAAA |
| ATOM | 1993 | CA | GLY | A | 274 | 13.937 | 3.078 | 2.814 | 1.00 | 32.26 | AAAA |
| ATOM | 1994 | C | GLY | A | 274 | 13.725 | 2.683 | 1.362 | 1.00 | 32.80 | AAAA |
| ATOM | 1995 | O | GLY | A | 274 | 14.652 | 2.226 | 0.692 | 1.00 | 33.38 | AAAA |
| ATOM | 1996 | N | LEU | A | 275 | 12.501 | 2.862 | 0.873 | 1.00 | 32.88 | AAAA |
| ATOM | 1997 | CA | LEU | A | 275 | 12.169 | 2.494 | −0.497 | 1.00 | 32.70 | AAAA |
| ATOM | 1998 | CB | LEU | A | 275 | 11.266 | 1.262 | −0.502 | 1.00 | 32.79 | AAAA |
| ATOM | 1999 | CG | LEU | A | 275 | 11.869 | −0.138 | −0.431 | 1.00 | 33.70 | AAAA |
| ATOM | 2000 | CD1 | LEU | A | 275 | 10.762 | −1.133 | −0.114 | 1.00 | 33.69 | AAAA |
| ATOM | 2001 | CD2 | LEU | A | 275 | 12.538 | −0.484 | −1.762 | 1.00 | 32.25 | AAAA |
| ATOM | 2002 | C | LEU | A | 275 | 11.479 | 3.568 | −1.324 | 1.00 | 33.39 | AAAA |
| ATOM | 2003 | O | LEU | A | 275 | 10.638 | 4.320 | −0.819 | 1.00 | 32.48 | AAAA |
| ATOM | 2004 | N | PRO | A | 276 | 11.835 | 3.654 | −2.617 | 1.00 | 32.76 | AAAA |
| ATOM | 2005 | CD | PRO | A | 276 | 13.022 | 3.048 | −3.244 | 1.00 | 32.59 | AAAA |
| ATOM | 2006 | CA | PRO | A | 276 | 11.221 | 4.636 | −3.513 | 1.00 | 32.07 | AAAA |
| ATOM | 2007 | CB | PRO | A | 276 | 12.049 | 4.510 | −4.791 | 1.00 | 32.16 | AAAA |

TABLE 1-continued

ATOMIC COORDINATES OF *E. COLI* MURG PROTEIN

| ATOM | 2008 | CG  | PRO | A | 276 | 13.383  | 4.072  | -4.296  | 1.00 | 33.28 | AAAA |
|------|------|-----|-----|---|-----|---------|--------|---------|------|-------|------|
| ATOM | 2009 | C   | PRO | A | 276 | 9.794   | 4.143  | -3.722  | 1.00 | 31.63 | AAAA |
| ATOM | 2010 | O   | PRO | A | 276 | 9.531   | 2.936  | -3.651  | 1.00 | 30.32 | AAAA |
| ATOM | 2011 | N   | ALA | A | 277 | 8.864   | 5.049  | -3.976  | 1.00 | 31.27 | AAAA |
| ATOM | 2012 | CA  | ALA | A | 277 | 7.504   | 4.604  | -4.180  | 1.00 | 30.99 | AAAA |
| ATOM | 2013 | CB  | ALA | A | 277 | 6.764   | 4.558  | -2.842  | 1.00 | 30.75 | AAAA |
| ATOM | 2014 | C   | ALA | A | 277 | 6.722   | 5.450  | -5.163  | 1.00 | 30.92 | AAAA |
| ATOM | 2015 | O   | ALA | A | 277 | 6.948   | 6.652  | -5.295  | 1.00 | 32.61 | AAAA |
| ATOM | 2016 | N   | LEU | A | 278 | 5.809   | 4.796  | -5.865  | 1.00 | 31.01 | AAAA |
| ATOM | 2017 | CA  | LEU | A | 278 | 4.928   | 5.476  | -6.796  | 1.00 | 31.08 | AAAA |
| ATOM | 2018 | CB  | LEU | A | 278 | 4.884   | 4.758  | -8.146  | 1.00 | 31.98 | AAAA |
| ATOM | 2019 | CG  | LEU | A | 278 | 4.135   | 5.526  | -9.241  | 1.00 | 32.77 | AAAA |
| ATOM | 2020 | CD1 | LEU | A | 278 | 4.770   | 6.895  | -9.412  | 1.00 | 34.58 | AAAA |
| ATOM | 2021 | CD2 | LEU | A | 278 | 4.181   | 4.756  | -10.543 | 1.00 | 31.93 | AAAA |
| ATOM | 2022 | C   | LEU | A | 278 | 3.576   | 5.375  | -6.101  | 1.00 | 30.98 | AAAA |
| ATOM | 2023 | O   | LEU | A | 278 | 2.887   | 4.357  | -6.197  | 1.00 | 31.03 | AAAA |
| ATOM | 2024 | N   | PHE | A | 279 | 3.218   | 6.424  | -5.369  | 1.00 | 30.84 | AAAA |
| ATOM | 2025 | CA  | PHE | A | 279 | 1.964   | 6.447  | -4.633  | 1.00 | 29.87 | AAAA |
| ATOM | 2026 | CB  | PHE | A | 279 | 2.051   | 7.460  | -3.489  | 1.00 | 29.31 | AAAA |
| ATOM | 2027 | CG  | PHE | A | 279 | 2.948   | 7.033  | -2.353  | 1.00 | 26.86 | AAAA |
| ATOM | 2028 | CD1 | PHE | A | 279 | 3.961   | 7.870  | -1.902  | 1.00 | 27.25 | AAAA |
| ATOM | 2029 | CD2 | PHE | A | 279 | 2.751   | 5.817  | -1.710  | 1.00 | 26.40 | AAAA |
| ATOM | 2030 | CE1 | PHE | A | 279 | 4.765   | 7.506  | -0.821  | 1.00 | 27.90 | AAAA |
| ATOM | 2031 | CE2 | PHE | A | 279 | 3.549   | 5.439  | -0.630  | 1.00 | 25.57 | AAAA |
| ATOM | 2032 | CZ  | PHE | A | 279 | 4.555   | 6.286  | -0.186  | 1.00 | 25.90 | AAAA |
| ATOM | 2033 | C   | PHE | A | 279 | 0.765   | 6.773  | -5.508  | 1.00 | 30.70 | AAAA |
| ATOM | 2034 | O   | PHE | A | 279 | 0.790   | 7.719  | -6.294  | 1.00 | 30.85 | AAAA |
| ATOM | 2035 | N   | VAL | A | 280 | -0.281  | 5.968  | -5.367  | 1.00 | 31.23 | AAAA |
| ATOM | 2036 | CA  | VAL | A | 280 | -1.523  | 6.161  | -6.101  | 1.00 | 32.57 | AAAA |
| ATOM | 2037 | CB  | VAL | A | 280 | -1.867  | 4.924  | -6.954  | 1.00 | 33.12 | AAAA |
| ATOM | 2038 | CG1 | VAL | A | 280 | -3.196  | 5.122  | -7.661  | 1.00 | 32.63 | AAAA |
| ATOM | 2039 | CG2 | VAL | A | 280 | -0.768  | 4.688  | -7.979  | 1.00 | 33.54 | AAAA |
| ATOM | 2040 | C   | VAL | A | 280 | -2.598  | 6.394  | -5.036  | 1.00 | 33.46 | AAAA |
| ATOM | 2041 | O   | VAL | A | 280 | -3.320  | 5.478  | -4.643  | 1.00 | 32.49 | AAAA |
| ATOM | 2042 | N   | PRO | A | 281 | -2.695  | 7.640  | -4.546  | 1.00 | 34.67 | AAAA |
| ATOM | 2043 | CD  | PRO | A | 281 | -1.917  | 8.789  | -5.036  | 1.00 | 34.47 | AAAA |
| ATOM | 2044 | CA  | PRO | A | 281 | -3.652  | 8.061  | -3.518  | 1.00 | 36.79 | AAAA |
| ATOM | 2045 | CB  | PRO | A | 281 | -3.475  | 9.578  | -3.478  | 1.00 | 36.20 | AAAA |
| ATOM | 2046 | CG  | PRO | A | 281 | -2.060  | 9.772  | -3.909  | 1.00 | 36.53 | AAAA |
| ATOM | 2047 | C   | PRO | A | 281 | -5.097  | 7.676  | -3.801  | 1.00 | 38.44 | AAAA |
| ATOM | 2048 | O   | PRO | A | 281 | -5.564  | 7.763  | -4.936  | 1.00 | 38.62 | AAAA |
| ATOM | 2049 | N   | PHE | A | 282 | -5.800  | 7.237  | -2.763  | 1.00 | 41.21 | AAAA |
| ATOM | 2050 | CA  | PHE | A | 282 | -7.206  | 6.887  | -2.910  | 1.00 | 44.31 | AAAA |
| ATOM | 2051 | CB  | PHE | A | 282 | -7.722  | 6.169  | -1.664  | 1.00 | 45.63 | AAAA |
| ATOM | 2052 | CG  | PHE | A | 282 | -9.142  | 5.697  | -1.785  | 1.00 | 47.68 | AAAA |
| ATOM | 2053 | CD1 | PHE | A | 282 | -9.452  | 4.570  | -2.542  | 1.00 | 48.21 | AAAA |
| ATOM | 2054 | CD2 | PHE | A | 282 | -10.176 | 6.387  | -1.156  | 1.00 | 48.55 | AAAA |
| ATOM | 2055 | CE1 | PHE | A | 282 | -10.772 | 4.136  | -2.673  | 1.00 | 49.11 | AAAA |
| ATOM | 2056 | CE2 | PHE | A | 282 | -11.501 | 5.963  | -1.280  | 1.00 | 49.07 | AAAA |
| ATOM | 2057 | CZ  | PHE | A | 282 | -11.799 | 4.833  | -2.041  | 1.00 | 48.80 | AAAA |
| ATOM | 2058 | C   | PHE | A | 282 | -7.908  | 8.233  | -3.052  | 1.00 | 45.26 | AAAA |
| ATOM | 2059 | O   | PHE | A | 282 | -7.720  | 9.121  | -2.224  | 1.00 | 45.48 | AAAA |
| ATOM | 2060 | N   | GLN | A | 283 | -8.706  | 8.387  | -4.101  | 1.00 | 47.00 | AAAA |
| ATOM | 2061 | CA  | GLN | A | 283 | -9.399  | 9.648  | -4.339  | 1.00 | 48.78 | AAAA |
| ATOM | 2062 | CB  | GLN | A | 283 | -9.958  | 9.677  | -5.768  | 1.00 | 48.98 | AAAA |
| ATOM | 2063 | CG  | GLN | A | 283 | -10.606 | 11.000 | -6.170  | 1.00 | 50.07 | AAAA |
| ATOM | 2064 | CD  | GLN | A | 283 | -9.649  | 12.179 | -6.082  | 1.00 | 50.05 | AAAA |
| ATOM | 2065 | OE1 | GLN | A | 283 | -9.206  | 12.556 | -4.997  | 1.00 | 50.12 | AAAA |
| ATOM | 2066 | NE2 | GLN | A | 283 | -9.321  | 12.762 | -7.230  | 1.00 | 50.62 | AAAA |
| ATOM | 2067 | C   | GLN | A | 283 | -10.519 | 9.918  | -3.335  | 1.00 | 49.60 | AAAA |
| ATOM | 2068 | O   | GLN | A | 283 | -11.317 | 9.035  | -3.018  | 1.00 | 49.68 | AAAA |
| ATOM | 2069 | N   | HIS | A | 284 | -10.558 | 11.151 | -2.838  | 1.00 | 50.76 | AAAA |
| ATOM | 2070 | CA  | HIS | A | 284 | -11.570 | 11.579 | -1.875  | 1.00 | 51.60 | AAAA |
| ATOM | 2071 | CB  | HIS | A | 284 | -11.329 | 10.918 | -0.515  | 1.00 | 52.12 | AAAA |
| ATOM | 2072 | CG  | HIS | A | 284 | -12.436 | 11.140 | 0.469   | 1.00 | 52.63 | AAAA |
| ATOM | 2073 | CD2 | HIS | A | 284 | -13.327 | 10.280 | 1.017   | 1.00 | 52.98 | AAAA |
| ATOM | 2074 | ND1 | HIS | A | 284 | -12.733 | 12.381 | 0.991   | 1.00 | 52.98 | AAAA |
| ATOM | 2075 | CE1 | HIS | A | 284 | -13.758 | 12.276 | 1.817   | 1.00 | 52.69 | AAAA |
| ATOM | 2076 | NE2 | HIS | A | 284 | -14.138 | 11.011 | 1.851   | 1.00 | 52.96 | AAAA |
| ATOM | 2077 | C   | HIS | A | 284 | -11.497 | 13.098 | -1.745  | 1.00 | 52.04 | AAAA |
| ATOM | 2078 | O   | HIS | A | 284 | -10.451 | 13.697 | -2.000  | 1.00 | 52.03 | AAAA |
| ATOM | 2079 | N   | LYS | A | 285 | -12.604 | 13.719 | -1.347  | 1.00 | 52.27 | AAAA |
| ATOM | 2080 | CA  | LYS | A | 285 | -12.653 | 15.171 | -1.210  | 1.00 | 52.70 | AAAA |
| ATOM | 2081 | CB  | LYS | A | 285 | -14.018 | 15.604 | -0.669  | 1.00 | 53.61 | AAAA |
| ATOM | 2082 | CG  | LYS | A | 285 | -14.256 | 17.111 | -0.701  | 1.00 | 55.17 | AAAA |
| ATOM | 2083 | CD  | LYS | A | 285 | -14.503 | 17.634 | -2.122  | 1.00 | 56.00 | AAAA |
| ATOM | 2084 | CE  | LYS | A | 285 | -13.244 | 17.625 | -2.984  | 1.00 | 56.62 | AAAA |

TABLE 1-continued

ATOMIC COORDINATES OF E. COLI MURG PROTEIN

| ATOM | 2085 | NZ | LYS | A | 285 | −13.513 | 18.075 | −4.383 | 1.00 | 56.60 | AAAA |
|---|---|---|---|---|---|---|---|---|---|---|---|
| ATOM | 2086 | C | LYS | A | 285 | −11.552 | 15.746 | −0.319 | 1.00 | 52.35 | AAAA |
| ATOM | 2087 | O | LYS | A | 285 | −10.988 | 16.800 | −0.619 | 1.00 | 51.96 | AAAA |
| ATOM | 2088 | N | ASP | A | 286 | −11.246 | 15.054 | 0.773 | 1.00 | 51.71 | AAAA |
| ATOM | 2089 | CA | ASP | A | 286 | −10.218 | 15.521 | 1.693 | 1.00 | 51.34 | AAAA |
| ATOM | 2090 | CB | ASP | A | 286 | −10.405 | 14.869 | 3.067 | 1.00 | 53.33 | AAAA |
| ATOM | 2091 | CG | ASP | A | 286 | −10.003 | 13.403 | 3.083 | 1.00 | 55.00 | AAAA |
| ATOM | 2092 | OD1 | ASP | A | 286 | −10.412 | 12.648 | 2.174 | 1.00 | 56.57 | AAAA |
| ATOM | 2093 | OD2 | ASP | A | 286 | −9.280 | 13.004 | 4.018 | 1.00 | 56.62 | AAAA |
| ATOM | 2094 | C | ASP | A | 286 | −8.817 | 15.230 | 1.164 | 1.00 | 49.69 | AAAA |
| ATOM | 2095 | O | ASP | A | 286 | −7.840 | 15.829 | 1.616 | 1.00 | 49.71 | AAAA |
| ATOM | 2096 | N | ARG | A | 287 | −8.724 | 14.315 | 0.203 | 1.00 | 47.93 | AAAA |
| ATOM | 2097 | CA | ARG | A | 287 | −7.436 | 13.944 | −0.380 | 1.00 | 45.79 | AAAA |
| ATOM | 2098 | CB | ARG | A | 287 | −6.848 | 15.121 | −1.156 | 1.00 | 45.56 | AAAA |
| ATOM | 2099 | CG | ARG | A | 287 | −7.744 | 15.660 | −2.251 | 1.00 | 45.87 | AAAA |
| ATOM | 2100 | CD | ARG | A | 287 | −7.172 | 16.949 | −2.801 | 1.00 | 45.75 | AAAA |
| ATOM | 2101 | NE | ARG | A | 287 | −5.999 | 16.724 | −3.637 | 1.00 | 46.20 | AAAA |
| ATOM | 2102 | CZ | ARG | A | 287 | −4.981 | 17.573 | −3.733 | 1.00 | 46.22 | AAAA |
| ATOM | 2103 | NH1 | ARG | A | 287 | −4.986 | 18.702 | −3.037 | 1.00 | 46.26 | AAAA |
| ATOM | 2104 | NH2 | ARG | A | 287 | −3.962 | 17.297 | −4.533 | 1.00 | 46.42 | AAAA |
| ATOM | 2105 | C | ARG | A | 287 | −6.464 | 13.533 | 0.722 | 1.00 | 44.13 | AAAA |
| ATOM | 2106 | O | ARG | A | 287 | −5.279 | 13.870 | 0.685 | 1.00 | 43.87 | AAAA |
| ATOM | 2107 | N | GLN | A | 288 | −6.975 | 12.804 | 1.704 | 1.00 | 42.92 | AAAA |
| ATOM | 2108 | CA | GLN | A | 288 | −6.157 | 12.359 | 2.824 | 1.00 | 42.41 | AAAA |
| ATOM | 2109 | CB | GLN | A | 288 | −6.955 | 11.395 | 3.704 | 1.00 | 42.02 | AAAA |
| ATOM | 2110 | CG | GLN | A | 288 | −6.226 | 10.947 | 4.958 | 1.00 | 41.95 | AAAA |
| ATOM | 2111 | CD | GLN | A | 288 | −7.033 | 9.951 | 5.766 | 1.00 | 42.04 | AAAA |
| ATOM | 2112 | OE1 | GLN | A | 288 | −7.356 | 8.860 | 5.288 | 1.00 | 41.14 | AAAA |
| ATOM | 2113 | NE2 | GLN | A | 288 | −7.369 | 10.322 | 6.997 | 1.00 | 41.32 | AAAA |
| ATOM | 2114 | C | GLN | A | 288 | −4.867 | 11.682 | 2.372 | 1.00 | 41.36 | AAAA |
| ATOM | 2115 | O | GLN | A | 288 | −3.772 | 12.113 | 2.734 | 1.00 | 41.61 | AAAA |
| ATOM | 2116 | N | GLN | A | 289 | −4.999 | 10.626 | 1.575 | 1.00 | 41.32 | AAAA |
| ATOM | 2117 | CA | GLN | A | 289 | −3.835 | 9.886 | 1.105 | 1.00 | 40.21 | AAAA |
| ATOM | 2118 | CB | GLN | A | 289 | −4.267 | 8.678 | 0.280 | 1.00 | 39.57 | AAAA |
| ATOM | 2119 | CG | GLN | A | 289 | −5.126 | 7.703 | 1.068 | 1.00 | 37.69 | AAAA |
| ATOM | 2120 | CD | GLN | A | 289 | −4.976 | 6.274 | 0.595 | 1.00 | 37.80 | AAAA |
| ATOM | 2121 | OE1 | GLN | A | 289 | −4.422 | 6.014 | −0.475 | 1.00 | 35.48 | AAAA |
| ATOM | 2122 | NE2 | GLN | A | 289 | −5.478 | 5.337 | 1.388 | 1.00 | 36.57 | AAAA |
| ATOM | 2123 | C | GLN | A | 289 | −2.862 | 10.744 | 0.318 | 1.00 | 40.38 | AAAA |
| ATOM | 2124 | O | GLN | A | 289 | −1.661 | 10.469 | 0.301 | 1.00 | 40.11 | AAAA |
| ATOM | 2125 | N | TYR | A | 290 | −3.373 | 11.782 | −0.335 | 1.00 | 40.27 | AAAA |
| ATOM | 2126 | CA | TYR | A | 290 | −2.504 | 12.678 | −1.081 | 1.00 | 39.93 | AAAA |
| ATOM | 2127 | CB | TYR | A | 290 | −3.316 | 13.715 | −1.860 | 1.00 | 41.72 | AAAA |
| ATOM | 2128 | CG | TYR | A | 290 | −2.473 | 14.873 | −2.352 | 1.00 | 43.41 | AAAA |
| ATOM | 2129 | CD1 | TYR | A | 290 | −1.590 | 14.716 | −3.421 | 1.00 | 44.44 | AAAA |
| ATOM | 2130 | CE1 | TYR | A | 290 | −0.764 | 15.763 | −3.836 | 1.00 | 45.65 | AAAA |
| ATOM | 2131 | CD2 | TYR | A | 290 | −2.513 | 16.109 | −1.709 | 1.00 | 43.91 | AAAA |
| ATOM | 2132 | CE2 | TYR | A | 290 | −1.695 | 17.161 | −2.111 | 1.00 | 45.19 | AAAA |
| ATOM | 2133 | CZ | TYR | A | 290 | −0.821 | 16.981 | −3.174 | 1.00 | 46.54 | AAAA |
| ATOM | 2134 | OH | TYR | A | 290 | 0.003 | 18.014 | −3.566 | 1.00 | 47.98 | AAAA |
| ATOM | 2135 | C | TYR | A | 290 | −1.604 | 13.399 | −0.085 | 1.00 | 39.33 | AAAA |
| ATOM | 2136 | O | TYR | A | 290 | −0.396 | 13.529 | −0.296 | 1.00 | 39.19 | AAAA |
| ATOM | 2137 | N | TRP | A | 291 | −2.202 | 13.871 | 1.005 | 1.00 | 38.32 | AAAA |
| ATOM | 2138 | CA | TRP | A | 291 | −1.451 | 14.585 | 2.025 | 1.00 | 37.84 | AAAA |
| ATOM | 2139 | CB | TRP | A | 291 | −2.409 | 15.307 | 2.979 | 1.00 | 37.98 | AAAA |
| ATOM | 2140 | CG | TRP | A | 291 | −3.211 | 16.366 | 2.286 | 1.00 | 39.40 | AAAA |
| ATOM | 2141 | CD2 | TRP | A | 291 | −2.721 | 17.612 | 1.778 | 1.00 | 39.83 | AAAA |
| ATOM | 2142 | CE2 | TRP | A | 291 | −3.810 | 18.270 | 1.162 | 1.00 | 40.18 | AAAA |
| ATOM | 2143 | CE3 | TRP | A | 291 | −1.467 | 18.238 | 1.781 | 1.00 | 40.07 | AAAA |
| ATOM | 2144 | CD1 | TRP | A | 291 | −4.540 | 16.319 | 1.969 | 1.00 | 38.96 | AAAA |
| ATOM | 2145 | NE1 | TRP | A | 291 | −4.908 | 17.459 | 1.294 | 1.00 | 39.51 | AAAA |
| ATOM | 2146 | CZ2 | TRP | A | 291 | −3.684 | 19.525 | 0.554 | 1.00 | 40.53 | AAAA |
| ATOM | 2147 | CZ3 | TRP | A | 291 | −1.340 | 19.488 | 1.177 | 1.00 | 41.40 | AAAA |
| ATOM | 2148 | CH2 | TRP | A | 291 | −2.446 | 20.116 | 0.572 | 1.00 | 40.92 | AAAA |
| ATOM | 2149 | C | TRP | A | 291 | −0.506 | 13.680 | 2.803 | 1.00 | 36.79 | AAAA |
| ATOM | 2150 | O | TRP | A | 291 | 0.515 | 14.141 | 3.306 | 1.00 | 36.64 | AAAA |
| ATOM | 2151 | N | ASN | A | 292 | −0.841 | 12.397 | 2.907 | 1.00 | 36.82 | AAAA |
| ATOM | 2152 | CA | ASN | A | 292 | 0.030 | 11.467 | 3.619 | 1.00 | 37.08 | AAAA |
| ATOM | 2153 | CB | ASN | A | 292 | −0.658 | 10.116 | 3.842 | 1.00 | 36.47 | AAAA |
| ATOM | 2154 | CG | ASN | A | 292 | −1.841 | 10.203 | 4.783 | 1.00 | 36.02 | AAAA |
| ATOM | 2155 | OD1 | ASN | A | 292 | −1.924 | 11.104 | 5.618 | 1.00 | 35.88 | AAAA |
| ATOM | 2156 | ND2 | ASN | A | 292 | −2.757 | 9.248 | 4.667 | 1.00 | 35.26 | AAAA |
| ATOM | 2157 | C | ASN | A | 292 | 1.302 | 11.246 | 2.803 | 1.00 | 37.41 | AAAA |
| ATOM | 2158 | O | ASN | A | 292 | 2.402 | 11.170 | 3.353 | 1.00 | 36.90 | AAAA |
| ATOM | 2159 | N | ALA | A | 293 | 1.138 | 11.166 | 1.485 | 1.00 | 38.20 | AAAA |
| ATOM | 2160 | CA | ALA | A | 293 | 2.253 | 10.936 | 0.567 | 1.00 | 38.64 | AAAA |
| ATOM | 2161 | CB | ALA | A | 293 | 1.729 | 10.343 | −0.737 | 1.00 | 37.83 | AAAA |

TABLE 1-continued

ATOMIC COORDINATES OF E. COLI MURG PROTEIN

| ATOM | 2162 | C | ALA | A | 293 | 3.085 | 12.176 | 0.267 | 1.00 | 39.51 | AAAA |
|---|---|---|---|---|---|---|---|---|---|---|---|
| ATOM | 2163 | O | ALA | A | 293 | 4.311 | 12.094 | 0.158 | 1.00 | 39.51 | AAAA |
| ATOM | 2164 | N | LEU | A | 294 | 2.422 | 13.321 | 0.137 | 1.00 | 40.40 | AAAA |
| ATOM | 2165 | CA | LEU | A | 294 | 3.101 | 14.575 | −0.169 | 1.00 | 40.96 | AAAA |
| ATOM | 2166 | CB | LEU | A | 294 | 2.166 | 15.757 | 0.101 | 1.00 | 41.41 | AAAA |
| ATOM | 2167 | CG | LEU | A | 294 | 2.666 | 17.155 | −0.272 | 1.00 | 41.36 | AAAA |
| ATOM | 2168 | CD1 | LEU | A | 294 | 3.231 | 17.168 | −1.688 | 1.00 | 41.61 | AAAA |
| ATOM | 2169 | CD2 | LEU | A | 294 | 1.510 | 18.136 | −0.147 | 1.00 | 41.60 | AAAA |
| ATOM | 2170 | C | LEU | A | 294 | 4.419 | 14.762 | 0.585 | 1.00 | 42.04 | AAAA |
| ATOM | 2171 | O | LEU | A | 294 | 5.404 | 15.228 | 0.013 | 1.00 | 42.14 | AAAA |
| ATOM | 2172 | N | PRO | A | 295 | 4.459 | 14.401 | 1.877 | 1.00 | 42.80 | AAAA |
| ATOM | 2173 | CD | PRO | A | 295 | 3.351 | 14.022 | 2.772 | 1.00 | 42.95 | AAAA |
| ATOM | 2174 | CA | PRO | A | 295 | 5.706 | 14.560 | 2.634 | 1.00 | 43.42 | AAAA |
| ATOM | 2175 | CB | PRO | A | 295 | 5.336 | 14.032 | 4.015 | 1.00 | 43.51 | AAAA |
| ATOM | 2176 | CG | PRO | A | 295 | 3.889 | 14.406 | 4.128 | 1.00 | 43.40 | AAAA |
| ATOM | 2177 | C | PRO | A | 295 | 6.900 | 13.813 | 2.022 | 1.00 | 44.05 | AAAA |
| ATOM | 2178 | O | PRO | A | 295 | 8.007 | 14.349 | 1.957 | 1.00 | 44.17 | AAAA |
| ATOM | 2179 | N | LEU | A | 296 | 6.682 | 12.577 | 1.581 | 1.00 | 44.41 | AAAA |
| ATOM | 2180 | CA | LEU | A | 296 | 7.766 | 11.800 | 0.980 | 1.00 | 45.13 | AAAA |
| ATOM | 2181 | CB | LEU | A | 296 | 7.373 | 10.324 | 0.852 | 1.00 | 44.54 | AAAA |
| ATOM | 2182 | CG | LEU | A | 296 | 7.424 | 9.484 | 2.130 | 1.00 | 44.46 | AAAA |
| ATOM | 2183 | CD1 | LEU | A | 296 | 6.951 | 8.069 | 1.840 | 1.00 | 43.91 | AAAA |
| ATOM | 2184 | CD2 | LEU | A | 296 | 8.844 | 9.469 | 2.667 | 1.00 | 44.76 | AAAA |
| ATOM | 2185 | C | LEU | A | 296 | 8.151 | 12.346 | −0.391 | 1.00 | 45.53 | AAAA |
| ATOM | 2186 | O | LEU | A | 296 | 9.333 | 12.406 | −0.732 | 1.00 | 45.28 | AAAA |
| ATOM | 2187 | N | GLU | A | 297 | 7.155 | 12.747 | −1.174 | 1.00 | 46.35 | AAAA |
| ATOM | 2188 | CA | GLU | A | 297 | 7.421 | 13.291 | −2.502 | 1.00 | 47.94 | AAAA |
| ATOM | 2189 | CB | GLU | A | 297 | 6.113 | 13.563 | −3.251 | 1.00 | 48.43 | AAAA |
| ATOM | 2190 | CG | GLU | A | 297 | 6.306 | 14.349 | −4.544 | 1.00 | 49.91 | AAAA |
| ATOM | 2191 | CD | GLU | A | 297 | 5.014 | 14.543 | −5.318 | 1.00 | 51.34 | AAAA |
| ATOM | 2192 | OE1 | GLU | A | 297 | 4.562 | 13.586 | −5.981 | 1.00 | 51.89 | AAAA |
| ATOM | 2193 | OE2 | GLU | A | 297 | 4.446 | 15.655 | −5.257 | 1.00 | 52.41 | AAAA |
| ATOM | 2194 | C | GLU | A | 297 | 8.225 | 14.579 | −2.393 | 1.00 | 48.46 | AAAA |
| ATOM | 2195 | O | GLU | A | 297 | 9.155 | 14.806 | −3.165 | 1.00 | 48.78 | AAAA |
| ATOM | 2196 | N | LYS | A | 298 | 7.860 | 15.421 | −1.431 | 1.00 | 49.07 | AAAA |
| ATOM | 2197 | CA | LYS | A | 298 | 8.556 | 16.685 | −1.226 | 1.00 | 49.76 | AAAA |
| ATOM | 2198 | CB | LYS | A | 298 | 7.914 | 17.468 | −0.077 | 1.00 | 50.85 | AAAA |
| ATOM | 2199 | CG | LYS | A | 298 | 8.644 | 18.753 | 0.277 | 1.00 | 52.14 | AAAA |
| ATOM | 2200 | CD | LYS | A | 298 | 8.032 | 19.429 | 1.492 | 1.00 | 53.44 | AAAA |
| ATOM | 2201 | CE | LYS | A | 298 | 8.820 | 20.675 | 1.882 | 1.00 | 53.80 | AAAA |
| ATOM | 2202 | NZ | LYS | A | 298 | 8.281 | 21.309 | 3.116 | 1.00 | 54.32 | AAAA |
| ATOM | 2203 | C | LYS | A | 298 | 10.022 | 16.420 | −0.908 | 1.00 | 49.36 | AAAA |
| ATOM | 2204 | O | LYS | A | 298 | 10.904 | 17.180 | −1.305 | 1.00 | 50.01 | AAAA |
| ATOM | 2205 | N | ALA | A | 299 | 10.275 | 15.335 | −0.138 | 1.00 | 48.67 | AAAA |
| ATOM | 2206 | CA | ALA | A | 299 | 11.635 | 14.975 | 0.182 | 1.00 | 47.48 | AAAA |
| ATOM | 2207 | CB | ALA | A | 299 | 11.615 | 14.001 | 1.353 | 1.00 | 47.29 | AAAA |
| ATOM | 2208 | C | ALA | A | 299 | 12.354 | 14.356 | −1.009 | 1.00 | 46.69 | AAAA |
| ATOM | 2209 | O | ALA | A | 299 | 13.554 | 14.098 | −0.953 | 1.00 | 46.67 | AAAA |
| ATOM | 2210 | N | GLY | A | 300 | 11.613 | 14.133 | −2.090 | 1.00 | 45.80 | AAAA |
| ATOM | 2211 | CA | GLY | A | 300 | 12.197 | 13.538 | −3.278 | 1.00 | 44.79 | AAAA |
| ATOM | 2212 | C | GLY | A | 300 | 12.399 | 12.042 | −3.119 | 1.00 | 44.04 | AAAA |
| ATOM | 2213 | O | GLY | A | 300 | 13.343 | 11.472 | −3.665 | 1.00 | 44.02 | AAAA |
| ATOM | 2214 | N | ALA | A | 301 | 11.505 | 11.404 | −2.370 | 1.00 | 43.01 | AAAA |
| ATOM | 2215 | CA | ALA | A | 301 | 11.589 | 9.967 | −2.131 | 1.00 | 42.10 | AAAA |
| ATOM | 2216 | CB | ALA | A | 301 | 11.514 | 9.684 | −0.632 | 1.00 | 42.10 | AAAA |
| ATOM | 2217 | C | ALA | A | 301 | 10.484 | 9.209 | −2.858 | 1.00 | 41.88 | AAAA |
| ATOM | 2218 | O | ALA | A | 301 | 10.480 | 7.976 | −2.882 | 1.00 | 41.48 | AAAA |
| ATOM | 2219 | N | ALA | A | 302 | 9.549 | 9.941 | −3.453 | 1.00 | 40.88 | AAAA |
| ATOM | 2220 | CA | ALA | A | 302 | 8.451 | 9.303 | −4.156 | 1.00 | 40.59 | AAAA |
| ATOM | 2221 | CB | ALA | A | 302 | 7.411 | 8.818 | −3.153 | 1.00 | 39.61 | AAAA |
| ATOM | 2222 | C | ALA | A | 302 | 7.786 | 10.197 | −5.191 | 1.00 | 40.72 | AAAA |
| ATOM | 2223 | O | ALA | A | 302 | 8.123 | 11.372 | −5.340 | 1.00 | 40.90 | AAAA |
| ATOM | 2224 | N | LYS | A | 303 | 6.837 | 9.610 | −5.910 | 1.00 | 41.39 | AAAA |
| ATOM | 2225 | CA | LYS | A | 303 | 6.073 | 10.309 | −6.930 | 1.00 | 41.79 | AAAA |
| ATOM | 2226 | CB | LYS | A | 303 | 6.455 | 9.807 | −8.325 | 1.00 | 41.86 | AAAA |
| ATOM | 2227 | CG | LYS | A | 303 | 5.540 | 10.295 | −9.442 | 1.00 | 43.46 | AAAA |
| ATOM | 2228 | CD | LYS | A | 303 | 5.608 | 11.807 | −9.614 | 1.00 | 44.98 | AAAA |
| ATOM | 2229 | CE | LYS | A | 303 | 4.676 | 12.284 | −10.729 | 1.00 | 46.33 | AAAA |
| ATOM | 2230 | NZ | LYS | A | 303 | 4.767 | 13.759 | −10.957 | 1.00 | 46.15 | AAAA |
| ATOM | 2231 | C | LYS | A | 303 | 4.603 | 10.022 | −6.671 | 1.00 | 41.86 | AAAA |
| ATOM | 2232 | O | LYS | A | 303 | 4.219 | 8.873 | −6.441 | 1.00 | 41.54 | AAAA |
| ATOM | 2233 | N | ILE | A | 304 | 3.782 | 11.065 | −6.702 | 1.00 | 41.98 | AAAA |
| ATOM | 2234 | CA | ILE | A | 304 | 2.354 | 10.905 | −6.475 | 1.00 | 42.52 | AAAA |
| ATOM | 2235 | CB | ILE | A | 304 | 1.808 | 11.961 | −5.492 | 1.00 | 42.27 | AAAA |
| ATOM | 2236 | CG2 | ILE | A | 304 | 0.321 | 11.738 | −5.278 | 1.00 | 41.77 | AAAA |
| ATOM | 2237 | CG1 | ILE | A | 304 | 2.554 | 11.889 | −4.159 | 1.00 | 42.76 | AAAA |
| ATOM | 2238 | CD1 | ILE | A | 304 | 2.094 | 12.921 | −3.140 | 1.00 | 41.84 | AAAA |

TABLE 1-continued

ATOMIC COORDINATES OF E. COLI MURG PROTEIN

| | | | | | | | | | | |
|---|---|---|---|---|---|---|---|---|---|---|
| ATOM | 2239 | C | ILE | A | 304 | 1.580 | 11.047 | −7.777 | 1.00 | 43.43 AAAA |
| ATOM | 2240 | O | ILE | A | 304 | 1.818 | 11.969 | −8.555 | 1.00 | 43.89 AAAA |
| ATOM | 2241 | N | ILE | A | 305 | 0.649 | 10.129 | −8.006 | 1.00 | 44.38 AAAA |
| ATOM | 2242 | CA | ILE | A | 305 | −0.177 | 10.164 | −9.199 | 1.00 | 45.28 AAAA |
| ATOM | 2243 | CB | ILE | A | 305 | 0.287 | 9.124 | −10.247 | 1.00 | 44.81 AAAA |
| ATOM | 2244 | CG2 | ILE | A | 305 | −0.610 | 9.188 | −11.478 | 1.00 | 43.86 AAAA |
| ATOM | 2245 | CG1 | ILE | A | 305 | 1.738 | 9.400 | −10.647 | 1.00 | 44.38 AAAA |
| ATOM | 2246 | CD1 | ILE | A | 305 | 2.305 | 8.405 | −11.647 | 1.00 | 45.12 AAAA |
| ATOM | 2247 | C | ILE | A | 305 | −1.620 | 9.870 | −8.807 | 1.00 | 47.13 AAAA |
| ATOM | 2248 | O | ILE | A | 305 | −1.985 | 8.724 | −8.550 | 1.00 | 46.47 AAAA |
| ATOM | 2249 | N | GLU | A | 306 | −2.435 | 10.918 | −8.745 | 1.00 | 49.50 AAAA |
| ATOM | 2250 | CA | GLU | A | 306 | −3.839 | 10.761 | −8.396 | 1.00 | 51.69 AAAA |
| ATOM | 2251 | CB | GLU | A | 306 | −4.430 | 12.110 | −7.987 | 1.00 | 51.85 AAAA |
| ATOM | 2252 | CG | GLU | A | 306 | −3.603 | 12.818 | −6.927 | 1.00 | 51.67 AAAA |
| ATOM | 2253 | CD | GLU | A | 306 | −4.324 | 13.990 | −6.296 | 1.00 | 52.25 AAAA |
| ATOM | 2254 | OE1 | GLU | A | 306 | −5.351 | 13.763 | −5.621 | 1.00 | 52.52 AAAA |
| ATOM | 2255 | OE2 | GLU | A | 306 | −3.861 | 15.135 | −6.472 | 1.00 | 52.12 AAAA |
| ATOM | 2256 | C | GLU | A | 306 | −4.552 | 10.202 | −9.619 | 1.00 | 53.21 AAAA |
| ATOM | 2257 | O | GLU | A | 306 | −4.180 | 10.515 | −10.749 | 1.00 | 53.53 AAAA |
| ATOM | 2258 | N | GLN | A | 307 | −5.570 | 9.376 | −9.393 | 1.00 | 55.39 AAAA |
| ATOM | 2259 | CA | GLN | A | 307 | −6.313 | 8.750 | −10.483 | 1.00 | 57.63 AAAA |
| ATOM | 2260 | CB | GLN | A | 307 | −7.553 | 8.035 | −9.934 | 1.00 | 58.22 AAAA |
| ATOM | 2261 | CG | GLN | A | 307 | −7.213 | 6.925 | −8.937 | 1.00 | 59.17 AAAA |
| ATOM | 2262 | CD | GLN | A | 307 | −8.196 | 5.766 | −8.970 | 1.00 | 59.83 AAAA |
| ATOM | 2263 | OE1 | GLN | A | 307 | −8.110 | 4.840 | −8.160 | 1.00 | 60.26 AAAA |
| ATOM | 2264 | NE2 | GLN | A | 307 | −9.131 | 5.807 | −9.912 | 1.00 | 60.69 AAAA |
| ATOM | 2265 | C | GLN | A | 307 | −6.703 | 9.663 | −11.648 | 1.00 | 58.47 AAAA |
| ATOM | 2266 | O | GLN | A | 307 | −6.774 | 9.208 | −12.791 | 1.00 | 58.81 AAAA |
| ATOM | 2267 | N | PRO | A | 308 | −6.968 | 10.956 | −11.385 | 1.00 | 59.24 AAAA |
| ATOM | 2268 | CD | PRO | A | 308 | −7.113 | 11.674 | −10.105 | 1.00 | 59.76 AAAA |
| ATOM | 2269 | CA | PRO | A | 308 | −7.334 | 11.825 | −12.507 | 1.00 | 59.72 AAAA |
| ATOM | 2270 | CB | PRO | A | 308 | −7.360 | 13.209 | −11.870 | 1.00 | 59.96 AAAA |
| ATOM | 2271 | CG | PRO | A | 308 | −7.896 | 12.914 | −10.510 | 1.00 | 60.00 AAAA |
| ATOM | 2272 | C | PRO | A | 308 | −6.318 | 11.723 | −13.641 | 1.00 | 59.84 AAAA |
| ATOM | 2273 | O | PRO | A | 308 | −6.685 | 11.496 | −14.795 | 1.00 | 60.34 AAAA |
| ATOM | 2274 | N | GLN | A | 309 | −5.042 | 11.881 | −13.305 | 1.00 | 59.45 AAAA |
| ATOM | 2275 | CA | GLN | A | 309 | −3.985 | 11.794 | −14.303 | 1.00 | 58.69 AAAA |
| ATOM | 2276 | CB | GLN | A | 309 | −2.992 | 12.947 | −14.135 | 1.00 | 59.92 AAAA |
| ATOM | 2277 | CG | GLN | A | 309 | −2.082 | 12.838 | −12.920 | 1.00 | 60.97 AAAA |
| ATOM | 2278 | CD | GLN | A | 309 | −1.077 | 13.975 | −12.843 | 1.00 | 61.96 AAAA |
| ATOM | 2279 | OE1 | GLN | A | 309 | −0.180 | 13.974 | −11.997 | 1.00 | 62.79 AAAA |
| ATOM | 2280 | NE2 | GLN | A | 309 | −1.226 | 14.956 | −13.728 | 1.00 | 62.49 AAAA |
| ATOM | 2281 | C | GLN | A | 309 | −3.250 | 10.459 | −14.204 | 1.00 | 57.53 AAAA |
| ATOM | 2282 | O | GLN | A | 309 | −2.078 | 10.358 | −14.567 | 1.00 | 57.67 AAAA |
| ATOM | 2283 | N | LEU | A | 310 | −3.947 | 9.437 | −13.711 | 1.00 | 55.75 AAAA |
| ATOM | 2284 | CA | LEU | A | 310 | −3.364 | 8.107 | −13.570 | 1.00 | 53.92 AAAA |
| ATOM | 2285 | CB | LEU | A | 310 | −3.799 | 7.473 | −12.241 | 1.00 | 53.77 AAAA |
| ATOM | 2286 | CG | LEU | A | 310 | −3.242 | 6.108 | −11.804 | 1.00 | 53.75 AAAA |
| ATOM | 2287 | CD1 | LEU | A | 310 | −3.810 | 4.998 | −12.669 | 1.00 | 54.14 AAAA |
| ATOM | 2288 | CD2 | LEU | A | 310 | −1.727 | 6.123 | −11.876 | 1.00 | 52.88 AAAA |
| ATOM | 2289 | C | LEU | A | 310 | −3.813 | 7.243 | −14.740 | 1.00 | 52.48 AAAA |
| ATOM | 2290 | O | LEU | A | 310 | −5.003 | 7.162 | −15.044 | 1.00 | 53.10 AAAA |
| ATOM | 2291 | N | SER | A | 311 | −2.852 | 6.603 | −15.395 | 1.00 | 49.96 AAAA |
| ATOM | 2292 | CA | SER | A | 311 | −3.136 | 5.748 | −16.540 | 1.00 | 47.96 AAAA |
| ATOM | 2293 | CB | SER | A | 311 | −3.409 | 6.599 | −17.778 | 1.00 | 47.62 AAAA |
| ATOM | 2294 | OG | SER | A | 311 | −2.232 | 7.287 | −18.168 | 1.00 | 46.72 AAAA |
| ATOM | 2295 | C | SER | A | 311 | −1.936 | 4.849 | −16.815 | 1.00 | 46.16 AAAA |
| ATOM | 2296 | O | SER | A | 311 | −0.873 | 5.018 | −16.212 | 1.00 | 45.34 AAAA |
| ATOM | 2297 | N | VAL | A | 312 | −2.113 | 3.907 | −17.736 | 1.00 | 44.77 AAAA |
| ATOM | 2298 | CA | VAL | A | 312 | −1.056 | 2.972 | −18.103 | 1.00 | 43.52 AAAA |
| ATOM | 2299 | CB | VAL | A | 312 | −1.496 | 2.066 | −19.278 | 1.00 | 43.96 AAAA |
| ATOM | 2300 | CG1 | VAL | A | 312 | −0.373 | 1.112 | −19.656 | 1.00 | 43.81 AAAA |
| ATOM | 2301 | CG2 | VAL | A | 312 | −2.740 | 1.285 | −18.892 | 1.00 | 43.95 AAAA |
| ATOM | 2302 | C | VAL | A | 312 | 0.215 | 3.712 | −18.498 | 1.00 | 42.79 AAAA |
| ATOM | 2303 | O | VAL | A | 312 | 1.284 | 3.488 | −17.922 | 1.00 | 41.92 AAAA |
| ATOM | 2304 | N | ASP | A | 313 | 0.096 | 4.610 | −19.470 | 1.00 | 42.00 AAAA |
| ATOM | 2305 | CA | ASP | A | 313 | 1.252 | 5.364 | −19.939 | 1.00 | 41.37 AAAA |
| ATOM | 2306 | CB | ASP | A | 313 | 0.877 | 6.203 | −21.163 | 1.00 | 43.96 AAAA |
| ATOM | 2307 | CG | ASP | A | 313 | 0.506 | 5.345 | −22.357 | 1.00 | 46.32 AAAA |
| ATOM | 2308 | OD1 | ASP | A | 313 | 1.334 | 4.496 | −22.755 | 1.00 | 47.81 AAAA |
| ATOM | 2309 | OD2 | ASP | A | 313 | −0.610 | 5.514 | −22.896 | 1.00 | 48.38 AAAA |
| ATOM | 2310 | C | ASP | A | 313 | 1.856 | 6.249 | −18.864 | 1.00 | 39.53 AAAA |
| ATOM | 2311 | O | ASP | A | 313 | 3.069 | 6.452 | −18.832 | 1.00 | 39.95 AAAA |
| ATOM | 2312 | N | ALA | A | 314 | 1.015 | 6.768 | −17.978 | 1.00 | 38.08 AAAA |
| ATOM | 2313 | CA | ALA | A | 314 | 1.492 | 7.629 | −16.905 | 1.00 | 36.44 AAAA |
| ATOM | 2314 | CB | ALA | A | 314 | 0.306 | 8.233 | −16.156 | 1.00 | 36.79 AAAA |
| ATOM | 2315 | C | ALA | A | 314 | 2.382 | 6.844 | −15.939 | 1.00 | 35.41 AAAA |

TABLE 1-continued

ATOMIC COORDINATES OF E. COLI MURG PROTEIN

| ATOM | 2316 | O | ALA | A | 314 | 3.448 | 7.313 | −15.535 | 1.00 | 35.44 | AAAA |
|---|---|---|---|---|---|---|---|---|---|---|---|
| ATOM | 2317 | N | VAL | A | 315 | 1.940 | 5.648 | −15.569 | 1.00 | 34.29 | AAAA |
| ATOM | 2318 | CA | VAL | A | 315 | 2.708 | 4.809 | −14.652 | 1.00 | 33.44 | AAAA |
| ATOM | 2319 | CB | VAL | A | 315 | 1.886 | 3.592 | −14.169 | 1.00 | 33.40 | AAAA |
| ATOM | 2320 | CG1 | VAL | A | 315 | 2.707 | 2.775 | −13.180 | 1.00 | 33.12 | AAAA |
| ATOM | 2321 | CG2 | VAL | A | 315 | 0.588 | 4.059 | −13.521 | 1.00 | 32.76 | AAAA |
| ATOM | 2322 | C | VAL | A | 315 | 3.970 | 4.295 | −15.328 | 1.00 | 32.88 | AAAA |
| ATOM | 2323 | O | VAL | A | 315 | 5.071 | 4.426 | −14.792 | 1.00 | 32.35 | AAAA |
| ATOM | 2324 | N | ALA | A | 316 | 3.805 | 3.708 | −16.508 | 1.00 | 33.02 | AAAA |
| ATOM | 2325 | CA | ALA | A | 316 | 4.940 | 3.172 | −17.250 | 1.00 | 34.17 | AAAA |
| ATOM | 2326 | CB | ALA | A | 316 | 4.469 | 2.616 | −18.593 | 1.00 | 33.68 | AAAA |
| ATOM | 2327 | C | ALA | A | 316 | 6.002 | 4.252 | −17.456 | 1.00 | 34.75 | AAAA |
| ATOM | 2328 | O | ALA | A | 316 | 7.190 | 4.026 | −17.211 | 1.00 | 34.70 | AAAA |
| ATOM | 2329 | N | ASN | A | 317 | 5.578 | 5.434 | −17.889 | 1.00 | 35.49 | AAAA |
| ATOM | 2330 | CA | ASN | A | 317 | 6.524 | 6.518 | −18.108 | 1.00 | 35.27 | AAAA |
| ATOM | 2331 | CB | ASN | A | 317 | 5.815 | 7.738 | −18.694 | 1.00 | 37.74 | AAAA |
| ATOM | 2332 | CG | ASN | A | 317 | 5.395 | 7.518 | −20.128 | 1.00 | 38.86 | AAAA |
| ATOM | 2333 | OD1 | ASN | A | 317 | 6.099 | 6.855 | −20.889 | 1.00 | 39.80 | AAAA |
| ATOM | 2334 | ND2 | ASN | A | 317 | 4.252 | 8.077 | −20.511 | 1.00 | 40.96 | AAAA |
| ATOM | 2335 | C | ASN | A | 317 | 7.272 | 6.916 | −16.847 | 1.00 | 35.18 | AAAA |
| ATOM | 2336 | O | ASN | A | 317 | 8.458 | 7.239 | −16.904 | 1.00 | 34.36 | AAAA |
| ATOM | 2337 | N | THR | A | 318 | 6.592 | 6.891 | −15.704 | 1.00 | 34.31 | AAAA |
| ATOM | 2338 | CA | THR | A | 318 | 7.251 | 7.262 | −14.456 | 1.00 | 34.35 | AAAA |
| ATOM | 2339 | CB | THR | A | 318 | 6.245 | 7.358 | −13.282 | 1.00 | 34.55 | AAAA |
| ATOM | 2340 | OG1 | THR | A | 318 | 5.353 | 8.460 | −13.498 | 1.00 | 34.46 | AAAA |
| ATOM | 2341 | CG2 | THR | A | 318 | 6.984 | 7.568 | −11.969 | 1.00 | 34.42 | AAAA |
| ATOM | 2342 | C | THR | A | 318 | 8.335 | 6.252 | −14.093 | 1.00 | 34.52 | AAAA |
| ATOM | 2343 | O | THR | A | 318 | 9.464 | 6.624 | −13.783 | 1.00 | 34.11 | AAAA |
| ATOM | 2344 | N | LEU | A | 319 | 7.987 | 4.971 | −14.139 | 1.00 | 35.35 | AAAA |
| ATOM | 2345 | CA | LEU | A | 319 | 8.937 | 3.918 | −13.801 | 1.00 | 35.23 | AAAA |
| ATOM | 2346 | CB | LEU | A | 319 | 8.233 | 2.556 | −13.804 | 1.00 | 34.91 | AAAA |
| ATOM | 2347 | CG | LEU | A | 319 | 7.142 | 2.362 | −12.743 | 1.00 | 34.50 | AAAA |
| ATOM | 2348 | CD1 | LEU | A | 319 | 6.445 | 1.031 | −12.956 | 1.00 | 34.48 | AAAA |
| ATOM | 2349 | CD2 | LEU | A | 319 | 7.761 | 2.432 | −11.351 | 1.00 | 35.13 | AAAA |
| ATOM | 2350 | C | LEU | A | 319 | 10.107 | 3.907 | −14.777 | 1.00 | 35.72 | AAAA |
| ATOM | 2351 | O | LEU | A | 319 | 11.264 | 3.830 | −14.370 | 1.00 | 34.85 | AAAA |
| ATOM | 2352 | N | ALA | A | 320 | 9.801 | 3.997 | −16.067 | 1.00 | 36.49 | AAAA |
| ATOM | 2353 | CA | ALA | A | 320 | 10.832 | 3.989 | −17.096 | 1.00 | 38.10 | AAAA |
| ATOM | 2354 | CB | ALA | A | 320 | 10.192 | 4.051 | −18.472 | 1.00 | 37.58 | AAAA |
| ATOM | 2355 | C | ALA | A | 320 | 11.809 | 5.144 | −16.924 | 1.00 | 38.94 | AAAA |
| ATOM | 2356 | O | ALA | A | 320 | 12.939 | 5.087 | −17.410 | 1.00 | 39.51 | AAAA |
| ATOM | 2357 | N | GLY | A | 321 | 11.375 | 6.186 | −16.219 | 1.00 | 38.88 | AAAA |
| ATOM | 2358 | CA | GLY | A | 321 | 12.224 | 7.347 | −16.013 | 1.00 | 38.68 | AAAA |
| ATOM | 2359 | C | GLY | A | 321 | 13.117 | 7.303 | −14.788 | 1.00 | 38.70 | AAAA |
| ATOM | 2360 | O | GLY | A | 321 | 13.881 | 8.235 | −14.542 | 1.00 | 38.64 | AAAA |
| ATOM | 2361 | N | TRP | A | 322 | 13.028 | 6.230 | −14.010 | 1.00 | 38.46 | AAAA |
| ATOM | 2362 | CA | TRP | A | 322 | 13.855 | 6.108 | −12.820 | 1.00 | 38.53 | AAAA |
| ATOM | 2363 | CB | TRP | A | 322 | 13.008 | 5.688 | −11.611 | 1.00 | 39.41 | AAAA |
| ATOM | 2364 | CG | TRP | A | 322 | 12.047 | 6.748 | −11.146 | 1.00 | 40.01 | AAAA |
| ATOM | 2365 | CD2 | TRP | A | 322 | 10.898 | 6.558 | −10.307 | 1.00 | 40.49 | AAAA |
| ATOM | 2366 | CE2 | TRP | A | 322 | 10.330 | 7.833 | −10.081 | 1.00 | 41.27 | AAAA |
| ATOM | 2367 | CE3 | TRP | A | 322 | 10.295 | 5.436 | −9.722 | 1.00 | 40.54 | AAAA |
| ATOM | 2368 | CD1 | TRP | A | 322 | 12.126 | 8.091 | −11.389 | 1.00 | 39.97 | AAAA |
| ATOM | 2369 | NE1 | TRP | A | 322 | 11.098 | 8.749 | −10.752 | 1.00 | 40.69 | AAAA |
| ATOM | 2370 | CZ2 | TRP | A | 322 | 9.186 | 8.018 | −9.293 | 1.00 | 41.67 | AAAA |
| ATOM | 2371 | CZ3 | TRP | A | 322 | 9.155 | 5.619 | −8.938 | 1.00 | 41.40 | AAAA |
| ATOM | 2372 | CH2 | TRP | A | 322 | 8.615 | 6.903 | −8.732 | 1.00 | 41.69 | AAAA |
| ATOM | 2373 | C | TRP | A | 322 | 14.984 | 5.109 | −13.027 | 1.00 | 38.48 | AAAA |
| ATOM | 2374 | O | TRP | A | 322 | 14.743 | 3.929 | −13.271 | 1.00 | 38.22 | AAAA |
| ATOM | 2375 | N | SER | A | 323 | 16.217 | 5.596 | −12.935 | 1.00 | 38.13 | AAAA |
| ATOM | 2376 | CA | SER | A | 323 | 17.395 | 4.753 | −13.101 | 1.00 | 38.51 | AAAA |
| ATOM | 2377 | CB | SER | A | 323 | 18.573 | 5.590 | −13.591 | 1.00 | 38.51 | AAAA |
| ATOM | 2378 | OG | SER | A | 323 | 18.994 | 6.489 | −12.582 | 1.00 | 39.52 | AAAA |
| ATOM | 2379 | C | SER | A | 323 | 17.739 | 4.150 | −11.744 | 1.00 | 38.37 | AAAA |
| ATOM | 2380 | O | SER | A | 323 | 17.188 | 4.566 | −10.725 | 1.00 | 37.29 | AAAA |
| ATOM | 2381 | N | ARG | A | 324 | 18.647 | 3.178 | −11.723 | 1.00 | 37.86 | AAAA |
| ATOM | 2382 | CA | ARG | A | 324 | 19.030 | 2.563 | −10.461 | 1.00 | 37.82 | AAAA |
| ATOM | 2383 | CB | ARG | A | 324 | 19.924 | 1.341 | −10.688 | 1.00 | 36.36 | AAAA |
| ATOM | 2384 | CG | ARG | A | 324 | 19.130 | 0.077 | −10.959 | 1.00 | 34.77 | AAAA |
| ATOM | 2385 | CD | ARG | A | 324 | 19.978 | −1.176 | −10.849 | 1.00 | 33.04 | AAAA |
| ATOM | 2386 | NE | ARG | A | 324 | 19.143 | −2.372 | −10.888 | 1.00 | 31.23 | AAAA |
| ATOM | 2387 | CZ | ARG | A | 324 | 18.318 | −2.738 | −9.908 | 1.00 | 29.95 | AAAA |
| ATOM | 2388 | NH1 | ARG | A | 324 | 18.228 | −2.006 | −8.808 | 1.00 | 28.46 | AAAA |
| ATOM | 2389 | NH2 | ARG | A | 324 | 17.562 | −3.815 | −10.041 | 1.00 | 28.17 | AAAA |
| ATOM | 2390 | C | ARG | A | 324 | 19.731 | 3.571 | −9.569 | 1.00 | 38.78 | AAAA |
| ATOM | 2391 | O | ARG | A | 324 | 19.532 | 3.578 | −8.354 | 1.00 | 38.12 | AAAA |
| ATOM | 2392 | N | GLU | A | 325 | 20.551 | 4.428 | −10.169 | 1.00 | 39.55 | AAAA |

TABLE 1-continued

ATOMIC COORDINATES OF *E. COLI* MURG PROTEIN

| ATOM | 2393 | CA | GLU | A | 325 | 21.251 | 5.447 | −9.401 | 1.00 | 40.60 | AAAA |
|---|---|---|---|---|---|---|---|---|---|---|---|
| ATOM | 2394 | CB | GLU | A | 325 | 22.208 | 6.236 | −10.304 | 1.00 | 42.74 | AAAA |
| ATOM | 2395 | CG | GLU | A | 325 | 22.642 | 7.589 | −9.745 | 1.00 | 46.19 | AAAA |
| ATOM | 2396 | CD | GLU | A | 325 | 23.197 | 7.517 | −8.327 | 1.00 | 48.10 | AAAA |
| ATOM | 2397 | OE1 | GLU | A | 325 | 23.535 | 8.586 | −7.770 | 1.00 | 49.61 | AAAA |
| ATOM | 2398 | OE2 | GLU | A | 325 | 23.297 | 6.403 | −7.768 | 1.00 | 49.87 | AAAA |
| ATOM | 2399 | C | GLU | A | 325 | 20.214 | 6.380 | −8.784 | 1.00 | 39.88 | AAAA |
| ATOM | 2400 | O | GLU | A | 325 | 20.324 | 6.771 | −7.623 | 1.00 | 39.45 | AAAA |
| ATOM | 2401 | N | THR | A | 326 | 19.202 | 6.725 | −9.572 | 1.00 | 39.89 | AAAA |
| ATOM | 2402 | CA | THR | A | 326 | 18.130 | 7.591 | −9.102 | 1.00 | 40.25 | AAAA |
| ATOM | 2403 | CB | THR | A | 326 | 17.139 | 7.912 | −10.240 | 1.00 | 40.72 | AAAA |
| ATOM | 2404 | OG1 | THR | A | 326 | 17.828 | 8.593 | −11.298 | 1.00 | 42.28 | AAAA |
| ATOM | 2405 | CG2 | THR | A | 326 | 16.006 | 8.795 | −9.730 | 1.00 | 41.64 | AAAA |
| ATOM | 2406 | C | THR | A | 326 | 17.371 | 6.897 | −7.968 | 1.00 | 39.76 | AAAA |
| ATOM | 2407 | O | THR | A | 326 | 17.108 | 7.497 | −6.925 | 1.00 | 39.87 | AAAA |
| ATOM | 2408 | N | LEU | A | 327 | 17.027 | 5.628 | −8.175 | 1.00 | 38.46 | AAAA |
| ATOM | 2409 | CA | LEU | A | 327 | 16.294 | 4.867 | −7.169 | 1.00 | 37.41 | AAAA |
| ATOM | 2410 | CB | LEU | A | 327 | 15.968 | 3.466 | −7.697 | 1.00 | 36.19 | AAAA |
| ATOM | 2411 | CG | LEU | A | 327 | 14.952 | 3.426 | −8.843 | 1.00 | 35.32 | AAAA |
| ATOM | 2412 | CD1 | LEU | A | 327 | 14.802 | 2.002 | −9.370 | 1.00 | 35.07 | AAAA |
| ATOM | 2413 | CD2 | LEU | A | 327 | 13.614 | 3.961 | −8.354 | 1.00 | 34.69 | AAAA |
| ATOM | 2414 | C | LEU | A | 327 | 17.050 | 4.774 | −5.845 | 1.00 | 37.39 | AAAA |
| ATOM | 2415 | O | LEU | A | 327 | 16.437 | 4.807 | −4.778 | 1.00 | 36.80 | AAAA |
| ATOM | 2416 | N | LEU | A | 328 | 18.375 | 4.665 | −5.909 | 1.00 | 37.58 | AAAA |
| ATOM | 2417 | CA | LEU | A | 328 | 19.184 | 4.593 | −4.693 | 1.00 | 38.35 | AAAA |
| ATOM | 2418 | CB | LEU | A | 328 | 20.662 | 4.368 | −5.030 | 1.00 | 38.95 | AAAA |
| ATOM | 2419 | CG | LEU | A | 328 | 21.636 | 4.544 | −3.854 | 1.00 | 40.10 | AAAA |
| ATOM | 2420 | CD1 | LEU | A | 328 | 21.303 | 3.551 | −2.752 | 1.00 | 39.51 | AAAA |
| ATOM | 2421 | CD2 | LEU | A | 328 | 23.068 | 4.349 | −4.330 | 1.00 | 40.30 | AAAA |
| ATOM | 2422 | C | LEU | A | 328 | 19.039 | 5.899 | −3.926 | 1.00 | 38.68 | AAAA |
| ATOM | 2423 | O | LEU | A | 328 | 18.929 | 5.906 | −2.697 | 1.00 | 38.65 | AAAA |
| ATOM | 2424 | N | THR | A | 329 | 19.048 | 7.004 | −4.664 | 1.00 | 39.35 | AAAA |
| ATOM | 2425 | CA | THR | A | 329 | 18.908 | 8.326 | −4.068 | 1.00 | 39.98 | AAAA |
| ATOM | 2426 | CB | THR | A | 329 | 19.002 | 9.433 | −5.136 | 1.00 | 40.05 | AAAA |
| ATOM | 2427 | OG1 | THR | A | 329 | 20.280 | 9.364 | −5.782 | 1.00 | 41.54 | AAAA |
| ATOM | 2428 | CG2 | THR | A | 329 | 18.841 | 10.808 | −4.497 | 1.00 | 40.35 | AAAA |
| ATOM | 2429 | C | THR | A | 329 | 17.557 | 8.425 | −3.367 | 1.00 | 39.68 | AAAA |
| ATOM | 2430 | O | THR | A | 329 | 17.485 | 8.743 | −2.179 | 1.00 | 39.91 | AAAA |
| ATOM | 2431 | N | MET | A | 330 | 16.492 | 8.147 | −4.111 | 1.00 | 39.51 | AAAA |
| ATOM | 2432 | CA | MET | A | 330 | 15.143 | 8.190 | −3.564 | 1.00 | 38.79 | AAAA |
| ATOM | 2433 | CB | MET | A | 330 | 14.141 | 7.718 | −4.617 | 1.00 | 38.09 | AAAA |
| ATOM | 2434 | CG | MET | A | 330 | 14.011 | 8.657 | −5.804 | 1.00 | 36.84 | AAAA |
| ATOM | 2435 | SD | MET | A | 330 | 12.977 | 7.980 | −7.108 | 1.00 | 37.95 | AAAA |
| ATOM | 2436 | CE | MET | A | 330 | 11.332 | 8.342 | −6.478 | 1.00 | 37.58 | AAAA |
| ATOM | 2437 | C | MET | A | 330 | 15.037 | 7.315 | −2.319 | 1.00 | 39.71 | AAAA |
| ATOM | 2438 | O | MET | A | 330 | 14.418 | 7.703 | −1.326 | 1.00 | 39.60 | AAAA |
| ATOM | 2439 | N | ALA | A | 331 | 15.646 | 6.135 | −2.381 | 1.00 | 39.50 | AAAA |
| ATOM | 2440 | CA | ALA | A | 331 | 15.625 | 5.202 | −1.266 | 1.00 | 40.36 | AAAA |
| ATOM | 2441 | CB | ALA | A | 331 | 16.378 | 3.928 | −1.634 | 1.00 | 39.91 | AAAA |
| ATOM | 2442 | C | ALA | A | 331 | 16.243 | 5.843 | −0.032 | 1.00 | 40.98 | AAAA |
| ATOM | 2443 | O | ALA | A | 331 | 15.662 | 5.805 | 1.052 | 1.00 | 40.34 | AAAA |
| ATOM | 2444 | N | GLU | A | 332 | 17.422 | 6.435 | −0.201 | 1.00 | 41.85 | AAAA |
| ATOM | 2445 | CA | GLU | A | 332 | 18.102 | 7.087 | 0.911 | 1.00 | 42.77 | AAAA |
| ATOM | 2446 | CB | GLU | A | 332 | 19.470 | 7.607 | 0.465 | 1.00 | 44.04 | AAAA |
| ATOM | 2447 | CG | GLU | A | 332 | 20.414 | 6.500 | 0.016 | 1.00 | 46.55 | AAAA |
| ATOM | 2448 | CD | GLU | A | 332 | 21.822 | 6.994 | −0.248 | 1.00 | 48.04 | AAAA |
| ATOM | 2449 | OE1 | GLU | A | 332 | 21.981 | 7.923 | −1.065 | 1.00 | 49.87 | AAAA |
| ATOM | 2450 | OE2 | GLU | A | 332 | 22.770 | 6.449 | 0.359 | 1.00 | 49.38 | AAAA |
| ATOM | 2451 | C | GLU | A | 332 | 17.246 | 8.228 | 1.445 | 1.00 | 42.38 | AAAA |
| ATOM | 2452 | O | GLU | A | 332 | 17.156 | 8.435 | 2.653 | 1.00 | 42.66 | AAAA |
| ATOM | 2453 | N | ARG | A | 333 | 16.619 | 8.969 | 0.540 | 1.00 | 41.80 | AAAA |
| ATOM | 2454 | CA | ARG | A | 333 | 15.752 | 10.067 | 0.937 | 1.00 | 42.25 | AAAA |
| ATOM | 2455 | CB | ARG | A | 333 | 15.212 | 10.784 | −0.306 | 1.00 | 43.43 | AAAA |
| ATOM | 2456 | CG | ARG | A | 333 | 16.184 | 11.793 | −0.926 | 1.00 | 45.99 | AAAA |
| ATOM | 2457 | CD | ARG | A | 333 | 15.844 | 12.060 | −2.389 | 1.00 | 48.51 | AAAA |
| ATOM | 2458 | NE | ARG | A | 333 | 16.415 | 13.301 | −2.913 | 1.00 | 50.45 | AAAA |
| ATOM | 2459 | CZ | ARG | A | 333 | 17.703 | 13.631 | −2.859 | 1.00 | 52.07 | AAAA |
| ATOM | 2460 | NH1 | ARG | A | 333 | 18.585 | 12.814 | −2.297 | 1.00 | 52.45 | AAAA |
| ATOM | 2461 | NH2 | ARG | A | 333 | 18.112 | 14.784 | −3.377 | 1.00 | 51.94 | AAAA |
| ATOM | 2462 | C | ARG | A | 333 | 14.594 | 9.519 | 1.777 | 1.00 | 41.39 | AAAA |
| ATOM | 2463 | O | ARG | A | 333 | 14.275 | 10.060 | 2.834 | 1.00 | 40.21 | AAAA |
| ATOM | 2464 | N | ALA | A | 334 | 13.981 | 8.435 | 1.308 | 1.00 | 40.03 | AAAA |
| ATOM | 2465 | CA | ALA | A | 334 | 12.859 | 7.825 | 2.014 | 1.00 | 39.84 | AAAA |
| ATOM | 2466 | CB | ALA | A | 334 | 12.356 | 6.612 | 1.241 | 1.00 | 38.43 | AAAA |
| ATOM | 2467 | C | ALA | A | 334 | 13.239 | 7.417 | 3.435 | 1.00 | 40.05 | AAAA |
| ATOM | 2468 | O | ALA | A | 334 | 12.493 | 7.665 | 4.386 | 1.00 | 40.41 | AAAA |
| ATOM | 2469 | N | ARG | A | 335 | 14.404 | 6.797 | 3.577 | 1.00 | 39.11 | AAAA |

TABLE 1-continued

ATOMIC COORDINATES OF E. COLI MURG PROTEIN

| ATOM | 2470 | CA | ARG | A | 335 | 14.874 | 6.351 | 4.881 | 1.00 | 40.00 | AAAA |
|---|---|---|---|---|---|---|---|---|---|---|---|
| ATOM | 2471 | CB | ARG | A | 335 | 16.137 | 5.506 | 4.719 | 1.00 | 39.98 | AAAA |
| ATOM | 2472 | CG | ARG | A | 335 | 16.631 | 4.865 | 6.000 | 1.00 | 40.54 | AAAA |
| ATOM | 2473 | CD | ARG | A | 335 | 15.653 | 3.814 | 6.501 | 1.00 | 42.08 | AAAA |
| ATOM | 2474 | NE | ARG | A | 335 | 16.263 | 2.949 | 7.507 | 1.00 | 42.95 | AAAA |
| ATOM | 2475 | CZ | ARG | A | 335 | 16.403 | 1.634 | 7.373 | 1.00 | 43.43 | AAAA |
| ATOM | 2476 | NH1 | ARG | A | 335 | 15.972 | 1.024 | 6.274 | 1.00 | 43.17 | AAAA |
| ATOM | 2477 | NH2 | ARG | A | 335 | 16.983 | 0.927 | 8.335 | 1.00 | 43.96 | AAAA |
| ATOM | 2478 | C | ARG | A | 335 | 15.167 | 7.527 | 5.802 | 1.00 | 40.09 | AAAA |
| ATOM | 2479 | O | ARG | A | 335 | 14.877 | 7.479 | 6.997 | 1.00 | 39.35 | AAAA |
| ATOM | 2480 | N | ALA | A | 336 | 15.745 | 8.581 | 5.237 | 1.00 | 40.52 | AAAA |
| ATOM | 2481 | CA | ALA | A | 336 | 16.089 | 9.774 | 6.001 | 1.00 | 41.50 | AAAA |
| ATOM | 2482 | CB | ALA | A | 336 | 16.850 | 10.754 | 5.116 | 1.00 | 41.05 | AAAA |
| ATOM | 2483 | C | ALA | A | 336 | 14.847 | 10.447 | 6.573 | 1.00 | 42.00 | AAAA |
| ATOM | 2484 | O | ALA | A | 336 | 14.905 | 11.087 | 7.621 | 1.00 | 42.49 | AAAA |
| ATOM | 2485 | N | ALA | A | 337 | 13.725 | 10.300 | 5.879 | 1.00 | 42.58 | AAAA |
| ATOM | 2486 | CA | ALA | A | 337 | 12.475 | 10.903 | 6.320 | 1.00 | 42.55 | AAAA |
| ATOM | 2487 | CB | ALA | A | 337 | 11.656 | 11.338 | 5.111 | 1.00 | 42.34 | AAAA |
| ATOM | 2488 | C | ALA | A | 337 | 11.670 | 9.932 | 7.174 | 1.00 | 42.43 | AAAA |
| ATOM | 2489 | O | ALA | A | 337 | 10.444 | 10.000 | 7.209 | 1.00 | 44.01 | AAAA |
| ATOM | 2490 | N | SER | A | 338 | 12.360 | 9.035 | 7.868 | 1.00 | 41.93 | AAAA |
| ATOM | 2491 | CA | SER | A | 338 | 11.686 | 8.053 | 8.708 | 1.00 | 41.12 | AAAA |
| ATOM | 2492 | CB | SER | A | 338 | 12.097 | 6.641 | 8.293 | 1.00 | 40.73 | AAAA |
| ATOM | 2493 | OG | SER | A | 338 | 11.504 | 5.671 | 9.139 | 1.00 | 40.32 | AAAA |
| ATOM | 2494 | C | SER | A | 338 | 11.964 | 8.235 | 10.198 | 1.00 | 40.88 | AAAA |
| ATOM | 2495 | O | SER | A | 338 | 13.042 | 8.674 | 10.594 | 1.00 | 41.46 | AAAA |
| ATOM | 2496 | N | ILE | A | 339 | 10.971 | 7.898 | 11.013 | 1.00 | 40.11 | AAAA |
| ATOM | 2497 | CA | ILE | A | 339 | 11.080 | 7.985 | 12.461 | 1.00 | 39.66 | AAAA |
| ATOM | 2498 | CB | ILE | A | 339 | 10.061 | 8.992 | 13.038 | 1.00 | 39.74 | AAAA |
| ATOM | 2499 | CG2 | ILE | A | 339 | 10.249 | 9.118 | 14.544 | 1.00 | 38.88 | AAAA |
| ATOM | 2500 | CG1 | ILE | A | 339 | 10.249 | 10.354 | 12.361 | 1.00 | 39.75 | AAAA |
| ATOM | 2501 | CD1 | ILE | A | 339 | 9.263 | 11.423 | 12.804 | 1.00 | 40.42 | AAAA |
| ATOM | 2502 | C | ILE | A | 339 | 10.788 | 6.576 | 12.978 | 1.00 | 40.19 | AAAA |
| ATOM | 2503 | O | ILE | A | 339 | 9.653 | 6.102 | 12.923 | 1.00 | 39.97 | AAAA |
| ATOM | 2504 | N | PRO | A | 340 | 11.821 | 5.886 | 13.484 | 1.00 | 40.75 | AAAA |
| ATOM | 2505 | CD | PRO | A | 340 | 13.225 | 6.336 | 13.448 | 1.00 | 40.95 | AAAA |
| ATOM | 2506 | CA | PRO | A | 340 | 11.728 | 4.520 | 14.012 | 1.00 | 40.57 | AAAA |
| ATOM | 2507 | CB | PRO | A | 340 | 13.161 | 4.021 | 13.877 | 1.00 | 41.22 | AAAA |
| ATOM | 2508 | CG | PRO | A | 340 | 13.944 | 5.244 | 14.222 | 1.00 | 41.12 | AAAA |
| ATOM | 2509 | C | PRO | A | 340 | 11.180 | 4.294 | 15.424 | 1.00 | 40.38 | AAAA |
| ATOM | 2510 | O | PRO | A | 340 | 10.841 | 3.163 | 15.776 | 1.00 | 40.48 | AAAA |
| ATOM | 2511 | N | ASP | A | 341 | 11.080 | 5.345 | 16.232 | 1.00 | 39.43 | AAAA |
| ATOM | 2512 | CA | ASP | A | 341 | 10.603 | 5.174 | 17.603 | 1.00 | 38.32 | AAAA |
| ATOM | 2513 | CB | ASP | A | 341 | 11.668 | 5.696 | 18.578 | 1.00 | 38.62 | AAAA |
| ATOM | 2514 | CG | ASP | A | 341 | 12.044 | 7.146 | 18.317 | 1.00 | 39.54 | AAAA |
| ATOM | 2515 | OD1 | ASP | A | 341 | 11.727 | 7.658 | 17.221 | 1.00 | 38.30 | AAAA |
| ATOM | 2516 | OD2 | ASP | A | 341 | 12.668 | 7.771 | 19.209 | 1.00 | 40.07 | AAAA |
| ATOM | 2517 | C | ASP | A | 341 | 9.241 | 5.789 | 17.939 | 1.00 | 37.27 | AAAA |
| ATOM | 2518 | O | ASP | A | 341 | 9.014 | 6.235 | 19.066 | 1.00 | 35.88 | AAAA |
| ATOM | 2519 | N | ALA | A | 342 | 8.329 | 5.789 | 16.971 | 1.00 | 36.20 | AAAA |
| ATOM | 2520 | CA | ALA | A | 342 | 6.996 | 6.349 | 17.181 | 1.00 | 34.98 | AAAA |
| ATOM | 2521 | CB | ALA | A | 342 | 6.150 | 6.156 | 15.927 | 1.00 | 35.84 | AAAA |
| ATOM | 2522 | C | ALA | A | 342 | 6.280 | 5.744 | 18.389 | 1.00 | 34.17 | AAAA |
| ATOM | 2523 | O | ALA | A | 342 | 5.843 | 6.465 | 19.289 | 1.00 | 33.36 | AAAA |
| ATOM | 2524 | N | THR | A | 343 | 6.159 | 4.421 | 18.410 | 1.00 | 33.49 | AAAA |
| ATOM | 2525 | CA | THR | A | 343 | 5.481 | 3.747 | 19.512 | 1.00 | 33.39 | AAAA |
| ATOM | 2526 | CB | THR | A | 343 | 5.567 | 2.211 | 19.362 | 1.00 | 33.34 | AAAA |
| ATOM | 2527 | OG1 | THR | A | 343 | 4.951 | 1.818 | 18.128 | 1.00 | 34.05 | AAAA |
| ATOM | 2528 | CG2 | THR | A | 343 | 4.851 | 1.519 | 20.516 | 1.00 | 33.82 | AAAA |
| ATOM | 2529 | C | THR | A | 343 | 6.067 | 4.155 | 20.865 | 1.00 | 33.89 | AAAA |
| ATOM | 2530 | O | THR | A | 343 | 5.340 | 4.591 | 21.756 | 1.00 | 32.15 | AAAA |
| ATOM | 2531 | N | GLU | A | 344 | 7.383 | 4.027 | 21.007 | 1.00 | 34.87 | AAAA |
| ATOM | 2532 | CA | GLU | A | 344 | 8.055 | 4.379 | 22.257 | 1.00 | 35.80 | AAAA |
| ATOM | 2533 | CB | GLU | A | 344 | 9.553 | 4.054 | 22.177 | 1.00 | 37.79 | AAAA |
| ATOM | 2534 | CG | GLU | A | 344 | 9.892 | 2.570 | 22.029 | 1.00 | 41.45 | AAAA |
| ATOM | 2535 | CD | GLU | A | 344 | 9.963 | 2.101 | 20.581 | 1.00 | 44.16 | AAAA |
| ATOM | 2536 | OE1 | GLU | A | 344 | 10.311 | 0.917 | 20.357 | 1.00 | 45.57 | AAAA |
| ATOM | 2537 | OE2 | GLU | A | 344 | 9.676 | 2.910 | 19.668 | 1.00 | 45.28 | AAAA |
| ATOM | 2538 | C | GLU | A | 344 | 7.886 | 5.856 | 22.590 | 1.00 | 35.95 | AAAA |
| ATOM | 2539 | O | GLU | A | 344 | 7.751 | 6.233 | 23.754 | 1.00 | 35.12 | AAAA |
| ATOM | 2540 | N | ARG | A | 345 | 7.896 | 6.689 | 21.559 | 1.00 | 35.83 | AAAA |
| ATOM | 2541 | CA | ARG | A | 345 | 7.759 | 8.127 | 21.731 | 1.00 | 36.32 | AAAA |
| ATOM | 2542 | CB | ARG | A | 345 | 7.999 | 8.803 | 20.386 | 1.00 | 38.26 | AAAA |
| ATOM | 2543 | CG | ARG | A | 345 | 8.268 | 10.280 | 20.448 | 1.00 | 41.85 | AAAA |
| ATOM | 2544 | CD | ARG | A | 345 | 9.006 | 10.686 | 19.194 | 1.00 | 44.45 | AAAA |
| ATOM | 2545 | NE | ARG | A | 345 | 9.194 | 12.128 | 19.098 | 1.00 | 47.27 | AAAA |
| ATOM | 2546 | CZ | ARG | A | 345 | 9.855 | 12.721 | 18.111 | 1.00 | 47.66 | AAAA |

TABLE 1-continued

ATOMIC COORDINATES OF E. COLI MURG PROTEIN

| ATOM | 2547 | NH1 | ARG | A | 345 | 10.390 | 11.988 | 17.144 | 1.00 | 48.37 | AAAA |
|---|---|---|---|---|---|---|---|---|---|---|---|
| ATOM | 2548 | NH2 | ARG | A | 345 | 9.974 | 14.042 | 18.090 | 1.00 | 48.27 | AAAA |
| ATOM | 2549 | C | ARG | A | 345 | 6.384 | 8.510 | 22.289 | 1.00 | 35.99 | AAAA |
| ATOM | 2550 | O | ARG | A | 345 | 6.285 | 9.209 | 23.302 | 1.00 | 35.24 | AAAA |
| ATOM | 2551 | N | VAL | A | 346 | 5.324 | 8.052 | 21.630 | 1.00 | 34.14 | AAAA |
| ATOM | 2552 | CA | VAL | A | 346 | 3.975 | 8.355 | 22.092 | 1.00 | 33.40 | AAAA |
| ATOM | 2553 | CB | VAL | A | 346 | 2.909 | 7.816 | 21.110 | 1.00 | 33.26 | AAAA |
| ATOM | 2554 | CG1 | VAL | A | 346 | 1.516 | 7.969 | 21.709 | 1.00 | 33.83 | AAAA |
| ATOM | 2555 | CG2 | VAL | A | 346 | 3.005 | 8.565 | 19.793 | 1.00 | 32.47 | AAAA |
| ATOM | 2556 | C | VAL | A | 346 | 3.770 | 7.727 | 23.466 | 1.00 | 33.14 | AAAA |
| ATOM | 2557 | O | VAL | A | 346 | 3.172 | 8.336 | 24.352 | 1.00 | 32.24 | AAAA |
| ATOM | 2558 | N | ALA | A | 347 | 4.280 | 6.510 | 23.643 | 1.00 | 32.01 | AAAA |
| ATOM | 2559 | CA | ALA | A | 347 | 4.159 | 5.813 | 24.917 | 1.00 | 32.80 | AAAA |
| ATOM | 2560 | CB | ALA | A | 347 | 4.831 | 4.447 | 24.839 | 1.00 | 31.97 | AAAA |
| ATOM | 2561 | C | ALA | A | 347 | 4.788 | 6.639 | 26.031 | 1.00 | 33.01 | AAAA |
| ATOM | 2562 | O | ALA | A | 347 | 4.214 | 6.769 | 27.114 | 1.00 | 32.22 | AAAA |
| ATOM | 2563 | N | ASN | A | 348 | 5.968 | 7.193 | 25.758 | 1.00 | 33.65 | AAAA |
| ATOM | 2564 | CA | ASN | A | 348 | 6.681 | 8.009 | 26.738 | 1.00 | 35.77 | AAAA |
| ATOM | 2565 | CB | ASN | A | 348 | 8.078 | 8.382 | 26.228 | 1.00 | 37.45 | AAAA |
| ATOM | 2566 | CG | ASN | A | 348 | 8.996 | 7.183 | 26.119 | 1.00 | 40.90 | AAAA |
| ATOM | 2567 | OD1 | ASN | A | 348 | 8.998 | 6.308 | 26.989 | 1.00 | 43.23 | AAAA |
| ATOM | 2568 | ND2 | ASN | A | 348 | 9.795 | 7.140 | 25.057 | 1.00 | 42.50 | AAAA |
| ATOM | 2569 | C | ASN | A | 348 | 5.912 | 9.281 | 27.074 | 1.00 | 35.43 | AAAA |
| ATOM | 2570 | O | ASN | A | 348 | 5.824 | 9.662 | 28.240 | 1.00 | 34.83 | AAAA |
| ATOM | 2571 | N | GLU | A | 349 | 5.372 | 9.943 | 26.051 | 1.00 | 35.34 | AAAA |
| ATOM | 2572 | CA | GLU | A | 349 | 4.600 | 11.164 | 26.264 | 1.00 | 34.80 | AAAA |
| ATOM | 2573 | CB | GLU | A | 349 | 4.203 | 11.802 | 24.932 | 1.00 | 36.04 | AAAA |
| ATOM | 2574 | CG | GLU | A | 349 | 5.277 | 12.681 | 24.323 | 1.00 | 38.86 | AAAA |
| ATOM | 2575 | CD | GLU | A | 349 | 5.713 | 13.801 | 25.257 | 1.00 | 40.72 | AAAA |
| ATOM | 2576 | OE1 | GLU | A | 349 | 4.836 | 14.458 | 25.860 | 1.00 | 41.85 | AAAA |
| ATOM | 2577 | OE2 | GLU | A | 349 | 6.933 | 14.033 | 25.385 | 1.00 | 42.23 | AAAA |
| ATOM | 2578 | C | GLU | A | 349 | 3.357 | 10.863 | 27.084 | 1.00 | 32.75 | AAAA |
| ATOM | 2579 | O | GLU | A | 349 | 2.962 | 11.658 | 27.932 | 1.00 | 32.53 | AAAA |
| ATOM | 2580 | N | VAL | A | 350 | 2.737 | 9.716 | 26.827 | 1.00 | 31.83 | AAAA |
| ATOM | 2581 | CA | VAL | A | 350 | 1.556 | 9.323 | 27.583 | 1.00 | 31.06 | AAAA |
| ATOM | 2582 | CB | VAL | A | 350 | 0.952 | 8.000 | 27.049 | 1.00 | 31.68 | AAAA |
| ATOM | 2583 | CG1 | VAL | A | 350 | 0.006 | 7.406 | 28.081 | 1.00 | 31.12 | AAAA |
| ATOM | 2584 | CG2 | VAL | A | 350 | 0.205 | 8.260 | 25.753 | 1.00 | 31.66 | AAAA |
| ATOM | 2585 | C | VAL | A | 350 | 1.949 | 9.135 | 29.048 | 1.00 | 30.82 | AAAA |
| ATOM | 2586 | O | VAL | A | 350 | 1.239 | 9.579 | 29.953 | 1.00 | 30.31 | AAAA |
| ATOM | 2587 | N | SER | A | 351 | 3.087 | 8.486 | 29.276 | 1.00 | 29.94 | AAAA |
| ATOM | 2588 | CA | SER | A | 351 | 3.569 | 8.248 | 30.635 | 1.00 | 31.15 | AAAA |
| ATOM | 2589 | CB | SER | A | 351 | 4.830 | 7.378 | 30.610 | 1.00 | 31.12 | AAAA |
| ATOM | 2590 | OG | SER | A | 351 | 5.292 | 7.138 | 31.926 | 1.00 | 32.12 | AAAA |
| ATOM | 2591 | C | SER | A | 351 | 3.880 | 9.558 | 31.351 | 1.00 | 30.90 | AAAA |
| ATOM | 2592 | O | SER | A | 351 | 3.556 | 9.731 | 32.527 | 1.00 | 30.97 | AAAA |
| ATOM | 2593 | N | ARG | A | 352 | 4.511 | 10.478 | 30.633 | 1.00 | 31.65 | AAAA |
| ATOM | 2594 | CA | ARG | A | 352 | 4.873 | 11.771 | 31.193 | 1.00 | 33.50 | AAAA |
| ATOM | 2595 | CB | ARG | A | 352 | 5.681 | 12.572 | 30.172 | 1.00 | 35.69 | AAAA |
| ATOM | 2596 | CG | ARG | A | 352 | 6.406 | 13.776 | 30.753 | 1.00 | 40.36 | AAAA |
| ATOM | 2597 | CD | ARG | A | 352 | 6.877 | 14.713 | 29.652 | 1.00 | 43.61 | AAAA |
| ATOM | 2598 | NE | ARG | A | 352 | 5.742 | 15.305 | 28.947 | 1.00 | 47.26 | AAAA |
| ATOM | 2599 | CZ | ARG | A | 352 | 5.846 | 16.181 | 27.952 | 1.00 | 49.17 | AAAA |
| ATOM | 2600 | NH1 | ARG | A | 352 | 7.043 | 16.575 | 27.532 | 1.00 | 50.34 | AAAA |
| ATOM | 2601 | NH2 | ARG | A | 352 | 4.751 | 16.670 | 27.381 | 1.00 | 49.80 | AAAA |
| ATOM | 2602 | C | ARG | A | 352 | 3.623 | 12.558 | 31.588 | 1.00 | 33.09 | AAAA |
| ATOM | 2603 | O | ARG | A | 352 | 3.570 | 13.159 | 32.660 | 1.00 | 33.61 | AAAA |
| ATOM | 2604 | N | VAL | A | 353 | 2.622 | 12.554 | 30.713 | 1.00 | 32.09 | AAAA |
| ATOM | 2605 | CA | VAL | A | 353 | 1.380 | 13.272 | 30.975 | 1.00 | 32.29 | AAAA |
| ATOM | 2606 | CB | VAL | A | 353 | 0.490 | 13.307 | 29.714 | 1.00 | 31.98 | AAAA |
| ATOM | 2607 | CG1 | VAL | A | 353 | −0.897 | 13.828 | 30.062 | 1.00 | 30.21 | AAAA |
| ATOM | 2608 | CG2 | VAL | A | 353 | 1.129 | 14.200 | 28.665 | 1.00 | 30.41 | AAAA |
| ATOM | 2609 | C | VAL | A | 353 | 0.596 | 12.660 | 32.131 | 1.00 | 32.54 | AAAA |
| ATOM | 2610 | O | VAL | A | 353 | 0.075 | 13.379 | 32.985 | 1.00 | 32.79 | AAAA |
| ATOM | 2611 | N | ALA | A | 354 | 0.513 | 11.335 | 32.159 | 1.00 | 32.97 | AAAA |
| ATOM | 2612 | CA | ALA | A | 354 | −0.206 | 10.650 | 33.224 | 1.00 | 34.65 | AAAA |
| ATOM | 2613 | CB | ALA | A | 354 | −0.157 | 9.145 | 33.007 | 1.00 | 33.53 | AAAA |
| ATOM | 2614 | C | ALA | A | 354 | 0.391 | 11.002 | 34.583 | 1.00 | 35.84 | AAAA |
| ATOM | 2615 | O | ALA | A | 354 | −0.316 | 11.026 | 35.588 | 1.00 | 36.31 | AAAA |
| ATOM | 2616 | N | ARG | A | 355 | 1.694 | 11.271 | 34.609 | 1.00 | 38.21 | AAAA |
| ATOM | 2617 | CA | ARG | A | 355 | 2.382 | 11.619 | 35.852 | 1.00 | 41.12 | AAAA |
| ATOM | 2618 | CB | ARG | A | 355 | 3.637 | 11.141 | 35.802 | 1.00 | 42.43 | AAAA |
| ATOM | 2619 | CG | ARG | A | 355 | 3.976 | 9.627 | 35.701 | 1.00 | 44.93 | AAAA |
| ATOM | 2620 | CD | ARG | A | 355 | 5.416 | 9.190 | 35.457 | 1.00 | 47.18 | AAAA |
| ATOM | 2621 | NE | ARG | A | 355 | 5.482 | 7.790 | 35.042 | 1.00 | 48.82 | AAAA |
| ATOM | 2622 | CZ | ARG | A | 355 | 5.248 | 6.754 | 35.842 | 1.00 | 50.06 | AAAA |
| ATOM | 2623 | NH1 | ARG | A | 355 | 4.939 | 6.947 | 37.117 | 1.00 | 50.68 | AAAA |

TABLE 1-continued

ATOMIC COORDINATES OF *E. COLI* MURG PROTEIN

| ATOM | 2624 | NH2 | ARG | A | 355 | 5.302 | 5.519 | 35.360 | 1.00 | 50.06 | AAAA |
|---|---|---|---|---|---|---|---|---|---|---|---|
| ATOM | 2625 | C | ARG | A | 355 | 2.333 | 13.125 | 36.103 | 1.00 | 42.42 | AAAA |
| ATOM | 2626 | O | ARG | A | 355 | 2.883 | 13.621 | 37.086 | 1.00 | 42.30 | AAAA |
| ATOM | 2627 | N | ALA | A | 356 | 1.660 | 13.840 | 35.203 | 1.00 | 43.60 | AAAA |
| ATOM | 2628 | CA | ALA | A | 356 | 1.504 | 15.289 | 35.294 | 1.00 | 44.67 | AAAA |
| ATOM | 2629 | CB | ALA | A | 356 | 0.702 | 15.651 | 36.547 | 1.00 | 45.12 | AAAA |
| ATOM | 2630 | C | ALA | A | 356 | 2.830 | 16.042 | 35.288 | 1.00 | 45.36 | AAAA |
| ATOM | 2631 | O | ALA | A | 356 | 2.980 | 17.042 | 35.989 | 1.00 | 45.40 | AAAA |
| ATOM | 2632 | N | LEU | A | 357 | 3.779 | 15.569 | 34.487 | 1.00 | 46.31 | AAAA |
| ATOM | 2633 | CA | LEU | A | 357 | 5.093 | 16.201 | 34.392 | 1.00 | 47.87 | AAAA |
| ATOM | 2634 | CB | LEU | A | 357 | 6.122 | 15.212 | 33.843 | 1.00 | 47.62 | AAAA |
| ATOM | 2635 | CG | LEU | A | 357 | 6.465 | 14.017 | 34.734 | 1.00 | 47.58 | AAAA |
| ATOM | 2636 | CD1 | LEU | A | 357 | 7.330 | 13.041 | 33.958 | 1.00 | 47.32 | AAAA |
| ATOM | 2637 | CD2 | LEU | A | 357 | 7.187 | 14.497 | 35.985 | 1.00 | 47.50 | AAAA |
| ATOM | 2638 | C | LEU | A | 357 | 5.064 | 17.438 | 33.505 | 1.00 | 48.87 | AAAA |
| ATOM | 2639 | OT1 | LEU | A | 357 | 5.458 | 18.518 | 33.993 | 1.00 | 50.17 | AAAA |
| ATOM | 2640 | OT2 | LEU | A | 357 | 4.659 | 17.313 | 32.330 | 1.00 | 50.17 | AAAA |
| ATOM | 2641 | CB | LYS | B | 7 | −5.082 | −44.913 | −47.742 | 1.00 | 46.68 | BBBB |
| ATOM | 2642 | CG | LYS | B | 7 | −4.666 | −44.949 | −49.196 | 1.00 | 49.02 | BBBB |
| ATOM | 2643 | CD | LYS | B | 7 | −3.162 | −44.896 | −49.340 | 1.00 | 49.96 | BBBB |
| ATOM | 2644 | CE | LYS | B | 7 | −2.769 | −45.054 | −50.794 | 1.00 | 50.91 | BBBB |
| ATOM | 2645 | NZ | LYS | B | 7 | −1.300 | −45.222 | −50.954 | 1.00 | 52.39 | BBBB |
| ATOM | 2646 | C | LYS | B | 7 | −6.742 | −45.658 | −46.035 | 1.00 | 43.87 | BBBB |
| ATOM | 2647 | O | LYS | B | 7 | −7.135 | −44.760 | −45.287 | 1.00 | 43.90 | BBBB |
| ATOM | 2648 | N | LYS | B | 7 | −7.490 | −44.434 | −48.090 | 1.00 | 46.26 | BBBB |
| ATOM | 2649 | CA | LYS | B | 7 | −6.512 | −45.403 | −47.519 | 1.00 | 45.28 | BBBB |
| ATOM | 2650 | N | ARG | B | 8 | −6.486 | −46.895 | −45.620 | 1.00 | 41.24 | BBBB |
| ATOM | 2651 | CA | ARG | B | 8 | −6.682 | −47.303 | −44.240 | 1.00 | 38.63 | BBBB |
| ATOM | 2652 | CB | ARG | B | 8 | −7.493 | −48.600 | −44.201 | 1.00 | 40.59 | BBBB |
| ATOM | 2653 | CG | ARG | B | 8 | −8.927 | −48.466 | −44.677 | 1.00 | 43.69 | BBBB |
| ATOM | 2654 | CD | ARG | B | 8 | −9.417 | −49.774 | −45.269 | 1.00 | 46.42 | BBBB |
| ATOM | 2655 | NE | ARG | B | 8 | −10.866 | −49.789 | −45.425 | 1.00 | 50.16 | BBBB |
| ATOM | 2656 | CZ | ARG | B | 8 | −11.722 | −49.833 | −44.408 | 1.00 | 51.89 | BBBB |
| ATOM | 2657 | NH1 | ARG | B | 8 | −11.268 | −49.869 | −43.165 | 1.00 | 52.20 | BBBB |
| ATOM | 2658 | NH2 | ARG | B | 8 | −13.031 | −49.841 | −44.631 | 1.00 | 53.20 | BBBB |
| ATOM | 2659 | C | ARG | B | 8 | −5.371 | −47.512 | −43.495 | 1.00 | 35.87 | BBBB |
| ATOM | 2660 | O | ARG | B | 8 | −4.474 | −48.206 | −43.973 | 1.00 | 34.76 | BBBB |
| ATOM | 2661 | N | LEU | B | 9 | −5.272 | −46.899 | −42.321 | 1.00 | 32.91 | BBBB |
| ATOM | 2662 | CA | LEU | B | 9 | −4.094 | −47.039 | −41.477 | 1.00 | 30.88 | BBBB |
| ATOM | 2663 | CB | LEU | B | 9 | −3.390 | −45.694 | −41.278 | 1.00 | 30.40 | BBBB |
| ATOM | 2664 | CG | LEU | B | 9 | −2.381 | −45.626 | −40.119 | 1.00 | 29.02 | BBBB |
| ATOM | 2665 | CD1 | LEU | B | 9 | −1.157 | −46.466 | −40.442 | 1.00 | 29.47 | BBBB |
| ATOM | 2666 | CD2 | LEU | B | 9 | −1.975 | −44.178 | −39.873 | 1.00 | 29.56 | BBBB |
| ATOM | 2667 | C | LEU | B | 9 | −4.513 | −47.562 | −40.115 | 1.00 | 29.67 | BBBB |
| ATOM | 2668 | O | LEU | B | 9 | −5.505 | −47.101 | −39.543 | 1.00 | 28.43 | BBBB |
| ATOM | 2669 | N | MET | B | 10 | −3.772 | −48.541 | −39.604 | 1.00 | 27.75 | BBBB |
| ATOM | 2670 | CA | MET | B | 10 | −4.048 | −49.055 | −38.275 | 1.00 | 26.66 | BBBB |
| ATOM | 2671 | CB | MET | B | 10 | −4.268 | −50.571 | −38.274 | 1.00 | 27.09 | BBBB |
| ATOM | 2672 | CG | MET | B | 10 | −4.496 | −51.113 | −36.869 | 1.00 | 28.55 | BBBB |
| ATOM | 2673 | SD | MET | B | 10 | −5.474 | −52.612 | −36.799 | 1.00 | 29.60 | BBBB |
| ATOM | 2674 | CE | MET | B | 10 | −7.126 | −51.913 | −36.618 | 1.00 | 29.41 | BBBB |
| ATOM | 2675 | C | MET | B | 10 | −2.826 | −48.691 | −37.448 | 1.00 | 25.08 | BBBB |
| ATOM | 2676 | O | MET | B | 10 | −1.690 | −48.971 | −37.839 | 1.00 | 24.38 | BBBB |
| ATOM | 2677 | N | VAL | B | 11 | −3.062 | −48.037 | −36.317 | 1.00 | 23.45 | BBBB |
| ATOM | 2678 | CA | VAL | B | 11 | −1.982 | −47.605 | −35.449 | 1.00 | 23.16 | BBBB |
| ATOM | 2679 | CB | VAL | B | 11 | −2.159 | −46.116 | −35.029 | 1.00 | 23.01 | BBBB |
| ATOM | 2680 | CG1 | VAL | B | 11 | −0.971 | −45.666 | −34.184 | 1.00 | 20.91 | BBBB |
| ATOM | 2681 | CG2 | VAL | B | 11 | −2.305 | −45.225 | −36.276 | 1.00 | 23.82 | BBBB |
| ATOM | 2682 | C | VAL | B | 11 | −1.935 | −48.461 | −34.184 | 1.00 | 23.59 | BBBB |
| ATOM | 2683 | O | VAL | B | 11 | −2.962 | −48.712 | −33.567 | 1.00 | 23.24 | BBBB |
| ATOM | 2684 | N | MET | B | 12 | −0.734 | −48.902 | −33.817 | 1.00 | 23.68 | BBBB |
| ATOM | 2685 | CA | MET | B | 12 | −0.523 | −49.707 | −32.613 | 1.00 | 24.54 | BBBB |
| ATOM | 2686 | CB | MET | B | 12 | 0.192 | −51.019 | −32.971 | 1.00 | 24.28 | BBBB |
| ATOM | 2687 | CG | MET | B | 12 | −0.402 | −51.726 | −34.188 | 1.00 | 25.19 | BBBB |
| ATOM | 2688 | SD | MET | B | 12 | 0.399 | −53.284 | −34.669 | 1.00 | 26.54 | BBBB |
| ATOM | 2689 | CE | MET | B | 12 | 1.990 | −52.691 | −35.289 | 1.00 | 22.99 | BBBB |
| ATOM | 2690 | C | MET | B | 12 | 0.361 | −48.840 | −31.720 | 1.00 | 25.31 | BBBB |
| ATOM | 2691 | O | MET | B | 12 | 1.546 | −48.645 | −32.006 | 1.00 | 23.88 | BBBB |
| ATOM | 2692 | N | ALA | B | 13 | −0.224 | −48.292 | −30.657 | 1.00 | 27.08 | BBBB |
| ATOM | 2693 | CA | ALA | B | 13 | 0.508 | −47.410 | −29.752 | 1.00 | 29.43 | BBBB |
| ATOM | 2694 | CB | ALA | B | 13 | 0.747 | −46.074 | −30.429 | 1.00 | 28.82 | BBBB |
| ATOM | 2695 | C | ALA | B | 13 | −0.239 | −47.192 | −28.436 | 1.00 | 31.80 | BBBB |
| ATOM | 2696 | O | ALA | B | 13 | −1.143 | −46.350 | −28.352 | 1.00 | 32.16 | BBBB |
| ATOM | 2697 | N | GLY | B | 14 | 0.150 | −47.934 | −27.405 | 1.00 | 32.46 | BBBB |
| ATOM | 2698 | CA | GLY | B | 14 | −0.513 | −47.804 | −26.120 | 1.00 | 33.82 | BBBB |
| ATOM | 2699 | C | GLY | B | 14 | −0.107 | −46.595 | −25.299 | 1.00 | 34.82 | BBBB |
| ATOM | 2700 | O | GLY | B | 14 | 0.975 | −46.040 | −25.479 | 1.00 | 35.47 | BBBB |

TABLE 1-continued

ATOMIC COORDINATES OF E. COLI MURG PROTEIN

| ATOM | 2701 | N   | GLY | B | 15 | −0.986 | −46.188 | −24.385 | 1.00 | 35.56 | BBBB |
|------|------|-----|-----|---|----|--------|---------|---------|------|-------|------|
| ATOM | 2702 | CA  | GLY | B | 15 | −0.700 | −45.047 | −23.536 | 1.00 | 36.08 | BBBB |
| ATOM | 2703 | C   | GLY | B | 15 | 0.539  | −45.254 | −22.683 | 1.00 | 36.84 | BBBB |
| ATOM | 2704 | O   | GLY | B | 15 | 1.293  | −44.311 | −22.426 | 1.00 | 36.03 | BBBB |
| ATOM | 2705 | N   | THR | B | 16 | 0.755  | −46.488 | −22.240 | 1.00 | 36.65 | BBBB |
| ATOM | 2706 | CA  | THR | B | 16 | 1.920  | −46.787 | −21.421 | 1.00 | 38.51 | BBBB |
| ATOM | 2707 | CB  | THR | B | 16 | 1.926  | −48.258 | −20.974 | 1.00 | 38.51 | BBBB |
| ATOM | 2708 | OG1 | THR | B | 16 | 0.686  | −48.558 | −20.321 | 1.00 | 38.39 | BBBB |
| ATOM | 2709 | CG2 | THR | B | 16 | 3.075  | −48.518 | −20.005 | 1.00 | 39.11 | BBBB |
| ATOM | 2710 | C   | THR | B | 16 | 3.158  | −46.497 | −22.264 | 1.00 | 38.35 | BBBB |
| ATOM | 2711 | O   | THR | B | 16 | 3.191  | −46.798 | −23.460 | 1.00 | 39.90 | BBBB |
| ATOM | 2712 | N   | GLY | B | 17 | 4.168  | −45.897 | −21.649 | 1.00 | 37.68 | BBBB |
| ATOM | 2713 | CA  | GLY | B | 17 | 5.367  | −45.567 | −22.392 | 1.00 | 36.57 | BBBB |
| ATOM | 2714 | C   | GLY | B | 17 | 5.161  | −44.303 | −23.211 | 1.00 | 35.56 | BBBB |
| ATOM | 2715 | O   | GLY | B | 17 | 6.079  | −43.843 | −23.890 | 1.00 | 35.03 | BBBB |
| ATOM | 2716 | N   | GLY | B | 18 | 3.949  | −43.752 | −23.150 | 1.00 | 33.83 | BBBB |
| ATOM | 2717 | CA  | GLY | B | 18 | 3.631  | −42.529 | −23.872 | 1.00 | 33.48 | BBBB |
| ATOM | 2718 | C   | GLY | B | 18 | 3.825  | −42.593 | −25.378 | 1.00 | 33.12 | BBBB |
| ATOM | 2719 | O   | GLY | B | 18 | 4.345  | −41.650 | −25.984 | 1.00 | 35.38 | BBBB |
| ATOM | 2720 | N   | HIS | B | 19 | 3.416  | −43.699 | −25.988 | 1.00 | 30.26 | BBBB |
| ATOM | 2721 | CA  | HIS | B | 19 | 3.548  | −43.865 | −27.435 | 1.00 | 28.22 | BBBB |
| ATOM | 2722 | CB  | HIS | B | 19 | 3.772  | −45.349 | −27.779 | 1.00 | 25.81 | BBBB |
| ATOM | 2723 | CG  | HIS | B | 19 | 4.957  | −45.966 | −27.094 | 1.00 | 25.35 | BBBB |
| ATOM | 2724 | CD2 | HIS | B | 19 | 6.281  | −45.694 | −27.184 | 1.00 | 24.18 | BBBB |
| ATOM | 2725 | ND1 | HIS | B | 19 | 4.845  | −47.025 | −26.217 | 1.00 | 24.57 | BBBB |
| ATOM | 2726 | CE1 | HIS | B | 19 | 6.046  | −47.380 | −25.798 | 1.00 | 23.08 | BBBB |
| ATOM | 2727 | NE2 | HIS | B | 19 | 6.936  | −46.589 | −26.369 | 1.00 | 25.51 | BBBB |
| ATOM | 2728 | C   | HIS | B | 19 | 2.280  | −43.370 | −28.144 | 1.00 | 27.91 | BBBB |
| ATOM | 2729 | O   | HIS | B | 19 | 2.300  | −43.049 | −29.337 | 1.00 | 26.91 | BBBB |
| ATOM | 2730 | N   | VAL | B | 20 | 1.180  | −43.310 | −27.402 | 1.00 | 27.65 | BBBB |
| ATOM | 2731 | CA  | VAL | B | 20 | −0.098 | −42.894 | −27.965 | 1.00 | 27.77 | BBBB |
| ATOM | 2732 | CB  | VAL | B | 20 | −1.248 | −43.080 | −26.942 | 1.00 | 28.57 | BBBB |
| ATOM | 2733 | CG1 | VAL | B | 20 | −1.082 | −42.114 | −25.787 | 1.00 | 30.03 | BBBB |
| ATOM | 2734 | CG2 | VAL | B | 20 | −2.602 | −42.873 | −27.631 | 1.00 | 26.82 | BBBB |
| ATOM | 2735 | C   | VAL | B | 20 | −0.140 | −41.452 | −28.470 | 1.00 | 27.57 | BBBB |
| ATOM | 2736 | O   | VAL | B | 20 | −0.771 | −41.172 | −29.486 | 1.00 | 27.12 | BBBB |
| ATOM | 2737 | N   | PHE | B | 21 | 0.528  | −40.543 | −27.770 | 1.00 | 28.03 | BBBB |
| ATOM | 2738 | CA  | PHE | B | 21 | 0.517  | −39.136 | −28.160 | 1.00 | 29.00 | BBBB |
| ATOM | 2739 | CB  | PHE | B | 21 | 1.215  | −38.289 | −27.094 | 1.00 | 30.27 | BBBB |
| ATOM | 2740 | CG  | PHE | B | 21 | 0.565  | −38.383 | −25.746 | 1.00 | 33.59 | BBBB |
| ATOM | 2741 | CD1 | PHE | B | 21 | −0.764 | −37.999 | −25.578 | 1.00 | 33.84 | BBBB |
| ATOM | 2742 | CD2 | PHE | B | 21 | 1.256  | −38.909 | −24.659 | 1.00 | 35.22 | BBBB |
| ATOM | 2743 | CE1 | PHE | B | 21 | −1.397 | −38.142 | −24.350 | 1.00 | 35.17 | BBBB |
| ATOM | 2744 | CE2 | PHE | B | 21 | 0.630  | −39.057 | −23.422 | 1.00 | 36.08 | BBBB |
| ATOM | 2745 | CZ  | PHE | B | 21 | −0.700 | −38.673 | −23.269 | 1.00 | 35.65 | BBBB |
| ATOM | 2746 | C   | PHE | B | 21 | 1.129  | −38.898 | −29.535 | 1.00 | 28.53 | BBBB |
| ATOM | 2747 | O   | PHE | B | 21 | 0.521  | −38.236 | −30.378 | 1.00 | 28.69 | BBBB |
| ATOM | 2748 | N   | PRO | B | 22 | 2.336  | −39.430 | −29.781 | 1.00 | 27.41 | BBBB |
| ATOM | 2749 | CD  | PRO | B | 22 | 3.251  | −40.074 | −28.819 | 1.00 | 27.82 | BBBB |
| ATOM | 2750 | CA  | PRO | B | 22 | 2.986  | −39.252 | −31.086 | 1.00 | 26.12 | BBBB |
| ATOM | 2751 | CB  | PRO | B | 22 | 4.362  | −39.884 | −30.883 | 1.00 | 27.48 | BBBB |
| ATOM | 2752 | CG  | PRO | B | 22 | 4.594  | −39.757 | −29.403 | 1.00 | 28.99 | BBBB |
| ATOM | 2753 | C   | PRO | B | 22 | 2.188  | −39.972 | −32.176 | 1.00 | 26.37 | BBBB |
| ATOM | 2754 | O   | PRO | B | 22 | 2.129  | −39.522 | −33.321 | 1.00 | 24.40 | BBBB |
| ATOM | 2755 | N   | GLY | B | 23 | 1.585  | −41.102 | −31.807 | 1.00 | 24.71 | BBBB |
| ATOM | 2756 | CA  | GLY | B | 23 | 0.787  | −41.864 | −32.752 | 1.00 | 25.07 | BBBB |
| ATOM | 2757 | C   | GLY | B | 23 | −0.459 | −41.088 | −33.144 | 1.00 | 25.00 | BBBB |
| ATOM | 2758 | O   | GLY | B | 23 | −0.913 | −41.144 | −34.295 | 1.00 | 23.40 | BBBB |
| ATOM | 2759 | N   | LEU | B | 24 | −1.014 | −40.366 | −32.176 | 1.00 | 24.65 | BBBB |
| ATOM | 2760 | CA  | LEU | B | 24 | −2.201 | −39.551 | −32.401 | 1.00 | 25.32 | BBBB |
| ATOM | 2761 | CB  | LEU | B | 24 | −2.732 | −39.017 | −31.064 | 1.00 | 25.08 | BBBB |
| ATOM | 2762 | CG  | LEU | B | 24 | −3.594 | −39.997 | −30.264 | 1.00 | 23.58 | BBBB |
| ATOM | 2763 | CD1 | LEU | B | 24 | −3.823 | −39.482 | −28.828 | 1.00 | 25.41 | BBBB |
| ATOM | 2764 | CD2 | LEU | B | 24 | −4.919 | −40.192 | −30.998 | 1.00 | 24.78 | BBBB |
| ATOM | 2765 | C   | LEU | B | 24 | −1.843 | −38.397 | −33.336 | 1.00 | 25.69 | BBBB |
| ATOM | 2766 | O   | LEU | B | 24 | −2.634 | −38.017 | −34.204 | 1.00 | 25.99 | BBBB |
| ATOM | 2767 | N   | ALA | B | 25 | −0.644 | −37.850 | −33.164 | 1.00 | 24.89 | BBBB |
| ATOM | 2768 | CA  | ALA | B | 25 | −0.197 | −36.754 | −34.013 | 1.00 | 25.94 | BBBB |
| ATOM | 2769 | CB  | ALA | B | 25 | 1.195  | −36.278 | −33.590 | 1.00 | 25.12 | BBBB |
| ATOM | 2770 | C   | ALA | B | 25 | −0.171 | −37.207 | −35.469 | 1.00 | 27.14 | BBBB |
| ATOM | 2771 | O   | ALA | B | 25 | −0.626 | −36.483 | −36.354 | 1.00 | 27.46 | BBBB |
| ATOM | 2772 | N   | VAL | B | 26 | 0.368  | −38.403 | −35.709 | 1.00 | 26.50 | BBBB |
| ATOM | 2773 | CA  | VAL | B | 26 | 0.466  | −38.955 | −37.056 | 1.00 | 25.70 | BBBB |
| ATOM | 2774 | CB  | VAL | B | 26 | 1.373  | −40.226 | −37.081 | 1.00 | 26.22 | BBBB |
| ATOM | 2775 | CG1 | VAL | B | 26 | 1.410  | −40.833 | −38.479 | 1.00 | 26.25 | BBBB |
| ATOM | 2776 | CG2 | VAL | B | 26 | 2.778  | −39.861 | −36.631 | 1.00 | 24.56 | BBBB |
| ATOM | 2777 | C   | VAL | B | 26 | −0.908 | −39.310 | −37.612 | 1.00 | 26.20 | BBBB |

TABLE 1-continued

ATOMIC COORDINATES OF *E. COLI* MURG PROTEIN

| ATOM | 2778 | O | VAL | B | 26 | −1.178 | −39.091 | −38.796 | 1.00 | 25.87 | BBBB |
|------|------|-----|-----|---|----|--------|---------|---------|------|-------|------|
| ATOM | 2779 | N | ALA | B | 27 | −1.777 | −39.851 | −36.764 | 1.00 | 24.68 | BBBB |
| ATOM | 2780 | CA | ALA | B | 27 | −3.116 | −40.222 | −37.199 | 1.00 | 26.15 | BBBB |
| ATOM | 2781 | CB | ALA | B | 27 | −3.868 | −40.909 | −36.066 | 1.00 | 26.23 | BBBB |
| ATOM | 2782 | C | ALA | B | 27 | −3.888 | −38.984 | −37.661 | 1.00 | 27.60 | BBBB |
| ATOM | 2783 | O | ALA | B | 27 | −4.492 | −38.985 | −38.736 | 1.00 | 27.05 | BBBB |
| ATOM | 2784 | N | HIS | B | 28 | −3.864 | −37.933 | −36.847 | 1.00 | 27.68 | BBBB |
| ATOM | 2785 | CA | HIS | B | 28 | −4.574 | −36.702 | −37.190 | 1.00 | 29.32 | BBBB |
| ATOM | 2786 | CB | HIS | B | 28 | −4.498 | −35.693 | −36.039 | 1.00 | 27.05 | BBBB |
| ATOM | 2787 | CG | HIS | B | 28 | −5.491 | −35.957 | −34.952 | 1.00 | 27.65 | BBBB |
| ATOM | 2788 | CD2 | HIS | B | 28 | −5.327 | −36.213 | −33.632 | 1.00 | 26.92 | BBBB |
| ATOM | 2789 | ND1 | HIS | B | 28 | −6.850 | −36.010 | −35.188 | 1.00 | 27.29 | BBBB |
| ATOM | 2790 | CE1 | HIS | B | 28 | −7.479 | −36.290 | −34.060 | 1.00 | 26.85 | BBBB |
| ATOM | 2791 | NE2 | HIS | B | 28 | −6.578 | −36.417 | −33.101 | 1.00 | 27.78 | BBBB |
| ATOM | 2792 | C | HIS | B | 28 | −4.018 | −36.095 | −38.462 | 1.00 | 30.24 | BBBB |
| ATOM | 2793 | O | HIS | B | 28 | −4.766 | −35.589 | −39.297 | 1.00 | 31.14 | BBBB |
| ATOM | 2794 | N | HIS | B | 29 | −2.702 | −36.164 | −38.618 | 1.00 | 31.42 | BBBB |
| ATOM | 2795 | CA | HIS | B | 29 | −2.070 | −35.623 | −39.806 | 1.00 | 32.38 | BBBB |
| ATOM | 2796 | CB | HIS | B | 29 | −0.554 | −35.764 | −39.720 | 1.00 | 33.49 | BBBB |
| ATOM | 2797 | CG | HIS | B | 29 | 0.177 | −34.957 | −40.743 | 1.00 | 35.61 | BBBB |
| ATOM | 2798 | CD2 | HIS | B | 29 | 0.667 | −35.292 | −41.960 | 1.00 | 36.38 | BBBB |
| ATOM | 2799 | ND1 | HIS | B | 29 | 0.436 | −33.612 | −40.583 | 1.00 | 37.53 | BBBB |
| ATOM | 2800 | CE1 | HIS | B | 29 | 1.055 | −33.155 | −41.657 | 1.00 | 37.93 | BBBB |
| ATOM | 2801 | NE2 | HIS | B | 29 | 1.207 | −34.154 | −42.508 | 1.00 | 37.24 | BBBB |
| ATOM | 2802 | C | HIS | B | 29 | −2.567 | −36.324 | −41.068 | 1.00 | 33.00 | BBBB |
| ATOM | 2803 | O | HIS | B | 29 | −2.845 | −35.674 | −42.078 | 1.00 | 33.02 | BBBB |
| ATOM | 2804 | N | LEU | B | 30 | −2.676 | −37.650 | −41.012 | 1.00 | 31.69 | BBBB |
| ATOM | 2805 | CA | LEU | B | 30 | −3.136 | −38.417 | −42.162 | 1.00 | 32.00 | BBBB |
| ATOM | 2806 | CB | LEU | B | 30 | −2.701 | −39.883 | −42.033 | 1.00 | 30.44 | BBBB |
| ATOM | 2807 | CG | LEU | B | 30 | −1.191 | −40.099 | −42.203 | 1.00 | 29.95 | BBBB |
| ATOM | 2808 | CD1 | LEU | B | 30 | −0.823 | −41.550 | −41.898 | 1.00 | 28.64 | BBBB |
| ATOM | 2809 | CD2 | LEU | B | 30 | −0.785 | −39.736 | −43.621 | 1.00 | 28.97 | BBBB |
| ATOM | 2810 | C | LEU | B | 30 | −4.641 | −38.332 | −42.375 | 1.00 | 32.37 | BBBB |
| ATOM | 2811 | O | LEU | B | 30 | −5.109 | −38.414 | −43.507 | 1.00 | 33.16 | BBBB |
| ATOM | 2812 | N | MET | B | 31 | −5.401 | −38.168 | −41.297 | 1.00 | 33.50 | BBBB |
| ATOM | 2813 | CA | MET | B | 31 | −6.849 | −38.064 | −41.424 | 1.00 | 34.91 | BBBB |
| ATOM | 2814 | CB | MET | B | 31 | −7.514 | −38.061 | −40.048 | 1.00 | 35.67 | BBBB |
| ATOM | 2815 | CG | MET | B | 31 | −7.536 | −39.424 | −39.391 | 1.00 | 36.44 | BBBB |
| ATOM | 2816 | SD | MET | B | 31 | −8.407 | −39.436 | −37.827 | 1.00 | 37.84 | BBBB |
| ATOM | 2817 | CE | MET | B | 31 | −7.095 | −39.039 | −36.719 | 1.00 | 37.80 | BBBB |
| ATOM | 2818 | C | MET | B | 31 | −7.197 | −36.786 | −42.173 | 1.00 | 35.99 | BBBB |
| ATOM | 2819 | O | MET | B | 31 | −8.224 | −36.710 | −42.847 | 1.00 | 37.36 | BBBB |
| ATOM | 2820 | N | ALA | B | 32 | −6.326 | −35.791 | −42.052 | 1.00 | 36.39 | BBBB |
| ATOM | 2821 | CA | ALA | B | 32 | −6.510 | −34.511 | −42.722 | 1.00 | 37.55 | BBBB |
| ATOM | 2822 | CB | ALA | B | 32 | −5.622 | −33.458 | −42.073 | 1.00 | 36.85 | BBBB |
| ATOM | 2823 | C | ALA | B | 32 | −6.151 | −34.663 | −44.205 | 1.00 | 38.60 | BBBB |
| ATOM | 2824 | O | ALA | B | 32 | −6.392 | −33.760 | −45.013 | 1.00 | 38.04 | BBBB |
| ATOM | 2825 | N | GLN | B | 33 | −5.569 | −35.809 | −44.555 | 1.00 | 38.35 | BBBB |
| ATOM | 2826 | CA | GLN | B | 33 | −5.182 | −36.070 | −45.938 | 1.00 | 38.24 | BBBB |
| ATOM | 2827 | CB | GLN | B | 33 | −3.792 | −36.706 | −46.011 | 1.00 | 39.81 | BBBB |
| ATOM | 2828 | CG | GLN | B | 33 | −2.771 | −36.162 | −45.028 | 1.00 | 41.67 | BBBB |
| ATOM | 2829 | CD | GLN | B | 33 | −2.269 | −34.781 | −45.384 | 1.00 | 41.96 | BBBB |
| ATOM | 2830 | OE1 | GLN | B | 33 | −1.735 | −34.559 | −46.471 | 1.00 | 41.35 | BBBB |
| ATOM | 2831 | NE2 | GLN | B | 33 | −2.423 | −33.843 | −44.456 | 1.00 | 42.42 | BBBB |
| ATOM | 2832 | C | GLN | B | 33 | −6.187 | −37.027 | −46.556 | 1.00 | 36.70 | BBBB |
| ATOM | 2833 | O | GLN | B | 33 | −5.970 | −37.541 | −47.647 | 1.00 | 36.47 | BBBB |
| ATOM | 2834 | N | GLY | B | 34 | −7.281 | −37.274 | −45.845 | 1.00 | 36.09 | BBBB |
| ATOM | 2835 | CA | GLY | B | 34 | −8.305 | −38.169 | −46.353 | 1.00 | 35.75 | BBBB |
| ATOM | 2836 | C | GLY | B | 34 | −8.219 | −39.600 | −45.837 | 1.00 | 35.33 | BBBB |
| ATOM | 2837 | O | GLY | B | 34 | −9.075 | −40.426 | −46.146 | 1.00 | 34.43 | BBBB |
| ATOM | 2838 | N | TRP | B | 35 | −7.196 | −39.896 | −45.042 | 1.00 | 35.23 | BBBB |
| ATOM | 2839 | CA | TRP | B | 35 | −7.016 | −41.246 | −44.508 | 1.00 | 34.58 | BBBB |
| ATOM | 2840 | CB | TRP | B | 35 | −5.618 | −41.400 | −43.908 | 1.00 | 35.03 | BBBB |
| ATOM | 2841 | CG | TRP | B | 35 | −4.511 | −41.558 | −44.901 | 1.00 | 34.87 | BBBB |
| ATOM | 2842 | CD2 | TRP | B | 35 | −3.666 | −42.704 | −45.060 | 1.00 | 35.81 | BBBB |
| ATOM | 2843 | CE2 | TRP | B | 35 | −2.733 | −42.399 | −46.076 | 1.00 | 35.60 | BBBB |
| ATOM | 2844 | CE3 | TRP | B | 35 | −3.605 | −43.961 | −44.441 | 1.00 | 36.59 | BBBB |
| ATOM | 2845 | CD1 | TRP | B | 35 | −4.075 | −40.633 | −45.803 | 1.00 | 35.62 | BBBB |
| ATOM | 2846 | NE1 | TRP | B | 35 | −3.004 | −41.129 | −46.513 | 1.00 | 34.95 | BBBB |
| ATOM | 2847 | CZ2 | TRP | B | 35 | −1.746 | −43.305 | −46.488 | 1.00 | 37.19 | BBBB |
| ATOM | 2848 | CZ3 | TRP | B | 35 | −2.620 | −44.865 | −44.852 | 1.00 | 36.85 | BBBB |
| ATOM | 2849 | CH2 | TRP | B | 35 | −1.705 | −44.528 | −45.867 | 1.00 | 36.87 | BBBB |
| ATOM | 2850 | C | TRP | B | 35 | −8.022 | −41.670 | −43.449 | 1.00 | 34.58 | BBBB |
| ATOM | 2851 | O | TRP | B | 35 | −8.546 | −40.850 | −42.699 | 1.00 | 33.58 | BBBB |
| ATOM | 2852 | N | GLN | B | 36 | −8.295 | −42.969 | −43.410 | 1.00 | 34.54 | BBBB |
| ATOM | 2853 | CA | GLN | B | 36 | −9.175 | −43.535 | −42.402 | 1.00 | 35.40 | BBBB |
| ATOM | 2854 | CB | GLN | B | 36 | −10.095 | −44.596 | −43.003 | 1.00 | 37.42 | BBBB |

TABLE 1-continued

ATOMIC COORDINATES OF *E. COLI* MURG PROTEIN

| ATOM | 2855 | CG | GLN | B | 36 | −11.219 | −44.027 | −43.862 | 1.00 | 41.66 | BBBB |
|---|---|---|---|---|---|---|---|---|---|---|---|
| ATOM | 2856 | CD | GLN | B | 36 | −11.996 | −45.103 | −44.601 | 1.00 | 44.12 | BBBB |
| ATOM | 2857 | OE1 | GLN | B | 36 | −12.988 | −44.816 | −45.277 | 1.00 | 45.76 | BBBB |
| ATOM | 2858 | NE2 | GLN | B | 36 | −11.546 | −46.350 | −44.480 | 1.00 | 44.99 | BBBB |
| ATOM | 2859 | C | GLN | B | 36 | −8.183 | −44.186 | −41.451 | 1.00 | 34.89 | BBBB |
| ATOM | 2860 | O | GLN | B | 36 | −7.272 | −44.885 | −41.889 | 1.00 | 34.58 | BBBB |
| ATOM | 2861 | N | VAL | B | 37 | −8.336 | −43.941 | −40.158 | 1.00 | 35.26 | BBBB |
| ATOM | 2862 | CA | VAL | B | 37 | −7.417 | −44.516 | −39.184 | 1.00 | 34.16 | BBBB |
| ATOM | 2863 | CB | VAL | B | 37 | −6.561 | −43.417 | −38.509 | 1.00 | 34.99 | BBBB |
| ATOM | 2864 | GC1 | VAL | B | 37 | −5.630 | −44.032 | −37.479 | 1.00 | 34.72 | BBBB |
| ATOM | 2865 | CG2 | VAL | B | 37 | −5.755 | −42.668 | −39.552 | 1.00 | 34.06 | BBBB |
| ATOM | 2866 | C | VAL | B | 37 | −8.166 | −45.288 | −38.109 | 1.00 | 34.02 | BBBB |
| ATOM | 2867 | O | VAL | B | 37 | −9.207 | −44.849 | −37.618 | 1.00 | 33.01 | BBBB |
| ATOM | 2868 | N | ARG | B | 38 | −7.629 | −46.451 | −37.758 | 1.00 | 32.20 | BBBB |
| ATOM | 2869 | CA | ARG | B | 38 | −8.219 | −47.286 | −36.730 | 1.00 | 31.56 | BBBB |
| ATOM | 2870 | CB | ARG | B | 38 | −8.811 | −48.554 | −37.344 | 1.00 | 33.53 | BBBB |
| ATOM | 2871 | CG | ARG | B | 38 | −9.706 | −49.324 | −36.397 | 1.00 | 36.77 | BBBB |
| ATOM | 2872 | CD | ARG | B | 38 | −11.107 | −49.511 | −36.975 | 1.00 | 38.80 | BBBB |
| ATOM | 2873 | NE | ARG | B | 38 | −12.000 | −50.108 | −35.989 | 1.00 | 41.24 | BBBB |
| ATOM | 2874 | CZ | ARG | B | 38 | −13.304 | −50.293 | −36.161 | 1.00 | 43.18 | BBBB |
| ATOM | 2875 | NH1 | ARG | B | 38 | −13.892 | −49.927 | −37.294 | 1.00 | 43.21 | BBBB |
| ATOM | 2876 | NH2 | ARG | B | 38 | −14.026 | −50.839 | −35.189 | 1.00 | 44.37 | BBBB |
| ATOM | 2877 | C | ARG | B | 38 | −7.097 | −47.628 | −35.751 | 1.00 | 30.48 | BBBB |
| ATOM | 2878 | O | ARG | B | 38 | −5.936 | −47.742 | −36.134 | 1.00 | 29.62 | BBBB |
| ATOM | 2879 | N | TRP | B | 39 | −7.447 | −47.782 | −34.484 | 1.00 | 28.40 | BBBB |
| ATOM | 2880 | CA | TRP | B | 39 | −6.456 | −48.070 | −33.471 | 1.00 | 27.41 | BBBB |
| ATOM | 2881 | CB | TRP | B | 39 | −6.696 | −47.145 | −32.291 | 1.00 | 27.98 | BBBB |
| ATOM | 2882 | CG | TRP | B | 39 | −5.480 | −46.788 | −31.568 | 1.00 | 28.00 | BBBB |
| ATOM | 2883 | CD2 | TRP | B | 39 | −4.677 | −45.627 | −31.784 | 1.00 | 28.42 | BBBB |
| ATOM | 2884 | CE2 | TRP | B | 39 | −3.625 | −45.673 | −30.851 | 1.00 | 28.85 | BBBB |
| ATOM | 2885 | CE3 | TRP | B | 39 | −4.749 | −44.549 | −32.680 | 1.00 | 29.78 | BBBB |
| ATOM | 2886 | CD1 | TRP | B | 39 | −4.898 | −47.476 | −30.549 | 1.00 | 28.26 | BBBB |
| ATOM | 2887 | NE1 | TRP | B | 39 | −3.783 | −46.812 | −30.111 | 1.00 | 28.48 | BBBB |
| ATOM | 2888 | CZ2 | TRP | B | 39 | −2.648 | −44.684 | −30.778 | 1.00 | 30.55 | BBBB |
| ATOM | 2889 | CZ3 | TRP | B | 39 | −3.770 | −43.561 | −32.610 | 1.00 | 29.22 | BBBB |
| ATOM | 2890 | CH2 | TRP | B | 39 | −2.734 | −43.639 | −31.662 | 1.00 | 30.90 | BBBB |
| ATOM | 2891 | C | TRP | B | 39 | −6.478 | −49.517 | −32.999 | 1.00 | 25.82 | BBBB |
| ATOM | 2892 | O | TRP | B | 39 | −7.509 | −50.176 | −33.055 | 1.00 | 24.87 | BBBB |
| ATOM | 2893 | N | LEU | B | 40 | −5.323 | −50.004 | −32.549 | 1.00 | 25.21 | BBBB |
| ATOM | 2894 | CA | LEU | B | 40 | −5.200 | −51.364 | −32.026 | 1.00 | 24.71 | BBBB |
| ATOM | 2895 | CB | LEU | B | 40 | −4.326 | −52.221 | −32.952 | 1.00 | 25.21 | BBBB |
| ATOM | 2896 | CG | LEU | B | 40 | −4.416 | −53.754 | −32.868 | 1.00 | 26.95 | BBBB |
| ATOM | 2897 | CD1 | LEU | B | 40 | −3.037 | −54.334 | −32.571 | 1.00 | 27.63 | BBBB |
| ATOM | 2898 | CD2 | LEU | B | 40 | −5.421 | −54.179 | −31.817 | 1.00 | 26.69 | BBBB |
| ATOM | 2899 | C | LEU | B | 40 | −4.535 | −51.235 | −30.655 | 1.00 | 23.33 | BBBB |
| ATOM | 2900 | O | LEU | B | 40 | −3.387 | −50.824 | −30.563 | 1.00 | 23.43 | BBBB |
| ATOM | 2901 | N | GLY | B | 41 | −5.260 | −51.567 | −29.591 | 1.00 | 24.01 | BBBB |
| ATOM | 2902 | CA | GLY | B | 41 | −4.691 | −51.450 | −28.257 | 1.00 | 23.47 | BBBB |
| ATOM | 2903 | C | GLY | B | 41 | −5.292 | −52.479 | −27.322 | 1.00 | 23.99 | BBBB |
| ATOM | 2904 | O | GLY | B | 41 | −5.797 | −53.498 | −27.785 | 1.00 | 22.90 | BBBB |
| ATOM | 2905 | N | THR | B | 42 | −5.225 | −52.225 | −26.017 | 1.00 | 26.62 | BBBB |
| ATOM | 2906 | CA | THR | B | 42 | −5.787 | −53.141 | −25.027 | 1.00 | 29.84 | BBBB |
| ATOM | 2907 | CB | THR | B | 42 | −4.693 | −53.715 | −24.092 | 1.00 | 30.17 | BBBB |
| ATOM | 2908 | OG1 | THR | B | 42 | −4.019 | −52.647 | −23.418 | 1.00 | 30.77 | BBBB |
| ATOM | 2909 | CG2 | THR | B | 42 | −3.683 | −54.514 | −24.900 | 1.00 | 31.30 | BBBB |
| ATOM | 2910 | C | THR | B | 42 | −6.852 | −52.420 | −24.200 | 1.00 | 32.04 | BBBB |
| ATOM | 2911 | O | THR | B | 42 | −6.737 | −51.226 | −23.924 | 1.00 | 31.27 | BBBB |
| ATOM | 2912 | N | ALA | B | 43 | −7.881 | −53.160 | −23.801 | 1.00 | 35.37 | BBBB |
| ATOM | 2913 | CA | ALA | B | 43 | −9.000 | −52.595 | −23.047 | 1.00 | 38.81 | BBBB |
| ATOM | 2914 | CB | ALA | B | 43 | −10.063 | −53.669 | −22.835 | 1.00 | 38.49 | BBBB |
| ATOM | 2915 | C | ALA | B | 43 | −8.671 | −51.928 | −21.713 | 1.00 | 41.06 | BBBB |
| ATOM | 2916 | O | ALA | B | 43 | −9.224 | −50.875 | −21.391 | 1.00 | 42.22 | BBBB |
| ATOM | 2917 | N | ASP | B | 44 | −7.777 | −52.521 | −20.931 | 1.00 | 43.18 | BBBB |
| ATOM | 2918 | CA | ASP | B | 44 | −7.455 | −51.942 | −19.632 | 1.00 | 44.47 | BBBB |
| ATOM | 2919 | CB | ASP | B | 44 | −7.311 | −53.057 | −18.586 | 1.00 | 46.93 | BBBB |
| ATOM | 2920 | CG | ASP | B | 44 | −8.646 | −53.724 | −18.255 | 1.00 | 48.65 | BBBB |
| ATOM | 2921 | OD1 | ASP | B | 44 | −9.553 | −53.026 | −17.753 | 1.00 | 50.52 | BBBB |
| ATOM | 2922 | OD2 | ASP | B | 44 | −8.791 | −54.943 | −18.498 | 1.00 | 49.40 | BBBB |
| ATOM | 2923 | C | ASP | B | 44 | −6.236 | −51.025 | −19.598 | 1.00 | 44.13 | BBBB |
| ATOM | 2924 | O | ASP | B | 44 | −5.520 | −50.968 | −18.595 | 1.00 | 45.05 | BBBB |
| ATOM | 2925 | N | ARG | B | 45 | −6.001 | −50.307 | −20.692 | 1.00 | 42.34 | BBBB |
| ATOM | 2926 | CA | ARG | B | 45 | −4.887 | −49.367 | −20.763 | 1.00 | 40.44 | BBBB |
| ATOM | 2927 | CB | ARG | B | 45 | −3.802 | −49.869 | −21.725 | 1.00 | 41.87 | BBBB |
| ATOM | 2928 | CG | ARG | B | 45 | −2.935 | −50.994 | −21.149 | 1.00 | 43.86 | BBBB |
| ATOM | 2929 | CD | ARG | B | 45 | −2.218 | −50.541 | −19.881 | 1.00 | 45.24 | BBBB |
| ATOM | 2930 | NE | ARG | B | 45 | −1.385 | −51.582 | −19.277 | 1.00 | 46.96 | BBBB |
| ATOM | 2931 | CZ | ARG | B | 45 | −1.840 | −52.753 | −18.839 | 1.00 | 47.69 | BBBB |

TABLE 1-continued

ATOMIC COORDINATES OF E. COLI MURG PROTEIN

| ATOM | 2932 | NH1 | ARG | B | 45 | −3.130 | −53.051 | −18.937 | 1.00 | 48.59 | BBBB |
|---|---|---|---|---|---|---|---|---|---|---|---|
| ATOM | 2933 | NH2 | ARG | B | 45 | −1.005 | −53.626 | −18.289 | 1.00 | 48.33 | BBBB |
| ATOM | 2934 | C | ARG | B | 45 | −5.390 | −47.992 | −21.195 | 1.00 | 38.74 | BBBB |
| ATOM | 2935 | O | ARG | B | 45 | −6.486 | −47.866 | −21.738 | 1.00 | 37.69 | BBBB |
| ATOM | 2936 | N | MET | B | 46 | −4.567 | −46.977 | −20.955 | 1.00 | 37.09 | BBBB |
| ATOM | 2937 | CA | MET | B | 46 | −4.881 | −45.581 | −21.249 | 1.00 | 36.33 | BBBB |
| ATOM | 2938 | CB | MET | B | 46 | −3.644 | −44.725 | −20.945 | 1.00 | 37.92 | BBBB |
| ATOM | 2939 | CG | MET | B | 46 | −3.873 | −43.222 | −20.952 | 1.00 | 40.65 | BBBB |
| ATOM | 2940 | SD | MET | B | 46 | −3.420 | −42.436 | −22.517 | 1.00 | 44.22 | BBBB |
| ATOM | 2941 | CE | MET | B | 46 | −1.720 | −41.959 | −22.168 | 1.00 | 41.80 | BBBB |
| ATOM | 2942 | C | MET | B | 46 | −5.430 | −45.239 | −22.643 | 1.00 | 34.96 | BBBB |
| ATOM | 2943 | O | MET | B | 46 | −6.264 | −44.338 | −22.774 | 1.00 | 33.21 | BBBB |
| ATOM | 2944 | N | GLU | B | 47 | −4.976 | −45.941 | −23.678 | 1.00 | 32.85 | BBBB |
| ATOM | 2945 | CA | GLU | B | 47 | −5.458 | −45.655 | −25.029 | 1.00 | 31.79 | BBBB |
| ATOM | 2946 | CB | GLU | B | 47 | −4.624 | −46.402 | −26.080 | 1.00 | 30.62 | BBBB |
| ATOM | 2947 | CG | GLU | B | 47 | −4.755 | −47.922 | −26.051 | 1.00 | 29.85 | BBBB |
| ATOM | 2948 | CD | GLU | B | 47 | −3.793 | −48.597 | −25.082 | 1.00 | 29.78 | BBBB |
| ATOM | 2949 | OE1 | GLU | B | 47 | −3.188 | −47.895 | −24.247 | 1.00 | 28.76 | BBBB |
| ATOM | 2950 | OE2 | GLU | B | 47 | −3.649 | −49.840 | −25.156 | 1.00 | 29.01 | BBBB |
| ATOM | 2951 | C | GLU | B | 47 | −6.938 | −46.017 | −25.191 | 1.00 | 31.81 | BBBB |
| ATOM | 2952 | O | GLU | B | 47 | −7.626 | −45.476 | −26.055 | 1.00 | 31.31 | BBBB |
| ATOM | 2953 | N | ALA | B | 48 | −7.428 | −46.924 | −24.352 | 1.00 | 31.55 | BBBB |
| ATOM | 2954 | CA | ALA | B | 48 | −8.821 | −47.344 | −24.414 | 1.00 | 32.58 | BBBB |
| ATOM | 2955 | CB | ALA | B | 48 | −9.085 | −48.450 | −23.384 | 1.00 | 33.19 | BBBB |
| ATOM | 2956 | C | ALA | B | 48 | −9.761 | −46.168 | −24.164 | 1.00 | 33.37 | BBBB |
| ATOM | 2957 | C | ALA | B | 48 | −10.860 | −46.114 | −24.716 | 1.00 | 33.81 | BBBB |
| ATOM | 2958 | N | ASP | B | 49 | −9.328 | −45.232 | −23.328 | 1.00 | 34.05 | BBBB |
| ATOM | 2959 | CA | ASP | B | 49 | −10.143 | −44.065 | −23.009 | 1.00 | 35.60 | BBBB |
| ATOM | 2960 | CB | ASP | B | 49 | −10.033 | −43.736 | −21.514 | 1.00 | 36.58 | BBBB |
| ATOM | 2961 | CG | ASP | B | 49 | −10.645 | −44.812 | −20.628 | 1.00 | 39.54 | BBBB |
| ATOM | 2962 | OD1 | ASP | B | 49 | −11.835 | −45.144 | −20.825 | 1.00 | 40.82 | BBBB |
| ATOM | 2963 | OD2 | ASP | B | 49 | −9.939 | −45.323 | −19.730 | 1.00 | 39.49 | BBBB |
| ATOM | 2964 | C | ASP | B | 49 | −9.768 | −42.832 | −23.831 | 1.00 | 34.79 | BBBB |
| ATOM | 2965 | O | ASP | B | 49 | −10.637 | −42.064 | −24.241 | 1.00 | 35.85 | BBBB |
| ATOM | 2966 | N | LEU | B | 50 | −8.478 | −42.648 | −24.088 | 1.00 | 34.06 | BBBB |
| ATOM | 2967 | CA | LEU | B | 50 | −8.026 | −41.484 | −24.840 | 1.00 | 33.49 | BBBB |
| ATOM | 2968 | CB | LEU | B | 50 | −6.526 | −41.264 | −24.635 | 1.00 | 33.25 | BBBB |
| ATOM | 2969 | CG | LEU | B | 50 | −6.001 | −39.986 | −25.299 | 1.00 | 33.36 | BBBB |
| ATOM | 2970 | CD1 | LEU | B | 50 | −6.679 | −38.771 | −24.659 | 1.00 | 34.04 | BBBB |
| ATOM | 2971 | CD2 | LEU | B | 50 | −4.496 | −39.894 | −25.157 | 1.00 | 33.08 | BBBB |
| ATOM | 2972 | C | LEU | B | 50 | −8.320 | −41.486 | −26.337 | 1.00 | 33.52 | BBBB |
| ATOM | 2973 | O | LEU | B | 50 | −8.769 | −40.477 | −26.882 | 1.00 | 32.52 | BBBB |
| ATOM | 2974 | N | VAL | B | 51 | −8.073 | −42.605 | −27.011 | 1.00 | 32.94 | BBBB |
| ATOM | 2975 | CA | VAL | B | 51 | −8.299 | −42.641 | −28.449 | 1.00 | 32.68 | BBBB |
| ATOM | 2976 | CB | VAL | B | 51 | −7.829 | −43.982 | −29.058 | 1.00 | 33.06 | BBBB |
| ATOM | 2977 | CG1 | VAL | B | 51 | −8.115 | −44.013 | −30.565 | 1.00 | 31.54 | BBBB |
| ATOM | 2978 | CG2 | VAL | B | 51 | −6.329 | −44.145 | −28.813 | 1.00 | 31.45 | BBBB |
| ATOM | 2979 | C | VAL | B | 51 | −9.747 | −42.348 | −28.829 | 1.00 | 33.08 | BBBB |
| ATOM | 2980 | O | VAL | B | 51 | −10.000 | −41.623 | −29.792 | 1.00 | 32.88 | BBBB |
| ATOM | 2981 | N | PRO | B | 52 | −10.721 | −42.900 | −28.085 | 1.00 | 33.67 | BBBB |
| ATOM | 2982 | CD | PRO | B | 52 | −10.667 | −44.012 | −27.119 | 1.00 | 33.29 | BBBB |
| ATOM | 2983 | CA | PRO | B | 52 | −12.111 | −42.601 | −28.453 | 1.00 | 34.43 | BBBB |
| ATOM | 2984 | CB | PRO | B | 52 | −12.915 | −43.465 | −27.489 | 1.00 | 34.36 | BBBB |
| ATOM | 2985 | CG | PRO | B | 52 | −12.021 | −44.661 | −27.307 | 1.00 | 33.77 | BBBB |
| ATOM | 2986 | C | PRO | B | 52 | −12.422 | −41.111 | −28.294 | 1.00 | 35.67 | BBBB |
| ATOM | 2987 | O | PRO | B | 52 | −13.219 | −40.548 | −29.048 | 1.00 | 36.65 | BBBB |
| ATOM | 2988 | N | LYS | B | 53 | −11.790 | −40.478 | −27.310 | 1.00 | 35.75 | BBBB |
| ATOM | 2989 | CA | LYS | B | 53 | −11.998 | −39.054 | −27.064 | 1.00 | 36.73 | BBBB |
| ATOM | 2990 | CB | LYS | B | 53 | −11.334 | −38.633 | −25.746 | 1.00 | 37.14 | BBBB |
| ATOM | 2991 | CG | LYS | B | 53 | −12.020 | −39.207 | −24.514 | 1.00 | 38.38 | BBBB |
| ATOM | 2992 | CD | LYS | B | 53 | −11.368 | −38.746 | −23.218 | 1.00 | 39.34 | BBBB |
| ATOM | 2993 | CE | LYS | B | 53 | −12.057 | −39.379 | −22.012 | 1.00 | 40.74 | BBBB |
| ATOM | 2994 | NZ | LYS | B | 53 | −11.352 | −39.092 | −20.725 | 1.00 | 40.94 | BBBB |
| ATOM | 2995 | C | LYS | B | 53 | −11.445 | −38.231 | −28.220 | 1.00 | 36.11 | BBBB |
| ATOM | 2996 | O | LYS | B | 53 | −11.703 | −37.036 | −28.323 | 1.00 | 36.71 | BBBB |
| ATOM | 2997 | N | HIS | B | 54 | −10.688 | −38.881 | −29.096 | 1.00 | 35.60 | BBBB |
| ATOM | 2998 | CA | HIS | B | 54 | −10.116 | −38.212 | −30.259 | 1.00 | 34.62 | BBBB |
| ATOM | 2999 | CB | HIS | B | 54 | −8.666 | −38.647 | −30.464 | 1.00 | 34.78 | BBBB |
| ATOM | 3000 | CG | HIS | B | 54 | −7.676 | −37.810 | −29.721 | 1.00 | 33.79 | BBBB |
| ATOM | 3001 | CD2 | HIS | B | 54 | −7.360 | −37.760 | −28.406 | 1.00 | 33.76 | BBBB |
| ATOM | 3002 | ND1 | HIS | B | 54 | −6.884 | −36.869 | −30.343 | 1.00 | 34.27 | BBBB |
| ATOM | 3003 | CE1 | HIS | B | 54 | −6.120 | −36.277 | −29.441 | 1.00 | 34.41 | BBBB |
| ATOM | 3004 | NE2 | HIS | B | 54 | −6.390 | −36.799 | −28.258 | 1.00 | 33.91 | BBBB |
| ATOM | 3005 | C | HIS | B | 54 | −10.919 | −38.524 | −31.512 | 1.00 | 34.28 | BBBB |
| ATOM | 3006 | O | HIS | B | 54 | −10.487 | −38.224 | −32.620 | 1.00 | 34.99 | BBBB |
| ATOM | 3007 | N | GLY | B | 55 | −12.082 | −39.140 | −31.325 | 1.00 | 34.47 | BBBB |
| ATOM | 3008 | CA | GLY | B | 55 | −12.938 | −39.481 | −32.447 | 1.00 | 35.34 | BBBB |

TABLE 1-continued

ATOMIC COORDINATES OF E. COLI MURG PROTEIN

| ATOM | 3009 | C | GLY | B | 55 | −12.427 | −40.619 | −33.310 | 1.00 | 36.18 | BBBB |
|---|---|---|---|---|---|---|---|---|---|---|---|
| ATOM | 3010 | O | GLY | B | 55 | −12.883 | −40.799 | −34.442 | 1.00 | 35.99 | BBBB |
| ATOM | 3011 | N | ILE | B | 56 | −11.490 | −41.399 | −32.776 | 1.00 | 35.32 | BBBB |
| ATOM | 3012 | CA | ILE | B | 56 | −10.909 | −42.517 | −33.514 | 1.00 | 33.81 | BBBB |
| ATOM | 3013 | CB | ILE | B | 56 | −9.374 | −42.445 | −33.462 | 1.00 | 33.36 | BBBB |
| ATOM | 3014 | CG2 | ILE | B | 56 | −8.761 | −43.602 | −34.245 | 1.00 | 32.87 | BBBB |
| ATOM | 3015 | CG1 | ILE | B | 56 | −8.916 | −41.097 | −34.029 | 1.00 | 32.05 | BBBB |
| ATOM | 3016 | CD1 | ILE | B | 56 | −7.461 | −40.792 | −33.818 | 1.00 | 30.35 | BBBB |
| ATOM | 3017 | C | ILE | B | 56 | −11.375 | −43.859 | −32.956 | 1.00 | 34.45 | BBBB |
| ATOM | 3018 | O | ILE | B | 56 | −11.394 | −44.069 | −31.738 | 1.00 | 34.26 | BBBB |
| ATOM | 3019 | N | GLU | B | 57 | −11.764 | −44.758 | −33.855 | 1.00 | 33.40 | BBBB |
| ATOM | 3020 | CA | GLU | B | 57 | −12.228 | −46.083 | −33.467 | 1.00 | 34.16 | BBBB |
| ATOM | 3021 | CB | GLU | B | 57 | −12.905 | −46.769 | −34.651 | 1.00 | 37.41 | BBBB |
| ATOM | 3022 | CG | GLU | B | 57 | −14.064 | −45.982 | −35.244 | 1.00 | 42.10 | BBBB |
| ATOM | 3023 | CD | GLU | B | 57 | −14.653 | −46.659 | −36.465 | 1.00 | 45.50 | BBBB |
| ATOM | 3024 | OE1 | GLU | B | 57 | −13.903 | −46.875 | −37.448 | 1.00 | 46.39 | BBBB |
| ATOM | 3025 | OE2 | GLU | B | 57 | −15.866 | −46.977 | −36.441 | 1.00 | 48.36 | BBBB |
| ATOM | 3026 | C | GLU | B | 57 | −11.044 | −46.923 | −33.005 | 1.00 | 33.01 | BBBB |
| ATOM | 3027 | O | GLU | B | 57 | −9.931 | −46.769 | −33.504 | 1.00 | 31.58 | BBBB |
| ATOM | 3028 | N | ILE | B | 58 | −11.287 | −47.817 | −32.056 | 1.00 | 31.85 | BBBB |
| ATOM | 3029 | CA | ILE | B | 58 | −10.217 | −48.658 | −31.553 | 1.00 | 31.38 | BBBB |
| ATOM | 3030 | CB | ILE | B | 58 | −9.651 | −48.099 | −30.223 | 1.00 | 30.95 | BBBB |
| ATOM | 3031 | CG2 | ILE | B | 58 | −10.769 | −47.946 | −29.205 | 1.00 | 31.48 | BBBB |
| ATOM | 3032 | CG1 | ILE | B | 58 | −8.553 | −49.030 | −29.690 | 1.00 | 31.13 | BBBB |
| ATOM | 3033 | CD1 | ILE | B | 58 | −7.736 | −48.437 | −28.572 | 1.00 | 29.87 | BBBB |
| ATOM | 3034 | C | ILE | B | 58 | −10.647 | −50.102 | −31.357 | 1.00 | 31.67 | BBBB |
| ATOM | 3035 | O | ILE | B | 58 | −11.716 | −50.384 | −30.801 | 1.00 | 30.68 | BBBB |
| ATOM | 3036 | N | ASP | B | 59 | −9.807 | −51.011 | −31.844 | 1.00 | 30.76 | BBBB |
| ATOM | 3037 | CA | ASP | B | 59 | −10.039 | −52.442 | −31.720 | 1.00 | 31.09 | BBBB |
| ATOM | 3038 | CB | ASP | B | 59 | −9.732 | −53.153 | −33.037 | 1.00 | 31.37 | BBBB |
| ATOM | 3039 | CG | ASP | B | 59 | −10.766 | −52.863 | −34.104 | 1.00 | 32.68 | BBBB |
| ATOM | 3040 | OD1 | ASP | B | 59 | −11.969 | −53.037 | −33.812 | 1.00 | 32.40 | BBBB |
| ATOM | 3041 | OD2 | ASP | B | 59 | −10.378 | −52.468 | −35.224 | 1.00 | 33.40 | BBBB |
| ATOM | 3042 | C | ASP | B | 59 | −9.119 | −52.950 | −30.618 | 1.00 | 30.50 | BBBB |
| ATOM | 3043 | O | ASP | B | 59 | −7.987 | −52.491 | −30.492 | 1.00 | 30.24 | BBBB |
| ATOM | 3044 | N | PHE | B | 60 | −9.608 | −53.888 | −29.815 | 1.00 | 30.65 | BBBB |
| ATOM | 3045 | CA | PHE | B | 60 | −8.809 | −54.410 | −28.713 | 1.00 | 30.32 | BBBB |
| ATOM | 3046 | CB | PHE | B | 60 | −9.560 | −54.239 | −27.385 | 1.00 | 30.74 | BBBB |
| ATOM | 3047 | CG | PHE | B | 60 | −9.925 | −52.815 | −27.058 | 1.00 | 32.14 | BBBB |
| ATOM | 3048 | CD1 | PHE | B | 60 | −11.250 | −52.392 | −27.129 | 1.00 | 33.15 | BBBB |
| ATOM | 3049 | CD2 | PHE | B | 60 | −8.955 | −51.908 | −26.649 | 1.00 | 31.57 | BBBB |
| ATOM | 3050 | CE1 | PHE | B | 60 | −11.605 | −51.083 | −26.791 | 1.00 | 34.05 | BBBB |
| ATOM | 3051 | CE2 | PHE | B | 60 | −9.294 | −50.598 | −26.310 | 1.00 | 33.00 | BBBB |
| ATOM | 3052 | CZ | PHE | B | 60 | −10.626 | −50.185 | −26.380 | 1.00 | 33.82 | BBBB |
| ATOM | 3053 | C | PHE | B | 60 | −8.430 | −55.878 | −28.846 | 1.00 | 29.86 | BBBB |
| ATOM | 3054 | O | PHE | B | 60 | −9.154 | −56.668 | −29.445 | 1.00 | 29.93 | BBBB |
| ATOM | 3055 | N | ILE | B | 61 | −7.271 | −56.229 | −28.295 | 1.00 | 29.38 | BBBB |
| ATOM | 3056 | CA | ILE | B | 61 | −6.832 | −57.616 | −28.269 | 1.00 | 28.55 | BBBB |
| ATOM | 3057 | CB | ILE | B | 61 | −5.674 | −57.923 | −29.258 | 1.00 | 28.48 | BBBB |
| ATOM | 3058 | CG2 | ILE | B | 61 | −6.123 | −57.650 | −30.694 | 1.00 | 27.65 | BBBB |
| ATOM | 3059 | CG1 | ILE | B | 61 | −4.422 | −57.126 | −28.892 | 1.00 | 26.70 | BBBB |
| ATOM | 3060 | CD1 | ILE | B | 61 | −3.177 | −57.615 | −29.638 | 1.00 | 27.03 | BBBB |
| ATOM | 3061 | C | ILE | B | 61 | −6.344 | −57.855 | −26.848 | 1.00 | 29.13 | BBBB |
| ATOM | 3062 | O | ILE | B | 61 | −6.124 | −56.906 | −26.091 | 1.00 | 28.80 | BBBB |
| ATOM | 3063 | N | ARG | B | 62 | −6.186 | −59.116 | −26.473 | 1.00 | 29.38 | BBBB |
| ATOM | 3064 | CA | ARG | B | 62 | −5.709 | −59.416 | −25.133 | 1.00 | 30.76 | BBBB |
| ATOM | 3065 | CB | ARG | B | 62 | −6.630 | −60.447 | −24.461 | 1.00 | 32.36 | BBBB |
| ATOM | 3066 | CG | ARG | B | 62 | −6.130 | −60.955 | −23.114 | 1.00 | 35.99 | BBBB |
| ATOM | 3067 | CD | ARG | B | 62 | −5.438 | −59.859 | −22.311 | 1.00 | 37.86 | BBBB |
| ATOM | 3068 | NE | ARG | B | 62 | −6.297 | −58.718 | −22.004 | 1.00 | 40.01 | BBBB |
| ATOM | 3069 | CZ | ARG | B | 62 | −5.840 | −57.504 | −21.711 | 1.00 | 39.09 | BBBB |
| ATOM | 3070 | NH1 | ARG | B | 62 | −4.536 | −57.275 | −21.690 | 1.00 | 39.24 | BBBB |
| ATOM | 3071 | NH2 | ARG | B | 62 | −6.686 | −56.518 | −21.439 | 1.00 | 40.03 | BBBB |
| ATOM | 3072 | C | ARG | B | 62 | −4.274 | −59.923 | −25.156 | 1.00 | 29.32 | BBBB |
| ATOM | 3073 | O | ARG | B | 62 | −3.933 | −60.809 | −25.934 | 1.00 | 28.65 | BBBB |
| ATOM | 3074 | N | ILE | B | 63 | −3.428 | −59.342 | −24.313 | 1.00 | 30.07 | BBBB |
| ATOM | 3075 | CA | ILE | B | 63 | −2.036 | −59.770 | −24.231 | 1.00 | 31.38 | BBBB |
| ATOM | 3076 | CB | ILE | B | 63 | −1.081 | −58.745 | −24.883 | 1.00 | 30.06 | BBBB |
| ATOM | 3077 | CG2 | ILE | B | 63 | −1.442 | −58.567 | −26.353 | 1.00 | 30.41 | BBBB |
| ATOM | 3078 | CG1 | ILE | B | 63 | −1.143 | −57.411 | −24.137 | 1.00 | 29.94 | BBBB |
| ATOM | 3079 | CD1 | ILE | B | 63 | −0.128 | −56.384 | −24.632 | 1.00 | 29.62 | BBBB |
| ATOM | 3080 | C | ILE | B | 63 | −1.623 | −59.981 | −22.775 | 1.00 | 33.08 | BBBB |
| ATOM | 3081 | O | ILE | B | 63 | −0.444 | −59.872 | −22.430 | 1.00 | 33.21 | BBBB |
| ATOM | 3082 | N | SER | B | 64 | −2.603 | −60.284 | −21.927 | 1.00 | 35.38 | BBBB |
| ATOM | 3083 | CA | SER | B | 64 | −2.356 | −60.520 | −20.505 | 1.00 | 37.51 | BBBB |
| ATOM | 3084 | CB | SER | B | 64 | −3.652 | −60.912 | −19.792 | 1.00 | 38.82 | BBBB |
| ATOM | 3085 | OG | SER | B | 64 | −4.558 | −59.823 | −19.750 | 1.00 | 42.88 | BBBB |

TABLE 1-continued

ATOMIC COORDINATES OF *E. COLI* MURG PROTEIN

| ATOM | 3086 | C | SER | B | 64 | −1.326 | −61.622 | −20.311 | 1.00 | 37.32 | BBBB |
|---|---|---|---|---|---|---|---|---|---|---|---|
| ATOM | 3087 | O | SER | B | 64 | −1.411 | −62.682 | −20.933 | 1.00 | 37.86 | BBBB |
| ATOM | 3088 | N | GLY | B | 65 | −0.356 | −61.370 | −19.441 | 1.00 | 37.81 | BBBB |
| ATOM | 3089 | CA | GLY | B | 65 | 0.679 | −62.355 | −19.199 | 1.00 | 37.13 | BBBB |
| ATOM | 3090 | C | GLY | B | 65 | 1.798 | −62.283 | −20.226 | 1.00 | 36.26 | BBBB |
| ATOM | 3091 | O | GLY | B | 65 | 2.858 | −62.889 | −20.038 | 1.00 | 37.57 | BBBB |
| ATOM | 3092 | N | LEU | B | 66 | 1.577 | −61.539 | −21.307 | 1.00 | 34.63 | BBBB |
| ATOM | 3093 | CA | LEU | B | 66 | 2.591 | −61.413 | −22.355 | 1.00 | 33.17 | BBBB |
| ATOM | 3094 | CB | LEU | B | 66 | 1.936 | −61.470 | −23.735 | 1.00 | 32.08 | BBBB |
| ATOM | 3095 | CG | LEU | B | 66 | 1.162 | −62.747 | −24.061 | 1.00 | 32.52 | BBBB |
| ATOM | 3096 | CD1 | LEU | B | 66 | 0.563 | −62.626 | −25.445 | 1.00 | 31.38 | BBBB |
| ATOM | 3097 | CD2 | LEU | B | 66 | 2.093 | −63.957 | −23.984 | 1.00 | 31.67 | BBBB |
| ATOM | 3098 | C | LEU | B | 66 | 3.414 | −60.133 | −22.246 | 1.00 | 32.72 | BBBB |
| ATOM | 3099 | O | LEU | B | 66 | 4.451 | −60.002 | −22.893 | 1.00 | 33.13 | BBBB |
| ATOM | 3100 | N | ARG | B | 67 | 2.953 | −59.185 | −21.440 | 1.00 | 31.54 | BBBB |
| ATOM | 3101 | CA | ARG | B | 67 | 3.671 | −57.928 | −21.277 | 1.00 | 30.90 | BBBB |
| ATOM | 3102 | CB | ARG | B | 67 | 2.888 | −56.984 | −20.363 | 1.00 | 32.28 | BBBB |
| ATOM | 3103 | CG | ARG | B | 67 | 1.540 | −56.576 | −20.913 | 1.00 | 34.65 | BBBB |
| ATOM | 3104 | CD | ARG | B | 67 | 0.926 | −55.440 | −20.097 | 1.00 | 36.69 | BBBB |
| ATOM | 3105 | NE | ARG | B | 67 | −0.259 | −54.889 | −20.748 | 1.00 | 38.28 | BBBB |
| ATOM | 3106 | CZ | ARG | B | 67 | −1.425 | −55.519 | −20.853 | 1.00 | 39.05 | BBBB |
| ATOM | 3107 | NH1 | ARG | B | 62 | −1.583 | −56.734 | −20.341 | 1.00 | 39.61 | BBBB |
| ATOM | 3108 | NH2 | ARG | B | 67 | −2.434 | −54.935 | −21.487 | 1.00 | 39.52 | BBBB |
| ATOM | 3109 | C | ARG | B | 67 | 5.071 | −58.142 | −20.713 | 1.00 | 29.99 | BBBB |
| ATOM | 3110 | O | ARG | B | 67 | 5.294 | −59.034 | −19.889 | 1.00 | 28.67 | BBBB |
| ATOM | 3111 | N | GLY | B | 68 | 6.014 | −57.321 | −21.165 | 1.00 | 27.75 | BBBB |
| ATOM | 3112 | CA | GLY | B | 68 | 7.380 | −57.427 | −20.685 | 1.00 | 26.79 | BBBB |
| ATOM | 3113 | C | GLY | B | 68 | 8.166 | −58.579 | −21.280 | 1.00 | 25.41 | BBBB |
| ATOM | 3114 | O | GLY | B | 68 | 9.326 | −58.779 | −20.943 | 1.00 | 26.04 | BBBB |
| ATOM | 3115 | N | LYS | B | 69 | 7.546 | −59.342 | −22.170 | 1.00 | 24.55 | BBBB |
| ATOM | 3116 | CA | LYS | B | 69 | 8.238 | −60.463 | −22.796 | 1.00 | 23.93 | BBBB |
| ATOM | 3117 | CB | LYS | B | 69 | 7.284 | −61.641 | −23.033 | 1.00 | 24.12 | BBBB |
| ATOM | 3118 | CG | LYS | B | 69 | 6.757 | −62.360 | −21.794 | 1.00 | 25.08 | BBBB |
| ATOM | 3119 | CD | LYS | B | 69 | 5.887 | −63.553 | −22.224 | 1.00 | 25.44 | BBBB |
| ATOM | 3120 | CE | LYS | B | 69 | 5.357 | −64.358 | −21.035 | 1.00 | 28.31 | BBBB |
| ATOM | 3121 | NZ | LYS | B | 69 | 6.468 | −64.877 | −20.175 | 1.00 | 29.71 | BBBB |
| ATOM | 3122 | C | LYS | B | 69 | 8.825 | −60.062 | −24.142 | 1.00 | 23.32 | BBBB |
| ATOM | 3123 | O | LYS | B | 69 | 8.151 | −59.404 | −24.944 | 1.00 | 21.96 | BBBB |
| ATOM | 3124 | N | GLY | B | 70 | 10.075 | −60.470 | −24.374 | 1.00 | 22.48 | BBBB |
| ATOM | 3125 | CA | GLY | B | 70 | 10.755 | −60.229 | −25.636 | 1.00 | 22.26 | BBBB |
| ATOM | 3126 | C | GLY | B | 70 | 10.308 | −61.337 | −26.588 | 1.00 | 22.17 | BBBB |
| ATOM | 3127 | O | GLY | B | 70 | 9.512 | −62.183 | −26.195 | 1.00 | 21.62 | BBBB |
| ATOM | 3128 | N | ILE | B | 71 | 10.819 | −61.373 | −27.814 | 1.00 | 21.85 | BBBB |
| ATOM | 3129 | CA | ILE | B | 71 | 10.357 | −62.386 | −28.762 | 1.00 | 23.55 | BBBB |
| ATOM | 3130 | CB | ILE | B | 71 | 10.926 | −62.142 | −30.181 | 1.00 | 23.52 | BBBB |
| ATOM | 3131 | CG2 | ILE | B | 71 | 12.435 | −62.375 | −30.192 | 1.00 | 25.96 | BBBB |
| ATOM | 3132 | CG1 | ILE | B | 71 | 10.264 | −63.096 | −31.182 | 1.00 | 24.18 | BBBB |
| ATOM | 3133 | CD1 | ILE | B | 71 | 8.745 | −62.981 | −31.263 | 1.00 | 25.73 | BBBB |
| ATOM | 3134 | C | ILE | B | 71 | 10.616 | −63.840 | −28.359 | 1.00 | 23.88 | BBBB |
| ATOM | 3135 | O | ILE | B | 71 | 9.775 | −64.707 | −28.592 | 1.00 | 21.66 | BBBB |
| ATOM | 3136 | N | LYS | B | 72 | 11.764 | −64.119 | −27.751 | 1.00 | 23.82 | BBBB |
| ATOM | 3137 | CA | LYS | B | 72 | 12.038 | −65.491 | −27.343 | 1.00 | 24.92 | BBBB |
| ATOM | 3138 | CB | LYS | B | 72 | 13.491 | −65.634 | −26.875 | 1.00 | 26.86 | BBBB |
| ATOM | 3139 | CG | LYS | B | 72 | 14.496 | −65.590 | −28.019 | 1.00 | 31.29 | BBBB |
| ATOM | 3140 | CD | LYS | B | 72 | 15.925 | −65.791 | −27.518 | 1.00 | 36.00 | BBBB |
| ATOM | 3141 | CE | LYS | B | 72 | 16.926 | −65.816 | −28.671 | 1.00 | 38.82 | BBBB |
| ATOM | 3142 | NZ | LYS | B | 72 | 18.342 | −65.957 | −28.192 | 1.00 | 41.21 | BBBB |
| ATOM | 3143 | C | LYS | B | 72 | 11.068 | −65.925 | −26.245 | 1.00 | 23.73 | BBBB |
| ATOM | 3144 | O | LYS | B | 72 | 10.592 | −67.062 | −26.245 | 1.00 | 24.08 | BBBB |
| ATOM | 3145 | N | ALA | B | 73 | 10.765 | −65.016 | −25.322 | 1.00 | 21.62 | BBBB |
| ATOM | 3146 | CA | ALA | B | 73 | 9.839 | −65.306 | −24.233 | 1.00 | 21.18 | BBBB |
| ATOM | 3147 | CB | ALA | B | 73 | 9.895 | −64.196 | −23.187 | 1.00 | 22.25 | BBBB |
| ATOM | 3148 | C | ALA | B | 73 | 8.412 | −65.454 | −24.771 | 1.00 | 20.36 | BBBB |
| ATOM | 3149 | O | ALA | B | 73 | 7.619 | −66.250 | −24.267 | 1.00 | 18.97 | BBBB |
| ATOM | 3150 | N | LEU | B | 74 | 8.076 | −64.673 | −25.791 | 1.00 | 20.23 | BBBB |
| ATOM | 3151 | CA | LEU | B | 74 | 6.745 | −64.762 | −26.387 | 1.00 | 19.36 | BBBB |
| ATOM | 3152 | CB | LEU | B | 74 | 6.540 | −63.643 | −27.417 | 1.00 | 18.42 | BBBB |
| ATOM | 3153 | CG | LEU | B | 74 | 6.422 | −62.208 | −26.884 | 1.00 | 18.80 | BBBB |
| ATOM | 3154 | CD1 | LEU | B | 74 | 6.473 | −61.197 | −28.039 | 1.00 | 19.86 | BBBB |
| ATOM | 3155 | CD2 | LEU | B | 74 | 5.109 | −62.071 | −26.104 | 1.00 | 19.45 | BBBB |
| ATOM | 3156 | C | LEU | B | 74 | 6.549 | −66.110 | −27.069 | 1.00 | 19.37 | BBBB |
| ATOM | 3157 | O | LEU | B | 74 | 5.539 | −66.779 | −26.863 | 1.00 | 20.01 | BBBB |
| ATOM | 3158 | N | ILE | B | 75 | 7.520 | −66.507 | −27.883 | 1.00 | 20.59 | BBBB |
| ATOM | 3159 | CA | ILE | B | 75 | 7.434 | −67.768 | −28.601 | 1.00 | 21.18 | BBBB |
| ATOM | 3160 | CB | ILE | B | 75 | 8.571 | −67.896 | −29.641 | 1.00 | 22.95 | BBBB |
| ATOM | 3161 | CG2 | ILE | B | 75 | 8.334 | −69.108 | −30.527 | 1.00 | 25.38 | BBBB |
| ATOM | 3162 | CG1 | ILE | B | 75 | 8.598 | −66.657 | −30.540 | 1.00 | 26.82 | BBBB |

TABLE 1-continued

ATOMIC COORDINATES OF *E. COLI* MURG PROTEIN

| ATOM | 3163 | CD1 | ILE | B | 75 | 7.304 | −66.442 | −31.327 | 1.00 | 28.48 | BBBB |
|---|---|---|---|---|---|---|---|---|---|---|---|
| ATOM | 3164 | C | ILE | B | 75 | 7.488 | −68.942 | −27.624 | 1.00 | 21.20 | BBBB |
| ATOM | 3165 | O | ILE | B | 75 | 7.125 | −70.063 | −27.979 | 1.00 | 21.59 | BBBB |
| ATOM | 3166 | N | ALA | B | 76 | 7.940 | −68.680 | −2.399 | 1.00 | 20.49 | BBBB |
| ATOM | 3167 | CA | ALA | B | 76 | 7.996 | −69.726 | −25.374 | 1.00 | 21.72 | BBBB |
| ATOM | 3168 | CB | ALA | B | 76 | 9.026 | −69.372 | −24.305 | 1.00 | 21.92 | BBBB |
| ATOM | 3169 | C | ALA | B | 76 | 6.624 | −69.904 | −24.732 | 1.00 | 21.54 | BBBB |
| ATOM | 3170 | O | ALA | B | 76 | 6.441 | −70.778 | −23.875 | 1.00 | 20.75 | BBBB |
| ATOM | 3171 | N | ALA | B | 77 | 5.668 | −69.066 | −25.145 | 1.00 | 20.61 | BBBB |
| ATOM | 3172 | CA | ALA | B | 77 | 4.289 | −69.121 | −24.655 | 1.00 | 21.07 | BBBB |
| ATOM | 3173 | CB | ALA | B | 77 | 3.937 | −67.830 | −23.924 | 1.00 | 20.10 | BBBB |
| ATOM | 3174 | C | ALA | B | 77 | 3.383 | −69.298 | −25.881 | 1.00 | 21.69 | BBBB |
| ATOM | 3175 | O | ALA | B | 77 | 2.567 | −68.430 | −26.199 | 1.00 | 21.93 | BBBB |
| ATOM | 3176 | N | PRO | B | 78 | 3.507 | −70.446 | −26.564 | 1.00 | 22.38 | BBBB |
| ATOM | 3177 | CD | PRO | B | 78 | 4.211 | −71.603 | −25.976 | 1.00 | 21.89 | BBBB |
| ATOM | 3178 | CA | PRO | B | 78 | 2.772 | −70.846 | −27.771 | 1.00 | 20.95 | BBBB |
| ATOM | 3179 | CB | PRO | B | 78 | 3.027 | −72.350 | −27.861 | 1.00 | 22.21 | BBBB |
| ATOM | 3180 | CG | PRO | B | 78 | 4.288 | −72.547 | −27.117 | 1.00 | 24.07 | BBBB |
| ATOM | 3181 | C | PRO | B | 78 | 1.278 | −70.535 | −27.813 | 1.00 | 21.19 | BBBB |
| ATOM | 3182 | O | PRO | B | 78 | 0.789 | −69.939 | −28.776 | 1.00 | 19.68 | BBBB |
| ATOM | 3183 | N | LEU | B | 79 | 0.544 | −70.961 | −26.790 | 1.00 | 21.21 | BBBB |
| ATOM | 3184 | CA | LEU | B | 79 | −0.896 | −70.728 | −26.783 | 1.00 | 21.32 | BBBB |
| ATOM | 3185 | CB | LEU | B | 79 | −1.569 | −71.476 | −25.630 | 1.00 | 20.99 | BBBB |
| ATOM | 3186 | CG | LEU | B | 79 | −1.397 | −72.988 | −25.617 | 1.00 | 22.40 | BBBB |
| ATOM | 3187 | CD1 | LEU | B | 79 | −2.504 | −73.619 | −24.772 | 1.00 | 22.01 | BBBB |
| ATOM | 3188 | CD2 | LEU | B | 79 | −1.438 | −73.521 | −27.021 | 1.00 | 23.82 | BBBB |
| ATOM | 3189 | C | LEU | B | 79 | −1.275 | −69.263 | −26.707 | 1.00 | 21.17 | BBBB |
| ATOM | 3190 | O | LEU | B | 79 | −2.125 | −68.800 | −27.481 | 1.00 | 20.44 | BBBB |
| ATOM | 3191 | N | ARG | B | 80 | −0.656 | −68.529 | −25.788 | 1.00 | 20.91 | BBBB |
| ATOM | 3192 | CA | ARG | B | 80 | −0.980 | −67.115 | −25.637 | 1.00 | 21.30 | BBBB |
| ATOM | 3193 | CB | ARG | B | 80 | −0.444 | −66.583 | −24.312 | 1.00 | 22.12 | BBBB |
| ATOM | 3194 | CG | ARG | B | 80 | −1.286 | −67.051 | −23.118 | 1.00 | 24.03 | BBBB |
| ATOM | 3195 | CD | ARG | B | 80 | −0.610 | −66.738 | −21.807 | 1.00 | 23.42 | BBBB |
| ATOM | 3196 | NE | ARG | B | 80 | 0.581 | −67.556 | −21.610 | 1.00 | 24.59 | BBBB |
| ATOM | 3197 | CZ | ARG | B | 80 | 1.466 | −67.351 | −20.642 | 1.00 | 26.08 | BBBB |
| ATOM | 3198 | NH1 | ARG | B | 80 | 1.290 | −66.349 | −19.787 | 1.00 | 26.92 | BBBB |
| ATOM | 3199 | NH2 | ARG | B | 80 | 2.514 | −68.152 | −20.519 | 1.00 | 27.22 | BBBB |
| ATOM | 3200 | C | ARG | B | 80 | −0.526 | −66.233 | −26.790 | 1.00 | 21.29 | BBBB |
| ATOM | 3201 | O | ARG | B | 80 | −1.278 | −65.355 | −27.223 | 1.00 | 21.47 | BBBB |
| ATOM | 3202 | N | ILE | B | 81 | 0.683 | −66.448 | −27.303 | 1.00 | 19.29 | BBBB |
| ATOM | 3203 | CA | ILE | B | 81 | 1.113 | −65.621 | −28.421 | 1.00 | 19.47 | BBBB |
| ATOM | 3204 | CB | ILE | B | 81 | 2.639 | −65.793 | −28.730 | 1.00 | 17.92 | BBBB |
| ATOM | 3205 | CG2 | ILE | B | 81 | 2.949 | −67.200 | −29.206 | 1.00 | 17.33 | BBBB |
| ATOM | 3206 | CG1 | ILE | B | 81 | 3.067 | −64.753 | −29.769 | 1.00 | 18.63 | BBBB |
| ATOM | 3207 | CD1 | ILE | B | 81 | 2.746 | −63.318 | −29.346 | 1.00 | 17.46 | BBBB |
| ATOM | 3208 | C | ILE | B | 81 | 0.256 | −65.937 | −29.654 | 1.00 | 18.99 | BBBB |
| ATOM | 3209 | O | ILE | B | 81 | −0.149 | −65.028 | −30.378 | 1.00 | 19.38 | BBBB |
| ATOM | 3210 | N | PHE | B | 82 | −0.056 | −67.211 | −29.880 | 1.00 | 19.39 | BBBB |
| ATOM | 3211 | CA | PHE | B | 82 | −0.875 | −67.582 | −31.038 | 1.00 | 19.15 | BBBB |
| ATOM | 3212 | CB | PHE | B | 82 | −1.057 | −69.103 | −31.136 | 1.00 | 19.27 | BBBB |
| ATOM | 3213 | CG | PHE | B | 82 | −1.811 | −69.548 | −32.368 | 1.00 | 19.87 | BBBB |
| ATOM | 3214 | CD1 | PHE | B | 82 | −1.180 | −69.602 | −33.603 | 1.00 | 20.87 | BBBB |
| ATOM | 3215 | CD2 | PHE | B | 82 | −3.154 | −69.898 | −32.289 | 1.00 | 21.11 | BBBB |
| ATOM | 3216 | CE1 | PHE | B | 82 | −1.872 | −70.002 | −34.753 | 1.00 | 21.20 | BBBB |
| ATOM | 3217 | CE2 | PHE | B | 82 | −3.857 | −70.297 | −33.429 | 1.00 | 22.26 | BBBB |
| ATOM | 3218 | CZ | PHE | B | 82 | −3.212 | −70.349 | −34.663 | 1.00 | 22.14 | BBBB |
| ATOM | 3219 | C | PHE | B | 82 | −2.250 | −66.931 | −30.959 | 1.00 | 19.94 | BBBB |
| ATOM | 3220 | O | PHE | B | 82 | −2.777 | −66.444 | −31.970 | 1.00 | 19.64 | BBBB |
| ATOM | 3221 | N | ASN | B | 83 | −2.832 | −66.923 | −29.764 | 1.00 | 19.29 | BBBB |
| ATOM | 3222 | CA | ASN | B | 83 | −4.150 | −66.332 | −29.577 | 1.00 | 20.90 | BBBB |
| ATOM | 3223 | CB | ASN | B | 83 | −4.693 | −66.641 | −28.178 | 1.00 | 20.55 | BBBB |
| ATOM | 3224 | CG | ASN | B | 83 | −6.158 | −66.244 | −28.028 | 1.00 | 22.79 | BBBB |
| ATOM | 3225 | OD1 | ASN | B | 83 | −6.505 | −65.374 | −27.229 | 1.00 | 25.14 | BBBB |
| ATOM | 3226 | ND2 | ASN | B | 83 | −7.018 | −66.877 | −28.807 | 1.00 | 20.47 | BBBB |
| ATOM | 3227 | C | ASN | B | 83 | −4.178 | −64.821 | −29.812 | 1.00 | 20.83 | BBBB |
| ATOM | 3228 | O | ASN | B | 83 | −5.086 | −64.316 | −30.472 | 1.00 | 21.92 | BBBB |
| ATOM | 3229 | N | ALA | B | 84 | −3.203 | −64.092 | −29.275 | 1.00 | 19.74 | BBBB |
| ATOM | 3230 | CA | ALA | B | 84 | −3.177 | −62.647 | −29.484 | 1.00 | 19.30 | BBBB |
| ATOM | 3231 | CB | ALA | B | 84 | −2.060 | −62.008 | −28.662 | 1.00 | 18.59 | BBBB |
| ATOM | 3232 | C | ALA | B | 84 | −2.967 | −62.380 | −30.981 | 1.00 | 19.94 | BBBB |
| ATOM | 3233 | O | ALA | B | 84 | −3.561 | −61.459 | −31.552 | 1.00 | 19.69 | BBBB |
| ATOM | 3234 | N | TRP | B | 85 | −2.118 | −63.197 | −31.603 | 1.00 | 19.77 | BBBB |
| ATOM | 3235 | CA | TRP | B | 85 | −1.820 | −63.111 | −33.032 | 1.00 | 20.56 | BBBB |
| ATOM | 3236 | CB | TRP | B | 85 | −0.754 | −64.148 | −33.396 | 1.00 | 21.46 | BBBB |
| ATOM | 3237 | CG | TRP | B | 85 | −0.365 | −64.167 | −34.856 | 1.00 | 23.00 | BBBB |
| ATOM | 3238 | CD2 | TRP | B | 85 | −0.588 | −65.232 | −35.785 | 1.00 | 23.69 | BBBB |
| ATOM | 3239 | CE2 | TRP | B | 85 | −0.024 | −64.835 | −37.022 | 1.00 | 24.14 | BBBB |

TABLE 1-continued

ATOMIC COORDINATES OF E. COLI MURG PROTEIN

| ATOM | 3240 | CE3 | TRP | B | 85 | −1.206 | −66.486 | −35.693 | 1.00 | 24.79 | BBBB |
|---|---|---|---|---|---|---|---|---|---|---|---|
| ATOM | 3241 | CD1 | TRP | B | 85 | 0.301 | −63.189 | −35.548 | 1.00 | 23.17 | BBBB |
| ATOM | 3242 | NE1 | TRP | B | 85 | 0.509 | −63.585 | −36.848 | 1.00 | 24.28 | BBBB |
| ATOM | 3243 | CZ2 | TRP | B | 85 | −0.060 | −65.650 | −38.160 | 1.00 | 24.90 | BBBB |
| ATOM | 3244 | CZ3 | TRP | B | 85 | −1.243 | −67.299 | −36.827 | 1.00 | 25.45 | BBBB |
| ATOM | 3245 | CH2 | TRP | B | 85 | −0.671 | −66.875 | −38.045 | 1.00 | 25.15 | BBBB |
| ATOM | 3246 | C | TRP | B | 85 | −3.090 | −63.354 | −33.865 | 1.00 | 21.76 | BBBB |
| ATOM | 3247 | O | TRP | B | 85 | −3.339 | −62.658 | −34.859 | 1.00 | 20.40 | BBBB |
| ATOM | 3248 | N | ARG | B | 86 | −3.885 | −64.346 | −33.467 | 1.00 | 22.03 | BBBB |
| ATOM | 3249 | CA | ARG | B | 86 | −5.140 | −64.660 | −34.166 | 1.00 | 23.28 | BBBB |
| ATOM | 3250 | CB | ARG | B | 86 | −5.754 | −65.965 | −33.623 | 1.00 | 24.72 | BBBB |
| ATOM | 3251 | CG | ARG | B | 86 | −4.999 | −67.236 | −34.021 | 1.00 | 27.21 | BBBB |
| ATOM | 3252 | CD | ARG | B | 86 | −5.368 | −67.725 | −35.418 | 1.00 | 29.60 | BBBB |
| ATOM | 3253 | NE | ARG | B | 86 | −6.626 | −68.477 | −35.422 | 1.00 | 31.45 | BBBB |
| ATOM | 3254 | CZ | ARG | B | 86 | −7.185 | −69.004 | −36.508 | 1.00 | 31.37 | BBBB |
| ATOM | 3255 | NH1 | ARG | B | 86 | −6.607 | −68.862 | −37.696 | 1.00 | 32.19 | BBBB |
| ATOM | 3256 | NH2 | ARG | B | 86 | −8.314 | −69.694 | −36.405 | 1.00 | 31.39 | BBBB |
| ATOM | 3257 | C | ARG | B | 86 | −6.151 | −63.517 | −34.007 | 1.00 | 22.98 | BBBB |
| ATOM | 3258 | O | ARG | B | 86 | −6.890 | −63.195 | −34.942 | 1.00 | 21.37 | BBBB |
| ATOM | 3259 | N | GLN | B | 87 | −6.190 | −62.916 | −32.821 | 1.00 | 22.90 | BBBB |
| ATOM | 3260 | CA | GLN | B | 87 | −7.101 | −61.802 | −32.567 | 1.00 | 24.07 | BBBB |
| ATOM | 3261 | CB | GLN | B | 87 | −7.046 | −61.382 | −31.097 | 1.00 | 24.33 | BBBB |
| ATOM | 3262 | CG | GLN | B | 87 | −7.873 | −62.280 | −30.187 | 1.00 | 27.24 | BBBB |
| ATOM | 3263 | CD | GLN | B | 87 | −7.720 | −61.943 | −28.723 | 1.00 | 28.81 | BBBB |
| ATOM | 3264 | OE1 | GLN | B | 87 | −8.567 | −62.296 | −27.908 | 1.00 | 33.25 | BBBB |
| ATOM | 3265 | NE2 | GLN | B | 87 | −6.632 | −61.275 | −28.375 | 1.00 | 29.95 | BBBB |
| ATOM | 3266 | C | GLN | B | 87 | −6.738 | −60.618 | −33.457 | 1.00 | 23.85 | BBBB |
| ATOM | 3267 | O | GLN | B | 87 | −7.613 | −60.012 | −34.077 | 1.00 | 24.02 | BBBB |
| ATOM | 3268 | N | ALA | B | 88 | −5.449 | −60.293 | −33.521 | 1.00 | 23.39 | BBBB |
| ATOM | 3269 | CA | ALA | B | 88 | −4.996 | −59.183 | −34.355 | 1.00 | 23.78 | BBBB |
| ATOM | 3270 | CB | ALA | B | 88 | −3.508 | −58.909 | −34.116 | 1.00 | 23.33 | BBBB |
| ATOM | 3271 | C | ALA | B | 88 | −5.257 | −59.485 | −35.831 | 1.00 | 24.73 | BBBB |
| ATOM | 3272 | O | ALA | B | 88 | −5.655 | −58.595 | −36.592 | 1.00 | 24.72 | BBBB |
| ATOM | 3273 | N | ARG | B | 89 | −5.038 | −60.735 | −36.244 | 1.00 | 24.26 | BBBB |
| ATOM | 3274 | CA | ARG | B | 89 | −5.285 | −61.111 | −37.636 | 1.00 | 24.94 | BBBB |
| ATOM | 3275 | CB | ARG | B | 89 | −4.904 | −62.575 | −37.893 | 1.00 | 25.14 | BBBB |
| ATOM | 3276 | CG | ARG | B | 89 | −3.461 | −62.774 | −38.353 | 1.00 | 24.54 | BBBB |
| ATOM | 3277 | CD | ARG | B | 89 | −3.142 | −64.253 | −38.510 | 1.00 | 25.50 | BBBB |
| ATOM | 3278 | NE | ARG | B | 89 | −3.809 | −64.901 | −39.641 | 1.00 | 24.93 | BBBB |
| ATOM | 3279 | CZ | ARG | B | 89 | −3.329 | −64.930 | −40.882 | 1.00 | 25.90 | BBBB |
| ATOM | 3280 | NH1 | ARG | B | 89 | −2.178 | −64.336 | −41.170 | 1.00 | 25.98 | BBBB |
| ATOM | 3281 | NH2 | ARG | B | 89 | −3.979 | −65.596 | −41.831 | 1.00 | 26.36 | BBBB |
| ATOM | 3282 | C | ARG | B | 89 | −6.752 | −60.909 | −38.013 | 1.00 | 25.29 | BBBB |
| ATOM | 3283 | O | ARG | B | 89 | −7.056 | −60.420 | −39.104 | 1.00 | 24.27 | BBBB |
| ATOM | 3284 | N | ALA | B | 90 | −7.658 | −61.296 | −37.118 | 1.00 | 24.61 | BBBB |
| ATOM | 3285 | CA | ALA | B | 90 | −9.088 | −61.151 | −37.383 | 1.00 | 26.16 | BBBB |
| ATOM | 3286 | CB | ALA | B | 90 | −9.907 | −61.775 | −36.254 | 1.00 | 25.77 | BBBB |
| ATOM | 3287 | C | ALA | B | 90 | −9.440 | −59.673 | −37.538 | 1.00 | 26.83 | BBBB |
| ATOM | 3288 | O | ALA | B | 90 | −10.213 | −59.301 | −38.421 | 1.00 | 27.71 | BBBB |
| ATOM | 3289 | N | ILE | B | 91 | −8.862 | −58.837 | −36.685 | 1.00 | 26.92 | BBBB |
| ATOM | 3290 | CA | ILE | B | 91 | −9.108 | −57.400 | −36.733 | 1.00 | 26.97 | BBBB |
| ATOM | 3291 | CB | ILE | B | 91 | −8.408 | −56.682 | −35.565 | 1.00 | 27.03 | BBBB |
| ATOM | 3292 | CG2 | ILE | B | 91 | −8.327 | −55.175 | −35.837 | 1.00 | 25.82 | BBBB |
| ATOM | 3293 | CG1 | ILE | B | 91 | −9.161 | −56.962 | −34.260 | 1.00 | 24.58 | BBBB |
| ATOM | 3294 | CD1 | ILE | B | 91 | −8.435 | −56.490 | −33.021 | 1.00 | 24.65 | BBBB |
| ATOM | 3295 | C | ILE | B | 91 | −8.618 | −56.787 | −38.040 | 1.00 | 28.07 | BBBB |
| ATOM | 3296 | O | ILE | B | 91 | −9.289 | −55.934 | −38.629 | 1.00 | 28.41 | BBBB |
| ATOM | 3297 | N | MET | B | 92 | −7.451 | −57.227 | −38.496 | 1.00 | 27.92 | BBBB |
| ATOM | 3298 | CA | MET | B | 92 | −6.872 | −56.693 | −39.717 | 1.00 | 29.03 | BBBB |
| ATOM | 3299 | CB | MET | B | 92 | −5.366 | −56.912 | −39.712 | 1.00 | 27.34 | BBBB |
| ATOM | 3300 | CG | MET | B | 92 | −4.686 | −56.235 | −38.536 | 1.00 | 26.09 | BBBB |
| ATOM | 3301 | SD | MET | B | 92 | −2.919 | −56.413 | −38.602 | 1.00 | 25.72 | BBBB |
| ATOM | 3302 | CE | MET | B | 92 | −2.413 | −55.394 | −37.218 | 1.00 | 24.09 | BBBB |
| ATOM | 3303 | C | MET | B | 92 | −7.488 | −57.257 | −40.988 | 1.00 | 30.07 | BBBB |
| ATOM | 3304 | O | MET | B | 92 | −7.417 | −56.628 | −42.046 | 1.00 | 30.66 | BBBB |
| ATOM | 3305 | N | LYS | B | 93 | −8.082 | −58.441 | −40.894 | 1.00 | 30.96 | BBBB |
| ATOM | 3306 | CA | LYS | B | 93 | −8.735 | −59.038 | −42.050 | 1.00 | 33.20 | BBBB |
| ATOM | 3307 | CB | LYS | B | 93 | −8.969 | −60.537 | −41.826 | 1.00 | 34.31 | BBBB |
| ATOM | 3308 | CG | LYS | B | 93 | −7.689 | −61.369 | −41.860 | 1.00 | 36.71 | BBBB |
| ATOM | 3309 | CD | LYS | B | 93 | −7.956 | −62.847 | −41.576 | 1.00 | 38.43 | BBBB |
| ATOM | 3310 | CE | LYS | B | 93 | −8.781 | −63.491 | −42.683 | 1.00 | 38.82 | BBBB |
| ATOM | 3311 | NZ | LYS | B | 93 | −9.197 | −64.881 | −42.344 | 1.00 | 40.70 | BBBB |
| ATOM | 3312 | C | LYS | B | 93 | −10.067 | −58.314 | −42.252 | 1.00 | 33.65 | BBBB |
| ATOM | 3313 | O | LYS | B | 93 | −10.524 | −58.143 | −43.382 | 1.00 | 34.76 | BBBB |
| ATOM | 3314 | N | ALA | B | 94 | −10.672 | −57.877 | −41.147 | 1.00 | 33.00 | BBBB |
| ATOM | 3315 | CA | ALA | B | 94 | −11.943 | −57.157 | −41.183 | 1.00 | 33.62 | BBBB |
| ATOM | 3316 | CB | ALA | B | 94 | −12.641 | −57.260 | −39.833 | 1.00 | 33.62 | BBBB |

TABLE 1-continued

ATOMIC COORDINATES OF E. COLI MURG PROTEIN

| ATOM | 3317 | C | ALA | B | 94 | −11.752 | −55.684 | −41.559 | 1.00 | 33.95 | BBBB |
|---|---|---|---|---|---|---|---|---|---|---|---|
| ATOM | 3318 | O | ALA | B | 94 | −12.484 | −55.153 | −42.397 | 1.00 | 33.20 | BBBB |
| ATOM | 3319 | N | TYR | B | 95 | −10.772 | −55.028 | −40.943 | 1.00 | 33.15 | BBBB |
| ATOM | 3320 | CA | TYR | B | 95 | −10.504 | −53.620 | −41.224 | 1.00 | 33.83 | BBBB |
| ATOM | 3321 | CB | TYR | B | 95 | −9.722 | −52.992 | −40.060 | 1.00 | 33.92 | BBBB |
| ATOM | 3322 | CG | TYR | B | 95 | −9.383 | −51.525 | −40.249 | 1.00 | 34.38 | BBBB |
| ATOM | 3323 | CD1 | TYR | B | 95 | −10.381 | −50.585 | −40.499 | 1.00 | 36.04 | BBBB |
| ATOM | 3324 | CE1 | TYR | B | 95 | −10.071 | −49.240 | −40.702 | 1.00 | 36.49 | BBBB |
| ATOM | 3325 | CD2 | TYR | B | 95 | −8.063 | −51.082 | −40.202 | 1.00 | 34.89 | BBBB |
| ATOM | 3326 | CE2 | TYR | B | 95 | −7.741 | −49.741 | −40.401 | 1.00 | 35.72 | BBBB |
| ATOM | 3327 | CZ | TYR | B | 95 | −8.750 | −48.826 | −40.655 | 1.00 | 36.79 | BBBB |
| ATOM | 3328 | OH | TYR | B | 95 | −8.436 | −47.502 | −40.874 | 1.00 | 37.60 | BBBB |
| ATOM | 3329 | C | TYR | B | 95 | −9.743 | −53.418 | −42.538 | 1.00 | 34.06 | BBBB |
| ATOM | 3330 | O | TYR | B | 95 | −9.919 | −52.404 | −43.214 | 1.00 | 33.85 | BBBB |
| ATOM | 3331 | N | LYS | B | 96 | −8.902 | −54.386 | −42.896 | 1.00 | 33.76 | BBBB |
| ATOM | 3332 | CA | LYS | B | 96 | −8.104 | −54.327 | −44.122 | 1.00 | 33.85 | BBBB |
| ATOM | 3333 | CB | LYS | B | 96 | −9.004 | −54.476 | −45.353 | 1.00 | 35.14 | BBBB |
| ATOM | 3334 | CG | LYS | B | 96 | −9.707 | −55.812 | −45.463 | 1.00 | 37.16 | BBBB |
| ATOM | 3335 | CD | LYS | B | 96 | −10.649 | −55.843 | −46.661 | 1.00 | 38.58 | BBBB |
| ATOM | 3336 | CE | LYS | B | 96 | −11.388 | −57.170 | −46.752 | 1.00 | 40.07 | BBBB |
| ATOM | 3337 | NZ | LYS | B | 96 | −12.319 | −57.218 | −47.925 | 1.00 | 41.29 | BBBB |
| ATOM | 3338 | C | LYS | B | 96 | −7.278 | −53.049 | −44.262 | 1.00 | 33.75 | BBBB |
| ATOM | 3339 | O | LYS | B | 96 | −7.489 | −52.258 | −45.189 | 1.00 | 34.55 | BBBB |
| ATOM | 3340 | N | PRO | B | 97 | −6.326 | −52.825 | −43.345 | 1.00 | 32.59 | BBBB |
| ATOM | 3341 | CD | PRO | B | 97 | −6.004 | −53.620 | −42.143 | 1.00 | 32.37 | BBBB |
| ATOM | 3342 | CA | PRO | B | 97 | −5.490 | −51.623 | −43.419 | 1.00 | 31.82 | BBBB |
| ATOM | 3343 | CB | PRO | B | 97 | −4.850 | −51.568 | −42.038 | 1.00 | 31.66 | BBBB |
| ATOM | 3344 | CG | PRO | B | 97 | −4.686 | −53.025 | −41.704 | 1.00 | 31.53 | BBBB |
| ATOM | 3345 | C | PRO | B | 97 | −4.458 | −51.769 | −44.530 | 1.00 | 31.60 | BBBB |
| ATOM | 3346 | O | PRO | B | 97 | −4.052 | −52.881 | −44.860 | 1.00 | 32.52 | BBBB |
| ATOM | 3347 | N | ASP | B | 98 | −4.037 | −50.651 | −45.112 | 1.00 | 31.25 | BBBB |
| ATOM | 3348 | CA | ASP | B | 98 | −3.049 | −50.685 | −46.188 | 1.00 | 29.78 | BBBB |
| ATOM | 3349 | CB | ASP | B | 98 | −3.234 | −49.488 | −47.117 | 1.00 | 32.00 | BBBB |
| ATOM | 3350 | CG | ASP | B | 98 | −4.562 | −49.519 | −47.837 | 1.00 | 34.21 | BBBB |
| ATOM | 3351 | OD1 | ASP | B | 98 | −5.281 | −48.498 | −47.795 | 1.00 | 35.37 | BBBB |
| ATOM | 3352 | OD2 | ASP | B | 98 | −4.888 | −50.566 | −48.443 | 1.00 | 35.10 | BBBB |
| ATOM | 3353 | C | ASP | B | 98 | −1.654 | −50.660 | −45.603 | 1.00 | 28.70 | BBBB |
| ATOM | 3354 | O | ASP | B | 98 | −0.672 | −50.973 | −46.274 | 1.00 | 26.48 | BBBB |
| ATOM | 3355 | N | VAL | B | 99 | −1.573 | −50.278 | −44.337 | 1.00 | 26.88 | BBBB |
| ATOM | 3356 | CA | VAL | B | 99 | −0.296 | −50.214 | −43.660 | 1.00 | 26.75 | BBBB |
| ATOM | 3357 | CB | VAL | B | 99 | 0.500 | −48.973 | −44.132 | 1.00 | 27.35 | BBBB |
| ATOM | 3358 | CG1 | VAL | B | 99 | −0.305 | −47.718 | −43.867 | 1.00 | 29.45 | BBBB |
| ATOM | 3359 | CG2 | VAL | B | 99 | 1.841 | −48.908 | −43.443 | 1.00 | 27.48 | BBBB |
| ATOM | 3360 | C | VAL | B | 99 | −0.552 | −50.134 | −42.162 | 1.00 | 25.92 | BBBB |
| ATOM | 3361 | O | VAL | B | 99 | −1.585 | −49.627 | −41.723 | 1.00 | 25.04 | BBBB |
| ATOM | 3362 | N | VAL | B | 100 | 0.374 | −50.664 | −41.377 | 1.00 | 24.63 | BBBB |
| ATOM | 3363 | CA | VAL | B | 100 | 0.227 | −50.613 | −39.936 | 1.00 | 23.59 | BBBB |
| ATOM | 3364 | CB | VAL | B | 100 | 0.120 | −52.026 | −39.327 | 1.00 | 24.97 | BBBB |
| ATOM | 3365 | CG1 | VAL | B | 100 | 0.139 | −51.941 | −37.811 | 1.00 | 24.71 | BBBB |
| ATOM | 3366 | CG2 | VAL | B | 100 | −1.172 | −52.683 | −39.782 | 1.00 | 22.62 | BBBB |
| ATOM | 3367 | C | VAL | B | 100 | 1.428 | −49.881 | −39.382 | 1.00 | 22.74 | BBBB |
| ATOM | 3368 | O | VAL | B | 100 | 2.551 | −50.093 | −39.830 | 1.00 | 24.62 | BBBB |
| ATOM | 3369 | N | LEU | B | 101 | 1.178 | −49.001 | −38.419 | 1.00 | 21.89 | BBBB |
| ATOM | 3370 | CA | LEU | B | 101 | 2.214 | −48.199 | −37.797 | 1.00 | 21.59 | BBBB |
| ATOM | 3371 | CB | LEU | B | 101 | 1.823 | −46.716 | −37.853 | 1.00 | 22.86 | BBBB |
| ATOM | 3372 | CG | LEU | B | 101 | 2.850 | −45.580 | −37.892 | 1.00 | 24.72 | BBBB |
| ATOM | 3373 | CD1 | LEU | B | 101 | 2.237 | −44.385 | −37.174 | 1.00 | 25.30 | BBBB |
| ATOM | 3374 | CD2 | LEU | B | 101 | 4.168 | −45.954 | −37.273 | 1.00 | 24.45 | BBBB |
| ATOM | 3375 | C | LEU | B | 101 | 2.349 | −48.604 | −36.336 | 1.00 | 20.83 | BBBB |
| ATOM | 3376 | O | LEU | B | 101 | 1.370 | −48.581 | −35.595 | 1.00 | 21.35 | BBBB |
| ATOM | 3377 | N | GLY | B | 102 | 3.556 | −48.986 | −35.936 | 1.00 | 20.96 | BBBB |
| ATOM | 3378 | CA | GLY | B | 102 | 3.796 | −49.357 | −34.549 | 1.00 | 19.23 | BBBB |
| ATOM | 3379 | C | GLY | B | 102 | 4.655 | −48.282 | −33.918 | 1.00 | 18.45 | BBBB |
| ATOM | 3380 | O | GLY | B | 102 | 5.765 | −48.016 | −34.381 | 1.00 | 18.70 | BBBB |
| ATOM | 3381 | N | MET | B | 103 | 4.155 | −47.660 | −32.857 | 1.00 | 18.01 | BBBB |
| ATOM | 3382 | CA | MET | B | 103 | 4.892 | −46.597 | −32.191 | 1.00 | 18.93 | BBBB |
| ATOM | 3383 | CB | MET | B | 103 | 3.928 | −45.477 | −31.781 | 1.00 | 20.02 | BBBB |
| ATOM | 3384 | CG | MET | B | 103 | 3.121 | −44.888 | −32.944 | 1.00 | 21.61 | BBBB |
| ATOM | 3385 | SD | MET | B | 103 | 4.212 | −44.135 | −34.157 | 1.00 | 23.45 | BBBB |
| ATOM | 3386 | CE | MET | B | 103 | 4.718 | −42.680 | −33.271 | 1.00 | 21.40 | BBBB |
| ATOM | 3387 | C | MET | B | 103 | 5.612 | −47.128 | −30.957 | 1.00 | 18.98 | BBBB |
| ATOM | 3388 | O | MET | B | 103 | 6.134 | −46.357 | −30.158 | 1.00 | 17.96 | BBBB |
| ATOM | 3389 | N | GLY | B | 104 | 5.640 | −48.450 | −30.827 | 1.00 | 21.56 | BBBB |
| ATOM | 3390 | CA | GLY | B | 104 | 6.275 | −49.080 | −29.686 | 1.00 | 21.89 | BBBB |
| ATOM | 3391 | C | GLY | B | 104 | 5.192 | −49.614 | −28.764 | 1.00 | 23.28 | BBBB |
| ATOM | 3392 | O | GLY | B | 104 | 4.009 | −49.353 | −28.980 | 1.00 | 22.50 | BBBB |
| ATOM | 3393 | N | GLY | B | 105 | 5.583 | −50.364 | −27.741 | 1.00 | 23.01 | BBBB |

TABLE 1-continued

ATOMIC COORDINATES OF *E. COLI* MURG PROTEIN

| ATOM | 3394 | CA | GLY | B | 105 | 4.593 | −50.905 | −26.827 | 1.00 | 23.54 | BBBB |
|---|---|---|---|---|---|---|---|---|---|---|---|
| ATOM | 3395 | C | GLY | B | 105 | 4.358 | −52.380 | −27.078 | 1.00 | 23.17 | BBBB |
| ATOM | 3396 | O | GLY | B | 105 | 4.449 | −52.844 | −28.214 | 1.00 | 22.69 | BBBB |
| ATOM | 3397 | N | TYR | B | 106 | 4.018 | −53.118 | −26.026 | 1.00 | 22.87 | BBBB |
| ATOM | 3398 | CA | TYR | B | 106 | 3.818 | −54.554 | −26.159 | 1.00 | 22.37 | BBBB |
| ATOM | 3399 | CB | TYR | B | 106 | 3.632 | −55.181 | −24.774 | 1.00 | 25.08 | BBBB |
| ATOM | 3400 | CG | TYR | B | 106 | 4.864 | −55.008 | −23.929 | 1.00 | 28.19 | BBBB |
| ATOM | 3401 | CD1 | TYR | B | 106 | 4.869 | −54.153 | −22.830 | 1.00 | 31.96 | BBBB |
| ATOM | 3402 | CE1 | TYR | B | 106 | 6.043 | −53.915 | −22.108 | 1.00 | 33.13 | BBBB |
| ATOM | 3403 | CD2 | TYR | B | 106 | 6.058 | −55.631 | −24.282 | 1.00 | 31.27 | BBBB |
| ATOM | 3404 | CE2 | TYR | B | 106 | 7.234 | −55.400 | −23.569 | 1.00 | 32.27 | BBBB |
| ATOM | 3405 | CZ | TYR | B | 106 | 7.219 | −54.541 | −22.487 | 1.00 | 33.19 | BBBB |
| ATOM | 3406 | OH | TYR | B | 106 | 8.388 | −54.291 | −21.802 | 1.00 | 35.95 | BBBB |
| ATOM | 3407 | C | TYR | B | 106 | 2.719 | −55.018 | −27.100 | 1.00 | 20.52 | BBBB |
| ATOM | 3408 | O | TYR | B | 106 | 2.867 | −56.052 | −27.746 | 1.00 | 20.50 | BBBB |
| ATOM | 3409 | N | VAL | B | 107 | 1.628 | −54.270 | −27.205 | 1.00 | 19.06 | BBBB |
| ATOM | 3410 | CA | VAL | B | 107 | 0.557 | −54.694 | −28.099 | 1.00 | 18.06 | BBBB |
| ATOM | 3411 | CB | VAL | B | 107 | −0.690 | −53.774 | −27.978 | 1.00 | 20.95 | BBBB |
| ATOM | 3412 | CG1 | VAL | B | 107 | −0.407 | −52.407 | −28.589 | 1.00 | 21.39 | BBBB |
| ATOM | 3413 | CG2 | VAL | B | 107 | −1.879 | −54.433 | −28.658 | 1.00 | 21.30 | BBBB |
| ATOM | 3414 | C | VAL | B | 107 | 1.015 | −54.743 | −29.559 | 1.00 | 17.45 | BBBB |
| ATOM | 3415 | O | VAL | B | 107 | 0.502 | −55.536 | −30.346 | 1.00 | 16.99 | BBBB |
| ATOM | 3416 | N | SER | B | 108 | 1.991 | −53.916 | −29.918 | 1.00 | 17.96 | BBBB |
| ATOM | 3417 | CA | SER | B | 108 | 2.488 | −53.892 | −31.290 | 1.00 | 19.67 | BBBB |
| ATOM | 3418 | CB | SER | B | 108 | 3.424 | −52.691 | −31.508 | 1.00 | 19.56 | BBBB |
| ATOM | 3419 | OG | SER | B | 108 | 4.666 | −52.824 | −30.837 | 1.00 | 19.63 | BBBB |
| ATOM | 3420 | C | SER | B | 108 | 3.197 | −55.187 | −31.694 | 1.00 | 20.38 | BBBB |
| ATOM | 3421 | O | SER | B | 108 | 3.385 | −55.449 | −32.884 | 1.00 | 21.25 | BBBB |
| ATOM | 3422 | N | GLY | B | 109 | 3.595 | −55.995 | −30.710 | 1.00 | 19.59 | BBBB |
| ATOM | 3423 | CA | GLY | B | 109 | 4.251 | −57.256 | −31.023 | 1.00 | 20.03 | BBBB |
| ATOM | 3424 | C | GLY | B | 109 | 3.311 | −58.170 | −31.792 | 1.00 | 19.61 | BBBB |
| ATOM | 3425 | O | GLY | B | 109 | 3.579 | −58.517 | −32.940 | 1.00 | 19.24 | BBBB |
| ATOM | 3426 | N | PRO | B | 110 | 2.206 | −58.606 | −31.173 | 1.00 | 19.20 | BBBB |
| ATOM | 3427 | CD | PRO | B | 110 | 1.914 | −58.528 | −29.729 | 1.00 | 19.94 | BBBB |
| ATOM | 3428 | CA | PRO | B | 110 | 1.251 | −59.478 | −31.855 | 1.00 | 18.99 | BBBB |
| ATOM | 3429 | CB | PRO | B | 110 | 0.198 | −59.737 | −30.778 | 1.00 | 20.41 | BBBB |
| ATOM | 3430 | CG | PRO | B | 110 | 0.998 | −59.720 | −29.515 | 1.00 | 19.81 | BBBB |
| ATOM | 3431 | C | PRO | B | 110 | 0.651 | −58.761 | −33.075 | 1.00 | 19.22 | BBBB |
| ATOM | 3432 | O | PRO | B | 110 | 0.406 | −59.371 | −34.116 | 1.00 | 17.13 | BBBB |
| ATOM | 3433 | N | GLY | B | 111 | 0.407 | −57.462 | −32.927 | 1.00 | 19.03 | BBBB |
| ATOM | 3434 | CA | GLY | B | 111 | −0.160 | −56.702 | −34.025 | 1.00 | 19.60 | BBBB |
| ATOM | 3435 | C | GLY | B | 111 | 0.764 | −56.714 | −35.226 | 1.00 | 19.59 | BBBB |
| ATOM | 3436 | O | GLY | B | 111 | 0.330 | −56.979 | −36.339 | 1.00 | 21.10 | BBBB |
| ATOM | 3437 | N | GLY | B | 112 | 2.043 | −56.429 | −34.995 | 1.00 | 19.78 | BBBB |
| ATOM | 3438 | CA | GLY | B | 112 | 3.014 | −56.417 | −36.074 | 1.00 | 19.97 | BBBB |
| ATOM | 3439 | C | GLY | B | 112 | 3.147 | −57.783 | −36.724 | 1.00 | 20.43 | BBBB |
| ATOM | 3440 | O | GLY | B | 112 | 3.233 | −57.896 | −37.949 | 1.00 | 19.94 | BBBB |
| ATOM | 3441 | N | LEU | B | 113 | 3.167 | −58.828 | −35.903 | 1.00 | 19.26 | BBBB |
| ATOM | 3442 | CA | LEU | B | 113 | 3.265 | −60.184 | −36.429 | 1.00 | 19.49 | BBBB |
| ATOM | 3443 | CB | LEU | B | 113 | 3.405 | −61.198 | −35.289 | 1.00 | 18.38 | BBBB |
| ATOM | 3444 | CG | LEU | B | 113 | 4.777 | −61.270 | −34.605 | 1.00 | 20.59 | BBBB |
| ATOM | 3445 | CD1 | LEU | B | 113 | 4.656 | −62.059 | −33.311 | 1.00 | 20.01 | BBBB |
| ATOM | 3446 | CD2 | LEU | B | 113 | 5.794 | −61.914 | −35.538 | 1.00 | 20.23 | BBBB |
| ATOM | 3447 | C | LEU | B | 113 | 2.040 | −60.521 | −37.274 | 1.00 | 18.73 | BBBB |
| ATOM | 3448 | O | LEU | B | 113 | 2.143 | −61.252 | −38.255 | 1.00 | 18.44 | BBBB |
| ATOM | 3449 | N | ALA | B | 114 | 0.875 | −60.010 | −36.892 | 1.00 | 18.96 | BBBB |
| ATOM | 3450 | CA | ALA | B | 114 | −0.334 | −60.292 | −37.661 | 1.00 | 18.70 | BBBB |
| ATOM | 3451 | CB | ALA | B | 114 | −1.562 | −59.855 | −36.889 | 1.00 | 16.45 | BBBB |
| ATOM | 3452 | C | ALA | B | 114 | −0.288 | −59.578 | −39.019 | 1.00 | 19.30 | BBBB |
| ATOM | 3453 | O | ALA | B | 114 | −0.602 | −60.167 | −40.052 | 1.00 | 20.62 | BBBB |
| ATOM | 3454 | N | ALA | B | 115 | 0.082 | −58.303 | −39.000 | 1.00 | 20.57 | BBBB |
| ATOM | 3455 | CA | ALA | B | 115 | 0.167 | −57.516 | −40.229 | 1.00 | 21.84 | BBBB |
| ATOM | 3456 | CB | ALA | B | 115 | 0.636 | −56.108 | −39.911 | 1.00 | 19.85 | BBBB |
| ATOM | 3457 | C | ALA | B | 115 | 1.140 | −58.192 | −41.189 | 1.00 | 21.58 | BBBB |
| ATOM | 3458 | O | ALA | B | 115 | 0.815 | −58.464 | −42.345 | 1.00 | 22.14 | BBBB |
| ATOM | 3459 | N | TRP | B | 116 | 2.334 | −58.476 | −40.688 | 1.00 | 22.12 | BBBB |
| ATOM | 3460 | CA | TRP | B | 116 | 3.365 | −59.126 | −41.478 | 1.00 | 23.22 | BBBB |
| ATOM | 3461 | CB | TRP | B | 116 | 4.584 | −59.367 | −40.579 | 1.00 | 26.08 | BBBB |
| ATOM | 3462 | CG | TRP | B | 116 | 5.699 | −60.136 | −41.204 | 1.00 | 27.40 | BBBB |
| ATOM | 3463 | CD2 | TRP | B | 116 | 6.168 | −61.418 | −40.793 | 1.00 | 28.77 | BBBB |
| ATOM | 3464 | CE2 | TRP | B | 116 | 7.234 | −61.771 | −41.655 | 1.00 | 30.37 | BBBB |
| ATOM | 3465 | CE3 | TRP | B | 116 | 5.794 | −62.308 | −39.778 | 1.00 | 30.49 | BBBB |
| ATOM | 3466 | CD1 | TRP | B | 116 | 6.473 | −59.761 | −42.271 | 1.00 | 28.30 | BBBB |
| ATOM | 3467 | NE1 | TRP | B | 116 | 7.401 | −60.742 | −42.547 | 1.00 | 29.04 | BBBB |
| ATOM | 3468 | CZ2 | TRP | B | 116 | 7.929 | −62.981 | −41.529 | 1.00 | 31.08 | BBBB |
| ATOM | 3469 | CZ3 | TRP | B | 116 | 6.485 | −63.510 | −39.653 | 1.00 | 31.85 | BBBB |
| ATOM | 3470 | CH2 | TRP | B | 116 | 7.541 | −63.834 | −40.527 | 1.00 | 32.27 | BBBB |

TABLE 1-continued

ATOMIC COORDINATES OF E. COLI MURG PROTEIN

| ATOM | 3471 | C | TRP | B | 116 | 2.871 | −60.434 | −42.123 | 1.00 | 23.55 | BBBB |
|------|------|------|-----|---|-----|--------|---------|---------|------|-------|------|
| ATOM | 3472 | O | TRP | B | 116 | 3.048 | −60.643 | −43.329 | 1.00 | 22.19 | BBBB |
| ATOM | 3473 | N | SER | B | 117 | 2.231 | −61.304 | −41.338 | 1.00 | 21.35 | BBBB |
| ATOM | 3474 | CA | SER | B | 117 | 1.735 | −62.573 | −41.873 | 1.00 | 22.61 | BBBB |
| ATOM | 3475 | CB | SER | B | 117 | 1.167 | −63.462 | −40.756 | 1.00 | 20.72 | BBBB |
| ATOM | 3476 | OG | SER | B | 117 | 0.010 | −62.889 | −40.169 | 1.00 | 22.72 | BBBB |
| ATOM | 3477 | C | SER | B | 117 | 0.665 | −62.383 | −42.940 | 1.00 | 23.56 | BBBB |
| ATOM | 3478 | O | SER | B | 117 | 0.463 | −63.262 | −43.780 | 1.00 | 23.11 | BBBB |
| ATOM | 3479 | N | LEU | B | 118 | −0.020 | −61.242 | −42.905 | 1.00 | 24.40 | BBBB |
| ATOM | 3480 | CA | LEU | B | 118 | −1.069 | −60.957 | −43.882 | 1.00 | 25.70 | BBBB |
| ATOM | 3481 | CB | LEU | B | 118 | −2.195 | −60.155 | −43.227 | 1.00 | 25.80 | BBBB |
| ATOM | 3482 | CG | LEU | B | 118 | −3.012 | −60.889 | −42.159 | 1.00 | 26.56 | BBBB |
| ATOM | 3483 | CD1 | LEU | B | 118 | −3.905 | −59.895 | −41.433 | 1.00 | 26.62 | BBBB |
| ATOM | 3484 | CD2 | LEU | B | 118 | −3.841 | −62.000 | −42.801 | 1.00 | 26.51 | BBBB |
| ATOM | 3485 | C | LEU | B | 118 | −0.539 | −60.193 | −45.094 | 1.00 | 26.87 | BBBB |
| ATOM | 3486 | O | LEU | B | 118 | −1.292 | −59.878 | −46.021 | 1.00 | 26.69 | BBBB |
| ATOM | 3487 | N | GLY | B | 119 | 0.755 | −59.898 | −45.085 | 1.00 | 26.39 | BBBB |
| ATOM | 3488 | CA | GLY | B | 119 | 1.354 | −59.174 | −46.192 | 1.00 | 27.80 | BBBB |
| ATOM | 3489 | C | GLY | B | 119 | 1.142 | −57.671 | −46.120 | 1.00 | 27.64 | BBBB |
| ATOM | 3490 | O | GLY | B | 119 | 1.293 | −56.972 | −47.122 | 1.00 | 28.49 | BBBB |
| ATOM | 3491 | N | ILE | B | 120 | 0.786 | −57.173 | −44.940 | 1.00 | 25.88 | BBBB |
| ATOM | 3492 | CA | ILE | B | 120 | 0.568 | −55.744 | −44.731 | 1.00 | 24.85 | BBBB |
| ATOM | 3493 | CB | ILE | B | 120 | −0.507 | −55.497 | −43.652 | 1.00 | 24.64 | BBBB |
| ATOM | 3494 | CG2 | ILE | B | 120 | −0.648 | −54.000 | −43.397 | 1.00 | 24.49 | BBBB |
| ATOM | 3495 | CG1 | ILE | B | 120 | −1.839 | −56.112 | −44.093 | 1.00 | 24.61 | BBBB |
| ATOM | 3496 | CD1 | ILE | B | 120 | −2.891 | −56.170 | −42.991 | 1.00 | 23.34 | BBBB |
| ATOM | 3497 | C | ILE | B | 120 | 1.879 | −55.121 | −44.272 | 1.00 | 24.55 | BBBB |
| ATOM | 3498 | O | ILE | B | 120 | 2.465 | −55.551 | −43.275 | 1.00 | 23.69 | BBBB |
| ATOM | 3499 | N | PRO | B | 121 | 2.365 | −54.098 | −44.995 | 1.00 | 23.85 | BBBB |
| ATOM | 3500 | CD | PRO | B | 121 | 1.780 | −53.400 | −46.154 | 1.00 | 23.64 | BBBB |
| ATOM | 3501 | CA | PRO | B | 121 | 3.625 | −53.477 | −44.591 | 1.00 | 22.63 | BBBB |
| ATOM | 3502 | CB | PRO | B | 121 | 3.872 | −52.440 | −45.691 | 1.00 | 23.83 | BBBB |
| ATOM | 3503 | CG | PRO | B | 121 | 2.485 | −52.053 | −46.102 | 1.00 | 23.96 | BBBB |
| ATOM | 3504 | C | PRO | B | 121 | 3.583 | −52.869 | −43.196 | 1.00 | 22.21 | BBBB |
| ATOM | 3505 | O | PRO | B | 121 | 2.617 | −52.208 | −42.810 | 1.00 | 22.46 | BBBB |
| ATOM | 3506 | N | VAL | B | 122 | 4.641 | −53.114 | −42.437 | 1.00 | 21.69 | BBBB |
| ATOM | 3507 | CA | VAL | B | 122 | 4.743 | −52.594 | −41.083 | 1.00 | 22.03 | BBBB |
| ATOM | 3508 | CB | VAL | B | 122 | 5.184 | −53.694 | −40.095 | 1.00 | 21.80 | BBBB |
| ATOM | 3509 | CG1 | VAL | B | 122 | 5.426 | −53.085 | −38.724 | 1.00 | 21.97 | BBBB |
| ATOM | 3510 | CG2 | VAL | B | 122 | 4.133 | −54.789 | −40.035 | 1.00 | 22.19 | BBBB |
| ATOM | 3511 | C | VAL | B | 122 | 5.754 | −51.465 | −41.021 | 1.00 | 21.29 | BBBB |
| ATOM | 3512 | O | VAL | B | 122 | 6.892 | −51.605 | −41.479 | 1.00 | 22.83 | BBBB |
| ATOM | 3513 | N | VAL | B | 123 | 5.330 | −50.338 | −40.464 | 1.00 | 20.94 | BBBB |
| ATOM | 3514 | CA | VAL | B | 123 | 6.200 | −49.184 | −40.310 | 1.00 | 20.82 | BBBB |
| ATOM | 3515 | CB | VAL | B | 123 | 5.580 | −47.902 | −40.932 | 1.00 | 22.16 | BBBB |
| ATOM | 3516 | CG1 | VAL | B | 123 | 6.516 | −46.722 | −40.709 | 1.00 | 20.83 | BBBB |
| ATOM | 3517 | CG2 | VAL | B | 123 | 5.322 | −48.111 | −42.420 | 1.00 | 22.66 | BBBB |
| ATOM | 3518 | C | VAL | B | 123 | 6.338 | −48.953 | −38.812 | 1.00 | 21.09 | BBBB |
| ATOM | 3519 | O | VAL | B | 123 | 5.341 | −48.986 | −38.093 | 1.00 | 21.48 | BBBB |
| ATOM | 3520 | N | LEU | B | 124 | 7.557 | −48.720 | −38.340 | 1.00 | 20.53 | BBBB |
| ATOM | 3521 | CA | LEU | B | 124 | 7.749 | −48.485 | −36.915 | 1.00 | 22.10 | BBBB |
| ATOM | 3522 | CB | LEU | B | 124 | 8.578 | −49.606 | −36.286 | 1.00 | 22.00 | BBBB |
| ATOM | 3523 | CG | LEU | B | 124 | 8.160 | −51.051 | −36.551 | 1.00 | 22.45 | BBBB |
| ATOM | 3524 | CD1 | LEU | B | 124 | 9.196 | −51.974 | −35.905 | 1.00 | 23.90 | BBBB |
| ATOM | 3525 | CD2 | LEU | B | 124 | 6.765 | −51.313 | −36.003 | 1.00 | 22.34 | BBBB |
| ATOM | 3526 | C | LEU | B | 124 | 8.452 | −47.172 | −36.633 | 1.00 | 22.36 | BBBB |
| ATOM | 3527 | O | LEU | B | 124 | 9.218 | −46.660 | −37.461 | 1.00 | 20.75 | BBBB |
| ATOM | 3528 | N | HIS | B | 125 | 8.182 | −46.638 | −35.447 | 1.00 | 21.40 | BBBB |
| ATOM | 3529 | CA | HIS | B | 125 | 8.814 | −45.413 | −34.981 | 1.00 | 21.42 | BBBB |
| ATOM | 3530 | CB | HIS | B | 125 | 7.858 | −44.218 | −35.067 | 1.00 | 21.57 | BBBB |
| ATOM | 3531 | CG | HIS | B | 125 | 8.432 | −42.948 | −34.511 | 1.00 | 23.73 | BBBB |
| ATOM | 3532 | CD2 | HIS | B | 125 | 8.300 | −42.368 | −33.295 | 1.00 | 22.15 | BBBB |
| ATOM | 3533 | ND1 | HIS | B | 125 | 9.274 | −42.127 | −35.236 | 1.00 | 26.23 | BBBB |
| ATOM | 3534 | CE1 | HIS | B | 125 | 9.631 | −41.095 | −34.490 | 1.00 | 24.20 | BBBB |
| ATOM | 3535 | NE2 | HIS | B | 125 | 9.054 | −41.218 | −33.307 | 1.00 | 26.07 | BBBB |
| ATOM | 3536 | C | HIS | B | 125 | 9.196 | −45.642 | −33.519 | 1.00 | 21.70 | BBBB |
| ATOM | 3537 | O | HIS | B | 125 | 8.378 | −46.117 | −32.725 | 1.00 | 19.81 | BBBB |
| ATOM | 3538 | N | GLU | B | 126 | 10.444 | −45.332 | −33.286 | 1.00 | 21.20 | BBBB |
| ATOM | 3539 | CA | GLU | B | 126 | 10.947 | −45.452 | −31.817 | 1.00 | 22.15 | BBBB |
| ATOM | 3540 | CB | GLU | B | 126 | 12.252 | −46.246 | −31.790 | 1.00 | 21.99 | BBBB |
| ATOM | 3541 | CG | GLU | B | 126 | 12.958 | −46.206 | −30.439 | 1.00 | 22.04 | BBBB |
| ATOM | 3542 | CD | GLU | B | 126 | 12.119 | −46.824 | −29.338 | 1.00 | 21.43 | BBBB |
| ATOM | 3543 | OE1 | GLU | B | 126 | 11.767 | −48.014 | −29.471 | 1.00 | 21.92 | BBBB |
| ATOM | 3544 | OE2 | GLU | B | 126 | 11.807 | −46.124 | −28.349 | 1.00 | 21.08 | BBBB |
| ATOM | 3545 | C | GLU | B | 126 | 11.205 | −44.027 | −31.326 | 1.00 | 21.93 | BBBB |
| ATOM | 3546 | O | GLU | B | 126 | 12.016 | −43.300 | −31.908 | 1.00 | 21.33 | BBBB |
| ATOM | 3547 | N | GLN | B | 127 | 10.520 | −43.624 | −30.259 | 1.00 | 22.62 | BBBB |

TABLE 1-continued

ATOMIC COORDINATES OF E. COLI MURG PROTEIN

| ATOM | 3548 | CA | GLN | B | 127 | 10.682 | −42.270 | −29.735 | 1.00 | 22.81 | BBBB |
|---|---|---|---|---|---|---|---|---|---|---|---|
| ATOM | 3549 | CB | GLN | B | 127 | 9.414 | −41.814 | −28.989 | 1.00 | 23.56 | BBBB |
| ATOM | 3550 | CG | GLN | B | 127 | 8.147 | −41.783 | −29.830 | 1.00 | 24.46 | BBBB |
| ATOM | 3551 | CD | GLN | B | 127 | 7.312 | −43.041 | −29.687 | 1.00 | 25.85 | BBBB |
| ATOM | 3552 | OE1 | GLN | B | 127 | 6.842 | −43.366 | −28.591 | 1.00 | 23.78 | BBBB |
| ATOM | 3553 | NE2 | GLN | B | 127 | 7.119 | −43.758 | −30.797 | 1.00 | 24.91 | BBBB |
| ATOM | 3554 | C | GLN | B | 127 | 11.874 | −42.087 | −28.809 | 1.00 | 22.39 | BBBB |
| ATOM | 3555 | O | GLN | B | 127 | 12.399 | −40.976 | −28.682 | 1.00 | 22.43 | BBBB |
| ATOM | 3556 | N | ASN | B | 128 | 12.314 | −43.173 | −28.177 | 1.00 | 22.35 | BBBB |
| ATOM | 3557 | CA | ASN | B | 128 | 13.406 | −43.097 | −27.216 | 1.00 | 22.96 | BBBB |
| ATOM | 3558 | CB | ASN | B | 128 | 13.136 | −44.080 | −26.064 | 1.00 | 22.85 | BBBB |
| ATOM | 3559 | CG | ASN | B | 128 | 11.742 | −43.919 | −25.474 | 1.00 | 23.25 | BBBB |
| ATOM | 3560 | OD1 | ASN | B | 128 | 10.804 | −44.632 | −25.848 | 1.00 | 26.04 | BBBB |
| ATOM | 3561 | ND2 | ASN | B | 128 | 11.597 | −42.975 | −24.556 | 1.00 | 22.68 | BBBB |
| ATOM | 3562 | C | ASN | B | 128 | 14.824 | −43.314 | −27.742 | 1.00 | 23.87 | BBBB |
| ATOM | 3563 | O | ASN | B | 128 | 15.026 | −43.856 | −28.830 | 1.00 | 24.05 | BBBB |
| ATOM | 3564 | N | GLY | B | 129 | 15.798 | −42.885 | −26.940 | 1.00 | 24.35 | BBBB |
| ATOM | 3565 | CA | GLY | B | 129 | 17.203 | −43.019 | −27.294 | 1.00 | 25.36 | BBBB |
| ATOM | 3566 | C | GLY | B | 129 | 17.642 | −44.468 | −27.280 | 1.00 | 25.97 | BBBB |
| ATOM | 3567 | O | GLY | B | 129 | 18.643 | −44.836 | −27.891 | 1.00 | 25.48 | BBBB |
| ATOM | 3568 | N | ILE | B | 130 | 16.886 | −45.290 | −26.565 | 1.00 | 26.18 | BBBB |
| ATOM | 3569 | CA | ILE | B | 130 | 17.160 | −46.716 | −26.488 | 1.00 | 28.00 | BBBB |
| ATOM | 3570 | CB | ILE | B | 130 | 17.480 | −47.145 | −25.033 | 1.00 | 28.45 | BBBB |
| ATOM | 3571 | CG2 | ILE | B | 130 | 16.323 | −46.785 | −24.102 | 1.00 | 28.52 | BBBB |
| ATOM | 3572 | CG1 | ILE | B | 130 | 17.776 | −48.642 | −24.986 | 1.00 | 29.33 | BBBB |
| ATOM | 3673 | CD1 | ILE | B | 130 | 18.097 | −49.149 | −23.593 | 1.00 | 31.39 | BBBB |
| ATOM | 3574 | C | ILE | B | 130 | 15.909 | −47.435 | −26.999 | 1.00 | 27.44 | BBBB |
| ATOM | 3575 | O | ILE | B | 130 | 14.793 | −47.103 | −26.610 | 1.00 | 28.58 | BBBB |
| ATOM | 3576 | N | ALA | B | 131 | 16.097 | −48.405 | −27.887 | 1.00 | 26.98 | BBBB |
| ATOM | 3577 | CA | ALA | B | 131 | 14.978 | −49.139 | −28.461 | 1.00 | 25.88 | BBBB |
| ATOM | 3578 | CB | ALA | B | 131 | 15.485 | −50.102 | −29.525 | 1.00 | 25.02 | BBBB |
| ATOM | 3579 | C | ALA | B | 131 | 14.171 | −49.901 | −27.413 | 1.00 | 25.20 | BBBB |
| ATOM | 3580 | O | ALA | B | 131 | 14.732 | −50.544 | −26.533 | 1.00 | 25.01 | BBBB |
| ATOM | 3581 | N | GLY | B | 132 | 12.851 | −49.814 | −27.506 | 1.00 | 24.52 | BBBB |
| ATOM | 3582 | CA | GLY | B | 132 | 12.007 | −50.532 | −26.568 | 1.00 | 24.05 | BBBB |
| ATOM | 3583 | C | GLY | B | 132 | 12.150 | −52.019 | −26.831 | 1.00 | 23.35 | BBBB |
| ATOM | 3584 | O | GLY | B | 132 | 12.582 | −52.419 | −27.904 | 1.00 | 22.89 | BBBB |
| ATOM | 3585 | N | LEU | B | 133 | 11.788 | −52.846 | −25.860 | 1.00 | 23.38 | BBBB |
| ATOM | 3586 | CA | LEU | B | 133 | 11.903 | −54.293 | −26.020 | 1.00 | 24.54 | BBBB |
| ATOM | 3587 | CB | LEU | B | 133 | 11.328 | −54.996 | −24.786 | 1.00 | 25.48 | BBBB |
| ATOM | 3588 | CG | LEU | B | 133 | 11.388 | −56.527 | −24.780 | 1.00 | 27.50 | BBBB |
| ATOM | 3589 | CD1 | LEU | B | 133 | 12.840 | −56.984 | −24.866 | 1.00 | 28.69 | BBBB |
| ATOM | 3590 | CD2 | LEU | B | 133 | 10.735 | −57.059 | −23.509 | 1.00 | 28.04 | BBBB |
| ATOM | 3591 | C | LEU | B | 133 | 11.209 | −54.833 | −27.276 | 1.00 | 22.84 | BBBB |
| ATOM | 3592 | O | LEU | B | 133 | 11.784 | −55.019 | −28.027 | 1.00 | 21.86 | BBBB |
| ATOM | 3593 | N | THR | B | 134 | 9.975 | −54.401 | −27.499 | 1.00 | 21.72 | BBBB |
| ATOM | 3594 | CA | THR | B | 134 | 9.202 | −54.860 | −28.639 | 1.00 | 21.22 | BBBB |
| ATOM | 3595 | CB | THR | B | 134 | 7.716 | −54.509 | −28.449 | 1.00 | 20.99 | BBBB |
| ATOM | 3596 | OG1 | THR | B | 134 | 7.257 | −55.075 | −27.210 | 1.00 | 20.94 | BBBB |
| ATOM | 3597 | CG2 | THR | B | 134 | 6.872 | −55.073 | −29.600 | 1.00 | 20.64 | BBBB |
| ATOM | 3598 | C | THR | B | 134 | 9.693 | −54.326 | −29.986 | 1.00 | 20.62 | BBBB |
| ATOM | 3599 | O | THR | B | 134 | 9.843 | −55.091 | −30.932 | 1.00 | 20.33 | BBBB |
| ATOM | 3600 | N | ASN | B | 135 | 9.932 | −53.021 | −30.075 | 1.00 | 21.24 | BBBB |
| ATOM | 3601 | CA | ASN | B | 135 | 10.407 | −52.419 | −31.324 | 1.00 | 20.50 | BBBB |
| ATOM | 3602 | CB | ASN | B | 135 | 10.637 | −50.911 | −31.142 | 1.00 | 19.58 | BBBB |
| ATOM | 3603 | CG | ASN | B | 135 | 9.457 | −50.058 | −31.597 | 1.00 | 19.93 | BBBB |
| ATOM | 3604 | OD1 | ASN | B | 135 | 9.454 | −48.837 | −31.390 | 1.00 | 21.78 | BBBB |
| ATOM | 3605 | ND2 | ASN | B | 135 | 8.467 | −50.677 | −32.219 | 1.00 | 17.21 | BBBB |
| ATOM | 3606 | C | ASN | B | 135 | 11.724 | −53.064 | −31.767 | 1.00 | 20.78 | BBBB |
| ATOM | 3607 | O | ASN | B | 135 | 11.945 | −53.290 | −32.953 | 1.00 | 20.41 | BBBB |
| ATOM | 3608 | N | LYS | B | 136 | 12.595 | −53.366 | −30.809 | 1.00 | 21.46 | BBBB |
| ATOM | 3609 | CA | LYS | B | 136 | 13.886 | −53.949 | −31.144 | 1.00 | 22.79 | BBBB |
| ATOM | 3610 | CB | LYS | B | 136 | 14.713 | −54.196 | −29.879 | 1.00 | 24.70 | BBBB |
| ATOM | 3611 | CG | LYS | B | 136 | 16.183 | −54.424 | −30.178 | 1.00 | 27.75 | BBBB |
| ATOM | 3612 | CD | LYS | B | 136 | 16.998 | −54.494 | −28.902 | 1.00 | 30.17 | BBBB |
| ATOM | 3613 | CE | LYS | B | 136 | 18.479 | −54.671 | −29.203 | 1.00 | 32.33 | BBBB |
| ATOM | 3614 | NZ | LYS | B | 136 | 19.278 | −54.641 | −27.944 | 1.00 | 33.37 | BBBB |
| ATOM | 3615 | C | LYS | B | 136 | 13.793 | −55.229 | −31.966 | 1.00 | 23.46 | BBBB |
| ATOM | 3616 | O | LYS | B | 136 | 14.561 | −55.407 | −32.912 | 1.00 | 23.71 | BBBB |
| ATOM | 3617 | N | TRP | B | 137 | 12.868 | −56.127 | −31.633 | 1.00 | 21.78 | BBBB |
| ATOM | 3618 | CA | TRP | B | 137 | 12.753 | −57.345 | −32.424 | 1.00 | 22.06 | BBBB |
| ATOM | 3619 | CB | TRP | B | 137 | 12.361 | −58.552 | −31.553 | 1.00 | 21.20 | BBBB |
| ATOM | 3620 | CG | TRP | B | 137 | 10.990 | −58.525 | −30.922 | 1.00 | 20.23 | BBBB |
| ATOM | 3621 | CD2 | TRP | B | 137 | 9.748 | −58.877 | −31.544 | 1.00 | 18.68 | BBBB |
| ATOM | 3622 | CE2 | TRP | B | 137 | 8.743 | −58.780 | −30.555 | 1.00 | 18.97 | BBBB |
| ATOM | 3623 | CE3 | TRP | B | 137 | 9.383 | −59.270 | −32.840 | 1.00 | 19.75 | BBBB |
| ATOM | 3624 | CD1 | TRP | B | 137 | 10.696 | −58.231 | −29.618 | 1.00 | 19.62 | BBBB |

TABLE 1-continued

ATOMIC COORDINATES OF E. COLI MURG PROTEIN

| ATOM | 3625 | NE1 | TRP | B | 137 | 9.349 | −58.385 | −29.390 | 1.00 | 19.31 | BBBB |
|---|---|---|---|---|---|---|---|---|---|---|---|
| ATOM | 3626 | CZ2 | TRP | B | 137 | 7.401 | −59.058 | −30.821 | 1.00 | 18.18 | BBBB |
| ATOM | 3627 | CZ3 | TRP | B | 137 | 8.046 | −59.549 | −33.107 | 1.00 | 18.87 | BBBB |
| ATOM | 3628 | CH2 | TRP | B | 137 | 7.072 | −59.440 | −32.099 | 1.00 | 18.94 | BBBB |
| ATOM | 3629 | C | TRP | B | 137 | 11.768 | −57.202 | −33.574 | 1.00 | 21.75 | BBBB |
| ATOM | 3630 | O | TRP | B | 137 | 11.936 | −57.822 | −34.623 | 1.00 | 21.76 | BBBB |
| ATOM | 3631 | N | LEU | B | 138 | 10.741 | −56.381 | −33.386 | 1.00 | 21.61 | BBBB |
| ATOM | 3632 | CA | LEU | B | 138 | 9.744 | −56.188 | −34.431 | 1.00 | 23.15 | BBBB |
| ATOM | 3633 | CB | LEU | B | 138 | 8.618 | −55.305 | −33.886 | 1.00 | 23.87 | BBBB |
| ATOM | 3634 | CG | LEU | B | 138 | 7.312 | −55.155 | −34.664 | 1.00 | 26.48 | BBBB |
| ATOM | 3635 | CD1 | LEU | B | 138 | 6.672 | −56.508 | −34.915 | 1.00 | 25.34 | BBBB |
| ATOM | 3636 | CD2 | LEU | B | 138 | 6.383 | −54.267 | −33.851 | 1.00 | 25.90 | BBBB |
| ATOM | 3637 | C | LEU | B | 138 | 10.384 | −55.558 | −35.676 | 1.00 | 23.07 | BBBB |
| ATOM | 3638 | O | LEU | B | 138 | 9.958 | −55.801 | −36.809 | 1.00 | 22.68 | BBBB |
| ATOM | 3639 | N | ALA | B | 139 | 11.423 | −54.763 | −35.453 | 1.00 | 23.34 | BBBB |
| ATOM | 3640 | CA | ALA | B | 139 | 12.128 | −54.092 | −36.542 | 1.00 | 25.29 | BBBB |
| ATOM | 3641 | CB | ALA | B | 139 | 13.298 | −53.287 | −35.984 | 1.00 | 24.97 | BBBB |
| ATOM | 3642 | C | ALA | B | 139 | 12.624 | −55.064 | −37.610 | 1.00 | 26.83 | BBBB |
| ATOM | 3643 | O | ALA | B | 139 | 12.829 | −54.672 | −38.754 | 1.00 | 27.29 | BBBB |
| ATOM | 3644 | N | LYS | B | 140 | 12.801 | −56.332 | −37.241 | 1.00 | 27.38 | BBBB |
| ATOM | 3645 | CA | LYS | B | 140 | 13.279 | −57.337 | −38.182 | 1.00 | 28.05 | BBBB |
| ATOM | 3646 | CB | LYS | B | 140 | 13.893 | −58.501 | −37.401 | 1.00 | 29.91 | BBBB |
| ATOM | 3647 | CG | LYS | B | 140 | 15.134 | −58.057 | −36.635 | 1.00 | 31.62 | BBBB |
| ATOM | 3648 | CD | LYS | B | 140 | 15.719 | −59.149 | −35.757 | 1.00 | 33.53 | BBBB |
| ATOM | 3649 | CE | LYS | B | 140 | 16.974 | −58.634 | −35.055 | 1.00 | 34.46 | BBBB |
| ATOM | 3650 | NZ | LYS | B | 140 | 17.692 | −59.713 | −34.320 | 1.00 | 36.17 | BBBB |
| ATOM | 3651 | C. | LYS | B | 140 | 12.254 | −57.833 | −39.212 | 1.00 | 27.83 | BBBB |
| ATOM | 3652 | O | LYS | B | 140 | 12.602 | −58.562 | −40.142 | 1.00 | 27.80 | BBBB |
| ATOM | 3653 | N | ILE | B | 141 | 10.992 | −57.445 | −39.052 | 1.00 | 26.40 | BBBB |
| ATOM | 3654 | CA | ILE | B | 141 | 9.963 | −57.818 | −40.016 | 1.00 | 26.09 | BBBB |
| ATOM | 3655 | CB | ILE | B | 141 | 8.854 | −58.721 | −39.405 | 1.00 | 26.39 | BBBB |
| ATOM | 3656 | CG2 | ILE | B | 141 | 9.401 | −60.118 | −39.145 | 1.00 | 28.33 | BBBB |
| ATOM | 3657 | CG1 | ILE | B | 141 | 8.298 | −58.092 | −38.127 | 1.00 | 26.45 | BBBB |
| ATOM | 3658 | CD1 | ILE | B | 141 | 7.136 | −58.845 | −37.549 | 1.00 | 26.95 | BBBB |
| ATOM | 3659 | C | ILE | B | 141 | 9.316 | −56.542 | −40.530 | 1.00 | 25.81 | BBBB |
| ATOM | 3660 | O | ILE | B | 141 | 8.353 | −56.586 | −41.305 | 1.00 | 26.10 | BBBB |
| ATOM | 3661 | N | ALA | B | 142 | 9.856 | −55.405 | −40.097 | 1.00 | 23.78 | BBBB |
| ATOM | 3662 | CA | ALA | B | 142 | 9.331 | −54.107 | −40.498 | 1.00 | 25.03 | BBBB |
| ATOM | 3663 | CB | ALA | B | 142 | 9.717 | −53.046 | −39.466 | 1.00 | 24.89 | BBBB |
| ATOM | 3664 | C | ALA | B | 142 | 9.816 | −53.680 | −41.880 | 1.00 | 25.08 | BBBB |
| ATOM | 3665 | O | ALA | B | 142 | 10.973 | −53.894 | −42.237 | 1.00 | 24.93 | BBBB |
| ATOM | 3666 | N | THR | B | 143 | 8.920 | −53.075 | −42.651 | 1.00 | 25.03 | BBBB |
| ATOM | 3667 | CA | THR | B | 143 | 9.262 | −52.595 | −43.984 | 1.00 | 26.10 | BBBB |
| ATOM | 3668 | CB | THR | B | 143 | 7.987 | −52.318 | −44.816 | 1.00 | 25.75 | BBBB |
| ATOM | 3669 | OG1 | THR | B | 143 | 7.249 | −53.534 | −44.970 | 1.00 | 25.54 | BBBB |
| ATOM | 3670 | CG2 | THR | B | 143 | 8.345 | −51.782 | −46.207 | 1.00 | 26.92 | BBBB |
| ATOM | 3671 | C | THE | B | 143 | 10.079 | −51.310 | −43.863 | 1.00 | 26.63 | BBBB |
| ATOM | 3672 | O | THR | B | 143 | 10.996 | −51.061 | −44.656 | 1.00 | 27.13 | BBBB |
| ATOM | 3673 | N | LYS | B | 144 | 9.753 | −50.506 | −42.853 | 1.00 | 24.95 | BBBB |
| ATOM | 3674 | CA | LYS | B | 144 | 10.436 | −49.238 | −42.618 | 1.00 | 24.73 | BBBB |
| ATOM | 3675 | CB | LYS | B | 144 | 9.688 | −48.103 | −43.329 | 1.00 | 26.20 | BBBB |
| ATOM | 3676 | CG | LYS | B | 144 | 10.202 | −46.710 | −43.013 | 1.00 | 27.44 | BBBB |
| ATOM | 3677 | CO | LYS | B | 144 | 11.602 | −46.480 | −43.558 | 1.00 | 29.01 | BBBB |
| ATOM | 3678 | CE. | LYS | B | 144 | 12.055 | −45.051 | −43.293 | 1.00 | 29.74 | BBBB |
| ATOM | 3679 | NZ | LYS | B | 144 | 13.406 | −44.774 | −43.854 | 1.00 | 31.29 | BBBB |
| ATOM | 3680 | C | LYS | B | 144 | 10.506 | −48.943 | −41.125 | 1.00 | 24.61 | BBBB |
| ATOM | 3681 | O | LYS | B | 144 | 9.493 | −49.008 | −40.423 | 1.00 | 23.36 | BBBB |
| ATOM | 3682 | N | VAL | B | 145 | 11.707 | −48.623 | −40.656 | 1.00 | 23.68 | BBBB |
| ATOM | 3683 | CA | VAL | B | 145 | 11.947 | −48.311 | −39.252 | 1.00 | 23.62 | BBBB |
| ATOM | 3684 | CB | VAL | B | 145 | 12.981 | −49.279 | −38.617 | 1.00 | 23.66 | BBBB |
| ATOM | 3685 | CG1 | VAL | B | 145 | 13.083 | −49.014 | −37.114 | 1.00 | 24.44 | BBBB |
| ATOM | 3686 | CG2 | VAL | B | 145 | 12.589 | −50.724 | −38.878 | 1.00 | 23.51 | BBBB |
| ATOM | 3687 | C | VAL | B | 145 | 12.510 | −46.900 | −39.125 | 1.00 | 24.09 | BBBB |
| ATOM | 3688 | O | VAL | B | 145 | 13.473 | −46.545 | −39.808 | 1.00 | 23.68 | BBBB |
| ATOM | 3689 | N | MET | B | 146 | 11.902 | −46.103 | −38.251 | 1.00 | 23.84 | BBBB |
| ATOM | 3690 | CA | MET | B | 146 | 12.338 | −44.736 | −37.993 | 1.00 | 23.15 | BBBB |
| ATOM | 3691 | CB | MET | B | 146 | 11.274 | −43.729 | −38.448 | 1.00 | 24.72 | BBBB |
| ATOM | 3692 | CG | MET | B | 146 | 11.130 | −43.577 | −39.970 | 1.00 | 21.76 | BBBB |
| ATOM | 3693 | SD | MET | B | 146 | 9.649 | −42.636 | −40.468 | 1.00 | 25.05 | BBBB |
| ATOM | 3694 | CE | MET | B | 146 | 8.376 | −43.846 | −40.325 | 1.00 | 21.96 | BBBB |
| ATOM | 3695 | C | MET | B | 146 | 12.567 | −44.593 | −36.488 | 1.00 | 24.69 | BBBB |
| ATOM | 3696 | O | MET | B | 146 | 11.963 | −45.311 | −35.689 | 1.00 | 22.43 | BBBB |
| ATOM | 3697 | N | GLN | B | 147 | 13.456 | −43.678 | −36.112 | 1.00 | 23.37 | BBBB |
| ATOM | 3698 | CA | GLN | B | 147 | 13.762 | −43.418 | −34.712 | 1.00 | 25.05 | BBBB |
| ATOM | 3699 | CB | GLN | B | 147 | 15.067 | −44.114 | +34.301 | 1.00 | 24.99 | BBBB |
| ATOM | 3700 | CG | GLN | B | 147 | 16.259 | −43.750 | −35.169 | 1.00 | 26.10 | BBBB |
| ATOM | 3701 | CD | GLN | B | 147 | 17.527 | −44.508 | −34.803 | 1.00 | 26.65 | BBBB |

TABLE 1-continued

ATOMIC COORDINATES OF E. COLI MURG PROTEIN

| ATOM | 3702 | OE1 | GLN | B | 147 | 18.425 | −44.671 | −35.637 | 1.00 | 28.62 | BBBB |
|---|---|---|---|---|---|---|---|---|---|---|---|
| ATOM | 3703 | NE2 | GLN | B | 147 | 17.615 | −44.966 | −33.558 | 1.00 | 26.05 | BBBB |
| ATOM | 3704 | C | GLN | B | 147 | 13.880 | −41.911 | −34.515 | 1.00 | 26.28 | BBBB |
| ATOM | 3705 | O | GLN | B | 147 | 14.292 | −41.177 | −35.430 | 1.00 | 25.02 | BBBB |
| ATOM | 3706 | N | ALA | B | 148 | 13.518 | −41.452 | −33.323 | 1.00 | 26.58 | BBBB |
| ATOM | 3707 | CA | ALA | B | 148 | 13.559 | −40.032 | −33.009 | 1.00 | 26.88 | BBBB |
| ATOM | 3708 | CB | ALA | B | 148 | 12.853 | −39.776 | −31.685 | 1.00 | 26.71 | BBBB |
| ATOM | 3709 | C | ALA | B | 148 | 14.983 | −39.502 | −32.954 | 1.00 | 27.88 | BBBB |
| ATOM | 3710 | O | ALA | B | 148 | 15.293 | −38.463 | −33.545 | 1.00 | 27.38 | BBBB |
| ATOM | 3711 | N | PHE | B | 149 | 15.847 | −40.219 | −32.242 | 1.00 | 27.92 | BBBB |
| ATOM | 3712 | CA | PHE | B | 149 | 17.239 | −39.820 | −32.098 | 1.00 | 29.39 | BBBB |
| ATOM | 3713 | CB | PHE | B | 149 | 17.596 | −39.631 | −30.617 | 1.00 | 28.95 | BBBB |
| ATOM | 3714 | CG | PHE | B | 149 | 16.549 | −38.910 | −29.821 | 1.00 | 28.91 | BBBB |
| ATOM | 3715 | CD1 | PHE | B | 149 | 15.745 | −39.603 | −28.929 | 1.00 | 27.96 | BBBB |
| ATOM | 3716 | CD2 | PHE | B | 149 | 16.372 | −37.537 | −29.957 | 1.00 | 29.03 | BBBB |
| ATOM | 3717 | CE1 | PHE | B | 149 | 14.779 | −38.945 | −28.178 | 1.00 | 28.64 | BBBB |
| ATOM | 3718 | CE2 | PHE | B | 149 | 15.406 | −36.866 | −29.211 | 1.00 | 30.10 | BBBB |
| ATOM | 3719 | CZ | PHE | B | 149 | 14.608 | −37.575 | −28.317 | 1.00 | 29.02 | BBBB |
| ATOM | 3720 | C | PHE | B | 149 | 18.153 | −40.893 | −32.673 | 1.00 | 30.03 | BBBB |
| ATOM | 3721 | O | PHE | B | 149 | 17.750 | −42.036 | −32.849 | 1.00 | 30.05 | BBBB |
| ATOM | 3722 | N | PRO | B | 150 | 19.401 | −40.530 | −32.991 | 1.00 | 31.73 | BBBB |
| ATOM | 3723 | CD | PRO | B | 150 | 20.018 | −39.192 | −33.018 | 1.00 | 32.39 | BBBB |
| ATOM | 3724 | CA | PRO | B | 150 | 20.310 | −41.541 | −33.535 | 1.00 | 31.87 | BBBB |
| ATOM | 3725 | CB | PRO | B | 150 | 21.418 | −40.698 | −34.154 | 1.00 | 33.07 | BBBB |
| ATOM | 3726 | CG | PRO | B | 150 | 21.480 | −39.517 | −33.238 | 1.00 | 33.70 | BBBB |
| ATOM | 3727 | C | PRO | B | 150 | 20.809 | −42.411 | −32.376 | 1.00 | 31.93 | BBBB |
| ATOM | 3728 | O | PRO | B | 150 | 20.873 | −41.945 | −31.239 | 1.00 | 31.39 | BBBB |
| ATOM | 3729 | N | GLY | B | 151 | 21.130 | −43.671 | −32.651 | 1.00 | 31.67 | BBBB |
| ATOM | 3730 | CA | GLY | B | 151 | 21.629 | −44.537 | −31.595 | 1.00 | 32.62 | BBBB |
| ATOM | 3731 | C | GLY | B | 151 | 20.717 | −45.655 | −31.112 | 1.00 | 32.88 | BBBB |
| ATOM | 3732 | O | GLY | B | 151 | 21.206 | −46.690 | −30.657 | 1.00 | 32.98 | BBBB |
| ATOM | 3733 | N | ALA | B | 152 | 19.403 | −45.458 | −31.196 | 1.00 | 32.24 | BBBB |
| ATOM | 3734 | CA | ALA | B | 152 | 18.447 | −46.476 | −30.753 | 1.00 | 32.71 | BBBB |
| ATOM | 3735 | CB | ALA | B | 152 | 17.020 | −45.924 | −30.817 | 1.00 | 31.78 | BBBB |
| ATOM | 3736 | C | ALA | B | 152 | 18.582 | −47.708 | −31.643 | 1.00 | 33.00 | BBBB |
| ATOM | 3737 | O | ALA | B | 152 | 18.528 | −48.842 | −31.169 | 1.00 | 32.08 | BBBB |
| ATOM | 3738 | N | PHE | B | 153 | 18.732 | −47.462 | −32.941 | 1.00 | 33.66 | BBBB |
| ATOM | 3739 | CA | PHE | B | 153 | 18.925 | −48.506 | −33.937 | 1.00 | 34.83 | BBBB |
| ATOM | 3740 | CB | PHE | B | 153 | 17.734 | −48.611 | −34.893 | 1.00 | 33.64 | BBBB |
| ATOM | 3741 | CG | PHE | B | 153 | 16.518 | −49.244 | −34.289 | 1.00 | 32.97 | BBBB |
| ATOM | 3742 | CD1 | PHE | B | 153 | 15.468 | −48.461 | −33.823 | 1.00 | 31.93 | BBBB |
| ATOM | 3743 | CD2 | PHE | B | 153 | 16.421 | −50.628 | −34.184 | 1.00 | 32.46 | BBBB |
| ATOM | 3744 | CE1 | PHE | B | 153 | 14.339 | −49.049 | −33.265 | 1.00 | 32.18 | BBBB |
| ATOM | 3745 | CE2 | PHE | B | 153 | 15.294 | −51.224 | −33.626 | 1.00 | 31.75 | BBBB |
| ATOM | 3746 | CZ | PHE | B | 153 | 14.254 | −50.435 | −33.166 | 1.00 | 31.22 | BBBB |
| ATOM | 3747 | C | PHE | B | 153 | 20.155 | −48.075 | −34.723 | 1.00 | 36.90 | BBBB |
| ATOM | 3748 | O | PHE | B | 153 | 20.407 | −46.878 | −34.879 | 1.00 | 37.54 | BBBB |
| ATOM | 3749 | N | PRO | B | 154 | 20.944 | −49.040 | −35.220 | 1.00 | 38.15 | BBBB |
| ATOM | 3750 | CD | PRO | B | 154 | 20.845 | −50.482 | −34.932 | 1.00 | 38.37 | BBBB |
| ATOM | 3751 | CA | PRO | B | 154 | 22.158 | −48.751 | −35.993 | 1.00 | 38.97 | BBBB |
| ATOM | 3752 | CB | PRO | B | 154 | 22.706 | −50.143 | −36.302 | 1.00 | 39.31 | BBBB |
| ATOM | 3753 | CG | PRO | B | 154 | 22.274 | −50.941 | −35.108 | 1.00 | 39.50 | BBBB |
| ATOM | 3754 | C | PRO | B | 154 | 21.964 | −47.921 | −37.266 | 1.00 | 39.90 | BBBB |
| ATOM | 3755 | O | PRO | B | 154 | 22.697 | −46.958 | −37.496 | 1.00 | 39.89 | BBBB |
| ATOM | 3756 | N | ASN | B | 155 | 20.979 | −48.280 | −38.088 | 1.00 | 40.46 | BBBB |
| ATOM | 3757 | CA | ASN | B | 155 | 20.765 | −47.568 | −39.346 | 1.00 | 41.08 | BBBB |
| ATOM | 3758 | CB | ASN | B | 155 | 21.135 | −48.488 | −40.510 | 1.00 | 43.63 | BBBB |
| ATOM | 3759 | CG | ASN | B | 155 | 22.618 | −48.753 | −40.585 | 1.00 | 45.00 | BBBB |
| ATOM | 3760 | OD1 | ASN | B | 155 | 23.401 | −47.861 | −40.922 | 1.00 | 46.41 | BBBB |
| ATOM | 3761 | ND2 | ASN | B | 155 | 23.019 | −49.978 | −40.259 | 1.00 | 45.20 | BBBB |
| ATOM | 3762 | C | ASN | B | 155 | 19.393 | −46.966 | −39.627 | 1.00 | 40.73 | BBBB |
| ATOM | 3763 | O | ASN | B | 155 | 19.145 | −46.501 | −40.742 | 1.00 | 41.01 | BBBB |
| ATOM | 3764 | N | ALA | B | 156 | 18.507 | −46.956 | −38.638 | 1.00 | 38.93 | BBBB |
| ATOM | 3765 | CA | ALA | B | 156 | 17.170 | −46.407 | −38.843 | 1.00 | 37.55 | BBBB |
| ATOM | 3766 | CB | ALA | B | 156 | 16.304 | −46.689 | −37.618 | 1.00 | 37.34 | BBBB |
| ATOM | 3767 | C | ALA | B | 156 | 17.209 | −44.909 | −39.123 | 1.00 | 36.36 | BBBB |
| ATOM | 3768 | O | ALA | B | 156 | 17.934 | −44.171 | −38.459 | 1.00 | 36.95 | BBBB |
| ATOM | 3769 | N | GLU | B | 157 | 16.428 | −44.464 | −40.107 | 1.00 | 35.76 | BBBB |
| ATOM | 3770 | CA | GLU | B | 157 | 16.367 | −43.044 | −40.460 | 1.00 | 34.40 | BBBB |
| ATOM | 3771 | CB | GLU | B | 157 | 15.375 | −42.815 | −41.613 | 1.00 | 34.84 | BBBB |
| ATOM | 3772 | CG | GLU | B | 157 | 15.246 | −41.349 | −42.055 | 1.00 | 34.91 | BBBB |
| ATOM | 3773 | CD | GLU | B | 157 | 14.171 | −41.123 | −43.117 | 1.00 | 36.66 | BBBB |
| ATOM | 3774 | OE1 | GLU | B | 157 | 13.952 | −39.951 | −43.509 | 1.00 | 37.67 | BBBB |
| ATOM | 3775 | OE2 | GLU | B | 157 | 13.543 | −42.107 | −43.563 | 1.00 | 35.62 | BBBB |
| ATOM | 3776 | C | GLU | B | 157 | 15.922 | −42.249 | −39.231 | 1.00 | 33.89 | BBBB |
| ATOM | 3777 | O | GLU | B | 157 | 14.941 | −42.605 | −38.574 | 1.00 | 33.04 | BBBB |
| ATOM | 3778 | N | VAL | B | 158 | 16.655 | −41.185 | −38.915 | 1.00 | 32.73 | BBBB |

TABLE 1-continued

ATOMIC COORDINATES OF *E. COLI* MURG PROTEIN

| ATOM | 3779 | CA  | VAL | B | 158 | 16.337 | −40.344 | −37.764 | 1.00 | 31.16 | BBBB |
|------|------|-----|-----|---|-----|--------|---------|---------|------|-------|------|
| ATOM | 3780 | CB  | VAL | B | 158 | 17.606 | −39.680 | −37.202 | 1.00 | 31.85 | BBBB |
| ATOM | 3781 | CG1 | VAL | B | 158 | 17.238 | −38.729 | −36.073 | 1.00 | 31.22 | BBBB |
| ATOM | 3782 | CG2 | VAL | B | 158 | 18.574 | −40.752 | −36.708 | 1.00 | 31.41 | BBBB |
| ATOM | 3783 | C   | VAL | B | 158 | 15.352 | −39.260 | −38.178 | 1.00 | 30.27 | BBBB |
| ATOM | 3784 | O   | VAL | B | 158 | 15.649 | −38.445 | −39.053 | 1.00 | 30.18 | BBBB |
| ATOM | 3785 | N   | VAL | B | 159 | 14.186 | −39.241 | −37.544 | 1.00 | 28.57 | BBBB |
| ATOM | 3786 | CA  | VAL | B | 159 | 13.155 | −38.265 | −37.889 | 1.00 | 28.10 | BBBB |
| ATOM | 3787 | CB  | VAL | B | 159 | 11.942 | −38.963 | −38.535 | 1.00 | 27.81 | BBBB |
| ATOM | 3788 | CG1 | VAL | B | 159 | 12.365 | −39.667 | −39.819 | 1.00 | 28.61 | BBBB |
| ATOM | 3789 | CG2 | VAL | B | 159 | 11.336 | −39.962 | −37.548 | 1.00 | 27.61 | BBBB |
| ATOM | 3790 | C   | VAL | B | 159 | 12.636 | −37.430 | −36.725 | 1.00 | 27.64 | BBBB |
| ATOM | 3791 | O   | VAL | B | 159 | 11.757 | −36.591 | −36.918 | 1.00 | 27.97 | BBBB |
| ATOM | 3792 | N   | GLY | B | 160 | 13.168 | −37.662 | −35.527 | 1.00 | 27.60 | BBBB |
| ATOM | 3793 | CA  | GLY | B | 160 | 12.724 | −36.921 | −34.355 | 1.00 | 26.93 | BBBB |
| ATOM | 3794 | C   | GLY | B | 160 | 11.331 | −37.312 | −33.883 | 1.00 | 26.66 | BBBB |
| ATOM | 3795 | O   | GLY | B | 160 | 10.757 | −38.275 | −34.384 | 1.00 | 26.71 | BBBB |
| ATOM | 3796 | N   | ASN | B | 161 | 10.797 | −36.569 | −32.914 | 1.00 | 25.68 | BBBB |
| ATOM | 3797 | CA  | ASN | B | 161 | 9.456  | −36.807 | −32.375 | 1.00 | 25.27 | BBBB |
| ATOM | 3798 | CB  | ASN | B | 161 | 9.481  | −36.963 | −30.849 | 1.00 | 23.89 | BBBB |
| ATOM | 3799 | CG  | ASN | B | 161 | 10.042 | −38.285 | −30.401 | 1.00 | 22.91 | BBBB |
| ATOM | 3800 | OD1 | ASN | B | 161 | 9.600  | −39.335 | −30.850 | 1.00 | 22.70 | BBBB |
| ATOM | 3801 | ND2 | ASN | B | 161 | 11.017 | −38.243 | −29.496 | 1.00 | 22.71 | BBBB |
| ATOM | 3802 | C   | ASN | B | 161 | 8.556  | −35.618 | −32.670 | 1.00 | 25.39 | BBBB |
| ATOM | 3803 | O   | ASN | B | 161 | 9.028  | −34.499 | −32.821 | 1.00 | 25.45 | BBBB |
| ATOM | 3804 | N   | PRO | B | 162 | 7.241  | −35.849 | −32.741 | 1.00 | 26.08 | BBBB |
| ATOM | 3805 | CD  | PRO | B | 162 | 6.533  | −37.140 | −32.710 | 1.00 | 25.20 | BBBB |
| ATOM | 3806 | CA  | PRO | B | 162 | 6.315  | −34.747 | −33.004 | 1.00 | 26.14 | BBBB |
| ATOM | 3807 | CB  | PRO | B | 162 | 4.952  | −35.431 | −32.976 | 1.00 | 25.76 | BBBB |
| ATOM | 3808 | CG  | PRO | B | 162 | 5.255  | −36.821 | −33.430 | 1.00 | 26.48 | BBBB |
| ATOM | 3809 | C   | PRO | B | 162 | 6.455  | −33.728 | −31.866 | 1.00 | 27.00 | BBBB |
| ATOM | 3810 | O   | PRO | B | 162 | 6.652  | −34.102 | −30.703 | 1.00 | 25.08 | BBBB |
| ATOM | 3811 | N   | VAL | B | 163 | 6.355  | −32.446 | −32.203 | 1.00 | 27.54 | BBBB |
| ATOM | 3812 | CA  | VAL | B | 163 | 6.456  | −31.379 | −31.216 | 1.00 | 27.75 | BBBB |
| ATOM | 3813 | CB  | VAL | B | 163 | 7.748  | −30.561 | −31.421 | 1.00 | 28.81 | BBBB |
| ATOM | 3814 | CG1 | VAL | B | 163 | 7.839  | −29.451 | −30.381 | 1.00 | 28.20 | BBBB |
| ATOM | 3815 | CG2 | VAL | B | 163 | 8.958  | −31.471 | −31.335 | 1.00 | 27.87 | BBBB |
| ATOM | 3816 | C   | VAL | B | 163 | 5.261  | −30.440 | −31.365 | 1.00 | 29.43 | BBBB |
| ATOM | 3817 | O   | VAL | B | 163 | 4.777  | −30.227 | −32.476 | 1.00 | 28.49 | BBBB |
| ATOM | 3818 | N   | ARG | B | 164 | 4.790  | −29.891 | −30.246 | 1.00 | 29.93 | BBBB |
| ATOM | 3819 | CA  | ARG | B | 164 | 3.667  | −28.953 | −30.246 | 1.00 | 32.36 | BBBB |
| ATOM | 3820 | CB  | ARG | B | 164 | 3.430  | −28.411 | −28.833 | 1.00 | 34.56 | BBBB |
| ATOM | 3821 | CG  | ARG | B | 164 | 2.967  | −29.439 | −27.832 | 1.00 | 38.34 | BBBB |
| ATOM | 3822 | CD  | ARG | B | 164 | 3.067  | −28.889 | −26.417 | 1.00 | 41.59 | BBBB |
| ATOM | 3823 | NE  | ARG | B | 164 | 2.481  | −27.555 | −26.299 | 1.00 | 44.08 | BBBB |
| ATOM | 3824 | CZ  | ARG | B | 164 | 2.307  | −26.919 | −25.144 | 1.00 | 45.79 | BBBB |
| ATOM | 3825 | NH1 | ARG | B | 164 | 2.673  | −27.499 | −24.008 | 1.00 | 46.89 | BBBB |
| ATOM | 3826 | NH2 | ARG | B | 164 | 1.769  | −25.705 | −25.123 | 1.00 | 47.50 | BBBB |
| ATOM | 3827 | C   | ARG | B | 164 | 3.939  | −27.775 | −31.187 | 1.00 | 31.56 | BBBB |
| ATOM | 3828 | O   | ARG | B | 164 | 5.031  | −27.212 | −31.191 | 1.00 | 30.03 | BBBB |
| ATOM | 3829 | N   | THR | B | 165 | 2.928  | −27.401 | −31.965 | 1.00 | 32.06 | BBBB |
| ATOM | 3830 | CA  | THR | B | 165 | 3.038  | −26.307 | −32.924 | 1.00 | 31.74 | BBBB |
| ATOM | 3831 | CB  | THR | B | 165 | 1.701  | −26.104 | −33.678 | 1.00 | 32.51 | BBBB |
| ATOM | 3832 | OG1 | THR | B | 165 | 1.198  | −27.375 | −34.094 | 1.00 | 32.54 | BBBB |
| ATOM | 3833 | CG2 | THR | B | 165 | 1.907  | −25.239 | −34.916 | 1.00 | 32.14 | BBBB |
| ATOM | 3834 | C   | THR | B | 165 | 3.445  | −24.976 | −32.295 | 1.00 | 31.49 | BBBB |
| ATOM | 3835 | O   | THR | B | 165 | 4.236  | −24.238 | −32.872 | 1.00 | 31.48 | BBBB |
| ATOM | 3836 | N   | ASP | B | 166 | 2.907  | −24.664 | −31.120 | 1.00 | 30.86 | BBBB |
| ATOM | 3837 | CA  | ASP | B | 166 | 3.252  | −23.404 | −30.466 | 1.00 | 30.64 | BBBB |
| ATOM | 3838 | CB  | ASP | B | 166 | 2.358  | −23.163 | −29.242 | 1.00 | 33.08 | BBBB |
| ATOM | 3839 | CG  | ASP | B | 166 | 2.185  | −24.400 | −28.384 | 1.00 | 35.24 | BBBB |
| ATOM | 3840 | OD1 | ASP | B | 166 | 1.315  | −24.373 | −27.485 | 1.00 | 38.19 | BBBB |
| ATOM | 3841 | OD2 | ASP | B | 166 | 2.908  | −25.393 | −28.603 | 1.00 | 37.17 | BBBB |
| ATOM | 3842 | C   | ASP | B | 166 | 4.729  | −23.338 | −30.084 | 1.00 | 28.64 | BBBB |
| ATOM | 3843 | O   | ASP | B | 166 | 5.321  | −22.259 | −30.076 | 1.00 | 27.92 | BBBB |
| ATOM | 3844 | N   | VAL | B | 167 | 5.328  | −24.485 | −29.773 | 1.00 | 27.08 | BBBB |
| ATOM | 3845 | CA  | VAL | B | 167 | 6.746  | −24.503 | −29.440 | 1.00 | 25.91 | BBBB |
| ATOM | 3846 | CB  | VAL | B | 167 | 7.171  | −25.824 | −28.757 | 1.00 | 25.96 | BBBB |
| ATOM | 3847 | CG1 | VAL | B | 167 | 8.687  | −25.844 | −28.586 | 1.00 | 24.67 | BBBB |
| ATOM | 3848 | CG2 | VAL | B | 167 | 6.482  | −25.964 | −27.396 | 1.00 | 26.22 | BBBB |
| ATOM | 3849 | C   | VAL | B | 167 | 7.548  | −24.361 | −30.736 | 1.00 | 25.54 | BBBB |
| ATOM | 3850 | O   | VAL | B | 167 | 8.548  | −23.642 | −30.787 | 1.00 | 25.58 | BBBB |
| ATOM | 3851 | N   | LEU | B | 168 | 7.108  | −25.059 | −31.778 | 1.00 | 26.75 | BBBB |
| ATOM | 3852 | CA  | LEU | B | 168 | 7.780  | −25.002 | −33.075 | 1.00 | 28.46 | BBBB |
| ATOM | 3853 | CB  | LEU | B | 168 | 7.085  | −25.930 | −34.080 | 1.00 | 28.40 | BBBB |
| ATOM | 3854 | CG  | LEU | B | 168 | 7.205  | −27.440 | −33.890 | 1.00 | 28.67 | BBBB |
| ATOM | 3855 | CD1 | LEU | B | 168 | 6.254  | −28.161 | −34.854 | 1.00 | 30.19 | BBBB |

TABLE 1-continued

ATOMIC COORDINATES OF *E. COLI* MURG PROTEIN

| ATOM | 3856 | CD2 | LEU | B | 168 | 8.647 | −27.868 | −34.129 | 1.00 | 28.82 | BBBB |
|------|------|-----|-----|---|-----|-------|---------|---------|------|-------|------|
| ATOM | 3857 | C | LEU | B | 168 | 7.766 | −23.584 | −33.632 | 1.00 | 29.14 | BBBB |
| ATOM | 3858 | O | LEU | B | 168 | 8.667 | −23.186 | −34.369 | 1.00 | 29.57 | BBBB |
| ATOM | 3859 | N | ALA | B | 169 | 6.741 | −22.823 | −33.267 | 1.00 | 30.35 | BBBB |
| ATOM | 3860 | CA | ALA | B | 169 | 6.580 | −21.455 | −33.756 | 1.00 | 31.43 | BBBB |
| ATOM | 3861 | CB | ALA | B | 169 | 5.118 | −21.030 | −33.624 | 1.00 | 33.26 | BBBB |
| ATOM | 3862 | C | ALA | B | 169 | 7.472 | −20.427 | −33.078 | 1.00 | 32.03 | BBBB |
| ATOM | 3863 | O | ALA | B | 169 | 7.562 | −19.284 | −33.536 | 1.00 | 31.95 | BBBB |
| ATOM | 3864 | N | LEU | B | 170 | 8.131 | −20.824 | −31.993 | 1.00 | 30.53 | BBBB |
| ATOM | 3865 | CA | LEU | B | 170 | 9.002 | −19.905 | −31.268 | 1.00 | 29.60 | BBBB |
| ATOM | 3866 | CB | LEU | B | 170 | 9.601 | −20.595 | −30.041 | 1.00 | 28.66 | BBBB |
| ATOM | 3867 | CG | LEU | B | 170 | 8.623 | −20.954 | −28.923 | 1.00 | 28.67 | BBBB |
| ATOM | 3868 | CD1 | LEU | B | 170 | 9.322 | −21.845 | −27.907 | 1.00 | 27.66 | BBBB |
| ATOM | 3869 | CD2 | LEU | B | 170 | 8.096 | −19.675 | −28.277 | 1.00 | 27.21 | BBBB |
| ATOM | 3870 | C | LEU | B | 170 | 10.138 | −19.363 | −32.127 | 1.00 | 29.76 | BBBB |
| ATOM | 3871 | O | LEU | B | 170 | 10.670 | −20.064 | −32.983 | 1.00 | 29.07 | BBBB |
| ATOM | 3872 | N | PRO | B | 171 | 10.525 | −18.099 | −31.897 | 1.00 | 29.71 | BBBB |
| ATOM | 3873 | CD | PRO | B | 171 | 9.874 | −17.138 | −30.989 | 1.00 | 30.67 | BBBB |
| ATOM | 3874 | CA | PRO | B | 171 | 11.611 | −17.457 | −32.642 | 1.00 | 30.11 | BBBB |
| ATOM | 3875 | CB | PRO | B | 171 | 11.665 | −16.054 | −32.033 | 1.00 | 29.54 | BBBB |
| ATOM | 3876 | CG | PRO | B | 171 | 10.261 | −15.810 | −31.605 | 1.00 | 30.96 | BBBB |
| ATOM | 3877 | C | PRO | B | 171 | 12.900 | −18.226 | −32.374 | 1.00 | 30.39 | BBBB |
| ATOM | 3878 | O | PRO | B | 171 | 12.999 | −18.933 | −31.363 | 1.00 | 30.16 | BBBB |
| ATOM | 3879 | N | LEU | B | 172 | 13.883 | −18.097 | −33.263 | 1.00 | 28.62 | BBBB |
| ATOM | 3880 | CA | LEU | B | 172 | 15.157 | −18.780 | −33.062 | 1.00 | 28.33 | BBBB |
| ATOM | 3881 | CB | LEU | B | 172 | 16.106 | −18.557 | −34.247 | 1.00 | 29.88 | BBBB |
| ATOM | 3882 | CG | LEU | B | 172 | 15.800 | −19.149 | −35.628 | 1.00 | 32.18 | BBBB |
| ATOM | 3883 | CD1 | LEU | B | 172 | 15.593 | −20.656 | −35.510 | 1.00 | 32.75 | BBBB |
| ATOM | 3884 | CD2 | LEU | B | 172 | 14.573 | −18.476 | −36.222 | 1.00 | 33.92 | BBBB |
| ATOM | 3885 | C | LEU | B | 172 | 15.805 | −18.206 | −31.805 | 1.00 | 26.61 | BBBB |
| ATOM | 3886 | O | LEU | B | 172 | 15.478 | −17.093 | −31.388 | 1.00 | 26.45 | BBBB |
| ATOM | 3887 | N | PRO | B | 173 | 16.735 | −18.959 | −31.190 | 1.00 | 25.73 | BBBB |
| ATOM | 3888 | CD | PRO | B | 173 | 17.093 | −20.345 | −31.550 | 1.00 | 24.63 | BBBB |
| ATOM | 3889 | CA | PRO | B | 173 | 17.450 | −18.550 | −29.977 | 1.00 | 25.25 | BBBB |
| ATOM | 3890 | CB | PRO | B | 173 | 18.512 | −19.635 | −29.827 | 1.00 | 25.04 | BBBB |
| ATOM | 3891 | CG | PRO | B | 173 | 17.818 | −20.831 | −30.309 | 1.00 | 24.90 | BBBB |
| ATOM | 3892 | C | PRO | B | 173 | 18.066 | −17.145 | −29.999 | 1.00 | 24.24 | BBBB |
| ATOM | 3893 | O | PRO | B | 173 | 17.791 | −16.337 | −29.116 | 1.00 | 22.89 | BBBB |
| ATOM | 3894 | N | GLN | B | 174 | 18.899 | −16.850 | −30.995 | 1.00 | 24.48 | BBBB |
| ATOM | 3895 | CA | GLN | B | 174 | 19.526 | −15.527 | −31.049 | 1.00 | 25.46 | BBBB |
| ATOM | 3896 | CB | GLN | B | 174 | 20.384 | −15.382 | −32.313 | 1.00 | 26.10 | BBBB |
| ATOM | 3897 | CG | GLN | B | 174 | 21.173 | −14.070 | −32.382 | 1.00 | 26.21 | BBBB |
| ATOM | 3898 | CD | GLN | B | 174 | 20.325 | −12.883 | −32.812 | 1.00 | 26.24 | BBBB |
| ATOM | 3899 | OE1 | GLN | B | 174 | 20.634 | −11.732 | −32.491 | 1.00 | 26.98 | BBBB |
| ATOM | 3900 | NE2 | GLN | B | 174 | 19.258 | −13.154 | −33.550 | 1.00 | 25.58 | BBBB |
| ATOM | 3901 | C | GLN | B | 174 | 18.485 | −14.408 | −30.981 | 1.00 | 25.33 | BBBB |
| ATOM | 3902 | O | GLN | B | 174 | 18.646 | −13.432 | −30.249 | 1.00 | 24.63 | BBBB |
| ATOM | 3903 | N | GLN | B | 175 | 17.402 | −14.555 | −31.726 | 1.00 | 26.49 | BBBB |
| ATOM | 3904 | CA | GLN | B | 175 | 16.365 | −13.525 | −31.718 | 1.00 | 28.47 | BBBB |
| ATOM | 3905 | CB | GLN | B | 175 | 15.333 | −13.819 | −32.809 | 1.00 | 29.48 | BBBB |
| ATOM | 3906 | CG | GLN | B | 175 | 14.206 | −12.805 | −32.888 | 1.00 | 33.70 | BBBB |
| ATOM | 3907 | CD | GLN | B | 175 | 13.324 | −13.006 | −34.109 | 1.00 | 35.20 | BBBB |
| ATOM | 3908 | OE1 | GLN | B | 175 | 12.247 | −12.422 | −34.215 | 1.00 | 38.98 | BBBB |
| ATOM | 3909 | NE2 | GLN | B | 175 | 13.785 | −13.828 | −35.042 | 1.00 | 37.92 | BBBB |
| ATOM | 3910 | C | GLN | B | 175 | 15.678 | −13.430 | −30.355 | 1.00 | 27.54 | BBBB |
| ATOM | 3911 | O | GLN | B | 175 | 15.521 | −12.346 | −29.796 | 1.00 | 26.49 | BBBB |
| ATOM | 3912 | N | ARG | B | 176 | 15.288 | −14.578 | −29.818 | 1.00 | 28.19 | BBBB |
| ATOM | 3913 | CA | ARG | B | 176 | 14.611 | −14.635 | −28.525 | 1.00 | 29.01 | BBBB |
| ATOM | 3914 | CB | ARG | B | 176 | 14.183 | −16.088 | −28.260 | 1.00 | 32.12 | BBBB |
| ATOM | 3915 | CG | ARG | B | 176 | 13.783 | −16.410 | −26.825 | 1.00 | 34.95 | BBBB |
| ATOM | 3916 | CD | ARG | B | 176 | 12.879 | −17.638 | −26.779 | 1.00 | 26.93 | BBBB |
| ATOM | 3917 | NE | ARG | B | 176 | 13.401 | −18.749 | −27.566 | 1.00 | 37.99 | BBBB |
| ATOM | 3918 | CZ | ARG | B | 176 | 14.458 | −19.480 | −27.231 | 1.00 | 40.44 | BBBB |
| ATOM | 3919 | NH1 | ARG | B | 176 | 15.121 | −19.233 | −26.107 | 1.00 | 41.22 | BBBB |
| ATOM | 3920 | NH2 | ARG | B | 176 | 14.866 | −20.451 | −28.040 | 1.00 | 42.79 | BBBB |
| ATOM | 3921 | C | ARG | B | 176 | 15.449 | −14.094 | −27.357 | 1.00 | 28.58 | BBBB |
| ATOM | 3922 | O | ARG | B | 176 | 14.933 | −13.414 | −26.467 | 1.00 | 26.70 | BBBB |
| ATOM | 3923 | N | LEU | B | 177 | 16.744 | −14.382 | −27.384 | 1.00 | 28.60 | BBBB |
| ATOM | 3924 | CA | LEU | B | 177 | 17.673 | −13.970 | −26.331 | 1.00 | 29.90 | BBBB |
| ATOM | 3925 | CB | LEU | B | 177 | 18.729 | −15.071 | −26.140 | 1.00 | 30.05 | BBBB |
| ATOM | 3926 | CG | LEU | B | 177 | 18.323 | −16.402 | −25.484 | 1.00 | 31.35 | BBBB |
| ATOM | 3927 | CD1 | LEU | B | 177 | 16.893 | −16.755 | −25.807 | 1.00 | 31.63 | BBBB |
| ATOM | 3928 | CD2 | LEU | B | 177 | 19.266 | −17.504 | −25.948 | 1.00 | 30.16 | BBBB |
| ATOM | 3929 | C | LEU | B | 177 | 18.384 | −12.637 | −26.594 | 1.00 | 30.48 | BBBB |
| ATOM | 3930 | O | LEU | B | 177 | 19.148 | −12.161 | −25.752 | 1.00 | 30.67 | BBBB |
| ATOM | 3931 | N | ALA | B | 178 | 18.128 | −12.036 | −27.752 | 1.00 | 31.18 | BBBB |
| ATOM | 3932 | CA | ALA | B | 178 | 18.766 | −10.776 | −28.131 | 1.00 | 30.78 | BBBB |

TABLE 1-continued

ATOMIC COORDINATES OF E. COLI MURG PROTEIN

| ATOM | 3933 | CB  | ALA | B | 178 | 18.238 | −10.319 | −29.496 | 1.00 | 32.30 | BBBB |
|------|------|-----|-----|---|-----|--------|---------|---------|------|-------|------|
| ATOM | 3934 | C   | ALA | B | 178 | 18.639 | −9.636  | −27.123 | 1.00 | 31.11 | BBBB |
| ATOM | 3935 | O   | ALA | B | 178 | 17.537 | −9.253  | −26.726 | 1.00 | 30.59 | BBBB |
| ATOM | 3936 | N   | GLY | B | 179 | 19.792 | −9.105  | −26.718 | 1.00 | 30.45 | BBBB |
| ATOM | 3937 | CA  | GLY | B | 179 | 19.846 | −7.993  | −25.784 | 1.00 | 30.10 | BBBB |
| ATOM | 3938 | C   | GLY | B | 179 | 19.392 | −8.298  | −24.374 | 1.00 | 29.54 | BBBB |
| ATOM | 3939 | O   | GLY | B | 179 | 19.288 | −7.405  | −23.537 | 1.00 | 28.79 | BBBB |
| ATOM | 3940 | N   | ARG | B | 180 | 19.129 | −9.568  | −24.101 | 1.00 | 29.31 | BBBB |
| ATOM | 3941 | CA  | ARG | B | 180 | 18.676 | −9.965  | −22.787 | 1.00 | 28.97 | BBBB |
| ATOM | 3942 | CB  | ARG | B | 180 | 18.120 | −11.391 | −22.868 | 1.00 | 28.73 | BBBB |
| ATOM | 3943 | CG  | ARG | B | 180 | 17.281 | −11.815 | −21.693 | 1.00 | 25.80 | BBBB |
| ATOM | 3944 | CD  | ARG | B | 180 | 16.813 | −13.245 | −21.869 | 1.00 | 24.21 | BBBB |
| ATOM | 3945 | NE  | ARG | B | 180 | 15.595 | −13.363 | −22.665 | 1.00 | 23.27 | BBBB |
| ATOM | 3946 | CZ  | ARG | B | 180 | 14.898 | −14.489 | −22.776 | 1.00 | 24.65 | BBBB |
| ATOM | 3947 | NH1 | ARG | B | 180 | 15.316 | −15.579 | −22.146 | 1.00 | 21.06 | BBBB |
| ATOM | 3948 | NH2 | ARG | B | 180 | 13.777 | −14.529 | −23.491 | 1.00 | 23.07 | BBBB |
| ATOM | 3949 | C   | ARG | B | 180 | 19.818 | −9.874  | −21.769 | 1.00 | 30.52 | BBBB |
| ATOM | 3950 | O   | ARG | B | 180 | 20.916 | −10.398 | −21.980 | 1.00 | 30.32 | BBBB |
| ATOM | 3951 | N   | GLU | B | 181 | 19.562 | −9.171  | −20.677 | 1.00 | 30.40 | BBBB |
| ATOM | 3952 | CA  | GLU | B | 181 | 20.545 | −9.027  | −19.621 | 1.00 | 31.79 | BBBB |
| ATOM | 3953 | CB  | GLU | B | 181 | 21.157 | −7.617  | −19.650 | 1.00 | 34.59 | BBBB |
| ATOM | 3954 | CG  | GLU | B | 181 | 22.130 | −7.422  | −20.826 | 1.00 | 38.85 | BBBB |
| ATOM | 3955 | CD  | GLU | B | 181 | 22.659 | −6.001  | −20.957 | 1.00 | 41.19 | BBBB |
| ATOM | 3956 | OE1 | GLU | B | 181 | 23.274 | −5.495  | −19.996 | 1.00 | 43.24 | BBBB |
| ATOM | 3957 | OE2 | GLU | B | 181 | 22.467 | −5.392  | −22.032 | 1.00 | 43.11 | BBBB |
| ATOM | 3958 | C   | GLU | B | 181 | 19.815 | −9.307  | −18.313 | 1.00 | 31.51 | BBBB |
| ATOM | 3959 | O   | GLU | B | 181 | 18.605 | −9.543  | −18.313 | 1.00 | 33.44 | BBBB |
| ATOM | 3960 | N   | GLY | B | 182 | 20.535 | −9.314  | −17.203 | 1.00 | 29.65 | BBBB |
| ATOM | 3961 | CA  | GLY | B | 182 | 19.871 | −9.586  | −15.943 | 1.00 | 27.75 | BBBB |
| ATOM | 3962 | C   | GLY | B | 182 | 19.989 | −11.051 | −15.565 | 1.00 | 25.32 | BBBB |
| ATOM | 3963 | O   | GLY | B | 182 | 20.573 | −11.830 | −16.311 | 1.00 | 22.00 | BBBB |
| ATOM | 3964 | N   | PRO | B | 183 | 19.414 | −11.455 | −14.423 | 1.00 | 23.79 | BBBB |
| ATOM | 3965 | CD  | PRO | B | 183 | 18.562 | −10.609 | −13.572 | 1.00 | 24.07 | BBBB |
| ATOM | 3966 | CA  | PRO | B | 183 | 19.450 | −12.832 | −13.913 | 1.00 | 22.93 | BBBB |
| ATOM | 3967 | CB  | PRO | B | 183 | 18.480 | −12.796 | −12.727 | 1.00 | 23.23 | BBBB |
| ATOM | 3968 | CG  | PRO | B | 183 | 18.549 | −11.381 | −12.271 | 1.00 | 24.61 | BBBB |
| ATOM | 3969 | C   | PRO | B | 183 | 19.063 | −13.912 | −14.905 | 1.00 | 21.77 | BBBB |
| ATOM | 3970 | O   | PRO | B | 183 | 18.117 | −13.758 | −15.683 | 1.00 | 21.04 | BBBB |
| ATOM | 3971 | N   | VAL | B | 184 | 19.805 | −15.011 | −14.867 | 1.00 | 19.40 | BBBB |
| ATOM | 3972 | CA  | VAL | B | 184 | 19.524 | −16.146 | −15.729 | 1.00 | 18.01 | BBBB |
| ATOM | 3973 | CB  | VAL | B | 184 | 20.597 | −17.248 | −15.549 | 1.00 | 17.45 | BBBB |
| ATOM | 3974 | CG1 | VAL | B | 184 | 20.171 | −18.534 | −16.249 | 1.00 | 15.59 | BBBB |
| ATOM | 3975 | CG2 | VAL | B | 184 | 21.931 | −16.753 | −16.121 | 1.00 | 18.46 | BBBB |
| ATOM | 3976 | C   | VAL | B | 184 | 18.155 | −16.650 | −15.283 | 1.00 | 18.17 | BBBB |
| ATOM | 3977 | O   | VAL | B | 184 | 17.931 | −16.882 | −14.092 | 1.00 | 16.37 | BBBB |
| ATOM | 3978 | N   | ARG | B | 185 | 17.244 | −16.771 | −16.245 | 1.00 | 17.91 | BBBB |
| ATOM | 3979 | CA  | ARG | B | 185 | 15.873 | −17.216 | −16.011 | 1.00 | 17.62 | BBBB |
| ATOM | 3980 | CB  | ARG | B | 185 | 14.966 | −16.622 | −17.092 | 1.00 | 17.65 | BBBB |
| ATOM | 3981 | CG  | ARG | B | 185 | 15.036 | −15.110 | −17.160 | 1.00 | 18.62 | BBBB |
| ATOM | 3982 | CD  | ARG | B | 185 | 14.344 | −14.624 | −18.420 | 1.00 | 20.39 | BBBB |
| ATOM | 3983 | NE  | ARG | B | 185 | 14.307 | −13.173 | −18.516 | 1.00 | 19.72 | BBBB |
| ATOM | 3984 | CZ  | ARG | B | 185 | 13.647 | −12.520 | −19.466 | 1.00 | 20.23 | BBBB |
| ATOM | 3985 | NH1 | ARG | B | 185 | 12.977 | −13.197 | −20.391 | 1.00 | 19.85 | BBBB |
| ATOM | 3986 | NH2 | ARG | B | 185 | 13.650 | −11.197 | −19.487 | 1.00 | 23.44 | BBBB |
| ATOM | 3987 | C   | ARG | B | 185 | 15.804 | −18.740 | −16.037 | 1.00 | 16.88 | BBBB |
| ATOM | 3988 | O   | ARG | B | 185 | 15.971 | −19.367 | −17.087 | 1.00 | 15.75 | BBBB |
| ATOM | 3989 | N   | VAL | B | 186 | 15.566 | −19.326 | −14.870 | 1.00 | 15.97 | BBBB |
| ATOM | 3990 | CA  | VAL | B | 186 | 15.508 | −20.771 | −14.741 | 1.00 | 16.47 | BBBB |
| ATOM | 3991 | CB  | VAL | B | 186 | 16.259 | −21.245 | −13.476 | 1.00 | 15.51 | BBBB |
| ATOM | 3992 | CG1 | VAL | B | 186 | 16.316 | −22.770 | −13.448 | 1.00 | 17.66 | BBBB |
| ATOM | 3993 | CG2 | VAL | B | 186 | 17.652 | −20.626 | −13.430 | 1.00 | 16.97 | BBBB |
| ATOM | 3994 | C   | VAL | B | 186 | 14.076 | −21.282 | −14.644 | 1.00 | 16.41 | BBBB |
| ATOM | 3995 | O   | VAL | B | 186 | 13.343 | −20.920 | −13.732 | 1.00 | 18.33 | BBBB |
| ATOM | 3996 | N   | LEU | B | 187 | 13.695 | −22.128 | −15.588 | 1.00 | 15.92 | BBBB |
| ATOM | 3997 | CA  | LEU | B | 187 | 12.361 | −22.710 | −15.604 | 1.00 | 16.75 | BBBB |
| ATOM | 3998 | CB  | LEU | B | 187 | 11.813 | −22.701 | −17.035 | 1.00 | 16.85 | BBBB |
| ATOM | 3999 | CG  | LEU | B | 187 | 10.445 | −23.340 | −17.276 | 1.00 | 18.63 | BBBB |
| ATOM | 4000 | CD1 | LEU | B | 187 | 9.368  | −22.478 | −16.625 | 1.00 | 19.42 | BBBB |
| ATOM | 4001 | CD2 | LEU | B | 187 | 10.198 | −23.449 | −18.783 | 1.00 | 19.11 | BBBB |
| ATOM | 4002 | C   | LEU | B | 187 | 12.450 | −24.146 | −15.085 | 1.00 | 16.85 | BBBB |
| ATOM | 4003 | O   | LEU | B | 187 | 13.115 | −24.982 | −15.688 | 1.00 | 17.18 | BBBB |
| ATOM | 4004 | N   | VAL | B | 188 | 11.788 | −24.426 | −13.964 | 1.00 | 18.20 | BBBB |
| ATOM | 4005 | CA  | VAL | B | 188 | 11.774 | −25.775 | −13.381 | 1.00 | 18.41 | BBBB |
| ATOM | 4006 | CB  | VAL | B | 188 | 11.902 | −25.714 | −11.842 | 1.00 | 18.98 | BBBB |
| ATOM | 4007 | CG1 | VAL | B | 188 | 12.088 | −27.126 | −11.270 | 1.00 | 18.50 | BBBB |
| ATOM | 4008 | CG2 | VAL | B | 188 | 13.061 | −24.818 | −11.449 | 1.00 | 18.83 | BBBB |
| ATOM | 4009 | C   | VAL | B | 188 | 10.434 | −26.440 | −13.739 | 1.00 | 19.88 | BBBB |

TABLE 1-continued

ATOMIC COORDINATES OF E. COLI MURG PROTEIN

| ATOM | 4010 | O | VAL | B | 188 | 9.371 | −25.967 | −13.336 | 1.00 | 20.39 | BBBB |
|---|---|---|---|---|---|---|---|---|---|---|---|
| ATOM | 4011 | N | VAL | B | 189 | 10.493 | −27.532 | −14.496 | 1.00 | 21.55 | BBBB |
| ATOM | 4012 | CA | VAL | B | 189 | 9.298 | −28.234 | −14.948 | 1.00 | 22.11 | BBBB |
| ATOM | 4013 | CB | VAL | B | 189 | 9.299 | −28.342 | −16.488 | 1.00 | 22.50 | BBBB |
| ATOM | 4014 | CG1 | VAL | B | 189 | 8.009 | −29.013 | −16.981 | 1.00 | 22.70 | BBBB |
| ATOM | 4015 | CG2 | VAL | B | 189 | 9.470 | −26.943 | −17.101 | 1.00 | 21.26 | BBBB |
| ATOM | 4016 | C | VAL | B | 189 | 9.191 | −29.639 | −14.351 | 1.00 | 23.90 | BBBB |
| ATOM | 4017 | O | VAL | B | 189 | 10.067 | −30.478 | −14.559 | 1.00 | 23.61 | BBBB |
| ATOM | 4018 | N | GLY | B | 190 | 8.111 | −29.887 | −13.615 | 1.00 | 25.60 | BBBB |
| ATOM | 4019 | CA | GLY | B | 190 | 7.914 | −31.188 | −12.994 | 1.00 | 27.28 | BBBB |
| ATOM | 4020 | C | GLY | B | 190 | 6.808 | −32.026 | −13.604 | 1.00 | 29.67 | BBBB |
| ATOM | 4021 | O | GLY | B | 190 | 6.668 | −33.208 | −13.283 | 1.00 | 29.86 | BBBB |
| ATOM | 4022 | N | GLY | B | 191 | 6.025 | −31.430 | −14.497 | 1.00 | 30.56 | BBBB |
| ATOM | 4023 | CA | GLY | B | 191 | 4.935 | −32.163 | −15.115 | 1.00 | 31.94 | BBBB |
| ATOM | 4024 | C | GLY | B | 191 | 3.676 | −32.104 | −14.269 | 1.00 | 33.11 | BBBB |
| ATOM | 4025 | O | GLY | B | 191 | 3.691 | −31.556 | −13.165 | 1.00 | 32.41 | BBBB |
| ATOM | 4026 | N | SER | B | 192 | 2.687 | −32.673 | −14.779 | 1.00 | 34.23 | BBBB |
| ATOM | 4027 | CA | SER | B | 192 | 1.313 | −32.665 | −14.064 | 1.00 | 35.91 | BBBB |
| ATOM | 4028 | CB | SER | B | 192 | 0.283 | −33.532 | −14.801 | 1.00 | 36.87 | BBBB |
| ATOM | 4029 | OG | SER | B | 192 | 0.702 | −34.887 | −14.877 | 1.00 | 39.58 | BBBB |
| ATOM | 4030 | C | SER | B | 192 | 1.419 | −33.128 | −12.609 | 1.00 | 36.41 | BBBB |
| ATOM | 4031 | O | SER | B | 192 | 0.862 | −32.499 | −11.714 | 1.00 | 35.78 | BBBB |
| ATOM | 4032 | N | GLN | B | 193 | 2.134 | −34.225 | −12.380 | 1.00 | 37.60 | BBBB |
| ATOM | 4033 | CA | GLN | B | 193 | 2.292 | −34.763 | −11.033 | 1.00 | 38.53 | BBBB |
| ATOM | 4034 | CB | GLN | B | 193 | 2.584 | −36.263 | −11.096 | 1.00 | 41.10 | BBBB |
| ATOM | 4035 | CG | GLN | B | 193 | 1.501 | −37.082 | −11.779 | 1.00 | 45.38 | BBBB |
| ATOM | 4036 | CD | GLN | B | 193 | 0.152 | −36.948 | −11.099 | 1.00 | 47.81 | BBBB |
| ATOM | 4037 | OE1 | GLN | B | 193 | −0.484 | −35.892 | −11.149 | 1.00 | 49.50 | BBBB |
| ATOM | 4038 | NE2 | GLN | B | 193 | −0.290 | −38.023 | −10.452 | 1.00 | 49.36 | BBBB |
| ATOM | 4039 | C | GLN | B | 193 | 3.405 | −34.072 | −10.260 | 1.00 | 37.76 | BBBB |
| ATOM | 4040 | O | GLN | B | 193 | 3.458 | −34.146 | −9.030 | 1.00 | 37.02 | BBBB |
| ATOM | 4041 | N | GLY | B | 194 | 4.291 | −33.398 | −10.986 | 1.00 | 36.47 | BBBB |
| ATOM | 4042 | CA | GLY | B | 194 | 5.398 | −32.711 | −10.350 | 1.00 | 35.02 | BBBB |
| ATOM | 4043 | C | GLY | B | 194 | 6.584 | −33.630 | −10.146 | 1.00 | 34.51 | BBBB |
| ATOM | 4044 | O | GLY | B | 194 | 6.442 | −34.851 | −10.191 | 1.00 | 34.26 | BBBB |
| ATOM | 4045 | N | ALA | B | 195 | 7.761 | −33.045 | −9.938 | 1.00 | 33.54 | BBBB |
| ATOM | 4046 | CA | ALA | B | 195 | 8.977 | −33.819 | −9.709 | 1.00 | 33.12 | BBBB |
| ATOM | 4047 | CB | ALA | B | 195 | 10.073 | −33.387 | −10.679 | 1.00 | 33.17 | BBBB |
| ATOM | 4048 | C | ALA | B | 195 | 9.423 | −33.590 | −8.267 | 1.00 | 32.87 | BBBB |
| ATOM | 4049 | O | ALA | B | 195 | 9.955 | −32.533 | −7.923 | 1.00 | 31.47 | BBBB |
| ATOM | 4050 | N | ALA | B | 196 | 9.195 | −34.592 | −7.426 | 1.00 | 32.81 | BBBB |
| ATOM | 4051 | CA | ARG | B | 196 | 9.538 | −34.512 | −6.010 | 1.00 | 32.63 | BBBB |
| ATOM | 4052 | CB | ARG | B | 196 | 9.373 | −35.891 | −5.361 | 1.00 | 35.51 | BBBB |
| ATOM | 4053 | CG | ARG | B | 196 | 10.382 | −36.954 | −5.830 | 1.00 | 39.68 | BBBB |
| ATOM | 4054 | CD | ARG | B | 196 | 10.317 | −37.224 | −7.329 | 1.00 | 41.52 | BBBB |
| ATOM | 4055 | NE | ARG | B | 196 | 9.007 | −37.722 | −7.738 | 1.00 | 43.02 | BBBB |
| ATOM | 4056 | CZ | ARG | B | 196 | 8.661 | −37.955 | −8.997 | 1.00 | 42.91 | BBBB |
| ATOM | 4057 | NH1 | ARG | B | 196 | 9.527 | −37.735 | −9.975 | 1.00 | 44.39 | BBBB |
| ATOM | 4058 | NH2 | ARG | B | 196 | 7.449 | −38.408 | −9.279 | 1.00 | 45.18 | BBBB |
| ATOM | 4059 | C | ARG | B | 196 | 10.940 | −33.977 | −5.729 | 1.00 | 30.96 | BBBB |
| ATOM | 4060 | O | ARG | B | 196 | 11.108 | −33.035 | −4.957 | 1.00 | 29.99 | BBBB |
| ATOM | 4061 | N | ILE | B | 197 | 11.942 | −34.573 | −6.367 | 1.00 | 29.47 | BBBB |
| ATOM | 4062 | CA | ILE | B | 197 | 13.329 | −34.168 | −6.164 | 1.00 | 28.10 | BBBB |
| ATOM | 4063 | CB | ILE | B | 197 | 14.284 | −35.109 | −6.946 | 1.00 | 28.46 | BBBB |
| ATOM | 4064 | CG2 | ILE | B | 197 | 13.984 | −35.041 | −8.430 | 1.00 | 27.99 | BBBB |
| ATOM | 4065 | CG1 | ILE | B | 197 | 15.742 | −34.749 | −6.657 | 1.00 | 28.64 | BBBB |
| ATOM | 4066 | CD1 | ILE | B | 197 | 16.212 | −35.158 | −5.281 | 1.00 | 30.51 | BBBB |
| ATOM | 4067 | C | ILE | B | 197 | 13.579 | −32.703 | −6.554 | 1.00 | 27.65 | BBBB |
| ATOM | 4068 | O | ILE | B | 197 | 14.378 | −32.013 | −5.921 | 1.00 | 27.21 | BBBB |
| ATOM | 4069 | N | LEU | B | 198 | 12.897 | −32.223 | −7.590 | 1.00 | 27.07 | BBBB |
| ATOM | 4070 | CA | LEU | B | 198 | 13.069 | −30.833 | −8.003 | 1.00 | 26.58 | BBBB |
| ATOM | 4071 | CB | LEU | B | 198 | 12.504 | −30.616 | −9.412 | 1.00 | 25.88 | BBBB |
| ATOM | 4072 | CG | LEU | B | 198 | 13.196 | −31.408 | −10.524 | 1.00 | 25.40 | BBBB |
| ATOM | 4073 | CD1 | LEU | B | 198 | 12.625 | −31.007 | −11.874 | 1.00 | 26.54 | BBBB |
| ATOM | 4074 | CD2 | LEU | B | 198 | 14.692 | −31.146 | −10.493 | 1.00 | 25.94 | BBBB |
| ATOM | 4075 | C | LEU | B | 198 | 12.388 | −29.893 | −7.006 | 1.00 | 26.41 | BBBB |
| ATOM | 4076 | O | LEU | B | 198 | 12.930 | −28.835 | −6.667 | 1.00 | 26.35 | BBBB |
| ATOM | 4077 | N | ASN | B | 199 | 11.205 | −30.274 | −6.532 | 1.00 | 26.01 | BBBB |
| ATOM | 4078 | CA | ASN | B | 199 | 10.497 | −29.447 | −5.563 | 1.00 | 27.07 | BBBB |
| ATOM | 4079 | CB | ASN | B | 199 | 9.123 | −30.035 | −5.238 | 1.00 | 26.63 | BBBB |
| ATOM | 4080 | CG | ASN | B | 199 | 8.212 | −30.050 | −6.434 | 1.00 | 27.62 | BBBB |
| ATOM | 4081 | OD1 | ASN | B | 199 | 8.519 | −29.434 | −7.460 | 1.00 | 26.33 | BBBB |
| ATOM | 4082 | ND2 | ASN | B | 199 | 7.080 | −30.749 | −6.320 | 1.00 | 24.20 | BBBB |
| ATOM | 4083 | C | ASN | B | 199 | 11.308 | −29.319 | −4.282 | 1.00 | 27.65 | BBBB |
| ATOM | 4084 | O | ASN | B | 199 | 11.207 | −28.321 | −3.581 | 1.00 | 28.19 | BBBB |
| ATOM | 4085 | N | GLN | B | 200 | 12.124 | −30.328 | −3.994 | 1.00 | 28.38 | BBBB |
| ATOM | 4086 | CA | GLN | B | 200 | 12.955 | −30.326 | −2.794 | 1.00 | 30.10 | BBBB |

TABLE 1-continued

ATOMIC COORDINATES OF E. COLI MURG PROTEIN

| ATOM | 4087 | CB | GLN | B | 200 | 13.158 | −31.764 | −2.301 | 1.00 | 31.91 | BBBB |
|---|---|---|---|---|---|---|---|---|---|---|---|
| ATOM | 4088 | CG | GLN | B | 200 | 11.883 | −32.453 | −1.827 | 1.00 | 35.02 | BBBB |
| ATOM | 4089 | CD | GLN | B | 200 | 12.056 | −33.956 | −1.632 | 1.00 | 37.49 | BBBB |
| ATOM | 4090 | CO1 | GLN | B | 200 | 11.204 | −34.619 | −1.032 | 1.00 | 38.76 | BBBB |
| ATOM | 4091 | NE2 | GLN | B | 200 | 13.155 | −34.502 | −2.151 | 1.00 | 37.28 | BBBB |
| ATOM | 4092 | C | GLN | B | 200 | 14.319 | −29.675 | −3.011 | 1.00 | 30.18 | BBBB |
| ATOM | 4093 | C | GLN | B | 200 | 14.834 | −28.975 | −2.135 | 1.00 | 31.13 | BBBB |
| ATOM | 4094 | N | THR | B | 201 | 14.897 | −29.884 | −4.187 | 1.00 | 28.94 | BBBB |
| ATOM | 4095 | CA | THR | B | 201 | 16.215 | −29.345 | −4.474 | 1.00 | 27.34 | BBBB |
| ATOM | 4096 | CB | THR | B | 201 | 16.915 | −30.181 | −5.567 | 1.00 | 28.81 | BBBB |
| ATOM | 4097 | OG1 | THR | B | 201 | 16.988 | −31.553 | −5.149 | 1.00 | 28.92 | BBBB |
| ATOM | 4098 | CG2 | THR | B | 201 | 18.331 | −29.654 | −5.817 | 1.00 | 28.29 | BBBB |
| ATOM | 4099 | C | THR | B | 201 | 16.313 | −27.871 | −4.869 | 1.00 | 25.78 | BBBB |
| ATOM | 4100 | O | THR | B | 201 | 17.137 | −27.138 | −4.331 | 1.00 | 24.91 | BBBB |
| ATOM | 4101 | N | MET | B | 202 | 15.479 | −27.430 | −5.800 | 1.00 | 24.08 | BBBB |
| ATOM | 4102 | CA | MET | B | 202 | 15.567 | −26.048 | −6.268 | 1.00 | 23.68 | BBBB |
| ATOM | 4103 | CB | MET | B | 202 | 14.558 | −25.827 | −7.397 | 1.00 | 22.29 | BBBB |
| ATOM | 4104 | CG | MET | B | 202 | 14.856 | −26.685 | −8.633 | 1.00 | 22.80 | BBBB |
| ATOM | 4105 | SD | MET | B | 202 | 16.590 | −26.614 | −9.190 | 1.00 | 25.93 | BBBB |
| ATOM | 4106 | CE | MET | B | 202 | 16.814 | −24.877 | −9.345 | 1.00 | 22.63 | BBBB |
| ATOM | 4107 | C | MET | B | 202 | 15.489 | −24.926 | −5.229 | 1.00 | 23.47 | BBBB |
| ATOM | 4108 | O | MET | B | 202 | 16.189 | −23.929 | −5.354 | 1.00 | 24.40 | BBBB |
| ATOM | 4109 | N | PRO | B | 203 | 14.636 | −25.059 | −4.192 | 1.00 | 24.12 | BBBB |
| ATOM | 4110 | CD | PRO | B | 203 | 13.518 | −25.991 | −3.970 | 1.00 | 22.27 | BBBB |
| ATOM | 4111 | CA | PRO | B | 203 | 14.608 | −23.963 | −3.220 | 1.00 | 23.84 | BBBB |
| ATOM | 4112 | CB | PRO | B | 203 | 13.553 | −24.424 | −2.217 | 1.00 | 24.46 | BBBB |
| ATOM | 4113 | CG | PRO | B | 203 | 12.593 | −25.178 | −3.084 | 1.00 | 24.04 | BBBB |
| ATOM | 4114 | C | PRO | B | 203 | 15.987 | −23.731 | −2.573 | 1.00 | 24.07 | BBBB |
| ATOM | 4115 | O | PRO | B | 203 | 16.395 | −22.593 | −2.343 | 1.00 | 23.18 | BBBB |
| ATOM | 4116 | N | GLN | B | 204 | 16.706 | −24.814 | −2.290 | 1.00 | 25.26 | BBBB |
| ATOM | 4117 | CA | GLN | B | 204 | 18.033 | −24.708 | −1.684 | 1.00 | 26.34 | BBBB |
| ATOM | 4118 | CB | GLN | B | 204 | 18.474 | −26.078 | −1.157 | 1.00 | 28.67 | BBBB |
| ATOM | 4119 | CG | GLN | B | 204 | 17.555 | −26.626 | −0.065 | 1.00 | 33.65 | BBBB |
| ATOM | 4120 | CD | GLN | B | 204 | 17.885 | −28.059 | 0.328 | 1.00 | 37.09 | BBBB |
| ATOM | 4121 | OE1 | GLN | B | 204 | 18.991 | −28.354 | 0.792 | 1.00 | 39.30 | BBBB |
| ATOM | 4122 | NE2 | GLN | B | 204 | 16.924 | −28.960 | 0.140 | 1.00 | 38.32 | BBBB |
| ATOM | 4123 | C | GLN | B | 204 | 19.030 | −24.177 | −2.717 | 1.00 | 25.36 | BBBB |
| ATOM | 4124 | O | GLN | B | 204 | 19.985 | −23.466 | −2.385 | 1.00 | 24.98 | BBBB |
| ATOM | 4125 | N | VAL | B | 205 | 18.806 | −24.522 | −3.978 | 1.00 | 24.46 | BBBB |
| ATOM | 4126 | CA | VAL | B | 205 | 19.672 | −24.033 | −5.043 | 1.00 | 24.44 | BBBB |
| ATOM | 4127 | CB | VAL | B | 205 | 19.288 | −24.634 | −6.409 | 1.00 | 24.84 | BBBB |
| ATOM | 4128 | CG1 | VAL | B | 205 | 20.039 | −23.906 | −7.534 | 1.00 | 23.72 | BBBB |
| ATOM | 4129 | CG2 | VAL | B | 205 | 19.614 | −26.110 | −6.428 | 1.00 | 22.91 | BBBB |
| ATOM | 4130 | C | VAL | B | 205 | 19.511 | −22.515 | −5.110 | 1.00 | 23.79 | BBBB |
| ATOM | 4131 | O | VAL | B | 205 | 20.487 | −21.789 | −5.270 | 1.00 | 25.25 | BBBB |
| ATOM | 4132 | N | ALA | B | 206 | 18.273 | −22.044 | −4.972 | 1.00 | 24.12 | BBBB |
| ATOM | 4133 | CA | ALA | B | 206 | 17.980 | −20.610 | −5.013 | 1.00 | 22.84 | BBBB |
| ATOM | 4134 | CB | ALA | B | 206 | 16.466 | −20.377 | −4.908 | 1.00 | 21.55 | BBBB |
| ATOM | 4135 | C | ALA | B | 206 | 18.700 | −19.862 | −3.890 | 1.00 | 24.09 | BBBB |
| ATOM | 4136 | O | ALA | B | 206 | 19.174 | −18.740 | −4.081 | 1.00 | 24.90 | BBBB |
| ATOM | 4137 | N | ALA | B | 207 | 18.768 | −20.477 | −2.713 | 1.00 | 25.15 | BBBB |
| ATOM | 4138 | CA | ALA | B | 207 | 19.442 | −19.857 | −1.576 | 1.00 | 26.65 | BBBB |
| ATOM | 4139 | CB | ALA | B | 207 | 19.260 | −20.710 | −0.324 | 1.00 | 27.83 | BBBB |
| ATOM | 4140 | C | ALA | B | 207 | 20.924 | −19.686 | −1.879 | 1.00 | 26.96 | BBBB |
| ATOM | 4141 | O | ALA | B | 207 | 21.537 | −18.693 | −1.493 | 1.00 | 27.82 | BBBB |
| ATOM | 4142 | N | LYS | B | 208 | 21.498 | −20.651 | −2.586 | 1.00 | 27.19 | BBBB |
| ATOM | 4143 | CA | LYS | B | 208 | 22.915 | −20.595 | −2.919 | 1.00 | 28.31 | BBBB |
| ATOM | 4144 | CB | LYS | B | 208 | 23.432 | −21.989 | −3.300 | 1.00 | 29.85 | BBBB |
| ATOM | 4145 | CG | LYS | B | 208 | 23.030 | −23.088 | −2.329 | 1.00 | 32.97 | BBBB |
| ATOM | 4146 | CD | LYS | B | 208 | 23.264 | −22.667 | −0.886 | 1.00 | 35.74 | BBBB |
| ATOM | 4147 | CE | LYS | B | 208 | 22.689 | −23.689 | 0.084 | 1.00 | 37.28 | BBBB |
| ATOM | 4148 | NZ | LYS | B | 208 | 21.227 | −23.899 | −0.135 | 1.00 | 35.29 | BBBB |
| ATOM | 4149 | C | LYS | B | 208 | 23.237 | −19.624 | −4.050 | 1.00 | 27.83 | BBBB |
| ATOM | 4150 | O | LYS | B | 208 | 24.286 | −18.978 | −4.033 | 1.00 | 27.46 | BBBB |
| ATOM | 4151 | N | LEU | B | 209 | 22.341 | −19.517 | −5.028 | 1.00 | 26.04 | BBBB |
| ATOM | 4152 | CA | LEU | B | 209 | 22.577 | −18.640 | −6.171 | 1.00 | 25.68 | BBBB |
| ATOM | 4153 | CB | LEU | B | 209 | 21.975 | −19.268 | −7.435 | 1.00 | 25.08 | BBBB |
| ATOM | 4154 | CG | LEU | B | 209 | 22.534 | −20.638 | −7.844 | 1.00 | 25.01 | BBBB |
| ATOM | 4155 | CD1 | LEU | B | 209 | 21.797 | −21.151 | −9.074 | 1.00 | 25.67 | BBBB |
| ATOM | 4156 | CD2 | LEU | B | 209 | 24.029 | −20.528 | −8.119 | 1.00 | 25.13 | BBBB |
| ATOM | 4157 | C | LEU | B | 209 | 22.075 | −17.200 | −6.007 | 1.00 | 25.59 | BBBB |
| ATOM | 4158 | O | LEU | B | 209 | 22.496 | −16.313 | −6.742 | 1.00 | 25.26 | BBBB |
| ATOM | 4159 | N | GLY | B | 210 | 21.185 | −16.970 | −5.045 | 1.00 | 26.27 | BBBB |
| ATOM | 4160 | CA | GLY | B | 210 | 20.675 | −15.628 | −4.804 | 1.00 | 26.56 | BBBB |
| ATOM | 4161 | C | GLY | B | 210 | 20.238 | −14.836 | −6.030 | 1.00 | 27.75 | BBBB |
| ATOM | 4162 | O | GLY | B | 210 | 19.518 | −15.349 | −6.889 | 1.00 | 27.68 | BBBB |
| ATOM | 4163 | N | ASP | B | 211 | 20.696 | −13.585 | −6.105 | 1.00 | 27.93 | BBBB |

TABLE 1-continued

ATOMIC COORDINATES OF E. COLI MURG PROTEIN

| ATOM | 4164 | CA | ASP | B | 211 | 20.370 | −12.647 | −7.190 | 1.00 | 28.28 | BBBB |
|---|---|---|---|---|---|---|---|---|---|---|---|
| ATOM | 4165 | CB | ASP | B | 211 | 21.011 | −11.283 | −6.906 | 1.00 | 29.89 | BBBB |
| ATOM | 4166 | CG | ASP | B | 211 | 20.351 | −10.545 | −5.768 | 1.00 | 31.43 | BBBB |
| ATOM | 4167 | OD1 | ASP | B | 211 | 20.864 | −9.469 | −5.398 | 1.00 | 32.43 | BBBB |
| ATOM | 4168 | OD2 | ASP | B | 211 | 19.323 | −11.025 | −5.249 | 1.00 | 33.41 | BBBB |
| ATOM | 4169 | C | ASP | B | 211 | 20.768 | −13.035 | −8.615 | 1.00 | 27.77 | BBBB |
| ATOM | 4170 | O | ASP | B | 211 | 20.320 | −12.397 | −9.578 | 1.00 | 26.32 | BBBB |
| ATOM | 4171 | N | SER | B | 212 | 21.616 | −14.048 | −8.753 | 1.00 | 25.75 | BBBB |
| ATOM | 4172 | CA | SER | B | 212 | 22.098 | −14.474 | −10.067 | 1.00 | 25.73 | BBBB |
| ATOM | 4173 | CB | SER | B | 212 | 23.331 | −15.376 | −9.904 | 1.00 | 26.63 | BBBB |
| ATOM | 4174 | OG | SER | B | 212 | 22.971 | −16.596 | −9.282 | 1.00 | 26.71 | BBBB |
| ATOM | 4175 | C | SER | B | 212 | 21.062 | −15.185 | −10.943 | 1.00 | 23.61 | BBBB |
| ATOM | 4176 | O | SER | B | 212 | 21.262 | −15.334 | −12.147 | 1.00 | 22.28 | BBBB |
| ATOM | 4177 | N | VAL | B | 213 | 19.969 | −15.644 | −10.344 | 1.00 | 23.16 | BBBB |
| ATOM | 4178 | CA | VAL | B | 213 | 18.925 | −16.308 | −11.116 | 1.00 | 20.76 | BBBB |
| ATOM | 4179 | CB | VAL | B | 213 | 18.952 | −17.867 | −10.989 | 1.00 | 21.69 | BBBB |
| ATOM | 4180 | CG1 | VAL | B | 213 | 20.318 | −18.423 | −11.375 | 1.00 | 19.84 | BBBB |
| ATOM | 4181 | CG2 | VAL | B | 213 | 18.564 | −18.288 | −9.576 | 1.00 | 20.36 | BBBB |
| ATOM | 4182 | C | VAL | B | 213 | 17.535 | −15.871 | −10.677 | 1.00 | 21.41 | BBBB |
| ATOM | 4183 | O | VAL | B | 213 | 17.328 | −15.396 | −9.554 | 1.00 | 20.58 | BBBB |
| ATOM | 4184 | N | THR | B | 214 | 16.593 | −16.021 | −11.595 | 1.00 | 19.82 | BBBB |
| ATOM | 4185 | CA | THR | B | 214 | 15.204 | −15.726 | −11.337 | 1.00 | 19.60 | BBBB |
| ATOM | 4186 | CB | THR | B | 214 | 14.718 | −14.478 | −12.126 | 1.00 | 21.35 | BBBB |
| ATOM | 4187 | OG1 | THR | B | 214 | 13.323 | −14.273 | −11.870 | 1.00 | 21.93 | BBBB |
| ATOM | 4188 | CG2 | THR | B | 214 | 14.983 | −14.633 | −13.622 | 1.00 | 19.52 | BBBB |
| ATOM | 4189 | C | THR | B | 214 | 14.543 | −17.021 | −11.791 | 1.00 | 20.24 | BBBB |
| ATOM | 4190 | O | THR | B | 214 | 14.803 | −17.533 | −12.893 | 1.00 | 18.70 | BBBB |
| ATOM | 4191 | N | ILE | B | 215 | 13.706 | −17.569 | −10.921 | 1.00 | 19.21 | BBBB |
| ATOM | 4192 | CA | ILE | B | 215 | 13.076 | −18.850 | −11.169 | 1.00 | 18.75 | BBBB |
| ATOM | 4193 | CB | ILE | B | 215 | 13.417 | −19.828 | −10.008 | 1.00 | 18.82 | BBBB |
| ATOM | 4194 | CG2 | ILE | B | 215 | 12.690 | −21.157 | −10.194 | 1.00 | 19.53 | BBBB |
| ATOM | 4195 | CG1 | ILE | B | 215 | 14.934 | −20.030 | −9.931 | 1.00 | 19.76 | BBBB |
| ATOM | 4196 | CD1 | ILE | B | 215 | 15.421 | −20.656 | −8.600 | 1.00 | 19.40 | BBBB |
| ATOM | 4197 | C | ILE | B | 215 | 11.568 | −18.837 | −11.315 | 1.00 | 19.26 | BBBB |
| ATOM | 4198 | O | ILE | B | 215 | 10.874 | −18.025 | −10.699 | 1.00 | 18.28 | BBHB |
| ATOM | 4199 | N | TRP | B | 216 | 11.089 | −19.737 | −12.167 | 1.00 | 18.93 | BBBB |
| ATOM | 4200 | CA | TRP | B | 216 | 9.661 | −19.973 | −12.378 | 1.00 | 19.34 | BBBB |
| ATOM | 4201 | CB | TRP | B | 216 | 9.222 | −19.631 | −13.797 | 1.00 | 18.97 | BBBB |
| ATOM | 4202 | CG | TRP | B | 216 | 7.757 | −19.897 | −14.065 | 1.00 | 20.09 | BBBB |
| ATOM | 4203 | CD2 | TRP | B | 216 | 7.015 | −19.467 | −15.211 | 1.00 | 19.61 | BBBB |
| ATOM | 4204 | CE2 | TRP | B | 216 | 5.705 | −19.988 | −15.085 | 1.00 | 19.98 | BBBB |
| ATOM | 4205 | CE3 | TRP | B | 216 | 7.329 | −18.690 | −16.333 | 1.00 | 19.39 | BBBB |
| ATOM | 4206 | CD1 | TRP | B | 216 | 6.888 | −20.639 | −13.303 | 1.00 | 19.30 | BBBB |
| ATOM | 4207 | NE1 | TRP | B | 216 | 5.653 | −20.700 | −13.914 | 1.00 | 20.95 | BBBB |
| ATOM | 4208 | CZ2 | TRP | B | 216 | 4.713 | −19.759 | −16.043 | 1.00 | 22.06 | BBBB |
| ATOM | 4209 | CZ3 | TRP | B | 216 | 6.336 | −18.459 | −17.288 | 1.00 | 20.42 | BBBB |
| ATOM | 4210 | CH2 | TRP | B | 216 | 5.047 | −18.993 | −17.134 | 1.00 | 21.16 | BBBB |
| ATOM | 4211 | C | TRP | B | 216 | 9.629 | −21.479 | −12.176 | 1.00 | 19.95 | BBBB |
| ATOM | 4212 | O | TRP | B | 216 | 10.114 | −22.241 | −13.010 | 1.00 | 19.91 | BBBB |
| ATOM | 4213 | N | HIS | B | 217 | 9.067 | −21.897 | −11.050 | 1.00 | 21.62 | BBBB |
| ATOM | 4214 | CA | HIS | B | 217 | 9.015 | −23.303 | −10.680 | 1.00 | 21.06 | BBBB |
| ATOM | 4215 | CB | HIS | B | 217 | 9.553 | −23.419 | −9.242 | 1.00 | 20.56 | BBBB |
| ATOM | 4216 | CG | HIS | B | 217 | 9.717 | −24.824 | −8.747 | 1.00 | 21.95 | BBBB |
| ATOM | 4217 | CD2 | HIS | B | 217 | 8.915 | −25.910 | −8.846 | 1.00 | 22.12 | BBBB |
| ATOM | 4218 | ND1 | HIS | B | 217 | 10.807 | −25.219 | −8.002 | 1.00 | 23.39 | BBBB |
| ATOM | 4219 | CE1 | HIS | B | 217 | 10.670 | −26.490 | −7.663 | 1.00 | 21.82 | BBBB |
| ATOM | 4220 | NE2 | HIS | B | 217 | 9.530 | −26.933 | −8.162 | 1.00 | 22.14 | BHBB |
| ATOM | 4221 | C | HIS | B | 217 | 7.596 | −23.870 | −10.795 | 1.00 | 21.27 | BBBB |
| ATOM | 4222 | O | HIS | B | 217 | 6.655 | −23.334 | −10.214 | 1.00 | 21.69 | BBBB |
| ATOM | 4223 | N | GLN | B | 218 | 7.448 | −24.940 | −11.567 | 1.00 | 20.83 | BBBB |
| ATOM | 4224 | CA | GLN | B | 218 | 6.149 | −25.594 | −11.735 | 1.00 | 24.30 | BBHB |
| ATOM | 4225 | CB | GLN | B | 218 | 5.915 | −25.935 | −13.206 | 1.00 | 23.84 | BBBB |
| ATOM | 4226 | CG | GLN | B | 218 | 4.561 | −26.558 | −13.495 | 1.00 | 25.91 | BBBB |
| ATOM | 4227 | CD | GLN | B | 218 | 4.637 | −28.060 | −13.673 | 1.00 | 26.52 | BBBB |
| ATOM | 4228 | OE1 | GLN | B | 218 | 3.757 | −28.793 | −13.214 | 1.00 | 28.05 | BBBB |
| ATOM | 4229 | NE2 | GLN | B | 218 | 5.680 | −28.529 | −14.360 | 1.00 | 25.20 | BBBB |
| ATOM | 4230 | C | GLN | B | 218 | 6.173 | −26.854 | −10.854 | 1.00 | 24.64 | BBBB |
| ATOM | 4231 | O | GLN | B | 218 | 6.780 | −27.866 | −11.199 | 1.00 | 25.73 | BBBB |
| ATOM | 4232 | N | SER | B | 219 | 5.502 | −26.756 | −9.709 | 1.00 | 26.38 | BBBB |
| ATOM | 4233 | CA | SER | B | 219 | 5.463 | −27.800 | −8.684 | 1.00 | 26.73 | BBBB |
| ATOM | 4234 | CB | SER | B | 219 | 4.947 | −27.188 | −7.380 | 1.00 | 28.26 | BBBB |
| ATOM | 4235 | OG | SER | B | 219 | 3.563 | −26.881 | −7.488 | 1.00 | 26.22 | BBBB |
| ATOM | 4236 | C | SER | B | 219 | 4.689 | −29.096 | −8.914 | 1.00 | 27.58 | BBBB |
| ATOM | 4237 | O | SER | B | 219 | 5.014 | −30.122 | −8.320 | 1.00 | 26.39 | BBBB |
| ATOM | 4238 | N | GLY | B | 220 | 3.662 | −29.054 | −9.750 | 1.00 | 28.58 | BBBB |
| ATOM | 4239 | CA | GLY | B | 220 | 2.855 | −30.242 | −9.961 | 1.00 | 30.53 | BBBB |
| ATOM | 4240 | C | GLY | B | 220 | 1.596 | −30.110 | −9.111 | 1.00 | 31.96 | BBBB |

TABLE 1-continued

ATOMIC COORDINATES OF E. COLI MURG PROTEIN

| ATOM | 4241 | O   | GLY | B | 220 | 1.523  | -29.248 | -8.233 | 1.00 | 30.92 | BBBB |
|------|------|-----|-----|---|-----|--------|---------|--------|------|-------|------|
| ATOM | 4242 | N   | LYS | B | 221 | 0.608  | -30.965 | -9.358 | 1.00 | 33.93 | BBBB |
| ATOM | 4243 | CA  | LYS | B | 221 | -0.657 | -30.914 | -8.628 | 1.00 | 35.12 | BBBB |
| ATOM | 4244 | CB  | LYS | B | 221 | -1.573 | -32.049 | -9.094 | 1.00 | 37.88 | BBBB |
| ATOM | 4245 | CG  | LYS | B | 221 | -2.942 | -32.055 | -8.427 | 1.00 | 40.51 | BBBB |
| ATOM | 4246 | CD  | LYS | B | 221 | -3.792 | -33.215 | -8.934 | 1.00 | 42.62 | BBBB |
| ATOM | 4247 | CE  | LYS | B | 221 | -5.162 | -33.249 | -8.260 | 1.00 | 43.67 | BBBB |
| ATOM | 4248 | NZ  | LYS | B | 221 | -6.002 | -34.383 | -8.763 | 1.00 | 45.38 | BBBB |
| ATOM | 4249 | C   | LYS | B | 221 | -0.545 | -30.950 | -7.103 | 1.00 | 35.13 | BBBB |
| ATOM | 4250 | O   | LYS | B | 221 | 0.110  | -31.823 | -6.531 | 1.00 | 34.60 | BBBB |
| ATOM | 4251 | N   | GLY | B | 222 | -1.187 | -29.979 | -6.461 | 1.00 | 34.79 | BBBB |
| ATOM | 4252 | CA  | GLY | B | 222 | -1.195 | -29.899 | -5.011 | 1.00 | 35.34 | BBBB |
| ATOM | 4253 | C   | GLY | B | 222 | 0.111  | -29.594 | -4.299 | 1.00 | 35.61 | BBBB |
| ATOM | 4254 | O   | GLY | B | 222 | 0.163  | -29.678 | -3.071 | 1.00 | 35.51 | BBBB |
| ATOM | 4255 | N   | SER | B | 223 | 1.158  | -29.234 | -5.038 | 1.00 | 34.65 | BBBB |
| ATOM | 4256 | CA  | SER | B | 223 | 2.451  | -28.934 | -4.418 | 1.00 | 33.98 | BBBB |
| ATOM | 4257 | CB  | SER | B | 223 | 3.552  | -29.781 | -5.062 | 1.00 | 35.02 | BBBB |
| ATOM | 4258 | OG  | SER | B | 223 | 3.303  | -31.168 | -4.897 | 1.00 | 36.07 | BBBB |
| ATOM | 4259 | C   | SER | B | 223 | 2.839  | -27.454 | -4.504 | 1.00 | 33.55 | BBBB |
| ATOM | 4260 | O   | SER | B | 223 | 3.930  | -27.063 | -4.086 | 1.00 | 31.72 | BBBB |
| ATOM | 4261 | N   | GLN | B | 224 | 1.941  | -26.639 | -5.044 | 1.00 | 33.22 | BBBB |
| ATOM | 4262 | CA  | GLN | B | 224 | 2.187  | -25.208 | -5.186 | 1.00 | 33.71 | BBBB |
| ATOM | 4263 | CB  | GLN | B | 224 | 0.954  | -24.539 | -5.799 | 1.00 | 35.45 | BBBB |
| ATOM | 4264 | CG  | GLN | B | 224 | 1.160  | -23.120 | -6.337 | 1.00 | 37.82 | BBBB |
| ATOM | 4265 | CD  | GLN | B | 224 | 1.344  | -22.076 | -5.249 | 1.00 | 40.08 | BBBB |
| ATOM | 4266 | CE1 | GLN | B | 224 | 0.669  | -22.111 | -4.217 | 1.00 | 40.97 | BBBB |
| ATOM | 4267 | NE2 | GLN | B | 224 | 2.244  | -21.124 | -5.486 | 1.00 | 40.08 | BBBB |
| ATOM | 4268 | C   | GLN | B | 224 | 2.510  | -24.560 | -3.840 | 1.00 | 33.86 | BBBB |
| ATOM | 4269 | O   | GLN | B | 224 | 3.512  | -23.856 | -3.697 | 1.00 | 33.38 | BBBB |
| ATOM | 4270 | N   | GLN | B | 225 | 1.659  | -24.814 | -2.850 | 1.00 | 33.06 | BBBB |
| ATOM | 4271 | CA  | GLN | B | 225 | 1.823  | -24.239 | -1.519 | 1.00 | 32.32 | BBBB |
| ATOM | 4272 | CB  | GLN | B | 225 | 0.624  | -24.619 | -0.640 | 1.00 | 35.12 | BBBB |
| ATOM | 4273 | CG  | GLN | B | 225 | -0.743 | -24.143 | -1.151 | 1.00 | 36.85 | BBBB |
| ATOM | 4274 | CD  | GLN | B | 225 | -1.144 | -24.751 | -2.495 | 1.00 | 39.09 | BBBB |
| ATOM | 4275 | CE1 | GLN | B | 225 | -0.914 | -25.937 | -2.759 | 1.00 | 39.42 | BBBB |
| ATOM | 4276 | NE2 | GLN | B | 225 | -1.768 | -23.937 | -3.345 | 1.00 | 40.13 | BBBB |
| ATOM | 4277 | C   | GLN | B | 225 | 3.117  | -24.606 | -0.788 | 1.00 | 30.73 | BBBB |
| ATOM | 4278 | O   | GLN | B | 225 | 3.766  | -23.742 | -0.202 | 1.00 | 30.36 | BBBB |
| ATOM | 4279 | N   | SER | B | 226 | 3.494  | -25.878 | -0.817 | 1.00 | 29.26 | BBBB |
| ATOM | 4280 | CA  | SER | B | 226 | 4.701  | -26.309 | -0.122 | 1.00 | 28.30 | BBBB |
| ATOM | 4281 | CB  | SER | B | 226 | 4.727  | -27.834 | -0.003 | 1.00 | 29.10 | BBBB |
| ATOM | 4282 | OG  | SER | B | 226 | 4.563  | -28.461 | -1.254 | 1.00 | 32.61 | BBBB |
| ATOM | 4283 | C   | SER | B | 226 | 5.991  | -25.809 | -0.771 | 1.00 | 26.41 | BBBB |
| ATOM | 4284 | O   | SER | B | 226 | 6.950  | -25.486 | -0.073 | 1.00 | 25.24 | BBBB |
| ATOM | 4285 | N   | VAL | B | 227 | 6.019  | -25.738 | -2.099 | 1.00 | 25.21 | BBBB |
| ATOM | 4286 | CA  | VAL | B | 227 | 7.214  | -25.247 | -2.791 | 1.00 | 24.28 | BBBB |
| ATOM | 4287 | CB  | VAL | B | 227 | 7.150  | -25.527 | -4.317 | 1.00 | 23.32 | BBBB |
| ATOM | 4288 | CG1 | VAL | B | 227 | 8.368  | -24.914 | -5.028 | 1.00 | 20.67 | BBBB |
| ATOM | 4289 | CG2 | VAL | B | 227 | 7.117  | -27.024 | -4.563 | 1.00 | 22.45 | BBBB |
| ATOM | 4290 | C   | VAL | B | 227 | 7.335  | -23.743 | -2.545 | 1.00 | 24.34 | BBBB |
| ATOM | 4291 | O   | VAL | B | 227 | 8.421  | -23.240 | -2.281 | 1.00 | 25.50 | BBBB |
| ATOM | 4292 | N   | GLU | B | 228 | 6.209  | -23.035 | -2.623 | 1.00 | 26.12 | BBBB |
| ATOM | 4293 | CA  | GLU | B | 228 | 6.178  | -21.592 | -2.387 | 1.00 | 27.23 | BBBB |
| ATOM | 4294 | CB  | GLU | B | 228 | 4.735  | -21.075 | -2.476 | 1.00 | 28.60 | BBBB |
| ATOM | 4295 | CG  | GLU | B | 228 | 4.558  | -19.586 | -2.184 | 1.00 | 30.24 | BBBB |
| ATOM | 4296 | CD  | GLU | B | 228 | 4.938  | -18.688 | -3.356 | 1.00 | 31.99 | BBBB |
| ATOM | 4297 | OE1 | GLU | B | 228 | 5.012  | -17.452 | -3.159 | 1.00 | 31.68 | BBBB |
| ATOM | 4298 | OE2 | GLU | B | 228 | 5.154  | -19.212 | -4.471 | 1.00 | 32.04 | BBBB |
| ATOM | 4299 | C   | GLU | B | 228 | 6.746  | -21.327 | -0.994 | 1.00 | 27.95 | BBBB |
| ATOM | 4300 | O   | GLU | B | 228 | 7.511  | -20.383 | -0.787 | 1.00 | 27.32 | BBBB |
| ATOM | 4301 | N   | GLN | B | 229 | 6.374  | -22.178 | -0.041 | 1.00 | 28.66 | BBBB |
| ATOM | 4302 | CA  | GLN | B | 229 | 6.853  | -22.046 | 1.329  | 1.00 | 28.38 | BBBB |
| ATOM | 4303 | CB  | GLN | B | 229 | 6.082  | -22.990 | 2.261  | 1.00 | 31.03 | BBBB |
| ATOM | 4304 | CG  | GLN | B | 229 | 6.570  | -22.946 | 3.700  | 1.00 | 35.48 | BBBB |
| ATOM | 4305 | CD  | GLN | B | 229 | 5.780  | -23.860 | 4.615  | 1.00 | 38.01 | BBBB |
| ATOM | 4306 | OE1 | GLN | B | 229 | 4.548  | -23.810 | 4.645  | 1.00 | 39.26 | BBBB |
| ATOM | 4307 | NE2 | GLN | B | 229 | 6.484  | -24.697 | 5.370  | 1.00 | 38.61 | BBBB |
| ATOM | 4308 | C   | GLN | B | 229 | 8.338  | -22.362 | 1.407  | 1.00 | 27.09 | BBBB |
| ATOM | 4309 | O   | GLN | B | 229 | 9.084  | -21.697 | 2.124  | 1.00 | 28.29 | BBBB |
| ATOM | 4310 | N   | ALA | B | 230 | 8.771  | -23.385 | 0.677  | 1.00 | 26.97 | BBBB |
| ATOM | 4311 | CA  | ALA | B | 230 | 10.185 | -23.754 | 0.682  | 1.00 | 26.18 | BBBB |
| ATOM | 4312 | CB  | ALA | B | 230 | 10.412 | -24.984 | -0.184 | 1.00 | 25.07 | BBBB |
| ATOM | 4313 | C   | ALA | B | 230 | 11.054 | -22.588 | 0.192  | 1.00 | 26.36 | BBBB |
| ATOM | 4314 | O   | ALA | B | 230 | 12.119 | -22.317 | 0.755  | 1.00 | 25.04 | BBBB |
| ATOM | 4315 | N   | TYR | B | 231 | 10.605 | -21.895 | -0.854 | 1.00 | 25.85 | BBBB |
| ATOM | 4316 | CA  | TYR | B | 231 | 11.371 | -20.766 | -1.366 | 1.00 | 25.47 | BBBB |
| ATOM | 4317 | CB  | TYR | B | 231 | 10.762 | -20.248 | -2.678 | 1.00 | 24.72 | BBBB |

TABLE 1-continued

ATOMIC COORDINATES OF E. COLI MURG PROTEIN

| ATOM | 4318 | CG | TYR | B | 231 | 11.236 | −21.014 | −3.905 | 1.00 | 23.66 | BBBB |
|---|---|---|---|---|---|---|---|---|---|---|---|
| ATOM | 4319 | CD1 | TYR | B | 231 | 12.546 | −20.869 | −4.381 | 1.00 | 23.97 | BBBB |
| ATOM | 4320 | CE1 | TYR | B | 231 | 13.006 | −21.599 | −5.488 | 1.00 | 21.40 | BBBB |
| ATOM | 4321 | CD2 | TYR | B | 231 | 10.393 | −21.905 | −4.567 | 1.00 | 22.63 | BBBB |
| ATOM | 4322 | CE2 | TYR | B | 231 | 10.841 | −22.641 | −5.681 | 1.00 | 22.71 | BBBB |
| ATOM | 4323 | CZ | TYR | B | 231 | 12.151 | −22.480 | −6.128 | 1.00 | 21.91 | BBBB |
| ATOM | 4324 | OH | TYR | B | 231 | 12.600 | −23.214 | −7.199 | 1.00 | 21.69 | BBBB |
| ATOM | 4325 | C | TYR | B | 231 | 11.450 | −19.639 | −0.336 | 1.00 | 26.53 | BBBB |
| ATOM | 4326 | O | TYR | B | 231 | 12.498 | −19.011 | −0.175 | 1.00 | 26.32 | BBBB |
| ATOM | 4327 | N | ALA | B | 232 | 10.345 | −19.380 | 0.361 | 1.00 | 26.28 | BBBB |
| ATOM | 4328 | CA | ALA | B | 232 | 10.342 | −18.322 | 1.368 | 1.00 | 27.51 | BBBB |
| ATOM | 4329 | CB | ALA | B | 232 | 8.930 | −18.109 | 1.910 | 1.00 | 28.09 | BBBB |
| ATOM | 4330 | C | ALA | B | 232 | 11.303 | −18.695 | 2.499 | 1.00 | 28.03 | BBBB |
| ATOM | 4331 | O | ALA | B | 232 | 12.069 | −17.858 | 2.983 | 1.00 | 27.93 | BBBB |
| ATOM | 4332 | N | GLU | B | 233 | 11.263 | −19.958 | 2.911 | 1.00 | 29.43 | BBBB |
| ATOM | 4333 | CA | GLU | B | 233 | 12.145 | −20.441 | 3.966 | 1.00 | 30.87 | BBBB |
| ATOM | 4334 | CB | GLU | B | 233 | 11.772 | −21.877 | 4.344 | 1.00 | 33.60 | BBBB |
| ATOM | 4335 | CG | GLU | B | 233 | 10.491 | −21.973 | 5.170 | 1.00 | 37.67 | BBBB |
| ATOM | 4336 | CD | GLU | B | 233 | 10.077 | −23.404 | 5.461 | 1.00 | 40.35 | BBBB |
| ATOM | 4337 | OE1 | GLU | B | 233 | 10.964 | −24.283 | 5.525 | 1.00 | 42.97 | BBBB |
| ATOM | 4338 | OE2 | GLU | B | 233 | 8.864 | −23.649 | 5.641 | 1.00 | 41.95 | BBBB |
| ATOM | 4339 | C | GLU | B | 233 | 13.606 | −20.369 | 3.530 | 1.00 | 30.58 | BBBB |
| ATOM | 4340 | O | GLU | B | 233 | 14.499 | −20.202 | 4.359 | 1.00 | 30.82 | BBBB |
| ATOM | 4341 | N | ALA | B | 234 | 13.850 | −20.485 | 2.227 | 1.00 | 29.17 | BBBB |
| ATOM | 4342 | CA | ALA | B | 234 | 15.215 | −20.417 | 1.714 | 1.00 | 28.48 | BBBB |
| ATOM | 4343 | CB | ALA | B | 234 | 15.310 | −21.110 | 0.354 | 1.00 | 27.71 | BBBB |
| ATOM | 4344 | C | ALA | B | 234 | 15.649 | −18.961 | 1.588 | 1.00 | 27.73 | BBBB |
| ATOM | 4345 | O | ALA | B | 234 | 16.787 | −18.677 | 1.213 | 1.00 | 27.34 | BBBB |
| ATOM | 4346 | N | GLY | B | 235 | 14.731 | −18.045 | 1.890 | 1.00 | 26.74 | BBBB |
| ATOM | 4347 | CA | GLY | B | 235 | 15.033 | −16.627 | 1.815 | 1.00 | 26.23 | BBBB |
| ATOM | 4348 | C | GLY | B | 235 | 14.946 | −16.009 | 0.426 | 1.00 | 26.13 | BBBB |
| ATOM | 4349 | O | GLY | B | 235 | 15.483 | −14.924 | 0.198 | 1.00 | 25.67 | BBBB |
| ATOM | 4350 | N | GLN | B | 236 | 14.284 | −16.696 | −0.502 | 1.00 | 25.36 | BBBB |
| ATOM | 4351 | CA | GLN | B | 236 | 14.121 | −16.198 | −1.870 | 1.00 | 25.53 | BBBB |
| ATOM | 4352 | CB | GLN | B | 236 | 14.940 | −17.043 | −2.852 | 1.00 | 25.84 | BBBB |
| ATOM | 4353 | CG | GLN | B | 236 | 16.436 | −17.074 | −2.603 | 1.00 | 27.18 | BBBB |
| ATOM | 4354 | CD | GLN | B | 236 | 17.080 | −15.705 | −2.661 | 1.00 | 28.96 | BBBB |
| ATOM | 4355 | OE1 | GLN | B | 236 | 16.686 | −14.850 | −3.456 | 1.00 | 30.03 | BBBB |
| ATOM | 4356 | NE2 | GLN | B | 236 | 18.092 | −15.495 | −1.829 | 1.00 | 29.39 | BBBB |
| ATOM | 4357 | C | GLN | B | 236 | 12.641 | −16.298 | −2.232 | 1.00 | 24.12 | BBBB |
| ATOM | 4358 | O | GLN | B | 236 | 12.262 | −17.002 | −3.167 | 1.00 | 23.31 | BBBB |
| ATOM | 4359 | N | PRO | B | 237 | 11.783 | −15.578 | −1.497 | 1.00 | 24.40 | BBBB |
| ATOM | 4360 | CD | PRO | B | 237 | 12.143 | −14.580 | −0.473 | 1.00 | 24.52 | BBBB |
| ATOM | 4361 | CA | PRO | B | 237 | 10.336 | −15.587 | −1.720 | 1.00 | 24.65 | BBBB |
| ATOM | 4362 | CB | PRO | B | 237 | 9.808 | −14.798 | −0.527 | 1.00 | 25.37 | BBBB |
| ATOM | 4363 | CG | PRO | B | 237 | 10.862 | −13.773 | −0.340 | 1.00 | 25.24 | BBBB |
| ATOM | 4364 | C | PRO | B | 237 | 9.837 | −15.012 | −3.043 | 1.00 | 25.33 | BBBB |
| ATOM | 4365 | O | PRO | B | 237 | 8.720 | −15.313 | −3.465 | 1.00 | 24.93 | BBBB |
| ATOM | 4366 | N | GLN | B | 238 | 10.663 | −14.197 | −3.690 | 1.00 | 24.47 | BBBB |
| ATOM | 4367 | CA | GLN | B | 238 | 10.277 | −13.558 | −4.945 | 1.00 | 24.29 | BBBB |
| ATOM | 4368 | CB | GLN | B | 238 | 11.281 | −12.455 | −5.306 | 1.00 | 23.76 | BBBB |
| ATOM | 4369 | CG | GLN | B | 238 | 12.622 | −12.945 | −5.852 | 1.00 | 25.22 | BBBB |
| ATOM | 4370 | CD | GLN | B | 238 | 13.535 | −13.523 | −4.783 | 1.00 | 26.90 | BBBB |
| ATOM | 4371 | OE1 | GLN | B | 238 | 13.188 | −13.550 | −3.600 | 1.00 | 28.05 | BBBB |
| ATOM | 4372 | NE2 | GLN | B | 238 | 14.712 | −13.983 | −5.195 | 1.00 | 25.61 | BBBB |
| ATOM | 4373 | C | GLN | B | 238 | 10.108 | −14.489 | −6.143 | 1.00 | 23.41 | BBBB |
| ATOM | 4374 | O | GLN | B | 238 | 9.485 | −14.112 | −7.139 | 1.00 | 20.49 | BBBB |
| ATOM | 4375 | N | HIS | B | 239 | 10.655 | −15.700 | −6.069 | 1.00 | 22.66 | BBBB |
| ATOM | 4376 | CA | HIS | B | 239 | 10.526 | −16.608 | −7.201 | 1.00 | 22.08 | BBBB |
| ATOM | 4377 | CB | HIS | B | 239 | 11.432 | −17.829 | −7.008 | 1.00 | 22.41 | BBBB |
| ATOM | 4378 | CG | HIS | B | 239 | 12.891 | −17.488 | −6.998 | 1.00 | 20.93 | BBBB |
| ATOM | 4379 | CD2 | HIS | B | 239 | 13.869 | −17.774 | −6.104 | 1.00 | 20.09 | BBBB |
| ATOM | 4380 | ND1 | HIS | B | 239 | 13.488 | −16.743 | −7.992 | 1.00 | 20.30 | BBBB |
| ATOM | 4381 | CE1 | HIS | B | 239 | 14.769 | −16.582 | −7.711 | 1.00 | 22.38 | BBBB |
| ATOM | 4382 | NE2 | HIS | B | 239 | 15.025 | −17.197 | −6.569 | 1.00 | 19.62 | BBBB |
| ATOM | 4383 | C | HIS | B | 239 | 9.076 | −17.024 | −7.433 | 1.00 | 22.98 | BBBB |
| ATOM | 4384 | O | HIS | B | 239 | 8.293 | −17.161 | −6.490 | 1.00 | 21.86 | BBBB |
| ATOM | 4385 | N | LYS | B | 240 | 8.727 | −17.209 | −8.703 | 1.00 | 21.76 | BBBB |
| ATOM | 4386 | CA | LYS | B | 240 | 7.375 | −17.589 | −9.105 | 1.00 | 23.26 | BBBB |
| ATOM | 4387 | CB | LYS | B | 240 | 7.112 | −17.102 | −10.534 | 1.00 | 23.38 | BBBB |
| ATOM | 4388 | CG | LYS | B | 240 | 5.718 | −17.385 | −11.079 | 1.00 | 24.06 | BBBB |
| ATOM | 4389 | CD | LYS | B | 240 | 5.701 | −17.155 | −12.585 | 1.00 | 23.93 | BBBB |
| ATOM | 4390 | CE | LYS | B | 240 | 4.315 | −17.309 | −13.193 | 1.00 | 23.72 | BBBB |
| ATOM | 4391 | NZ | LYS | B | 240 | 3.478 | −16.129 | −12.884 | 1.00 | 21.82 | BBBB |
| ATOM | 4392 | C | LYS | B | 240 | 7.149 | −19.091 | −9.046 | 1.00 | 23.38 | BBBB |
| ATOM | 4393 | O | LYS | B | 240 | 7.922 | −19.871 | −9.607 | 1.00 | 23.06 | BBBB |
| ATOM | 4394 | N | VAL | B | 241 | 6.075 | −19.497 | −8.378 | 1.00 | 23.98 | BBBB |

TABLE 1-continued

ATOMIC COORDINATES OF E. COLI MURG PROTEIN

| ATOM | 4395 | CA | VAL | B | 241 | 5.740 | −20.911 | −8.277 | 1.00 | 23.78 | BBBB |
|---|---|---|---|---|---|---|---|---|---|---|---|
| ATOM | 4396 | CB | VAL | B | 241 | 5.858 | −21.428 | −6.833 | 1.00 | 24.03 | BBBB |
| ATOM | 4397 | CG1 | VAL | B | 241 | 5.548 | −22.923 | −6.803 | 1.00 | 24.14 | BBBB |
| ATOM | 4398 | CG2 | VAL | B | 241 | 7.242 | −21.144 | −6.281 | 1.00 | 23.49 | BBBB |
| ATOM | 4399 | C | VAL | B | 241 | 4.299 | −21.136 | −8.723 | 1.00 | 24.15 | BBBB |
| ATOM | 4400 | O | VAL | B | 241 | 3.380 | −20.528 | −8.184 | 1.00 | 24.63 | BBBB |
| ATOM | 4401 | N | THR | B | 242 | 4.103 | −22.000 | −9.710 | 1.00 | 24.22 | BBBB |
| ATOM | 4402 | CA | THR | B | 242 | 2.758 | −22.301 | −10.177 | 1.00 | 25.93 | BBBB |
| ATOM | 4403 | CB | THR | B | 242 | 2.513 | −21.812 | −11.615 | 1.00 | 25.89 | BBBB |
| ATOM | 4404 | OG1 | THR | B | 242 | 3.466 | −22.419 | 12.492 | 1.00 | 27.48 | BBBB |
| ATOM | 4405 | CG2 | THR | B | 242 | 2.639 | −20.299 | −11.697 | 1.00 | 26.82 | BBBB |
| ATOM | 4406 | C | THR | B | 242 | 2.555 | −23.809 | −10.135 | 1.00 | 26.29 | BBBB |
| ATOM | 4407 | O | THR | B | 242 | 3.503 | −24.577 | −10.303 | 1.00 | 26.75 | BBBB |
| ATOM | 4408 | N | GLU | B | 243 | 1.319 | −24.228 | −9.898 | 1.00 | 26.70 | BBBB |
| ATOM | 4409 | CA | GLU | B | 243 | 0.999 | −25.651 | −9.837 | 1.00 | 27.03 | BBBB |
| ATOM | 4410 | CB | GLU | B | 243 | −0.473 | −25.828 | −9.445 | 1.00 | 29.00 | BBBB |
| ATOM | 4411 | CG | GLU | B | 243 | −0.831 | −27.218 | −8.962 | 1.00 | 30.88 | BBBB |
| ATOM | 4412 | CD | GLU | B | 243 | −2.297 | −27.341 | −8.583 | 1.00 | 33.00 | BBBB |
| ATOM | 4413 | OE1 | GLU | B | 243 | −2.682 | −28.402 | −8.048 | 1.00 | 33.66 | BBBB |
| ATOM | 4414 | OE2 | GLU | B | 243 | −3.063 | −26.383 | −8.827 | 1.00 | 32.17 | BBBB |
| ATOM | 4415 | C | GLU | B | 243 | 1.256 | −26.289 | −11.202 | 1.00 | 26.61 | BBBB |
| ATOM | 4416 | O | GLU | B | 243 | 1.841 | −27.370 | −11.304 | 1.00 | 26.48 | BBBB |
| ATOM | 4417 | N | PHE | B | 244 | 0.807 | −25.602 | −12.248 | 1.00 | 26.54 | BBBB |
| ATOM | 4418 | CA | PHE | B | 244 | 0.964 | −26.068 | −13.620 | 1.00 | 26.54 | BBBB |
| ATOM | 4419 | CB | PHE | B | 244 | −0.376 | −26.553 | −14.186 | 1.00 | 29.14 | BBBB |
| ATOM | 4420 | CG | PHE | B | 244 | −1.110 | −27.531 | −13.307 | 1.00 | 30.15 | BBBB |
| ATOM | 4421 | CD1 | PHE | B | 244 | −0.622 | −28.817 | −13.107 | 1.00 | 32.26 | BBBB |
| ATOM | 4422 | CD2 | PHE | B | 244 | −2.318 | −27.172 | −12.716 | 1.00 | 31.10 | BBBB |
| ATOM | 4423 | CE1 | PHE | B | 244 | −1.335 | −29.744 | −12.328 | 1.00 | 33.63 | BBBB |
| ATOM | 4424 | CE2 | PHE | B | 244 | −3.040 | −28.083 | −11.938 | 1.00 | 32.04 | BBBB |
| ATOM | 4425 | CZ | PHE | B | 244 | −2.549 | −29.371 | −11.744 | 1.00 | 32.59 | BBBB |
| ATOM | 4426 | C | PHE | B | 244 | 1.420 | −24.915 | −14.507 | 1.00 | 25.60 | BBBB |
| ATOM | 4427 | O | PHE | B | 244 | 1.604 | −23.794 | −14.053 | 1.00 | 24.93 | BBBB |
| ATOM | 4428 | N | ILE | B | 245 | 1.591 | −25.223 | −15.786 | 1.00 | 27.02 | BBBB |
| ATOM | 4429 | CA | ILE | B | 245 | 1.932 | −24.242 | −16.802 | 1.00 | 28.48 | BBBB |
| ATOM | 4430 | CB | ILE | B | 245 | 3.441 | −24.226 | −17.159 | 1.00 | 28.41 | BBBB |
| ATOM | 4431 | CG2 | ILE | B | 245 | 3.676 | −23.348 | −18.399 | 1.00 | 27.05 | BBBB |
| ATOM | 4432 | CG1 | ILE | B | 245 | 4.245 | −23.663 | −15.983 | 1.00 | 27.10 | BBBB |
| ATOM | 4433 | CD1 | ILE | B | 245 | 5.734 | −23.543 | −16.256 | 1.00 | 27.28 | BBBB |
| ATOM | 4434 | C | ILE | B | 245 | 1.127 | −24.721 | −18.000 | 1.00 | 30.75 | BBBB |
| ATOM | 4435 | O | ILE | B | 245 | 1.428 | −25.753 | −18.595 | 1.00 | 31.41 | BBBB |
| ATOM | 4436 | N | ASP | B | 246 | 0.071 | −23.997 | −18.331 | 1.00 | 33.46 | BBBB |
| ATOM | 4437 | CA | ASP | B | 246 | −0.754 | −24.396 | −19.457 | 1.00 | 36.00 | BBBB |
| ATOM | 4438 | CB | ASP | B | 246 | −2.143 | −23.754 | −19.342 | 1.00 | 39.42 | BBBB |
| ATOM | 4439 | CG | ASP | B | 246 | −2.083 | −22.246 | −19.141 | 1.00 | 42.83 | BBBB |
| ATOM | 4440 | OD1 | ASP | B | 246 | −1.447 | −21.795 | −18.162 | 1.00 | 44.54 | BBBB |
| ATOM | 4441 | OD2 | ASP | B | 246 | −2.678 | −21.511 | −19.962 | 1.00 | 45.41 | BBBB |
| ATOM | 4442 | C | ASP | B | 246 | −0.088 | −24.020 | −20.780 | 1.00 | 35.70 | BBBB |
| ATOM | 4443 | O | ASP | B | 246 | −0.155 | −24.768 | −21.758 | 1.00 | 38.58 | BBBB |
| ATOM | 4444 | N | ASP | B | 247 | 0.582 | −22.876 | −20.794 | 1.00 | 33.18 | BBBB |
| ATOM | 4445 | CA | ASP | B | 247 | 1.245 | −22.392 | −21.999 | 1.00 | 30.74 | BBBB |
| ATOM | 4446 | CB | ASP | B | 247 | 0.936 | −20.904 | −22.182 | 1.00 | 29.62 | BBBB |
| ATOM | 4447 | CG | ASP | B | 247 | 1.344 | −20.380 | −23.548 | 1.00 | 30.15 | BBBB |
| ATOM | 4448 | OE1 | ASP | B | 247 | 2.161 | −21.036 | −24.225 | 1.00 | 27.57 | BBBB |
| ATOM | 4449 | OD2 | ASP | B | 247 | 0.854 | −19.296 | −23.935 | 1.00 | 29.19 | BBBB |
| ATOM | 4450 | C | ASP | B | 247 | 2.754 | −22.607 | −21.892 | 1.00 | 28.87 | BBBB |
| ATOM | 4451 | O | ASP | B | 247 | 3.494 | −21.695 | −21.525 | 1.00 | 27.28 | BBBB |
| ATOM | 4452 | N | MET | B | 248 | 3.204 | −23.818 | −22.205 | 1.00 | 27.72 | BBBB |
| ATOM | 4453 | CA | MET | B | 248 | 4.625 | −24.136 | −22.138 | 1.00 | 28.41 | BBBB |
| ATOM | 4454 | CB | MET | B | 248 | 4.856 | −25.623 | −22.405 | 1.00 | 29.48 | BBBB |
| ATOM | 4455 | CG | MET | B | 248 | 4.952 | −26.469 | −21.150 | 1.00 | 34.21 | BBBB |
| ATOM | 4456 | SD | MET | B | 248 | 6.277 | −25.936 | −20.049 | 1.00 | 38.21 | BBBB |
| ATOM | 4457 | CE | MET | B | 248 | 5.611 | −26.499 | −18.479 | 1.00 | 37.90 | BBBB |
| ATOM | 4458 | C | MET | B | 248 | 5.429 | −23.313 | −23.132 | 1.00 | 27.22 | BBBB |
| ATOM | 4459 | O | MET | B | 248 | 6.578 | −22.965 | −22.873 | 1.00 | 27.06 | BBBB |
| ATOM | 4460 | N | ALA | B | 249 | 4.827 | −23.009 | −24.279 | 1.00 | 26.23 | BBBB |
| ATOM | 4461 | CA | ALA | B | 249 | 5.512 | −22.216 | −25.290 | 1.00 | 24.67 | BBBB |
| ATOM | 4462 | CB | ALA | B | 249 | 4.625 | −22.069 | −26.537 | 1.00 | 25.39 | BBBB |
| ATOM | 4463 | C | ALA | B | 249 | 5.870 | −20.843 | −24.721 | 1.00 | 24.03 | BBBB |
| ATOM | 4464 | O | ALA | B | 249 | 6.971 | −20.338 | −24.932 | 1.00 | 23.78 | BBBB |
| ATOM | 4465 | N | ALA | B | 250 | 4.942 | −20.241 | −23.983 | 1.00 | 23.39 | BBBB |
| ATOM | 4466 | CA | ALA | B | 250 | 5.188 | −18.933 | −23.390 | 1.00 | 21.78 | BBBB |
| ATOM | 4467 | CB | ALA | B | 250 | 3.898 | −18.376 | −22.797 | 1.00 | 23.21 | BBBB |
| ATOM | 4468 | C | ALA | B | 250 | 6.277 | −19.011 | −22.313 | 1.00 | 21.84 | BBBB |
| ATOM | 4469 | O | ALA | B | 250 | 7.091 | −18.092 | −22.176 | 1.00 | 20.78 | BBBB |
| ATOM | 4470 | N | ALA | B | 251 | 6.291 | −20.099 | −21.548 | 1.00 | 20.34 | BBBB |
| ATOM | 4471 | CA | ALA | B | 251 | 7.301 | −20.259 | −20.501 | 1.00 | 20.85 | BBBB |

TABLE 1-continued

ATOMIC COORDINATES OF *E. COLI* MURG PROTEIN

| ATOM | 4472 | CB | ALA | B | 251 | 6.920 | −21.405 | −19.568 | 1.00 | 19.79 | BBBB |
|---|---|---|---|---|---|---|---|---|---|---|---|
| ATOM | 4473 | C | ALA | B | 251 | 8.685 | −20.512 | −21.123 | 1.00 | 20.95 | BBBB |
| ATOM | 4474 | O | ALA | B | 251 | 9.689 | −19.980 | −20.648 | 1.00 | 21.14 | BBBB |
| ATOM | 4475 | N | TYR | B | 252 | 8.723 | −21.314 | −22.184 | 1.00 | 21.27 | BBBB |
| ATOM | 4476 | CA | TYR | B | 252 | 9.972 | −21.616 | −22.886 | 1.00 | 22.78 | BBBB |
| ATOM | 4477 | CB | TYR | B | 252 | 9.726 | −22.661 | −23.980 | 1.00 | 21.62 | BBBB |
| ATOM | 4478 | CG | TYR | B | 252 | 9.662 | −24.100 | −23.505 | 1.00 | 23.34 | BBBB |
| ATOM | 4479 | CD1 | TYR | B | 252 | 9.003 | −25.065 | −24.261 | 1.00 | 22.88 | BBBB |
| ATOM | 4480 | CE1 | TYR | B | 252 | 8.961 | −26.392 | −23.861 | 1.00 | 24.81 | BBBB |
| ATOM | 4481 | CD2 | TYR | B | 252 | 10.288 | −24.505 | −22.319 | 1.00 | 22.30 | BBBB |
| ATOM | 4482 | CE2 | TYR | B | 252 | 10.253 | −25.838 | −21.912 | 1.00 | 23.56 | BBBB |
| ATOM | 4483 | CZ | TYR | B | 252 | 9.590 | −26.772 | −22.687 | 1.00 | 24.26 | BBBB |
| ATOM | 4484 | OH | TYR | B | 252 | 9.554 | −28.088 | −22.305 | 1.00 | 25.57 | BBBB |
| ATOM | 4485 | C | TYR | B | 252 | 10.566 | −20.354 | −23.516 | 1.00 | 23.57 | BBBB |
| ATOM | 4486 | O | TYR | B | 252 | 11.784 | −20.180 | −23.550 | 1.00 | 23.91 | BBBB |
| ATOM | 4487 | N | ALA | B | 253 | 9.699 | −19.473 | −24.007 | 1.00 | 23.22 | BBBB |
| ATOM | 4488 | CA | ALA | B | 253 | 10.131 | −18.224 | −24.636 | 1.00 | 23.54 | BBBB |
| ATOM | 4489 | CB | ALA | B | 253 | 8.931 | −17.512 | −25.275 | 1.00 | 24.59 | BBBB |
| ATOM | 4490 | C | ALA | B | 253 | 10.783 | −17.305 | −23.617 | 1.00 | 23.30 | BBBB |
| ATOM | 4491 | O | ALA | B | 253 | 11.699 | −16.546 | −23.945 | 1.00 | 23.04 | BBBB |
| ATOM | 4492 | N | TRP | B | 254 | 10.299 | −17.369 | −22.379 | 1.00 | 20.49 | BBBB |
| ATOM | 4493 | CA | TRP | B | 254 | 10.829 | −16.534 | −21.303 | 1.00 | 19.76 | BBBB |
| ATOM | 4494 | CB | TRP | B | 254 | 9.808 | −16.467 | −20.151 | 1.00 | 19.57 | BBBB |
| ATOM | 4495 | CG | TRP | B | 254 | 10.381 | −15.981 | −18.841 | 1.00 | 19.57 | BBBB |
| ATOM | 4496 | CD2 | TRP | B | 254 | 10.870 | −16.796 | −17.762 | 1.00 | 19.25 | BBBB |
| ATOM | 4497 | CE2 | TRP | B | 254 | 11.369 | −15.922 | −16.771 | 1.00 | 18.94 | BBBB |
| ATOM | 4498 | CE3 | TRP | B | 254 | 10.939 | −18.178 | −17.543 | 1.00 | 19.18 | BBBB |
| ATOM | 4499 | CD1 | TRP | B | 254 | 10.591 | −14.691 | −18.470 | 1.00 | 19.03 | BBBB |
| ATOM | 4500 | NE1 | TRP | B | 254 | 11.185 | −14.643 | −17.226 | 1.00 | 20.30 | BBBB |
| ATOM | 4501 | CZ2 | TRP | B | 254 | 11.931 | −16.382 | −15.572 | 1.00 | 20.01 | BBBB |
| ATOM | 4502 | CZ3 | TRP | B | 254 | 11.504 | −18.642 | −16.346 | 1.00 | 20.05 | BBBB |
| ATOM | 4503 | CH2 | TRP | B | 254 | 11.991 | −17.743 | −15.380 | 1.00 | 18.31 | BBBB |
| ATOM | 4504 | C | TRP | B | 254 | 12.156 | −17.059 | −20.755 | 1.00 | 19.33 | BBBB |
| ATOM | 4505 | O | TRP | B | 254 | 13.084 | −16.293 | −20.496 | 1.00 | 19.25 | BBBB |
| ATOM | 4506 | N | ALA | B | 255 | 12.234 | −18.373 | −20.597 | 1.00 | 18.90 | BBBB |
| ATOM | 4507 | CA | ALA | B | 255 | 13.399 | −19.025 | −20.003 | 1.00 | 19.51 | BBBB |
| ATOM | 4508 | CB | ALA | B | 255 | 13.082 | −20.507 | −19.788 | 1.00 | 18.83 | BBBB |
| ATOM | 4509 | C | ALA | B | 255 | 14.737 | −18.901 | −20.713 | 1.00 | 18.88 | BBBB |
| ATOM | 4510 | O | ALA | B | 255 | 14.803 | −18.688 | −21.918 | 1.00 | 19.40 | BBBB |
| ATOM | 4511 | N | ASP | B | 256 | 15.803 | −19.036 | −19.927 | 1.00 | 19.01 | BBBB |
| ATOM | 4512 | CA | ASP | B | 256 | 17.176 | −19.026 | −20.434 | 1.00 | 17.58 | BBBB |
| ATOM | 4513 | CB | ASP | B | 256 | 18.078 | −18.185 | −19.534 | 1.00 | 18.47 | BBBB |
| ATOM | 4514 | CG | ASP | B | 256 | 17.954 | −16.699 | −19.795 | 1.00 | 18.05 | BBBB |
| ATOM | 4515 | OD1 | ASP | B | 256 | 17.845 | −15.944 | −18.806 | 1.00 | 16.89 | BBBB |
| ATOM | 4516 | OD2 | ASP | B | 256 | 17.983 | −16.287 | −20.982 | 1.00 | 19.53 | BBBB |
| ATOM | 4517 | C | ASP | B | 256 | 17.657 | −20.481 | −20.379 | 1.00 | 18.01 | BBBB |
| ATOM | 4518 | O | ASP | B | 256 | 18.459 | −20.929 | −21.198 | 1.00 | 16.11 | BBBB |
| ATOM | 4519 | N | VAL | B | 257 | 17.147 | −21.216 | −19.396 | 1.00 | 17.49 | BBBB |
| ATOM | 4520 | CA | VAL | B | 257 | 17.535 | −22.603 | −19.194 | 1.00 | 18.53 | BBBB |
| ATOM | 4521 | CB | VAL | B | 257 | 18.831 | −22.681 | −18.332 | 1.00 | 17.72 | BBBB |
| ATOM | 4522 | CG1 | VAL | B | 257 | 18.586 | −22.069 | −16.966 | 1.00 | 19.19 | BBBB |
| ATOM | 4523 | CG2 | VAL | B | 257 | 19.286 | −24.129 | −18.200 | 1.00 | 20.40 | BBBB |
| ATOM | 4524 | C | VAL | B | 257 | 16.400 | −23.363 | −18.501 | 1.00 | 18.31 | BBBB |
| ATOM | 4525 | O | VAL | B | 257 | 15.659 | −22.795 | −17.703 | 1.00 | 19.74 | BBBB |
| ATOM | 4526 | N | VAL | B | 258 | 16.263 | −24.643 | −18.818 | 1.00 | 18.74 | BBBB |
| ATOM | 4527 | CA | VAL | B | 258 | 15.208 | −25.456 | −18.234 | 1.00 | 19.32 | BBBB |
| ATOM | 4528 | CB | VAL | B | 258 | 14.328 | −26.100 | −19.337 | 1.00 | 19.89 | BBBB |
| ATOM | 4529 | CG1 | VAL | B | 258 | 13.101 | −26.754 | −18.714 | 1.00 | 19.81 | BBBB |
| ATOM | 4530 | CG2 | VAL | B | 258 | 13.907 | −25.041 | −20.364 | 1.00 | 21.59 | BBBB |
| ATOM | 4531 | C | VAL | B | 258 | 15.799 | −26.585 | −17.389 | 1.00 | 19.70 | BBBB |
| ATOM | 4532 | O | VAL | B | 258 | 16.808 | −27.175 | −17.758 | 1.00 | 18.96 | BBBB |
| ATOM | 4533 | N | VAL | B | 259 | 15.167 | −26.861 | −16.253 | 1.00 | 20.24 | BBBB |
| ATOM | 4534 | CA | VAL | B | 259 | 15.581 | −27.957 | −15.374 | 1.00 | 19.85 | BBBB |
| ATOM | 4535 | CB | VAL | B | 259 | 15.850 | −27.483 | −13.936 | 1.00 | 20.08 | BBBB |
| ATOM | 4536 | CG1 | VAL | B | 259 | 16.222 | −28.689 | −13.059 | 1.00 | 20.22 | BBBB |
| ATOM | 4537 | CG2 | VAL | B | 259 | 16.966 | −26.453 | −13.930 | 1.00 | 17.86 | BBBB |
| ATOM | 4538 | C | VAL | B | 259 | 14.382 | −28.890 | −15.371 | 1.00 | 20.02 | BBBB |
| ATOM | 4539 | O | VAL | B | 259 | 13.301 | −28.500 | −14.942 | 1.00 | 21.88 | BBBB |
| ATOM | 4540 | N | CYS | B | 260 | 14.562 | −30.111 | −15.867 | 1.00 | 21.70 | BBBB |
| ATOM | 4541 | CA | CYS | B | 260 | 13.454 | −31.055 | −15.946 | 1.00 | 22.00 | BBBB |
| ATOM | 4542 | CB | CYS | B | 260 | 12.494 | −30.618 | −17.057 | 1.00 | 22.77 | BBBB |
| ATOM | 4543 | SC | CYS | B | 260 | 13.297 | −30.506 | −18.711 | 1.00 | 22.15 | BBBB |
| ATOM | 4544 | C | CYS | B | 260 | 13.903 | −32.478 | −16.242 | 1.00 | 21.86 | BBBB |
| ATOM | 4545 | O | CYS | B | 260 | 15.087 | −32.730 | −16.496 | 1.00 | 21.34 | BBBB |
| ATOM | 4546 | N | ARG | B | 261 | 12.937 | −33.397 | −16.212 | 1.00 | 22.34 | BBBB |
| ATOM | 4547 | CA | ARG | B | 261 | 13.170 | −34.800 | −16.515 | 1.00 | 23.75 | BBBB |
| ATOM | 4548 | CB | ARG | B | 261 | 11.964 | −35.663 | −16.104 | 1.00 | 27.16 | BBBB |

TABLE 1-continued

ATOMIC COORDINATES OF *E. COLI* MURG PROTEIN

| ATOM | 4549 | CG | ARG | B | 261 | 11.376 | −35.337 | −14.738 | 1.00 | 31.82 | BBBB |
|------|------|-----|-----|---|-----|--------|---------|---------|------|-------|------|
| ATOM | 4550 | CD | ARG | B | 261 | 11.490 | −36.473 | −13.732 | 1.00 | 36.33 | BBBB |
| ATOM | 4551 | NE | ARG | B | 261 | 12.865 | −36.721 | −13.323 | 1.00 | 38.48 | BBBB |
| ATOM | 4552 | CZ | ARG | B | 261 | 13.218 | −37.176 | −12.125 | 1.00 | 37.25 | BBBB |
| ATOM | 4553 | NB1 | ARG | B | 261 | 12.295 | −37.433 | −11.204 | 1.00 | 38.46 | BBBB |
| ATOM | 4554 | NH2 | ARG | B | 261 | 14.499 | −37.370 | −11.848 | 1.00 | 36.79 | BBBB |
| ATOM | 4555 | C | ARG | B | 261 | 13.351 | −34.871 | −18.032 | 1.00 | 23.98 | BBBB |
| ATOM | 4556 | O | ARG | B | 261 | 13.117 | −33.883 | −18.746 | 1.00 | 22.44 | BBBB |
| ATOM | 4557 | N | SER | B | 262 | 13.740 | −36.038 | −18.527 | 1.00 | 22.00 | BBBB |
| ATOM | 4558 | CA | SER | B | 262 | 13.975 | −36.189 | −19.948 | 1.00 | 23.18 | BBBB |
| ATOM | 4559 | CB | SER | B | 262 | 15.481 | −36.377 | −20.203 | 1.00 | 24.45 | BBBB |
| ATOM | 4560 | OG | SER | B | 262 | 16.043 | −37.326 | −19.311 | 1.00 | 25.79 | BBBB |
| ATOM | 4561 | C | SER | B | 262 | 13.173 | −37.263 | −20.676 | 1.00 | 22.90 | BBBB |
| ATOM | 4562 | O | SER | B | 262 | 13.738 | −38.179 | −21.274 | 1.00 | 23.25 | BBBB |
| ATOM | 4563 | N | GLY | B | 263 | 11.850 | −37.151 | −20.619 | 1.00 | 22.74 | BBBB |
| ATOM | 4564 | CA | GLY | B | 263 | 11.026 | −38.079 | −21.361 | 1.00 | 22.85 | BBBB |
| ATOM | 4565 | C | GLY | B | 263 | 11.392 | −37.793 | −22.813 | 1.00 | 24.06 | BBBB |
| ATOM | 4566 | O | GLY | B | 263 | 11.908 | −36.705 | −23.121 | 1.00 | 22.75 | BBBB |
| ATOM | 4567 | N | ALA | B | 264 | 11.130 | −38.739 | −23.708 | 1.00 | 23.37 | BBBB |
| ATOM | 4568 | CA | ALA | B | 264 | 11.482 | −38.564 | −25.115 | 1.00 | 24.25 | BBBB |
| ATOM | 4569 | CB | ALA | B | 264 | 11.133 | −39.829 | −25.894 | 1.00 | 24.58 | BBBB |
| ATOM | 4570 | C | ALA | B | 264 | 10.843 | −37.343 | −25.783 | 1.00 | 24.29 | BBBB |
| ATOM | 4571 | O | ALA | B | 264 | 11.523 | −36.572 | −26.470 | 1.00 | 24.33 | BBBB |
| ATOM | 4572 | N | LEU | B | 265 | 9.541 | −37.167 | −25.596 | 1.00 | 24.44 | BBBB |
| ATOM | 4573 | CA | LEU | B | 265 | 8.846 | −36.037 | −26.205 | 1.00 | 24.66 | BBBB |
| ATOM | 4574 | CB | LEU | B | 265 | 7.332 | −36.183 | −26.011 | 1.00 | 25.33 | BBBB |
| ATOM | 4575 | CG | LEU | B | 265 | 6.760 | −37.544 | −26.426 | 1.00 | 27.97 | BBBB |
| ATOM | 4576 | CD1 | LEU | B | 265 | 5.242 | −37.541 | −26.258 | 1.00 | 28.21 | BBBB |
| ATOM | 4577 | CD2 | LEU | B | 265 | 7.146 | −37.856 | −27.878 | 1.00 | 27.40 | BBBB |
| ATOM | 4578 | C | LEU | B | 265 | 9.331 | −34.717 | −25.613 | 1.00 | 24.47 | BBBB |
| ATOM | 4579 | O | LEU | B | 265 | 9.374 | −33.693 | −26.301 | 1.00 | 23.85 | BBBB |
| ATOM | 4580 | N | THR | B | 266 | 9.702 | −34.747 | −24.338 | 1.00 | 22.12 | BBBB |
| ATOM | 4581 | CA | THR | B | 266 | 10.194 | −33.557 | −23.657 | 1.00 | 22.34 | BBBB |
| ATOM | 4582 | CB | THR | B | 266 | 10.348 | −33.803 | −22.140 | 1.00 | 22.35 | BBBB |
| ATOM | 4583 | OE1 | THR | B | 266 | 9.061 | −34.087 | −21.583 | 1.00 | 24.46 | BBBB |
| ATOM | 4584 | CG2 | THR | B | 266 | 10.945 | −32.573 | −21.444 | 1.00 | 24.00 | BBBB |
| ATOM | 4585 | C | THR | B | 266 | 11.535 | −33.117 | −24.226 | 1.00 | 21.15 | BBBB |
| ATOM | 4586 | O | THR | B | 266 | 11.761 | −31.926 | −24.442 | 1.00 | 20.35 | BBBB |
| ATOM | 4587 | N | VAL | B | 267 | 12.427 | −34.075 | −24.461 | 1.00 | 20.46 | BBBB |
| ATOM | 4588 | CA | VAL | B | 267 | 13.730 | −33.762 | −25.023 | 1.00 | 21.11 | BBBB |
| ATOM | 4589 | CB | VAL | B | 267 | 14.614 | −35.039 | −25.114 | 1.00 | 21.54 | BBBB |
| ATOM | 4590 | CG1 | VAL | B | 267 | 15.903 | −34.740 | −25.865 | 1.00 | 20.72 | BBBB |
| ATOM | 4591 | CG2 | VAL | B | 267 | 14.938 | −35.541 | −23.708 | 1.00 | 20.45 | BBBB |
| ATOM | 4592 | C | VAL | B | 267 | 13.548 | −33.138 | −26.416 | 1.00 | 21.34 | BBBB |
| ATOM | 4593 | O | VAL | B | 267 | 14.188 | −32.135 | −26.747 | 1.00 | 19.99 | BBBB |
| ATOM | 4594 | N | SER | B | 268 | 12.663 | −33.717 | −27.222 | 1.00 | 21.61 | BBBB |
| ATOM | 4595 | CA | SER | B | 268 | 12.411 | −33.191 | −28.567 | 1.00 | 21.96 | BBBB |
| ATOM | 4596 | CB | SER | B | 268 | 11.474 | −34.121 | −29.344 | 1.00 | 21.57 | BBBB |
| ATOM | 4597 | OG | SER | B | 268 | 12.141 | −35.316 | −29.721 | 1.00 | 24.06 | BBBB |
| ATOM | 4598 | C | SER | B | 268 | 11.817 | −31.790 | −28.519 | 1.00 | 21.81 | BBBB |
| ATOM | 4599 | O | SER | B | 268 | 12.158 | −30.933 | −29.336 | 1.00 | 22.60 | BBBB |
| ATOM | 4600 | N | GLU | B | 269 | 10.928 | −31.563 | −27.557 | 1.00 | 21.64 | BBBB |
| ATOM | 4601 | CA | GLU | B | 269 | 10.282 | −30.272 | −27.378 | 1.00 | 21.95 | BBBB |
| ATOM | 4602 | CB | GLU | B | 269 | 9.213 | −30.399 | −26.292 | 1.00 | 24.72 | BBBB |
| ATOM | 4603 | CG | GLU | B | 269 | 8.480 | −29.128 | −25.940 | 1.00 | 27.67 | BBBB |
| ATOM | 4604 | CD | GLU | B | 269 | 7.385 | −29.380 | −24.908 | 1.00 | 30.05 | BBBB |
| ATOM | 4605 | OE1 | GLU | B | 269 | 6.325 | −29.915 | −25.287 | 1.00 | 31.50 | BBBB |
| ATOM | 4606 | OE2 | GLU | B | 269 | 7.591 | −29.057 | −23.719 | 1.00 | 29.84 | BBBB |
| ATOM | 4607 | C | GLU | B | 269 | 11.321 | −29.214 | −26.999 | 1.00 | 21.68 | BBBB |
| ATOM | 4608 | O | GLU | B | 269 | 11.301 | −28.095 | −27.518 | 1.00 | 18.12 | BBBB |
| ATOM | 4609 | N | ILE | B | 270 | 12.224 | −29.581 | −26.092 | 1.00 | 19.43 | BBBB |
| ATOM | 4610 | CA | ILE | B | 270 | 13.295 | −28.698 | −25.638 | 1.00 | 20.62 | BBBB |
| ATOM | 4611 | CB | ILE | B | 270 | 14.157 | −29.391 | −24.533 | 1.00 | 20.30 | BBBB |
| ATOM | 4612 | CG2 | ILE | B | 270 | 15.415 | −28.595 | −24.266 | 1.00 | 19.17 | BBBB |
| ATOM | 4613 | CG1 | ILE | B | 270 | 13.337 | −29.574 | −23.254 | 1.00 | 21.32 | BBBB |
| ATOM | 4614 | CD1 | ILE | B | 270 | 12.926 | −28.291 | −22.583 | 1.00 | 23.40 | BBBB |
| ATOM | 4615 | C | ILE | B | 270 | 14.214 | −28.314 | −26.806 | 1.00 | 20.58 | BBBB |
| ATOM | 4616 | O | ILE | B | 270 | 14.595 | −27.151 | −26.954 | 1.00 | 20.50 | BBBB |
| ATOM | 4617 | N | ALA | B | 271 | 14.574 | −29.298 | −27.624 | 1.00 | 21.29 | BBBB |
| ATOM | 4618 | CA | ALA | B | 271 | 15.440 | −29.058 | −28.776 | 1.00 | 22.45 | BBBB |
| ATOM | 4619 | CB | ALA | B | 271 | 15.741 | −30.376 | −29.485 | 1.00 | 23.36 | BBBB |
| ATOM | 4620 | C | ALA | B | 271 | 14.766 | −28.084 | −29.745 | 1.00 | 23.03 | BBBB |
| ATOM | 4621 | O | ALA | B | 271 | 15.400 | −27.156 | −30.259 | 1.00 | 23.57 | BBBB |
| ATOM | 4622 | N | ALA | B | 272 | 13.479 | −28.301 | −29.988 | 1.00 | 21.81 | BBBB |
| ATOM | 4623 | CA | ALA | B | 272 | 12.719 | −27.451 | −30.898 | 1.00 | 22.17 | BBBB |
| ATOM | 4624 | CB | ALA | B | 272 | 11.335 | −28.053 | −31.131 | 1.00 | 22.15 | BBBB |
| ATOM | 4625 | C | ALA | B | 272 | 12.590 | −26.030 | −30.355 | 1.00 | 22.78 | BBBB |

TABLE 1-continued

ATOMIC COORDINATES OF *E. COLI* MURG PROTEIN

| ATOM | 4626 | O | ALA | B | 272 | 12.585 | −25.058 | −31.122 | 1.00 | 21.77 | BBBB |
|---|---|---|---|---|---|---|---|---|---|---|---|
| ATOM | 4627 | N | ALA | B | 273 | 12.474 | −25.907 | −29.034 | 1.00 | 21.06 | BBBB |
| ATOM | 4628 | CA | ALA | B | 273 | 12.361 | −24.596 | −28.407 | 1.00 | 21.97 | BBBB |
| ATOM | 4629 | CB | ALA | B | 273 | 11.919 | −24.737 | −26.949 | 1.00 | 20.63 | BBBB |
| ATOM | 4630 | C | ALA | B | 273 | 13.699 | −23.867 | −28.468 | 1.00 | 21.83 | BBBB |
| ATOM | 4631 | O | ALA | B | 273 | 13.754 | −22.642 | −28.344 | 1.00 | 22.67 | BBBB |
| ATOM | 4632 | N | GLY | B | 274 | 14.773 | −24.621 | −28.656 | 1.00 | 20.90 | BBBB |
| ATOM | 4633 | CA | GLY | B | 274 | 16.093 | −24.023 | −28.709 | 1.00 | 21.07 | BBBB |
| ATOM | 4634 | C | GLY | B | 274 | 16.498 | −23.549 | −27.327 | 1.00 | 21.48 | BBBB |
| ATOM | 4635 | O | GLY | B | 274 | 16.961 | −22.421 | −27.154 | 1.00 | 20.01 | BBBB |
| ATOM | 4636 | N | LEU | B | 275 | 16.331 | −24.420 | −26.333 | 1.00 | 19.66 | BBBB |
| ATOM | 4637 | CA | LEU | B | 275 | 16.666 | −24.057 | −24.966 | 1.00 | 19.78 | BBBB |
| ATOM | 4638 | CB | LEU | B | 275 | 15.402 | −24.068 | −24.102 | 1.00 | 21.30 | BBBB |
| ATOM | 4639 | CG | LEU | B | 275 | 14.451 | −22.870 | −24.202 | 1.00 | 24.60 | BBBB |
| ATOM | 4640 | CD1 | LEU | B | 275 | 13.220 | −23.136 | −23.349 | 1.00 | 26.44 | BBBB |
| ATOM | 4641 | CD2 | LEU | B | 275 | 15.159 | −21.609 | −23.725 | 1.00 | 24.02 | BBBB |
| ATOM | 4642 | C | LEU | B | 275 | 17.698 | −24.970 | −24.318 | 1.00 | 18.79 | BBBB |
| ATOM | 4643 | O | LEU | B | 275 | 17.679 | −26.180 | −24.524 | 1.00 | 19.36 | BBBB |
| ATOM | 4644 | N | PRO | B | 276 | 18.634 | −24.389 | −23.554 | 1.00 | 17.27 | BBBB |
| ATOM | 4645 | CD | PRO | B | 276 | 18.925 | −22.955 | −23.416 | 1.00 | 16.95 | BBBB |
| ATOM | 4646 | CA | PRO | B | 276 | 19.651 | −25.199 | −22.875 | 1.00 | 16.62 | BBBB |
| ATOM | 4647 | CB | PRO | B | 276 | 20.619 | −24.162 | −22.317 | 1.00 | 17.27 | BBBB |
| ATOM | 4648 | CG | PRO | B | 276 | 20.408 | −22.957 | −23.195 | 1.00 | 18.59 | BBBB |
| ATOM | 4649 | C | PRO | B | 276 | 18.900 | −25.900 | −21.746 | 1.00 | 17.23 | BBBB |
| ATOM | 4650 | O | PRO | B | 276 | 17.944 | −25.340 | −21.189 | 1.00 | 15.14 | BBBB |
| ATOM | 4651 | N | ALA | B | 277 | 19.316 | −27.110 | −21.396 | 1.00 | 17.01 | BBBB |
| ATOM | 4652 | CA | ALA | B | 277 | 18.638 | −27.807 | −20.321 | 1.00 | 15.80 | BBBB |
| ATOM | 4653 | CB | ALA | B | 277 | 17.641 | −28.805 | −20.895 | 1.00 | 17.01 | BBBB |
| ATOM | 4654 | C | ALA | B | 277 | 19.591 | −28.526 | −19.382 | 1.00 | 17.37 | BBBB |
| ATOM | 4655 | O | ALA | B | 277 | 20.710 | −28.891 | −19.755 | 1.00 | 17.09 | BBBB |
| ATOM | 4656 | N | LEU | B | 278 | 19.147 | −28.673 | −18.138 | 1.00 | 17.14 | BBBB |
| ATOM | 4657 | CA | LEU | B | 278 | 19.896 | −29.429 | −17.145 | 1.00 | 18.48 | BBBB |
| ATOM | 4658 | CB | LEU | B | 278 | 20.140 | −28.619 | −15.869 | 1.00 | 19.19 | BBBB |
| ATOM | 4659 | CG | LEU | B | 278 | 21.084 | −29.308 | −14.868 | 1.00 | 20.85 | BBBB |
| ATOM | 4660 | CD1 | LEU | B | 278 | 21.283 | −28.411 | −13.668 | 1.00 | 21.11 | BBBB |
| ATOM | 4661 | CD2 | LEU | B | 278 | 20.497 | −30.647 | −14.433 | 1.00 | 19.16 | BBBB |
| ATOM | 4662 | C | LEU | B | 278 | 18.884 | −30.535 | −16.898 | 1.00 | 19.62 | BBBB |
| ATOM | 4663 | O | LEU | B | 278 | 17.870 | −30.330 | −16.218 | 1.00 | 20.77 | BBBB |
| ATOM | 4664 | N | PHE | B | 279 | 19.149 | −31.691 | −17.495 | 1.00 | 19.50 | BBBB |
| ATOM | 4665 | CA | PHE | B | 279 | 18.266 | −32.838 | −17.392 | 1.00 | 21.59 | BBBB |
| ATOM | 4666 | CB | PHE | B | 279 | 18.385 | −33.700 | −18.651 | 1.00 | 21.07 | BBBB |
| ATOM | 4667 | CG | PHE | B | 279 | 17.740 | −33.099 | −19.876 | 1.00 | 19.35 | BBBB |
| ATOM | 4668 | CD1 | PHE | B | 279 | 18.481 | −32.898 | −21.035 | 1.00 | 19.42 | BBBB |
| ATOM | 4669 | CD2 | PHE | B | 279 | 16.379 | −32.794 | −19.888 | 1.00 | 18.16 | BBBB |
| ATOM | 4670 | CE1 | PHE | B | 279 | 17.874 | −32.405 | −22.203 | 1.00 | 19.06 | BBBB |
| ATOM | 4671 | CE2 | PHE | B | 279 | 15.759 | −32.298 | −21.052 | 1.00 | 17.65 | BBBB |
| ATOM | 4672 | CZ | PHE | B | 279 | 16.515 | −32.108 | −22.208 | 1.00 | 15.61 | BBBB |
| ATOM | 4673 | C | PHE | B | 279 | 18.525 | −33.709 | −16.167 | 1.00 | 22.86 | BBBB |
| ATOM | 4674 | O | PHE | B | 279 | 19.671 | −34.065 | −15.871 | 1.00 | 23.32 | BBBB |
| ATOM | 4675 | N | VAL | B | 280 | 17.445 | −34.037 | −15.461 | 1.00 | 23.88 | BBBB |
| ATOM | 4676 | CA | VAL | B | 280 | 17.502 | −34.902 | −14.281 | 1.00 | 25.67 | BBBB |
| ATOM | 4677 | CB | VAL | B | 280 | 16.883 | −34.223 | −13.048 | 1.00 | 26.89 | BBBB |
| ATOM | 4678 | CG1 | VAL | B | 280 | 16.954 | −35.159 | −11.847 | 1.00 | 28.12 | BBBB |
| ATOM | 4679 | CG2 | VAL | B | 280 | 17.631 | −32.929 | −12.742 | 1.00 | 27.70 | BBBB |
| ATOM | 4680 | C | VAL | B | 280 | 16.690 | −36.136 | −14.658 | 1.00 | 25.65 | BBBB |
| ATOM | 4681 | O | VAL | B | 280 | 15.509 | −36.239 | −14.346 | 1.00 | 24.57 | BBBB |
| ATOM | 4682 | N | PRO | B | 281 | 17.324 | −37.080 | −15.370 | 1.00 | 27.08 | BBBB |
| ATOM | 4683 | CD | PRO | B | 281 | 18.750 | −37.057 | −15.726 | 1.00 | 27.31 | BBBB |
| ATOM | 4684 | CA | PRO | B | 281 | 16.698 | −38.320 | −15.824 | 1.00 | 29.05 | BBBB |
| ATOM | 4685 | CB | PRO | B | 281 | 17.851 | −39.071 | −16.492 | 1.00 | 29.44 | BBBB |
| ATOM | 4686 | CG | PRO | B | 281 | 18.791 | −37.992 | −16.895 | 1.00 | 29.67 | BBBB |
| ATOM | 4687 | C | PRO | B | 281 | 16.092 | −39.121 | −14.684 | 1.00 | 31.51 | BBBB |
| ATOM | 4688 | O | PRO | B | 281 | 16.675 | −39.223 | −13.603 | 1.00 | 32.26 | BBBB |
| ATOM | 4689 | N | PHE | B | 282 | 14.908 | −39.668 | −14.923 | 1.00 | 33.83 | BBBB |
| ATOM | 4690 | CA | PHE | B | 282 | 14.246 | −40.496 | −13.926 | 1.00 | 37.13 | BBBB |
| ATOM | 4691 | CB | PHE | B | 282 | 12.818 | −40.808 | −14.372 | 1.00 | 38.38 | BBBB |
| ATOM | 4692 | CG | PHE | B | 282 | 12.032 | −41.606 | −13.377 | 1.00 | 40.57 | BBBB |
| ATOM | 4693 | CD1 | PHE | B | 282 | 11.720 | −41.074 | −12.130 | 1.00 | 41.80 | BBBB |
| ATOM | 4694 | CD2 | PHE | B | 282 | 11.590 | −42.886 | −13.689 | 1.00 | 41.65 | BBBB |
| ATOM | 4695 | CE1 | PHE | B | 282 | 10.975 | −41.806 | −11.209 | 1.00 | 42.03 | BBBB |
| ATOM | 4696 | CE2 | PHE | B | 282 | 10.843 | −43.628 | −12.773 | 1.00 | 42.49 | BBBB |
| ATOM | 4697 | CZ | PHE | B | 282 | 10.536 | −43.085 | −11.532 | 1.00 | 41.74 | BBBB |
| ATOM | 4698 | C | PHE | B | 282 | 15.078 | −41.776 | −13.880 | 1.00 | 38.09 | BBBB |
| ATOM | 4699 | O | PHE | B | 282 | 15.357 | −42.373 | −14.921 | 1.00 | 38.33 | BBBB |
| ATOM | 4700 | N | GLN | B | 283 | 15.492 | −42.197 | −12.690 | 1.00 | 39.70 | BBBB |
| ATOM | 4701 | CA | GLN | B | 283 | 16.319 | −43.395 | −12.591 | 1.00 | 41.11 | BBBB |
| ATOM | 4702 | CB | GLN | B | 283 | 17.010 | −43.477 | −11.223 | 1.00 | 41.41 | BBBB |

TABLE 1-continued

ATOMIC COORDINATES OF *E. COLI* MURG PROTEIN

| ATOM | 4703 | CG | GLN | B | 283 | 17.953 | −44.676 | −11.096 | 1.00 | 42.60 | BBBB |
|------|------|-----|-----|---|-----|--------|---------|---------|------|-------|------|
| ATOM | 4704 | CD | GLN | B | 283 | 19.143 | −44.605 | −12.051 | 1.00 | 42.87 | BBBB |
| ATOM | 4705 | OE1 | GLN | B | 283 | 20.199 | −44.068 | −11.712 | 1.00 | 43.66 | BBBB |
| ATOM | 4706 | NE2 | GLN | B | 283 | 18.969 | −45.135 | −13.254 | 1.00 | 42.46 | BBBB |
| ATOM | 4707 | C | GLN | B | 283 | 15.543 | −44.679 | −12.846 | 1.00 | 41.60 | BBBB |
| ATOM | 4708 | O | GLN | B | 283 | 14.382 | −44.809 | −12.462 | 1.00 | 40.91 | BBBB |
| ATOM | 4709 | N | HIS | B | 284 | 16.211 | −45.618 | −13.511 | 1.00 | 42.92 | BBBB |
| ATOM | 4710 | CA | HIS | B | 284 | 15.641 | −46.917 | −13.843 | 1.00 | 43.69 | BBBB |
| ATOM | 4711 | CB | HIS | B | 284 | 14.508 | −46.760 | −14.858 | 1.00 | 43.91 | BBBB |
| ATOM | 4712 | CG | HIS | B | 284 | 13.795 | −48.039 | −15.165 | 1.00 | 44.71 | BBBB |
| ATOM | 4713 | CD2 | HIS | B | 284 | 12.574 | −48.489 | −14.793 | 1.00 | 44.80 | BBBB |
| ATOM | 4714 | ND1 | HIS | B | 284 | 14.360 | −49.044 | −15.923 | 1.00 | 44.69 | BBBB |
| ATOM | 4715 | CE1 | HIS | B | 284 | 13.516 | −50.058 | −16.002 | 1.00 | 45.06 | BBBB |
| ATOM | 4716 | NE2 | HIS | B | 284 | 12.425 | −49.747 | −15.325 | 1.00 | 44.90 | BBBB |
| ATOM | 4717 | C | HIS | B | 284 | 16.749 | −47.788 | −14.424 | 1.00 | 44.09 | BBBB |
| ATOM | 4718 | O | HIS | B | 284 | 17.602 | −47.302 | −15.164 | 1.00 | 43.02 | BBBB |
| ATOM | 4719 | N | LYS | B | 285 | 16.740 | −49.074 | −14.085 | 1.00 | 44.90 | BBBB |
| ATOM | 4720 | CA | LYS | B | 285 | 17.767 | −49.993 | −14.571 | 1.00 | 45.34 | BBBB |
| ATOM | 4721 | CB | LYS | B | 285 | 17.386 | −51.436 | −14.222 | 1.00 | 46.84 | BBBB |
| ATOM | 4722 | CG | LYS | B | 285 | 18.541 | −52.425 | −14.327 | 1.00 | 49.53 | BBBB |
| ATOM | 4723 | CD | LYS | B | 285 | 18.140 | −53.802 | −13.807 | 1.00 | 51.08 | BBBB |
| ATOM | 4724 | CE | LYS | B | 285 | 19.325 | −54.759 | −13.780 | 1.00 | 51.58 | BBBB |
| ATOM | 4725 | NZ | LYS | B | 285 | 18.931 | −56.115 | −13.292 | 1.00 | 52.11 | BBBB |
| ATOM | 4726 | C | LYS | B | 285 | 17.969 | −49.853 | −16.079 | 1.00 | 45.02 | BBBB |
| ATOM | 4727 | O | LYS | B | 285 | 19.067 | −50.070 | −16.595 | 1.00 | 45.49 | BBBB |
| ATOM | 4728 | N | ASP | B | 286 | 16.903 | −49.478 | −16.777 | 1.00 | 44.33 | BBBB |
| ATOM | 4729 | CA | ASP | B | 286 | 16.949 | −49.299 | −18.222 | 1.00 | 43.26 | BBBB |
| ATOM | 4730 | CB | ASP | B | 286 | 15.532 | −49.379 | −18.794 | 1.00 | 45.91 | BBBB |
| ATOM | 4731 | CG | ASP | B | 286 | 15.511 | −49.354 | −20.304 | 1.00 | 48.32 | BBBB |
| ATOM | 4732 | OD1 | ASP | B | 286 | 15.971 | −50.338 | −20.925 | 1.00 | 49.52 | BBBB |
| ATOM | 4733 | OD2 | ASP | B | 286 | 15.037 | −48.346 | −20.872 | 1.00 | 51.04 | BBBB |
| ATOM | 4734 | C | ASP | B | 286 | 17.573 | −47.947 | −18.582 | 1.00 | 40.92 | BBBB |
| ATOM | 4735 | O | ASP | B | 286 | 18.179 | −47.796 | −19.643 | 1.00 | 40.31 | BBBB |
| ATOM | 4736 | N | ARG | B | 287 | 17.415 | −46.972 | −17.689 | 1.00 | 38.60 | BBBB |
| ATOM | 4737 | CA | ARG | B | 287 | 17.951 | −45.623 | −17.883 | 1.00 | 36.28 | BBBB |
| ATOM | 4738 | CB | ARG | B | 287 | 19.477 | −45.650 | −17.910 | 1.00 | 37.28 | BBBB |
| ATOM | 4739 | CG | ARG | B | 287 | 20.116 | −46.263 | −16.687 | 1.00 | 40.54 | BBBB |
| ATOM | 4740 | CD | ARG | B | 287 | 21.605 | −46.395 | −16.906 | 1.00 | 42.34 | BBBB |
| ATOM | 4741 | NE | ARG | B | 287 | 22.291 | −45.113 | −16.802 | 1.00 | 44.33 | BBBB |
| ATOM | 4742 | CZ | ARG | B | 287 | 23.449 | −44.842 | −17.392 | 1.00 | 45.20 | BBBB |
| ATOM | 4743 | NH1 | ARG | B | 287 | 24.045 | −45.764 | −18.135 | 1.00 | 45.60 | BBBB |
| ATOM | 4744 | NH2 | ARG | B | 287 | 24.019 | −43.656 | −17.227 | 1.00 | 45.68 | BBBB |
| ATOM | 4745 | C | ARG | B | 287 | 17.449 | −45.005 | −19.180 | 1.00 | 33.59 | BBBB |
| ATOM | 4746 | O | ARG | B | 287 | 18.167 | −44.255 | −19.844 | 1.00 | 32.61 | BBBB |
| ATOM | 4747 | N | GLN | B | 288 | 16.212 | −45.321 | −19.533 | 1.00 | 30.94 | BBBB |
| ATOM | 4748 | CA | GLN | B | 288 | 15.622 | −44.804 | −20.755 | 1.00 | 30.77 | BBBB |
| ATOM | 4749 | CB | GLN | B | 288 | 14.143 | −45.158 | −20.810 | 1.00 | 30.59 | BBBB |
| ATOM | 4750 | CG | GLN | B | 288 | 13.473 | −44.772 | −22.109 | 1.00 | 29.73 | BBBB |
| ATOM | 4751 | CD | GLN | B | 288 | 11.981 | −44.971 | −22.044 | 1.00 | 28.04 | BBBB |
| ATOM | 4752 | OE1 | GLN | B | 288 | 11.294 | −44.295 | −21.279 | 1.00 | 29.59 | BBBB |
| ATOM | 4753 | NE2 | GLN | B | 288 | 11.468 | −45.905 | −22.838 | 1.00 | 26.98 | BBBB |
| ATOM | 4754 | C | GLN | B | 288 | 15.783 | −43.291 | −20.885 | 1.00 | 29.70 | BBBB |
| ATOM | 4755 | O | GLN | B | 288 | 16.268 | −42.801 | −21.902 | 1.00 | 29.79 | BBBB |
| ATOM | 4756 | N | GLN | B | 289 | 15.378 | −42.554 | −19.857 | 1.00 | 29.38 | BBBB |
| ATOM | 4757 | CA | GLN | B | 289 | 15.474 | −41.099 | −19.904 | 1.00 | 29.46 | HBBH |
| ATOM | 4758 | CB | GLN | B | 289 | 14.772 | −40.472 | −18.700 | 1.00 | 29.25 | BBBB |
| ATOM | 4759 | CG | GLN | B | 289 | 13.265 | −40.416 | −18.883 | 1.00 | 29.32 | BBBB |
| ATOM | 4760 | CD | GLN | B | 289 | 12.575 | −39.585 | −17.826 | 1.00 | 29.84 | BBBB |
| ATOM | 4761 | OE1 | GLN | B | 289 | 13.191 | −38.728 | −17.188 | 1.00 | 29.52 | BBBB |
| ATOM | 4762 | NE2 | GLN | B | 289 | 11.281 | −39.821 | −17.647 | 1.00 | 28.95 | BBBB |
| ATOM | 4763 | C | GLN | B | 289 | 16.906 | −40.613 | −20.005 | 1.00 | 29.36 | BBBB |
| ATOM | 4764 | O | GLN | B | 289 | 17.173 | −39.557 | −20.585 | 1.00 | 29.12 | BBBB |
| ATOM | 4765 | N | TYR | B | 290 | 17.835 | −41.374 | −19.442 | 1.00 | 28.95 | BBBB |
| ATOM | 4766 | CA | TYR | B | 290 | 19.228 | −40.984 | −19.550 | 1.00 | 29.55 | BBBB |
| ATOM | 4767 | CB | TYR | B | 290 | 20.136 | −41.934 | −18.768 | 1.00 | 31.40 | BBBB |
| ATOM | 4768 | CG | TYR | B | 290 | 21.587 | −41.780 | −19.148 | 1.00 | 33.37 | BBBB |
| ATOM | 4769 | CD1 | TYR | B | 290 | 22.332 | −40.682 | −18.717 | 1.00 | 34.57 | BBBB |
| ATOM | 4770 | CE1 | TYR | B | 290 | 23.644 | −40.490 | −19.148 | 1.00 | 35.97 | BBBB |
| ATOM | 4771 | CD2 | TYR | B | 290 | 22.192 | −42.684 | −20.017 | 1.00 | 34.90 | BBBB |
| ATOM | 4772 | CE2 | TYR | B | 290 | 23.497 | −42.500 | −20.453 | 1.00 | 36.03 | BBBB |
| ATOM | 4773 | CZ | TYR | B | 290 | 24.214 | −41.402 | −20.019 | 1.00 | 36.29 | BBBB |
| ATOM | 4774 | OH | TYR | B | 290 | 25.499 | −41.215 | −20.475 | 1.00 | 39.44 | BBBB |
| ATOM | 4775 | C | TYR | B | 290 | 19.593 | −41.042 | −21.032 | 1.00 | 28.80 | BBBB |
| ATOM | 4776 | O | TYR | B | 290 | 20.192 | −40.113 | −21.567 | 1.00 | 29.22 | BBBB |
| ATOM | 4777 | N | TRP | B | 291 | 19.227 | −42.135 | −21.697 | 1.00 | 27.57 | BBBB |
| ATOM | 4778 | CA | TRP | B | 291 | 19.542 | −42.282 | −23.116 | 1.00 | 28.07 | BBBB |
| ATOM | 4779 | CB | TRP | B | 291 | 19.217 | −43.705 | −23.599 | 1.00 | 29.42 | BBBB |

TABLE 1-continued

ATOMIC COORDINATES OF *E. COLI* MURG PROTEIN

| ATOM | 4780 | CG  | TRP | B | 291 | 20.070 | −44.750 | −22.936 | 1.00 | 31.82 | BBBB |
|------|------|-----|-----|---|-----|--------|---------|---------|------|-------|------|
| ATOM | 4781 | CD2 | TRP | B | 291 | 21.487 | −44.908 | −23.069 | 1.00 | 33.22 | BBBB |
| ATOM | 4782 | CE2 | TRP | B | 291 | 21.873 | −45.966 | −22.213 | 1.00 | 33.81 | BBBB |
| ATOM | 4783 | CE3 | TRP | B | 291 | 22.470 | −44.257 | −23.826 | 1.00 | 33.13 | BBBB |
| ATOM | 4784 | CD1 | TRP | B | 291 | 19.663 | −45.695 | −22.035 | 1.00 | 32.62 | BBBB |
| ATOM | 4785 | NE1 | TRP | B | 291 | 20.741 | −46.428 | −21.595 | 1.00 | 33.43 | BBBB |
| ATOM | 4786 | CZ2 | TRP | B | 291 | 23.203 | −46.387 | −22.093 | 1.00 | 34.69 | BBBB |
| ATOM | 4787 | CZ3 | TRP | B | 291 | 23.794 | −44.676 | −23.707 | 1.00 | 35.41 | BBBB |
| ATOM | 4788 | CH2 | TRP | B | 291 | 24.146 | −45.732 | −22.845 | 1.00 | 35.26 | BBBB |
| ATOM | 4789 | C   | TRP | B | 291 | 18.808 | −41.256 | −23.978 | 1.00 | 26.84 | BBBB |
| ATOM | 4790 | O   | TRP | B | 291 | 19.283 | −40.900 | −25.058 | 1.00 | 26.55 | BBBB |
| ATOM | 4791 | N   | ASN | B | 292 | 17.658 | −40.779 | −23.508 | 1.00 | 25.52 | BBBB |
| ATOM | 4792 | CA  | ASN | B | 292 | 16.902 | −39.784 | −24.270 | 1.00 | 26.06 | BBBB |
| ATOM | 4793 | CB  | ASN | B | 292 | 15.484 | −39.599 | −23.709 | 1.00 | 24.78 | BBBB |
| ATOM | 4794 | CG  | ASN | B | 292 | 14.590 | −40.811 | −23.928 | 1.00 | 24.46 | BBBB |
| ATOM | 4795 | OD1 | ASN | B | 292 | 14.842 | −41.641 | −24.798 | 1.00 | 25.33 | BBBB |
| ATOM | 4796 | ND2 | ASN | B | 292 | 13.523 | −40.900 | −23.146 | 1.00 | 23.83 | BBBB |
| ATOM | 4797 | C   | ASN | B | 292 | 17.605 | −38.427 | −24.258 | 1.00 | 25.99 | BBBB |
| ATOM | 4798 | O   | ASN | B | 292 | 17.566 | −37.687 | −25.244 | 1.00 | 26.18 | BBBB |
| ATOM | 4799 | N   | ALA | B | 293 | 18.242 | −38.105 | −23.139 | 1.00 | 25.66 | BBBB |
| ATOM | 4800 | CA  | ALA | B | 293 | 18.926 | −36.822 | −22.979 | 1.00 | 25.69 | BBBB |
| ATOM | 4801 | CB  | ALA | B | 293 | 18.940 | −36.422 | −21.506 | 1.00 | 24.17 | BBBB |
| ATOM | 4802 | C   | ALA | B | 293 | 20.346 | −36.800 | −23.521 | 1.00 | 25.67 | BBBB |
| ATOM | 4803 | O   | ALA | B | 293 | 20.855 | −35.743 | −23.902 | 1.00 | 25.52 | BBBB |
| ATOM | 4804 | N   | LEU | B | 294 | 20.978 | −37.969 | −23.560 | 1.00 | 25.62 | BBBB |
| ATOM | 4805 | CA  | LEU | B | 294 | 22.354 | −38.088 | −24.032 | 1.00 | 25.90 | BBBB |
| ATOM | 4806 | CB  | LEU | B | 294 | 22.745 | −39.566 | −24.121 | 1.00 | 26.51 | BBBB |
| ATOM | 4807 | CG  | LEU | B | 294 | 24.226 | −39.864 | −24.350 | 1.00 | 28.12 | BBBB |
| ATOM | 4808 | CD1 | LEU | B | 294 | 25.085 | −39.055 | −23.380 | 1.00 | 28.29 | BBBB |
| ATOM | 4809 | CD2 | LEU | B | 294 | 24.470 | −41.368 | −24.169 | 1.00 | 28.15 | BBBB |
| ATOM | 4810 | C   | LEU | B | 294 | 22.644 | −37.392 | −25.359 | 1.00 | 25.66 | BBBB |
| ATOM | 4811 | O   | LEU | B | 294 | 23.677 | −36.741 | −25.507 | 1.00 | 24.79 | BBBB |
| ATOM | 4812 | N   | PRO | B | 295 | 21.748 | −37.532 | −26.351 | 1.00 | 26.24 | BBBB |
| ATOM | 4813 | CD  | PRO | B | 295 | 20.560 | −38.400 | −26.437 | 1.00 | 25.75 | BBBB |
| ATOM | 4814 | CA  | PRO | B | 295 | 21.998 | −36.870 | −27.635 | 1.00 | 26.15 | BBBB |
| ATOM | 4815 | CB  | PRO | B | 295 | 20.740 | −37.201 | −28.439 | 1.00 | 26.70 | BBBB |
| ATOM | 4816 | CG  | PRO | B | 295 | 20.382 | −38.548 | −27.932 | 1.00 | 26.84 | BBBB |
| ATOM | 4817 | C   | PRO | B | 295 | 22.219 | −35.358 | −27.480 | 1.00 | 25.78 | BBBB |
| ATOM | 4818 | O   | PRO | B | 295 | 23.138 | −34.792 | −28.069 | 1.00 | 25.05 | BBBB |
| ATOM | 4819 | N   | LEU | B | 296 | 21.375 | −34.703 | −26.688 | 1.00 | 25.66 | BBBB |
| ATOM | 4820 | CA  | LEU | B | 296 | 21.521 | −33.265 | −26.481 | 1.00 | 25.42 | BBBB |
| ATOM | 4821 | CB  | LEU | B | 296 | 20.283 | −32.685 | −25.779 | 1.00 | 24.45 | BBBB |
| ATOM | 4822 | CG  | LEU | B | 296 | 19.066 | −32.458 | −26.679 | 1.00 | 25.59 | BBBB |
| ATOM | 4823 | CD1 | LEU | B | 296 | 17.968 | −31.718 | −25.911 | 1.00 | 23.56 | BBBB |
| ATOM | 4824 | CD2 | LEU | B | 296 | 19.496 | −31.630 | −27.893 | 1.00 | 25.87 | BBBB |
| ATOM | 4825 | C   | LEU | B | 296 | 22.784 | −32.935 | −25.688 | 1.00 | 26.07 | BBBB |
| ATOM | 4826 | O   | LEU | B | 296 | 23.435 | −31.917 | −25.944 | 1.00 | 25.26 | BBBB |
| ATOM | 4827 | N   | GLU | B | 297 | 23.143 | −33.785 | −24.730 | 1.00 | 26.14 | BBBB |
| ATOM | 4828 | CA  | GLU | B | 297 | 24.354 | −33.530 | −23.953 | 1.00 | 28.78 | BBBB |
| ATOM | 4829 | CB  | GLU | B | 297 | 24.470 | −34.483 | −22.755 | 1.00 | 29.05 | BBBB |
| ATOM | 4830 | CG  | GLU | B | 297 | 25.716 | −34.210 | −21.908 | 1.00 | 30.81 | BBBB |
| ATOM | 4831 | CD  | GLU | B | 297 | 25.812 | −35.087 | −20.671 | 1.00 | 31.84 | BBBB |
| ATOM | 4832 | OE1 | GLU | B | 297 | 25.655 | −34.555 | −19.551 | 1.00 | 31.74 | BBBB |
| ATOM | 4833 | OE2 | GLU | B | 297 | 26.045 | −36.307 | −20.820 | 1.00 | 31.56 | BBBB |
| ATOM | 4834 | C   | GLU | B | 297 | 25.577 | −33.686 | −24.846 | 1.00 | 29.06 | BBBB |
| ATOM | 4835 | O   | GLU | B | 297 | 26.528 | −32.910 | −24.746 | 1.00 | 29.11 | BBBB |
| ATOM | 4836 | N   | LYS | B | 298 | 25.543 | −34.688 | −25.722 | 1.00 | 31.21 | BBBB |
| ATOM | 4837 | CA  | LYS | B | 298 | 26.644 | −34.947 | −26.648 | 1.00 | 31.90 | BBBB |
| ATOM | 4838 | CB  | LYS | B | 298 | 26.379 | −36.216 | −27.464 | 1.00 | 33.65 | BBBB |
| ATOM | 4839 | CG  | LYS | B | 298 | 26.519 | −37.514 | −26.680 | 1.00 | 36.05 | BBBB |
| ATOM | 4840 | CD  | LYS | B | 298 | 26.251 | −38.734 | −27.568 | 1.00 | 37.69 | BBBB |
| ATOM | 4841 | CE  | LYS | B | 298 | 26.461 | −40.033 | −26.801 | 1.00 | 38.51 | BBBB |
| ATOM | 4842 | NZ  | LYS | B | 298 | 26.094 | −41.235 | −27.607 | 1.00 | 39.05 | BBBB |
| ATOM | 4843 | C   | LYS | B | 298 | 26.829 | −33.768 | −27.598 | 1.00 | 31.69 | BBBB |
| ATOM | 4844 | O   | LYS | B | 298 | 27.945 | −33.455 | −27.998 | 1.00 | 30.87 | BBBB |
| ATOM | 4845 | N   | ALA | B | 299 | 25.725 | −33.116 | −27.952 | 1.00 | 31.63 | BBBB |
| ATOM | 4846 | CA  | ALA | B | 299 | 25.773 | −31.965 | −28.847 | 1.00 | 30.38 | BBBB |
| ATOM | 4847 | CB  | ALA | B | 299 | 24.415 | −31.778 | −29.521 | 1.00 | 30.22 | BBBB |
| ATOM | 4848 | C   | ALA | B | 299 | 26.173 | −30.685 | −28.106 | 1.00 | 29.94 | BBBB |
| ATOM | 4849 | O   | ALA | B | 299 | 26.278 | −29.615 | −28.709 | 1.00 | 30.96 | BBBB |
| ATOM | 4850 | N   | GLY | B | 300 | 26.398 | −30.796 | −26.801 | 1.00 | 27.41 | BBBB |
| ATOM | 4851 | CA  | GLY | B | 300 | 26.777 | −29.635 | −26.017 | 1.00 | 26.18 | BBBB |
| ATOM | 4852 | C   | GLY | B | 300 | 25.619 | −28.665 | −25.810 | 1.00 | 25.19 | BBBB |
| ATOM | 4853 | O   | GLY | B | 300 | 25.832 | −27.466 | −25.644 | 1.00 | 24.70 | BBBB |
| ATOM | 4854 | N   | ALA | B | 301 | 24.392 | −29.179 | −25.820 | 1.00 | 23.51 | BBBB |
| ATOM | 4855 | CA  | ALA | B | 301 | 23.214 | −28.333 | −25.638 | 1.00 | 22.50 | BBBB |
| ATOM | 4856 | CB  | ALA | B | 301 | 22.174 | −28.644 | −26.717 | 1.00 | 23.44 | BBBB |

TABLE 1-continued

ATOMIC COORDINATES OF E. COLI MURG PROTEIN

| ATOM | 4857 | C | ALA | B | 301 | 22.591 | −28.510 | −24.254 | 1.00 | 22.09 | BBBB |
|------|------|-----|-----|---|-----|--------|---------|---------|------|-------|------|
| ATOM | 4858 | O | ALA | B | 301 | 21.705 | −27.746 | −23.863 | 1.00 | 19.90 | BBBB |
| ATOM | 4859 | N | ALA | B | 302 | 23.066 | −29.504 | −23.507 | 1.00 | 20.94 | BBBB |
| ATOM | 4860 | CA | ALA | B | 302 | 22.516 | −29.770 | −22.186 | 1.00 | 21.78 | BBBB |
| ATOM | 4861 | CB | ALA | B | 302 | 21.243 | −30.595 | −22.327 | 1.00 | 20.10 | BBBB |
| ATOM | 4862 | C | ALA | B | 302 | 23.503 | −30.507 | −21.288 | 1.00 | 22.69 | BBBB |
| ATOM | 4863 | O | ALA | B | 302 | 24.561 | −30.948 | −21.739 | 1.00 | 22.25 | BBBB |
| ATOM | 4864 | N | LYS | B | 303 | 23.156 | −30.613 | −20.009 | 1.00 | 24.62 | BBBB |
| ATOM | 4865 | CA | LYS | B | 303 | 23.979 | −31.340 | −19.048 | 1.00 | 25.86 | BBBB |
| ATOM | 4866 | CB | LYS | B | 303 | 24.632 | −30.401 | −18.036 | 1.00 | 27.85 | BBBB |
| ATOM | 4867 | CG | LYS | B | 303 | 25.466 | −31.146 | −16.986 | 1.00 | 29.37 | BBBB |
| ATOM | 4868 | CD | LYS | B | 303 | 26.150 | −30.186 | −16.025 | 1.00 | 32.41 | BBBB |
| ATOM | 4869 | CE | LYS | B | 303 | 27.083 | −30.912 | −15.056 | 1.00 | 33.22 | BBBB |
| ATOM | 4870 | NZ | LYS | B | 303 | 27.827 | −29.952 | −14.181 | 1.00 | 33.62 | BBBB |
| ATOM | 4871 | C | LYS | B | 303 | 23.083 | −32.319 | −18.302 | 1.00 | 26.41 | BBBB |
| ATOM | 4872 | O | LYS | B | 303 | 22.015 | −31.948 | −17.802 | 1.00 | 25.76 | BBBB |
| ATOM | 4873 | N | ILE | B | 304 | 23.520 | −33.570 | −18.234 | 1.00 | 25.65 | BBBB |
| ATOM | 4874 | CA | ILE | B | 304 | 22.753 | −34.598 | −17.550 | 1.00 | 27.17 | BBBB |
| ATOM | 4875 | CB | ILE | B | 304 | 22.786 | −35.946 | −18.316 | 1.00 | 27.06 | BBBB |
| ATOM | 4876 | CG2 | ILE | B | 304 | 21.977 | −36.996 | −17.555 | 1.00 | 28.49 | BBBB |
| ATOM | 4877 | CG1 | ILE | B | 304 | 22.242 | −35.769 | −19.733 | 1.00 | 27.61 | BBBB |
| ATOM | 4878 | CD1 | ILE | B | 304 | 22.380 | −37.009 | −20.599 | 1.00 | 27.05 | BBBB |
| ATOM | 4879 | C | ILE | B | 304 | 23.308 | −34.855 | −16.160 | 1.00 | 27.00 | BBBB |
| ATOM | 4880 | O | ILE | B | 304 | 24.511 | −35.012 | −15.986 | 1.00 | 27.46 | BBBB |
| ATOM | 4881 | N | ILE | B | 305 | 22.428 | −34.869 | −15.168 | 1.00 | 27.22 | BBBB |
| ATOM | 4882 | CA | ILE | B | 305 | 22.843 | −35.178 | −13.813 | 1.00 | 29.01 | BBBB |
| ATOM | 4883 | CB | ILE | B | 305 | 22.713 | −33.977 | −12.858 | 1.00 | 28.91 | BBBB |
| ATOM | 4884 | CG2 | ILE | B | 305 | 23.063 | −34.416 | −11.432 | 1.00 | 30.98 | BBBB |
| ATOM | 4885 | CG1 | ILE | B | 305 | 23.660 | −32.855 | −13.299 | 1.00 | 29.51 | BBBB |
| ATOM | 4886 | CD1 | ILE | B | 305 | 23.674 | −31.653 | −12.367 | 1.00 | 29.43 | BBBB |
| ATOM | 4887 | C | ILE | B | 305 | 21.934 | −36.302 | −13.351 | 1.00 | 29.64 | BBBB |
| ATOM | 4888 | O | ILE | B | 305 | 20.806 | −36.067 | −12.932 | 1.00 | 29.25 | BBBB |
| ATOM | 4889 | N | GLU | B | 306 | 22.429 | −37.532 | −13.467 | 1.00 | 32.18 | BBBB |
| ATOM | 4890 | CA | GLU | B | 306 | 21.664 | −38.702 | −13.061 | 1.00 | 34.65 | BBBB |
| ATOM | 4891 | CB | GLU | B | 306 | 22.356 | −39.989 | −13.530 | 1.00 | 34.79 | BBBB |
| ATOM | 4892 | CG | GLU | B | 306 | 22.529 | −40.067 | −15.035 | 1.00 | 36.39 | BBBB |
| ATOM | 4893 | CD | GLU | B | 306 | 23.114 | −41.388 | −15.504 | 1.00 | 36.86 | BBBB |
| ATOM | 4894 | OE1 | GLU | B | 306 | 22.468 | −42.433 | −15.289 | 1.00 | 36.59 | BBBB |
| ATOM | 4895 | OE2 | GLU | B | 306 | 24.214 | −41.378 | −16.099 | 1.00 | 37.75 | BBBB |
| ATOM | 4896 | C | GLU | B | 306 | 21.531 | −38.704 | −11.552 | 1.00 | 35.50 | BBBB |
| ATOM | 4897 | O | GLU | B | 306 | 22.241 | −37.984 | −10.858 | 1.00 | 35.55 | BBBB |
| ATOM | 4898 | N | GLN | B | 307 | 20.612 | −39.514 | −11.048 | 1.00 | 38.41 | BBBB |
| ATOM | 4899 | CA | GLN | B | 307 | 20.377 | −39.599 | −9.613 | 1.00 | 40.54 | BBBB |
| ATOM | 4900 | CB | GLN | B | 307 | 19.397 | −40.734 | −9.322 | 1.00 | 40.99 | BBBB |
| ATOM | 4901 | CG | GLN | B | 307 | 18.896 | −40.769 | −7.896 | 1.00 | 42.76 | BBBB |
| ATOM | 4902 | CD | GLN | B | 307 | 17.879 | −41.867 | −7.681 | 1.00 | 44.33 | BBBB |
| ATOM | 4903 | OE1 | GLN | B | 307 | 18.181 | −43.051 | −7.847 | 1.00 | 44.46 | BBBB |
| ATOM | 4904 | NE2 | GLN | B | 307 | 16.659 | −41.481 | −7.318 | 1.00 | 45.30 | BBBB |
| ATOM | 4905 | C | GLN | B | 307 | 21.647 | −39.784 | −8.776 | 1.00 | 40.94 | BBBB |
| ATOM | 4906 | O | GLN | B | 307 | 21.796 | −39.154 | −7.732 | 1.00 | 41.24 | BBBB |
| ATOM | 4907 | N | PRO | B | 308 | 22.580 | −40.648 | −9.224 | 1.00 | 42.16 | BBBB |
| ATOM | 4908 | CD | PRO | B | 308 | 22.456 | −41.593 | −10.349 | 1.00 | 42.40 | BBBB |
| ATOM | 4909 | CA | PRO | B | 308 | 23.828 | −40.891 | −8.484 | 1.00 | 43.20 | BBBB |
| ATOM | 4910 | CB | PRO | B | 308 | 24.533 | −41.954 | −9.329 | 1.00 | 43.16 | BBBB |
| ATOM | 4911 | CG | PRO | B | 308 | 23.395 | −42.708 | −9.938 | 1.00 | 43.10 | BBBB |
| ATOM | 4912 | C | PRO | B | 308 | 24.719 | −39.668 | −8.250 | 1.00 | 43.82 | BBBB |
| ATOM | 4913 | O | PRO | B | 308 | 25.652 | −39.724 | −7.449 | 1.00 | 44.24 | BBBB |
| ATOM | 4914 | N | GLN | B | 309 | 24.442 | −38.569 | −8.944 | 1.00 | 44.04 | BBBB |
| ATOM | 4915 | CA | GLN | B | 309 | 25.247 | −37.361 | −8.787 | 1.00 | 43.46 | BBBB |
| ATOM | 4916 | CB | GLN | B | 309 | 26.071 | −37.104 | −10.056 | 1.00 | 44.98 | BBBB |
| ATOM | 4917 | CG | GLN | B | 309 | 27.183 | −38.113 | −10.329 | 1.00 | 46.93 | BBBB |
| ATOM | 4918 | CD | GLN | B | 309 | 26.683 | −39.437 | −10.885 | 1.00 | 47.93 | BBBB |
| ATOM | 4919 | OE1 | GLN | B | 309 | 27.459 | −40.376 | −11.054 | 1.00 | 48.87 | BBBB |
| ATOM | 4920 | NE2 | GLN | B | 309 | 25.388 | −39.515 | −11.179 | 1.00 | 49.17 | BBBB |
| ATOM | 4921 | C | GLN | B | 309 | 24.417 | −36.119 | −8.479 | 1.00 | 42.87 | BBBB |
| ATOM | 4922 | O | GLN | B | 309 | 24.955 | −35.013 | −8.404 | 1.00 | 43.33 | BBBB |
| ATOM | 4923 | N | LEU | B | 310 | 23.113 | −36.297 | −8.289 | 1.00 | 41.06 | BBBB |
| ATOM | 4924 | CA | LEU | B | 310 | 22.232 | −35.166 | −8.022 | 1.00 | 39.65 | BBBB |
| ATOM | 4925 | CB | LEU | B | 310 | 20.779 | −35.549 | −8.330 | 1.00 | 39.95 | BBBB |
| ATOM | 4926 | CG | LEU | B | 310 | 19.730 | −34.437 | −8.480 | 1.00 | 39.98 | BBBB |
| ATOM | 4927 | CD1 | LEU | B | 310 | 19.545 | −33.699 | −7.166 | 1.00 | 41.39 | BBBB |
| ATOM | 4928 | CD2 | LEU | B | 310 | 20.160 | −33.472 | −9.580 | 1.00 | 40.19 | BBBB |
| ATOM | 4929 | C | LEU | B | 310 | 22.342 | −34.659 | −6.591 | 1.00 | 38.83 | BBBB |
| ATOM | 4930 | O | LEU | B | 310 | 22.246 | −35.428 | −5.634 | 1.00 | 39.25 | BBBB |
| ATOM | 4931 | N | SER | B | 311 | 22.541 | −33.354 | −6.457 | 1.00 | 36.17 | BBBB |
| ATOM | 4932 | CA | SER | B | 311 | 22.660 | −32.714 | −5.154 | 1.00 | 34.90 | BBBB |
| ATOM | 4933 | CB | SER | B | 311 | 24.059 | −32.928 | −4.569 | 1.00 | 35.08 | BBBB |

TABLE 1-continued

ATOMIC COORDINATES OF E. COLI MURG PROTEIN

| ATOM | 4934 | OG  | SER | B | 311 | 25.022 | -32.135 | -5.248  | 1.00 | 33.92 | BBBB |
|------|------|-----|-----|---|-----|--------|---------|---------|------|-------|------|
| ATOM | 4935 | C   | SER | B | 311 | 22.434 | -31.227 | -5.357  | 1.00 | 33.51 | BBBB |
| ATOM | 4936 | O   | SER | B | 311 | 22.476 | -30.741 | -6.485  | 1.00 | 33.60 | BBBB |
| ATOM | 4937 | N   | VAL | B | 312 | 22.202 | -30.509 | -4.266  | 1.00 | 32.42 | BBBB |
| ATOM | 4938 | CA  | VAL | B | 312 | 21.990 | -29.074 | -4.341  | 1.00 | 31.50 | BBBB |
| ATOM | 4939 | CB  | VAL | B | 312 | 21.707 | -28.482 | -2.938  | 1.00 | 31.69 | BBBB |
| ATOM | 4940 | CG1 | VAL | B | 312 | 21.546 | -26.976 | -3.023  | 1.00 | 31.54 | BBBB |
| ATOM | 4941 | CG2 | VAL | B | 312 | 20.445 | -29.106 | -2.362  | 1.00 | 31.93 | BBBB |
| ATOM | 4942 | C   | VAL | B | 312 | 23.228 | -28.417 | -4.946  | 1.00 | 31.40 | BBBB |
| ATOM | 4943 | O   | VAL | B | 312 | 23.123 | -27.612 | -5.875  | 1.00 | 30.04 | BBBB |
| ATOM | 4944 | N   | ASP | B | 313 | 24.406 | -28.780 | -4.444  | 1.00 | 30.18 | BBBB |
| ATOM | 4945 | CA  | ASP | B | 313 | 25.642 | -28.202 | -4.957  | 1.00 | 29.61 | BBBB |
| ATOM | 4946 | CB  | ASP | B | 313 | 26.840 | -28.656 | -4.120  | 1.00 | 32.36 | BBBB |
| ATOM | 4947 | CG  | ASP | B | 313 | 26.817 | -28.085 | -2.718  | 1.00 | 34.21 | BBBB |
| ATOM | 4948 | OD1 | ASP | B | 313 | 26.662 | -26.855 | -2.578  | 1.00 | 36.52 | BBBB |
| ATOM | 4949 | OD2 | ASP | B | 313 | 26.958 | -28.865 | -1.751  | 1.00 | 38.92 | BBBB |
| ATOM | 4950 | C   | ASP | B | 313 | 25.910 | -28.516 | -6.425  | 1.00 | 28.84 | BBBB |
| ATOM | 4951 | O   | ASP | B | 313 | 26.442 | -27.677 | -7.146  | 1.00 | 28.96 | BBBB |
| ATOM | 4952 | N   | ALA | B | 314 | 25.555 | -29.719 | -6.868  | 1.00 | 26.61 | BBBB |
| ATOM | 4953 | CA  | ALA | B | 314 | 25.782 | -30.099 | -8.254  | 1.00 | 26.47 | BBBB |
| ATOM | 4954 | CB  | ALA | B | 314 | 25.441 | -31.575 | -8.460  | 1.00 | 26.05 | BBBB |
| ATOM | 4955 | C   | ALA | B | 314 | 24.928 | -29.220 | -9.174  | 1.00 | 25.78 | BBBB |
| ATOM | 4956 | O   | ALA | B | 314 | 25.412 | -28.714 | -10.187 | 1.00 | 24.94 | BBBB |
| ATOM | 4957 | N   | VAL | B | 315 | 23.661 | -29.046 | -8.815  | 1.00 | 25.00 | BBBB |
| ATOM | 4958 | CA  | VAL | B | 315 | 22.755 | -28.215 | -9.612  | 1.00 | 25.33 | BBBB |
| ATOM | 4959 | CB  | VAL | B | 315 | 21.305 | -28.298 | -9.088  | 1.00 | 24.74 | BBBB |
| ATOM | 4960 | CG1 | VAL | B | 315 | 20.392 | -27.382 | -9.898  | 1.00 | 23.53 | BBBB |
| ATOM | 4961 | CG2 | VAL | B | 315 | 20.810 | -29.738 | -9.172  | 1.00 | 25.69 | BBBB |
| ATOM | 4962 | C   | VAL | B | 315 | 23.222 | -26.764 | -9.561  | 1.00 | 25.02 | BBBB |
| ATOM | 4963 | O   | VAL | B | 315 | 23.398 | -26.125 | -10.590 | 1.00 | 25.73 | BBBB |
| ATOM | 4964 | N   | ALA | B | 316 | 23.445 | -26.251 | -8.359  | 1.00 | 26.04 | BBBB |
| ATOM | 4965 | CA  | ALA | B | 316 | 23.888 | -24.872 | -8.199  | 1.00 | 27.13 | BBBB |
| ATOM | 4966 | CB  | ALA | B | 316 | 24.059 | -24.545 | -6.714  | 1.00 | 27.12 | BBBB |
| ATOM | 4967 | C   | ALA | B | 316 | 25.185 | -24.584 | -8.955  | 1.00 | 28.17 | BBBB |
| ATOM | 4968 | O   | ALA | B | 316 | 25.289 | -23.572 | -9.652  | 1.00 | 27.04 | BBBB |
| ATOM | 4969 | N   | ASN | B | 317 | 26.178 | -25.463 | -8.823  | 1.00 | 28.72 | BBBB |
| ATOM | 4970 | CA  | ASN | B | 317 | 27.444 | -25.246 | -9.518  | 1.00 | 28.52 | BBBB |
| ATOM | 4971 | CB  | ASN | B | 317 | 28.493 | -26.271 | -9.081  | 1.00 | 31.30 | BBBB |
| ATOM | 4972 | CG  | ASN | B | 317 | 28.940 | -26.068 | -7.645  | 1.00 | 34.01 | BBBB |
| ATOM | 4973 | OD1 | ASN | B | 317 | 29.091 | -24.933 | -7.183  | 1.00 | 33.87 | BBBB |
| ATOM | 4974 | ND2 | ASN | B | 317 | 29.170 | -27.171 | -6.933  | 1.00 | 35.63 | BBBB |
| ATOM | 4975 | C   | ASN | B | 317 | 27.270 | -25.310 | -11.026 | 1.00 | 27.23 | BBBB |
| ATOM | 4976 | O   | ASN | B | 317 | 27.887 | -24.543 | -11.765 | 1.00 | 26.36 | BBBB |
| ATOM | 4977 | N   | THR | B | 318 | 26.424 | -26.224 | -11.482 | 1.00 | 26.95 | BBBB |
| ATOM | 4978 | CA  | THR | B | 318 | 26.174 | -26.371 | -12.906 | 1.00 | 27.04 | BBBB |
| ATOM | 4979 | CB  | THR | B | 318 | 25.203 | -27.537 | -13.189 | 1.00 | 27.91 | BBBB |
| ATOM | 4980 | OG1 | THR | B | 318 | 25.843 | -28.779 | -12.872 | 1.00 | 30.24 | BBBB |
| ATOM | 4981 | CG2 | THR | B | 318 | 24.784 | -27.539 | -14.655 | 1.00 | 27.49 | BBBB |
| ATOM | 4982 | C   | THR | B | 318 | 25.579 | -25.087 | -13.480 | 1.00 | 26.50 | BBBB |
| ATOM | 4983 | O   | THR | B | 318 | 26.085 | -24.548 | -14.465 | 1.00 | 26.71 | BBBB |
| ATOM | 4984 | N   | LEU | B | 319 | 24.516 | -24.588 | -12.859 | 1.00 | 24.75 | BBBB |
| ATOM | 4985 | CA  | LEU | B | 319 | 23.883 | -23.370 | -13.357 | 1.00 | 25.21 | BBBB |
| ATOM | 4986 | CB  | LEU | B | 319 | 22.579 | -23.090 | -12.600 | 1.00 | 23.70 | BBBB |
| ATOM | 4987 | CG  | LEU | B | 319 | 21.496 | -24.153 | -12.803 | 1.00 | 23.20 | BBBB |
| ATOM | 4988 | CD1 | LEU | B | 319 | 20.384 | -23.962 | -11.785 | 1.00 | 22.93 | BBBB |
| ATOM | 4989 | CD2 | LEU | B | 319 | 20.963 | -24.065 | -14.237 | 1.00 | 22.39 | BBBB |
| ATOM | 4990 | C   | LEU | B | 319 | 24.814 | -22.169 | -13.253 | 1.00 | 25.23 | BBBB |
| ATOM | 4991 | O   | LEU | B | 319 | 24.888 | -21.368 | -14.168 | 1.00 | 25.17 | BBBB |
| ATOM | 4992 | N   | ALA | B | 320 | 25.540 | -22.055 | -12.147 | 1.00 | 24.41 | BBBB |
| ATOM | 4993 | CA  | ALA | B | 320 | 26.445 | -20.931 | -11.957 | 1.00 | 24.59 | BBBB |
| ATOM | 4994 | CB  | ALA | B | 320 | 27.069 | -20.987 | -10.547 | 1.00 | 24.46 | BBBB |
| ATOM | 4995 | C   | ALA | B | 320 | 27.549 | -20.865 | -13.010 | 1.00 | 24.21 | BBBB |
| ATOM | 4996 | O   | ALA | B | 320 | 28.091 | -19.800 | -13.281 | 1.00 | 24.35 | BBBB |
| ATOM | 4997 | N   | GLY | B | 321 | 27.878 | -22.005 | -13.601 | 1.00 | 24.35 | BBBB |
| ATOM | 4998 | CA  | GLY | B | 321 | 28.934 | -22.031 | -14.591 | 1.00 | 24.34 | BBBB |
| ATOM | 4999 | C   | GLY | B | 321 | 28.509 | -21.642 | -15.993 | 1.00 | 24.34 | BBBB |
| ATOM | 5000 | O   | GLY | B | 321 | 29.345 | -21.585 | -16.890 | 1.00 | 24.63 | BBBB |
| ATOM | 5001 | N   | TRP | B | 322 | 27.225 | -21.357 | -16.188 | 1.00 | 22.62 | BBBB |
| ATOM | 5002 | CA  | TRP | B | 322 | 26.738 | -21.007 | -17.521 | 1.00 | 21.72 | BBBB |
| ATOM | 5003 | CB  | TRP | B | 322 | 25.499 | -21.841 | -17.858 | 1.00 | 20.09 | BBBB |
| ATOM | 5004 | CG  | TRP | B | 322 | 25.763 | -23.318 | -17.973 | 1.00 | 19.85 | BBBB |
| ATOM | 5005 | CD2 | TRP | B | 322 | 24.789 | -24.370 | -17.939 | 1.00 | 19.16 | BBBB |
| ATOM | 5006 | CE2 | TRP | B | 322 | 25.479 | -25.584 | -18.164 | 1.00 | 20.31 | BBBB |
| ATOM | 5007 | CE3 | TRP | B | 322 | 23.403 | -24.406 | -17.742 | 1.00 | 19.35 | BBBB |
| ATOM | 5008 | CD1 | TRP | B | 322 | 26.973 | -23.925 | -18.204 | 1.00 | 19.51 | BBBB |
| ATOM | 5009 | NE1 | TRP | B | 322 | 26.806 | -25.281 | -18.323 | 1.00 | 18.84 | BBBB |
| ATOM | 5010 | CZ2 | TRP | B | 322 | 24.825 | -26.825 | -18.198 | 1.00 | 20.00 | BBBB |

TABLE 1-continued

ATOMIC COORDINATES OF E. COLI MURG PROTEIN

| ATOM | 5011 | CZ3 | TRP | B | 322 | 22.749 | −25.646 | −17.775 | 1.00 | 19.90 | BBBB |
|---|---|---|---|---|---|---|---|---|---|---|---|
| ATOM | 5012 | CH2 | TRP | B | 322 | 23.467 | −26.836 | −18.003 | 1.00 | 20.26 | BBBB |
| ATOM | 5013 | C | TRP | B | 322 | 26.422 | −19.524 | −17.722 | 1.00 | 21.61 | BBBB |
| ATOM | 5014 | O | TRP | B | 322 | 25.390 | −19.030 | −17.271 | 1.00 | 21.25 | BBBB |
| ATOM | 5015 | N | SER | B | 323 | 27.320 | −18.824 | −18.409 | 1.00 | 19.53 | BBBB |
| ATOM | 5016 | CA | SER | B | 323 | 27.141 | −17.404 | −18.692 | 1.00 | 19.04 | BBBB |
| ATOM | 5017 | CB | SER | B | 323 | 28.456 | −16.807 | −19.186 | 1.00 | 18.51 | BBBB |
| ATOM | 5018 | OG | SER | B | 323 | 28.793 | −17.374 | −20.447 | 1.00 | 16.33 | BBBB |
| ATOM | 5019 | C | SER | B | 323 | 26.099 | −17.239 | −19.799 | 1.00 | 18.26 | BBBB |
| ATOM | 5020 | O | SER | B | 323 | 25.690 | −18.216 | −20.426 | 1.00 | 16.71 | BBBB |
| ATOM | 5021 | N | ARG | B | 324 | 25.690 | −15.999 | −20.053 | 1.00 | 19.12 | BBBB |
| ATOM | 5022 | CA | ARG | B | 324 | 24.725 | −15.741 | −21.112 | 1.00 | 18.09 | BBBB |
| ATOM | 5023 | CB | ARG | B | 324 | 24.298 | −14.268 | −21.108 | 1.00 | 19.15 | BBBB |
| ATOM | 5024 | CG | ARG | B | 324 | 23.266 | −13.973 | −20.031 | 1.00 | 20.58 | BBBB |
| ATOM | 5025 | CD | ARG | B | 324 | 22.508 | −12.662 | −20.220 | 1.00 | 22.13 | BBBB |
| ATOM | 5026 | NE | ARG | B | 324 | 21.345 | −12.641 | −19.331 | 1.00 | 21.36 | BBBB |
| ATOM | 5027 | CZ | ARG | B | 324 | 20.268 | −13.403 | −19.510 | 1.00 | 21.63 | BBBB |
| ATOM | 5028 | NH1 | ARG | B | 324 | 20.206 | −14.224 | −20.549 | 1.00 | 20.63 | BBBB |
| ATOM | 5029 | NH2 | ARG | B | 324 | 19.269 | −13.378 | −18.633 | 1.00 | 22.19 | BBBB |
| ATOM | 5030 | C | ARG | B | 324 | 25.288 | −16.145 | −22.481 | 1.00 | 17.79 | BBBB |
| ATOM | 5031 | O | ARG | B | 324 | 24.540 | −16.611 | −23.341 | 1.00 | 17.56 | BBBB |
| ATOM | 5032 | N | GLU | B | 325 | 26.597 | −15.975 | −22.686 | 1.00 | 17.74 | BBBB |
| ATOM | 5033 | CA | GLU | B | 325 | 27.220 | −16.368 | −23.954 | 1.00 | 16.96 | BBBB |
| ATOM | 5034 | CB | GLU | B | 325 | 28.690 | −15.907 | −24.028 | 1.00 | 17.92 | BBBB |
| ATOM | 5035 | CG | GLU | B | 325 | 29.361 | −16.398 | −25.319 | 1.00 | 18.50 | BBBB |
| ATOM | 5036 | CD | GLU | B | 325 | 30.844 | −16.068 | −25.454 | 1.00 | 19.03 | BBBB |
| ATOM | 5037 | OE1 | GLU | B | 325 | 31.446 | −16.562 | −26.433 | 1.00 | 18.89 | BBBB |
| ATOM | 5038 | OE2 | GLU | B | 325 | 31.408 | −15.325 | −24.615 | 1.00 | 20.56 | BBBB |
| ATOM | 5039 | C | GLU | B | 325 | 27.164 | −17.894 | −24.110 | 1.00 | 16.65 | BBBB |
| ATOM | 5040 | O | GLU | B | 325 | 26.838 | −18.428 | −25.172 | 1.00 | 15.39 | BBBB |
| ATOM | 5041 | N | THR | B | 326 | 27.500 | −18.603 | −23.042 | 1.00 | 16.67 | BBBB |
| ATOM | 5042 | CA | THR | B | 326 | 27.460 | −20.055 | −23.070 | 1.00 | 16.39 | BBBB |
| ATOM | 5043 | CB | THR | B | 326 | 27.967 | −20.635 | −21.725 | 1.00 | 16.62 | BBBB |
| ATOM | 5044 | OG1 | THR | B | 326 | 29.346 | −20.294 | −21.561 | 1.00 | 18.31 | BBBB |
| ATOM | 5045 | CG2 | THR | B | 326 | 27.804 | −22.143 | −21.690 | 1.00 | 18.20 | BBBB |
| ATOM | 5046 | C | THR | B | 326 | 26.034 | −20.551 | −23.321 | 1.00 | 17.40 | BBBB |
| ATOM | 5047 | O | THR | B | 326 | 25.817 | −21.478 | −24.107 | 1.00 | 16.65 | BBBB |
| ATOM | 5048 | N | LEU | B | 327 | 25.068 | −19.932 | −22.643 | 1.00 | 17.90 | BBBB |
| ATOM | 5049 | CA | LEU | B | 327 | 23.659 | −20.305 | −22.780 | 1.00 | 17.27 | BBBB |
| ATOM | 5050 | CB | LEU | B | 327 | 22.791 | −19.514 | −21.791 | 1.00 | 17.35 | BBBB |
| ATOM | 5051 | CG | LEU | B | 327 | 22.922 | −19.919 | −20.309 | 1.00 | 16.74 | BBBB |
| ATOM | 5052 | CD1 | LEU | B | 327 | 22.192 | −18.930 | −19.416 | 1.00 | 14.82 | BBBB |
| ATOM | 5053 | CD2 | LEU | B | 327 | 22.361 | −21.312 | −20.129 | 1.00 | 18.13 | BBBB |
| ATOM | 5054 | C | LEU | B | 327 | 23.145 | −20.096 | −24.198 | 1.00 | 17.58 | BBBB |
| ATOM | 5055 | O | LEU | B | 327 | 22.352 | −20.899 | −24.692 | 1.00 | 16.08 | BBBB |
| ATOM | 5056 | N | LEU | B | 328 | 23.584 | −19.014 | −24.845 | 1.00 | 17.87 | BBBB |
| ATOM | 5057 | CA | LEU | B | 328 | 23.175 | −18.745 | −26.222 | 1.00 | 17.39 | BBBB |
| ATOM | 5058 | CB | LEU | B | 328 | 23.706 | −17.379 | −26.690 | 1.00 | 17.84 | BBBB |
| ATOM | 5059 | CG | LEU | B | 328 | 23.475 | −17.021 | −28.173 | 1.00 | 18.65 | BBBB |
| ATOM | 5060 | CD1 | LEU | B | 328 | 21.988 | −17.112 | −28.494 | 1.00 | 16.92 | BBBB |
| ATOM | 5061 | CD2 | LEU | B | 328 | 23.984 | −15.608 | −28.460 | 1.00 | 18.47 | BBBB |
| ATOM | 5062 | C | LEU | B | 328 | 23.716 | −19.868 | −27.111 | 1.00 | 17.74 | BBBB |
| ATOM | 5063 | O | LEU | B | 328 | 23.003 | −20.400 | −27.953 | 1.00 | 17.59 | BBBB |
| ATOM | 5064 | N | THR | B | 329 | 24.977 | −20.244 | −26.910 | 1.00 | 20.12 | BBBB |
| ATOM | 5065 | CA | THR | B | 329 | 25.567 | −21.335 | −27.688 | 1.00 | 21.30 | BBBB |
| ATOM | 5066 | CB | THR | B | 329 | 27.069 | −21.556 | −27.336 | 1.00 | 22.69 | BBBB |
| ATOM | 5067 | OG1 | THR | B | 329 | 27.866 | −20.591 | −28.029 | 1.00 | 25.80 | BBBB |
| ATOM | 5068 | CG2 | THR | B | 329 | 27.533 | −22.957 | −27.757 | 1.00 | 24.48 | BBBB |
| ATOM | 5069 | C | THR | B | 329 | 24.819 | −22.644 | −27.457 | 1.00 | 20.40 | BBBB |
| ATOM | 5070 | O | THR | B | 329 | 24.552 | −23.382 | −28.398 | 1.00 | 20.34 | BBBB |
| ATOM | 5071 | N | MET | B | 330 | 24.494 | −22.933 | −26.200 | 1.00 | 20.31 | BBBB |
| ATOM | 5072 | CA | MET | B | 330 | 23.771 | −24.153 | −25.870 | 1.00 | 19.91 | BBBB |
| ATOM | 5073 | CB | MET | B | 330 | 23.642 | −24.292 | −24.350 | 1.00 | 20.88 | BBBB |
| ATOM | 5074 | CG | MET | B | 330 | 24.957 | −24.571 | −23.647 | 1.00 | 21.37 | BBBB |
| ATOM | 5075 | SD | MET | B | 330 | 24.805 | −24.609 | −21.855 | 1.00 | 22.76 | BBBB |
| ATOM | 5076 | CE | MET | B | 330 | 24.118 | −26.250 | −21.622 | 1.00 | 22.37 | BBBB |
| ATOM | 5077 | C | MET | B | 330 | 22.389 | −24.149 | −26.519 | 1.00 | 19.43 | BBBB |
| ATOM | 5078 | O | MET | B | 330 | 21.924 | −25.167 | −27.029 | 1.00 | 20.85 | BBBB |
| ATOM | 5079 | N | ALA | B | 331 | 21.737 | −22.996 | −26.504 | 1.00 | 18.81 | BBBB |
| ATOM | 5080 | CA | ALA | B | 331 | 20.412 | −22.871 | −27.098 | 1.00 | 18.49 | BBBB |
| ATOM | 5081 | CB | ALA | B | 331 | 19.868 | −21.462 | −26.859 | 1.00 | 17.16 | BBBB |
| ATOM | 5082 | C | ALA | B | 331 | 20.481 | −23.162 | −28.594 | 1.00 | 19.04 | BBBB |
| ATOM | 5083 | O | ALA | B | 331 | 19.644 | −23.879 | −29.130 | 1.00 | 18.16 | BBBB |
| ATOM | 5084 | N | GLU | B | 332 | 21.489 | −22.613 | −29.269 | 1.00 | 19.87 | BBBB |
| ATOM | 5085 | CA | GLU | B | 332 | 21.626 | −22.827 | −30.704 | 1.00 | 21.47 | BBBB |
| ATOM | 5086 | CB | GLU | B | 332 | 22.709 | −21.912 | −31.274 | 1.00 | 22.13 | BBBB |
| ATOM | 5087 | CG | GLU | B | 332 | 22.328 | −20.455 | −31.143 | 1.00 | 24.10 | BBBB |

TABLE 1-continued

ATOMIC COORDINATES OF E. COLI MURG PROTEIN

| ATOM | 5088 | CD | GLU | B | 332 | 23.428 | −19.522 | −31.572 | 1.00 | 26.61 | BBBB |
|---|---|---|---|---|---|---|---|---|---|---|---|
| ATOM | 5089 | OE1 | GLU | B | 332 | 24.594 | −19.765 | −31.197 | 1.00 | 26.92 | BBBB |
| ATOM | 5090 | OE2 | GLU | B | 332 | 23.118 | −18.542 | −32.273 | 1.00 | 27.58 | BBBB |
| ATOM | 5091 | C | GLU | B | 332 | 21.921 | −24.280 | −31.025 | 1.00 | 22.44 | BBBB |
| ATOM | 5092 | O | GLU | B | 332 | 21.412 | −24.814 | −32.006 | 1.00 | 22.84 | BBBB |
| ATOM | 5093 | N | ARG | B | 333 | 22.739 | −24.923 | −30.200 | 1.00 | 22.30 | BBBB |
| ATOM | 5094 | CA | ARG | B | 333 | 23.040 | −26.330 | −30.408 | 1.00 | 23.77 | BBBB |
| ATOM | 5095 | CB | ARG | B | 333 | 24.117 | −26.789 | −29.427 | 1.00 | 25.03 | BBBB |
| ATOM | 5096 | CG | ARG | B | 333 | 25.503 | −26.222 | −29.737 | 1.00 | 26.79 | BBBB |
| ATOM | 5097 | CD | ARG | B | 333 | 26.443 | −26.467 | −28.570 | 1.00 | 28.88 | BBBB |
| ATOM | 5098 | NE | ARG | B | 333 | 27.810 | −26.041 | −28.846 | 1.00 | 29.09 | BBBB |
| ATOM | 5099 | CZ | ARG | B | 333 | 28.772 | −26.001 | −27.932 | 1.00 | 30.32 | BBBB |
| ATOM | 5100 | NH1 | ARG | B | 333 | 28.514 | −26.361 | −26.678 | 1.00 | 32.07 | BBBB |
| ATOM | 5101 | NH2 | ARG | B | 333 | 29.990 | −25.596 | −28.269 | 1.00 | 31.36 | BBBB |
| ATOM | 5102 | C | ARG | B | 333 | 21.763 | −27.147 | −30.218 | 1.00 | 23.13 | BBBB |
| ATOM | 5103 | O | ARG | B | 333 | 21.548 | −28.151 | −30.895 | 1.00 | 23.45 | BBBB |
| ATOM | 5104 | N | ALA | B | 334 | 20.907 | −26.713 | −29.299 | 1.00 | 22.82 | BBBB |
| ATOM | 5105 | CA | ALA | B | 334 | 19.648 | −27.420 | −29.063 | 1.00 | 22.88 | BBBB |
| ATOM | 5106 | CB | ALA | B | 334 | 18.915 | −26.800 | −27.882 | 1.00 | 22.08 | BBBB |
| ATOM | 5107 | C | ALA | B | 334 | 18.778 | −27.333 | −30.317 | 1.00 | 22.86 | BBBB |
| ATOM | 5108 | O | ALA | B | 334 | 18.285 | −28.339 | −30.827 | 1.00 | 21.38 | BBBB |
| ATOM | 5109 | N | ARG | B | 335 | 18.602 | −26.114 | −30.815 | 1.00 | 23.14 | BBBB |
| ATOM | 5110 | CA | ARG | B | 335 | 17.795 | −25.892 | −32.002 | 1.00 | 23.54 | BBBB |
| ATOM | 5111 | CB | ARG | B | 335 | 17.815 | −24.407 | −32.361 | 1.00 | 25.17 | BBBB |
| ATOM | 5112 | CG | ARG | B | 335 | 16.804 | −23.995 | −33.418 | 1.00 | 26.90 | BBBB |
| ATOM | 5113 | CD | ARG | B | 335 | 15.381 | −24.129 | −32.891 | 1.00 | 30.87 | BBBB |
| ATOM | 5114 | NE | ARG | B | 335 | 14.435 | −23.414 | −33.736 | 1.00 | 33.71 | BBBB |
| ATOM | 5115 | CZ | ARG | B | 335 | 13.607 | −22.469 | −33.301 | 1.00 | 35.57 | BBBB |
| ATOM | 5116 | NH1 | ARG | B | 335 | 13.601 | −22.123 | −32.016 | 1.00 | 34.54 | BBBB |
| ATOM | 5117 | NH2 | ARG | B | 335 | 12.791 | −21.862 | −34.157 | 1.00 | 35.17 | BBBB |
| ATOM | 5118 | C | ARG | B | 335 | 18.348 | −26.724 | −33.163 | 1.00 | 23.86 | BBBB |
| ATOM | 5119 | O | ARG | B | 335 | 17.595 | −27.360 | −33.902 | 1.00 | 22.38 | BBBB |
| ATOM | 5120 | N | ALA | B | 336 | 19.671 | −26.737 | −33.297 | 1.00 | 25.17 | BBBB |
| ATOM | 5121 | CA | ALA | B | 336 | 20.330 | −27.477 | −34.372 | 1.00 | 26.85 | BBBB |
| ATOM | 5122 | CB | ALA | B | 336 | 21.830 | −27.174 | −34.374 | 1.00 | 26.27 | BBBB |
| ATOM | 5123 | C | ALA | B | 336 | 20.101 | −28.985 | −34.288 | 1.00 | 27.80 | BBBB |
| ATOM | 5124 | O | ALA | B | 336 | 20.052 | −29.665 | −35.308 | 1.00 | 27.33 | BBBB |
| ATOM | 5125 | N | ALA | B | 337 | 19.959 | −29.501 | −33.072 | 1.00 | 29.45 | BBBB |
| ATOM | 5126 | CA | ALA | B | 337 | 19.740 | −30.925 | −32.865 | 1.00 | 30.89 | BBBB |
| ATOM | 5127 | CB | ALA | B | 337 | 20.205 | −31.320 | −31.467 | 1.00 | 31.47 | BBBB |
| ATOM | 5128 | C | ALA | B | 337 | 18.267 | −31.276 | −33.047 | 1.00 | 32.47 | BBBB |
| ATOM | 5129 | O | ALA | B | 337 | 17.887 | −32.445 | −33.029 | 1.00 | 34.14 | BBBB |
| ATOM | 5130 | N | SER | B | 338 | 17.442 | −30.254 | −33.229 | 1.00 | 31.76 | BBBB |
| ATOM | 5131 | CA | SER | B | 338 | 16.008 | −30.432 | −33.408 | 1.00 | 32.41 | BBBB |
| ATOM | 5132 | CB | SER | B | 338 | 15.286 | −29.140 | −33.029 | 1.00 | 31.94 | BBBB |
| ATOM | 5133 | OG | SER | B | 338 | 13.921 | −29.196 | −33.385 | 1.00 | 34.53 | BBBB |
| ATOM | 5134 | C | SER | B | 338 | 15.593 | −30.822 | −34.829 | 1.00 | 33.16 | BBBB |
| ATOM | 5135 | C | SER | B | 338 | 16.274 | −30.503 | −35.801 | 1.00 | 32.25 | BBBB |
| ATOM | 5136 | N | ILE | B | 339 | 14.466 | −31.523 | −34.921 | 1.00 | 33.44 | BBBB |
| ATOM | 5137 | CA | ILE | B | 339 | 13.882 | −31.941 | −36.187 | 1.00 | 34.35 | BBBB |
| ATOM | 5138 | CB | ILE | B | 339 | 13.989 | −33.472 | −36.384 | 1.00 | 35.51 | BBBB |
| ATOM | 5139 | CG2 | ILE | B | 339 | 13.271 | −33.880 | −37.658 | 1.00 | 35.53 | BBBB |
| ATOM | 5140 | CG1 | ILE | B | 339 | 15.463 | −33.887 | −36.450 | 1.00 | 36.09 | BBBB |
| ATOM | 5141 | CD1 | ILE | B | 339 | 15.688 | −35.378 | −36.667 | 1.00 | 37.71 | BBBB |
| ATOM | 5142 | C | ILE | B | 339 | 12.416 | −31.518 | −36.059 | 1.00 | 34.84 | BBBB |
| ATOM | 5143 | O | ILE | B | 339 | 11.601 | −32.229 | −35.479 | 1.00 | 35.09 | BBBB |
| ATOM | 5144 | N | PRO | B | 340 | 12.068 | −30.344 | −36.611 | 1.00 | 34.93 | BBBB |
| ATOM | 5145 | CD | PRO | B | 340 | 12.999 | −29.525 | −37.409 | 1.00 | 35.06 | BBBB |
| ATOM | 5146 | CA | PRO | B | 340 | 10.733 | −29.730 | −36.600 | 1.00 | 34.94 | BBBB |
| ATOM | 5147 | CB | PRO | B | 340 | 10.994 | −28.349 | −37.194 | 1.00 | 35.58 | BBBB |
| ATOM | 5148 | CG | PRO | B | 340 | 12.052 | −28.642 | −38.205 | 1.00 | 36.27 | BBBB |
| ATOM | 5149 | C | PRO | B | 340 | 9.551 | −30.409 | −37.284 | 1.00 | 34.07 | BBBB |
| ATOM | 5150 | O | PRO | B | 340 | 8.410 | −30.222 | −36.861 | 1.00 | 34.18 | BBBB |
| ATOM | 5151 | N | ASP | B | 341 | 9.803 | −31.180 | −38.334 | 1.00 | 33.42 | BBBB |
| ATOM | 5152 | CA | ASP | B | 341 | 8.711 | −31.820 | −39.056 | 1.00 | 33.33 | BBBB |
| ATOM | 5153 | CB | ASP | B | 341 | 8.802 | −31.448 | −40.536 | 1.00 | 35.03 | BBBB |
| ATOM | 5154 | CG | ASP | B | 341 | 10.101 | −31.886 | −41.159 | 1.00 | 37.02 | BBBB |
| ATOM | 5155 | OD1 | ASP | B | 341 | 11.125 | −31.907 | −40.443 | 1.00 | 37.17 | BBBB |
| ATOM | 5156 | OD2 | ASP | B | 341 | 10.102 | −32.200 | −42.367 | 1.00 | 40.57 | BBBB |
| ATOM | 5157 | C | ASP | B | 341 | 8.655 | −33.336 | −38.899 | 1.00 | 32.11 | BBBB |
| ATOM | 5158 | O | ASP | B | 341 | 8.377 | −34.066 | −39.854 | 1.00 | 30.74 | BBBB |
| ATOM | 5159 | N | ALA | B | 342 | 8.908 | −33.807 | −37.683 | 1.00 | 30.63 | BBBB |
| ATOM | 5160 | CA | ALA | B | 342 | 8.875 | −35.238 | −37.411 | 1.00 | 29.09 | BBBB |
| ATOM | 5161 | CB | ALA | B | 342 | 9.174 | −35.496 | −35.927 | 1.00 | 28.28 | BBBB |
| ATOM | 5162 | C | ALA | B | 342 | 7.530 | −35.844 | −37.792 | 1.00 | 28.32 | BBBB |
| ATOM | 5163 | O | ALA | B | 342 | 7.475 | −36.901 | −38.416 | 1.00 | 29.88 | BBBB |
| ATOM | 5164 | N | THR | B | 343 | 6.441 | −35.177 | −37.427 | 1.00 | 28.28 | BBBB |

TABLE 1-continued

ATOMIC COORDINATES OF E. COLI MURG PROTEIN

| ATOM | 5165 | CA | THR | B | 343 | 5.115 | −35.696 | −37.744 | 1.00 | 28.55 | BBBB |
|---|---|---|---|---|---|---|---|---|---|---|---|
| ATOM | 5166 | CB | THR | B | 343 | 3.998 | −34.765 | −37.205 | 1.00 | 29.04 | BBBB |
| ATOM | 5167 | OG1 | THR | B | 343 | 4.119 | −34.642 | −35.782 | 1.00 | 28.04 | BBBB |
| ATOM | 5168 | CG2 | THR | B | 343 | 2.628 | −35.330 | −37.528 | 1.00 | 28.54 | BBBB |
| ATOM | 5169 | C | THR | B | 343 | 4.934 | −35.882 | −39.254 | 1.00 | 29.50 | BBBB |
| ATOM | 5170 | O | THR | B | 343 | 4.533 | −36.952 | −39.711 | 1.00 | 28.08 | BBBB |
| ATOM | 5171 | N | GLU | B | 344 | 5.234 | −34.843 | −40.030 | 1.00 | 30.76 | BBBB |
| ATOM | 5172 | CA | GLU | B | 344 | 5.085 | −34.933 | −41.480 | 1.00 | 32.00 | BBBB |
| ATOM | 5173 | CB | GLU | B | 344 | 5.414 | −33.589 | −42.142 | 1.00 | 34.02 | BBBB |
| ATOM | 5174 | CG | GLU | B | 344 | 4.412 | −32.483 | −41.814 | 1.00 | 38.27 | BBBB |
| ATOM | 5175 | CD | GLU | B | 344 | 4.807 | −31.661 | −40.594 | 1.00 | 40.96 | BBBB |
| ATOM | 5176 | OE1 | GLU | B | 344 | 5.252 | −32.252 | −39.582 | 1.00 | 41.33 | BBBB |
| ATOM | 5177 | OE2 | GLU | B | 344 | 4.665 | −30.419 | −40.649 | 1.00 | 42.30 | BBBB |
| ATOM | 5178 | C | GLU | B | 344 | 5.970 | −36.032 | −42.056 | 1.00 | 31.14 | BBBB |
| ATOM | 5179 | O | GLU | B | 344 | 5.534 | −36.805 | −42.909 | 1.00 | 32.33 | BBBB |
| ATOM | 5180 | N | ARG | B | 345 | 7.209 | −36.106 | −41.587 | 1.00 | 30.66 | BBBB |
| ATOM | 5181 | CA | ARG | B | 345 | 8.138 | −37.123 | −42.067 | 1.00 | 31.44 | BBBB |
| ATOM | 5182 | CB | ARG | B | 345 | 9.494 | −36.986 | −41.376 | 1.00 | 33.54 | BBBB |
| ATOM | 5183 | CG | ARG | B | 345 | 10.293 | −35.772 | −41.793 | 1.00 | 37.73 | BBBB |
| ATOM | 5184 | CD | ARG | B | 345 | 11.716 | −35.880 | −41.284 | 1.00 | 40.70 | BBBB |
| ATOM | 5185 | NE | ARG | B | 345 | 12.580 | −34.864 | −41.873 | 1.00 | 44.36 | BBBB |
| ATOM | 5186 | CZ | ARG | B | 345 | 13.901 | −34.841 | −41.739 | 1.00 | 45.65 | BBBB |
| ATOM | 5187 | NH1 | ARG | B | 345 | 14.514 | −35.782 | −41.031 | 1.00 | 46.05 | BBBB |
| ATOM | 5188 | NH2 | ARG | B | 345 | 14.608 | −33.881 | −42.322 | 1.00 | 47.38 | BBBB |
| ATOM | 5189 | C | ARG | B | 345 | 7.626 | −38.545 | −41.854 | 1.00 | 30.89 | BBBB |
| ATOM | 5190 | O | ARG | B | 345 | 7.724 | −39.387 | −42.746 | 1.00 | 29.98 | BBBB |
| ATOM | 5191 | N | VAL | B | 346 | 7.086 | −38.818 | −40.670 | 1.00 | 29.72 | BBBB |
| ATOM | 5192 | CA | VAL | B | 346 | 6.578 | −40.151 | −40.384 | 1.00 | 28.61 | BBBB |
| ATOM | 5193 | CB | VAL | B | 346 | 6.197 | −40.298 | −38.885 | 1.00 | 27.90 | BBBB |
| ATOM | 5194 | CG1 | VAL | B | 346 | 5.612 | −41.680 | −38.625 | 1.00 | 27.30 | BBBB |
| ATOM | 5195 | CG2 | VAL | B | 346 | 7.419 | −40.060 | −38.024 | 1.00 | 27.32 | BBBB |
| ATOM | 5196 | C | VAL | B | 346 | 5.361 | −40.435 | −41.252 | 1.00 | 28.33 | BBBB |
| ATOM | 5197 | O | VAL | B | 346 | 5.248 | −41.511 | −41.847 | 1.00 | 28.30 | BBBB |
| ATOM | 5198 | N | ALA | B | 347 | 4.457 | −39.465 | −41.335 | 1.00 | 28.76 | BBBB |
| ATOM | 5199 | CA | ALA | B | 347 | 3.249 | −39.617 | −42.137 | 1.00 | 28.96 | BBBB |
| ATOM | 5200 | CB | ALA | B | 347 | 2.363 | −38.387 | −41.994 | 1.00 | 28.49 | BBBB |
| ATOM | 5201 | C | ALA | B | 347 | 3.596 | −39.844 | −43.606 | 1.00 | 30.26 | BBBB |
| ATOM | 5202 | O | ALA | B | 347 | 2.948 | −40.641 | −44.279 | 1.00 | 30.12 | BBBB |
| ATOM | 5203 | N | ASN | B | 348 | 4.613 | −39.142 | −44.098 | 1.00 | 32.77 | BBBB |
| ATOM | 5204 | CA | ASN | B | 348 | 5.035 | −39.286 | −45.493 | 1.00 | 34.56 | BBBB |
| ATOM | 5205 | CB | ASN | B | 348 | 6.045 | −38.195 | −45.868 | 1.00 | 35.68 | BBBB |
| ATOM | 5206 | CG | ASN | B | 348 | 5.384 | −36.846 | −46.123 | 1.00 | 37.21 | BBBB |
| ATOM | 5207 | OD1 | ASN | B | 348 | 4.157 | −36.719 | −46.081 | 1.00 | 38.48 | BBBB |
| ATOM | 5208 | ND2 | ASN | B | 348 | 6.199 | −35.831 | −46.393 | 1.00 | 38.38 | BBBB |
| ATOM | 5209 | C | ASN | B | 348 | 5.633 | −40.668 | −45.765 | 1.00 | 34.90 | BBBB |
| ATOM | 5210 | O | ASN | B | 348 | 5.433 | −41.233 | −46.841 | 1.00 | 34.59 | BBBB |
| ATOM | 5211 | N | GLU | B | 349 | 6.366 | −41.212 | −44.794 | 1.00 | 35.20 | BBBB |
| ATOM | 5212 | CA | GLU | B | 349 | 6.954 | −42.540 | −44.956 | 1.00 | 34.86 | BBBB |
| ATOM | 5213 | CB | GLU | B | 349 | 8.004 | −42.814 | −43.879 | 1.00 | 34.59 | BBBB |
| ATOM | 5214 | CG | GLU | B | 349 | 9.404 | −42.385 | −44.259 | 1.00 | 38.16 | BBBB |
| ATOM | 5215 | CD | GLU | B | 349 | 9.865 | −42.992 | −45.579 | 1.00 | 38.74 | BBBB |
| ATOM | 5216 | OE1 | GLU | B | 349 | 9.806 | −44.232 | −45.735 | 1.00 | 40.12 | BBBB |
| ATOM | 5217 | OE2 | GLU | B | 349 | 10.292 | −42.225 | −46.461 | 1.00 | 39.64 | BBBB |
| ATOM | 5218 | C | GLU | B | 349 | 5.872 | −43.607 | −44.895 | 1.00 | 33.96 | BBBB |
| ATOM | 5219 | O | GLU | B | 349 | 5.942 | −44.621 | −45.591 | 1.00 | 33.99 | BBBB |
| ATOM | 5220 | N | VAL | B | 350 | 4.875 | −43.377 | −44.051 | 1.00 | 33.91 | BBBB |
| ATOM | 5221 | CA | VAL | B | 350 | 3.767 | −44.306 | −43.919 | 1.00 | 33.79 | BBBB |
| ATOM | 5222 | CB | VAL | B | 350 | 2.848 | −43.907 | −42.744 | 1.00 | 33.70 | BBBB |
| ATOM | 5223 | CG1 | VAL | B | 350 | 1.554 | −44.695 | −42.798 | 1.00 | 32.22 | BBBB |
| ATOM | 5224 | CG2 | VAL | B | 350 | 3.568 | −44.154 | −41.425 | 1.00 | 32.24 | BBBB |
| ATOM | 5225 | C | VAL | B | 350 | 2.969 | −44.274 | −45.217 | 1.00 | 34.78 | BBBB |
| ATOM | 5226 | O | VAL | B | 350 | 2.411 | −45.285 | −45.645 | 1.00 | 34.85 | BBBB |
| ATOM | 5227 | N | SER | B | 351 | 2.925 | −43.102 | −45.844 | 1.00 | 35.34 | BBBB |
| ATOM | 5228 | CA | SER | B | 351 | 2.196 | −42.946 | −47.095 | 1.00 | 36.67 | BBBB |
| ATOM | 5229 | CB | SER | B | 351 | 2.024 | −41.462 | −47.425 | 1.00 | 37.32 | BBBB |
| ATOM | 5230 | OG | SER | B | 351 | 1.241 | −41.292 | −48.590 | 1.00 | 37.74 | BBBB |
| ATOM | 5231 | C | SER | B | 351 | 2.958 | −43.639 | −48.222 | 1.00 | 37.35 | BBBB |
| ATOM | 5232 | O | SER | B | 351 | 2.365 | −44.309 | −49.064 | 1.00 | 36.85 | BBBB |
| ATOM | 5233 | N | ARG | B | 352 | 4.277 | −43.482 | −48.223 | 1.00 | 37.89 | BBBB |
| ATOM | 5234 | CA | ARG | B | 352 | 5.114 | −44.088 | −49.251 | 1.00 | 40.03 | BBBB |
| ATOM | 5235 | CB | ARG | B | 352 | 6.557 | −43.600 | −49.114 | 1.00 | 41.58 | BBBB |
| ATOM | 5236 | CG | ARG | B | 352 | 7.470 | −44.069 | −50.232 | 1.00 | 44.46 | BBBB |
| ATOM | 5237 | CD | ARG | B | 352 | 8.906 | −44.157 | −49.759 | 1.00 | 47.36 | BBBB |
| ATOM | 5238 | NE | ARG | B | 352 | 9.097 | −45.271 | −48.832 | 1.00 | 49.57 | BBBB |
| ATOM | 5239 | CZ | ARG | B | 352 | 10.234 | −45.524 | −48.191 | 1.00 | 50.54 | BBBB |
| ATOM | 5240 | NH1 | ARG | B | 352 | 11.287 | −44.738 | −48.372 | 1.00 | 50.88 | BBBB |
| ATOM | 5241 | NH2 | ARG | B | 352 | 10.321 | −46.566 | −47.373 | 1.00 | 50.24 | BBBB |

TABLE 1-continued

ATOMIC COORDINATES OF E. COLI MURG PROTEIN

| ATOM | 5242 | C | ARG | B | 352 | 5.098 | −45.613 | −49.176 | 1.00 | 40.60 | BBBB |
|---|---|---|---|---|---|---|---|---|---|---|---|
| ATOM | 5243 | O | ARG | B | 352 | 5.101 | −46.292 | −50.204 | 1.00 | 39.84 | BBBB |
| ATOM | 5244 | N | VAL | B | 353 | 5.096 | −46.143 | −47.955 | 1.00 | 41.33 | BBBB |
| ATOM | 5245 | CA | VAL | B | 353 | 5.089 | −47.587 | −47.737 | 1.00 | 42.78 | BBBB |
| ATOM | 5246 | CB | VAL | B | 353 | 5.446 | −47.927 | −46.271 | 1.00 | 42.54 | BBBB |
| ATOM | 5247 | CG1 | VAL | B | 353 | 5.279 | −49.420 | −46.014 | 1.00 | 42.05 | BBBB |
| ATOM | 5248 | CG2 | VAL | B | 353 | 6.879 | −47.509 | −45.987 | 1.00 | 41.86 | BBBB |
| ATOM | 5249 | C | VAL | B | 353 | 3.742 | −48.206 | −48.095 | 1.00 | 43.85 | BBBB |
| ATOM | 5250 | O | VAL | B | 353 | 3.679 | −49.343 | −48.556 | 1.00 | 44.43 | BBBB |
| ATOM | 5251 | N | ALA | B | 354 | 2.664 | −47.465 | −47.871 | 1.00 | 45.85 | BBBB |
| ATOM | 5252 | CA | ALA | B | 354 | 1.336 | −47.957 | −48.212 | 1.00 | 47.24 | BBBB |
| ATOM | 5253 | CB | ALA | B | 354 | 0.264 | −47.043 | −47.628 | 1.00 | 46.79 | BBBB |
| ATOM | 5254 | C | ALA | B | 354 | 1.250 | −47.971 | −49.737 | 1.00 | 48.54 | BBBB |
| ATOM | 5255 | O | ALA | B | 354 | 0.531 | −48.780 | −50.324 | 1.00 | 48.48 | BBBB |
| ATOM | 5256 | N | ARG | B | 355 | 1.998 | −47.068 | −50.366 | 1.00 | 50.49 | BBBB |
| ATOM | 5257 | CA | ARG | B | 355 | 2.035 | −46.964 | −51.824 | 1.00 | 52.71 | BBBB |
| ATOM | 5258 | CB | ARG | B | 355 | 2.658 | −45.633 | −52.264 | 1.00 | 53.58 | BBBB |
| ATOM | 5259 | CG | ARG | B | 355 | 1.998 | −44.372 | −51.730 | 1.00 | 55.08 | BBBB |
| ATOM | 5260 | CD | ARG | B | 355 | 0.716 | −44.014 | −52.461 | 1.00 | 56.64 | BBBB |
| ATOM | 5261 | NE | ARG | B | 355 | 0.112 | −42.802 | −51.907 | 1.00 | 57.43 | BBBB |
| ATOM | 5262 | CZ | ARG | B | 355 | −1.054 | −42.296 | −52.299 | 1.00 | 58.24 | BBBB |
| ATOM | 5263 | NH1 | ARG | B | 355 | −1.758 | −42.896 | −53.252 | 1.00 | 58.53 | BBBB |
| ATOM | 5264 | NH2 | ARG | B | 355 | −1.519 | −41.186 | −51.738 | 1.00 | 58.87 | BBBB |
| ATOM | 5265 | C | ARG | B | 355 | 2.899 | −48.099 | −52.366 | 1.00 | 53.41 | BBBB |
| ATOM | 5266 | O | ARG | B | 355 | 2.966 | −48.319 | −53.575 | 1.00 | 53.50 | BBBB |
| ATOM | 5267 | N | ALA | B | 356 | 3.569 | −48.805 | −51.456 | 1.00 | 54.15 | BBBB |
| ATOM | 5268 | CA | ALA | B | 356 | 4.453 | −49.913 | −51.809 | 1.00 | 54.93 | BBBB |
| ATOM | 5269 | CB | ALA | B | 356 | 3.669 | −51.004 | −52.546 | 1.00 | 54.86 | BBBB |
| ATOM | 5270 | C | ALA | B | 356 | 5.611 | −49.417 | −52.671 | 1.00 | 55.63 | BBBB |
| ATOM | 5271 | O | ALA | B | 356 | 6.193 | −50.178 | −53.442 | 1.00 | 55.95 | BBBB |
| ATOM | 5272 | N | LEU | B | 357 | 5.942 | −48.136 | −52.526 | 1.00 | 56.45 | BBBB |
| ATOM | 5273 | CA | LEU | B | 357 | 7.023 | −47.522 | −53.289 | 1.00 | 57.81 | BBBB |
| ATOM | 5274 | CB | LEU | B | 357 | 6.871 | −45.997 | −53.290 | 1.00 | 58.04 | BBBB |
| ATOM | 5275 | CG | LEU | B | 357 | 5.595 | −45.422 | −53.915 | 1.00 | 58.29 | BBBB |
| ATOM | 5276 | CD1 | LEU | B | 357 | 5.624 | −43.903 | −53.820 | 1.00 | 58.36 | BBBB |
| ATOM | 5277 | CD2 | LEU | B | 357 | 5.485 | −45.859 | −55.370 | 1.00 | 58.62 | BBBB |
| ATOM | 5278 | C | LEU | B | 357 | 8.391 | −47.895 | −52.729 | 1.00 | 58.46 | BBBB |
| ATOM | 5279 | OT1 | LEU | B | 357 | 9.244 | −48.359 | −53.514 | 1.00 | 58.97 | BBBB |
| ATOM | 5280 | OT2 | LEU | B | 357 | 8.601 | −47.710 | −51.512 | 1.00 | 58.97 | BBBB |
| ATOM | 5281 | OH2 | WAT | W | 1 | −20.568 | 11.549 | 41.653 | 1.00 | 24.11 | WATR |
| ATOM | 5282 | OH2 | WAT | W | 4 | −7.219 | −67.275 | −41.843 | 1.00 | 35.35 | WATR |
| ATOM | 5283 | OH2 | WAT | W | 5 | 20.119 | −17.520 | −22.473 | 1.00 | 21.13 | WATR |
| ATOM | 5284 | OH2 | WAT | W | 6 | 18.858 | −19.701 | −23.468 | 1.00 | 18.31 | WATR |
| ATOM | 5285 | OH2 | WAT | W | 7 | 2.329 | −28.724 | −15.978 | 1.00 | 27.32 | WATR |
| ATOM | 5286 | OH2 | WAT | W | 8 | 9.484 | −48.435 | −27.938 | 1.00 | 23.67 | WATR |
| ATOM | 5287 | OH2 | WAT | W | 9 | 7.645 | −57.693 | −27.177 | 1.00 | 21.03 | WATR |
| ATOM | 5288 | OH2 | WAT | W | 10 | −1.542 | −8.422 | 1.824 | 1.00 | 29.71 | WATR |
| ATOM | 5289 | OH2 | WAT | W | 11 | 5.875 | −50.793 | −32.396 | 1.00 | 20.21 | WATR |
| ATOM | 5290 | OH2 | WAT | W | 12 | 27.592 | −18.174 | −27.779 | 1.00 | 22.52 | WATR |
| ATOM | 5291 | OH2 | WAT | W | 13 | 7.842 | −13.432 | −21.178 | 1.00 | 25.85 | WATR |
| ATOM | 5292 | OH2 | WAT | W | 14 | 4.845 | −57.924 | −27.444 | 1.00 | 24.35 | WATR |
| ATOM | 5293 | OH2 | WAT | W | 15 | 0.473 | −58.751 | −17.746 | 1.00 | 35.49 | WATR |
| ATOM | 5294 | OH2 | WAT | W | 16 | 7.998 | −52.522 | −25.785 | 1.00 | 22.34 | WATR |
| ATOM | 5295 | OH2 | WAT | W | 17 | −8.656 | 11.300 | 18.872 | 1.00 | 23.81 | WATR |
| ATOM | 5296 | OH2 | WAT | W | 18 | 8.711 | −45.913 | −29.121 | 1.00 | 21.55 | WATR |
| ATOM | 5297 | OH2 | WAT | W | 19 | 2.957 | −68.158 | −38.242 | 1.00 | 29.43 | WATR |
| ATOM | 5298 | OH2 | WAT | W | 20 | 16.486 | −11.742 | −16.567 | 1.00 | 22.13 | WATR |
| ATOM | 5299 | OH2 | WAT | W | 21 | −6.251 | 17.702 | 28.534 | 1.00 | 24.24 | WATR |
| ATOM | 5300 | OH2 | WAT | W | 22 | 12.670 | −47.636 | −24.808 | 1.00 | 25.87 | WATR |
| ATOM | 5301 | OH2 | WAT | W | 23 | 6.513 | −15.597 | −22.517 | 1.00 | 26.31 | WATR |
| ATOM | 5302 | OH2 | WAT | W | 24 | 7.536 | −66.906 | −21.753 | 1.00 | 21.48 | WATR |
| ATOM | 5303 | OH2 | WAT | W | 25 | −29.060 | 13.621 | 26.406 | 1.00 | 21.08 | WATR |
| ATOM | 5304 | OH2 | WAT | W | 26 | −5.240 | 10.154 | 13.527 | 1.00 | 29.62 | WATR |
| ATOM | 5305 | OH2 | WAT | W | 27 | 29.942 | −20.139 | −19.237 | 1.00 | 20.38 | WATR |
| ATOM | 5306 | OH2 | WAT | W | 28 | 18.996 | −28.763 | −24.427 | 1.00 | 20.28 | WATR |
| ATOM | 5307 | OH2 | WAT | W | 29 | 8.755 | −51.080 | −27.990 | 1.00 | 20.66 | WATR |
| ATOM | 5308 | OH2 | WAT | W | 30 | 4.215 | −64.684 | −43.328 | 1.00 | 39.67 | WATR |
| ATOM | 5309 | OH2 | WAT | W | 31 | 14.708 | −11.936 | −1.749 | 1.00 | 24.57 | WATR |
| ATOM | 5310 | OH2 | WAT | W | 32 | 28.140 | −13.870 | −21.266 | 1.00 | 18.93 | WATR |
| ATOM | 5311 | OH2 | WAT | W | 33 | 4.057 | −1.221 | 9.809 | 1.00 | 32.30 | WATR |
| ATOM | 5312 | OH2 | WAT | W | 34 | 4.784 | −56.759 | −43.904 | 1.00 | 25.99 | WATR |
| ATOM | 5313 | OH2 | WAT | W | 35 | −22.733 | 10.283 | 33.238 | 1.00 | 24.60 | WATR |
| ATOM | 5314 | OH2 | WAT | W | 36 | 0.540 | 14.225 | 10.932 | 1.00 | 26.89 | WATR |
| ATOM | 5315 | OH2 | WAT | W | 37 | −7.560 | 11.931 | 12.593 | 1.00 | 27.76 | WATR |
| ATOM | 5316 | OH2 | WAT | W | 38 | −7.966 | 17.043 | 30.555 | 1.00 | 20.04 | WATR |
| ATOM | 5317 | OH2 | WAT | W | 39 | 6.716 | −55.314 | −42.959 | 1.00 | 25.72 | WATR |
| ATOM | 5318 | OH2 | WAT | W | 40 | 6.833 | −32.402 | −3.845 | 1.00 | 32.49 | WATR |

TABLE 1-continued

ATOMIC COORDINATES OF E. COLI MURG PROTEIN

| ATOM | 5319 | OH2 | WAT | W | 41 | 30.445 | −20.104 | −25.459 | 1.00 | 27.97 | WATR |
|---|---|---|---|---|---|---|---|---|---|---|---|
| ATOM | 5320 | OH2 | WAT | W | 42 | 1.475 | −15.304 | −22.128 | 1.00 | 30.57 | WATR |
| ATOM | 5321 | OH2 | WAT | W | 43 | 15.703 | −42.835 | −31.237 | 1.00 | 26.74 | WATR |
| ATOM | 5322 | OH2 | WAT | W | 44 | 7.131 | −6.595 | −18.003 | 1.00 | 29.47 | WATR |
| ATOM | 5323 | OH2 | WAT | W | 45 | 30.256 | −23.202 | −11.163 | 1.00 | 33.81 | WATR |
| ATOM | 5324 | OH2 | WAT | W | 46 | −6.107 | −66.004 | −38.690 | 1.00 | 30.45 | WATR |
| ATOM | 5325 | OH2 | WAT | W | 47 | 17.631 | −17.241 | −5.864 | 1.00 | 28.69 | WATR |
| ATOM | 5326 | OH2 | WAT | W | 48 | 13.436 | −59.821 | −27.855 | 1.00 | 28.71 | WATR |
| ATOM | 5327 | OH2 | WAT | W | 49 | 11.395 | −15.293 | 2.925 | 1.00 | 29.36 | WATR |
| ATOM | 5328 | OH2 | WAT | W | 50 | 19.218 | −21.377 | −34.248 | 1.00 | 31.41 | WATR |
| ATOM | 5329 | OH2 | WAT | W | 51 | 11.973 | −11.890 | −15.788 | 1.00 | 35.59 | WATR |
| ATOM | 5330 | OH2 | WAT | W | 52 | 9.140 | −8.260 | −23.371 | 1.00 | 40.29 | WATR |
| ATOM | 5331 | OH2 | WAT | W | 53 | −19.061 | 14.438 | 38.966 | 1.00 | 38.01 | WATR |
| ATOM | 5332 | OH2 | WAT | W | 54 | −3.895 | −70.510 | −28.249 | 1.00 | 25.56 | WATR |
| ATOM | 5333 | OH2 | WAT | W | 55 | 20.909 | −23.456 | −34.213 | 1.00 | 26.74 | WATR |
| ATOM | 5334 | OH2 | WAT | W | 56 | −8.505 | 11.136 | 10.323 | 1.00 | 30.97 | WATR |
| ATOM | 5335 | OH2 | WAT | W | 57 | 22.022 | −15.529 | −23.223 | 1.00 | 26.74 | WATR |
| ATOM | 5336 | OH2 | WAT | W | 58 | 13.860 | −49.304 | −42.490 | 1.00 | 27.91 | WATR |
| ATOM | 5337 | OH2 | WAT | W | 59 | −9.455 | −6.552 | −9.720 | 1.00 | 41.70 | WATR |
| ATOM | 5338 | OH2 | WAT | W | 60 | 13.798 | −49.732 | −23.016 | 1.00 | 41.60 | WATR |
| ATOM | 5339 | OH2 | WAT | W | 61 | 15.881 | −60.461 | −31.910 | 1.00 | 48.66 | WATR |
| ATOM | 5340 | OH2 | WAT | W | 62 | −9.797 | 12.718 | 13.997 | 1.00 | 29.14 | WATR |
| ATOM | 5341 | OH2 | WAT | W | 63 | 16.793 | 0.356 | −6.115 | 1.00 | 26.17 | WATR |
| ATOM | 5342 | OH2 | WAT | W | 64 | 3.173 | 18.778 | 20.793 | 1.00 | 31.13 | WATR |
| ATOM | 5343 | OH2 | WAT | W | 65 | 13.433 | −11.079 | 0.672 | 1.00 | 27.40 | WATR |
| ATOM | 5344 | OH2 | WAT | W | 66 | 3.118 | −0.813 | 0.729 | 1.00 | 24.68 | WATR |
| ATOM | 5345 | OH2 | WAT | W | 67 | −22.179 | 3.583 | 26.978 | 1.00 | 32.28 | WATR |
| ATOM | 5346 | OH2 | WAT | W | 68 | 24.433 | −30.481 | −1.783 | 1.00 | 41.91 | WATR |
| ATOM | 5347 | OH2 | WAT | W | 69 | 4.384 | −66.131 | −41.203 | 1.00 | 34.75 | WATR |
| ATOM | 5348 | OH2 | WAT | W | 70 | 20.398 | −7.386 | −4.280 | 1.00 | 30.85 | WATR |
| ATOM | 5349 | OH2 | WAT | W | 71 | −2.444 | −70.752 | −22.067 | 1.00 | 25.46 | WATR |
| ATOM | 5350 | OH2 | WAT | W | 72 | −3.963 | −4.914 | −5.711 | 1.00 | 29.67 | WATR |
| ATOM | 5351 | OH2 | WAT | W | 73 | 17.663 | −11.040 | −34.488 | 1.00 | 30.24 | WATR |
| ATOM | 5352 | OH2 | WAT | W | 74 | 21.404 | −42.041 | −26.621 | 1.00 | 31.41 | WATR |
| ATOM | 5353 | OH2 | WAT | W | 75 | −1.110 | −15.319 | −1.089 | 1.00 | 31.51 | WATR |
| ATOM | 5354 | OH2 | WAT | W | 76 | 0.688 | 19.730 | 22.519 | 1.00 | 26.71 | WATR |
| ATOM | 5355 | OH2 | WAT | W | 77 | 12.113 | −69.335 | −26.593 | 1.00 | 27.11 | WATR |
| ATOM | 5356 | OH2 | WAT | W | 78 | 11.725 | −25.065 | −33.817 | 1.00 | 43.79 | WATR |
| ATOM | 5357 | OH2 | WAT | W | 79 | −25.519 | 9.450 | 22.092 | 1.00 | 28.18 | WATR |
| ATOM | 5358 | OH2 | WAT | W | 80 | −14.673 | 6.584 | 16.023 | 1.00 | 31.37 | WATR |
| ATOM | 5359 | OH2 | WAT | W | 81 | −2.250 | −0.253 | −1.741 | 1.00 | 29.99 | WATR |
| ATOM | 5360 | OH2 | WAT | W | 82 | −7.300 | 12.943 | 8.415 | 1.00 | 32.39 | WATR |
| ATOM | 5361 | OH2 | WAT | W | 83 | 1.712 | −13.629 | −13.904 | 1.00 | 34.08 | WATR |
| ATOM | 5362 | OH2 | WAT | W | 84 | 4.709 | −17.478 | −6.557 | 1.00 | 29.67 | WATR |
| ATOM | 5363 | OH2 | WAT | W | 85 | 10.070 | −57.496 | −44.450 | 1.00 | 48.39 | WATR |
| ATOM | 5364 | OH2 | WAT | W | 86 | 8.040 | −30.281 | −10.117 | 1.00 | 28.59 | WATR |
| ATOM | 5365 | OH2 | WAT | W | 87 | −1.967 | −32.372 | −38.643 | 1.00 | 31.55 | WATR |
| ATOM | 5366 | OH2 | WAT | W | 88 | −3.178 | −64.576 | −25.506 | 1.00 | 33.66 | WATR |
| ATOM | 5367 | OH2 | WAT | W | 89 | 15.762 | −9.860 | −10.400 | 1.00 | 34.29 | WATR |
| ATOM | 5368 | OH2 | WAT | W | 90 | 5.654 | −30.990 | −27.758 | 1.00 | 35.84 | WATR |
| ATOM | 5369 | OH2 | WAT | W | 91 | 14.959 | −46.096 | −42.270 | 1.00 | 35.21 | WATR |
| ATOM | 5370 | OH2 | WAT | W | 92 | 10.137 | −13.308 | −9.753 | 1.00 | 32.65 | WATR |
| ATOM | 5371 | OH2 | WAT | W | 93 | −4.480 | 6.624 | 6.614 | 1.00 | 27.37 | WATR |
| ATOM | 5372 | OH2 | WAT | W | 94 | −14.574 | 22.522 | 18.870 | 1.00 | 49.48 | WATR |
| ATOM | 5373 | OH2 | WAT | W | 95 | −11.031 | −42.768 | −39.637 | 1.00 | 37.63 | WATR |
| ATOM | 5374 | OH2 | WAT | W | 96 | 9.906 | −35.479 | −19.203 | 1.00 | 29.59 | WATR |
| ATOM | 5375 | OH2 | WAT | W | 97 | −0.990 | −0.781 | 36.951 | 1.00 | 37.27 | WATR |
| ATOM | 5376 | OH2 | WAT | W | 98 | −11.422 | 9.059 | 11.252 | 1.00 | 30.43 | WATR |
| ATOM | 5377 | OH2 | WAT | W | 99 | 8.118 | −36.710 | −22.371 | 1.00 | 34.85 | WATR |
| ATOM | 5378 | OH2 | WAT | W | 100 | 12.414 | −67.326 | −22.791 | 1.00 | 31.24 | WATR |
| ATOM | 5379 | OH2 | WAT | W | 101 | 28.541 | −24.603 | −31.049 | 1.00 | 40.14 | WATR |
| ATOM | 5380 | OH2 | WAT | W | 102 | 16.276 | −10.934 | −3.673 | 1.00 | 33.80 | WATR |
| ATOM | 5381 | OH2 | WAT | W | 103 | 30.979 | −13.264 | −22.953 | 1.00 | 24.73 | WATR |
| ATOM | 5382 | OH2 | WAT | W | 104 | 12.759 | −31.636 | −31.838 | 1.00 | 26.40 | WATR |
| ATOM | 5383 | OH2 | WAT | W | 105 | 23.507 | −29.661 | −32.187 | 1.00 | 29.62 | WATR |
| ATOM | 5384 | OH2 | WAT | W | 106 | 21.292 | −13.141 | −24.874 | 1.00 | 37.83 | WATR |
| ATOM | 5385 | OH2 | WAT | W | 107 | 10.171 | −32.960 | −15.580 | 1.00 | 26.59 | WATR |
| ATOM | 5386 | OH2 | WAT | W | 108 | −2.207 | 2.376 | 2.034 | 1.00 | 27.55 | WATR |
| ATOM | 5387 | OH2 | WAT | W | 109 | −6.984 | 22.588 | 16.082 | 1.00 | 39.01 | WATR |
| ATOM | 5388 | OH2 | WAT | W | 110 | 14.308 | −11.038 | −15.406 | 1.00 | 26.48 | WATR |
| ATOM | 5389 | OH2 | WAT | W | 111 | 10.612 | 9.749 | 24.161 | 1.00 | 40.18 | WATR |
| ATOM | 5390 | OH2 | WAT | W | 112 | 2.406 | −15.823 | −10.196 | 1.00 | 27.61 | WATR |
| ATOM | 5391 | OH2 | WAT | W | 113 | 6.310 | −68.984 | −20.661 | 1.00 | 40.25 | WATR |
| ATOM | 5392 | OH2 | WAT | W | 114 | 14.379 | −10.930 | −8.565 | 1.00 | 35.86 | WATR |
| ATOM | 5393 | OH2 | WAT | W | 115 | 24.183 | −35.475 | −30.338 | 1.00 | 35.17 | WATR |
| ATOM | 5394 | OH2 | WAT | W | 116 | 21.897 | −31.717 | −1.243 | 1.00 | 47.61 | WATR |
| ATOM | 5395 | OH2 | WAT | W | 117 | 24.065 | −17.545 | −13.707 | 1.00 | 32.24 | WATR |

TABLE 1-continued

ATOMIC COORDINATES OF E. COLI MURG PROTEIN

| ATOM | 5396 | OH2 | WAT | W | 118 | 16.772 | −51.926 | −25.940 | 1.00 | 38.66 | WATR |
|---|---|---|---|---|---|---|---|---|---|---|---|
| ATOM | 5397 | OH2 | WAT | W | 119 | −5.862 | 6.629 | 4.446 | 1.00 | 39.57 | WATR |
| ATOM | 5398 | OH2 | WAT | W | 120 | 14.133 | −57.303 | −28.159 | 1.00 | 30.19 | WATR |
| ATOM | 5399 | OH2 | WAT | W | 121 | −16.538 | −6.724 | 21.638 | 1.00 | 40.50 | WATR |
| ATOM | 5400 | OH2 | WAT | W | 122 | 19.669 | −18.487 | −33.216 | 1.00 | 38.38 | WATR |
| ATOM | 5401 | OH2 | WAT | W | 123 | 15.481 | 1.078 | −4.048 | 1.00 | 32.28 | WATR |
| ATOM | 5402 | OH2 | WAT | W | 124 | 20.395 | −13.033 | −2.072 | 1.00 | 49.69 | WATR |
| ATOM | 5403 | OH2 | WAT | W | 125 | 15.526 | −1.437 | −15.842 | 1.00 | 36.06 | WATR |
| ATOM | 5404 | OH2 | WAT | W | 126 | 7.297 | −29.419 | −1.509 | 1.00 | 34.75 | WATR |
| ATOM | 5405 | OH2 | WAT | W | 127 | 9.994 | −12.069 | −21.013 | 1.00 | 32.21 | WATR |
| ATOM | 5406 | OH2 | WAT | W | 128 | 17.433 | −42.825 | −16.713 | 1.00 | 31.02 | WATR |
| ATOM | 5407 | OH2 | WAT | W | 129 | −15.855 | 20.882 | 21.019 | 1.00 | 44.11 | WATR |
| ATOM | 5408 | OH2 | WAT | W | 130 | −6.351 | −7.687 | −14.067 | 1.00 | 35.04 | WATR |
| ATOM | 5409 | OH2 | WAT | W | 131 | 7.954 | −17.872 | −1.475 | 1.00 | 28.45 | WATR |
| ATOM | 5410 | OH2 | WAT | W | 132 | 13.526 | −34.593 | −31.844 | 1.00 | 31.12 | WATR |
| ATOM | 5411 | OH2 | WAT | W | 133 | 9.992 | −41.228 | −23.098 | 1.00 | 26.45 | WATR |
| ATOM | 5412 | OH2 | WAT | W | 134 | 8.434 | 18.132 | 16.019 | 1.00 | 32.97 | WATR |
| ATOM | 5413 | OH2 | WAT | W | 135 | −1.208 | −33.658 | −36.216 | 1.00 | 38.33 | WATR |
| ATOM | 5414 | OH2 | WAT | W | 136 | −14.502 | 9.100 | 12.433 | 1.00 | 43.21 | WATR |
| ATOM | 5415 | OH2 | WAT | W | 137 | 14.394 | −43.675 | −17.325 | 1.00 | 32.32 | WATR |
| ATOM | 5416 | OH2 | WAT | W | 138 | −4.809 | −30.333 | −46.416 | 1.00 | 42.65 | WATR |
| ATOM | 5417 | OH2 | WAT | W | 139 | 18.861 | −35.072 | −35.671 | 1.00 | 43.56 | WATR |
| ATOM | 5418 | OH2 | WAT | W | 140 | −10.162 | −60.139 | −32.862 | 1.00 | 35.41 | WATR |
| ATOM | 5419 | OH2 | WAT | W | 141 | 6.740 | −32.411 | −35.303 | 1.00 | 38.57 | WATR |
| ATOM | 5420 | OH2 | WAT | W | 142 | −12.257 | −60.854 | −39.307 | 1.00 | 32.90 | WATR |
| ATOM | 5421 | OH2 | WAT | W | 143 | 18.910 | −40.984 | −13.084 | 1.00 | 43.43 | WATR |
| ATOM | 5422 | OH2 | WAT | W | 144 | 18.857 | −49.375 | −28.645 | 1.00 | 31.34 | WATR |
| ATOM | 5423 | OH2 | WAT | W | 145 | 0.235 | −17.424 | −16.608 | 1.00 | 38.85 | WATR |
| ATOM | 5424 | OH2 | WAT | W | 146 | 14.236 | −11.252 | −24.086 | 1.00 | 27.79 | WATR |
| ATOM | 5425 | OH2 | WAT | W | 147 | 31.513 | −22.336 | −22.128 | 1.00 | 43.18 | WATR |
| ATOM | 5426 | OH2 | WAT | W | 148 | −5.314 | −70.396 | −26.090 | 1.00 | 43.91 | WATR |
| ATOM | 5427 | OH2 | WAT | W | 149 | −7.717 | −64.969 | −36.808 | 1.00 | 26.30 | WATR |
| ATOM | 5428 | OH2 | WAT | W | 150 | 22.584 | −12.594 | −4.179 | 1.00 | 46.91 | WATR |
| ATOM | 5429 | OH2 | WAT | W | 151 | −12.388 | 9.493 | 36.619 | 1.00 | 32.82 | WATR |
| ATOM | 5430 | OH2 | WAT | W | 152 | −14.517 | 16.479 | 37.760 | 1.00 | 39.52 | WATR |
| ATOM | 5431 | OH2 | WAT | W | 153 | −10.095 | −34.647 | −29.068 | 1.00 | 41.08 | WATR |
| ATOM | 5432 | OH2 | WAT | W | 154 | −5.233 | −4.134 | 31.160 | 1.00 | 35.31 | WATR |
| ATOM | 5433 | OH2 | WAT | W | 155 | −6.322 | 11.278 | −1.883 | 1.00 | 35.75 | WATR |
| ATOM | 5434 | OH2 | WAT | W | 156 | 10.262 | −9.572 | −16.736 | 1.00 | 42.40 | WATR |
| ATOM | 5435 | OH2 | WAT | W | 157 | 22.929 | −10.414 | −23.566 | 1.00 | 36.66 | WATR |
| ATOM | 5436 | OH2 | WAT | W | 158 | −15.987 | 3.994 | 16.559 | 1.00 | 37.22 | WATR |
| ATOM | 5437 | OH2 | WAT | W | 159 | 13.385 | −44.923 | −46.826 | 1.00 | 41.55 | WATR |
| ATOM | 5438 | OH2 | WAT | W | 160 | 26.508 | −13.616 | −18.049 | 1.00 | 25.93 | WATR |
| ATOM | 5439 | OH2 | WAT | W | 161 | 4.671 | −66.907 | −17.861 | 1.00 | 31.54 | WATR |
| ATOM | 5440 | OH2 | WAT | W | 162 | −12.589 | 12.262 | 11.825 | 1.00 | 32.71 | WATR |
| ATOM | 5441 | OH2 | WAT | W | 163 | 13.899 | −62.269 | −25.144 | 1.00 | 30.71 | WATR |
| ATOM | 5442 | OH2 | WAT | W | 164 | −31.053 | 15.663 | 19.272 | 1.00 | 30.19 | WATR |
| ATOM | 5443 | OH2 | WAT | W | 165 | 9.797 | −47.899 | −25.140 | 1.00 | 26.79 | WATR |
| ATOM | 5444 | OH2 | WAT | W | 166 | 0.877 | −51.774 | −25.619 | 1.00 | 30.02 | WATR |
| ATOM | 5445 | OH2 | WAT | W | 167 | −17.088 | 16.246 | 37.180 | 1.00 | 25.63 | WATR |
| ATOM | 5446 | OH2 | WAT | W | 168 | 0.855 | −52.086 | −22.078 | 1.00 | 40.99 | WATR |
| ATOM | 5447 | OH2 | WAT | W | 169 | −14.873 | 18.295 | 21.203 | 1.00 | 40.28 | WATR |
| ATOM | 5448 | OH2 | WAT | W | 170 | 11.913 | −62.134 | −35.641 | 1.00 | 41.33 | WATR |
| ATOM | 5449 | OH2 | WAT | W | 171 | 25.783 | −23.984 | −33.162 | 1.00 | 44.03 | WATR |
| ATOM | 5450 | OH2 | WAT | W | 172 | 7.169 | −50.047 | −23.737 | 1.00 | 47.85 | WATR |
| ATOM | 5451 | OH2 | WAT | W | 173 | 20.074 | −42.845 | −14.939 | 1.00 | 32.87 | WATR |
| ATOM | 5452 | OH2 | WAT | W | 174 | 8.765 | 5.909 | 9.193 | 1.00 | 34.30 | WATR |
| ATOM | 5453 | OH2 | WAT | W | 175 | −4.953 | −64.494 | −45.351 | 1.00 | 47.11 | WATR |
| ATOM | 5454 | OH2 | WAT | W | 176 | 11.889 | −61.263 | −22.531 | 1.00 | 36.63 | WATR |
| ATOM | 5455 | OH2 | WAT | W | 177 | 2.149 | −49.169 | −24.836 | 1.00 | 39.21 | WATR |
| ATOM | 5456 | OH2 | WAT | W | 178 | −14.051 | 6.399 | 13.353 | 1.00 | 39.89 | WATR |
| ATOM | 5457 | OH2 | WAT | W | 179 | 8.488 | −46.760 | −23.118 | 1.00 | 45.24 | WATR |
| ATOM | 5458 | OH2 | WAT | W | 180 | −1.152 | −23.348 | −11.975 | 1.00 | 30.36 | WATR |
| ATOM | 5459 | OH2 | WAT | W | 181 | −7.002 | 3.531 | 7.051 | 1.00 | 44.50 | WATR |
| ATOM | 5460 | OH2 | WAT | W | 182 | −12.320 | −54.772 | −29.990 | 1.00 | 38.61 | WATR |
| ATOM | 5461 | OH2 | WAT | W | 183 | 6.790 | −54.559 | −47.733 | 1.00 | 44.05 | WATR |
| ATOM | 5462 | OH2 | WAT | W | 184 | 26.305 | −38.240 | −19.177 | 1.00 | 39.53 | WATR |
| ATOM | 5463 | OH2 | WAT | W | 185 | 20.402 | −58.179 | −34.391 | 1.00 | 46.11 | WATR |
| ATOM | 5464 | OH2 | WAT | W | 186 | 8.061 | −31.341 | −19.653 | 1.00 | 41.37 | WATR |
| ATOM | 5465 | OH2 | WAT | W | 187 | −7.549 | −15.619 | −5.482 | 1.00 | 40.60 | WATR |
| ATOM | 5466 | OH2 | WAT | W | 188 | −31.099 | 11.941 | 25.471 | 1.00 | 38.80 | WATR |
| ATOM | 5467 | OH2 | WAT | W | 189 | 28.566 | −25.441 | −15.103 | 1.00 | 34.75 | WATR |
| ATOM | 5468 | OH2 | WAT | W | 190 | −5.613 | −40.109 | −50.158 | 1.00 | 49.21 | WATR |
| ATOM | 5469 | OH2 | WAT | W | 191 | 17.024 | −13.428 | 1.709 | 1.00 | 39.93 | WATR |
| ATOM | 5470 | OH2 | WAT | W | 192 | −22.114 | 10.176 | 37.673 | 1.00 | 32.53 | WATR |
| ATOM | 5471 | OH2 | WAT | W | 193 | 10.204 | −29.330 | −20.066 | 1.00 | 27.24 | WATR |
| ATOM | 5472 | OH2 | WAT | W | 194 | 27.893 | −25.793 | −21.862 | 1.00 | 38.97 | WATR |

TABLE 1-continued

ATOMIC COORDINATES OF E. COLI MURG PROTEIN

| ATOM | 5473 | OH2 | WAT | W | 195 | -5.582 | 17.681 | 32.898 | 1.00 | 43.64 | WATR |
|---|---|---|---|---|---|---|---|---|---|---|---|
| ATOM | 5474 | OH2 | WAT | W | 196 | 23.004 | -45.224 | -27.870 | 1.00 | 43.04 | WATR |
| ATOM | 5475 | OH2 | WAT | W | 197 | 5.189 | -58.857 | -25.016 | 1.00 | 28.15 | WATR |
| ATOM | 5476 | OH2 | WAT | W | 198 | -7.740 | -56.165 | -24.052 | 1.00 | 35.98 | WATR |
| ATOM | 5477 | OH2 | WAT | W | 199 | -8.156 | 24.723 | 26.733 | 1.00 | 45.54 | WATR |
| ATOM | 5478 | OH2 | WAT | W | 200 | 23.286 | -32.333 | -33.400 | 1.00 | 38.12 | WATR |
| ATOM | 5479 | OH2 | WAT | W | 201 | 30.646 | -14.180 | -20.528 | 1.00 | 31.01 | WATR |
| ATOM | 5480 | OH2 | WAT | W | 202 | -8.238 | -4.609 | 29.299 | 1.00 | 39.76 | WATR |
| ATOM | 5481 | OH2 | WAT | W | 203 | 19.370 | 0.814 | -7.532 | 1.00 | 35.83 | WATR |
| ATOM | 5482 | OH2 | WAT | W | 204 | 0.885 | -27.619 | -1.442 | 1.00 | 47.04 | WATR |
| ATOM | 5483 | OH2 | WAT | W | 205 | 16.084 | -56.649 | -26.382 | 1.00 | 45.97 | WATR |
| ATOM | 5484 | OH2 | WAT | W | 206 | -0.698 | -19.360 | -9.869 | 1.00 | 37.53 | WATR |
| ATOM | 5485 | OH2 | WAT | W | 207 | 0.682 | -14.985 | -15.794 | 1.00 | 33.35 | WATR |
| ATOM | 5486 | OH2 | WAT | W | 208 | 1.646 | 17.427 | 31.991 | 1.00 | 40.39 | WATR |
| ATOM | 5487 | OH2 | WAT | W | 209 | -21.611 | 1.533 | 20.359 | 1.00 | 31.04 | WATR |
| ATOM | 5488 | OH2 | WAT | W | 210 | -5.143 | -55.137 | -45.825 | 1.00 | 30.17 | WATR |
| ATOM | 5489 | OH2 | WAT | W | 211 | -9.645 | 13.045 | 37.660 | 1.00 | 42.93 | WATR |
| ATOM | 5490 | OH2 | WAT | W | 212 | 22.096 | -11.242 | -30.224 | 1.00 | 48.12 | WATR |
| ATOM | 5491 | OH2 | WAT | W | 213 | -5.759 | 2.610 | -15.984 | 1.00 | 41.67 | WATR |
| ATOM | 5492 | OH2 | WAT | W | 214 | -4.323 | 7.731 | -7.331 | 1.00 | 37.92 | WATR |
| ATOM | 5493 | OH2 | WAT | W | 215 | -5.450 | 7.197 | 10.632 | 1.00 | 33.99 | WATR |
| ATOM | 5494 | OH2 | WAT | W | 216 | 2.330 | -32.635 | -34.500 | 1.00 | 38.85 | WATR |
| ATOM | 5495 | OH2 | WAT | W | 217 | -26.827 | 16.219 | 13.451 | 1.00 | 38.12 | WATR |
| ATOM | 5496 | OH2 | WAT | W | 218 | -10.887 | -51.427 | -23.191 | 1.00 | 39.81 | WATR |
| ATOM | 5497 | OH2 | WAT | W | 219 | -9.020 | 19.746 | -3.698 | 1.00 | 46.58 | WATR |
| ATOM | 5498 | OH2 | WAT | W | 220 | 9.054 | 6.622 | -0.709 | 1.00 | 34.14 | WATR |
| ATOM | 5499 | OH2 | WAT | W | 221 | 4.173 | -7.985 | -23.786 | 1.00 | 32.75 | WATR |
| ATOM | 5500 | OH2 | WAT | W | 222 | 0.983 | 16.806 | 3.910 | 1.00 | 40.83 | WATR |
| ATOM | 5501 | OH2 | WAT | W | 223 | 2.222 | -16.848 | -6.783 | 1.00 | 33.50 | WATR |
| ATOM | 5502 | OH2 | WAT | W | 224 | 13.627 | 1.072 | -15.114 | 1.00 | 37.51 | WATR |
| ATOM | 5503 | OH2 | WAT | W | 225 | 12.533 | -14.212 | -9.007 | 1.00 | 38.40 | WATR |
| ATOM | 5504 | OH2 | WAT | W | 226 | 1.404 | -7.852 | 5.396 | 1.00 | 38.55 | WATR |
| ATOM | 5505 | OH2 | WAT | W | 227 | 31.159 | -24.354 | -31.143 | 1.00 | 37.67 | WATR |
| ATOM | 5506 | OH2 | WAT | W | 228 | -13.047 | -60.728 | -42.282 | 1.00 | 42.18 | WATR |
| ATOM | 5507 | OH2 | WAT | W | 229 | 8.956 | -37.681 | -16.765 | 1.00 | 41.45 | WATR |
| ATOM | 5508 | OH2 | WAT | W | 230 | 28.749 | -13.637 | -16.860 | 1.00 | 42.34 | WATR |
| ATOM | 5509 | OH2 | WAT | W | 231 | -4.461 | 19.451 | 8.684 | 1.00 | 36.17 | WATR |
| ATOM | 5510 | OH2 | WAT | W | 232 | -9.785 | -66.504 | -35.701 | 1.00 | 44.07 | WATR |
| ATOM | 5511 | OH2 | WAT | W | 233 | 10.673 | -41.619 | -20.678 | 1.00 | 36.58 | WATR |
| ATOM | 5512 | OH2 | WAT | W | 234 | -15.694 | 1.684 | 32.613 | 1.00 | 44.04 | WATR |
| ATOM | 5513 | OH2 | WAT | W | 235 | 3.345 | 1.229 | 9.738 | 1.00 | 35.70 | WATR |
| ATOM | 5514 | OH2 | WAT | W | 236 | -6.256 | -68.913 | -30.401 | 1.00 | 36.72 | WATR |
| ATOM | 5515 | OH2 | WAT | W | 237 | 28.344 | -21.326 | -30.399 | 1.00 | 36.45 | WATR |
| ATOM | 5516 | OH2 | WAT | W | 238 | 2.876 | -34.368 | -17.344 | 1.00 | 42.48 | WATR |
| ATOM | 5517 | OH2 | WAT | W | 239 | 15.355 | -11.202 | 2.371 | 1.00 | 38.84 | WATR |
| ATOM | 5518 | OH2 | WAT | W | 240 | 27.066 | -22.336 | -6.437 | 1.00 | 37.37 | WATR |
| ATOM | 5519 | OH2 | WAT | W | 241 | 2.222 | 18.464 | 26.994 | 1.00 | 35.75 | WATR |
| ATOM | 5520 | OH2 | WAT | W | 242 | 15.052 | -9.829 | -31.019 | 1.00 | 44.31 | WATR |
| ATOM | 5521 | OH2 | WAT | W | 243 | 10.351 | -67.649 | -21.184 | 1.00 | 35.79 | WATR |
| ATOM | 5522 | OH2 | WAT | W | 244 | -13.173 | 14.269 | 38.605 | 1.00 | 41.50 | WATR |
| ATOM | 5523 | OH2 | WAT | W | 245 | -7.569 | 9.658 | 0.793 | 1.00 | 37.62 | WATR |
| ATOM | 5524 | OH2 | WAT | W | 246 | -2.167 | -47.395 | -19.605 | 1.00 | 45.90 | WATR |
| ATOM | 5525 | OH2 | WAT | W | 247 | 7.166 | 2.400 | 15.830 | 1.00 | 42.90 | WATR |
| ATOM | 5526 | OH2 | WAT | W | 248 | -11.231 | -10.901 | -10.057 | 1.00 | 45.28 | WATR |
| ATOM | 5527 | OH2 | WAT | W | 249 | 5.684 | -16.094 | -26.796 | 1.00 | 44.76 | WATR |
| ATOM | 5528 | OH2 | WAT | W | 250 | -4.745 | 3.667 | -18.932 | 1.00 | 46.20 | WATR |
| ATOM | 5529 | OH2 | WAT | W | 251 | -0.505 | -22.136 | -9.079 | 1.00 | 42.89 | WATR |
| ATOM | 5530 | OH2 | WAT | W | 252 | 16.668 | -37.987 | -7.767 | 1.00 | 35.76 | WATR |
| ATOM | 5531 | OH2 | WAT | W | 253 | 2.454 | -18.256 | -26.130 | 1.00 | 43.33 | WATR |
| ATOM | 5532 | OH2 | WAT | W | 254 | -8.367 | -39.960 | -21.638 | 1.00 | 43.07 | WATR |
| ATOM | 5533 | OH2 | WAT | W | 255 | 15.642 | 7.805 | 9.633 | 1.00 | 47.78 | WATR |
| ATOM | 5534 | OH2 | WAT | W | 256 | 13.660 | -24.331 | 1.932 | 1.00 | 42.50 | WATR |
| ATOM | 5535 | OH2 | WAT | W | 257 | 11.567 | -6.104 | -23.359 | 1.00 | 37.10 | WATR |
| ATOM | 5536 | OH2 | WAT | W | 258 | 18.941 | -16.698 | 0.528 | 1.00 | 40.97 | WATR |
| ATOM | 5537 | OH2 | WAT | W | 259 | -11.441 | -63.514 | -39.126 | 1.00 | 43.17 | WATR |
| ATOM | 5538 | OH2 | WAT | W | 260 | 28.664 | -39.605 | -22.853 | 1.00 | 42.65 | WATR |
| ATOM | 5539 | OH2 | WAT | W | 261 | 6.795 | -6.961 | 31.114 | 1.00 | 38.28 | WATR |
| ATOM | 5540 | OH2 | WAT | W | 262 | 7.077 | -14.349 | -24.858 | 1.00 | 41.00 | WATR |
| ATOM | 5541 | OH2 | WAT | W | 263 | -2.259 | -48.991 | -29.099 | 1.00 | 34.96 | WATR |
| ATOM | 5542 | OH2 | WAT | W | 264 | 21.812 | -44.128 | -35.641 | 1.00 | 44.51 | WATR |
| ATOM | 5543 | OH2 | WAT | W | 265 | -27.570 | 4.389 | 13.296 | 1.00 | 48.63 | WATR |
| ATOM | 5544 | OH2 | WAT | W | 266 | 13.573 | -27.185 | 0.220 | 1.00 | 43.56 | WATR |
| ATOM | 5545 | OH2 | WAT | W | 267 | 16.549 | 8.451 | -13.582 | 1.00 | 44.84 | WATR |
| ATOM | 5546 | OH2 | WAT | W | 268 | -9.142 | 9.107 | 36.872 | 1.00 | 37.66 | WATR |
| ATOM | 5547 | OH2 | WAT | W | 269 | 5.648 | -11.797 | -24.893 | 1.00 | 45.79 | WATR |
| ATOM | 5548 | OH2 | WAT | W | 270 | 3.619 | -14.850 | -23.652 | 1.00 | 34.09 | WATR |
| ATOM | 5549 | OH2 | WAT | W | 271 | -8.129 | -11.098 | -16.064 | 1.00 | 39.37 | WATR |

TABLE 1-continued

ATOMIC COORDINATES OF E. COLI MURG PROTEIN

| ATOM | 5550 | OH2 | WAT | W | 272 | −17.342 | 8.563 | 9.979 | 1.00 | 46.38 | WATR |
|---|---|---|---|---|---|---|---|---|---|---|---|
| ATOM | 5551 | OH2 | WAT | W | 273 | 8.798 | −36.348 | −46.119 | 1.00 | 37.71 | WATR |
| ATOM | 5552 | OH2 | WAT | W | 274 | 9.190 | −10.509 | −35.865 | 1.00 | 45.80 | WATR |
| ATOM | 5553 | OH2 | WAT | W | 275 | 13.545 | −13.441 | 3.898 | 1.00 | 42.83 | WATR |
| ATOM | 5554 | OH2 | WAT | W | 276 | −7.844 | 0.944 | −2.560 | 1.00 | 46.27 | WATR |
| ATOM | 5555 | OH2 | WAT | W | 277 | 0.478 | −47.721 | −55.170 | 1.00 | 46.25 | WATR |
| ATOM | 5556 | OH2 | WAT | W | 278 | 24.658 | −18.359 | −11.005 | 1.00 | 36.33 | WATR |
| ATOM | 5557 | OH2 | WAT | W | 279 | −4.675 | 21.561 | 12.155 | 1.00 | 37.17 | WATR |
| ATOM | 5558 | OH2 | WAT | W | 280 | 0.382 | 20.486 | 4.930 | 1.00 | 41.40 | WATR |
| ATOM | 5559 | OH2 | WAT | W | 281 | 5.919 | 18.010 | 25.033 | 1.00 | 41.72 | WATR |
| ATOM | 5560 | OH2 | WAT | W | 282 | −2.987 | −63.751 | −22.983 | 1.00 | 43.76 | WATR |
| ATOM | 5561 | OH2 | WAT | W | 283 | 8.990 | −33.134 | −17.898 | 1.00 | 40.17 | WATR |
| ATOM | 5562 | OH2 | WAT | W | 284 | 0.155 | −61.872 | −48.384 | 1.00 | 49.87 | WATR |
| ATOM | 5563 | OH2 | WAT | W | 285 | −10.443 | −56.965 | −24.681 | 1.00 | 48.02 | WATR |
| ATOM | 5564 | OH2 | WAT | W | 286 | 18.915 | −33.048 | −3.930 | 1.00 | 37.81 | WATR |
| ATOM | 5565 | OH2 | WAT | W | 287 | −16.181 | 11.706 | 12.277 | 1.00 | 41.77 | WATR |
| ATOM | 5566 | OH2 | WAT | W | 288 | 7.197 | 7.180 | 10.953 | 1.00 | 46.19 | WATR |
| ATOM | 5567 | OH2 | WAT | W | 289 | 31.934 | −26.155 | −26.053 | 1.00 | 38.77 | WATR |
| ATOM | 5568 | OH2 | WAT | W | 290 | −15.232 | −0.248 | −11.315 | 1.00 | 40.14 | WATR |
| ATOM | 5569 | OH2 | WAT | W | 291 | 9.450 | −27.963 | −1.396 | 1.00 | 41.29 | WATR |
| ATOM | 5570 | OH2 | WAT | W | 292 | −1.800 | 13.139 | −9.983 | 1.00 | 41.60 | WATR |
| ATOM | 5571 | OH2 | WAT | W | 293 | −7.766 | 5.988 | 9.798 | 1.00 | 40.11 | WATR |
| ATOM | 5572 | OH2 | WAT | W | 294 | 7.973 | 4.338 | 14.321 | 1.00 | 39.97 | WATR |
| ATOM | 5573 | OH2 | WAT | W | 295 | 23.449 | −40.563 | −27.347 | 1.00 | 40.59 | WATR |
| ATOM | 5574 | OH2 | WAT | W | 296 | −3.537 | −28.260 | −15.925 | 1.00 | 42.10 | WATR |
| ATOM | 5575 | OH2 | WAT | W | 297 | 28.052 | −32.620 | −12.168 | 1.00 | 48.03 | WATR |
| ATOM | 5576 | OH2 | WAT | W | 298 | 20.655 | −43.315 | −28.829 | 1.00 | 40.17 | WATR |
| ATOM | 5577 | S | SO4 | S | 1 | 1.273 | −70.953 | −23.009 | 1.00 | 22.99 | SO4 |
| ATOM | 5578 | O1 | SO4 | S | 1 | 1.720 | −71.882 | −24.053 | 1.00 | 21.18 | SO4 |
| ATOM | 5579 | O2 | SO4 | S | 1 | 0.908 | −69.659 | −23.626 | 1.00 | 22.47 | SO4 |
| ATOM | 5580 | O3 | SO4 | S | 1 | 2.337 | −70.752 | −22.018 | 1.00 | 23.88 | SO4 |
| ATOM | 5581 | O4 | SO4 | S | 1 | 0.088 | −71.522 | −22.328 | 1.00 | 22.50 | SO4 |
| TEREND | | | | | | | | | | | |

TABLE 2

ATOMIC COORDINATES OF E. COLI MURG C-ALPHA BACKBONE ATOMS

| ATOM | 2649 | CA | LYS | B | 7 | −6.512 | −45.403 | −47.519 | 1.00 | 45.28 | BBBB |
|---|---|---|---|---|---|---|---|---|---|---|---|
| ATOM | 2651 | CA | ARG | B | 8 | −6.682 | −47.303 | −44.240 | 1.00 | 38.63 | BBBB |
| ATOM | 2662 | CA | LEU | B | 9 | −4.094 | −47.039 | −41.477 | 1.00 | 30.88 | BBBB |
| ATOM | 2670 | CA | MET | B | 10 | −4.048 | −49.055 | −38.275 | 1.00 | 26.66 | BBBB |
| ATOM | 2678 | CA | VAL | B | 11 | −1.982 | −47.605 | −35.449 | 1.00 | 23.16 | BBBB |
| ATOM | 2685 | CA | MET | B | 12 | −0.523 | −49.707 | −32.613 | 1.00 | 24.54 | BBBB |
| ATOM | 2693 | CA | ALA | B | 13 | 0.508 | −47.410 | −29.752 | 1.00 | 29.43 | BBBB |
| ATOM | 2698 | CA | GLY | B | 14 | −0.513 | −47.804 | −26.120 | 1.00 | 33.82 | BBBB |
| ATOM | 2702 | CA | GLY | B | 15 | −0.700 | −45.047 | −23.536 | 1.00 | 36.08 | BBBB |
| ATOM | 2706 | CA | THR | B | 16 | 1.920 | −46.787 | −21.421 | 1.00 | 38.51 | BBBB |
| ATOM | 2713 | CA | GLY | B | 17 | 5.367 | −45.567 | −22.392 | 1.00 | 36.57 | BBBB |
| ATOM | 2717 | CA | GLY | B | 18 | 3.631 | −42.529 | −23.872 | 1.00 | 33.48 | BBBB |
| ATOM | 2721 | CA | HIS | B | 19 | 3.548 | −43.865 | −27.435 | 1.00 | 28.22 | BBBB |
| ATOM | 2731 | CA | VAL | B | 20 | −0.098 | −42.894 | −27.965 | 1.00 | 27.77 | BBBB |
| ATOM | 2738 | CA | PHE | B | 21 | 0.517 | −39.136 | −28.160 | 1.00 | 29.00 | BBBB |
| ATOM | 2750 | CA | PRO | B | 22 | 2.986 | −39.252 | −31.086 | 1.00 | 26.12 | BBBB |
| ATOM | 2756 | CA | GLY | B | 23 | 0.787 | −41.864 | −32.752 | 1.00 | 25.07 | BBBB |
| ATOM | 2760 | CA | LEU | B | 24 | −2.201 | −39.551 | −32.401 | 1.00 | 25.32 | BBBB |
| ATOM | 2768 | CA | ALA | B | 25 | −0.197 | −36.754 | −34.013 | 1.00 | 25.94 | BBBB |
| ATOM | 2773 | CA | VAL | B | 26 | 0.466 | −38.955 | −37.056 | 1.00 | 25.70 | BBBB |
| ATOM | 2780 | CA | ALA | B | 27 | −3.116 | −40.222 | −37.199 | 1.00 | 26.15 | BBBB |
| ATOM | 2785 | CA | HIS | B | 28 | −4.574 | −36.702 | −37.190 | 1.00 | 29.32 | BBBB |
| ATOM | 2795 | CA | HIS | B | 29 | −2.070 | −35.623 | −39.806 | 1.00 | 32.38 | BBBB |
| ATOM | 2805 | CA | LEU | B | 30 | −3.136 | −38.417 | −42.162 | 1.00 | 32.00 | BBBB |
| ATOM | 2813 | CA | MET | B | 31 | −6.849 | −38.064 | −41.424 | 1.00 | 34.91 | BBBB |
| ATOM | 2821 | CA | ALA | B | 32 | −6.510 | −34.511 | −42.722 | 1.00 | 37.55 | BBBB |
| ATOM | 2826 | CA | GLN | B | 33 | −5.182 | −36.070 | −45.938 | 1.00 | 38.24 | BBBB |
| ATOM | 2835 | CA | GLY | B | 34 | −8.305 | −38.169 | −46.353 | 1.00 | 35.75 | BBBB |
| ATOM | 2839 | CA | TRP | B | 35 | −7.016 | −41.246 | −44.508 | 1.00 | 34.58 | BBBB |
| ATOM | 2853 | CA | GLN | B | 36 | −9.175 | −43.535 | −42.402 | 1.00 | 35.40 | BBBB |
| ATOM | 2862 | CA | VAL | B | 37 | −7.417 | −44.516 | −39.184 | 1.00 | 34.16 | BBBB |
| ATOM | 2869 | CA | ARG | B | 38 | −8.219 | −47.286 | −36.730 | 1.00 | 31.56 | BBBB |
| ATOM | 2880 | CA | TRP | B | 39 | −6.456 | −48.070 | −33.471 | 1.00 | 27.41 | BBBB |
| ATOM | 2894 | CA | LEU | B | 40 | −5.200 | −51.364 | −32.026 | 1.00 | 24.71 | BBBB |
| ATOM | 2902 | CA | GLY | B | 41 | −4.691 | −51.450 | −28.257 | 1.00 | 23.47 | BBBB |

TABLE 2-continued

ATOMIC COORDINATES OF *E. COLI* MURG C-ALPHA BACKBONE ATOMS

| ATOM | 2906 | CA | THR | B | 42 | −5.787 | −53.141 | −25.027 | 1.00 | 29.84 | BBBB |
|---|---|---|---|---|---|---|---|---|---|---|---|
| ATOM | 2913 | CA | ALA | B | 43 | −9.000 | −52.595 | −23.047 | 1.00 | 38.81 | BBBB |
| ATOM | 2918 | CA | ASP | B | 44 | −7.455 | −51.942 | −19.632 | 1.00 | 44.47 | BBBB |
| ATOM | 2926 | CA | ARG | B | 45 | −4.887 | −49.367 | −20.763 | 1.00 | 40.44 | BBBB |
| ATOM | 2937 | CA | MET | B | 46 | −4.881 | −45.581 | −21.249 | 1.00 | 36.33 | BBBB |
| ATOM | 2945 | CA | GLU | B | 47 | −5.458 | −45.655 | −25.029 | 1.00 | 31.79 | BBBB |
| ATOM | 2954 | CA | ALA | B | 48 | −8.821 | −47.344 | −24.414 | 1.00 | 32.58 | BBBB |
| ATOM | 2959 | CA | ASP | B | 49 | −10.143 | −44.065 | −23.009 | 1.00 | 35.60 | BBBB |
| ATOM | 2967 | CA | LEU | B | 50 | −8.026 | −41.484 | −24.840 | 1.00 | 33.49 | BBBB |
| ATOM | 2975 | CA | VAL | B | 51 | −8.299 | −42.641 | −28.449 | 1.00 | 32.68 | BBBB |
| ATOM | 2983 | CA | PRO | B | 52 | −12.111 | −42.601 | −28.453 | 1.00 | 34.43 | BBBB |
| ATOM | 2989 | CA | LYS | B | 53 | −11.998 | −39.054 | −27.064 | 1.00 | 36.73 | BBBB |
| ATOM | 2998 | CA | HIS | B | 54 | −10.116 | −38.212 | −30.259 | 1.00 | 34.62 | BBBB |
| ATOM | 3008 | CA | GLY | B | 55 | −12.938 | −39.481 | −32.447 | 1.00 | 35.34 | BBBB |
| ATOM | 3012 | CA | ILE | B | 56 | −10.909 | −42.517 | −33.514 | 1.00 | 33.81 | BBBB |
| ATOM | 3020 | CA | GLU | B | 57 | −12.228 | −46.083 | −33.467 | 1.00 | 34.16 | BBBB |
| ATOM | 3029 | CA | ILE | B | 58 | −10.217 | −48.658 | −31.553 | 1.00 | 31.38 | BBBB |
| ATOM | 3037 | CA | ASP | B | 59 | −10.039 | −52.442 | −31.720 | 1.00 | 31.09 | BBBB |
| ATOM | 3045 | CA | PHE | B | 60 | −8.809 | −54.410 | −28.713 | 1.00 | 30.32 | BBBB |
| ATOM | 3056 | CA | ILE | B | 61 | −6.832 | −57.616 | −28.269 | 1.00 | 28.55 | BBBB |
| ATOM | 3064 | CA | ARG | B | 62 | −5.709 | −59.416 | −25.133 | 1.00 | 30.76 | BBBB |
| ATOM | 3075 | CA | ILE | B | 63 | −2.036 | −59.770 | −24.231 | 1.00 | 31.38 | BBBB |
| ATOM | 3083 | CA | SER | B | 64 | −2.356 | −60.520 | −20.505 | 1.00 | 37.51 | BBBB |
| ATOM | 3089 | CA | GLY | B | 65 | 0.679 | −62.355 | −19.199 | 1.00 | 37.13 | BBBB |
| ATOM | 3093 | CA | LEU | B | 66 | 2.591 | −61.413 | −22.355 | 1.00 | 33.17 | BBBB |
| ATOM | 3101 | CA | ARG | B | 67 | 3.671 | −57.928 | −21.277 | 1.00 | 30.90 | BBBB |
| ATOM | 3112 | CA | GLY | B | 68 | 7.380 | −57.427 | −20.685 | 1.00 | 26.79 | BBBB |
| ATOM | 3116 | CA | LYS | B | 69 | 8.238 | −60.463 | −22.796 | 1.00 | 23.93 | BBBB |
| ATOM | 3125 | CA | GLY | B | 70 | 10.755 | −60.229 | −25.636 | 1.00 | 22.26 | BBBB |
| ATOM | 3129 | CA | ILE | B | 71 | 10.357 | −62.386 | −28.762 | 1.00 | 23.55 | BBBB |
| ATOM | 3137 | CA | LYS | B | 72 | 12.038 | −65.491 | −27.343 | 1.00 | 24.92 | BBBB |
| ATOM | 3146 | CA | ALA | B | 73 | 9.839 | −65.306 | −24.233 | 1.00 | 21.18 | BBBB |
| ATOM | 3151 | CA | LEU | B | 74 | 6.745 | −64.762 | −26.387 | 1.00 | 19.36 | BBBB |
| ATOM | 3159 | CA | ILE | B | 75 | 7.434 | −67.768 | −28.601 | 1.00 | 21.18 | BBBB |
| ATOM | 3167 | CA | ALA | B | 76 | 7.996 | −69.726 | −25.374 | 1.00 | 21.72 | BBBB |
| ATOM | 3172 | CA | ALA | B | 77 | 4.289 | −69.121 | −24.655 | 1.00 | 21.07 | BBBB |
| ATOM | 3178 | CA | PRO | B | 78 | 2.772 | −70.846 | −27.771 | 1.00 | 20.95 | BBBB |
| ATOM | 3184 | CA | LEU | B | 79 | −0.896 | −70.728 | −26.783 | 1.00 | 21.32 | BBBB |
| ATOM | 3192 | CA | ARG | B | 80 | −0.980 | −67.115 | −25.637 | 1.00 | 21.30 | BBBB |
| ATOM | 3203 | CA | ILE | B | 81 | 1.113 | −65.621 | −28.421 | 1.00 | 19.47 | BBBB |
| ATOM | 3211 | CA | PHE | B | 82 | −0.875 | −67.582 | −31.038 | 1.00 | 19.15 | BBBB |
| ATOM | 3222 | CA | ASN | B | 83 | −4.150 | −66.332 | −29.577 | 1.00 | 20.90 | BBBB |
| ATOM | 3230 | CA | ALA | B | 84 | −3.177 | −62.647 | −29.484 | 1.00 | 19.30 | BBBB |
| ATOM | 3235 | CA | TRP | B | 85 | −1.820 | −63.111 | −33.032 | 1.00 | 20.56 | BBBB |
| ATOM | 3249 | CA | ARG | B | 86 | −5.140 | −64.660 | −34.166 | 1.00 | 23.28 | BBBB |
| ATOM | 3260 | CA | GLN | B | 87 | −7.101 | −61.802 | −32.567 | 1.00 | 24.07 | BBBB |
| ATOM | 3269 | CA | ALA | B | 88 | −4.996 | −59.183 | −34.355 | 1.00 | 23.78 | BBBB |
| ATOM | 3274 | CA | ARG | B | 89 | −5.285 | −61.111 | −37.636 | 1.00 | 24.94 | BBBB |
| ATOM | 3285 | CA | ALA | B | 90 | −9.088 | −61.151 | −37.383 | 1.00 | 26.16 | BBBB |
| ATOM | 3290 | CA | ILE | B | 91 | −9.108 | −57.400 | −36.733 | 1.00 | 26.97 | BBBB |
| ATOM | 3298 | CA | MET | B | 92 | −6.872 | −56.693 | −39.717 | 1.00 | 29.03 | BBBB |
| ATOM | 3306 | CA | LYS | B | 93 | −8.735 | −59.038 | −42.050 | 1.00 | 33.20 | BBBB |
| ATOM | 3315 | CA | ALA | B | 94 | −11.943 | −57.157 | −41.183 | 1.00 | 33.62 | BBBB |
| ATOM | 3320 | CA | TYR | B | 95 | −10.504 | −53.620 | −41.224 | 1.00 | 33.83 | BBBB |
| ATOM | 3332 | CA | LYS | B | 96 | −8.104 | −54.327 | −44.122 | 1.00 | 33.85 | BBBB |
| ATOM | 3342 | CA | PRO | B | 97 | −5.490 | −51.623 | −43.419 | 1.00 | 31.82 | BBBB |
| ATOM | 3348 | CA | ASP | B | 98 | −3.049 | −50.685 | −46.188 | 1.00 | 29.78 | BBBB |
| ATOM | 3356 | CA | VAL | B | 99 | −0.296 | −50.214 | −43.660 | 1.00 | 26.75 | BBBB |
| ATOM | 3363 | CA | VAL | B | 100 | 0.227 | −50.613 | −39.936 | 1.00 | 23.59 | BBBB |
| ATOM | 3370 | CA | LEU | B | 101 | 2.214 | −48.199 | −37.797 | 1.00 | 21.59 | BBBB |
| ATOM | 3378 | CA | GLY | B | 102 | 3.796 | −49.357 | −34.549 | 1.00 | 19.23 | BBBB |
| ATOM | 3382 | CA | MET | B | 103 | 4.892 | −46.597 | −32.191 | 1.00 | 18.93 | BBBB |
| ATOM | 3390 | CA | GLY | B | 104 | 6.275 | −49.080 | −29.686 | 1.00 | 21.89 | BBBB |
| ATOM | 3394 | CA | GLY | B | 105 | 4.593 | −50.905 | −26.827 | 1.00 | 23.54 | BBBB |
| ATOM | 3398 | CA | TYR | B | 106 | 3.818 | −54.554 | −26.159 | 1.00 | 22.37 | BBBB |
| ATOM | 3410 | CA | VAL | B | 107 | 0.557 | −54.694 | −28.099 | 1.00 | 18.06 | BBBB |
| ATOM | 3417 | CA | SER | B | 108 | 2.488 | −53.892 | −31.290 | 1.00 | 19.67 | BBBB |
| ATOM | 3423 | CA | GLY | B | 109 | 4.251 | −57.256 | −31.023 | 1.00 | 20.03 | BBBB |
| ATOM | 3428 | CA | PRO | B | 110 | 1.251 | −59.478 | −31.855 | 1.00 | 18.99 | BBBB |
| ATOM | 3434 | CA | GLY | B | 111 | −0.160 | −56.702 | −34.025 | 1.00 | 19.60 | BBBB |
| ATOM | 3438 | CA | GLY | B | 112 | 3.014 | −56.417 | −36.074 | 1.00 | 19.97 | BBBB |
| ATOM | 3442 | CA | LEU | B | 113 | 3.265 | −60.184 | −36.429 | 1.00 | 19.49 | BBBB |
| ATOM | 3450 | CA | ALA | B | 114 | −0.334 | −60.292 | −37.661 | 1.00 | 18.70 | BBBB |
| ATOM | 3455 | CA | ALA | B | 115 | 0.167 | −57.516 | −40.229 | 1.00 | 21.84 | BBBB |
| ATOM | 3460 | CA | TRP | B | 116 | 3.365 | −59.126 | −41.478 | 1.00 | 23.22 | BBBB |
| ATOM | 3474 | CA | SER | B | 117 | 1.735 | −62.573 | −41.873 | 1.00 | 22.61 | BBBB |

TABLE 2-continued

ATOMIC COORDINATES OF *E. COLI* MURG C-ALPHA
BACKBONE ATOMS

| ATOM | 3480 | CA | LEU | B | 118 | −1.069 | −60.957 | −43.882 | 1.00 | 25.70 | BBBB |
|------|------|----|----|---|-----|--------|---------|---------|------|-------|------|
| ATOM | 3488 | CA | GLY | B | 119 | 1.354 | −59.174 | −46.192 | 1.00 | 27.80 | BBBB |
| ATOM | 3492 | CA | ILE | B | 120 | 0.568 | −55.744 | −44.731 | 1.00 | 24.85 | BBBB |
| ATOM | 3501 | CA | PRO | B | 121 | 3.625 | −53.477 | −44.591 | 1.00 | 22.63 | BBBB |
| ATOM | 3507 | CA | VAL | B | 122 | 4.743 | −52.594 | −41.083 | 1.00 | 22.03 | BBBB |
| ATOM | 3514 | CA | VAL | B | 123 | 6.200 | −49.184 | −40.310 | 1.00 | 20.82 | BBBB |
| ATOM | 3521 | CA | LEU | B | 124 | 7.749 | −48.485 | −36.915 | 1.00 | 22.10 | BBBB |
| ATOM | 3529 | CA | HIS | B | 125 | 8.814 | −45.413 | −34.981 | 1.00 | 21.42 | BBBB |
| ATOM | 3539 | CA | GLU | B | 126 | 10.947 | −45.452 | −31.817 | 1.00 | 22.15 | BBBB |
| ATOM | 3548 | CA | GLN | B | 127 | 10.682 | −42.270 | −29.735 | 1.00 | 22.81 | BBBB |
| ATOM | 3557 | CA | ASN | B | 128 | 13.406 | −43.097 | −27.216 | 1.00 | 22.96 | BBBB |
| ATOM | 3565 | CA | GLY | B | 129 | 17.203 | −43.019 | −27.294 | 1.00 | 25.36 | BBBB |
| ATOM | 3569 | CA | ILE | B | 130 | 17.160 | −46.716 | −26.488 | 1.00 | 28.00 | BBBB |
| ATOM | 3577 | CA | ALA | B | 131 | 14.978 | −49.139 | −28.461 | 1.00 | 25.88 | BBBB |
| ATOM | 3582 | CA | GLY | B | 132 | 12.007 | −50.532 | −26.568 | 1.00 | 24.05 | BBBB |
| ATOM | 3586 | CA | LEU | B | 133 | 11.903 | −54.293 | −26.020 | 1.00 | 24.54 | BBBB |
| ATOM | 3594 | CA | THR | B | 134 | 9.202 | −54.860 | −28.639 | 1.00 | 21.22 | BBBB |
| ATOM | 3601 | CA | ASN | B | 135 | 10.407 | −52.419 | −31.324 | 1.00 | 20.50 | BBBB |
| ATOM | 3609 | CA | LYS | B | 136 | 13.886 | −53.949 | −31.144 | 1.00 | 22.79 | BBBB |
| ATOM | 3618 | CA | TRP | B | 137 | 12.753 | −57.345 | −32.424 | 1.00 | 22.06 | BBBB |
| ATOM | 3632 | CA | LEU | B | 138 | 9.744 | −56.188 | −34.431 | 1.00 | 23.15 | BBBB |
| ATOM | 3640 | CA | ALA | B | 139 | 12.128 | −54.092 | −36.542 | 1.00 | 25.29 | BBBB |
| ATOM | 3645 | CA | LYS | B | 140 | 13.279 | −57.337 | −38.182 | 1.00 | 28.05 | BBBB |
| ATOM | 3654 | CA | ILE | B | 141 | 9.963 | −57.818 | −40.016 | 1.00 | 26.09 | BBBB |
| ATOM | 3662 | CA | ALA | B | 142 | 9.331 | −54.107 | −40.498 | 1.00 | 25.03 | BBBB |
| ATOM | 3667 | CA | THR | B | 143 | 9.262 | −52.595 | −43.984 | 1.00 | 26.10 | BBBB |
| ATOM | 3674 | CA | LYS | B | 144 | 10.436 | −49.238 | −42.618 | 1.00 | 24.73 | BBBB |
| ATOM | 3683 | CA | VAL | B | 145 | 11.947 | −48.311 | −39.252 | 1.00 | 23.62 | BBBB |
| ATOM | 3690 | CA | MET | B | 146 | 12.338 | −44.736 | −37.993 | 1.00 | 23.15 | BBBB |
| ATOM | 3698 | CA | GLN | B | 147 | 13.762 | −43.418 | −34.712 | 1.00 | 25.05 | BBBB |
| ATOM | 3707 | CA | ALA | B | 148 | 13.559 | −40.032 | −33.009 | 1.00 | 26.88 | BBBB |
| ATOM | 3712 | CA | PHE | B | 149 | 17.239 | −39.820 | −32.098 | 1.00 | 29.39 | BBBB |
| ATOM | 3724 | CA | PRO | B | 150 | 20.310 | −41.541 | −33.535 | 1.00 | 31.87 | BBBB |
| ATOM | 3730 | CA | GLY | B | 151 | 21.629 | −44.537 | −31.595 | 1.00 | 32.62 | BBBB |
| ATOM | 3734 | CA | ALA | B | 152 | 18.447 | −46.476 | −30.753 | 1.00 | 32.71 | BBBB |
| ATOM | 3739 | CA | PHE | B | 153 | 18.925 | −48.506 | −33.937 | 1.00 | 34.83 | BBBB |
| ATOM | 3751 | CA | PRO | B | 154 | 22.158 | −48.751 | −35.993 | 1.00 | 38.97 | BBBB |
| ATOM | 3757 | CA | ASN | B | 155 | 20.765 | −47.568 | −39.346 | 1.00 | 41.08 | BBBB |
| ATOM | 3765 | CA | ALA | B | 156 | 17.170 | −46.407 | −38.843 | 1.00 | 37.55 | BBBB |
| ATOM | 3770 | CA | GLU | B | 157 | 16.367 | −43.044 | −40.460 | 1.00 | 34.40 | BBBB |
| ATOM | 3779 | CA | VAL | B | 158 | 16.337 | −40.344 | −37.764 | 1.00 | 31.16 | BBBB |
| ATOM | 3786 | CA | VAL | B | 159 | 13.155 | −38.265 | −37.889 | 1.00 | 28.10 | BBBB |
| ATOM | 3793 | CA | GLY | B | 160 | 12.724 | −36.921 | −34.355 | 1.00 | 26.93 | BBBB |
| ATOM | 3797 | CA | ASN | B | 161 | 9.456 | −36.807 | −32.375 | 1.00 | 25.27 | BBBB |
| ATOM | 3806 | CA | PRO | B | 162 | 6.315 | −34.747 | −33.004 | 1.00 | 26.14 | BBBB |
| ATOM | 3812 | CA | VAL | B | 163 | 6.456 | −31.379 | −31.216 | 1.00 | 27.75 | BBBB |
| ATOM | 3819 | CA | ARG | B | 164 | 3.667 | −28.953 | −30.246 | 1.00 | 32.36 | BBBB |
| ATOM | 3830 | CA | THR | B | 165 | 3.038 | −26.307 | −32.924 | 1.00 | 31.74 | BBBB |
| ATOM | 3837 | CA | ASP | B | 166 | 3.252 | −23.404 | −30.466 | 1.00 | 30.64 | BBBB |
| ATOM | 3845 | CA | VAL | B | 167 | 6.746 | −24.503 | −29.440 | 1.00 | 25.91 | BBBB |
| ATOM | 3852 | CA | LEU | B | 168 | 7.780 | −25.002 | −33.075 | 1.00 | 28.46 | BBBB |
| ATOM | 3860 | CA | ALA | B | 169 | 6.580 | −21.455 | −33.756 | 1.00 | 31.43 | BBBB |
| ATOM | 3865 | CA | LEU | B | 170 | 9.002 | −19.905 | −31.268 | 1.00 | 29.60 | BBBB |
| ATOM | 3874 | CA | PRO | B | 171 | 11.611 | −17.457 | −32.642 | 1.00 | 30.11 | BBBB |
| ATOM | 3880 | CA | LEU | B | 172 | 15.157 | −18.780 | −33.062 | 1.00 | 28.33 | BBBB |
| ATOM | 3889 | CA | PRO | B | 173 | 17.450 | −18.550 | −29.977 | 1.00 | 25.25 | BBBB |
| ATOM | 3895 | CA | GLN | B | 174 | 19.526 | −15.527 | −31.049 | 1.00 | 25.46 | BBBB |
| ATOM | 3904 | CA | GLN | B | 175 | 16.365 | −13.525 | −31.718 | 1.00 | 28.47 | BBBB |
| ATOM | 3913 | CA | ARG | B | 176 | 14.611 | −14.635 | −28.525 | 1.00 | 29.01 | BBBB |
| ATOM | 3924 | CA | LEU | B | 177 | 17.673 | −13.970 | −26.331 | 1.00 | 29.90 | BBBB |
| ATOM | 3932 | CA | ALA | B | 178 | 18.766 | −10.776 | −28.131 | 1.00 | 30.78 | BBBB |
| ATOM | 3937 | CA | GLY | B | 179 | 19.846 | −7.993 | −25.784 | 1.00 | 30.10 | BBBB |
| ATOM | 3941 | CA | ARG | B | 180 | 18.676 | −9.965 | −22.787 | 1.00 | 28.97 | BBBB |
| ATOM | 3952 | CA | GLU | B | 181 | 20.545 | −9.027 | −19.621 | 1.00 | 31.79 | BBBB |
| ATOM | 3961 | CA | GLY | B | 182 | 19.871 | −9.586 | −15.943 | 1.00 | 27.75 | BBBB |
| ATOM | 3966 | CA | PRO | B | 183 | 19.450 | −12.832 | −13.913 | 1.00 | 22.93 | BBBB |
| ATOM | 3972 | CA | VAL | B | 184 | 19.524 | −16.146 | −15.729 | 1.00 | 18.01 | BBBB |
| ATOM | 3979 | CA | ARG | B | 185 | 15.873 | −17.216 | −16.011 | 1.00 | 17.62 | BBBB |
| ATOM | 3990 | CA | VAL | B | 186 | 15.508 | −20.771 | −14.741 | 1.00 | 16.47 | BBBB |
| ATOM | 3997 | CA | LEU | B | 187 | 12.361 | −22.710 | −15.604 | 1.00 | 16.75 | BBBB |
| ATOM | 4005 | CA | VAL | B | 188 | 11.774 | −25.775 | −13.381 | 1.00 | 18.41 | BBBB |
| ATOM | 4012 | CA | VAL | B | 189 | 9.298 | −28.234 | −14.948 | 1.00 | 22.11 | BBBB |
| ATOM | 4019 | CA | GLY | B | 190 | 7.914 | −31.188 | −12.994 | 1.00 | 27.28 | BBBB |
| ATOM | 4023 | CA | GLY | B | 191 | 4.935 | −32.163 | −15.115 | 1.00 | 31.94 | BBBB |
| ATOM | 4027 | CA | SER | B | 192 | 1.313 | −32.665 | −14.064 | 1.00 | 35.91 | BBBB |
| ATOM | 4033 | CA | GLN | B | 193 | 2.292 | −34.763 | −11.033 | 1.00 | 38.53 | BBBB |

TABLE 2-continued

ATOMIC COORDINATES OF *E. COLI* MURG C-ALPHA
BACKBONE ATOMS

| ATOM | 4042 | CA | GLY | B | 194 | 5.398 | −32.711 | −10.350 | 1.00 | 35.02 | BBBB |
|---|---|---|---|---|---|---|---|---|---|---|---|
| ATOM | 4046 | CA | ALA | B | 195 | 8.977 | −33.819 | −9.709 | 1.00 | 33.12 | BBBB |
| ATOM | 4051 | CA | ARG | B | 196 | 9.538 | −34.512 | −6.010 | 1.00 | 32.63 | BBBB |
| ATOM | 4062 | CA | ILE | B | 197 | 13.329 | −34.168 | −6.164 | 1.00 | 28.10 | BBBB |
| ATOM | 4070 | CA | LEU | B | 198 | 13.069 | −30.833 | −8.003 | 1.00 | 26.58 | BBBB |
| ATOM | 4078 | CA | ASN | B | 199 | 10.497 | −29.447 | −5.563 | 1.00 | 27.07 | BBBB |
| ATOM | 4086 | CA | GLN | B | 200 | 12.955 | −30.326 | −2.794 | 1.00 | 30.10 | BBBB |
| ATOM | 4095 | CA | THR | B | 201 | 16.215 | −29.345 | −4.474 | 1.00 | 27.34 | BBBB |
| ATOM | 4102 | CA | MET | B | 202 | 15.567 | −26.048 | −6.268 | 1.00 | 23.68 | BBBB |
| ATOM | 4111 | CA | PRO | B | 203 | 14.608 | −23.963 | −3.220 | 1.00 | 23.84 | BBBB |
| ATOM | 4117 | CA | GLN | B | 204 | 18.033 | −24.708 | −1.684 | 1.00 | 26.34 | BBBB |
| ATOM | 4126 | CA | VAL | B | 205 | 19.672 | −24.033 | −5.043 | 1.00 | 24.44 | BBBB |
| ATOM | 4133 | CA | ALA | B | 206 | 17.980 | −20.610 | −5.013 | 1.00 | 22.84 | BBBB |
| ATOM | 4138 | CA | ALA | B | 207 | 19.442 | −19.857 | −1.576 | 1.00 | 26.65 | BBBB |
| ATOM | 4143 | CA | LYS | B | 208 | 22.915 | −20.595 | −2.919 | 1.00 | 28.31 | BBBB |
| ATOM | 4152 | CA | LEU | B | 209 | 22.577 | −18.640 | −6.171 | 1.00 | 25.68 | BBBB |
| ATOM | 4160 | CA | GLY | B | 210 | 20.675 | −15.628 | −4.804 | 1.00 | 26.56 | BBBB |
| ATOM | 4164 | CA | ASP | B | 211 | 20.370 | −12.647 | −7.190 | 1.00 | 28.28 | BBBB |
| ATOM | 4172 | CA | SER | B | 212 | 22.098 | −14.474 | −10.067 | 1.00 | 25.73 | BBBB |
| ATOM | 4178 | CA | VAL | B | 213 | 18.925 | −16.308 | −11.116 | 1.00 | 20.76 | BBBB |
| ATOM | 4185 | CA | THR | B | 214 | 15.204 | −15.726 | −11.337 | 1.00 | 19.60 | BBBB |
| ATOM | 4192 | CA | ILE | B | 215 | 13.076 | −18.850 | −11.169 | 1.00 | 18.75 | BBBB |
| ATOM | 4200 | CA | TRP | B | 216 | 9.661 | −19.973 | −12.378 | 1.00 | 19.34 | BBBB |
| ATOM | 4214 | CA | HIS | B | 217 | 9.015 | −23.303 | −10.680 | 1.00 | 21.06 | BBBB |
| ATOM | 4224 | CA | GLN | B | 218 | 6.149 | −25.594 | −11.735 | 1.00 | 24.30 | BBBB |
| ATOM | 4233 | CA | SER | B | 219 | 5.463 | −27.800 | −8.684 | 1.00 | 26.73 | BBBB |
| ATOM | 4239 | CA | GLY | B | 220 | 2.855 | −30.242 | −9.961 | 1.00 | 30.53 | BBBB |
| ATOM | 4243 | CA | LYS | B | 221 | −0.657 | −30.914 | −8.628 | 1.00 | 35.12 | BBBB |
| ATOM | 4252 | CA | GLY | B | 222 | −1.195 | −29.899 | −5.011 | 1.00 | 35.34 | BBBB |
| ATOM | 4256 | CA | SER | B | 223 | 2.451 | −28.934 | −4.418 | 1.00 | 33.98 | BBBB |
| ATOM | 4262 | CA | GLN | B | 224 | 2.187 | −25.208 | −5.186 | 1.00 | 33.71 | BBBB |
| ATOM | 4271 | CA | GLN | B | 225 | 1.823 | −24.239 | −1.519 | 1.00 | 32.32 | BBBB |
| ATOM | 4280 | CA | SER | B | 226 | 4.701 | −26.309 | −0.122 | 1.00 | 28.30 | BBBB |
| ATOM | 4286 | CA | VAL | B | 227 | 7.214 | −25.247 | −2.791 | 1.00 | 24.28 | BBBB |
| ATOM | 4293 | CA | GLU | B | 228 | 6.178 | −21.592 | −2.387 | 1.00 | 27.23 | BBBB |
| ATOM | 4302 | CA | GLN | B | 229 | 6.853 | −22.046 | 1.329 | 1.00 | 28.38 | BBBB |
| ATOM | 4311 | CA | ALA | B | 230 | 10.185 | −23.754 | 0.682 | 1.00 | 26.18 | BBBB |
| ATOM | 4316 | CA | TYR | B | 231 | 11.371 | −20.766 | −1.366 | 1.00 | 25.47 | BBBB |
| ATOM | 4328 | CA | ALA | B | 232 | 10.342 | −18.322 | 1.368 | 1.00 | 27.51 | BBBB |
| ATOM | 4333 | CA | GLU | B | 233 | 12.145 | −20.441 | 3.966 | 1.00 | 30.87 | BBBB |
| ATOM | 4342 | CA | ALA | B | 234 | 15.215 | −20.417 | 1.714 | 1.00 | 28.48 | BBBB |
| ATOM | 4347 | CA | GLY | B | 235 | 15.033 | −16.627 | 1.815 | 1.00 | 26.23 | BBBB |
| ATOM | 4351 | CA | GLN | B | 236 | 14.121 | −16.198 | −1.870 | 1.00 | 25.53 | BBBB |
| ATOM | 4361 | CA | PRO | B | 237 | 10.336 | −15.587 | −1.720 | 1.00 | 24.65 | BBBB |
| ATOM | 4367 | CA | GLN | B | 238 | 10.277 | −13.558 | −4.945 | 1.00 | 24.29 | BBBB |
| ATOM | 4376 | CA | HIS | B | 239 | 10.526 | −16.608 | −7.201 | 1.00 | 22.08 | BBBB |
| ATOM | 4386 | CA | LYS | B | 240 | 7.375 | −17.589 | −9.105 | 1.00 | 23.26 | BBBB |
| ATOM | 4395 | CA | VAL | B | 241 | 5.740 | −20.911 | −8.277 | 1.00 | 23.78 | BBBB |
| ATOM | 4402 | CA | THR | B | 242 | 2.758 | −22.301 | −10.177 | 1.00 | 25.93 | BBBB |
| ATOM | 4409 | CA | GLU | B | 243 | 0.999 | −25.651 | −9.837 | 1.00 | 27.03 | BBBB |
| ATOM | 4418 | CA | PHE | B | 244 | 0.964 | −26.068 | −13.620 | 1.00 | 26.54 | BBBB |
| ATOM | 4429 | CA | ILE | B | 245 | 1.932 | −24.242 | −16.802 | 1.00 | 28.48 | BBBB |
| ATOM | 4437 | CA | ASP | B | 246 | −0.754 | −24.396 | −19.457 | 1.00 | 36.00 | BBBB |
| ATOM | 4445 | CA | ASP | B | 247 | 1.245 | −22.392 | −21.999 | 1.00 | 30.74 | BBBB |
| ATOM | 4453 | CA | MET | B | 248 | 4.625 | −24.136 | −22.138 | 1.00 | 28.41 | BBBB |
| ATOM | 4461 | CA | ALA | B | 249 | 5.512 | −22.216 | −25.290 | 1.00 | 24.67 | BBBB |
| ATOM | 4466 | CA | ALA | B | 250 | 5.188 | −18.933 | −23.390 | 1.00 | 21.78 | BBBB |
| ATOM | 4471 | CA | ALA | B | 251 | 7.301 | −20.259 | −20.501 | 1.00 | 20.85 | BBBB |
| ATOM | 4476 | CA | TYR | B | 252 | 9.972 | −21.616 | −22.886 | 1.00 | 22.78 | BBBB |
| ATOM | 4488 | CA | ALA | B | 253 | 10.131 | −18.224 | −24.636 | 1.00 | 23.54 | BBBB |
| ATOM | 4493 | CA | TRP | B | 254 | 10.829 | −16.534 | −21.303 | 1.00 | 19.76 | BBBB |
| ATOM | 4507 | CA | ALA | B | 255 | 13.399 | −19.025 | −20.003 | 1.00 | 19.51 | BBBB |
| ATOM | 4512 | CA | ASP | B | 256 | 17.176 | −19.026 | −20.434 | 1.00 | 17.58 | BBBB |
| ATOM | 4520 | CA | VAL | B | 257 | 17.535 | −22.603 | −19.194 | 1.00 | 18.53 | BBBB |
| ATOM | 4527 | CA | VAL | B | 258 | 15.208 | −25.456 | −18.234 | 1.00 | 19.32 | BBBB |
| ATOM | 4534 | CA | VAL | B | 259 | 15.581 | −27.957 | −15.374 | 1.00 | 19.85 | BBBB |
| ATOM | 4541 | CA | CYS | B | 260 | 13.454 | −31.055 | −15.946 | 1.00 | 22.00 | BBBB |
| ATOM | 4547 | CA | ARG | B | 261 | 13.170 | −34.800 | −16.515 | 1.00 | 23.75 | BBBB |
| ATOM | 4558 | CA | SER | B | 262 | 13.975 | −36.189 | −19.948 | 1.00 | 23.18 | BBBB |
| ATOM | 4564 | CA | GLY | B | 263 | 11.026 | −38.079 | −21.361 | 1.00 | 22.85 | BBBB |
| ATOM | 4568 | CA | ALA | B | 264 | 11.482 | −38.564 | −25.115 | 1.00 | 24.25 | BBBB |
| ATOM | 4573 | CA | LEU | B | 265 | 8.846 | −36.037 | −26.205 | 1.00 | 24.66 | BBBB |
| ATOM | 4581 | CA | THR | B | 266 | 10.194 | −33.557 | −23.657 | 1.00 | 22.34 | BBBB |
| ATOM | 4588 | CA | VAL | B | 267 | 13.730 | −33.762 | −25.023 | 1.00 | 21.11 | BBBB |
| ATOM | 4595 | CA | SER | B | 268 | 12.411 | −33.191 | −28.567 | 1.00 | 21.96 | BBBB |
| ATOM | 4601 | CA | GLU | B | 269 | 10.282 | −30.272 | −27.378 | 1.00 | 21.95 | BBBB |

TABLE 2-continued

ATOMIC COORDINATES OF E. COLI MURG C-ALPHA BACKBONE ATOMS

| ATOM | 4610 | CA | ILE | B | 270 | 13.295 | −28.698 | −25.638 | 1.00 | 20.62 | BBBB |
|------|------|----|-----|---|-----|--------|---------|---------|------|-------|------|
| ATOM | 4618 | CA | ALA | B | 271 | 15.440 | −29.058 | −28.776 | 1.00 | 22.45 | BBBB |
| ATOM | 4623 | CA | ALA | B | 272 | 12.719 | −27.451 | −30.898 | 1.00 | 22.17 | BBBB |
| ATOM | 4628 | CA | ALA | B | 273 | 12.361 | −24.596 | −28.407 | 1.00 | 21.97 | BBBB |
| ATOM | 4633 | CA | GLY | B | 274 | 16.093 | −24.023 | −28.709 | 1.00 | 21.07 | BBBB |
| ATOM | 4637 | CA | LEU | B | 275 | 16.666 | −24.057 | −24.966 | 1.00 | 19.78 | BBBB |
| ATOM | 4646 | CA | PRO | B | 276 | 19.651 | −25.199 | −22.875 | 1.00 | 16.62 | BBBB |
| ATOM | 4652 | CA | ALA | B | 277 | 18.638 | −27.807 | −20.321 | 1.00 | 15.80 | BBBB |
| ATOM | 4657 | CA | LEU | B | 278 | 19.896 | −29.429 | −17.145 | 1.00 | 18.48 | BBBB |
| ATOM | 4665 | CA | PHE | B | 279 | 18.266 | −32.838 | −17.392 | 1.00 | 21.59 | BBBB |
| ATOM | 4676 | CA | VAL | B | 280 | 17.502 | −34.902 | −14.281 | 1.00 | 25.67 | BBBB |
| ATOM | 4684 | CA | PRO | B | 281 | 16.698 | −38.320 | −15.824 | 1.00 | 29.05 | BBBB |
| ATOM | 4690 | CA | PHE | B | 282 | 14.246 | −40.496 | −13.926 | 1.00 | 37.13 | BBBB |
| ATOM | 4701 | CA | GLN | B | 283 | 16.319 | −43.395 | −12.591 | 1.00 | 41.11 | BBBB |
| ATOM | 4710 | CA | HIS | B | 284 | 15.641 | −46.917 | −13.843 | 1.00 | 43.69 | BBBB |
| ATOM | 4720 | CA | LYS | B | 285 | 17.767 | −49.993 | −14.571 | 1.00 | 45.34 | BBBB |
| ATOM | 4729 | CA | ASP | B | 286 | 16.949 | −49.299 | −18.222 | 1.00 | 43.26 | BBBB |
| ATOM | 4737 | CA | ARG | B | 287 | 17.951 | −45.623 | −17.883 | 1.00 | 36.28 | BBBB |
| ATOM | 4748 | CA | GLN | B | 288 | 15.622 | −44.804 | −20.755 | 1.00 | 30.77 | BBBB |
| ATOM | 4757 | CA | GLN | B | 289 | 15.474 | −41.099 | −19.904 | 1.00 | 29.46 | BBBB |
| ATOM | 4766 | CA | TYR | B | 290 | 19.228 | −40.984 | −19.550 | 1.00 | 29.55 | BBBB |
| ATOM | 4778 | CA | TRP | B | 291 | 19.542 | −42.282 | −23.116 | 1.00 | 28.07 | BBBB |
| ATOM | 4792 | CA | ASN | B | 292 | 16.902 | −39.784 | −24.270 | 1.00 | 26.06 | BBBB |
| ATOM | 4800 | CA | ALA | B | 293 | 18.926 | −36.822 | −22.979 | 1.00 | 25.69 | BBBB |
| ATOM | 4805 | CA | LEU | B | 294 | 22.354 | −38.088 | −24.032 | 1.00 | 25.90 | BBBB |
| ATOM | 4814 | CA | PRO | B | 295 | 21.998 | −36.870 | −27.635 | 1.00 | 26.15 | BBBB |
| ATOM | 4820 | CA | LEU | B | 296 | 21.521 | −33.265 | −26.481 | 1.00 | 25.42 | BBBB |
| ATOM | 4828 | CA | GLU | B | 297 | 24.354 | −33.530 | −23.953 | 1.00 | 28.78 | BBBB |
| ATOM | 4837 | CA | LYS | B | 298 | 26.644 | −34.947 | −26.648 | 1.00 | 31.90 | BBBB |
| ATOM | 4846 | CA | ALA | B | 299 | 25.773 | −31.965 | −28.847 | 1.00 | 30.38 | BBBB |
| ATOM | 4851 | CA | GLY | B | 300 | 26.777 | −29.635 | −26.017 | 1.00 | 26.18 | BBBB |
| ATOM | 4855 | CA | ALA | B | 301 | 23.214 | −28.333 | −25.638 | 1.00 | 22.50 | BBBB |
| ATOM | 4860 | CA | ALA | B | 302 | 22.516 | −29.770 | −22.186 | 1.00 | 21.78 | BBBB |
| ATOM | 4865 | CA | LYS | B | 303 | 23.979 | −31.340 | −19.048 | 1.00 | 25.86 | BBBB |
| ATOM | 4874 | CA | ILE | B | 304 | 22.753 | −34.598 | −17.550 | 1.00 | 27.17 | BBBB |
| ATOM | 4882 | CA | ILE | B | 305 | 22.843 | −35.178 | −13.813 | 1.00 | 29.01 | BBBB |
| ATOM | 4890 | CA | GLU | B | 306 | 21.664 | −38.702 | −13.061 | 1.00 | 34.65 | BBBB |
| ATOM | 4899 | CA | GLN | B | 307 | 20.377 | −39.599 | −9.613 | 1.00 | 40.54 | BBBB |
| ATOM | 4909 | CA | PRO | B | 308 | 23.828 | −40.891 | −8.484 | 1.00 | 43.20 | BBBB |
| ATOM | 4915 | CA | GLN | B | 309 | 25.247 | −37.361 | −8.787 | 1.00 | 43.46 | BBBB |
| ATOM | 4924 | CA | LEU | B | 310 | 22.232 | −35.166 | −8.022 | 1.00 | 39.65 | BBBB |
| ATOM | 4932 | CA | SER | B | 311 | 22.660 | −32.714 | −5.154 | 1.00 | 34.90 | BBBB |
| ATOM | 4938 | CA | VAL | B | 312 | 21.990 | −29.074 | −4.341 | 1.00 | 31.50 | BBBB |
| ATOM | 4945 | CA | ASP | B | 313 | 25.642 | −28.202 | −4.957 | 1.00 | 29.61 | BBBB |
| ATOM | 4953 | CA | ALA | B | 314 | 25.782 | −30.099 | −8.254 | 1.00 | 26.47 | BBBB |
| ATOM | 4958 | CA | VAL | B | 315 | 22.755 | −28.215 | −9.612 | 1.00 | 25.33 | BBBB |
| ATOM | 4965 | CA | ALA | B | 316 | 23.888 | −24.872 | −8.199 | 1.00 | 27.13 | BBBB |
| ATOM | 4970 | CA | ASN | B | 317 | 27.444 | −25.246 | −9.518 | 1.00 | 28.52 | BBBB |
| ATOM | 4978 | CA | THR | B | 318 | 26.174 | −26.371 | −12.906 | 1.00 | 27.04 | BBBB |
| ATOM | 4985 | CA | LEU | B | 319 | 23.883 | −23.370 | −13.357 | 1.00 | 25.21 | BBBB |
| ATOM | 4993 | CA | ALA | B | 320 | 26.445 | −20.931 | −11.957 | 1.00 | 24.59 | BBBB |
| ATOM | 4998 | CA | GLY | B | 321 | 28.934 | −22.031 | −14.591 | 1.00 | 24.34 | BBBB |
| ATOM | 5002 | CA | TRP | B | 322 | 26.738 | −21.007 | −17.521 | 1.00 | 21.72 | BBBB |
| ATOM | 5016 | CA | SER | B | 323 | 27.141 | −17.404 | −18.692 | 1.00 | 19.04 | BBBB |
| ATOM | 5022 | CA | ARG | B | 324 | 24.725 | −15.741 | −21.112 | 1.00 | 18.09 | BBBB |
| ATOM | 5033 | CA | GLU | B | 325 | 27.220 | −16.368 | −23.954 | 1.00 | 16.96 | BBBB |
| ATOM | 5042 | CA | THR | B | 326 | 27.460 | −20.055 | −23.070 | 1.00 | 16.39 | BBBB |
| ATOM | 5049 | CA | LEU | B | 327 | 23.659 | −20.305 | −22.780 | 1.00 | 17.27 | BBBB |
| ATOM | 5057 | CA | LEU | B | 328 | 23.175 | −18.745 | −26.222 | 1.00 | 17.39 | BBBB |
| ATOM | 5065 | CA | THR | B | 329 | 25.567 | −21.335 | −27.688 | 1.00 | 21.30 | BBBB |
| ATOM | 5072 | CA | MET | B | 330 | 23.771 | −24.153 | −25.870 | 1.00 | 19.91 | BBBB |
| ATOM | 5080 | CA | ALA | B | 331 | 20.412 | −22.871 | −27.098 | 1.00 | 18.49 | BBBB |
| ATOM | 5085 | CA | GLU | B | 332 | 21.626 | −22.827 | −30.704 | 1.00 | 21.47 | BBBB |
| ATOM | 5094 | CA | ARG | B | 333 | 23.040 | −26.330 | −30.408 | 1.00 | 23.77 | BBBB |
| ATOM | 5105 | CA | ALA | B | 334 | 19.648 | −27.420 | −29.063 | 1.00 | 22.88 | BBBB |
| ATOM | 5110 | CA | ARG | B | 335 | 17.795 | −25.892 | −32.002 | 1.00 | 23.54 | BBBB |
| ATOM | 5121 | CA | ALA | B | 336 | 20.330 | −27.477 | −34.372 | 1.00 | 26.85 | BBBB |
| ATOM | 5126 | CA | ALA | B | 337 | 19.740 | −30.925 | −32.865 | 1.00 | 30.89 | BBBB |
| ATOM | 5131 | CA | SER | B | 338 | 16.008 | −30.432 | −33.408 | 1.00 | 32.41 | BBBB |
| ATOM | 5137 | CA | ILE | B | 339 | 13.882 | −31.941 | −36.187 | 1.00 | 34.35 | BBBB |
| ATOM | 5146 | CA | PRO | B | 340 | 10.733 | −29.730 | −36.600 | 1.00 | 34.94 | BBBB |
| ATOM | 5152 | CA | ASP | B | 341 | 8.711 | −31.820 | −39.056 | 1.00 | 33.33 | BBBB |
| ATOM | 5160 | CA | ALA | B | 342 | 8.875 | −35.238 | −37.411 | 1.00 | 29.09 | BBBB |
| ATOM | 5165 | CA | THR | B | 343 | 5.115 | −35.696 | −37.744 | 1.00 | 28.55 | BBBB |
| ATOM | 5172 | CA | GLU | B | 344 | 5.085 | −34.933 | −41.480 | 1.00 | 32.00 | BBBB |
| ATOM | 5181 | CA | ARG | B | 345 | 8.138 | −37.123 | −42.067 | 1.00 | 31.44 | BBBB |

TABLE 2-continued

**ATOMIC COORDINATES OF *E. COLI* MURG C-ALPHA BACKBONE ATOMS**

| ATOM | 5192 | CA | VAL | B | 346 | 6.578 | −40.151 | −40.384 | 1.00 | 28.61 | BBBB |
|---|---|---|---|---|---|---|---|---|---|---|---|
| ATOM | 5199 | CA | ALA | B | 347 | 3.249 | −39.617 | −42.137 | 1.00 | 28.96 | BBBB |
| ATOM | 5204 | CA | ASN | B | 348 | 5.035 | −39.286 | −45.493 | 1.00 | 34.56 | BBBB |
| ATOM | 5212 | CA | GLU | B | 349 | 6.954 | −42.540 | −44.956 | 1.00 | 34.86 | BBBB |
| ATOM | 5221 | CA | VAL | B | 350 | 3.767 | −44.306 | −43.919 | 1.00 | 33.79 | BBBB |
| ATOM | 5228 | CA | SER | B | 351 | 2.196 | −42.946 | −47.095 | 1.00 | 36.67 | BBBB |
| ATOM | 5234 | CA | ARG | B | 352 | 5.114 | −44.088 | −49.251 | 1.00 | 40.03 | BBBB |
| ATOM | 5245 | CA | VAL | B | 353 | 5.089 | −47.587 | −47.737 | 1.00 | 42.78 | BBBB |
| ATOM | 5252 | CA | ALA | B | 354 | 1.336 | −47.957 | −48.212 | 1.00 | 47.24 | BBBB |
| ATOM | 5257 | CA | ARG | B | 355 | 2.035 | −46.964 | −51.824 | 1.00 | 52.71 | BBBB |
| ATOM | 5268 | CA | ALA | B | 356 | 4.453 | −49.913 | −51.809 | 1.00 | 54.93 | BBBB |
| ATOM | 5273 | CA | LEU | B | 357 | 7.023 | −47.522 | −53.289 | 1.00 | 57.81 | BBBB |
| END | | | | | | | | | | | |

TABLE 3

**ATOMIC COORDINATES OF *E. COLI* MURG C-ALPHA BACKBONE AND CONSERVED AMINO ACID RESIDUES**

| ATOM | 2649 | CA | LYS | B | 7 | −6.512 | −45.403 | −47.519 | 1.00 | 45.23 | BBBB |
|---|---|---|---|---|---|---|---|---|---|---|---|
| ATOM | 2651 | CA | ARG | B | 8 | −6.682 | −47.303 | −44.240 | 1.00 | 38.63 | BBBB |
| ATOM | 2662 | CA | LEU | B | 9 | −4.094 | −47.039 | −41.477 | 1.00 | 30.88 | BBBB |
| ATOM | 2670 | CA | MET | B | 10 | −4.048 | −49.055 | −38.275 | 1.00 | 26.66 | BBBB |
| ATOM | 2678 | CA | VAL | B | 11 | −1.982 | −47.605 | −35.449 | 1.00 | 23.16 | BBBB |
| ATOM | 2685 | CA | MET | B | 12 | −0.523 | −49.707 | −32.613 | 1.00 | 24.54 | BBBB |
| ATOM | 2693 | CA | ALA | B | 13 | 0.508 | −47.410 | −29.752 | 1.00 | 29.43 | BBBB |
| ATOM | 2697 | N | GLY | B | 14 | 0.150 | −47.934 | −27.405 | 1.00 | 32.46 | BBBB |
| ATOM | 2698 | CA | GLY | B | 14 | −0.513 | −47.804 | −26.120 | 1.00 | 33.82 | BBBB |
| ATOM | 2699 | C | GLY | B | 14 | −0.107 | −46.595 | −25.299 | 1.00 | 34.82 | BBBB |
| ATOM | 2700 | O | GLY | B | 14 | 0.975 | −46.040 | −25.479 | 1.00 | 35.47 | BBBB |
| ATOM | 2701 | N | GLY | B | 15 | −0.986 | −46.188 | −24.385 | 1.00 | 35.56 | BBBB |
| ATOM | 2702 | CA | GLY | B | 15 | −0.700 | −45.047 | −23.536 | 1.00 | 36.08 | BBBB |
| ATOM | 2703 | C | GLY | B | 15 | 0.539 | −45.254 | −22.683 | 1.00 | 36.84 | BBBB |
| ATOM | 2704 | O | GLY | B | 15 | 1.293 | −44.311 | −22.426 | 1.00 | 36.03 | BBBB |
| ATOM | 2706 | CA | THR | B | 16 | 1.920 | −46.787 | −21.421 | 1.00 | 38.51 | BBBB |
| ATOM | 2713 | CA | GLY | B | 17 | 5.367 | −45.567 | −22.392 | 1.00 | 36.57 | BBBB |
| ATOM | 2716 | N | GLY | B | 18 | 3.949 | −43.752 | −23.150 | 1.00 | 33.83 | BBBB |
| ATOM | 2717 | CA | GLY | B | 18 | 3.631 | −42.529 | −23.872 | 1.00 | 33.48 | BBBB |
| ATOM | 2718 | C | GLY | B | 18 | 3.825 | −42.593 | −25.378 | 1.00 | 33.12 | BBBB |
| ATOM | 2719 | O | GLY | B | 18 | 4.345 | −41.650 | −25.984 | 1.00 | 35.38 | BBBB |
| ATOM | 2720 | N | HIS | B | 19 | 3.416 | −43.699 | −25.988 | 1.00 | 30.26 | BBBB |
| ATOM | 2721 | CA | HIS | B | 19 | 3.548 | −43.865 | −27.435 | 1.00 | 28.22 | BBBB |
| ATOM | 2722 | CB | HIS | B | 19 | 3.772 | −45.349 | −27.779 | 1.00 | 25.81 | BBBB |
| ATOM | 2723 | CG | HIS | B | 19 | 4.957 | −45.966 | −27.094 | 1.00 | 25.35 | BBBB |
| ATOM | 2724 | CD2 | HIS | B | 19 | 6.281 | −45.694 | −27.184 | 1.00 | 24.18 | BBBB |
| ATOM | 2725 | ND1 | HIS | B | 19 | 4.845 | −47.025 | −26.217 | 1.00 | 24.57 | BBBB |
| ATOM | 2726 | CE1 | HIS | B | 19 | 6.046 | −47.380 | −25.798 | 1.00 | 23.08 | BBBB |
| ATOM | 2727 | NE2 | HIS | B | 19 | 6.936 | −46.589 | −26.369 | 1.00 | 25.51 | BBBB |
| ATOM | 2728 | C | HIS | B | 19 | 2.280 | −43.370 | −28.144 | 1.00 | 27.91 | BBBB |
| ATOM | 2729 | O | HIS | B | 19 | 2.300 | −43.049 | −29.337 | 1.00 | 26.91 | BBBB |
| ATOM | 2731 | CA | VAL | B | 20 | −0.098 | −42.894 | −27.965 | 1.00 | 27.77 | BBBB |
| ATOM | 2738 | CA | PHE | B | 21 | 0.517 | −39.136 | −28.160 | 1.00 | 29.00 | BBBB |
| ATOM | 2750 | CA | PRO | B | 22 | 2.986 | −39.252 | −31.086 | 1.00 | 26.12 | BBBB |
| ATOM | 2756 | CA | GLY | B | 23 | 0.787 | −41.864 | −32.752 | 1.00 | 25.07 | BBBB |
| ATOM | 2760 | CA | LEU | B | 24 | −2.201 | −39.551 | −32.401 | 1.00 | 25.32 | BBBB |
| ATOM | 2768 | CA | ALA | B | 25 | −0.197 | −36.754 | −34.013 | 1.00 | 25.94 | BBBB |
| ATOM | 2773 | CA | VAL | B | 26 | 0.466 | −38.955 | −37.056 | 1.00 | 25.70 | BBBB |
| ATOM | 2780 | CA | ALA | B | 27 | −3.116 | −40.222 | −37.199 | 1.00 | 26.15 | BBBB |
| ATOM | 2785 | CA | HIS | B | 28 | −4.574 | −36.702 | −37.190 | 1.00 | 29.32 | BBBB |
| ATOM | 2795 | CA | HIS | B | 29 | −2.070 | −35.623 | −39.806 | 1.00 | 32.38 | BBBB |
| ATOM | 2805 | CA | LEU | B | 30 | −3.136 | −38.417 | −42.162 | 1.00 | 32.00 | BBBB |
| ATOM | 2813 | CA | MET | B | 31 | −6.849 | −38.064 | −41.424 | 1.00 | 34.91 | BBBB |
| ATOM | 2821 | CA | ALA | B | 32 | −6.510 | −34.511 | −42.722 | 1.00 | 37.55 | BBBB |
| ATOM | 2826 | CA | GLN | B | 33 | −5.182 | −36.070 | −45.938 | 1.00 | 38.24 | BBBB |
| ATOM | 2835 | CA | GLY | B | 34 | −8.305 | −38.169 | −46.353 | 1.00 | 35.75 | BBBB |
| ATOM | 2839 | CA | TRP | B | 35 | −7.016 | −41.246 | −44.508 | 1.00 | 34.58 | BBBB |
| ATOM | 2853 | CA | GLN | B | 36 | −9.175 | −43.535 | −42.402 | 1.00 | 35.40 | BBBB |
| ATOM | 2862 | CA | VAL | B | 37 | −7.417 | −44.516 | −39.184 | 1.00 | 34.16 | BBBB |
| ATOM | 2869 | CA | ARG | B | 38 | −8.219 | −47.286 | −36.730 | 1.00 | 31.56 | BBBB |
| ATOM | 2880 | CA | TRP | B | 39 | −6.456 | −48.070 | −33.471 | 1.00 | 27.41 | BBBB |
| ATOM | 2894 | CA | LEU | B | 40 | −5.200 | −51.364 | −32.026 | 1.00 | 24.71 | BBBB |
| ATOM | 2902 | CA | GLY | B | 41 | −4.691 | −51.450 | −28.257 | 1.00 | 23.47 | BBBB |
| ATOM | 2906 | CA | THR | B | 42 | −5.787 | −53.141 | −25.027 | 1.00 | 29.84 | BBBB |

TABLE 3-continued

ATOMIC COORDINATES OF E. COLI MURG C-ALPHA BACKBONE AND CONSERVED AMINO ACID RESIDUES

| ATOM | 2913 | CA | ALA | B | 43 | −9.000 | −52.595 | −23.047 | 1.00 | 38.81 | BBBB |
|---|---|---|---|---|---|---|---|---|---|---|---|
| ATOM | 2918 | CA | ASP | B | 44 | −7.455 | −51.942 | −19.632 | 1.00 | 44.47 | BBBB |
| ATOM | 2926 | CA | ARG | B | 45 | −4.887 | −49.367 | −20.763 | 1.00 | 40.44 | BBBB |
| ATOM | 2937 | CA | MET | B | 46 | −4.881 | −45.581 | −21.249 | 1.00 | 36.33 | BBBB |
| ATOM | 2945 | CA | GLU | B | 47 | −5.458 | −45.655 | −25.029 | 1.00 | 31.79 | BBBB |
| ATOM | 2954 | CA | ALA | B | 48 | −8.821 | −47.344 | −24.414 | 1.00 | 32.58 | BBBB |
| ATOM | 2959 | CA | ASP | B | 49 | −10.143 | −44.065 | −23.009 | 1.00 | 35.60 | BBBB |
| ATOM | 2967 | CA | LEU | B | 50 | −8.026 | −41.484 | −24.840 | 1.00 | 33.49 | BBBB |
| ATOM | 2975 | CA | VAL | B | 51 | −8.299 | −42.641 | −28.449 | 1.00 | 32.68 | BBBB |
| ATOM | 2983 | CA | PRO | B | 52 | −12.111 | −42.601 | −28.453 | 1.00 | 34.43 | BBBB |
| ATOM | 2989 | CA | LYS | B | 53 | −11.998 | −39.054 | −27.064 | 1.00 | 36.73 | BBBB |
| ATOM | 2998 | CA | HIS | B | 54 | −10.116 | −38.212 | −30.259 | 1.00 | 34.62 | BBBB |
| ATOM | 3008 | CA | GLY | B | 55 | −12.938 | −39.481 | −32.447 | 1.00 | 35.34 | BBBB |
| ATOM | 3012 | CA | ILE | B | 56 | −10.909 | −42.517 | −33.514 | 1.00 | 33.81 | BBBB |
| ATOM | 3020 | CA | GLU | B | 57 | −12.228 | −46.083 | −33.467 | 1.00 | 34.16 | BBBB |
| ATOM | 3029 | CA | ILE | B | 58 | −10.217 | −48.658 | −31.553 | 1.00 | 31.38 | BBBB |
| ATOM | 3037 | CA | ASP | B | 59 | −10.039 | −52.442 | −31.720 | 1.00 | 31.09 | BBBB |
| ATOM | 3045 | CA | PHE | B | 60 | −8.809 | −54.410 | −28.713 | 1.00 | 30.32 | BBBB |
| ATOM | 3056 | CA | ILE | B | 61 | −6.832 | −57.616 | −28.269 | 1.00 | 28.55 | BBBB |
| ATOM | 3064 | CA | ARG | B | 62 | −5.709 | −59.416 | −25.133 | 1.00 | 30.76 | BBBB |
| ATOM | 3075 | CA | ILE | B | 63 | −2.036 | −59.770 | −24.231 | 1.00 | 31.38 | BBBB |
| ATOM | 3083 | CA | SER | B | 64 | −2.356 | −60.520 | −20.505 | 1.00 | 37.51 | BBBB |
| ATOM | 3089 | CA | GLY | B | 65 | 0.679 | −62.355 | −19.199 | 1.00 | 37.13 | BBBB |
| ATOM | 3093 | CA | LEU | B | 66 | 2.591 | −61.413 | −22.355 | 1.00 | 33.17 | BBBB |
| ATOM | 3101 | CA | ARG | B | 67 | 3.671 | −57.928 | −21.277 | 1.00 | 30.90 | BBBB |
| ATOM | 3112 | CA | GLY | B | 68 | 7.380 | −57.427 | −20.685 | 1.00 | 26.79 | BBBB |
| ATOM | 3116 | CA | LYS | B | 69 | 8.238 | −60.463 | −22.796 | 1.00 | 23.93 | BBBB |
| ATOM | 3125 | CA | GLY | B | 70 | 10.755 | −60.229 | −25.636 | 1.00 | 22.26 | BBBB |
| ATOM | 3129 | CA | ILE | B | 71 | 10.357 | −62.386 | −28.762 | 1.00 | 23.55 | BBBB |
| ATOM | 3137 | CA | LYS | B | 72 | 12.038 | −65.491 | −27.343 | 1.00 | 24.92 | BBBB |
| ATOM | 3146 | CA | ALA | B | 73 | 9.839 | −65.306 | −24.233 | 1.00 | 21.18 | BBBB |
| ATOM | 3151 | CA | LEU | B | 74 | 6.745 | −64.762 | −26.387 | 1.00 | 19.36 | BBBB |
| ATOM | 3159 | CA | ILE | B | 75 | 7.434 | −67.768 | −28.601 | 1.00 | 21.18 | BBBB |
| ATOM | 3167 | CA | ALA | B | 76 | 7.996 | −69.726 | −25.374 | 1.00 | 21.72 | BBBB |
| ATOM | 3172 | CA | ALA | B | 77 | 4.289 | −69.121 | −24.655 | 1.00 | 21.07 | BBBB |
| ATOM | 3178 | CA | PRO | B | 78 | 2.772 | −70.846 | −27.771 | 1.00 | 20.95 | BBBB |
| ATOM | 3184 | CA | LEU | B | 79 | −0.896 | −70.728 | −26.783 | 1.00 | 21.32 | BBBB |
| ATOM | 3192 | CA | ARG | B | 80 | −0.980 | −67.115 | −25.637 | 1.00 | 21.30 | BBBB |
| ATOM | 3203 | CA | ILE | B | 81 | 1.113 | −65.621 | −28.421 | 1.00 | 19.47 | BBBB |
| ATOM | 3211 | CA | PHE | B | 82 | −0.875 | −67.582 | −31.038 | 1.00 | 19.15 | BBBB |
| ATOM | 3222 | CA | ASN | B | 83 | −4.150 | −66.332 | −29.577 | 1.00 | 20.90 | BBBB |
| ATOM | 3230 | CA | ALA | B | 84 | −3.177 | −62.647 | −29.484 | 1.00 | 19.30 | BBBB |
| ATOM | 3235 | CA | TRP | B | 85 | −1.820 | −63.111 | −33.032 | 1.00 | 20.56 | BBBB |
| ATOM | 3249 | CA | ARG | B | 86 | −5.140 | −64.660 | −34.166 | 1.00 | 23.28 | BBBB |
| ATOM | 3260 | CA | GLN | B | 87 | −7.101 | −61.802 | −32.567 | 1.00 | 24.07 | BBBB |
| ATOM | 3269 | CA | ALA | B | 88 | −4.996 | −59.183 | −34.355 | 1.00 | 23.78 | BBBB |
| ATOM | 3274 | CA | ARG | B | 89 | −5.285 | −61.111 | −37.636 | 1.00 | 24.94 | BBBB |
| ATOM | 3285 | CA | ALA | B | 90 | −9.088 | −61.151 | −37.383 | 1.00 | 26.16 | BBBB |
| ATOM | 3290 | CA | ILE | B | 91 | −9.108 | −57.400 | −36.733 | 1.00 | 26.97 | BBBB |
| ATOM | 3298 | CA | MET | B | 92 | −6.872 | −56.693 | −39.717 | 1.00 | 29.03 | BBBB |
| ATOM | 3306 | CA | LYS | B | 93 | −8.735 | −59.038 | −42.050 | 1.00 | 33.20 | BBBB |
| ATOM | 3315 | CA | ALA | B | 94 | −11.943 | −57.157 | −41.183 | 1.00 | 33.62 | BBBB |
| ATOM | 3320 | CA | TYR | B | 95 | −10.504 | −53.620 | −41.224 | 1.00 | 33.83 | BBBB |
| ATOM | 3332 | CA | LYS | B | 96 | −8.104 | −54.327 | −44.122 | 1.00 | 33.85 | BBBB |
| ATOM | 3342 | CA | PRO | B | 97 | −5.490 | −51.623 | −43.419 | 1.00 | 31.82 | BBBB |
| ATOM | 3348 | CA | ASP | B | 98 | −3.049 | −50.685 | −46.188 | 1.00 | 29.78 | BBBB |
| ATOM | 3356 | CA | VAL | B | 99 | −0.296 | −50.214 | −43.660 | 1.00 | 26.75 | BBBB |
| ATOM | 3363 | CA | VAL | B | 100 | 0.227 | −50.613 | −39.936 | 1.00 | 23.59 | BBBB |
| ATOM | 3370 | CA | LEU | B | 101 | 2.214 | −48.199 | −37.797 | 1.00 | 21.59 | BBBB |
| ATOM | 3378 | CA | GLY | B | 102 | 3.796 | −49.357 | −34.549 | 1.00 | 19.23 | BBBB |
| ATOM | 3382 | CA | MET | B | 103 | 4.892 | −46.597 | −32.191 | 1.00 | 18.93 | BBBB |
| ATOM | 3389 | N | GLY | B | 104 | 5.640 | −48.450 | −30.827 | 1.00 | 21.56 | BBBB |
| ATOM | 3390 | CA | GLY | B | 104 | 6.275 | −49.080 | −29.686 | 1.00 | 21.89 | BBBB |
| ATOM | 3391 | C | GLY | B | 104 | 5.192 | −49.614 | −28.764 | 1.00 | 23.28 | BBBB |
| ATOM | 3392 | O | GLY | B | 104 | 4.009 | −49.353 | −28.980 | 1.00 | 22.50 | BBBB |
| ATOM | 3394 | CA | GLY | B | 105 | 4.593 | −50.905 | −26.827 | 1.00 | 23.54 | BBBB |
| ATOM | 3398 | CA | TYR | B | 106 | 3.818 | −54.554 | −26.159 | 1.00 | 22.37 | BBBB |
| ATOM | 3410 | CA | VAL | B | 107 | 0.557 | −54.694 | −28.099 | 1.00 | 18.06 | BBBB |
| ATOM | 3417 | CA | SER | B | 108 | 2.488 | −53.892 | −31.290 | 1.00 | 19.67 | BBBB |
| ATOM | 3423 | CA | GLY | B | 109 | 4.251 | −57.256 | −31.023 | 1.00 | 20.03 | BBBB |
| ATOM | 3428 | CA | PRO | B | 110 | 1.251 | −59.478 | −31.855 | 1.00 | 18.99 | BBBB |
| ATOM | 3434 | CA | GLY | B | 111 | −0.160 | −56.702 | −34.025 | 1.00 | 19.60 | BBBB |
| ATOM | 3438 | CA | GLY | B | 112 | 3.014 | −56.417 | −36.074 | 1.00 | 19.97 | BBBB |
| ATOM | 3442 | CA | LEU | B | 113 | 3.265 | −60.184 | −36.429 | 1.00 | 19.49 | BBBB |
| ATOM | 3450 | CA | ALA | B | 114 | −0.334 | −60.292 | −37.661 | 1.00 | 18.70 | BBBB |
| ATOM | 3455 | CA | ALA | B | 115 | 0.167 | −57.516 | −40.229 | 1.00 | 21.84 | BBBB |

TABLE 3-continued

ATOMIC COORDINATES OF E. COLI MURG C-ALPHA
BACKBONE AND CONSERVED AMINO ACID RESIDUES

| ATOM | 3460 | CA | TRP | B | 116 | 3.365 | −59.126 | −41.478 | 1.00 | 23.22 | BBBB |
|------|------|-----|-----|---|-----|--------|---------|---------|------|-------|------|
| ATOM | 3474 | CA | SER | B | 117 | 1.735 | −62.573 | −41.873 | 1.00 | 22.61 | BBBB |
| ATOM | 3480 | CA | LEU | B | 118 | −1.069 | −60.957 | −43.882 | 1.00 | 25.70 | BBBB |
| ATOM | 3488 | CA | GLY | B | 119 | 1.354 | −59.174 | −46.192 | 1.00 | 27.80 | BBBB |
| ATOM | 3492 | CA | ILE | B | 120 | 0.568 | −55.744 | −44.731 | 1.00 | 24.85 | BBBB |
| ATOM | 3501 | CA | PRO | B | 121 | 3.625 | −53.477 | −44.591 | 1.00 | 22.63 | BBBB |
| ATOM | 3507 | CA | VAL | B | 122 | 4.743 | −52.594 | −41.083 | 1.00 | 22.03 | BBBB |
| ATOM | 3514 | CA | VAL | B | 123 | 6.200 | −49.184 | −40.310 | 1.00 | 20.82 | BBBB |
| ATOM | 3521 | CA | LEU | B | 124 | 7.749 | −48.485 | −36.915 | 1.00 | 22.10 | BBBB |
| ATOM | 3528 | N | HIS | B | 125 | 8.182 | −46.638 | −35.447 | 1.00 | 21.40 | BBBB |
| ATOM | 3529 | CA | HIS | B | 125 | 8.814 | −45.413 | −34.981 | 1.00 | 21.42 | BBBB |
| ATOM | 3530 | CB | HIS | B | 125 | 7.858 | −44.218 | −35.067 | 1.00 | 21.57 | BBBB |
| ATOM | 3531 | CG | HIS | B | 125 | 8.432 | −42.948 | −34.511 | 1.00 | 23.73 | BBBB |
| ATOM | 3532 | CD2 | HIS | B | 125 | 8.300 | −42.368 | −33.295 | 1.00 | 22.15 | BBBB |
| ATOM | 3533 | ND1 | HIS | B | 125 | 9.274 | −42.127 | −35.236 | 1.00 | 26.23 | BBBB |
| ATOM | 3534 | CE1 | HIS | B | 125 | 9.631 | −41.095 | −34.490 | 1.00 | 24.20 | BBBB |
| ATOM | 3535 | NE2 | HIS | B | 125 | 9.054 | −41.218 | −33.307 | 1.00 | 26.07 | BBBB |
| ATOM | 3536 | C | HIS | B | 125 | 9.196 | −45.642 | −33.519 | 1.00 | 21.70 | BBBB |
| ATOM | 3537 | O | HIS | B | 125 | 8.378 | −46.117 | −32.725 | 1.00 | 19.81 | BBBB |
| ATOM | 3538 | N | GLU | B | 126 | 10.444 | −45.332 | −33.186 | 1.00 | 21.20 | BBBB |
| ATOM | 3539 | CA | GLU | B | 126 | 10.947 | −45.452 | −31.817 | 1.00 | 22.15 | BBBB |
| ATOM | 3540 | CB | GLU | B | 126 | 12.252 | −46.246 | −31.790 | 1.00 | 21.99 | BBBB |
| ATOM | 3541 | CG | GLU | B | 126 | 12.958 | −46.206 | −30.439 | 1.00 | 22.04 | BBBB |
| ATOM | 3542 | CD | GLU | B | 126 | 12.119 | −46.824 | −29.338 | 1.00 | 21.43 | BBBB |
| ATOM | 3543 | OE1 | GLU | B | 126 | 11.767 | −48.014 | −29.471 | 1.00 | 21.92 | BBBB |
| ATOM | 3544 | OE2 | GLU | B | 126 | 11.807 | −46.124 | −28.349 | 1.00 | 21.08 | BBBB |
| ATOM | 3545 | C | GLU | B | 126 | 11.205 | −44.027 | −31.326 | 1.00 | 21.93 | BBBB |
| ATOM | 3546 | O | GLU | B | 126 | 12.016 | −43.300 | −31.908 | 1.00 | 21.33 | BBBB |
| ATOM | 3548 | CA | GLN | B | 127 | 10.682 | −42.270 | −29.735 | 1.00 | 22.81 | BBBB |
| ATOM | 3557 | CA | ASN | B | 128 | 13.406 | −43.097 | −27.216 | 1.00 | 22.96 | BBBB |
| ATOM | 3565 | CA | GLY | B | 129 | 17.203 | −43.019 | −27.294 | 1.00 | 25.36 | BBBB |
| ATOM | 3569 | CA | ILE | B | 130 | 17.160 | −46.716 | −26.488 | 1.00 | 28.00 | BBBB |
| ATOM | 3577 | CA | ALA | B | 131 | 14.978 | −49.139 | −28.461 | 1.00 | 25.88 | BBBB |
| ATOM | 3582 | CA | GLY | B | 132 | 12.007 | −50.532 | −26.568 | 1.00 | 24.05 | BBBB |
| ATOM | 3586 | CA | LEU | B | 133 | 11.903 | −54.293 | −26.020 | 1.00 | 24.54 | BBBB |
| ATOM | 3594 | CA | THR | B | 134 | 9.202 | −54.860 | −28.639 | 1.00 | 21.22 | BBBB |
| ATOM | 3601 | CA | ASN | B | 135 | 10.407 | −52.419 | −31.324 | 1.00 | 20.50 | BBBB |
| ATOM | 3609 | CA | LYS | B | 136 | 13.886 | −53.949 | −31.144 | 1.00 | 22.79 | BBBB |
| ATOM | 3618 | CA | TRP | B | 137 | 12.753 | −57.345 | −32.424 | 1.00 | 22.06 | BBBB |
| ATOM | 3632 | CA | LEU | B | 138 | 9.744 | −56.188 | −34.431 | 1.00 | 23.15 | BBBB |
| ATOM | 3640 | CA | ALA | B | 139 | 12.128 | −54.092 | −36.542 | 1.00 | 25.29 | BBBB |
| ATOM | 3645 | CA | LYS | B | 140 | 13.279 | −57.337 | −38.182 | 1.00 | 28.05 | BBBB |
| ATOM | 3654 | CA | ILE | B | 141 | 9.963 | −57.818 | −40.016 | 1.00 | 26.09 | BBBB |
| ATOM | 3662 | CA | ALA | B | 142 | 9.331 | −54.107 | −40.498 | 1.00 | 25.03 | BBBB |
| ATOM | 3667 | CA | THR | B | 143 | 9.262 | −52.595 | −43.984 | 1.00 | 26.10 | BBBB |
| ATOM | 3674 | CA | LYS | B | 144 | 10.436 | −49.238 | −42.618 | 1.00 | 24.73 | BBBB |
| ATOM | 3683 | CA | VAL | B | 145 | 11.947 | −48.311 | −39.252 | 1.00 | 23.62 | BBBB |
| ATOM | 3690 | CA | MET | B | 146 | 12.338 | −44.736 | −37.993 | 1.00 | 23.15 | BBBB |
| ATOM | 3698 | CA | GLN | B | 147 | 13.762 | −43.418 | −34.712 | 1.00 | 25.05 | BBBB |
| ATOM | 3707 | CA | ALA | B | 148 | 13.559 | −40.032 | −33.009 | 1.00 | 26.88 | BBBB |
| ATOM | 3712 | CA | PHE | B | 149 | 17.239 | −39.820 | −32.098 | 1.00 | 29.39 | BBBB |
| ATOM | 3724 | CA | PRO | B | 150 | 20.310 | −41.541 | −33.535 | 1.00 | 31.87 | BBBB |
| ATOM | 3730 | CA | GLY | B | 151 | 21.629 | −44.537 | −31.595 | 1.00 | 32.62 | BBBB |
| ATOM | 3734 | CA | ALA | B | 152 | 18.447 | −46.476 | −30.753 | 1.00 | 32.71 | BBBB |
| ATOM | 3739 | CA | PHE | B | 153 | 18.925 | −48.506 | −33.937 | 1.00 | 34.83 | BBBB |
| ATOM | 3751 | CA | PRO | B | 154 | 22.158 | −48.751 | −35.993 | 1.00 | 38.97 | BBBB |
| ATOM | 3757 | CA | ASN | B | 155 | 20.765 | −47.568 | −39.346 | 1.00 | 41.08 | BBBB |
| ATOM | 3765 | CA | ALA | B | 156 | 17.170 | −46.407 | −38.843 | 1.00 | 37.55 | BBBB |
| ATOM | 3770 | CA | GLU | B | 157 | 16.367 | −43.044 | −40.460 | 1.00 | 34.40 | BBBB |
| ATOM | 3779 | CA | VAL | B | 158 | 16.337 | −40.344 | −37.764 | 1.00 | 31.16 | BBBB |
| ATOM | 3786 | CA | VAL | B | 159 | 13.155 | −38.265 | −37.889 | 1.00 | 28.10 | BBBB |
| ATOM | 3793 | CA | GLY | B | 160 | 12.724 | −36.921 | −34.355 | 1.00 | 26.93 | BBBB |
| ATOM | 3797 | CA | ASN | B | 161 | 9.456 | −36.807 | −32.375 | 1.00 | 25.27 | BBBB |
| ATOM | 3806 | CA | PRO | B | 162 | 6.315 | −34.747 | −33.004 | 1.00 | 26.14 | BBBB |
| ATOM | 3812 | CA | VAL | B | 163 | 6.456 | −31.379 | −31.216 | 1.00 | 27.75 | BBBB |
| ATOM | 3819 | CA | ARG | B | 164 | 3.667 | −28.953 | −30.246 | 1.00 | 32.36 | BBBB |
| ATOM | 3830 | CA | THR | B | 165 | 3.038 | −26.307 | −32.924 | 1.00 | 31.74 | BBBB |
| ATOM | 3837 | CA | ASP | B | 166 | 3.252 | −23.404 | −30.466 | 1.00 | 30.64 | BBBB |
| ATOM | 3845 | CA | VAL | B | 167 | 6.746 | −24.503 | −29.440 | 1.00 | 25.91 | BBBB |
| ATOM | 3852 | CA | LEU | B | 168 | 7.780 | −25.002 | −33.075 | 1.00 | 28.46 | BBBB |
| ATOM | 3860 | CA | ALA | B | 169 | 6.580 | −21.455 | −33.756 | 1.00 | 31.43 | BBBB |
| ATOM | 3865 | CA | LEU | B | 170 | 9.002 | −19.905 | −31.268 | 1.00 | 29.60 | BBBB |
| ATOM | 3874 | CA | PRO | B | 171 | 11.611 | −17.457 | −32.642 | 1.00 | 30.11 | BBBB |
| ATOM | 3880 | CA | LEU | B | 172 | 15.157 | −18.780 | −33.062 | 1.00 | 28.33 | BBBB |
| ATOM | 3889 | CA | PRO | B | 173 | 17.450 | −18.550 | −29.977 | 1.00 | 25.25 | BBBB |
| ATOM | 3895 | CA | GLN | B | 174 | 19.526 | −15.527 | −31.049 | 1.00 | 25.46 | BBBB |

TABLE 3-continued

ATOMIC COORDINATES OF E. COLI MURG C-ALPHA
BACKBONE AND CONSERVED AMINO ACID RESIDUES

| ATOM | 3904 | CA | GLN | B | 175 | 16.365 | −13.525 | −31.718 | 1.00 | 28.47 | BBBB |
|---|---|---|---|---|---|---|---|---|---|---|---|
| ATOM | 3913 | CA | ARG | B | 176 | 14.611 | −14.635 | −28.525 | 1.00 | 29.01 | BBBB |
| ATOM | 3924 | CA | LEU | B | 177 | 17.673 | −13.970 | −26.331 | 1.00 | 29.90 | BBBB |
| ATOM | 3932 | CA | ALA | B | 178 | 18.766 | −10.776 | −28.131 | 1.00 | 30.78 | BBBB |
| ATOM | 3937 | CA | GLY | B | 179 | 19.846 | −7.993 | −25.784 | 1.00 | 30.10 | BBBB |
| ATOM | 3941 | CA | ARG | B | 180 | 18.676 | −9.965 | −22.787 | 1.00 | 28.97 | BBBB |
| ATOM | 3952 | CA | GLU | B | 181 | 20.545 | −9.027 | −19.621 | 1.00 | 31.79 | BBBB |
| ATOM | 3961 | CA | GLY | B | 182 | 19.871 | −9.586 | −15.943 | 1.00 | 27.75 | BBBB |
| ATOM | 3966 | CA | PRO | B | 183 | 19.450 | −12.832 | −13.913 | 1.00 | 22.93 | BBBB |
| ATOM | 3972 | CA | VAL | B | 184 | 19.524 | −16.146 | −15.729 | 1.00 | 18.01 | BBBB |
| ATOM | 3979 | CA | ARG | B | 185 | 15.873 | −17.216 | −16.011 | 1.00 | 17.62 | BBBB |
| ATOM | 3990 | CA | VAL | B | 186 | 15.508 | −20.771 | −14.741 | 1.00 | 16.47 | BBBB |
| ATOM | 3997 | CA | LEU | B | 187 | 12.361 | −22.710 | −15.604 | 1.00 | 16.75 | BBBB |
| ATOM | 4005 | CA | VAL | B | 188 | 11.774 | −25.775 | −13.381 | 1.00 | 18.41 | BBBB |
| ATOM | 4012 | CA | VAL | B | 189 | 9.298 | −28.234 | −14.948 | 1.00 | 22.11 | BBBB |
| ATOM | 4018 | N | GLY | B | 190 | 8.111 | −29.887 | −13.615 | 1.00 | 25.60 | BBBB |
| ATOM | 4019 | CA | GLY | B | 190 | 7.914 | −31.188 | −12.994 | 1.00 | 27.28 | BBBB |
| ATOM | 4020 | C | GLY | B | 190 | 6.808 | −32.026 | −13.604 | 1.00 | 29.67 | BBBB |
| ATOM | 4021 | O | GLY | B | 190 | 6.668 | −33.208 | −13.283 | 1.00 | 29.86 | BBBB |
| ATOM | 4022 | N | GLY | B | 191 | 6.025 | −31.430 | −14.497 | 1.00 | 30.56 | BBBB |
| ATOM | 4023 | CA | GLY | B | 191 | 4.935 | −32.163 | −15.115 | 1.00 | 31.94 | BBBB |
| ATOM | 4024 | C | GLY | B | 191 | 3.676 | −32.104 | −14.269 | 1.00 | 33.11 | BBBB |
| ATOM | 4025 | O | GLY | B | 191 | 3.691 | −31.556 | −13.165 | 1.00 | 32.14 | BBBB |
| ATOM | 4026 | N | SER | B | 192 | 2.587 | −32.673 | −14.779 | 1.00 | 34.23 | BBBB |
| ATOM | 4027 | CA | SER | B | 192 | 1.313 | −32.665 | −14.064 | 1.00 | 35.91 | BBBB |
| ATOM | 4028 | CB | SER | B | 192 | 0.283 | −33.532 | −14.801 | 1.00 | 36.87 | BBBB |
| ATOM | 4029 | OG | SER | B | 192 | 0.702 | −34.887 | −14.877 | 1.00 | 39.58 | BBBB |
| ATOM | 4030 | C | SER | B | 192 | 1.419 | −33.128 | −12.609 | 1.00 | 36.41 | BBBB |
| ATOM | 4031 | O | SER | B | 192 | 0.862 | −32.499 | −11.714 | 1.00 | 35.78 | BBBB |
| ATOM | 4033 | CA | GLN | B | 193 | 2.292 | −34.763 | −11.033 | 1.00 | 38.53 | BBBB |
| ATOM | 4041 | N | GLY | B | 194 | 4.291 | −33.398 | −10.986 | 1.00 | 36.47 | BBBB |
| ATOM | 4042 | CA | GLY | B | 194 | 5.398 | −32.711 | −10.350 | 1.00 | 35.02 | BBBB |
| ATOM | 4043 | C | GLY | B | 194 | 6.584 | −33.630 | −10.146 | 1.00 | 34.51 | BBBB |
| ATOM | 4044 | O | GLY | B | 194 | 6.442 | −34.851 | −10.191 | 1.00 | 34.26 | BBBB |
| ATOM | 4045 | N | ALA | B | 195 | 7.761 | −33.045 | −9.938 | 1.00 | 33.54 | BBBB |
| ATOM | 4046 | CA | ALA | B | 195 | 8.977 | −33.819 | −9.709 | 1.00 | 33.12 | BBBB |
| ATOM | 4047 | CB | ALA | B | 195 | 10.073 | −33.387 | −10.679 | 1.00 | 33.17 | BBBB |
| ATOM | 4048 | C | ALA | B | 195 | 9.423 | −33.590 | −8.267 | 1.00 | 32.87 | BBBB |
| ATOM | 4049 | O | ALA | B | 195 | 9.955 | −32.533 | −7.923 | 1.00 | 31.47 | BBBB |
| ATOM | 4051 | CA | ARG | B | 196 | 9.538 | −34.512 | −6.010 | 1.00 | 32.63 | BBBB |
| ATOM | 4062 | CA | ILE | B | 197 | 13.329 | −34.168 | −6.164 | 1.00 | 28.10 | BBBB |
| ATOM | 4070 | CA | LEU | B | 198 | 13.069 | −30.833 | −8.003 | 1.00 | 26.58 | BBBB |
| ATOM | 4078 | CA | ASN | B | 199 | 10.497 | −29.447 | −5.563 | 1.00 | 27.07 | BBBB |
| ATOM | 4086 | CA | GLN | B | 200 | 12.955 | −30.326 | −2.794 | 1.00 | 30.10 | BBBB |
| ATOM | 4095 | CA | THR | B | 201 | 16.215 | −29.345 | −4.474 | 1.00 | 27.34 | BBBB |
| ATOM | 4102 | CA | MET | B | 202 | 15.567 | −26.048 | −6.268 | 1.00 | 23.68 | BBBB |
| ATOM | 4111 | CA | PRO | B | 203 | 14.608 | −23.963 | −3.220 | 1.00 | 23.84 | BBBB |
| ATOM | 4117 | CA | GLN | B | 204 | 18.033 | −24.708 | −1.684 | 1.00 | 26.34 | BBBB |
| ATOM | 4126 | CA | VAL | B | 205 | 19.672 | −24.033 | −5.043 | 1.00 | 24.44 | BBBB |
| ATOM | 4133 | CA | ALA | B | 206 | 17.980 | −20.610 | −5.013 | 1.00 | 22.84 | BBBB |
| ATOM | 4138 | CA | ALA | B | 207 | 19.442 | −19.857 | −1.576 | 1.00 | 26.65 | BBBB |
| ATOM | 4143 | CA | LYS | B | 208 | 22.915 | −20.595 | −2.919 | 1.00 | 28.31 | BBBB |
| ATOM | 4152 | CA | LEU | B | 209 | 22.577 | −18.640 | −6.171 | 1.00 | 25.68 | BBBB |
| ATOM | 4160 | CA | GLY | B | 210 | 20.675 | −15.628 | −4.804 | 1.00 | 26.56 | BBBB |
| ATOM | 4164 | CA | ASP | B | 211 | 20.370 | −12.647 | −7.190 | 1.00 | 28.28 | BBBB |
| ATOM | 4172 | CA | SER | B | 212 | 22.098 | −14.474 | −10.067 | 1.00 | 25.73 | BBBB |
| ATOM | 4178 | CA | VAL | B | 213 | 18.925 | −16.308 | −11.116 | 1.00 | 20.76 | BBBB |
| ATOM | 4185 | CA | THR | B | 214 | 15.204 | −15.726 | −11.337 | 1.00 | 19.60 | BBBB |
| ATOM | 4192 | CA | ILE | B | 215 | 13.076 | −18.850 | −11.169 | 1.00 | 18.75 | BBBB |
| ATOM | 4200 | CA | TRP | B | 216 | 9.661 | −19.973 | −12.378 | 1.00 | 19.34 | BBBB |
| ATOM | 4214 | CA | HIS | B | 217 | 9.015 | −23.303 | −10.680 | 1.00 | 21.06 | BBBB |
| ATOM | 4224 | CA | GLN | B | 218 | 6.149 | −25.594 | −11.735 | 1.00 | 24.30 | BBBB |
| ATOM | 4233 | CA | SER | B | 219 | 5.463 | −27.800 | −8.684 | 1.00 | 26.73 | BBBB |
| ATOM | 4239 | CA | GLY | B | 220 | 2.855 | −30.242 | −9.961 | 1.00 | 30.53 | BBBB |
| ATOM | 4243 | CA | LYS | B | 221 | −0.657 | −30.914 | −8.628 | 1.00 | 35.12 | BBBB |
| ATOM | 4252 | CA | GLY | B | 222 | −1.195 | −29.899 | −5.011 | 1.00 | 35.34 | BBBB |
| ATOM | 4256 | CA | SER | B | 223 | 2.451 | −28.934 | −4.418 | 1.00 | 33.98 | BBBB |
| ATOM | 4262 | CA | GLN | B | 224 | 2.187 | −25.208 | −5.186 | 1.00 | 33.71 | BBBB |
| ATOM | 4271 | CA | GLN | B | 225 | 1.823 | −24.239 | −1.519 | 1.00 | 32.32 | BBBB |
| ATOM | 4280 | CA | SER | B | 226 | 4.701 | −26.309 | −0.122 | 1.00 | 28.30 | BBBB |
| ATOM | 4286 | CA | VAL | B | 227 | 7.214 | −25.247 | −2.791 | 1.00 | 24.28 | BBBB |
| ATOM | 4293 | CA | GLU | B | 228 | 6.178 | −21.592 | −2.387 | 1.00 | 27.23 | BBBB |
| ATOM | 4302 | CA | GLN | B | 229 | 6.853 | −22.046 | 1.329 | 1.00 | 28.38 | BBBB |
| ATOM | 4311 | CA | ALA | B | 230 | 10.185 | −23.754 | 0.682 | 1.00 | 26.18 | BBBB |
| ATOM | 4316 | CA | TYR | B | 231 | 11.371 | −20.766 | −1.366 | 1.00 | 25.47 | BBBB |
| ATOM | 4328 | CA | ALA | B | 232 | 10.342 | −18.322 | 1.368 | 1.00 | 27.51 | BBBB |

TABLE 3-continued

ATOMIC COORDINATES OF E. COLI MURG C-ALPHA
BACKBONE AND CONSERVED AMINO ACID RESIDUES

| ATOM | 4333 | CA  | GLU | B | 233 | 12.145  | −20.441 | 3.966   | 1.00 | 30.87 | BBBB |
|------|------|-----|-----|---|-----|---------|---------|---------|------|-------|------|
| ATOM | 4342 | CA  | ALA | B | 234 | 15.215  | −20.417 | 1.714   | 1.00 | 28.48 | BBBB |
| ATOM | 4347 | CA  | GLY | B | 235 | 15.033  | −16.627 | 1.815   | 1.00 | 26.23 | BBBB |
| ATOM | 4351 | CA  | GLN | B | 236 | 14.121  | −16.198 | −1.870  | 1.00 | 25.53 | BBBB |
| ATOM | 4361 | CA  | PRO | B | 237 | 10.336  | −15.587 | −1.720  | 1.00 | 24.65 | BBBB |
| ATOM | 4367 | CA  | GLN | B | 238 | 10.277  | −13.558 | −4.945  | 1.00 | 24.29 | BBBB |
| ATOM | 4376 | CA  | HIS | B | 239 | 10.526  | −16.608 | −7.201  | 1.00 | 22.08 | BBBB |
| ATOM | 4386 | CA  | LYS | B | 240 | 7.375   | −17.589 | −9.105  | 1.00 | 23.26 | BBBB |
| ATOM | 4395 | CA  | VAL | B | 241 | 5.740   | −20.911 | −8.277  | 1.00 | 23.78 | BBBB |
| ATOM | 4402 | CA  | THR | B | 242 | 2.758   | −22.301 | −10.177 | 1.00 | 25.93 | BBBB |
| ATOM | 4409 | CA  | GLU | B | 243 | 0.999   | −25.651 | −9.837  | 1.00 | 27.03 | BBBB |
| ATOM | 4418 | CA  | PHE | B | 244 | 0.964   | −26.068 | −13.620 | 1.00 | 26.54 | BBBB |
| ATOM | 4429 | CA  | ILE | B | 245 | 1.932   | −24.242 | −16.802 | 1.00 | 28.48 | BBBB |
| ATOM | 4437 | CA  | ASP | B | 246 | −0.754  | −24.396 | −19.457 | 1.00 | 36.00 | BBBB |
| ATOM | 4445 | CA  | ASP | B | 247 | 1.245   | −22.392 | −21.999 | 1.00 | 30.74 | BBBB |
| ATOM | 4453 | CA  | MET | B | 248 | 4.625   | −24.136 | −22.138 | 1.00 | 28.41 | BBBB |
| ATOM | 4461 | CA  | ALA | B | 249 | 5.512   | −22.216 | −25.290 | 1.00 | 24.67 | BBBB |
| ATOM | 4466 | CA  | ALA | B | 250 | 5.188   | −18.933 | −23.390 | 1.00 | 21.78 | BBBB |
| ATOM | 4471 | CA  | ALA | B | 251 | 7.301   | −20.259 | −20.501 | 1.00 | 20.85 | BBBB |
| ATOM | 4476 | CA  | TYR | B | 252 | 9.972   | −21.616 | −22.886 | 1.00 | 22.78 | BBBB |
| ATOM | 4488 | CA  | ALA | B | 253 | 10.131  | −18.224 | −24.636 | 1.00 | 23.54 | BBBB |
| ATOM | 4493 | CA  | TRP | B | 254 | 10.829  | −16.534 | −21.303 | 1.00 | 19.76 | BBBB |
| ATOM | 4507 | CA  | ALA | B | 255 | 13.399  | −19.025 | −20.003 | 1.00 | 19.51 | BBBB |
| ATOM | 4512 | CA  | ASP | B | 256 | 17.176  | −19.026 | −20.434 | 1.00 | 17.58 | BBBB |
| ATOM | 4520 | CA  | VAL | B | 257 | 17.535  | −22.603 | −19.194 | 1.00 | 18.53 | BBBB |
| ATOM | 4527 | CA  | VAL | B | 258 | 15.208  | −25.456 | −18.234 | 1.00 | 19.32 | BBBB |
| ATOM | 4534 | CA  | VAL | B | 259 | 15.581  | −27.957 | −15.374 | 1.00 | 19.85 | BBBB |
| ATOM | 4541 | CA  | CYS | B | 260 | 13.454  | −31.055 | −15.946 | 1.00 | 22.00 | BBBB |
| ATOM | 4546 | N   | ARG | B | 261 | 12.937  | −33.397 | −16.212 | 1.00 | 22.34 | BBBB |
| ATOM | 4547 | CA  | ARG | B | 261 | 13.170  | −34.800 | −16.515 | 1.00 | 23.75 | BBBB |
| ATOM | 4548 | CB  | ARG | B | 261 | 11.964  | −35.663 | −16.104 | 1.00 | 27.16 | BBBB |
| ATOM | 4549 | CG  | ARG | B | 261 | 11.376  | −35.337 | −14.738 | 1.00 | 31.82 | BBBB |
| ATOM | 4550 | CD  | ARG | B | 261 | 11.490  | −36.473 | −13.732 | 1.00 | 36.33 | BBBB |
| ATOM | 4551 | NE  | ARG | B | 261 | 12.865  | −36.721 | −13.323 | 1.00 | 38.48 | BBBB |
| ATOM | 4552 | CZ  | ARG | B | 261 | 13.218  | −37.176 | −12.125 | 1.00 | 37.25 | BBBB |
| ATOM | 4553 | NH1 | ARG | B | 261 | 12.295  | −37.433 | −11.204 | 1.00 | 38.46 | BBBB |
| ATOM | 4554 | NH2 | ARG | B | 261 | 14.499  | −37.370 | −11.848 | 1.00 | 36.79 | BBBB |
| ATOM | 4555 | C   | ARG | B | 261 | 13.351  | −34.871 | −18.032 | 1.00 | 23.98 | BBBB |
| ATOM | 4556 | O   | ARG | B | 261 | 13.117  | −33.883 | −18.746 | 1.00 | 22.44 | BBBB |
| ATOM | 4558 | CA  | SER | B | 262 | 13.975  | −36.189 | −19.948 | 1.00 | 23.18 | BBBB |
| ATOM | 4563 | N   | GLY | B | 263 | 11.850  | −37.151 | −20.619 | 1.00 | 22.74 | BBBB |
| ATOM | 4564 | CA  | GLY | B | 263 | 11.026  | −38.079 | −21.361 | 1.00 | 22.85 | BBBB |
| ATOM | 4565 | C   | GLY | B | 263 | 11.392  | −37.793 | −22.813 | 1.00 | 24.06 | BBBB |
| ATOM | 4566 | O   | GLY | B | 263 | 11.908  | −36.705 | −23.121 | 1.00 | 22.75 | BBBB |
| ATOM | 4567 | N   | ALA | B | 264 | 11.130  | −38.739 | −23.708 | 1.00 | 23.37 | BBBB |
| ATOM | 4568 | CA  | ALA | B | 264 | 11.482  | −38.564 | −25.115 | 1.00 | 24.25 | BBBB |
| ATOM | 4569 | CB  | ALA | B | 264 | 11.133  | −39.829 | −25.894 | 1.00 | 24.58 | BBBB |
| ATOM | 4570 | C   | ALA | B | 264 | 10.843  | −37.343 | −25.783 | 1.00 | 24.29 | BBBB |
| ATOM | 4571 | O   | ALA | B | 264 | 11.523  | −36.572 | −26.470 | 1.00 | 24.33 | BBBB |
| ATOM | 4573 | CA  | LEU | B | 265 | 8.846   | −36.037 | −26.205 | 1.00 | 24.66 | BBBB |
| ATOM | 4581 | CA  | THR | B | 266 | 10.194  | −33.557 | −23.657 | 1.00 | 22.34 | BBBB |
| ATOM | 4588 | CA  | VAL | B | 267 | 13.730  | −33.762 | −25.023 | 1.00 | 21.11 | BBBB |
| ATOM | 4595 | CA  | SER | B | 268 | 12.411  | −33.191 | −28.567 | 1.00 | 21.96 | BBBB |
| ATOM | 4600 | N   | GLU | B | 269 | 10.928  | −31.563 | −27.557 | 1.00 | 21.64 | BBBB |
| ATOM | 4601 | CA  | GLU | B | 269 | 10.282  | −30.272 | −27.378 | 1.00 | 21.95 | BBBB |
| ATOM | 4602 | CB  | GLU | B | 269 | 9.213   | −30.399 | −26.292 | 1.00 | 24.72 | BBBB |
| ATOM | 4603 | CG  | GLU | B | 269 | 8.480   | −29.128 | −25.940 | 1.00 | 27.67 | BBBB |
| ATOM | 4604 | CD  | GLU | B | 269 | 7.385   | −29.380 | −24.908 | 1.00 | 30.05 | BBBB |
| ATOM | 4605 | OE1 | GLU | B | 269 | 6.325   | −29.915 | −25.287 | 1.00 | 31.50 | BBBB |
| ATOM | 4606 | OE2 | GLU | B | 269 | 7.591   | −29.057 | −23.719 | 1.00 | 29.84 | BBBB |
| ATOM | 4607 | C   | GLU | B | 269 | 11.321  | −29.214 | −26.999 | 1.00 | 21.68 | BBBB |
| ATOM | 4608 | O   | GLU | B | 269 | 11.301  | −28.095 | −27.518 | 1.00 | 18.12 | BBBB |
| ATOM | 4610 | CA  | ILE | B | 270 | 13.295  | −28.698 | −25.638 | 1.00 | 20.62 | BBBB |
| ATOM | 4618 | CA  | ALA | B | 271 | 15.440  | −29.058 | −28.776 | 1.00 | 22.45 | BBBB |
| ATOM | 4623 | CA  | ALA | B | 272 | 12.719  | −27.451 | −30.898 | 1.00 | 22.17 | BBBB |
| ATOM | 4628 | CA  | ALA | B | 273 | 12.361  | −24.596 | −28.407 | 1.00 | 21.97 | BBBB |
| ATOM | 4633 | CA  | GLY | B | 274 | 16.093  | −24.023 | −28.709 | 1.00 | 21.07 | BBBB |
| ATOM | 4637 | CA  | LEU | B | 275 | 16.666  | −24.057 | −24.966 | 1.00 | 19.78 | BBBB |
| ATOM | 4646 | CA  | PRO | B | 276 | 19.651  | −25.199 | −22.875 | 1.00 | 16.62 | BBBB |
| ATOM | 4652 | CA  | ALA | B | 277 | 18.638  | −27.807 | −20.321 | 1.00 | 15.80 | BBBB |
| ATOM | 4657 | CA  | LEU | B | 278 | 19.896  | −29.429 | −17.145 | 1.00 | 18.48 | BBBB |
| ATOM | 4665 | CA  | PHE | B | 279 | 18.266  | −32.838 | −17.392 | 1.00 | 21.59 | BBBB |
| ATOM | 4676 | CA  | VAL | B | 280 | 17.502  | −34.902 | −14.281 | 1.00 | 25.67 | BBBB |
| ATOM | 4682 | N   | PRO | B | 281 | 17.324  | −37.080 | −15.370 | 1.00 | 27.08 | BBBB |
| ATOM | 4683 | CD  | PRO | B | 281 | 18.750  | −37.057 | −15.726 | 1.00 | 27.31 | BBBB |
| ATOM | 4684 | CA  | PRO | B | 281 | 16.698  | −38.320 | −15.824 | 1.00 | 29.05 | BBBB |

TABLE 3-continued

ATOMIC COORDINATES OF E. COLI MURG C-ALPHA
BACKBONE AND CONSERVED AMINO ACID RESIDUES

| ATOM | 4685 | CB | PRO | B | 281 | 17.851 | −39.071 | −16.492 | 1.00 | 29.44 | BBBB |
| --- | --- | --- | --- | --- | --- | --- | --- | --- | --- | --- | --- |
| ATOM | 4686 | CG | PRO | B | 281 | 18.791 | −37.992 | −16.895 | 1.00 | 29.67 | BBBB |
| ATOM | 4687 | C | PRO | B | 281 | 16.092 | −39.121 | −14.684 | 1.00 | 31.51 | BBBB |
| ATOM | 4688 | O | PRO | B | 281 | 16.675 | −39.223 | −13.603 | 1.00 | 32.26 | BBBB |
| ATOM | 4690 | CA | PHE | B | 282 | 14.246 | −40.496 | −13.926 | 1.00 | 37.13 | BBBB |
| ATOM | 4701 | CA | GLN | B | 283 | 16.319 | −43.395 | −12.591 | 1.00 | 41.11 | BBBB |
| ATOM | 4710 | CA | HIS | B | 284 | 15.641 | −46.917 | −13.843 | 1.00 | 43.69 | BBBB |
| ATOM | 4720 | CA | LYS | B | 285 | 17.767 | −49.993 | −14.571 | 1.00 | 45.34 | BBBB |
| ATOM | 4729 | CA | ASP | B | 286 | 16.949 | −49.299 | −18.222 | 1.00 | 43.26 | BBBB |
| ATOM | 4737 | CA | ARG | B | 287 | 17.951 | −45.623 | −17.883 | 1.00 | 36.28 | BBBB |
| ATOM | 4748 | CA | GLN | B | 288 | 15.622 | −44.804 | −20.755 | 1.00 | 30.77 | BBBB |
| ATOM | 4756 | N | GLN | B | 289 | 15.378 | −42.554 | −19.857 | 1.00 | 29.38 | BBBB |
| ATOM | 4757 | CA | GLN | B | 289 | 15.474 | −41.099 | −19.904 | 1.00 | 29.46 | BBBB |
| ATOM | 4758 | CB | GLN | B | 289 | 14.772 | −40.472 | −18.700 | 1.00 | 29.25 | BBBB |
| ATOM | 4759 | CG | GLN | B | 289 | 13.265 | −40.416 | −18.883 | 1.00 | 29.32 | BBBB |
| ATOM | 4760 | CD | GLN | B | 289 | 12.575 | −39.585 | −17.826 | 1.00 | 29.84 | BBBB |
| ATOM | 4761 | OE1 | GLN | B | 289 | 13.191 | −38.728 | −17.188 | 1.00 | 29.52 | BBBB |
| ATOM | 4762 | NE2 | GLN | B | 289 | 11.281 | −39.821 | −17.647 | 1.00 | 28.95 | BBBB |
| ATOM | 4763 | C | GLN | B | 289 | 16.906 | −40.613 | −20.005 | 1.00 | 29.36 | BBBB |
| ATOM | 4764 | O | GLN | B | 289 | 17.173 | −39.557 | −20.585 | 1.00 | 29.12 | BBBB |
| ATOM | 4766 | CA | TYR | B | 290 | 19.228 | −40.984 | −19.550 | 1.00 | 29.55 | BBBB |
| ATOM | 4778 | CA | TRP | B | 291 | 19.542 | −42.282 | −23.116 | 1.00 | 28.07 | BBBB |
| ATOM | 4791 | N | ASN | B | 292 | 17.658 | −40.779 | −23.508 | 1.00 | 25.52 | BBBB |
| ATOM | 4792 | CA | ASN | B | 292 | 16.902 | −39.784 | −24.270 | 1.00 | 26.06 | BBBB |
| ATOM | 4793 | CB | ASN | B | 292 | 15.484 | −39.599 | −23.709 | 1.00 | 24.78 | BBBB |
| ATOM | 4794 | CG | ASN | B | 292 | 14.590 | −40.811 | −23.928 | 1.00 | 24.46 | BBBB |
| ATOM | 4795 | OD1 | ASN | B | 292 | 14.842 | −41.641 | −24.798 | 1.00 | 25.33 | BBBB |
| ATOM | 4796 | ND2 | ASN | B | 292 | 13.523 | −40.900 | −23.146 | 1.00 | 23.83 | BBBB |
| ATOM | 4797 | C | ASN | B | 292 | 17.605 | −38.427 | −24.258 | 1.00 | 25.99 | BBBB |
| ATOM | 4798 | O | ASN | B | 292 | 17.566 | −37.687 | −25.244 | 1.00 | 26.18 | BBBB |
| ATOM | 4799 | N | ALA | B | 293 | 18.242 | −38.105 | −23.139 | 1.00 | 25.66 | BBBB |
| ATOM | 4800 | CA | ALA | B | 293 | 18.926 | −36.822 | −22.979 | 1.00 | 25.69 | BBBB |
| ATOM | 4801 | CB | ALA | B | 293 | 18.940 | −36.422 | −21.506 | 1.00 | 24.17 | BBBB |
| ATOM | 4802 | C | ALA | B | 293 | 20.346 | −36.800 | −23.521 | 1.00 | 25.67 | BBBB |
| ATOM | 4803 | O | ALA | B | 293 | 20.855 | −35.743 | −23.902 | 1.00 | 25.52 | BBBB |
| ATOM | 4805 | CA | LEU | B | 294 | 22.354 | −38.088 | −24.032 | 1.00 | 25.90 | BBBB |
| ATOM | 4814 | CA | PRO | B | 295 | 21.998 | −36.870 | −27.635 | 1.00 | 26.15 | BBBB |
| ATOM | 4820 | CA | LEU | B | 296 | 21.521 | −33.265 | −26.481 | 1.00 | 25.42 | BBBB |
| ATOM | 4828 | CA | GLU | B | 297 | 24.354 | −33.530 | −23.953 | 1.00 | 28.78 | BBBB |
| ATOM | 4837 | CA | LYS | B | 298 | 26.644 | −34.947 | −26.648 | 1.00 | 31.90 | BBBB |
| ATOM | 4846 | CA | ALA | B | 299 | 25.773 | −31.965 | −28.847 | 1.00 | 30.38 | BBBB |
| ATOM | 4851 | CA | GLY | B | 300 | 26.777 | −29.635 | −26.017 | 1.00 | 26.18 | BBBB |
| ATOM | 4855 | CA | ALA | B | 301 | 23.214 | −28.333 | −25.638 | 1.00 | 22.50 | BBBB |
| ATOM | 4860 | CA | ALA | B | 302 | 22.516 | −29.770 | −22.186 | 1.00 | 21.78 | BBBB |
| ATOM | 4865 | CA | LYS | B | 303 | 23.979 | −31.340 | −19.048 | 1.00 | 25.86 | BBBB |
| ATOM | 4874 | CA | ILE | B | 304 | 22.753 | −34.598 | −17.550 | 1.00 | 27.17 | BBBB |
| ATOM | 4882 | CA | ILE | B | 305 | 22.843 | −35.178 | −13.813 | 1.00 | 29.01 | BBBB |
| ATOM | 4890 | CA | GLU | B | 306 | 21.664 | −38.702 | −13.061 | 1.00 | 34.65 | BBBB |
| ATOM | 4899 | CA | GLN | B | 307 | 20.377 | −39.599 | −9.613 | 1.00 | 40.54 | BBBB |
| ATOM | 4909 | CA | PRO | B | 308 | 23.828 | −40.891 | −8.484 | 1.00 | 43.20 | BBBB |
| ATOM | 4915 | CA | GLN | B | 309 | 25.247 | −37.361 | −8.787 | 1.00 | 43.46 | BBBB |
| ATOM | 4924 | CA | LEU | B | 310 | 22.232 | −35.166 | −8.022 | 1.00 | 39.65 | BBBB |
| ATOM | 4932 | CA | SER | B | 311 | 22.660 | −32.714 | −5.154 | 1.00 | 34.90 | BBBB |
| ATOM | 4938 | CA | VAL | B | 312 | 21.990 | −29.074 | −4.341 | 1.00 | 31.50 | BBBB |
| ATOM | 4945 | CA | ASP | B | 313 | 25.642 | −28.202 | −4.957 | 1.00 | 29.61 | BBBB |
| ATOM | 4953 | CA | ALA | B | 314 | 25.782 | −30.099 | −8.254 | 1.00 | 26.47 | BBBB |
| ATOM | 4958 | CA | VAL | B | 315 | 22.755 | −28.215 | −9.612 | 1.00 | 25.33 | BBBB |
| ATOM | 4965 | CA | ALA | B | 316 | 23.888 | −24.872 | −8.199 | 1.00 | 27.13 | BBBB |
| ATOM | 4970 | CA | ASN | B | 317 | 27.444 | −25.246 | −9.518 | 1.00 | 28.52 | BBBB |
| ATOM | 4978 | CA | TBR | B | 318 | 26.174 | −26.371 | −12.906 | 1.00 | 27.04 | BBBB |
| ATOM | 4985 | CA | LEU | B | 319 | 23.883 | −23.370 | −13.357 | 1.00 | 25.21 | BBBB |
| ATOM | 4993 | CA | ALA | B | 320 | 26.445 | −20.931 | −11.957 | 1.00 | 24.59 | BBBB |
| ATOM | 4998 | CA | GLY | B | 321 | 28.934 | −22.031 | −14.591 | 1.00 | 24.34 | BBBB |
| ATOM | 5002 | CA | TRP | B | 322 | 26.738 | −21.007 | −17.521 | 1.00 | 21.72 | BBBB |
| ATOM | 5016 | CA | SER | B | 323 | 27.141 | −17.404 | −18.692 | 1.00 | 19.04 | BBBB |
| ATOM | 5022 | CA | ARG | B | 324 | 24.725 | −15.741 | −21.112 | 1.00 | 18.09 | BBBB |
| ATOM | 5033 | CA | GLU | B | 325 | 27.220 | −16.368 | −23.954 | 1.00 | 16.96 | BBBB |
| ATOM | 5042 | CA | THR | B | 326 | 27.460 | −20.055 | −23.070 | 1.00 | 16.39 | BBBB |
| ATOM | 5049 | CA | LEU | B | 327 | 23.659 | −20.305 | −22.780 | 1.00 | 17.27 | BBBB |
| ATOM | 5057 | CA | LEU | B | 328 | 23.175 | −18.745 | −26.222 | 1.00 | 17.39 | BBBB |
| ATOM | 5065 | CA | THR | B | 329 | 25.567 | −21.335 | −27.688 | 1.00 | 21.30 | BBBB |
| ATOM | 5072 | CA | MET | B | 330 | 23.771 | −24.153 | −25.870 | 1.00 | 19.91 | BBBB |
| ATOM | 5080 | CA | ALA | B | 331 | 20.412 | −22.871 | −27.098 | 1.00 | 18.49 | BBBB |
| ATOM | 5085 | CA | GLU | B | 332 | 21.626 | −22.827 | −30.704 | 1.00 | 21.47 | BBBB |
| ATOM | 5094 | CA | ARG | B | 333 | 23.040 | −26.330 | −30.408 | 1.00 | 23.77 | BBBB |
| ATOM | 5105 | CA | ALA | B | 334 | 19.648 | −27.420 | −29.063 | 1.00 | 22.88 | BBBB |

TABLE 3-continued

ATOMIC COORDINATES OF E. COLI MURG C-ALPHA
BACKBONE AND CONSERVED AMINO ACID RESIDUES

| ATOM | 5110 | CA | ARG | B | 335 | 17.795 | −25.892 | −32.002 | 1.00 | 23.54 | BBBB |
|------|------|----|-----|---|-----|--------|---------|---------|------|-------|------|
| ATOM | 5121 | CA | ALA | B | 336 | 20.330 | −27.477 | −34.372 | 1.00 | 26.85 | BBBB |
| ATOM | 5126 | CA | ALA | B | 337 | 19.740 | −30.925 | −32.865 | 1.00 | 30.89 | BBBB |
| ATOM | 5131 | CA | SER | B | 338 | 16.008 | −30.432 | −33.408 | 1.00 | 32.41 | BBBB |
| ATOM | 5137 | CA | ILE | B | 339 | 13.882 | −31.941 | −36.187 | 1.00 | 34.35 | BBBB |
| ATOM | 5146 | CA | PRO | B | 340 | 10.733 | −29.730 | −36.600 | 1.00 | 34.94 | BBBB |
| ATOM | 5152 | CA | ASP | B | 341 | 8.711  | −31.820 | −39.056 | 1.00 | 33.33 | BBBB |
| ATOM | 5160 | CA | ALA | B | 342 | 8.875  | −35.238 | −37.411 | 1.00 | 29.09 | BBBB |
| ATOM | 5165 | CA | THR | B | 343 | 5.115  | −35.696 | −37.744 | 1.00 | 28.55 | BBBB |
| ATOM | 5172 | CA | GLU | B | 344 | 5.085  | −34.933 | −41.480 | 1.00 | 32.00 | BBBB |
| ATOM | 5181 | CA | ARG | B | 345 | 8.138  | −37.123 | −42.067 | 1.00 | 31.44 | BBBB |
| ATOM | 5192 | CA | VAL | B | 346 | 6.578  | −40.151 | −40.384 | 1.00 | 28.61 | BBBB |
| ATOM | 5199 | CA | ALA | B | 347 | 3.249  | −39.617 | −42.137 | 1.00 | 28.96 | BBBB |
| ATOM | 5204 | CA | ASN | B | 348 | 5.035  | −39.286 | −45.493 | 1.00 | 34.56 | BBBB |
| ATOM | 5212 | CA | GLU | B | 349 | 6.954  | −42.540 | −44.956 | 1.00 | 34.86 | BBBB |
| ATOM | 5221 | CA | VAL | B | 350 | 3.767  | −44.306 | −43.919 | 1.00 | 33.79 | BBBB |
| ATOM | 5228 | CA | SER | B | 351 | 2.196  | −42.946 | −47.095 | 1.00 | 36.67 | BBBB |
| ATOM | 5234 | CA | ARG | B | 352 | 5.114  | −44.088 | −49.251 | 1.00 | 40.03 | BBBB |
| ATOM | 5245 | CA | VAL | B | 353 | 5.089  | −47.587 | −47.737 | 1.00 | 42.78 | BBBB |
| ATOM | 5252 | CA | ALA | B | 354 | 1.336  | −47.957 | −48.212 | 1.00 | 47.24 | BBBB |
| ATOM | 5257 | CA | ARG | B | 355 | 2.035  | −46.964 | −51.824 | 1.00 | 52.71 | BBBB |
| ATOM | 5268 | CA | ALA | B | 356 | 4.453  | −49.913 | −51.809 | 1.00 | 54.93 | BBBB |
| ATOM | 5273 | CA | LEU | B | 357 | 7.023  | −47.522 | −53.289 | 1.00 | 57.81 | BBBB |
| END  |      |    |     |   |     |        |         |         |      |       |      |

TABLE 4

ATOMIC COORDINATES OF THE
DONOR NUCLEOTIDE BINDING SITE

REMARK 4 1MUR COMPLIES WITH FORMAT V. 2.0, MAY 11, 2000

| ATOM | 1  | N   | LEU | B | 187 | 13.695 | −22.128 | −15.588 | 1.00 | 15.92 | N |
|------|----|-----|-----|---|-----|--------|---------|---------|------|-------|---|
| ATOM | 2  | CA  | LEU | B | 187 | 12.361 | −22.710 | −15.604 | 1.00 | 16.75 | C |
| ATOM | 3  | C   | LEU | B | 187 | 12.450 | −24.146 | −15.085 | 1.00 | 16.85 | C |
| ATOM | 4  | O   | LEU | B | 187 | 13.115 | −24.982 | −15.688 | 1.00 | 17.18 | O |
| ATOM | 5  | CB  | LEU | B | 187 | 11.813 | −22.701 | −17.035 | 1.00 | 16.85 | C |
| ATOM | 6  | CG  | LEU | B | 187 | 10.445 | −23.340 | −17.276 | 1.00 | 18.63 | C |
| ATOM | 7  | CD1 | LEU | B | 187 | 9.368  | −22.478 | −16.625 | 1.00 | 19.42 | C |
| ATOM | 8  | CD2 | LEU | B | 187 | 10.198 | −23.449 | −18.783 | 1.00 | 19.11 | C |
| ATOM | 9  | N   | VAL | B | 188 | 11.788 | −24.426 | −13.964 | 1.00 | 18.20 | N |
| ATOM | 10 | CA  | VAL | B | 188 | 11.774 | −25.775 | −13.381 | 1.00 | 18.41 | C |
| ATOM | 11 | C   | VAL | B | 188 | 10.434 | −26.440 | −13.739 | 1.00 | 19.88 | C |
| ATOM | 12 | O   | VAL | B | 188 | 9.371  | −25.967 | −13.336 | 1.00 | 20.39 | O |
| ATOM | 13 | CB  | VAL | B | 188 | 11.902 | −25.714 | −11.842 | 1.00 | 18.98 | C |
| ATOM | 14 | CG1 | VAL | B | 188 | 12.088 | −27.126 | −11.270 | 1.00 | 18.50 | C |
| ATOM | 15 | CG2 | VAL | B | 188 | 13.061 | −24.818 | −11.449 | 1.00 | 18.83 | C |
| ATOM | 16 | N   | VAL | B | 189 | 10.493 | −27.532 | −14.496 | 1.00 | 21.55 | N |
| ATOM | 17 | CA  | VAL | B | 189 | 9.298  | −28.234 | −14.948 | 1.00 | 22.11 | C |
| ATOM | 18 | C   | VAL | B | 189 | 9.191  | −29.639 | −14.351 | 1.00 | 23.90 | C |
| ATOM | 19 | O   | VAL | B | 189 | 10.067 | −30.478 | −14.559 | 1.00 | 23.61 | O |
| ATOM | 20 | CB  | VAL | B | 189 | 9.299  | −28.342 | −16.488 | 1.00 | 22.50 | C |
| ATOM | 21 | CG1 | VAL | B | 189 | 8.009  | −29.013 | −16.981 | 1.00 | 22.70 | C |
| ATOM | 22 | CG2 | VAL | B | 189 | 9.470  | −26.943 | −17.101 | 1.00 | 21.26 | C |
| ATOM | 23 | N   | GLY | B | 190 | 8.111  | −29.887 | −13.615 | 1.00 | 25.60 | N |
| ATOM | 24 | CA  | GLY | B | 190 | 7.914  | −31.188 | −12.994 | 1.00 | 27.28 | C |
| ATOM | 25 | C   | GLY | B | 190 | 6.808  | −32.026 | −13.604 | 1.00 | 29.67 | C |
| ATOM | 26 | O   | GLY | B | 190 | 6.668  | −33.208 | −13.283 | 1.00 | 29.86 | O |
| ATOM | 27 | N   | GLY | B | 191 | 6.025  | −31.430 | −14.497 | 1.00 | 30.56 | N |
| ATOM | 28 | CA  | GLY | B | 191 | 4.935  | −32.163 | −15.115 | 1.00 | 31.94 | C |
| ATOM | 29 | C   | GLY | B | 191 | 3.676  | −32.104 | −14.269 | 1.00 | 33.11 | C |
| ATOM | 30 | O   | GLY | B | 191 | 3.691  | −31.556 | −13.165 | 1.00 | 32.14 | O |
| ATOM | 31 | N   | ALA | B | 195 | 7.761  | −33.045 | −9.938  | 1.00 | 33.54 | N |
| ATOM | 32 | CA  | ALA | B | 195 | 8.977  | −33.819 | −9.709  | 1.00 | 33.12 | C |
| ATOM | 33 | C   | ALA | B | 195 | 9.423  | −33.590 | −8.267  | 1.00 | 32.87 | C |
| ATOM | 34 | O   | ALA | B | 195 | 9.955  | −32.533 | −7.923  | 1.00 | 31.47 | O |
| ATOM | 35 | CB  | ALA | B | 195 | 10.073 | −33.387 | −10.679 | 1.00 | 33.17 | C |
| ATOM | 36 | N   | LEU | B | 198 | 12.897 | −32.223 | −7.590  | 1.00 | 27.07 | N |
| ATOM | 37 | CA  | LEU | B | 198 | 13.069 | −30.833 | −8.003  | 1.00 | 26.58 | C |
| ATOM | 38 | C   | LEU | B | 198 | 12.388 | −29.893 | −7.006  | 1.00 | 26.41 | C |
| ATOM | 39 | O   | LEU | B | 198 | 12.930 | −28.835 | −6.667  | 1.00 | 26.35 | O |
| ATOM | 40 | CB  | LEU | B | 198 | 12.504 | −30.616 | −9.412  | 1.00 | 25.88 | C |
| ATOM | 41 | CG  | LEU | B | 198 | 13.196 | −31.408 | −10.524 | 1.00 | 25.40 | C |
| ATOM | 42 | CD1 | LEU | B | 198 | 12.625 | −31.007 | −11.874 | 1.00 | 26.54 | C |

TABLE 4-continued

ATOMIC COORDINATES OF THE
DONOR NUCLEOTIDE BINDING SITE

| ATOM | 43 | CD2 | LEU | B | 198 | 14.692 | −31.146 | −10.493 | 1.00 | 25.94 | C |
|---|---|---|---|---|---|---|---|---|---|---|---|
| ATOM | 44 | N | TYR | B | 252 | 8.723 | −21.314 | −22.184 | 1.00 | 21.27 | N |
| ATOM | 45 | CA | TYR | B | 252 | 9.972 | −21.616 | −22.886 | 1.00 | 22.78 | C |
| ATOM | 46 | C | TYR | B | 252 | 10.566 | −20.354 | −23.516 | 1.00 | 23.57 | C |
| ATOM | 47 | O | TYR | B | 252 | 11.784 | −20.180 | −23.550 | 1.00 | 23.91 | O |
| ATOM | 48 | CB | TYR | B | 252 | 9.726 | −22.661 | −23.980 | 1.00 | 21.62 | C |
| ATOM | 49 | CG | TYR | B | 252 | 9.662 | −24.100 | −23.505 | 1.00 | 23.34 | C |
| ATOM | 50 | CD1 | TYR | B | 252 | 9.003 | −25.065 | −24.261 | 1.00 | 22.88 | C |
| ATOM | 51 | CD2 | TYR | B | 252 | 10.288 | −24.505 | −22.319 | 1.00 | 22.30 | C |
| ATOM | 52 | CE1 | TYR | B | 252 | 8.961 | −26.392 | −23.861 | 1.00 | 24.81 | C |
| ATOM | 53 | CE2 | TYR | B | 252 | 10.253 | −25.838 | −21.912 | 1.00 | 23.56 | C |
| ATOM | 54 | CZ | TYR | B | 252 | 9.590 | −26.772 | −22.687 | 1.00 | 24.26 | C |
| ATOM | 55 | OH | TYR | B | 252 | 9.554 | −28.088 | −22.305 | 1.00 | 25.57 | O |
| ATOM | 56 | N | VAL | B | 258 | 16.263 | −24.643 | −18.818 | 1.00 | 18.74 | N |
| ATOM | 57 | CA | VAL | B | 258 | 15.208 | −25.456 | −18.234 | 1.00 | 19.32 | C |
| ATOM | 58 | C | VAL | B | 258 | 15.799 | −26.585 | −17.389 | 1.00 | 19.70 | C |
| ATOM | 59 | O | VAL | B | 258 | 16.808 | −27.175 | −17.758 | 1.00 | 18.96 | O |
| ATOM | 60 | CB | VAL | B | 258 | 14.328 | −26.100 | −19.337 | 1.00 | 19.89 | C |
| ATOM | 61 | CG1 | VAL | B | 258 | 13.101 | −26.754 | −18.714 | 1.00 | 19.81 | C |
| ATOM | 62 | CG2 | VAL | B | 258 | 13.907 | −25.041 | −20.364 | 1.00 | 21.59 | C |
| ATOM | 63 | N | VAL | B | 259 | 15.167 | −26.861 | −16.253 | 1.00 | 20.24 | N |
| ATOM | 64 | CA | VAL | B | 259 | 15.581 | −27.957 | −15.374 | 1.00 | 19.85 | C |
| ATOM | 65 | C | VAL | B | 259 | 14.382 | −28.890 | −15.371 | 1.00 | 20.02 | C |
| ATOM | 66 | O | VAL | B | 259 | 13.301 | −28.500 | −14.942 | 1.00 | 21.88 | O |
| ATOM | 67 | CB | VAL | B | 259 | 15.850 | −27.483 | −13.936 | 1.00 | 20.08 | C |
| ATOM | 68 | CG1 | VAL | B | 259 | 16.222 | −28.689 | −13.059 | 1.00 | 20.22 | C |
| ATOM | 69 | CG2 | VAL | B | 259 | 16.966 | −26.453 | −13.930 | 1.00 | 17.86 | C |
| ATOM | 70 | N | CYS | B | 260 | 14.562 | −30.111 | −15.867 | 1.00 | 21.70 | N |
| ATOM | 71 | CA | CYS | B | 260 | 13.454 | −31.055 | −15.946 | 1.00 | 22.00 | C |
| ATOM | 72 | C | CYS | B | 260 | 13.903 | −32.478 | −16.242 | 1.00 | 21.86 | C |
| ATOM | 73 | O | CYS | B | 260 | 15.087 | −32.730 | −16.496 | 1.00 | 21.34 | O |
| ATOM | 74 | CB | CYS | B | 260 | 12.494 | −30.618 | −17.057 | 1.00 | 22.77 | C |
| ATOM | 75 | SG | CYS | B | 260 | 13.297 | −30.506 | −18.711 | 1.00 | 22.15 | S |
| ATOM | 76 | N | ARG | B | 261 | 12.937 | −33.397 | −16.212 | 1.00 | 22.34 | N |
| ATOM | 77 | CA | ARG | B | 261 | 13.170 | −34.800 | −16.515 | 1.00 | 23.75 | C |
| ATOM | 78 | C | ARG | B | 261 | 13.351 | −34.871 | −18.032 | 1.00 | 23.98 | C |
| ATOM | 79 | O | ARG | B | 261 | 13.117 | −33.883 | −18.746 | 1.00 | 22.44 | O |
| ATOM | 80 | CB | ARG | B | 261 | 11.964 | −35.663 | −16.104 | 1.00 | 27.16 | C |
| ATOM | 81 | CG | ARG | B | 261 | 11.376 | −35.337 | −14.738 | 1.00 | 31.82 | C |
| ATOM | 82 | CD | ARG | B | 261 | 11.490 | −36.473 | −13.732 | 1.00 | 36.33 | C |
| ATOM | 83 | NE | ARG | B | 261 | 12.865 | −36.721 | −13.323 | 1.00 | 38.48 | N |
| ATOM | 84 | CZ | ARG | B | 261 | 13.218 | −37.176 | −12.125 | 1.00 | 37.25 | C |
| ATOM | 85 | NH1 | ARG | B | 261 | 12.295 | −37.433 | −11.204 | 1.00 | 38.46 | N |
| ATOM | 86 | NH2 | ARG | B | 261 | 14.499 | −37.370 | −11.848 | 1.00 | 36.79 | N |
| ATOM | 87 | N | SER | B | 262 | 13.740 | −36.038 | −18.527 | 1.00 | 22.00 | N |
| ATOM | 88 | CA | SER | B | 262 | 13.975 | −36.189 | −19.948 | 1.00 | 23.18 | C |
| ATOM | 89 | C | SER | B | 262 | 13.173 | −37.263 | −20.676 | 1.00 | 22.90 | C |
| ATOM | 90 | O | SER | B | 262 | 13.738 | −38.179 | −21.274 | 1.00 | 23.25 | O |
| ATOM | 91 | CB | SER | B | 262 | 15.481 | −36.377 | −20.203 | 1.00 | 24.45 | C |
| ATOM | 92 | OG | SER | B | 262 | 16.043 | −37.326 | −19.311 | 1.00 | 25.79 | O |
| ATOM | 93 | N | GLY | B | 263 | 11.850 | −37.151 | −20.619 | 1.00 | 22.74 | N |
| ATOM | 94 | CA | GLY | B | 263 | 11.026 | −38.079 | −21.361 | 1.00 | 22.85 | C |
| ATOM | 95 | C | GLY | B | 263 | 11.392 | −37.793 | −22.813 | 1.00 | 24.06 | C |
| ATOM | 96 | O | GLY | B | 263 | 11.908 | −36.705 | −23.121 | 1.00 | 22.75 | O |
| ATOM | 97 | N | ALA | B | 264 | 11.130 | −38.739 | −23.708 | 1.00 | 23.37 | N |
| ATOM | 98 | CA | ALA | B | 264 | 11.482 | −38.564 | −25.115 | 1.00 | 24.25 | C |
| ATOM | 99 | C | ALA | B | 264 | 10.843 | −37.343 | −25.783 | 1.00 | 24.29 | C |
| ATOM | 100 | O | ALA | B | 264 | 11.523 | −36.572 | −26.470 | 1.00 | 24.33 | O |
| ATOM | 101 | CB | ALA | B | 264 | 11.133 | −39.829 | −25.894 | 1.00 | 24.58 | C |
| ATOM | 102 | N | LEU | B | 265 | 9.541 | −37.167 | −25.596 | 1.00 | 24.44 | N |
| ATOM | 103 | CA | LEU | B | 265 | 8.846 | −36.037 | −26.205 | 1.00 | 24.66 | C |
| ATOM | 104 | C | LEU | B | 265 | 9.331 | −34.717 | −25.613 | 1.00 | 24.47 | C |
| ATOM | 105 | O | LEU | B | 265 | 9.374 | −33.693 | −26.301 | 1.00 | 23.85 | O |
| ATOM | 106 | CB | LEU | B | 265 | 7.332 | −36.183 | −26.011 | 1.00 | 25.33 | C |
| ATOM | 107 | CG | LEU | B | 265 | 6.760 | −37.544 | −26.426 | 1.00 | 27.97 | C |
| ATOM | 108 | CD1 | LEU | B | 265 | 5.242 | −37.541 | −26.258 | 1.00 | 28.21 | C |
| ATOM | 109 | CD2 | LEU | B | 265 | 7.146 | −37.856 | −27.878 | 1.00 | 27.40 | C |
| ATOM | 110 | N | THR | B | 266 | 9.702 | −34.747 | −24.338 | 1.00 | 22.12 | N |
| ATOM | 111 | CA | THR | B | 266 | 10.194 | −33.557 | −23.657 | 1.00 | 22.34 | C |
| ATOM | 112 | C | THR | B | 266 | 11.535 | −33.117 | −24.226 | 1.00 | 21.15 | C |
| ATOM | 113 | O | THR | B | 266 | 11.761 | −31.926 | −24.442 | 1.00 | 20.35 | O |
| ATOM | 114 | CB | THR | B | 266 | 10.348 | −33.803 | −22.140 | 1.00 | 22.35 | C |
| ATOM | 115 | CG1 | THR | B | 266 | 9.061 | −34.087 | −21.583 | 1.00 | 24.46 | O |
| ATOM | 116 | CG2 | THR | B | 266 | 10.945 | −32.573 | −21.444 | 1.00 | 24.00 | C |
| ATOM | 117 | N | VAL | B | 267 | 12.427 | −34.075 | −24.461 | 1.00 | 20.46 | N |
| ATOM | 118 | CA | VAL | B | 267 | 13.730 | −33.762 | −25.023 | 1.00 | 21.11 | C |

TABLE 4-continued

ATOMIC COORDINATES OF THE
DONOR NUCLEOTIDE BINDING SITE

| ATOM | 119 | C | VAL | B | 267 | 13.548 | −33.138 | −26.416 | 1.00 | 21.34 | C |
|---|---|---|---|---|---|---|---|---|---|---|---|
| ATOM | 120 | O | VAL | B | 267 | 14.188 | −32.135 | −26.747 | 1.00 | 19.99 | O |
| ATOM | 121 | CB | VAL | B | 267 | 14.614 | −35.039 | −25.114 | 1.00 | 21.54 | C |
| ATOM | 122 | CG1 | VAL | B | 267 | 15.903 | −34.740 | −25.865 | 1.00 | 20.72 | C |
| ATOM | 123 | CG2 | VAL | B | 267 | 14.938 | −35.541 | −23.708 | 1.00 | 20.45 | C |
| ATOM | 124 | N | SER | B | 268 | 12.663 | −33.717 | −27.222 | 1.00 | 21.61 | N |
| ATOM | 125 | CA | SER | B | 268 | 12.411 | −33.191 | −28.567 | 1.00 | 21.96 | C |
| ATOM | 126 | C | SER | B | 268 | 11.817 | −31.790 | −28.519 | 1.00 | 21.81 | C |
| ATOM | 127 | O | SER | B | 268 | 12.158 | −30.933 | −29.336 | 1.00 | 22.60 | O |
| ATOM | 128 | CB | SER | B | 268 | 11.474 | −34.121 | −29.344 | 1.00 | 21.57 | C |
| ATOM | 129 | OG | SER | B | 268 | 12.141 | −35.316 | −29.721 | 1.00 | 24.06 | O |
| ATOM | 130 | N | GLU | B | 269 | 10.928 | −31.563 | −27.557 | 1.00 | 21.64 | N |
| ATOM | 131 | CA | GLU | B | 269 | 10.282 | −30.272 | −27.378 | 1.00 | 21.95 | C |
| ATOM | 132 | C | GLU | B | 269 | 11.321 | −29.214 | −26.999 | 1.00 | 21.68 | C |
| ATOM | 133 | O | GLU | B | 269 | 11.301 | −28.095 | −27.518 | 1.00 | 18.12 | O |
| ATOM | 134 | CB | GLU | B | 269 | 9.213 | −30.399 | −26.292 | 1.00 | 24.72 | C |
| ATOM | 135 | CG | GLU | B | 269 | 8.480 | −29.128 | −25.940 | 1.00 | 27.67 | C |
| ATOM | 136 | CD | GLU | B | 269 | 7.385 | −29.380 | −24.908 | 1.00 | 30.05 | C |
| ATOM | 137 | OE1 | GLU | B | 269 | 6.325 | −29.915 | −25.287 | 1.00 | 31.50 | O |
| ATOM | 138 | OE2 | GLU | B | 269 | 7.591 | −29.057 | −23.719 | 1.00 | 29.84 | O |
| ATOM | 139 | N | ILE | B | 270 | 12.224 | −29.581 | −26.092 | 1.00 | 19.43 | N |
| ATOM | 140 | CA | ILE | B | 270 | 13.295 | −28.698 | −25.638 | 1.00 | 20.62 | C |
| ATOM | 141 | C | ILE | B | 270 | 14.214 | −28.314 | −26.806 | 1.00 | 20.58 | C |
| ATOM | 142 | O | ILE | B | 270 | 14.595 | −27.151 | −26.954 | 1.00 | 20.50 | O |
| ATOM | 143 | CB | ILE | B | 270 | 14.157 | −29.391 | −24.533 | 1.00 | 20.30 | C |
| ATOM | 144 | CG1 | ILE | B | 270 | 13.337 | −29.574 | −23.254 | 1.00 | 21.32 | C |
| ATOM | 145 | CG2 | ILE | B | 270 | 15.415 | −28.595 | −24.266 | 1.00 | 19.17 | C |
| ATOM | 146 | CD1 | ILE | B | 270 | 12.926 | −28.291 | −22.583 | 1.00 | 23.40 | C |
| ATOM | 147 | N | ALA | B | 277 | 19.316 | −27.110 | −21.396 | 1.00 | 17.01 | N |
| ATOM | 148 | CA | ALA | B | 277 | 18.638 | −27.807 | −20.321 | 1.00 | 15.80 | C |
| ATOM | 149 | C | ALA | B | 277 | 19.591 | −28.526 | −19.382 | 1.00 | 17.37 | C |
| ATOM | 150 | O | ALA | B | 277 | 20.710 | −28.891 | −19.755 | 1.00 | 17.09 | O |
| ATOM | 151 | CB | ALA | B | 277 | 17.641 | −28.805 | −20.895 | 1.00 | 17.01 | C |
| ATOM | 152 | N | LEU | B | 278 | 19.147 | −28.673 | −18.138 | 1.00 | 17.14 | N |
| ATOM | 153 | CA | LEU | B | 278 | 19.896 | −29.429 | −17.145 | 1.00 | 18.48 | C |
| ATOM | 154 | C | LEU | B | 278 | 18.884 | −30.535 | −16.898 | 1.00 | 19.62 | C |
| ATOM | 155 | O | LEU | B | 278 | 17.870 | −30.330 | −16.218 | 1.00 | 20.77 | O |
| ATOM | 156 | CB | LEU | B | 278 | 20.140 | −28.619 | −15.869 | 1.00 | 19.19 | C |
| ATOM | 157 | CG | LEU | B | 278 | 21.084 | −29.308 | −14.868 | 1.00 | 20.85 | C |
| ATOM | 158 | CD1 | LEU | B | 278 | 21.283 | −28.411 | −13.668 | 1.00 | 21.11 | C |
| ATOM | 159 | CD2 | LEU | B | 278 | 20.497 | −30.647 | −14.433 | 1.00 | 19.16 | C |
| ATOM | 160 | N | PHE | B | 279 | 19.149 | −31.691 | −17.495 | 1.00 | 19.50 | N |
| ATOM | 161 | CA | PHE | B | 279 | 18.266 | −32.838 | −17.392 | 1.00 | 21.59 | C |
| ATOM | 162 | C | PHE | B | 279 | 18.525 | −33.709 | −16.167 | 1.00 | 22.86 | C |
| ATOM | 163 | O | PHE | B | 279 | 19.671 | −34.065 | −15.871 | 1.00 | 23.32 | O |
| ATOM | 164 | CB | PHE | B | 279 | 18.385 | −33.700 | −18.651 | 1.00 | 21.07 | C |
| ATOM | 165 | OG | PHE | B | 279 | 17.740 | −33.099 | −19.876 | 1.00 | 19.35 | C |
| ATOM | 166 | CD1 | PHE | B | 279 | 18.481 | −32.898 | −21.035 | 1.00 | 19.42 | C |
| ATOM | 167 | CD2 | PHE | B | 279 | 16.379 | −32.794 | −19.888 | 1.00 | 18.16 | C |
| ATOM | 168 | CE1 | PHE | B | 279 | 17.874 | −32.405 | −22.203 | 1.00 | 19.06 | C |
| ATOM | 169 | CE2 | PHE | B | 279 | 15.759 | −32.298 | −21.052 | 1.00 | 17.65 | C |
| ATOM | 170 | CZ | PHE | B | 279 | 16.515 | −32.108 | −22.208 | 1.00 | 15.61 | C |
| ATOM | 171 | N | VAL | B | 280 | 17.445 | −34.037 | −15.461 | 1.00 | 23.88 | N |
| ATOM | 172 | CA | VAL | B | 280 | 17.502 | −34.902 | −14.281 | 1.00 | 25.67 | C |
| ATOM | 173 | C | VAL | B | 280 | 16.690 | −36.136 | −14.658 | 1.00 | 25.65 | C |
| ATOM | 174 | O | VAL | B | 280 | 15.509 | −36.239 | −14.346 | 1.00 | 24.57 | O |
| ATOM | 175 | CB | VAL | B | 280 | 16.883 | −34.223 | −13.048 | 1.00 | 26.89 | C |
| ATOM | 176 | CG1 | VAL | B | 280 | 16.954 | −35.159 | −11.847 | 1.00 | 28.12 | C |
| ATOM | 177 | CG2 | VAL | B | 280 | 17.631 | −32.929 | −12.742 | 1.00 | 27.70 | C |
| ATOM | 178 | N | PRO | B | 281 | 17.324 | −37.080 | −15.370 | 1.00 | 27.08 | N |
| ATOM | 179 | CA | PRO | B | 281 | 16.698 | −38.320 | −15.824 | 1.00 | 29.05 | C |
| ATOM | 180 | C | PRO | B | 281 | 16.092 | −39.121 | −14.684 | 1.00 | 31.51 | C |
| ATOM | 181 | O | PRO | B | 281 | 16.675 | −39.223 | −13.603 | 1.00 | 32.26 | O |
| ATOM | 182 | CB | PRO | B | 281 | 17.851 | −39.071 | −16.492 | 1.00 | 29.44 | C |
| ATOM | 183 | CG | PRO | B | 281 | 18.791 | −37.992 | −16.895 | 1.00 | 29.67 | C |
| ATOM | 184 | CD | PRO | B | 281 | 18.750 | −37.057 | −15.726 | 1.00 | 27.31 | C |
| ATOM | 185 | N | PHE | B | 282 | 14.908 | −39.668 | −14.923 | 1.00 | 33.83 | N |
| ATOM | 186 | CA | PHE | B | 282 | 14.246 | −40.496 | −13.926 | 1.00 | 37.13 | C |
| ATOM | 187 | C | PHE | B | 282 | 15.078 | −41.776 | −13.880 | 1.00 | 38.09 | C |
| ATOM | 188 | O | PHE | B | 282 | 15.357 | −42.373 | −14.921 | 1.00 | 38.33 | O |
| ATOM | 189 | CB | PHE | B | 282 | 12.818 | −40.808 | −14.372 | 1.00 | 38.38 | C |
| ATOM | 190 | CG | PHE | B | 282 | 12.032 | −41.606 | −13.377 | 1.00 | 40.57 | C |
| ATOM | 191 | CD1 | PHE | B | 282 | 11.720 | −41.074 | −12.130 | 1.00 | 41.80 | C |
| ATOM | 192 | CD2 | PHE | B | 282 | 11.590 | −42.886 | −13.689 | 1.00 | 41.65 | C |
| ATOM | 193 | CE1 | PHE | B | 282 | 10.975 | −41.806 | −11.209 | 1.00 | 42.03 | C |
| ATOM | 194 | CE2 | PHE | B | 282 | 10.843 | −43.628 | −12.773 | 1.00 | 42.49 | C |

TABLE 4-continued

ATOMIC COORDINATES OF THE
DONOR NUCLEOTIDE BINDING SITE

| ATOM | 195 | CZ | PHE | B | 282 | 10.536 | -43.085 | -11.532 | 1.00 | 41.74 | C |
|---|---|---|---|---|---|---|---|---|---|---|---|
| ATOM | 196 | N | GLN | B | 288 | 16.212 | -45.321 | -19.533 | 1.00 | 30.94 | N |
| ATOM | 197 | CA | GLN | B | 288 | 15.622 | -44.804 | -20.755 | 1.00 | 30.77 | C |
| ATOM | 198 | C | GLN | B | 288 | 15.783 | -43.291 | -20.885 | 1.00 | 29.70 | C |
| ATOM | 199 | O | GLN | B | 288 | 16.268 | -42.801 | -21.902 | 1.00 | 29.79 | O |
| ATOM | 200 | CB | GLN | B | 288 | 14.143 | -45.158 | -20.810 | 1.00 | 30.59 | C |
| ATOM | 201 | CG | GLN | B | 288 | 13.473 | -44.772 | -22.109 | 1.00 | 29.73 | C |
| ATOM | 202 | CD | GLN | B | 288 | 11.981 | -44.971 | -22.044 | 1.00 | 28.04 | C |
| ATOM | 203 | OE1 | GLN | B | 288 | 11.294 | -44.295 | -21.279 | 1.00 | 29.59 | O |
| ATOM | 204 | NE2 | GLN | B | 288 | 11.468 | -45.905 | -22.838 | 1.00 | 26.98 | N |
| ATOM | 205 | N | GLN | B | 289 | 15.378 | -42.554 | -19.857 | 1.00 | 29.38 | N |
| ATOM | 206 | CA | GLN | B | 289 | 15.474 | -41.099 | -19.904 | 1.00 | 29.46 | C |
| ATOM | 207 | C | GLN | B | 289 | 16.906 | -40.613 | -20.005 | 1.00 | 29.36 | C |
| ATOM | 208 | O | GLN | B | 289 | 17.173 | -39.557 | -20.585 | 1.00 | 29.12 | O |
| ATOM | 209 | CB | GLN | B | 289 | 14.772 | -40.472 | -18.700 | 1.00 | 29.25 | C |
| ATOM | 210 | CG | GLN | B | 289 | 13.265 | -40.416 | -18.883 | 1.00 | 29.32 | C |
| ATOM | 211 | CD | GLN | B | 289 | 12.575 | -39.585 | -17.826 | 1.00 | 29.84 | C |
| ATOM | 212 | OE1 | GLN | B | 289 | 13.191 | -38.728 | -17.188 | 1.00 | 29.52 | O |
| ATOM | 213 | NE2 | GLN | B | 289 | 11.281 | -39.821 | -17.647 | 1.00 | 28.95 | N |
| ATOM | 214 | N | TYR | B | 290 | 17.835 | -41.374 | -19.442 | 1.00 | 28.95 | N |
| ATOM | 215 | CA | TYR | B | 290 | 19.228 | -40.984 | -19.550 | 1.00 | 29.55 | C |
| ATOM | 216 | C | TYR | B | 290 | 19.593 | -41.042 | -21.032 | 1.00 | 28.80 | C |
| ATOM | 217 | O | TYR | B | 290 | 20.192 | -40.113 | -21.567 | 1.00 | 29.22 | O |
| ATOM | 218 | CB | TYR | B | 290 | 20.136 | -41.934 | -18.768 | 1.00 | 31.40 | C |
| ATOM | 219 | CG | TYR | B | 290 | 21.587 | -41.780 | -19.148 | 1.00 | 33.37 | C |
| ATOM | 220 | CD1 | TYR | B | 290 | 22.332 | -40.682 | -18.717 | 1.00 | 34.57 | C |
| ATOM | 221 | CD2 | TYR | B | 290 | 22.192 | -42.684 | -20.017 | 1.00 | 34.90 | C |
| ATOM | 222 | CE1 | TYR | B | 290 | 23.644 | -40.490 | -19.148 | 1.00 | 35.97 | C |
| ATOM | 223 | CE2 | TYR | B | 290 | 23.497 | -42.500 | -20.453 | 1.00 | 36.03 | C |
| ATOM | 224 | CZ | TYR | B | 290 | 24.214 | -41.402 | -20.019 | 1.00 | 36.29 | C |
| ATOM | 225 | OH | TYR | B | 290 | 25.499 | -41.215 | -20.475 | 1.00 | 39.44 | O |
| ATOM | 226 | N | ASN | B | 292 | 17.658 | -40.779 | -23.508 | 1.00 | 25.52 | N |
| ATOM | 227 | CA | ASN | B | 292 | 16.902 | -39.784 | -24.270 | 1.00 | 26.06 | C |
| ATOM | 228 | C | ASN | B | 292 | 17.605 | -38.427 | -24.258 | 1.00 | 25.99 | C |
| ATOM | 229 | O | ASN | B | 292 | 17.566 | -37.687 | -25.244 | 1.00 | 26.18 | O |
| ATOM | 230 | CB | ASN | B | 292 | 15.484 | -39.599 | -23.709 | 1.00 | 24.78 | C |
| ATOM | 231 | CG | ASN | B | 292 | 14.590 | -40.811 | -23.928 | 1.00 | 24.46 | C |
| ATOM | 232 | OD1 | ASN | B | 292 | 14.842 | -41.641 | -24.798 | 1.00 | 25.33 | O |
| ATOM | 233 | ND2 | ASN | B | 292 | 13.523 | -40.900 | -23.146 | 1.00 | 23.83 | N |
| ATOM | 234 | N | ALA | B | 293 | 18.242 | -38.105 | -23.139 | 1.00 | 25.66 | N |
| ATOM | 235 | CA | ALA | B | 293 | 18.926 | -36.822 | -22.979 | 1.00 | 25.69 | C |
| ATOM | 236 | C | ALA | B | 293 | 20.346 | -36.800 | -23.521 | 1.00 | 25.67 | C |
| ATOM | 237 | O | ALA | B | 293 | 20.855 | -35.743 | -23.902 | 1.00 | 25.52 | O |
| ATOM | 238 | CB | ALA | B | 293 | 18.940 | -36.422 | -21.506 | 1.00 | 24.17 | C |
| ATOM | 239 | N | LEU | B | 296 | 21.375 | -34.703 | -26.688 | 1.00 | 25.66 | N |
| ATOM | 240 | CA | LEU | B | 296 | 21.521 | -33.265 | -26.481 | 1.00 | 25.42 | C |
| ATOM | 241 | C | LEU | B | 296 | 22.784 | -32.935 | -25.688 | 1.00 | 26.07 | C |
| ATOM | 242 | O | LEU | B | 296 | 23.435 | -31.917 | -25.944 | 1.00 | 25.26 | O |
| ATOM | 243 | CB | LEU | B | 296 | 20.283 | -32.685 | -25.779 | 1.00 | 24.45 | C |
| ATOM | 244 | CG | LEU | B | 296 | 19.066 | -32.458 | -26.679 | 1.00 | 25.59 | C |
| ATOM | 245 | CD1 | LEU | B | 296 | 17.968 | -31.718 | -25.911 | 1.00 | 23.56 | C |
| ATOM | 246 | CD2 | LEU | B | 296 | 19.496 | -31.630 | -27.893 | 1.00 | 25.87 | C |
| ATOM | 247 | N | ALA | B | 302 | 23.066 | -29.504 | -23.507 | 1.00 | 20.94 | N |
| ATOM | 248 | CA | ALA | B | 302 | 22.516 | -29.770 | -22.186 | 1.00 | 21.78 | C |
| ATOM | 249 | C | ALA | B | 302 | 23.503 | -30.507 | -21.288 | 1.00 | 22.69 | C |
| ATOM | 250 | O | ALA | B | 302 | 24.561 | -30.948 | -21.739 | 1.00 | 22.25 | O |
| ATOM | 251 | CB | ALA | B | 302 | 21.243 | -30.595 | -22.327 | 1.00 | 20.10 | C |
| ATOM | 252 | N | LYS | B | 303 | 23.156 | -30.613 | -20.009 | 1.00 | 24.62 | N |
| ATOM | 253 | CA | LYS | B | 303 | 23.979 | -31.340 | -19.048 | 1.00 | 25.86 | C |
| ATOM | 254 | C | LYS | B | 303 | 23.083 | -32.319 | -18.302 | 1.00 | 26.41 | C |
| ATOM | 255 | O | LYS | B | 303 | 22.015 | -31.948 | -17.802 | 1.00 | 25.76 | O |
| ATOM | 256 | CB | LYS | B | 303 | 24.632 | -30.401 | -18.036 | 1.00 | 27.85 | C |
| ATOM | 257 | CG | LYS | B | 303 | 25.466 | -31.146 | -16.986 | 1.00 | 29.37 | C |
| ATOM | 258 | CD | LYS | B | 303 | 26.150 | -30.186 | -16.025 | 1.00 | 32.41 | C |
| ATOM | 259 | CE | LYS | B | 303 | 27.083 | -30.912 | -15.056 | 1.00 | 33.22 | C |
| ATOM | 260 | NZ | LYS | B | 303 | 27.827 | -29.952 | -14.181 | 1.00 | 33.62 | N |
| ATOM | 261 | N | ILE | B | 304 | 23.520 | -33.570 | -18.234 | 1.00 | 25.65 | N |
| ATOM | 262 | CA | ILE | B | 304 | 22.753 | -34.598 | -17.550 | 1.00 | 27.17 | C |
| ATOM | 263 | C | ILE | B | 304 | 23.308 | -34.855 | -16.160 | 1.00 | 27.00 | C |
| ATOM | 264 | O | ILE | B | 304 | 24.511 | -35.012 | -15.986 | 1.00 | 27.46 | O |
| ATOM | 265 | CB | ILE | B | 304 | 22.786 | -35.946 | -18.316 | 1.00 | 27.06 | C |
| ATOM | 266 | CG1 | ILE | B | 304 | 22.242 | -35.769 | -19.733 | 1.00 | 27.61 | C |
| ATOM | 267 | CG2 | ILE | B | 304 | 21.977 | -36.996 | -17.555 | 1.00 | 28.49 | C |
| ATOM | 268 | CD1 | ILE | B | 304 | 22.380 | -37.009 | -20.599 | 1.00 | 27.05 | C |
| ATOM | 269 | N | ILE | B | 305 | 22.428 | -34.869 | -15.168 | 1.00 | 27.22 | N |
| ATOM | 270 | CA | ILE | B | 305 | 22.843 | -35.178 | -13.813 | 1.00 | 29.01 | C |

TABLE 4-continued

ATOMIC COORDINATES OF THE DONOR NUCLEOTIDE BINDING SITE

| ATOM | 271 | C | ILE | B | 305 | 21.934 | −36.302 | −13.351 | 1.00 | 29.64 | C |
| --- | --- | --- | --- | --- | --- | --- | --- | --- | --- | --- | --- |
| ATOM | 272 | O | ILE | B | 305 | 20.806 | −36.067 | −12.932 | 1.00 | 29.25 | O |
| ATOM | 273 | CB | ILE | B | 305 | 22.713 | −33.977 | −12.858 | 1.00 | 28.91 | C |
| ATOM | 274 | CD1 | ILE | B | 305 | 23.660 | −32.855 | −13.299 | 1.00 | 29.51 | C |
| ATOM | 275 | CD2 | ILE | B | 305 | 23.063 | −34.416 | −11.432 | 1.00 | 30.98 | C |
| ATOM | 276 | CD1 | ILE | B | 305 | 23.674 | −31.653 | −12.367 | 1.00 | 29.43 | C |
| TER | | | | | | | | | | | |

TABLE 5

ATOMIC COORDINATES OF ACCEPTOR BINDING SITE

REMARK 4 1MUR COMPLIES WITH FORMAT V. 2.0, MAY 11, 2000

| ATOM | 1 | N | MET | B | 12 | −0.734 | −48.902 | −33.817 | 1.00 | 23.68 | N |
| --- | --- | --- | --- | --- | --- | --- | --- | --- | --- | --- | --- |
| ATOM | 2 | CA | MET | B | 12 | −0.523 | −49.707 | −32.613 | 1.00 | 24.54 | C |
| ATOM | 3 | C | MET | B | 12 | 0.361 | −48.840 | −31.720 | 1.00 | 25.31 | C |
| ATOM | 4 | O | MET | B | 12 | 1.546 | −48.645 | −32.006 | 1.00 | 23.88 | O |
| ATOM | 5 | CB | MET | B | 12 | 0.192 | −51.019 | −32.971 | 1.00 | 24.28 | C |
| ATOM | 6 | CG | MET | B | 12 | −0.402 | −51.726 | −34.188 | 1.00 | 25.19 | C |
| ATOM | 7 | SD | MET | B | 12 | 0.399 | −53.284 | −34.669 | 1.00 | 26.54 | S |
| ATOM | 8 | CE | MET | B | 12 | 1.990 | −52.691 | −35.289 | 1.00 | 22.99 | C |
| ATOM | 9 | N | ALA | B | 13 | −0.224 | −48.292 | −30.657 | 1.00 | 27.08 | N |
| ATOM | 10 | CA | ALA | B | 13 | 0.508 | −47.410 | −29.752 | 1.00 | 29.43 | C |
| ATOM | 11 | C | ALA | B | 13 | −0.239 | −47.192 | −28.436 | 1.00 | 31.80 | C |
| ATOM | 12 | O | ALA | B | 13 | −1.143 | −46.350 | −28.352 | 1.00 | 32.16 | O |
| ATOM | 13 | CB | ALA | B | 13 | 0.747 | −46.074 | −30.429 | 1.00 | 28.82 | C |
| ATOM | 14 | N | GLY | B | 14 | 0.150 | −47.934 | −27.405 | 1.00 | 32.46 | N |
| ATOM | 15 | CA | GLY | B | 14 | −0.513 | −47.804 | −26.120 | 1.00 | 33.82 | C |
| ATOM | 16 | C | GLY | B | 14 | −0.107 | −46.595 | −25.299 | 1.00 | 34.82 | C |
| ATOM | 17 | O | GLY | B | 14 | 0.975 | −46.040 | −25.479 | 1.00 | 35.47 | O |
| ATOM | 18 | N | GLY | B | 15 | −0.986 | −46.188 | −24.385 | 1.00 | 35.56 | N |
| ATOM | 19 | CA | GLY | B | 15 | −0.700 | −45.047 | −23.536 | 1.00 | 36.08 | C |
| ATOM | 20 | C | GLY | B | 15 | 0.539 | −45.254 | −22.683 | 1.00 | 36.84 | C |
| ATOM | 21 | O | GLY | B | 15 | 1.293 | −44.311 | −22.426 | 1.00 | 36.03 | O |
| ATOM | 22 | N | THR | B | 16 | 0.755 | −46.488 | −22.240 | 1.00 | 36.65 | N |
| ATOM | 23 | CA | THR | B | 16 | 1.920 | −46.787 | −21.421 | 1.00 | 38.51 | C |
| ATOM | 24 | C | THR | B | 16 | 3.158 | −46.497 | −22.264 | 1.00 | 38.35 | C |
| ATOM | 25 | O | THR | B | 16 | 3.191 | −46.798 | −23.460 | 1.00 | 39.90 | O |
| ATOM | 26 | CB | THR | B | 16 | 1.926 | −48.258 | −20.974 | 1.00 | 38.51 | C |
| ATOM | 27 | CG1 | THR | B | 16 | 0.686 | −48.558 | −20.321 | 1.00 | 38.39 | O |
| ATOM | 28 | CG2 | THR | B | 16 | 3.075 | −48.518 | −20.005 | 1.00 | 39.11 | C |
| ATOM | 29 | N | GLY | B | 17 | 4.168 | −45.897 | −21.649 | 1.00 | 37.68 | N |
| ATOM | 30 | CA | GLY | B | 17 | 5.367 | −45.567 | −22.392 | 1.00 | 36.57 | C |
| ATOM | 31 | C | GLY | B | 17 | 5.161 | −44.303 | −23.211 | 1.00 | 35.56 | C |
| ATOM | 32 | O | GLY | B | 17 | 6.079 | −43.843 | −23.890 | 1.00 | 35.03 | O |
| ATOM | 33 | N | GLY | B | 18 | 3.949 | −43.752 | −23.150 | 1.00 | 33.83 | N |
| ATOM | 34 | CA | GLY | B | 18 | 3.631 | −42.529 | −23.872 | 1.00 | 33.48 | C |
| ATOM | 35 | C | GLY | B | 18 | 3.825 | −42.593 | −25.378 | 1.00 | 33.12 | C |
| ATOM | 36 | O | GLY | B | 18 | 4.345 | −41.650 | −25.984 | 1.00 | 35.38 | O |
| ATOM | 37 | N | HIS | B | 19 | 3.416 | −43.699 | −25.988 | 1.00 | 30.26 | N |
| ATOM | 38 | CA | HIS | B | 19 | 3.548 | −43.865 | −27.435 | 1.00 | 28.22 | C |
| ATOM | 39 | C | HIS | B | 19 | 2.280 | −43.370 | −28.144 | 1.00 | 27.91 | C |
| ATOM | 40 | O | HIS | B | 19 | 2.300 | −43.049 | −29.337 | 1.00 | 26.91 | O |
| ATOM | 41 | CB | HIS | B | 19 | 3.772 | −45.349 | −27.779 | 1.00 | 25.81 | C |
| ATOM | 42 | CG | HIS | B | 19 | 4.957 | −45.966 | −27.094 | 1.00 | 25.35 | C |
| ATOM | 43 | ND1 | HIS | B | 19 | 4.845 | −47.025 | −26.217 | 1.00 | 24.57 | N |
| ATOM | 44 | CD2 | HIS | B | 19 | 6.281 | −45.694 | −27.184 | 1.00 | 24.18 | C |
| ATOM | 45 | CE1 | HIS | B | 19 | 6.046 | −47.380 | −25.798 | 1.00 | 23.08 | C |
| ATOM | 46 | NE2 | HIS | B | 19 | 6.936 | −46.589 | −26.369 | 1.00 | 25.51 | N |
| ATOM | 47 | N | VAL | B | 20 | 1.180 | −43.310 | −27.402 | 1.00 | 27.65 | N |
| ATOM | 48 | CA | VAL | B | 20 | −0.098 | −42.894 | −27.965 | 1.00 | 27.77 | C |
| ATOM | 49 | C | VAL | B | 20 | −0.140 | −41.452 | −28.470 | 1.00 | 27.57 | C |
| ATOM | 50 | O | VAL | B | 20 | −0.771 | −41.172 | −29.486 | 1.00 | 27.12 | O |
| ATOM | 51 | CB | VAL | B | 20 | −1.248 | −43.080 | −26.942 | 1.00 | 28.57 | C |
| ATOM | 52 | CG1 | VAL | B | 20 | −1.082 | −42.114 | −25.787 | 1.00 | 30.03 | C |
| ATOM | 53 | CG2 | VAL | B | 20 | −2.602 | −42.873 | −27.631 | 1.00 | 26.82 | C |
| ATOM | 54 | N | LEU | B | 40 | −5.323 | −50.004 | −32.549 | 1.00 | 25.21 | N |
| ATOM | 55 | CA | LEU | B | 40 | −5.200 | −51.364 | −32.026 | 1.00 | 24.71 | C |
| ATOM | 56 | C | LEU | B | 40 | −4.535 | −51.235 | −30.655 | 1.00 | 23.33 | C |
| ATOM | 57 | O | LEU | B | 40 | −3.387 | −50.824 | −30.563 | 1.00 | 23.43 | O |
| ATOM | 58 | CB | LEU | B | 40 | −4.326 | −52.221 | −32.952 | 1.00 | 25.21 | C |
| ATOM | 59 | CG | LEU | B | 40 | −4.416 | −53.754 | −32.868 | 1.00 | 26.95 | C |
| ATOM | 60 | CD1 | LEU | B | 40 | −3.037 | −54.334 | −32.571 | 1.00 | 27.63 | C |

TABLE 5-continued

ATOMIC COORDINATES OF ACCEPTOR BINDING SITE

| ATOM | 61 | CD2 | LEU | B | 40 | −5.421 | −54.179 | −31.817 | 1.00 | 26.69 | C |
|---|---|---|---|---|---|---|---|---|---|---|---|
| ATOM | 62 | N | GLU | B | 47 | −4.976 | −45.941 | −23.678 | 1.00 | 32.85 | N |
| ATOM | 63 | CA | GLU | B | 47 | −5.458 | −45.655 | −25.029 | 1.00 | 31.79 | C |
| ATOM | 64 | C | GLU | B | 47 | −6.938 | −46.017 | −25.191 | 1.00 | 31.81 | C |
| ATOM | 65 | O | GLU | B | 47 | −7.626 | −45.476 | −26.055 | 1.00 | 31.31 | O |
| ATOM | 66 | CB | GLU | B | 47 | −4.624 | −46.402 | −26.080 | 1.00 | 30.62 | C |
| ATOM | 67 | CG | GLU | B | 47 | −4.755 | −47.922 | −26.051 | 1.00 | 29.85 | C |
| ATOM | 68 | CD | GLU | B | 47 | −3.793 | −48.597 | −25.082 | 1.00 | 29.78 | C |
| ATOM | 69 | OE1 | GLU | B | 47 | −3.188 | −47.895 | −24.247 | 1.00 | 28.76 | O |
| ATOM | 70 | OE2 | GLU | B | 47 | −3.649 | −49.840 | −25.156 | 1.00 | 29.01 | O |
| ATOM | 71 | N | ILE | B | 63 | −3.428 | −59.342 | −24.313 | 1.00 | 30.07 | N |
| ATOM | 72 | CA | ILE | B | 63 | −2.036 | −59.770 | −24.231 | 1.00 | 31.38 | C |
| ATOM | 73 | C | ILE | B | 63 | −1.623 | −59.981 | −22.775 | 1.00 | 33.08 | C |
| ATOM | 74 | O | ILE | B | 63 | −0.444 | −59.872 | −22.430 | 1.00 | 33.21 | O |
| ATOM | 75 | CB | ILE | B | 63 | −1.081 | −58.745 | −24.883 | 1.00 | 30.06 | C |
| ATOM | 76 | CG1 | ILE | B | 63 | −1.143 | −57.411 | −24.137 | 1.00 | 29.94 | C |
| ATOM | 77 | CG2 | ILE | B | 63 | −1.442 | −58.567 | −26.353 | 1.00 | 30.41 | C |
| ATOM | 78 | CD1 | ILE | B | 63 | −0.128 | −56.384 | −24.632 | 1.00 | 29.62 | C |
| ATOM | 79 | N | ARG | B | 67 | 2.953 | −59.185 | −21.440 | 1.00 | 31.54 | N |
| ATOM | 80 | CA | ARG | B | 67 | 3.671 | −57.928 | −21.277 | 1.00 | 30.90 | C |
| ATOM | 81 | C | ARG | B | 67 | 5.071 | −58.142 | −20.713 | 1.00 | 29.99 | C |
| ATOM | 82 | O | ARG | B | 67 | 5.294 | −59.034 | −19.889 | 1.00 | 28.67 | O |
| ATOM | 83 | CB | ARG | B | 67 | 2.888 | −56.984 | −20.363 | 1.00 | 32.28 | C |
| ATOM | 84 | CC | ARG | B | 67 | 1.540 | −56.576 | −20.913 | 1.00 | 34.65 | C |
| ATOM | 85 | CD | ARG | B | 67 | 0.926 | −55.440 | −20.097 | 1.00 | 36.69 | C |
| ATOM | 86 | NE | ARG | B | 67 | −0.259 | −54.889 | −20.748 | 1.00 | 38.28 | N |
| ATOM | 87 | CZ | ARG | B | 67 | −1.425 | −55.519 | −20.853 | 1.00 | 39.05 | C |
| ATOM | 88 | NH1 | ARG | B | 67 | −1.583 | −56.734 | −20.341 | 1.00 | 39.61 | N |
| ATOM | 89 | NH2 | ARG | B | 67 | −2.434 | −54.935 | −21.487 | 1.00 | 39.52 | N |
| ATOM | 90 | N | GLY | B | 68 | 6.014 | −57.321 | −21.165 | 1.00 | 27.75 | N |
| ATOM | 91 | CA | GLY | B | 68 | 7.380 | −57.427 | −20.685 | 1.00 | 26.79 | C |
| ATOM | 92 | C | GLY | B | 68 | 8.166 | −58.579 | −21.280 | 1.00 | 25.41 | C |
| ATOM | 93 | O | GLY | B | 68 | 9.326 | −58.779 | −20.943 | 1.00 | 26.04 | O |
| ATOM | 94 | N | GLY | B | 102 | 3.556 | −48.986 | −35.936 | 1.00 | 20.96 | N |
| ATOM | 95 | CA | GLY | B | 102 | 3.796 | −49.357 | −34.549 | 1.00 | 19.23 | C |
| ATOM | 96 | C | GLY | B | 102 | 4.655 | −48.282 | −33.918 | 1.00 | 18.45 | C |
| ATOM | 97 | O | GLY | B | 102 | 5.765 | −48.016 | −34.381 | 1.00 | 18.70 | O |
| ATOM | 98 | N | MET | B | 103 | 4.155 | −47.660 | −32.857 | 1.00 | 18.01 | N |
| ATOM | 99 | CA | MET | B | 103 | 4.892 | −46.597 | −32.191 | 1.00 | 18.93 | C |
| ATOM | 100 | C | MET | B | 103 | 5.612 | −47.128 | −30.957 | 1.00 | 18.98 | C |
| ATOM | 101 | O | MET | B | 103 | 6.134 | −46.357 | −30.158 | 1.00 | 17.96 | O |
| ATOM | 102 | CB | MET | B | 103 | 3.928 | −45.477 | −31.781 | 1.00 | 20.02 | C |
| ATOM | 103 | CG | MET | B | 103 | 3.121 | −44.888 | −32.944 | 1.00 | 21.61 | C |
| ATOM | 104 | SD | MET | B | 103 | 4.212 | −44.135 | −34.157 | 1.00 | 23.45 | S |
| ATOM | 105 | CE | MET | B | 103 | 4.718 | −42.680 | −33.271 | 1.00 | 21.40 | C |
| ATOM | 106 | N | GLY | B | 104 | 5.640 | −48.450 | −30.827 | 1.00 | 21.56 | N |
| ATOM | 107 | CA | GLY | B | 104 | 6.275 | −49.080 | −29.686 | 1.00 | 21.89 | C |
| ATOM | 108 | C | GLY | B | 104 | 5.192 | −49.614 | −28.764 | 1.00 | 23.28 | C |
| ATOM | 109 | O | GLY | B | 104 | 4.009 | −49.353 | −28.980 | 1.00 | 22.50 | O |
| ATOM | 110 | N | GLY | B | 105 | 5.583 | −50.364 | −27.741 | 1.00 | 23.01 | N |
| ATOM | 111 | CA | GLY | B | 105 | 4.593 | −50.905 | −26.827 | 1.00 | 23.54 | C |
| ATOM | 112 | C | GLY | B | 105 | 4.358 | −52.380 | −27.078 | 1.00 | 23.17 | C |
| ATOM | 113 | O | GLY | B | 105 | 4.449 | −52.844 | −28.214 | 1.00 | 22.69 | O |
| ATOM | 114 | N | TYR | B | 106 | 4.018 | −53.118 | −26.026 | 1.00 | 22.87 | N |
| ATOM | 115 | CA | TYR | B | 106 | 3.818 | −54.554 | −26.159 | 1.00 | 22.37 | C |
| ATOM | 116 | C | TYR | B | 106 | 2.719 | −55.018 | −27.100 | 1.00 | 20.52 | C |
| ATOM | 117 | O | TYR | B | 106 | 2.867 | −56.052 | −27.746 | 1.00 | 20.50 | O |
| ATOM | 118 | CB | TYR | B | 106 | 3.632 | −55.181 | −24.774 | 1.00 | 25.08 | C |
| ATOM | 119 | CG | TYR | B | 106 | 4.864 | −55.008 | −23.929 | 1.00 | 28.19 | C |
| ATOM | 120 | CD1 | TYR | B | 106 | 4.869 | −54.153 | −22.830 | 1.00 | 31.96 | C |
| ATOM | 121 | CD2 | TYR | B | 106 | 6.058 | −55.631 | −24.282 | 1.00 | 31.27 | C |
| ATOM | 122 | CE1 | TYR | B | 106 | 6.043 | −53.915 | −22.108 | 1.00 | 33.13 | C |
| ATOM | 123 | CE2 | TYR | B | 106 | 7.234 | −55.400 | −23.569 | 1.00 | 32.27 | C |
| ATOM | 124 | CZ | TYR | B | 106 | 7.219 | −54.541 | −22.487 | 1.00 | 33.19 | C |
| ATOM | 125 | OH | TYR | B | 106 | 8.388 | −54.291 | −21.802 | 1.00 | 35.95 | O |
| ATOM | 126 | N | VAL | B | 107 | 1.628 | −54.270 | −27.205 | 1.00 | 19.06 | N |
| ATOM | 127 | CA | VAL | B | 107 | 0.557 | −54.694 | −28.099 | 1.00 | 18.06 | C |
| ATOM | 128 | C | VAL | B | 107 | 1.015 | −54.743 | −29.559 | 1.00 | 17.45 | C |
| ATOM | 129 | O | VAL | B | 107 | 0.502 | −55.536 | −30.346 | 1.00 | 16.99 | O |
| ATOM | 130 | CB | VAL | B | 107 | −0.690 | −53.774 | −27.978 | 1.00 | 20.95 | C |
| ATOM | 131 | CG1 | VAL | B | 107 | −0.407 | −52.407 | −28.589 | 1.00 | 21.39 | C |
| ATOM | 132 | CG2 | VAL | B | 107 | −1.879 | −54.433 | −28.658 | 1.00 | 21.30 | C |
| ATOM | 133 | N | SER | B | 108 | 1.991 | −53.916 | −29.918 | 1.00 | 17.96 | N |
| ATOM | 134 | CA | SER | B | 108 | 2.488 | −53.892 | −31.290 | 1.00 | 19.67 | C |
| ATOM | 135 | C | SER | B | 108 | 3.197 | −55.187 | −31.694 | 1.00 | 20.38 | C |
| ATOM | 136 | O | SER | B | 108 | 3.385 | −55.449 | −32.884 | 1.00 | 21.25 | O |
| ATOM | 137 | CB | SER | B | 108 | 3.424 | −52.691 | −31.508 | 1.00 | 19.56 | C |

TABLE 5-continued

ATOMIC COORDINATES OF ACCEPTOR BINDING SITE

| ATOM | 138 | OG | SER | B | 108 | 4.666 | −52.824 | −30.837 | 1.00 | 19.63 | O |
|------|-----|-----|-----|---|-----|-------|---------|---------|------|-------|---|
| ATOM | 139 | N | GLY | B | 109 | 3.595 | −55.995 | −30.710 | 1.00 | 19.59 | N |
| ATOM | 140 | CA | GLY | B | 109 | 4.251 | −57.256 | −31.023 | 1.00 | 20.03 | C |
| ATOM | 141 | C | GLY | B | 109 | 3.311 | −58.170 | −31.792 | 1.00 | 19.61 | C |
| ATOM | 142 | O | GLY | B | 109 | 3.579 | −58.517 | −32.940 | 1.00 | 19.24 | O |
| ATOM | 143 | N | PRO | B | 110 | 2.206 | −58.606 | −31.173 | 1.00 | 19.20 | N |
| ATOM | 144 | CA | PRO | B | 110 | 1.251 | −59.478 | −31.855 | 1.00 | 18.99 | C |
| ATOM | 145 | C | PRO | B | 110 | 0.651 | −58.761 | −33.075 | 1.00 | 19.22 | C |
| ATOM | 146 | O | PRO | B | 110 | 0.406 | −59.371 | −34.116 | 1.00 | 17.13 | O |
| ATOM | 147 | CB | PRO | B | 110 | 0.198 | −59.737 | −30.778 | 1.00 | 20.41 | C |
| ATOM | 148 | CG | PRO | B | 110 | 0.998 | −59.720 | −29.515 | 1.00 | 19.81 | C |
| ATOM | 149 | CD | PRO | B | 110 | 1.914 | −58.528 | −29.729 | 1.00 | 19.94 | C |
| ATOM | 150 | N | HIS | B | 125 | 8.182 | −46.638 | −35.447 | 1.00 | 21.40 | N |
| ATOM | 151 | CA | HIS | B | 125 | 8.814 | −45.413 | −34.981 | 1.00 | 21.42 | C |
| ATOM | 152 | C | HIS | B | 125 | 9.196 | −45.642 | −33.519 | 1.00 | 21.70 | C |
| ATOM | 153 | O | HIS | B | 125 | 8.378 | −46.117 | −32.725 | 1.00 | 19.81 | O |
| ATOM | 154 | CB | HIS | B | 125 | 7.858 | −44.218 | −35.067 | 1.00 | 21.57 | C |
| ATOM | 155 | CG | HIS | B | 125 | 8.432 | −42.948 | −34.511 | 1.00 | 23.73 | C |
| ATOM | 156 | ND1 | HIS | B | 125 | 9.274 | −42.127 | −35.236 | 1.00 | 26.23 | N |
| ATOM | 157 | CD2 | HIS | B | 125 | 8.300 | −42.368 | −33.295 | 1.00 | 22.15 | C |
| ATOM | 158 | CE1 | HIS | B | 125 | 9.631 | −41.095 | −34.490 | 1.00 | 24.20 | C |
| ATOM | 159 | NE2 | HIS | B | 125 | 9.054 | −41.218 | −33.307 | 1.00 | 26.07 | N |
| ATOM | 160 | N | GLU | B | 126 | 10.444 | −45.332 | −33.186 | 1.00 | 21.20 | N |
| ATOM | 161 | CA | GLU | B | 126 | 10.947 | −45.452 | −31.817 | 1.00 | 22.15 | C |
| ATOM | 162 | C | GLU | B | 126 | 11.205 | −44.027 | −31.326 | 1.00 | 21.93 | C |
| ATOM | 163 | O | GLU | B | 126 | 12.016 | −43.300 | −31.908 | 1.00 | 21.33 | O |
| ATOM | 164 | CB | GLU | B | 126 | 12.252 | −46.246 | −31.790 | 1.00 | 21.99 | C |
| ATOM | 165 | CG | GLU | B | 126 | 12.958 | −46.206 | −30.439 | 1.00 | 22.04 | C |
| ATOM | 166 | CD | GLU | B | 126 | 12.119 | −46.824 | −29.338 | 1.00 | 21.43 | C |
| ATOM | 167 | OE1 | GLU | B | 126 | 11.767 | −48.014 | −29.471 | 1.00 | 21.92 | O |
| ATOM | 168 | OE2 | GLU | B | 126 | 11.807 | −46.124 | −28.349 | 1.00 | 21.08 | O |
| ATOM | 169 | N | GLN | B | 127 | 10.520 | −43.624 | −30.259 | 1.00 | 22.62 | N |
| ATOM | 170 | CA | GLN | B | 127 | 10.682 | −42.270 | −29.735 | 1.00 | 22.81 | C |
| ATOM | 171 | C | GLN | B | 127 | 11.874 | −42.087 | −28.809 | 1.00 | 22.39 | C |
| ATOM | 172 | O | GLN | B | 127 | 12.399 | −40.976 | −28.682 | 1.00 | 22.43 | O |
| ATOM | 173 | CB | GLN | B | 127 | 9.414 | −41.814 | −28.989 | 1.00 | 23.56 | C |
| ATOM | 174 | CG | GLN | B | 127 | 8.147 | −41.783 | −29.830 | 1.00 | 24.46 | C |
| ATOM | 175 | CD | GLN | B | 127 | 7.312 | −43.041 | −29.687 | 1.00 | 25.85 | C |
| ATOM | 176 | OE1 | GLN | B | 127 | 6.842 | −43.366 | −28.591 | 1.00 | 23.78 | O |
| ATOM | 177 | NE2 | GLN | B | 127 | 7.119 | −43.758 | −30.797 | 1.00 | 24.91 | N |
| ATOM | 178 | N | ASN | B | 128 | 12.314 | −43.173 | −28.177 | 1.00 | 22.35 | N |
| ATOM | 179 | CA | ASN | B | 128 | 13.406 | −43.097 | −27.216 | 1.00 | 22.96 | C |
| ATOM | 180 | C | ASN | B | 128 | 14.824 | −43.314 | −27.742 | 1.00 | 23.87 | C |
| ATOM | 181 | O | ASN | B | 128 | 15.026 | −43.856 | −28.830 | 1.00 | 24.05 | O |
| ATOM | 182 | CB | ASN | B | 128 | 13.136 | −44.080 | −26.064 | 1.00 | 22.85 | C |
| ATOM | 183 | CG | ASN | B | 128 | 11.742 | −43.919 | −25.474 | 1.00 | 23.25 | C |
| ATOM | 184 | OD1 | ASN | B | 128 | 10.804 | −44.632 | −25.848 | 1.00 | 26.04 | O |
| ATOM | 185 | ND2 | ASN | B | 128 | 11.597 | −42.975 | −24.556 | 1.00 | 22.68 | N |
| ATOM | 186 | N | GLY | B | 132 | 12.851 | −49.814 | −27.506 | 1.00 | 24.52 | N |
| ATOM | 187 | CA | GLY | B | 132 | 12.007 | −50.532 | −26.568 | 1.00 | 24.05 | C |
| ATOM | 188 | C | GLY | B | 132 | 12.150 | −52.019 | −26.831 | 1.00 | 23.35 | C |
| ATOM | 189 | O | GLY | B | 132 | 12.582 | −52.419 | −27.904 | 1.00 | 22.89 | O |
| ATOM | 190 | N | LEU | B | 133 | 11.788 | −52.846 | −25.860 | 1.00 | 23.38 | N |
| ATOM | 191 | CA | LEU | B | 133 | 11.903 | −54.293 | −26.020 | 1.00 | 24.54 | C |
| ATOM | 192 | C | LEU | B | 133 | 11.209 | −54.833 | −27.276 | 1.00 | 22.84 | C |
| ATOM | 193 | O | LEU | B | 133 | 11.784 | −55.619 | −28.027 | 1.00 | 21.86 | O |
| ATOM | 194 | CB | LEU | B | 133 | 11.328 | −54.996 | −24.786 | 1.00 | 25.48 | C |
| ATOM | 195 | CG | LEU | B | 133 | 11.388 | −56.527 | −24.780 | 1.00 | 27.50 | C |
| ATOM | 196 | CD1 | LEU | B | 133 | 12.840 | −56.984 | −24.866 | 1.00 | 28.69 | C |
| ATOM | 197 | CD2 | LEU | B | 133 | 10.735 | −57.059 | −23.509 | 1.00 | 28.04 | C |
| ATOM | 198 | N | THR | B | 134 | 9.975 | −54.401 | −27.499 | 1.00 | 21.72 | N |
| ATOM | 199 | CA | THR | B | 134 | 9.202 | −54.860 | −28.639 | 1.00 | 21.22 | C |
| ATOM | 200 | C | THR | B | 134 | 9.693 | −54.326 | −29.986 | 1.00 | 20.62 | C |
| ATOM | 201 | O | THR | B | 134 | 9.843 | −55.091 | −30.932 | 1.00 | 20.33 | O |
| ATOM | 202 | CB | THR | B | 134 | 7.716 | −54.509 | −28.449 | 1.00 | 20.99 | C |
| ATOM | 203 | OG1 | THR | B | 134 | 7.257 | −55.075 | −27.210 | 1.00 | 20.94 | O |
| ATOM | 204 | CG2 | THR | B | 134 | 6.872 | −55.073 | −29.600 | 1.00 | 20.64 | C |
| ATOM | 205 | N | ASN | B | 135 | 9.932 | −53.021 | −30.075 | 1.00 | 21.24 | N |
| ATOM | 206 | CA | ASN | B | 135 | 10.407 | −52.419 | −31.324 | 1.00 | 20.50 | C |
| ATOM | 207 | C | ASN | B | 135 | 11.724 | −53.064 | −31.767 | 1.00 | 20.78 | C |
| ATOM | 208 | O | ASN | B | 135 | 11.945 | −53.290 | −32.953 | 1.00 | 20.41 | O |
| ATOM | 209 | CB | ASN | B | 135 | 10.637 | −50.911 | −31.142 | 1.00 | 19.58 | C |
| ATOM | 210 | CG | ASN | B | 135 | 9.457 | −50.058 | −31.597 | 1.00 | 19.93 | C |
| ATOM | 211 | OD1 | ASN | B | 135 | 9.454 | −48.837 | −31.390 | 1.00 | 21.78 | O |
| ATOM | 212 | ND2 | ASN | B | 135 | 8.467 | −50.677 | −32.219 | 1.00 | 17.21 | N |
| ATOM | 213 | N | LEU | B | 138 | 10.741 | −56.381 | −33.386 | 1.00 | 21.61 | N |
| ATOM | 214 | CA | LEU | B | 138 | 9.744 | −56.188 | −34.431 | 1.00 | 23.15 | C |

TABLE 5-continued

ATOMIC COORDINATES OF ACCEPTOR BINDING SITE

| ATOM | 215 | C | LEU | B | 138 | 10.384 | −55.558 | −35.676 | 1.00 | 23.07 | C |
|---|---|---|---|---|---|---|---|---|---|---|---|
| ATOM | 216 | O | LEU | B | 138 | 9.958 | −55.801 | −36.809 | 1.00 | 22.68 | O |
| ATOM | 217 | CB | LEU | B | 138 | 8.618 | −55.305 | −33.886 | 1.00 | 23.87 | C |
| ATOM | 218 | CG | LEU | B | 138 | 7.312 | −55.155 | −34.664 | 1.00 | 26.48 | C |
| ATOM | 219 | CD1 | LEU | B | 138 | 6.672 | −56.508 | −34.915 | 1.00 | 25.34 | C |
| ATOM | 220 | CD2 | LEU | B | 138 | 6.383 | −54.267 | −33.851 | 1.00 | 25.90 | C |
| TER | | | | | | | | | | | |

TABLE 6

ATOMIC COORDINATES OF MEMBRANE ASSOCIATION SITE

REMARK 4 1MUR COMPLIES WITH FORMAT V. 2.0, MAY 11, 2000

| ATOM | 1 | N | MET | B | 12 | −0.734 | −48.902 | −33.817 | 1.00 | 23.68 | N |
|---|---|---|---|---|---|---|---|---|---|---|---|
| ATOM | 2 | CA | MET | B | 12 | −0.523 | −49.707 | −32.613 | 1.00 | 24.54 | C |
| ATOM | 3 | C | MET | B | 12 | 0.361 | −48.840 | −31.720 | 1.00 | 25.31 | C |
| ATOM | 4 | O | MET | B | 12 | 1.546 | −48.645 | −32.006 | 1.00 | 23.88 | O |
| ATOM | 5 | CB | MET | B | 12 | 0.192 | −51.019 | −32.971 | 1.00 | 24.28 | C |
| ATOM | 6 | CG | MET | B | 12 | −0.402 | −51.726 | −34.188 | 1.00 | 25.19 | C |
| ATOM | 7 | SD | MET | B | 12 | 0.399 | −53.284 | −34.669 | 1.00 | 26.54 | S |
| ATOM | 8 | CE | MET | B | 12 | 1.990 | −52.691 | −35.289 | 1.00 | 22.99 | C |
| ATOM | 9 | N | LEU | B | 40 | −5.323 | −50.004 | −32.549 | 1.00 | 25.21 | N |
| ATOM | 10 | CA | LEU | B | 40 | −5.200 | −51.364 | −32.026 | 1.00 | 24.71 | C |
| ATOM | 11 | C | LEU | B | 40 | −4.535 | −51.235 | −30.655 | 1.00 | 23.33 | C |
| ATOM | 12 | O | LEU | B | 40 | −3.387 | −50.824 | −30.563 | 1.00 | 23.43 | O |
| ATOM | 13 | CB | LEU | B | 40 | −4.326 | −52.221 | −32.952 | 1.00 | 25.21 | C |
| ATOM | 14 | CG | LEU | B | 40 | −4.416 | −53.754 | −32.868 | 1.00 | 26.95 | C |
| ATOM | 15 | CD1 | LEU | B | 40 | −3.037 | −54.334 | −32.571 | 1.00 | 27.63 | C |
| ATOM | 16 | CD2 | LEU | B | 40 | −5.421 | −54.179 | −31.817 | 1.00 | 26.69 | C |
| ATOM | 17 | N | ILE | B | 61 | −7.271 | −56.229 | −28.295 | 1.00 | 29.38 | N |
| ATOM | 18 | CA | ILE | B | 61 | −6.832 | −57.616 | −28.269 | 1.00 | 28.55 | C |
| ATOM | 19 | C | ILE | B | 61 | −6.344 | −57.855 | −26.848 | 1.00 | 29.13 | C |
| ATOM | 20 | O | ILE | B | 61 | −6.124 | −56.906 | −26.091 | 1.00 | 28.80 | O |
| ATOM | 21 | CB | ILE | B | 61 | −5.674 | −57.923 | −29.258 | 1.00 | 28.48 | C |
| ATOM | 22 | CG1 | ILE | B | 61 | −4.422 | −57.126 | −28.892 | 1.00 | 26.70 | C |
| ATOM | 23 | CG2 | ILE | B | 61 | −6.123 | −57.650 | −30.694 | 1.00 | 27.65 | C |
| ATOM | 24 | CD1 | ILE | B | 61 | −3.177 | −57.615 | −29.638 | 1.00 | 27.03 | C |
| ATOM | 25 | N | ARG | B | 62 | −6.186 | −59.116 | −26.473 | 1.00 | 29.38 | N |
| ATOM | 26 | CA | ARG | B | 62 | −5.709 | −59.416 | −25.133 | 1.00 | 30.76 | C |
| ATOM | 27 | C | ARG | B | 62 | −4.274 | −59.923 | −25.156 | 1.00 | 29.32 | C |
| ATOM | 28 | O | ARG | B | 62 | −3.933 | −60.809 | −25.934 | 1.00 | 28.65 | O |
| ATOM | 29 | CB | ARG | B | 62 | −6.630 | −60.447 | −24.461 | 1.00 | 32.36 | C |
| ATOM | 30 | CG | ARG | B | 62 | −6.130 | −60.955 | −23.114 | 1.00 | 35.99 | C |
| ATOM | 31 | CD | ARG | B | 62 | −5.438 | −59.859 | −22.311 | 1.00 | 37.86 | C |
| ATOM | 32 | NE | ARG | B | 62 | −6.297 | −58.718 | −22.004 | 1.00 | 40.01 | N |
| ATOM | 33 | CZ | ARG | B | 62 | −5.840 | −57.504 | −21.711 | 1.00 | 39.09 | C |
| ATOM | 34 | NH1 | ARG | B | 62 | −4.536 | −57.275 | −21.690 | 1.00 | 39.24 | N |
| ATOM | 35 | NH2 | ARG | B | 62 | −6.686 | −56.518 | −21.439 | 1.00 | 40.03 | N |
| ATOM | 36 | N | ILE | B | 63 | −3.428 | −59.342 | −24.313 | 1.00 | 30.07 | N |
| ATOM | 37 | CA | ILE | B | 63 | −2.036 | −59.770 | −24.231 | 1.00 | 31.38 | C |
| ATOM | 38 | C | ILE | B | 63 | −1.623 | −59.981 | −22.775 | 1.00 | 33.08 | C |
| ATOM | 39 | O | ILE | B | 63 | −0.444 | −59.872 | −22.430 | 1.00 | 33.21 | O |
| ATOM | 40 | CB | ILE | B | 63 | −1.081 | −58.745 | −24.883 | 1.00 | 30.06 | C |
| ATOM | 41 | CG1 | ILE | B | 63 | −1.143 | −57.411 | −24.137 | 1.00 | 29.94 | C |
| ATOM | 42 | CG2 | ILE | B | 63 | −1.442 | −58.567 | −26.353 | 1.00 | 30.41 | C |
| ATOM | 43 | CD1 | ILE | B | 63 | −0.128 | −56.384 | −24.632 | 1.00 | 29.62 | C |
| ATOM | 44 | N | SER | B | 64 | −2.603 | −60.284 | −21.927 | 1.00 | 35.38 | N |
| ATOM | 45 | CA | SER | B | 64 | −2.356 | −60.520 | −20.505 | 1.00 | 37.51 | C |
| ATOM | 46 | C | SER | B | 64 | −1.326 | −61.622 | −20.311 | 1.00 | 37.32 | C |
| ATOM | 47 | O | SER | B | 64 | −1.411 | −62.682 | −20.933 | 1.00 | 37.86 | O |
| ATOM | 48 | CB | SER | B | 64 | −3.652 | −60.912 | −19.792 | 1.00 | 38.82 | C |
| ATOM | 49 | OG | SER | B | 64 | −4.558 | −59.823 | −19.750 | 1.00 | 42.88 | O |
| ATOM | 50 | N | GLY | B | 65 | −0.356 | −61.370 | −19.441 | 1.00 | 37.81 | N |
| ATOM | 51 | CA | GLY | B | 65 | 0.679 | −62.355 | −19.199 | 1.00 | 37.13 | C |
| ATOM | 52 | C | GLY | B | 65 | 1.798 | −62.283 | −20.226 | 1.00 | 36.76 | C |
| ATOM | 53 | O | GLY | B | 65 | 2.858 | −62.889 | −20.038 | 1.00 | 37.57 | O |
| ATOM | 54 | N | LEU | B | 66 | 1.577 | −61.539 | −21.307 | 1.00 | 34.63 | N |
| ATOM | 55 | CA | LEU | B | 66 | 2.591 | −61.413 | −22.355 | 1.00 | 33.17 | C |
| ATOM | 56 | C | LEU | B | 66 | 3.414 | −60.133 | −22.246 | 1.00 | 32.72 | C |
| ATOM | 57 | O | LEU | B | 66 | 4.451 | −60.002 | −22.893 | 1.00 | 33.13 | O |
| ATOM | 58 | CB | LEU | B | 66 | 1.936 | −61.470 | −23.735 | 1.00 | 32.08 | C |
| ATOM | 59 | CG | LEU | B | 66 | 1.162 | −62.747 | −24.061 | 1.00 | 32.52 | C |
| ATOM | 60 | CD1 | LEU | B | 66 | 0.563 | −62.626 | −25.445 | 1.00 | 31.38 | C |
| ATOM | 61 | CD2 | LEU | B | 66 | 2.093 | −63.957 | −23.984 | 1.00 | 31.67 | C |

TABLE 6-continued

ATOMIC COORDINATES OF MEMBRANE ASSOCIATION SITE

| ATOM | 62 | N | ARG | B | 67 | 2.953 | −59.185 | −21.440 | 1.00 | 31.54 | N |
|---|---|---|---|---|---|---|---|---|---|---|---|
| ATOM | 63 | CA | ARG | B | 67 | 3.671 | −57.928 | −21.277 | 1.00 | 30.90 | C |
| ATOM | 64 | C | ARG | B | 67 | 5.071 | −58.142 | −20.713 | 1.00 | 29.99 | C |
| ATOM | 65 | O | ARG | B | 67 | 5.294 | −59.034 | −19.889 | 1.00 | 28.67 | O |
| ATOM | 66 | CB | ARG | B | 67 | 2.888 | −56.984 | −20.363 | 1.00 | 32.28 | C |
| ATOM | 67 | CG | ARG | B | 67 | 1.540 | −56.576 | −20.913 | 1.00 | 34.65 | C |
| ATOM | 68 | CD | ARG | B | 67 | 0.926 | −55.440 | −20.097 | 1.00 | 36.69 | C |
| ATOM | 69 | NE | ARG | B | 67 | −0.259 | −54.889 | −20.748 | 1.00 | 38.28 | N |
| ATOM | 70 | CZ | ARG | B | 67 | −1.425 | −55.519 | −20.853 | 1.00 | 39.05 | C |
| ATOM | 71 | NH1 | ARG | B | 67 | −1.583 | −56.734 | −20.341 | 1.00 | 39.61 | N |
| ATOM | 72 | NH2 | ARG | B | 67 | −2.434 | −54.935 | −21.487 | 1.00 | 39.52 | N |
| ATOM | 73 | N | GLY | B | 68 | 6.014 | −57.321 | −21.165 | 1.00 | 27.75 | N |
| ATOM | 74 | CA | GLY | B | 68 | 7.380 | −57.427 | −20.685 | 1.00 | 26.79 | C |
| ATOM | 75 | C | GLY | B | 68 | 8.166 | −58.579 | −21.280 | 1.00 | 25.41 | C |
| ATOM | 76 | O | GLY | B | 68 | 9.326 | −58.779 | −20.943 | 1.00 | 26.04 | O |
| ATOM | 77 | N | LYS | B | 69 | 7.546 | −59.342 | −22.170 | 1.00 | 24.55 | N |
| ATOM | 78 | CA | LYS | B | 69 | 8.238 | −60.463 | −22.796 | 1.00 | 23.93 | C |
| ATOM | 79 | G | LYS | B | 69 | 8.825 | −60.062 | −24.142 | 1.00 | 23.32 | C |
| ATOM | 80 | O | LYS | B | 69 | 8.151 | −59.404 | −24.944 | 1.00 | 21.96 | O |
| ATOM | 81 | CB | LYS | B | 69 | 7.284 | −61.641 | −23.033 | 1.00 | 24.12 | C |
| ATOM | 82 | CG | LYS | B | 69 | 6.757 | −62.360 | −21.794 | 1.00 | 25.08 | C |
| ATOM | 83 | CD | LYS | B | 69 | 5.887 | −63.553 | −22.224 | 1.00 | 25.44 | C |
| ATOM | 84 | CE | LYS | B | 69 | 5.357 | −64.358 | −21.035 | 1.00 | 28.31 | C |
| ATOM | 85 | NZ | LYS | B | 69 | 6.468 | −64.877 | −20.175 | 1.00 | 29.71 | N |
| ATOM | 86 | N | GLY | B | 70 | 10.075 | −60.470 | −24.374 | 1.00 | 22.48 | N |
| ATOM | 87 | CA | GLY | B | 70 | 10.755 | −60.229 | −25.636 | 1.00 | 22.26 | C |
| ATOM | 88 | C | GLY | B | 70 | 10.308 | −61.337 | −26.588 | 1.00 | 22.17 | C |
| ATOM | 89 | O | GLY | B | 70 | 9.512 | −62.183 | −26.195 | 1.00 | 21.62 | O |
| ATOM | 90 | N | ILE | B | 71 | 10.819 | −61.373 | −27.814 | 1.00 | 21.85 | N |
| ATOM | 91 | CA | ILE | B | 71 | 10.357 | −62.386 | −28.762 | 1.00 | 23.55 | C |
| ATOM | 92 | C | ILE | B | 71 | 10.616 | −63.840 | −28.359 | 1.00 | 23.88 | C |
| ATOM | 93 | O | ILE | B | 71 | 9.775 | −64.707 | −28.592 | 1.00 | 21.66 | O |
| ATOM | 94 | CB | ILE | B | 71 | 10.926 | −62.142 | −30.181 | 1.00 | 23.52 | C |
| ATOM | 95 | CG1 | ILE | B | 71 | 10.264 | −63.096 | −31.182 | 1.00 | 24.18 | C |
| ATOM | 96 | CG2 | ILE | B | 71 | 12.435 | −62.375 | −30.192 | 1.00 | 25.96 | C |
| ATOM | 97 | CD1 | ILE | B | 71 | 8.745 | −62.981 | −31.263 | 1.00 | 25.73 | C |
| ATOM | 98 | N | LYS | B | 72 | 11.764 | −64.119 | −27.751 | 1.00 | 23.82 | N |
| ATOM | 99 | CA | LYS | B | 72 | 12.038 | −65.491 | −27.343 | 1.00 | 24.92 | C |
| ATOM | 100 | G | LYS | B | 72 | 11.068 | −65.925 | −26.245 | 1.00 | 23.73 | C |
| ATOM | 101 | O | LYS | B | 72 | 10.592 | −67.062 | −26.245 | 1.00 | 24.08 | O |
| ATOM | 102 | CB | LYS | B | 72 | 13.491 | −65.634 | −26.875 | 1.00 | 26.86 | C |
| ATOM | 103 | CG | LYS | B | 72 | 14.496 | −65.590 | −28.019 | 1.00 | 31.29 | C |
| ATOM | 104 | CD | LYS | B | 72 | 15.925 | −65.791 | −27.518 | 1.00 | 36.00 | C |
| ATOM | 105 | CE | LYS | B | 72 | 16.926 | −65.816 | −28.671 | 1.00 | 38.82 | C |
| ATOM | 106 | NZ | LYS | B | 72 | 18.342 | −65.957 | −28.192 | 1.00 | 41.21 | N |
| ATOM | 107 | N | ALA | B | 73 | 10.765 | −65.016 | −25.322 | 1.00 | 21.62 | N |
| ATOM | 108 | CA | ALA | B | 73 | 9.839 | −65.306 | −24.233 | 1.00 | 21.18 | C |
| ATOM | 109 | C | ALA | B | 73 | 8.412 | −65.454 | −24.771 | 1.00 | 20.36 | C |
| ATOM | 110 | O | ALA | B | 73 | 7.619 | −66.250 | −24.267 | 1.00 | 18.97 | O |
| ATOM | 111 | CB | ALA | B | 73 | 9.895 | −64.196 | −23.187 | 1.00 | 22.25 | C |
| ATOM | 112 | N | LEU | B | 74 | 8.076 | −64.673 | −25.791 | 1.00 | 20.23 | N |
| ATOM | 113 | CA | LEU | B | 74 | 6.745 | −64.762 | −26.387 | 1.00 | 19.36 | C |
| ATOM | 114 | C | LEU | B | 74 | 6.549 | −66.110 | −27.069 | 1.00 | 19.37 | C |
| ATOM | 115 | O | LEU | B | 74 | 5.539 | −66.779 | −26.863 | 1.00 | 20.01 | O |
| ATOM | 116 | CB | LEU | B | 74 | 6.540 | −63.643 | −27.417 | 1.00 | 18.42 | C |
| ATOM | 117 | CG | LEU | B | 74 | 6.422 | −62.208 | −26.884 | 1.00 | 18.80 | C |
| ATOM | 118 | CD1 | LEU | B | 74 | 6.473 | −61.197 | −28.039 | 1.00 | 19.86 | C |
| ATOM | 119 | CD2 | LEU | B | 74 | 5.109 | −62.071 | −26.104 | 1.00 | 19.45 | C |
| ATOM | 120 | N | ILE | B | 75 | 7.520 | −66.507 | −27.883 | 1.00 | 20.59 | N |
| ATOM | 121 | CA | ILE | B | 75 | 7.434 | −67.768 | −28.601 | 1.00 | 21.18 | C |
| ATOM | 122 | C | ILE | B | 75 | 7.488 | −68.942 | −27.624 | 1.00 | 21.20 | C |
| ATOM | 123 | O | ILE | B | 75 | 7.125 | −70.063 | −27.979 | 1.00 | 21.59 | O |
| ATOM | 124 | CB | ILE | B | 75 | 8.571 | −67.896 | −29.641 | 1.00 | 22.95 | C |
| ATOM | 125 | CG1 | ILE | B | 75 | 8.598 | −66.657 | −30.540 | 1.00 | 26.82 | C |
| ATOM | 126 | CG2 | ILE | B | 75 | 8.334 | −69.108 | −30.527 | 1.00 | 25.38 | C |
| ATOM | 127 | CD1 | ILE | B | 75 | 7.304 | −66.442 | −31.327 | 1.00 | 28.48 | C |
| ATOM | 128 | N | ALA | B | 76 | 7.940 | −68.680 | −26.399 | 1.00 | 20.49 | N |
| ATOM | 129 | CA | ALA | B | 76 | 7.996 | −69.726 | −25.374 | 1.00 | 21.72 | C |
| ATOM | 130 | C | ALA | B | 76 | 6.624 | −69.904 | −24.732 | 1.00 | 21.54 | C |
| ATOM | 131 | O | ALA | B | 76 | 6.441 | −70.778 | −23.875 | 1.00 | 20.75 | O |
| ATOM | 132 | CB | ALA | B | 76 | 9.026 | −69.372 | −24.305 | 1.00 | 21.92 | C |
| ATOM | 133 | N | ALA | B | 77 | 5.668 | −69.066 | −25.145 | 1.00 | 20.61 | N |
| ATOM | 134 | CA | ALA | B | 77 | 4.289 | −69.121 | −24.655 | 1.00 | 21.07 | C |
| ATOM | 135 | C | ALA | B | 77 | 3.383 | −69.298 | −25.881 | 1.00 | 21.69 | C |
| ATOM | 136 | O | ALA | B | 77 | 2.567 | −68.430 | −26.199 | 1.00 | 21.93 | O |
| ATOM | 137 | CB | ALA | B | 77 | 3.937 | −67.830 | −23.924 | 1.00 | 20.10 | C |
| ATOM | 138 | N | PRO | B | 78 | 3.507 | −70.446 | −26.564 | 1.00 | 22.38 | N |

TABLE 6-continued

ATOMIC COORDINATES OF MEMBRANE ASSOCIATION SITE

| ATOM | 139 | CA  | PRO | B | 78 | 2.772  | −70.846 | −27.771 | 1.00 | 20.95 | C |
|------|-----|-----|-----|---|----|--------|---------|---------|------|-------|---|
| ATOM | 140 | C   | PRO | B | 78 | 1.278  | −70.535 | −27.813 | 1.00 | 21.19 | C |
| ATOM | 141 | O   | PRO | B | 78 | 0.789  | −69.939 | −28.776 | 1.00 | 19.68 | O |
| ATOM | 142 | CB  | PRO | B | 78 | 3.027  | −72.350 | −27.861 | 1.00 | 22.21 | C |
| ATOM | 143 | CG  | PRO | B | 78 | 4.288  | −72.547 | −27.117 | 1.00 | 24.07 | C |
| ATOM | 144 | CD  | PRO | B | 78 | 4.211  | −71.603 | −25.976 | 1.00 | 21.89 | C |
| ATOM | 145 | N   | LEU | B | 79 | 0.544  | −70.961 | −26.790 | 1.00 | 21.21 | N |
| ATOM | 146 | CA  | LEU | B | 79 | −0.896 | −70.728 | −26.783 | 1.00 | 21.32 | C |
| ATOM | 147 | C   | LEU | B | 79 | −1.275 | −69.263 | −26.707 | 1.00 | 21.17 | C |
| ATOM | 148 | O   | LEU | B | 79 | −2.125 | −68.800 | −27.481 | 1.00 | 20.44 | O |
| ATOM | 149 | CB  | LEU | B | 79 | −1.569 | −71.476 | −25.630 | 1.00 | 20.99 | C |
| ATOM | 150 | CG  | LEU | B | 79 | −1.397 | −72.988 | −25.617 | 1.00 | 22.40 | C |
| ATOM | 151 | CD1 | LEU | B | 79 | −2.504 | −73.619 | −24.772 | 1.00 | 22.01 | C |
| ATOM | 152 | CD2 | LEU | B | 79 | −1.438 | −73.521 | −27.021 | 1.00 | 23.82 | C |
| ATOM | 153 | N   | ARG | B | 80 | −0.656 | −68.529 | −25.788 | 1.00 | 20.91 | N |
| ATOM | 154 | CA  | ARG | B | 80 | −0.980 | −67.115 | −25.637 | 1.00 | 21.30 | C |
| ATOM | 155 | C   | ARG | B | 80 | −0.526 | −66.233 | −26.790 | 1.00 | 21.29 | C |
| ATOM | 156 | O   | ARG | B | 80 | −1.278 | −65.355 | −27.223 | 1.00 | 21.47 | O |
| ATOM | 157 | CB  | ARG | B | 80 | −0.444 | −66.583 | −24.312 | 1.00 | 22.12 | C |
| ATOM | 158 | CG  | ARG | B | 80 | −1.286 | −67.051 | −23.118 | 1.00 | 24.03 | C |
| ATOM | 159 | CD  | ARG | B | 80 | −0.610 | −66.738 | −21.807 | 1.00 | 23.42 | C |
| ATOM | 160 | NE  | ARG | B | 80 | 0.581  | −67.556 | −21.610 | 1.00 | 24.59 | N |
| ATOM | 161 | CZ  | ARG | B | 80 | 1.466  | −67.351 | −20.642 | 1.00 | 26.08 | C |
| ATOM | 162 | NH1 | ARG | B | 80 | 1.290  | −66.349 | −19.787 | 1.00 | 26.92 | N |
| ATOM | 163 | NH2 | ARG | B | 80 | 2.514  | −68.152 | −20.519 | 1.00 | 27.22 | N |
| ATOM | 164 | N   | ILE | B | 81 | 0.683  | −66.448 | −27.303 | 1.00 | 19.29 | N |
| ATOM | 165 | CA  | ILE | B | 81 | 1.113  | −65.621 | −28.421 | 1.00 | 19.47 | C |
| ATOM | 166 | C   | ILE | B | 81 | 0.256  | −65.937 | −29.654 | 1.00 | 18.99 | C |
| ATOM | 167 | O   | ILE | B | 81 | −0.149 | −65.028 | −30.378 | 1.00 | 19.38 | O |
| ATOM | 168 | CB  | ILE | B | 81 | 2.639  | −65.793 | −28.730 | 1.00 | 17.92 | C |
| ATOM | 169 | CG1 | ILE | B | 81 | 3.067  | −64.753 | −29.769 | 1.00 | 18.63 | C |
| ATOM | 170 | CG2 | ILE | B | 81 | 2.949  | −67.200 | −29.206 | 1.00 | 17.33 | C |
| ATOM | 171 | CD1 | ILE | B | 81 | 2.746  | −63.318 | −29.346 | 1.00 | 17.46 | C |
| ATOM | 172 | N   | PHE | B | 82 | −0.056 | −67.211 | −29.880 | 1.00 | 19.39 | N |
| ATOM | 173 | CA  | PHE | B | 82 | −0.875 | −67.582 | −31.038 | 1.00 | 19.15 | C |
| ATOM | 174 | C   | PHE | B | 82 | −2.250 | −66.931 | −30.959 | 1.00 | 19.94 | C |
| ATOM | 175 | O   | PHE | B | 82 | −2.777 | −66.444 | −31.970 | 1.00 | 19.64 | O |
| ATOM | 176 | CB  | PHE | B | 82 | −1.057 | −69.103 | −31.136 | 1.00 | 19.27 | C |
| ATOM | 177 | CG  | PHE | B | 82 | −1.811 | −69.548 | −32.368 | 1.00 | 19.87 | C |
| ATOM | 178 | CD1 | PHE | B | 82 | −1.180 | −69.602 | −33.603 | 1.00 | 20.87 | C |
| ATOM | 179 | CD2 | PHE | B | 82 | −3.154 | −69.898 | −32.289 | 1.00 | 21.11 | C |
| ATOM | 180 | CE1 | PHE | B | 82 | −1.872 | −70.002 | −34.753 | 1.00 | 21.20 | C |
| ATOM | 181 | CE2 | PHE | B | 82 | −3.857 | −70.297 | −33.429 | 1.00 | 22.26 | C |
| ATOM | 182 | CZ  | PHE | B | 82 | −3.212 | −70.349 | −34.663 | 1.00 | 22.14 | C |
| ATOM | 183 | N   | ASN | B | 83 | −2.832 | −66.923 | −29.764 | 1.00 | 19.29 | N |
| ATOM | 184 | CA  | ASN | B | 83 | −4.150 | −66.332 | −29.577 | 1.00 | 20.90 | C |
| ATOM | 185 | C   | ASN | B | 83 | −4.178 | −64.821 | −29.812 | 1.00 | 20.83 | C |
| ATOM | 186 | O   | ASN | B | 83 | −5.086 | −64.316 | −30.472 | 1.00 | 21.92 | O |
| ATOM | 187 | CB  | ASN | B | 83 | −4.693 | −66.641 | −28.178 | 1.00 | 20.55 | C |
| ATOM | 188 | CG  | ASN | B | 83 | −6.158 | −66.244 | −28.028 | 1.00 | 22.79 | C |
| ATOM | 189 | OD1 | ASN | B | 83 | −6.505 | −65.374 | −27.229 | 1.00 | 25.14 | O |
| ATOM | 190 | ND2 | ASN | B | 83 | −7.018 | −66.877 | −28.807 | 1.00 | 20.47 | N |
| ATOM | 191 | N   | ALA | B | 84 | −3.203 | −64.092 | −29.275 | 1.00 | 19.74 | N |
| ATOM | 192 | CA  | ALA | B | 84 | −3.177 | −62.647 | −29.484 | 1.00 | 19.30 | C |
| ATOM | 193 | C   | ALA | B | 84 | −2.967 | −62.380 | −30.981 | 1.00 | 19.94 | C |
| ATOM | 194 | O   | ALA | B | 84 | −3.561 | −61.459 | −31.552 | 1.00 | 19.69 | O |
| ATOM | 195 | CB  | ALA | B | 84 | −2.060 | −62.008 | −28.662 | 1.00 | 18.59 | C |
| ATOM | 196 | N   | TRP | B | 85 | −2.118 | −63.197 | −31.603 | 1.00 | 19.77 | N |
| ATOM | 197 | CA  | TRP | B | 85 | −1.820 | −63.111 | −33.032 | 1.00 | 20.56 | C |
| ATOM | 198 | C   | TRP | B | 85 | −3.090 | −63.354 | −33.865 | 1.00 | 21.76 | C |
| ATOM | 199 | O   | TRP | B | 85 | −3.339 | −62.658 | −34.859 | 1.00 | 20.40 | O |
| ATOM | 200 | CB  | TRP | B | 85 | −0.754 | −64.148 | −33.396 | 1.00 | 21.46 | C |
| ATOM | 201 | CG  | TRP | B | 85 | −0.365 | −64.167 | −34.856 | 1.00 | 23.00 | C |
| ATOM | 202 | CD1 | TRP | B | 85 | 0.301  | −63.189 | −35.548 | 1.00 | 23.17 | C |
| ATOM | 203 | CD2 | TRP | B | 85 | −0.588 | −65.232 | −35.785 | 1.00 | 23.69 | C |
| ATOM | 204 | NE1 | TRP | B | 85 | 0.509  | −63.585 | −36.848 | 1.00 | 24.28 | N |
| ATOM | 205 | CE2 | TRP | B | 85 | −0.024 | −64.835 | −37.022 | 1.00 | 24.14 | C |
| ATOM | 206 | CE3 | TRP | B | 85 | −1.206 | −66.486 | −35.693 | 1.00 | 24.79 | C |
| ATOM | 207 | CZ2 | TRP | B | 85 | −0.060 | −65.650 | −38.160 | 1.00 | 24.90 | C |
| ATOM | 208 | CZ3 | TRP | B | 85 | −1.243 | −67.299 | −36.827 | 1.00 | 25.45 | C |
| ATOM | 209 | CH2 | TRP | B | 85 | −0.671 | −66.875 | −38.045 | 1.00 | 25.15 | C |
| ATOM | 210 | N   | ARG | B | 86 | −3.885 | −64.346 | −33.467 | 1.00 | 22.03 | N |
| ATOM | 211 | CA  | ARG | B | 86 | −5.140 | −64.660 | −34.166 | 1.00 | 23.28 | C |
| ATOM | 212 | C   | ARG | B | 86 | −6.151 | −63.517 | −34.007 | 1.00 | 22.98 | C |
| ATOM | 213 | O   | ARG | B | 86 | −6.890 | −63.195 | −34.942 | 1.00 | 21.37 | O |
| ATOM | 214 | CB  | ARG | B | 86 | −5.754 | −65.965 | −33.623 | 1.00 | 24.72 | C |
| ATOM | 215 | CG  | ARG | B | 86 | −4.999 | −67.236 | −34.021 | 1.00 | 27.21 | C |

TABLE 6-continued

ATOMIC COORDINATES OF MEMBRANE ASSOCIATION SITE

| ATOM | 216 | CD | ARG | B | 86 | −5.368 | −67.725 | −35.418 | 1.00 | 29.60 | C |
|---|---|---|---|---|---|---|---|---|---|---|---|
| ATOM | 217 | NE | ARG | B | 86 | −6.626 | −68.477 | −35.422 | 1.00 | 31.45 | N |
| ATOM | 218 | CZ | ARG | B | 86 | −7.185 | −69.004 | −36.508 | 1.00 | 31.37 | C |
| ATOM | 219 | NH1 | ARG | B | 86 | −6.607 | −68.862 | −37.696 | 1.00 | 32.19 | N |
| ATOM | 220 | NH2 | ARG | B | 86 | −8.314 | −69.694 | −36.405 | 1.00 | 31.39 | N |
| ATOM | 221 | N | GLN | B | 87 | −6.190 | −62.916 | −32.821 | 1.00 | 22.90 | N |
| ATOM | 222 | CA | GLN | B | 87 | −7.101 | −61.802 | −32.567 | 1.00 | 24.07 | C |
| ATOM | 223 | C | GLN | B | 87 | −6.738 | −60.618 | −33.457 | 1.00 | 23.85 | C |
| ATOM | 224 | O | GLN | B | 87 | −7.613 | −60.012 | −34.077 | 1.00 | 24.02 | O |
| ATOM | 225 | CB | GLN | B | 87 | −7.046 | −61.382 | −31.097 | 1.00 | 24.33 | C |
| ATOM | 226 | CG | GLN | B | 87 | −7.873 | −62.280 | −30.187 | 1.00 | 27.24 | C |
| ATOM | 227 | CD | GLN | B | 87 | −7.720 | −61.943 | −28.723 | 1.00 | 28.81 | C |
| ATOM | 228 | OE1 | GLN | B | 87 | −8.567 | −62.296 | −27.908 | 1.00 | 33.25 | O |
| ATOM | 229 | NE2 | GLN | B | 87 | −6.632 | −61.275 | −28.375 | 1.00 | 29.95 | N |
| ATOM | 230 | N | ALA | B | 88 | −5.449 | −60.293 | −33.521 | 1.00 | 23.39 | N |
| ATOM | 231 | CA | ALA | B | 88 | −4.996 | −59.183 | −34.355 | 1.00 | 23.78 | C |
| ATOM | 232 | C | ALA | B | 88 | −5.257 | −59.485 | −35.831 | 1.00 | 24.73 | C |
| ATOM | 233 | O | ALA | B | 88 | −5.655 | −58.595 | −36.592 | 1.00 | 24.72 | O |
| ATOM | 234 | CB | ALA | B | 88 | −3.508 | −58.909 | −34.116 | 1.00 | 23.33 | C |
| ATOM | 235 | N | ARG | B | 89 | −5.038 | −60.735 | −36.244 | 1.00 | 24.26 | N |
| ATOM | 236 | CA | ARG | B | 89 | −5.285 | −61.111 | −37.636 | 1.00 | 24.94 | C |
| ATOM | 237 | C | ARG | B | 89 | −6.752 | −60.909 | −38.013 | 1.00 | 25.29 | C |
| ATOM | 238 | O | ARG | B | 89 | −7.056 | −60.420 | −39.104 | 1.00 | 24.27 | O |
| ATOM | 239 | CB | ARG | B | 89 | −4.904 | −62.575 | −37.893 | 1.00 | 25.14 | C |
| ATOM | 240 | CG | ARG | B | 89 | −3.461 | −62.774 | −38.353 | 1.00 | 24.54 | C |
| ATOM | 241 | CD | ARG | B | 89 | −3.142 | −64.253 | −38.510 | 1.00 | 25.50 | C |
| ATOM | 242 | NE | ARG | B | 89 | −3.809 | −64.901 | −39.641 | 1.00 | 24.93 | N |
| ATOM | 243 | CZ | ARG | B | 89 | −3.329 | −64.930 | −40.882 | 1.00 | 25.90 | C |
| ATOM | 244 | NH1 | ARG | B | 89 | −2.178 | −64.336 | −41.170 | 1.00 | 25.98 | N |
| ATOM | 245 | NH2 | ARG | B | 89 | −3.979 | −65.596 | −41.831 | 1.00 | 26.36 | N |
| ATOM | 246 | N | GLY | B | 105 | 5.583 | −50.364 | −27.741 | 1.00 | 23.01 | N |
| ATOM | 247 | CA | GLY | B | 105 | 4.593 | −50.905 | −26.827 | 1.00 | 23.54 | C |
| ATOM | 248 | C | GLY | B | 105 | 4.358 | −52.380 | −27.078 | 1.00 | 23.17 | C |
| ATOM | 249 | O | GLY | B | 105 | 4.449 | −52.844 | −28.214 | 1.00 | 22.69 | O |
| ATOM | 250 | N | TYR | B | 106 | 4.018 | −53.118 | −26.026 | 1.00 | 22.87 | N |
| ATOM | 251 | CA | TYR | B | 106 | 3.818 | −54.554 | −26.159 | 1.00 | 22.37 | C |
| ATOM | 252 | C | TYR | B | 106 | 2.719 | −55.018 | −27.100 | 1.00 | 20.52 | C |
| ATOM | 253 | O | TYR | B | 106 | 2.867 | −56.052 | −27.746 | 1.00 | 20.50 | O |
| ATOM | 254 | CB | TYR | B | 106 | 3.632 | −55.181 | −24.774 | 1.00 | 25.08 | C |
| ATOM | 255 | CG | TYR | B | 106 | 4.864 | −55.008 | −23.929 | 1.00 | 28.19 | C |
| ATOM | 256 | CD1 | TYR | B | 106 | 4.869 | −54.153 | −22.830 | 1.00 | 31.96 | C |
| ATOM | 257 | CD2 | TYR | B | 106 | 6.058 | −55.631 | −24.282 | 1.00 | 31.27 | C |
| ATOM | 258 | CE1 | TYR | B | 106 | 6.043 | −53.915 | −22.108 | 1.00 | 33.13 | C |
| ATOM | 259 | CE2 | TYR | B | 106 | 7.234 | −55.400 | −23.569 | 1.00 | 32.27 | C |
| ATOM | 260 | CZ | TYR | B | 106 | 7.219 | −54.541 | −22.487 | 1.00 | 33.19 | C |
| ATOM | 261 | OH | TYR | B | 106 | 8.388 | −54.291 | −21.802 | 1.00 | 35.95 | O |
| ATOM | 262 | N | VAL | B | 107 | 1.628 | −54.270 | −27.205 | 1.00 | 19.06 | N |
| ATOM | 263 | CA | VAL | B | 107 | 0.557 | −54.694 | −28.099 | 1.00 | 18.06 | C |
| ATOM | 264 | C | VAL | B | 107 | 1.015 | −54.743 | −29.559 | 1.00 | 17.45 | C |
| ATOM | 265 | O | VAL | B | 107 | 0.502 | −55.536 | −30.346 | 1.00 | 16.99 | O |
| ATOM | 266 | CB | VAL | B | 107 | −0.690 | −53.774 | −27.978 | 1.00 | 20.95 | C |
| ATOM | 267 | CG1 | VAL | B | 107 | −0.407 | −52.407 | −28.589 | 1.00 | 21.39 | C |
| ATOM | 268 | CG2 | VAL | B | 107 | −1.879 | −54.433 | −28.658 | 1.00 | 21.30 | C |
| ATOM | 269 | N | SER | B | 108 | 1.991 | −53.916 | −29.918 | 1.00 | 17.96 | N |
| ATOM | 270 | CA | SER | B | 108 | 2.488 | −53.892 | −31.290 | 1.00 | 19.67 | C |
| ATOM | 271 | C | SER | B | 108 | 3.197 | −55.187 | −31.694 | 1.00 | 20.38 | C |
| ATOM | 272 | O | SER | B | 108 | 3.385 | −55.449 | −32.884 | 1.00 | 21.25 | O |
| ATOM | 273 | CB | SER | B | 108 | 3.424 | −52.691 | −31.508 | 1.00 | 19.56 | C |
| ATOM | 274 | OG | SER | B | 108 | 4.666 | −52.824 | −30.837 | 1.00 | 19.63 | O |
| ATOM | 275 | N | GLY | B | 109 | 3.595 | −55.995 | −30.710 | 1.00 | 19.59 | N |
| ATOM | 276 | CA | GLY | B | 109 | 4.251 | −57.256 | −31.023 | 1.00 | 20.03 | C |
| ATOM | 277 | C | GLY | B | 109 | 3.311 | −58.170 | −31.792 | 1.00 | 19.61 | C |
| ATOM | 278 | O | GLY | B | 109 | 3.579 | −58.517 | −32.940 | 1.00 | 19.24 | O |
| ATOM | 279 | N | PRO | B | 110 | 2.206 | −58.606 | −31.173 | 1.00 | 19.20 | N |
| ATOM | 280 | CA | PRO | B | 110 | 1.251 | −59.478 | −31.855 | 1.00 | 18.99 | C |
| ATOM | 281 | C | PRO | B | 110 | 0.651 | −58.761 | −33.075 | 1.00 | 19.22 | C |
| ATOM | 282 | O | PRO | B | 110 | 0.406 | −59.371 | −34.116 | 1.00 | 17.13 | O |
| ATOM | 283 | CB | PRO | B | 110 | 0.198 | −59.737 | −30.778 | 1.00 | 20.41 | C |
| ATOM | 284 | CG | PRO | B | 110 | 0.998 | −59.720 | −29.515 | 1.00 | 19.81 | C |
| ATOM | 285 | CD | PRO | B | 110 | 1.914 | −58.528 | −29.729 | 1.00 | 19.94 | C |
| ATOM | 286 | N | GLY | B | 111 | 0.407 | −57.462 | −32.927 | 1.00 | 19.03 | N |
| ATOM | 287 | CA | GLY | B | 111 | −0.160 | −56.702 | −34.025 | 1.00 | 19.60 | C |
| ATOM | 288 | C | GLY | B | 111 | 0.764 | −56.714 | −35.226 | 1.00 | 19.59 | C |
| ATOM | 289 | O | GLY | B | 111 | 0.330 | −56.979 | −36.339 | 1.00 | 21.10 | O |
| ATOM | 290 | N | GLY | B | 112 | 2.043 | −56.429 | −34.995 | 1.00 | 19.78 | N |
| ATOM | 291 | CA | GLY | B | 112 | 3.014 | −56.417 | −36.074 | 1.00 | 19.97 | C |
| ATOM | 292 | C | GLY | B | 112 | 3.147 | −57.783 | −36.724 | 1.00 | 20.43 | C |

TABLE 6-continued

ATOMIC COORDINATES OF MEMBRANE ASSOCIATION SITE

| ATOM | 293 | O | GLY | B | 112 | 3.233 | −57.896 | −37.949 | 1.00 | 19.94 | O |
|---|---|---|---|---|---|---|---|---|---|---|---|
| ATOM | 294 | N | LEU | B | 113 | 3.167 | −58.828 | −35.903 | 1.00 | 19.26 | N |
| ATOM | 295 | CA | LEU | B | 113 | 3.265 | −60.184 | −36.429 | 1.00 | 19.49 | C |
| ATOM | 296 | C | LEU | B | 113 | 2.040 | −60.521 | −37.274 | 1.00 | 18.73 | C |
| ATOM | 297 | O | LEU | B | 113 | 2.143 | −61.252 | −38.255 | 1.00 | 18.44 | O |
| ATOM | 298 | CB | LEU | B | 113 | 3.405 | −61.198 | −35.289 | 1.00 | 18.38 | C |
| ATOM | 299 | CG | LEU | B | 113 | 4.777 | −61.270 | −34.605 | 1.00 | 20.59 | C |
| ATOM | 300 | CD1 | LEU | B | 113 | 4.656 | −62.059 | −33.311 | 1.00 | 20.01 | C |
| ATOM | 301 | CD2 | LEU | B | 113 | 5.794 | −61.914 | −35.538 | 1.00 | 20.23 | C |
| ATOM | 302 | N | ALA | B | 114 | 0.875 | −60.010 | −36.892 | 1.00 | 18.96 | N |
| ATOM | 303 | CA | ALA | B | 114 | −0.334 | −60.292 | −37.661 | 1.00 | 18.70 | C |
| ATOM | 304 | C | ALA | B | 114 | −0.288 | −59.578 | −39.019 | 1.00 | 19.30 | C |
| ATOM | 305 | O | ALA | B | 114 | −0.602 | −60.167 | −40.052 | 1.00 | 20.62 | O |
| ATOM | 306 | CB | ALA | B | 114 | −1.562 | −59.855 | −36.889 | 1.00 | 16.45 | C |
| ATOM | 307 | N | ALA | B | 115 | 0.082 | −58.303 | −39.000 | 1.00 | 20.57 | N |
| ATOM | 308 | CA | ALA | B | 115 | 0.167 | −57.516 | −40.229 | 1.00 | 21.84 | C |
| ATOM | 309 | C | ALA | B | 115 | 1.140 | −58.192 | −41.189 | 1.00 | 21.58 | C |
| ATOM | 310 | O | ALA | B | 115 | 0.815 | −58.464 | −42.345 | 1.00 | 22.14 | O |
| ATOM | 311 | CB | ALA | B | 115 | 0.636 | −56.108 | −39.911 | 1.00 | 19.85 | C |
| ATOM | 312 | N | TRP | B | 116 | 2.334 | −58.476 | −40.688 | 1.00 | 22.12 | N |
| ATOM | 313 | CA | TRP | B | 116 | 3.365 | −59.126 | −41.478 | 1.00 | 23.22 | C |
| ATOM | 314 | C | TRP | B | 116 | 2.871 | −60.434 | −42.123 | 1.00 | 23.55 | C |
| ATOM | 315 | O | TRP | B | 116 | 3.048 | −60.643 | −43.329 | 1.00 | 22.19 | O |
| ATOM | 316 | CB | TRP | B | 116 | 4.584 | −59.367 | −40.579 | 1.00 | 26.08 | C |
| ATOM | 317 | CG | TRP | B | 116 | 5.699 | −60.136 | −41.204 | 1.00 | 27.40 | C |
| ATOM | 316 | CD1 | TRP | B | 116 | 6.473 | −59.761 | −42.271 | 1.00 | 28.30 | C |
| ATOM | 319 | CD2 | TRP | B | 116 | 6.168 | −61.418 | −40.793 | 1.00 | 28.77 | C |
| ATOM | 320 | NE1 | TRP | B | 116 | 7.401 | −60.742 | −42.547 | 1.00 | 29.04 | N |
| ATOM | 321 | CE2 | TRP | B | 116 | 7.234 | −61.771 | −41.655 | 1.00 | 30.37 | C |
| ATOM | 322 | CE3 | TRP | B | 116 | 5.794 | −62.308 | −39.778 | 1.00 | 30.49 | C |
| ATOM | 323 | CZ2 | TRP | B | 116 | 7.929 | −62.981 | −41.529 | 1.00 | 31.08 | C |
| ATOM | 324 | CZ3 | TRP | B | 116 | 6.485 | −63.510 | −39.653 | 1.00 | 31.85 | C |
| ATOM | 325 | CH2 | TRP | B | 116 | 7.541 | −63.834 | −40.527 | 1.00 | 32.27 | C |
| ATOM | 326 | N | SER | B | 117 | 2.231 | −61.304 | −41.338 | 1.00 | 21.35 | N |
| ATOM | 327 | CA | SER | B | 117 | 1.735 | −62.573 | −41.873 | 1.00 | 22.61 | C |
| ATOM | 328 | C | SER | B | 117 | 0.665 | −62.383 | −42.940 | 1.00 | 23.56 | C |
| ATOM | 329 | O | SER | B | 117 | 0.463 | −63.262 | −43.780 | 1.00 | 23.11 | O |
| ATOM | 330 | CB | SER | B | 117 | 1.167 | −63.462 | −40.756 | 1.00 | 20.72 | C |
| ATOM | 331 | OG | SER | B | 117 | 0.010 | −62.889 | −40.169 | 1.00 | 22.72 | O |
| ATOM | 332 | N | LEU | B | 133 | 11.788 | −52.846 | −25.860 | 1.00 | 23.38 | N |
| ATOM | 333 | CA | LEU | B | 133 | 11.903 | −54.293 | −26.020 | 1.00 | 24.54 | C |
| ATOM | 334 | C | LEU | B | 133 | 11.209 | −54.833 | −27.276 | 1.00 | 22.84 | C |
| ATOM | 335 | O | LEU | B | 133 | 11.784 | −55.619 | −28.027 | 1.00 | 21.86 | O |
| ATOM | 336 | CB | LEU | B | 133 | 11.328 | −54.996 | −24.786 | 1.00 | 25.48 | C |
| ATOM | 337 | CG | LEU | B | 133 | 11.388 | −56.527 | −24.780 | 1.00 | 27.50 | C |
| ATOM | 338 | CD1 | LEU | B | 133 | 12.840 | −56.984 | −24.866 | 1.00 | 28.69 | C |
| ATOM | 339 | CD2 | LEU | B | 133 | 10.735 | −57.059 | −23.509 | 1.00 | 28.04 | C |
| ATOM | 340 | N | THR | B | 134 | 9.975 | −54.401 | −27.499 | 1.00 | 21.72 | N |
| ATOM | 341 | CA | THR | B | 134 | 9.202 | −54.860 | −28.639 | 1.00 | 21.22 | C |
| ATOM | 342 | C | THR | B | 134 | 9.693 | −54.326 | −29.986 | 1.00 | 20.62 | C |
| ATOM | 343 | O | THR | B | 134 | 9.843 | −55.091 | −30.932 | 1.00 | 20.33 | O |
| ATOM | 344 | CB | THR | B | 134 | 7.716 | −54.509 | −28.449 | 1.00 | 20.99 | C |
| ATOM | 345 | OG1 | THR | B | 134 | 7.257 | −55.075 | −27.210 | 1.00 | 20.94 | O |
| ATOM | 346 | CG2 | THR | B | 134 | 6.872 | −55.073 | −29.600 | 1.00 | 20.64 | C |
| ATOM | 3608 | N | LYS | B | 136 | 12.595 | −53.366 | −30.809 | 1.00 | 21.46 | N |
| ATOM | 3609 | CA | LYS | B | 136 | 13.886 | −53.949 | −31.144 | 1.00 | 22.79 | C |
| ATOM | 3610 | CB | LYS | B | 136 | 14.713 | −54.196 | −29.879 | 1.00 | 24.70 | C |
| ATOM | 3611 | CG | LYS | B | 136 | 16.183 | −54.424 | −30.178 | 1.00 | 27.75 | C |
| ATOM | 3612 | CD | LYS | B | 136 | 16.998 | −54.494 | −28.902 | 1.00 | 30.17 | C |
| ATOM | 3613 | CE | LYS | B | 136 | 18.479 | −54.671 | −29.203 | 1.00 | 32.33 | C |
| ATOM | 3614 | NZ | LYS | B | 136 | 19.278 | −54.641 | −27.944 | 1.00 | 33.37 | N |
| ATOM | 3615 | C | LYS | B | 136 | 13.793 | −55.229 | −31.966 | 1.00 | 23.46 | C |
| ATOM | 3616 | O | LYS | B | 136 | 14.561 | −55.407 | −32.912 | 1.00 | 23.71 | O |
| ATOM | 347 | N | TRP | B | 137 | 12.868 | −56.127 | −31.633 | 1.00 | 21.78 | N |
| ATOM | 348 | CA | TRP | B | 137 | 12.753 | −57.345 | −32.424 | 1.00 | 22.06 | C |
| ATOM | 349 | C | TRP | B | 137 | 11.768 | −57.202 | −33.574 | 1.00 | 21.75 | C |
| ATOM | 350 | O | TRP | B | 137 | 11.936 | −57.822 | −34.623 | 1.00 | 21.76 | O |
| ATOM | 351 | CB | TRP | B | 137 | 12.361 | −58.552 | −31.553 | 1.00 | 21.20 | C |
| ATOM | 352 | CG | TRP | B | 137 | 10.990 | −58.525 | −30.922 | 1.00 | 20.23 | C |
| ATOM | 353 | CD1 | TRP | B | 137 | 10.696 | −58.231 | −29.618 | 1.00 | 19.62 | C |
| ATOM | 354 | CD2 | TRP | B | 137 | 9.748 | −58.877 | −31.544 | 1.00 | 18.68 | C |
| ATOM | 355 | NE1 | TRP | B | 137 | 9.349 | −58.385 | −29.390 | 1.00 | 19.31 | N |
| ATOM | 356 | CE2 | TRP | B | 137 | 8.743 | −58.780 | −30.555 | 1.00 | 18.97 | C |
| ATOM | 357 | CE3 | TRP | B | 137 | 9.383 | −59.270 | −32.840 | 1.00 | 19.75 | C |
| ATOM | 358 | CZ2 | TRP | B | 137 | 7.401 | −59.058 | −30.821 | 1.00 | 18.18 | C |
| ATOM | 359 | CZ3 | TRP | B | 137 | 8.046 | −59.549 | −33.107 | 1.00 | 18.87 | C |
| ATOM | 360 | CH2 | TRP | B | 137 | 7.072 | −59.440 | −32.099 | 1.00 | 18.94 | C |

TABLE 6-continued

ATOMIC COORDINATES OF MEMBRANE ASSOCIATION SITE

| ATOM | 361 | N | LEU | B | 138 | 10.741 | −56.381 | −33.386 | 1.00 | 21.61 | N |
|---|---|---|---|---|---|---|---|---|---|---|---|
| ATOM | 362 | CA | LEU | B | 138 | 9.744 | −56.188 | −34.431 | 1.00 | 23.15 | C |
| ATOM | 363 | C | LEU | B | 138 | 10.384 | −55.558 | −35.676 | 1.00 | 23.07 | C |
| ATOM | 364 | O | LEU | B | 138 | 9.958 | −55.801 | −36.809 | 1.00 | 22.68 | O |
| ATOM | 365 | CB | LEU | B | 138 | 8.618 | −55.305 | −33.886 | 1.00 | 23.87 | C |
| ATOM | 366 | CG | LEU | B | 138 | 7.312 | −55.155 | −34.664 | 1.00 | 26.48 | C |
| ATOM | 367 | CD1 | LEU | B | 138 | 6.672 | −56.508 | −34.915 | 1.00 | 25.34 | C |
| ATOM | 368 | CD2 | LEU | B | 138 | 6.383 | −54.267 | −33.851 | 1.00 | 25.90 | C |
| ATOM | 3644 | N | LYS | B | 140 | 12.801 | −56.332 | −37.241 | 1.00 | 27.38 | N |
| ATOM | 3645 | CA | LYS | B | 140 | 13.279 | −57.337 | −38.182 | 1.00 | 28.05 | C |
| ATOM | 3646 | CB | LYS | B | 140 | 13.893 | −58.501 | −37.401 | 1.00 | 29.91 | C |
| ATOM | 3647 | CG | LYS | B | 140 | 15.134 | −58.057 | −36.635 | 1.00 | 31.62 | C |
| ATOM | 3648 | CD | LYS | B | 140 | 15.719 | −59.149 | −35.757 | 1.00 | 33.53 | C |
| ATOM | 3649 | CE | LYS | B | 140 | 16.974 | −58.634 | −35.055 | 1.00 | 34.46 | C |
| ATOM | 3650 | NZ | LYS | B | 140 | 17.692 | −59.713 | −34.320 | 1.00 | 36.17 | N |
| ATOM | 3651 | C | LYS | B | 140 | 12.254 | −57.833 | −39.212 | 1.00 | 27.83 | C |
| ATOM | 3652 | O | LYS | B | 140 | 12.602 | −58.562 | −40.142 | 1.00 | 27.80 | O |
| ATOM | 369 | N | ILE | B | 141 | 10.992 | −57.445 | −39.052 | 1.00 | 26.40 | N |
| ATOM | 370 | CA | ILE | B | 141 | 9.963 | −57.818 | −40.016 | 1.00 | 26.09 | C |
| ATOM | 371 | C | ILE | B | 141 | 9.316 | −56.542 | −40.530 | 1.00 | 25.81 | C |
| ATOM | 372 | O | ILE | B | 141 | 8.353 | −56.586 | −41.305 | 1.00 | 26.10 | O |
| ATOM | 373 | CB | ILE | B | 141 | 8.854 | −58.721 | −39.405 | 1.00 | 26.39 | C |
| ATOM | 374 | CG1 | ILE | B | 141 | 8.298 | −58.092 | −38.127 | 1.00 | 26.45 | C |
| ATOM | 375 | CG2 | ILE | B | 141 | 9.401 | −60.118 | −39.145 | 1.00 | 28.33 | C |
| ATOM | 376 | CD1 | ILE | B | 141 | 7.136 | −58.845 | −37.549 | 1.00 | 26.95 | C |
| TER | | | | | | | | | | | |

The following examples are presented for purposes of illustration only and are not intended to limit the scope of the invention in any way.

EXAMPLE 1

This example describes the crystallization of the *E. coli* MurG protein and the determination of the coordinates of the three-dimensional crystal structure. This example also describes the identification of the donor nucleotide binding site, the acceptor binding site and the membrane association site of the MurG protein.

Abstract

The 1.9 Å X-ray structure of a membrane-associated glycosyltransferase involved in peptidoglycan biosynthesis is reported. This enzyme, MurG, contains two a/B open sheet domains separated by a deep cleft. The C-terminal domain contains the LTDP-GlcNAc binding site while the N-terminal domain contains the acceptor binding site and likely membrane association site. Combined with sequence data from other MurG homologs, this structure provides insight into the residues that are important in substrate binding and catalysis. We have also noted that a conserved region found in many UDP-sugar transferases maps to a $\beta/\alpha/\beta/\alpha$ supersecondary structural motif in the donor binding region of MurG, an observation that is be helpful in glycosyltransferase structure prediction.

Methods

Crystallization *E. coli* MurG containing a C-terminal LEH-HHHHHH sequence was purified as described (Ha et al., 1999) and concentrated to 10 mg ml—in 20 mM Tris-HCl, pH 7.9/150 mM NaCl/50 mM EDTA. The protein concentrate was mixed with UDP-GlcNAc in a 1:3 molar ratio. Crystals were grown at room temperature using the hanging-drop vapor-diffusion method by mixing equal volumes of protein with reservoir solution (0.1 M NaMES, pH 6.5/0.96 M (NH,), SO,/0.4% Triton X-100/10 mM DTT). Triclinic crystals with a typical size of 0.2 mm×0.1 mm×0.1 mm grew within a week. The crystals belong to the PI space group, with two molecules per asymmetric unit. The cell dimensions are a=60.613 Å, b=66.356 Å, c=67.902 Å, $\alpha$=64.294, $\beta$=83.520, $\gamma$=65.448.

Data Collection and Processing

All data sets were collected at 100 K on previously flash frozen crystals. Crystals were equilibrated in a cryoprotectant buffer with 0.1 M NaMES, pH 6.5, 1.44 M $(NH_4)_2SO_4$, 0.4% Triton X-100, and 20% glycerol. Heavy-atom soaks were carried out in the same buffer containing one of the following heavy-atom solutions: 2 mM $HgCl_2$, 1 mM $(NH_4)_2WS_4$, 1 mM $(NH_4)_2OsBr_6$. Crystals were flash-frozen in liquid nitrogen. $HgC_2$ (form A derivative) and $(NH_4)_2OsBr_6$ derivative data were collected at an R-AX1SIIC imaging plate detector mounted on a Rigaku 200HB generator. Native, $HgCl_2$ (form B derivative), and $(NH_4)_2WS_4$ derivative diffraction data were collected at beam-line BioCARS-14B at the Advanced Photon Source, at wavelengths 1.0092 Å, 0.9900 Å and 1.2147 Å respectively. Collection of data on the $HgCl_2$, derivative was initially designed for MAD phasing; however, the mercury derivative proved to be unstable to X-rays, and after a two-hour exposure to synchrotron radiation the form A derivative metamorphosed into a different mercury derivative (form B) that was suitable for MIR phasing. All the data were reduced using DENZO and SCALEPACK (Otwinowski & Minor, 1997), and processed with CCP4 programs (CCP4, 1994).

Structure Determination and Refinement

The structure was solved by multiple isomorphous replacement combined with anomalous scattering of mercuric derivatives (Table 1). Initial MIR phases calculated with program MLPHARE had a mean figure of merit of 0.44 to 2.5 Å, and were improved by solvent flattening and histogram matching using DM. An MIR map was generated which had continuous electron density for most regions of the protein. A model was built with the program 0 (Jones et al., 1991), and the structure was refined against 1.9 Å data using energy minimization, simulated annealing and B-factor refinement with the program CNS (Brunger et al., 1998). The N-terminal six residues and the C-terminal His-tag had no electron density and were not included in this model. There was no electron density for UDP-GlcNAc.

Results and Discussion

Overall Fold

The crystal structure of *E. coli* MurG was solved by a combination of multiple isomorphous replacement and anomalous scattering, and refined to 1.9 Å resolution.

Rossman domains typically contain at least one conserved glycine rich motif, with the consensus sequence GXGXXG, located at a turn between the carboxyl end of one β-strand and the amino terminus of the adjacent α-helix (Baker et al., 1992). This motif is involved in binding the negatively charged phosphates (Carugo & Argos, 1997). There are three glycine rich loops (G loops) in *E. coli* MurG (FIG. 3a) that may be variants on the phosphate binding loops found in other dinucleotide binding proteins (see below).

Sequence Homology

Amino acid sequences for eighteen MurG homologs are now available. The sequence similarity between *E. coli*

TABLE 1

Summary of crystallographic and refinement data

| Data set | Native | HgCl$_2$ (form A derivative) | HgCl$_2$ (form B derivative) | (NH$_4$)$_2$WS$_4$ | (NH$_4$)$_2$OsBr$_6$ |
|---|---|---|---|---|---|
| Resolution (Å) | 1.9 | 2.0 | 1.9 | 2.4 | 2.3 |
| Observations | 288,150 | 101,913 | 245,320 | 44,366 | 106,606 |
| Unique reflections | 65,567 | 53,391 | 65,581 | 27,950 | 36,443 |
| R$_{sym}$[1] (last shell) | 0.032 (0.187) | 0.043 (0.200) | 0.042 (0.296) | 0.031 (0.080) | 0.056 (0.302) |
| I/σ (last shell) | 41.9 (7.0) | 20.4 (2.9) | 29.0 (3.7) | 24.6 (8.2) | 19.6 (2.5) |
| Completeness (last shell) | 97.7% (96.4%) | 91.4% (66.6%) | 97.4% (94.0%) | 83.8% (62.0%) | 94.3% (78.6%) |
| MIR analysis (40.0-2.5 Å) | | | | | |
| Mean isomorphous difference[2] | | 0.163 | 0.130 | 0.068 | 0.134 |
| Phasing power[3] (last shell) | | 1.09 (0.73) | 0.57 (0.50) | 0.61 (0.24) | 0.61 (0.58) |
| R$_{cullis}$[4] (last shell) | | 0.81 (0.91) | 0.94 (0.96) | 0.92 (0.99) | 0.94 (0.95) |
| Anomalous R$_{cullis}$[4] (last shell) | | 0.96 (1.00) | 0.95 (1.00) | | |
| Refinement statistics | | | | | |
| Resolution | 40.0-1.9 Å | R.m.s.d.[7] | | | |
| Reflections (|F| > 2σ) | 61,989 | Bonds (Å) | | 0.006 | |
| Protein atoms (a.u.) | 5,280 | Angles (°) | | 1.29 | |
| Water Atoms | 298 | | | | |
| Sulfate groups | 1 | Ramachandran plot[8] | | | |
| R-factor[5] | 22.0% | Residues in most favored region | | 94.6% | |
| R-free[6] | 24.7% | Residues in additional allowed region | | 5.4% | |

[1]R$_{sym}$ = Σ| I$_i$ − <I> |/ΣI$_i$, where I$_i$ is the intensity of a reflection, and <I> is the average intensity of that reflection.
[2]Mean isomorphous difference = Σ |F$_{PH}$ − F$_p$|/ΣF$_{PH}$, where F$_{PH}$ and F$_p$ are the derivative and native structure factors respectively.
[3]Phasing power is the ratio of the mean calculated derivative structure factor to the mean lack of closure error.
[4]R$_{cullis}$ is the mean residual lack of closure error divided by the dispersive or anomalous difference.
[5]R-factor = Σ|Fobs| − |Fcalc| |/Σ|F|
[6]R-free is the R-factor calculated using 10% of the reflection data chosen randomly and omitted from the start of refinement.
[7]R.m.s.d., root-mean-square deviations from ideal bond lengths and bond angles.
[8]Calculated with program PROCHECK.

Figure 2A:
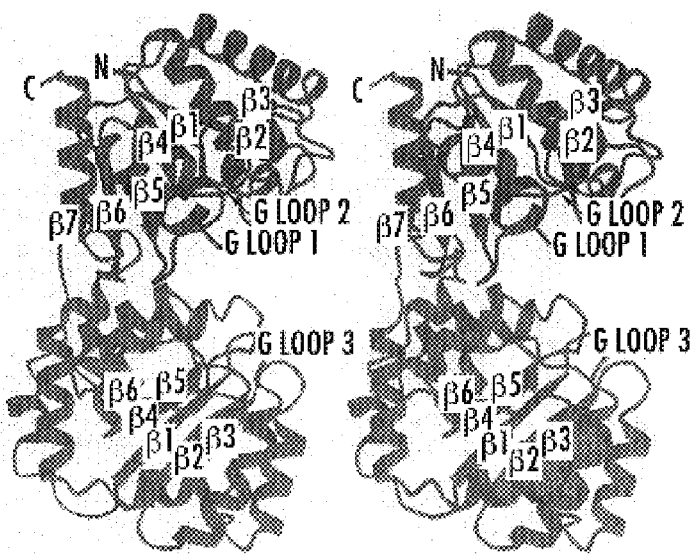
FIG. 2. Overall architecture of MurG. A. Stereo view of the MurG structure. The N domain is shown in purple; the C domain is shown in green. The figure was generated with the programs MOLSCRIPT (Klaulis, 1991) and RASTER31) (Merrit & Murphy, 1994). B. Topology diagram of MurG.
Figure 2B:
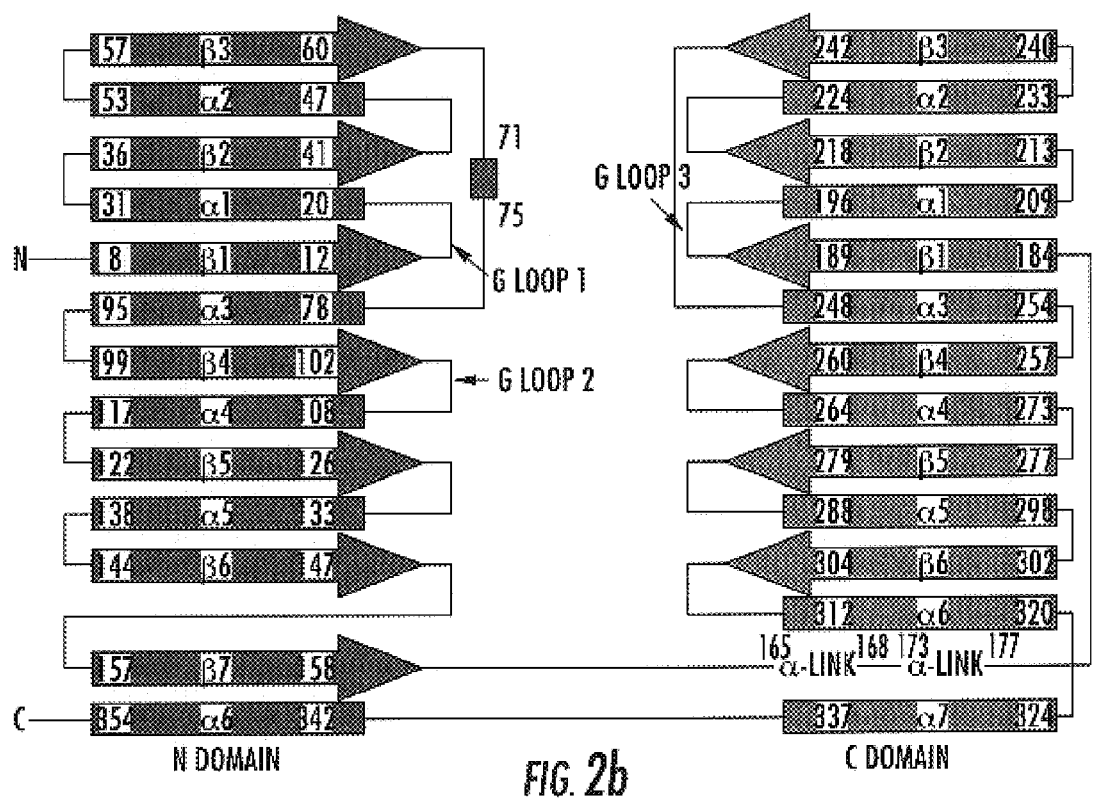

The structure consists of two domains separated by a deep cleft (FIG. 2a). Both domains exhibit an α/β open-sheet structure and have high structural homology despite minimal sequence homology (RMSD=2.02 over 85 aligned Cα atoms). The N-domain includes residues 7–163 and 341–357, and contains seven parallel β-strands and six α-helices, the last of which originates in the C-domain (FIG. 2b). The C-domain comprises residues 164–340 and contains six parallel β-strands and eight α-helices, including one irregular bipartite helix (α-link) that connects the N-domain to the first β-strand of the C-domain. The β-strands in both domains are ordered as for a typical Rossman fold. The N- and C-domains are joined by a short linker between the seventh β-strand of the N-domain and the α-link of the C-domain. This inter-domain linker and the peptide segment that joins the last helix of the C-domain to the last helix of the N-domain define the floor of the cleft between the two domains. The cleft itself is about 20 Å deep and 18 Å across at its widest point. Contacts <4 Å across the cleft are limited primarily to interactions between residues from C-α5 to the loop connecting N-β5 to N-α5.

Figure 3B:
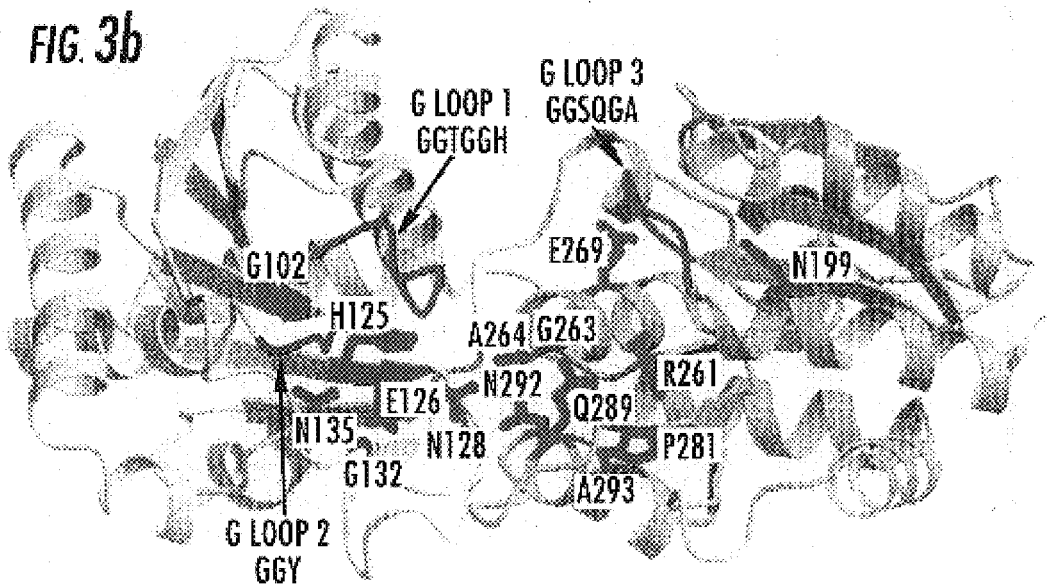

The α/β open-sheet motif (Rossman fold) adopted by both the N- and C-domains of MurG is characteristic of domains that bind nucleotides (Branden & Tooze, 1998). Classical MurG and homologs from other bacterial strains ranges from less than 30% to more than 90% depending on the evolutionary relationship between the organisms. In all MurG homologs, however, there are several invariant residues. FIG. 3a shows a sequence alignment for a subset of MurG homologs with the invariant and highly conserved residues indicated. These residues, which include the three G loops, have been highlighted in the *E. coli* MurG structure (FIG. 3b). Almost all of the invariant residues are located at or near the cleft between the two domains. Two of the G loops are found in the N domain (between N-β1/N-α1 and N-β4/N-α4) and one is found in the C-domain (between C-β1/C-α1). The strict conservation of the highlighted residues among different bacterial strains, and their location as determined from the *E. coli* MurG structure, implicates them in substrate binding and catalytic activity.

Structural Homology Reveals the Donor Binding Site

The three-dimensional backbone structure of *E. coli* MurG was compared to known protein structures, including the three other NDP-glycosyltransferase structures that have been reported (Chamok & Davies, 1999; Gastinel et al., 1999; Vrielink et al., 1994). The C-terminal domain was found to have significant structural homology (RMSD= 2.218 Å for 89 aligned C? atoms) to the C-terminal domain of phage T4 β-glucosyltransferase (BGT), an enzyme that catalyzes the glucosylation of hydroxymethyl-cytosines in duplex DNA. A co-crystal structure of BGT with UDP bound in the C-terminal domain reveals the topology of the UDP binding pocket and also shows important contacts to the nucleotide (Morera et al., 1999; Vrielink et al., 1994). These contacts include: a) hydrogen bonds from the backbone amide of I238 to the N3 and O4 positions of the base; b) hydrogen bonds between the carboxyl side chain of E272 and the O2' and O3' hydroxyls of the ribose ring; and c) contacts from a GGS motif in the loop following the first P-strand of the C domain to the alpha phosphate of UDP. The structurally homologous C-domain of MurG contains a topologically similar pocket (FIG. 4a). Furthermore, even though the two domains share only 11% sequence identity overall, there are identical residues in the same spatial location in E. coli MurG and in BGT. Based on this comparison, we have concluded that the C-domain of E. coli MurG is the UDP-GlcNAc binding site.

We have docked UDP-G1cNAc into the C-domain of E. coli MurG using the information on how UDP binds to BGT as a guide. As shown in FIG. 4b, the uracil is held in place by contacts from the N3 and O4 atoms to the backbone amide of I245. The O2' and O3' hydroxyls on the ribose sugar are within hydrogen bonding distance of the invariant glutamate residue (E269) in the middle of helix C-?4. The conserved GGS motif in G loop 3 is positioned to contact the alpha phosphate. When these contacts are made, the UDP-GlcNAc substrate fits nicely into a pocket in the C-domain, where it is surrounded by many of the invariant residues identified through sequence analysis of other MurG homologs. It is possible to propose roles for some of these invariant residues from the model. For example, the side chain of R261 can be rotated to contact the second phosphate; this contact may help explain why UDP binds significantly better to MurG than UMP. We propose that R261 plays an important role in catalysis by stabilizing the UDP leaving group via electrostatic interactions. The side chain of Q289 is within hydrogen bonding distance of the C4 hydroxyl of the GlcNAc sugar. This contact may explain why MurG can discriminate between UDP-G1cNAc and its C4 axial isomer, UDP-GalNAc (Ha et at., 1999).

The Acceptor Binding Site

Structural considerations suggest that the primary acceptor binding site is located in the N-terminal domain of MurG. This domain contains three highly conserved regions, two of which are glycine-rich loops that face the cleft (FIGS. 3a and 4c). These G loops are reminiscent of the phosphate binding loops found in other nucleotide binding proteins, and are most likely involved in binding to the diphosphate on Lipid I. The N-termini of the helices following each G loop form opposite walls of a small pocket between the G loops. The helix dipoles create a positively charged electrostatic field in the pocket that can stabilize the negative charged diphosphates. When the diphosphate of the acceptor is anchored in the pocket created by the G-loops, the MurNAc sugar emerges into the cleft between domains and the C4 hydroxyl can be directed towards the anomeric carbon of the G1cNAc for attack on the face opposite the UDP leaving group. The third conserved region in the N domain spans the loop from the end of N-?5 to the middle of N-?5. Kinetic analysis of mutants is required to evaluate the roles of these residues (Ha et al., 1999; Men et al., 1998).

Proposed Membrane Association Site

MurG associates with the cytoplasmic surface of bacterial membranes where it couples a soluble donor sugar to the membrane anchored acceptor sugar, Lipid I. Analysis of the E. coli MurG structure shows that there is a hydrophobic patch consisting of residues 175, L79, F82, W85 and W116 in the N-domain, which is surrounded by basic residues (K72, K140, K69, R80, R86, R89). We propose that this is the membrane association site and that association involves both hydrophobic and electrostatic interactions with the negatively charged bacterial membrane. The location of this patch in MurG is also consistent with the proposed acceptor binding site: membrane association at this patch would bring the two N-terminal G loops close to the membrane surface where the diphosphate portion of the acceptor is located (FIG. 4c). Moreover, the cleft between the two domains would remain accessible, consistent with the biochemical requirement that the soluble UDP-GlcNAc donor be able to find its binding site from the cytoplasm.

Implications for Other Glycosyltransferases

Glycosyltransferases that utilize an activated nucleotide sugar as a donor comprise a large family of enzymes in both prokaryotes and eukaryotes, and they play central roles in many important biological processes (Dennis et al., 1999; Koya et al., 1999; Verbert & Cacan, 1999). Glycosyltransferases are typically classified according to the nucleotide sugar they utilize, and it has frequently been noted that there is no significant sequence homology even among glycosyltransferases in the same family. This has made it difficult to identify common structural features and residues important in binding and catalysis. There are only three other glycosyltransferase structures available, and although none of them shows any sequence homology to MurG, a structural comparison indicates that one of them, BGT, contains a related donor binding site.

Figure 3C:
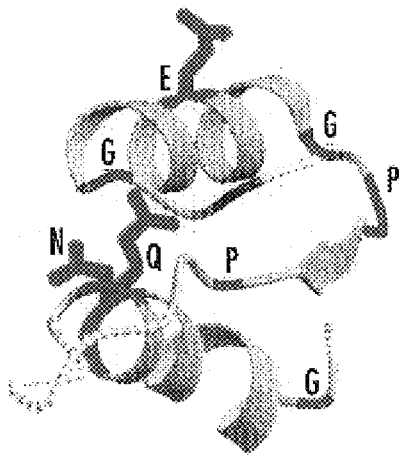

In addition to this structural homology, we have identified a strikingly similar sequence motif in the MurG family and certain other UDP-glycosyltransferase families. This sequence motif spans about a thirty amino acid stretch in the C-domain of MurG and includes most of the invariant residues found in that domain. As shown in FIG. 3a, a similar motif is found in the UDP-glucuronosyltransferases (Mackenzie, 1990). Certain residues are identical, including a number of prolines and glycines, and the spacing between them is invariant. This suggests that the UDP-glucuronosyltransferases contain a region of α/β supersecondary structure that is involved in a similar function as the corresponding region in MurG (FIG. 3c). This region binds the donor sugar. By analyzing the similarities and differences between the conserved residues in this subdomain in the MurG family and other UDP-glycosyltransferase families, it may be possible to identify—and perhaps alter— residues that are involved in determining donor selectivity. We note that it would be useful to be able to manipulate donor specificity because it would extend the utility of glycosyltransferases as reagents for glycosylation of complex molecules. Altered glycosyltransferases could also be useful for remodeling cell surfaces and for probing the biological roles of particular carbohydrate structures.

Conclusion

This first structure of a member of the MurG family of glycosyltransferases lays the groundwork for further mechanistic and structural investigations, which may lead to the design of inhibitors and perhaps even new antibiotics. The work also shows that there can be conserved subdomains even in very different glycosyltransferase families. Information on conserved subdomains will be useful for structure prediction and may help guide experiments directed towards changing substrate specificity.

EXAMPLE 2

This example describes a method of isolating the C-terminal domain of the E. coli MurG protein, expressing the domain in *E. coli* cells and utilizing nuclear magnetic resonance (NMR) to determine the ability of compounds to bind.

MurG can also be used to determine the ability of a chemical compound to bind to the C domain by a) determining the start of c domain based on the MurG crystal structure; b) independently expressing the C domain; and c) using NMR methods to identify binding site and/or bound conformation of ligand. The same procedure is used for the acceptor binding domains.

NMR methods are used to identify the protein binding sites and screen for ligands that bind. The MurG C-terminal domain region of the protein has been expressed independently. The C domain has a much lower molecular weight than the full-length protein. Therefore, the expression of the C domain results in much sharper NMR peaks which will facilitate the NMR interpretation. Also the proton chemical shifts are very sensitive to their environment. Binding of a compound will introduce local environment changes, thus changing the proton chemical shifts. In this way, residues involved in the binding can be differentiated easily from other amino-acid residues not involved in binding a ligand. This method has also been used to identify ligands that bind to low molecular weight drug targets (i.e., small proteins).

Relevant references to NMR techniques are: Discovering high-affinity ligands for proteins: SAR by NMR, S. Shuker, P. Hajduk, R. Meadows, and S. Fesik, Science 274, 1531 (1996); Lin Y, Nageswara Rao B D. Structural characterization of adenine nucleotides bound to *Escherichia coli* adenylate kinase. I. Adenosineconformations by proton two-dimensional transferred nuclear Overhauser effect spectroscopy. Biochemistry. 2000 Apr. 4;39(13):3636–46; and Fejzo J, et al., Chem Biol October 1999 6(10):755–69 (incorporated herein by reference).

The SHAPES strategy is also useful for NMR identification of binding residues, ligands and drug discover which is an NMR-based approach for lead generation in drug discovery. Recently, it has been shown that nuclear magnetic resonance (NMR) may be used to identify ligands that bind to low molecular weight protein drugtargets. Recognizing the utility of NMR as a very sensitive method for detecting binding, we have focused on developing alternative approaches that are applicable to larger molecular weight drug targets and do not require isotopic labeling. A new method for lead generation (SHAPES) uses NMR to detect the binding of a limited but diverse library of small molecules to a potential drug target. The compound scaffolds are derived from shapes most commonly found in known therapeutic agents. NMR detection of low (microM-mM) affinity binding is achieved using either differential line broadening or transferred NOE (nuclear Overhauser effect) NMR techniques. The SHAPES method for lead generation by NMR is useful for identifying potential lead classes of drugs early in a drug design program, and is easily integrated with other discovery tools such as virtual screening, high-throughput screening and combinatorial chemistry.

EXAMPLE 3

This example describes the method of using the three-dimensional structure of *E. coli* MurG to determine the crystal structures of its mutant, enzyme-ligand complex, and MurG homologs, which share the same folding motif.

First, a crystalline form of the new protein or the protein complex should be obtained. The *E. coli* MurG mutants should be crystallized in a condition very similar to what we have showed in the method section. The protein-ligand complex can be obtained by soaking the protein crystals in a ligand-containing buffer. Other MurG homologs can be expressed in a His-tagged fashion and purified using affinity colume. Presumably they can be crystallized in a similar way using a detergent as the additive. Next, the diffraction data should be collected and processed. After the data collection, the molecular replacement method is used to determine the unknown structure. Either the whole *E. coli* MurG protein or one single domain can serve as a search model. This search model can be rotated and translated until the correct orientation is located in the unit cell of this unknown structure. The search model may only represent part of the contents of the asymmetric unit. However, the location of the first model is now already available. While the first location of the search model is fixed, the second round of translation search can be carried out to search more molecules or domains in the asymmetric unit cell. The phases from the final model generated by molecular replacement can be used to calculate the electron density map. Finally, a model is built based on the electron density map, and the model needs to be refined using program CNS or XPLOR.

EXAMPLE 4

This example describes the method of using the three-dimensional coordinate structure of *E. coli* MurG to produce a protein fragment that can be used in an NMR-based lead discovery program. The crystal structure reveals the boundaries of the C domain and permits us to design a gene containing only the C domain from the gene containing both domains. The C domain starting at residue 164 and ending at residue 340 was cloned into an expression vector to generate a C-terminal His-tag fusion, It was over-expressed in *E. coli* cells and purified by affinity colume. The protein was shown to be monomeric by size exclusion chromatography and to be soluble at least up to 0.15 mM, a concentration more than adequate for NMR analysis. C domains from other MurG homologues can be similarly expressed and used.

EXAMPLE 5

This example describes the co-crystallization of a MurG protein with a ligand. A MurG-ligand complex is formed by either co-crystallizing MurG protein with appropriate ligand or soaking the MurG crystals in buffers containing appropriate ligand. Co-crystallization is done by pre-mixing the protein sample with a certain amount of substrate or substrate analogs. Then the hanging drop method is used to produce crystals as described infra.

Alternatively, ligans are incorporated into the crystals by soaking the protein crystals in the ligand containing buffer for a period of time to allow for infiltration into the crystal. The time ranges from a couple of hours to a couple of days. The concentration of ligand in the buffer ranges from several milimolar to several hundred mili molar.

Deposit of Coordinates

The crystal structure three-dimensional coordinates of the *E. coli* MurG as set forth in Table 1 were deposited with the Protein Data Bank and hare been assigned the indicated ID Code (Accession No.) 1F0K.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

REFERENCES

Baker P J, Britton K L, Rice D W, Rob A, Stillman T J. 1992. Structural consequences of sequence patterns in the fingerprint region of the nucleotide binding fold: Implications for nucleotide specificity. J. Mol. Biol 228: 662–671.

Benson T E, Filman D J, Walsh C T, Hogle J M. 1995. An enzyme-substrate complex involved in bacterial cell wall biosynthesis. *Nature Struct. Biol.* 2: 644–653.

Bertrand J A, Auger G, Fanchon E, Martin L, Blanot D, van Heijenoort J, Dideberg O. 1997. Crystal structure of UDP-N-acetylmuramoyl-L-alanine:D-glutamate ligase from *Escherichia coli*. *EMBO J.* 16: 3416–3425.

Branden C, Tooze J. 1998. *Introduction to Protein Structure*. New York: Gerland Publishing, Inc.

Brunger A T, Adams P D, Clore G M, Delano W L, Gros P, Grosse-Kunstleve R W, Jiang J-S, Kuszewski J, Nilges N, Pannu N S, Read R J, Rice L M, Simonson T, Warren G L. 1998. Crystallography and NMR system (CNS): a new software system for macromolecular structure determination. *Acta Crystallogr.* D 54. 905–921.

Bugg T D H, Walsh C T. 1993. Intracellular steps of bacterial cell wall peptidoglycan biosynthesis: enzymology, antibiotics, and antibiotic resistance. *Nat. Prod Rep.:* 199–215.

Bupp K, van Heijenoort J. 1993. The final step of peptidoglycan subunit assembly in *Escherichia coli* occurs in the cytoplasm. J. Bacteriol. 175: 1841–1843.

Carago O., Argos P. 1997. NADP-dependent enzymes. I: Conserved stereochemistry of cofactor binding. *Proteins* 28: 10–28.

CCP4. 1994. The CCP4 suite: programs for protein crystallography. Acta *Crystallogr. D* 50: 760–763.

Charnok S J, Davies G J. 1999. Structure of the nucleotide-diphospho sugar transferase, SpsA from *Bacillus subtilis*, in native and nucleotide-complexed forms. *Biochemisoy* 38: 6380–6385.

Dennis J W, Granovsky M, Warren C E. 1999. Glycoprotein glycosylation and cancer progression. Biochim. Biophys. Acia 1473: 21–34.

Fan C, Moews P C, Walsh C T, Knox J R. 1994. Vancomycin resistance: Structure of D-alanine:D-alanine ligase at 23A resolution. *Science* 266: 43–443.

Gastinel L N, Cambillau C, Bourne Y. 1999. Crystal structures of the bovine b4 galactosyltransferase catalytic domain and its complex with uridine diphosphogalactose. *EMBO J.* 18: 3546–3557.

Ha S, Chang E, Lo M-C, Men H, Park P, Ge M, Walker S. 1999. The kinetic characterization of *Escherichia coli* MurG using synthetic substrate analogues. *J. Am. Chem. Soc.* 121: 8415–8426.

Jones T A, Zou J-Y, Cowan S W, Kjeldgaard M. 1991. Improved methods for building protein models in electron density maps and the location of errors in these models. Acta Crystallogr. A 47: 110–119.

Klaulis P J. 1991. Molscript: a program to produce both detailed and schematic plots of protein structures. *J. Appl. Crystallogr.* 24: 946–950.

Koya D, Dennis J W, Warren C E, Takahara N, Schoen F J, Nishio Y, Nakajima T, Lipes M A, King G L. 1999. Overexpression of core 2 N-acetylglycosaminyltransferase enhances cytokine actions and induces hypertrophic myocardium in transgenic mice. *FASEB J.* 13: 2329–2337.

Mackenzie P I. 1990. Structure and regulation of UDP glucuronosyltransferases. In: Ruckpaut K, Rein H eds. *In Frontiers in Biotransformation: Principles, Mechanisms and Biological Consequences of Induction*, pp. 211–243. Berlin: Akademie-Verlag.

Men H, Park P, Ge M, Walker S. 1998. Substrate synthesis and activity assay for MurG. J. Am. Chem. Soc. 120: 2484–2485.

Merrit EA, Murphy M E. 1994. Raster3D Version 2.0: a program for photorealistic molecular graphics. Acta Crystallogr. D 50: 869–873.

Moréra S, Imberty A, Aschke-Sonnenborn U, Rüger W, Freemont P S. 1999. T4 phage β-glucosyltransferase: Substrate binding and proposed catalytic mechanism. *J. Mol. Biol.* 292: 717–730.

Otwinowski Z, Minor W. 1997. Processing of X-ray diffraction data collected in oscillation mode. *Methods Enzymol* 276: 307–326.

Skarzynski T, Mistry A, Wonacott A, Hutchinson S E, Kelly V A, Duncan K. 1996. Structure of UDP-N-acetylglucosamine enolpyruvyl transferase, an enzyme essential for the synthesis of bacterial peptidoglycan, complexed with substrate UDP-N-acetylghicosamine and the drug fosfomycin. Structure 4: 1465–1474.

Verbert A, Cacan R. 1999. Trafficking of oligomannosides released during N-glycosylation: a clearing mechanism of the rough endoplasmic reticulum. *Biochim. Biophys. Acta* 1473: 137–146.

Vrielink A, Rüger W, Driessen H P C, Freemont P S. 1994. Crystal structure of the DNA modifying enzyme b-glucosyltransferase in the presence and absence of the substrate uridine diphosphoglucose. *EMBO J.* 13: 3413–3422.

What is claimed is:

1. A method of obtaining a triclinic crystal composition of the bacterial membrane associated UDP-glycosyltransferase of SEQ ID NO: 1 (MurG protein), said method consisting of:
   (a) preparing a solution containing 10 mg/ml of MurG protein in 20 mM Tris-HCl buffer, pH 7.9, 150 mM NaCl, 50 mM EDTA, and three molar equivalent of UDP-GlcNAc to the MurG protein; and
   (b) growing a triclinic crystal at room temperature using the hanging drop-method by mixing equal volumes of the protein solution of (a) with a reservoir solution consisting of 0.1 M NaMES, pH 6.5, 0.96 M ammonium sulfate, 0.4% Triton X-100, and 10 mM DTT.

2. A crystalline composition produced according to the method of claim 1.

3. A crystalline composition according to claim 2 comprising MurG crystal molecules arranged in a P1 space group with two molecules per asymmetric unit so as to form a unit cell of dimensions a=60.613 Å, b=66.356 Å, c=67.902 Å, α=64.294°, β=83.520°, and γ=65.448°.

* * * * *

SEQUENCE LISTING

<160> NUMBER OF SEQ ID NOS: 8

<210> SEQ ID NO 1
<211> LENGTH: 364
<212> TYPE: PRT
<213> ORGANISM: Escherichia coli

<400> SEQUENCE: 1

Met Met Ser Gly Gln Gly Lys Arg Leu Met Val Met Ala Gly Gly Thr

```
              1               5              10              15
        Gly Gly His Val Phe Pro Gly Leu Ala Val Ala His His Leu Met Ala
                         20                  25                  30

Gln Gly Trp Gln Val Arg Trp Leu Gly Thr Ala Asp Arg Met Glu Ala
                         35                  40                  45

Asp Leu Val Pro Lys His Gly Ile Glu Ile Asp Phe Ile Arg Ile Ser
                         50                  55                  60

Gly Leu Arg Gly Lys Gly Ile Lys Ala Leu Ile Ala Ala Pro Leu Arg
         65                  70                  75                  80

Ile Phe Asn Ala Trp Arg Gln Ala Arg Ala Ile Met Lys Ala Tyr Lys
                         85                  90                  95

Pro Asp Val Val Leu Gly Met Gly Gly Tyr Val Ser Gly Pro Gly Gly
                        100                 105                 110

Leu Ala Ala Trp Ser Leu Gly Ile Pro Val Val Leu His Glu Gln Asn
                        115                 120                 125

Gly Ile Ala Gly Leu Thr Asn Lys Trp Leu Ala Arg Ile Ala Thr Lys
                        130                 135                 140

Val Met Gln Ala Glu Pro Gly Ala Phe Pro Asn Ala Glu Val Val Gly
        145                 150                 155                 160

Asn Pro Val Arg Thr Asp Val Leu Ala Leu Pro Leu Pro Gln Gln Arg
                        165                 170                 175

Leu Ala Gly Arg Glu Gly Pro Val Arg Val Leu Val Gly Gly Ser
                        180                 185                 190

Gln Gly Ala Arg Ile Leu Asn Gln Thr Met Pro Gln Val Ala Ala Lys
                        195                 200                 205

Leu Gly Asp Ser Val Ile Ile Trp His Gln Ser Gly Lys Gly Ser Gln
                        210                 215                 220

Gln Ser Val Glu Gln Ala Tyr Ala Glu Ala Gly Gln Pro Gln His Lys
        225                 230                 235                 240

Val Thr Glu Phe Ile Asp Asp Met Ala Ala Tyr Ala Trp Ala Asp
                        245                 250                 255

Val Val Val Cys Arg Ser Gly Ala Leu Thr Val Ser Glu Ile Ala Ala
                        260                 265                 270

Ala Gly Leu Pro Ala Leu Phe Val Pro Phe Gln His Lys Asp Arg Gln
                        275                 280                 285

Gln Tyr Trp Asn Ala Leu Pro Leu Glu Lys Ala Gly Ala Ala Lys Ile
                        290                 295                 300

Ile Glu Gln Pro Gln Leu Ser Val Asp Ala Val Ala Asn Thr Leu Ala
        305                 310                 315                 320

Gly Trp Ser Arg Glu Thr Leu Leu Thr Met Ala Glu Arg Ala Arg Ala
                        325                 330                 335

Ala Ser Ile Pro Asp Ala Thr Glu Arg Val Ala Asn Glu Val Ser Arg
                        340                 345                 350

Val Ala Arg Ala Leu Glu His His His His His His
                        355                 360

<210> SEQ ID NO 2
<211> LENGTH: 351
<212> TYPE: PRT
<213> ORGANISM: Haemophilus influenzae

<400> SEQUENCE: 2

Met Lys Asn Lys Lys Leu Leu Val Met Ala Gly Gly Thr Gly Gly His
         1               5                  10                  15
```

```
Val Phe Pro Ala Ile Ala Val Ala Gln Thr Leu Gln Lys Gln Glu Trp
            20                  25                  30

Asp Ile Cys Trp Leu Gly Thr Lys Asp Arg Met Glu Ala Gln Leu Val
        35                  40                  45

Pro Lys Tyr Gly Ile Pro Ile Arg Phe Ile Gln Ile Ser Gly Leu Arg
    50                  55                  60

Gly Lys Gly Ile Lys Ala Leu Leu Asn Ala Pro Phe Ala Ile Phe Arg
65                  70                  75                  80

Ala Val Leu Gln Ala Lys Lys Ile Ile Gln Glu Lys Pro Asp Ala
                85                  90                  95

Val Leu Gly Met Gly Gly Tyr Val Ser Gly Pro Ala Gly Val Ala Ala
            100                 105                 110

Lys Leu Cys Gly Val Pro Ile Ile Leu His Glu Gln Asn Ala Ile Ala
            115                 120                 125

Gly Leu Thr Asn Lys Leu Leu Gly Lys Ile Ala Thr Cys Val Leu Gln
130                 135                 140

Ala Phe Pro Thr Ala Phe Pro Met Ala Glu Val Val Gly Asn Pro Val
145                 150                 155                 160

Arg Glu Asp Leu Phe Glu Met Pro Asn Pro Asp Ile Arg Phe Ser Asp
            165                 170                 175

Arg Glu Glu Lys Leu Arg Val Leu Val Val Gly Gly Ser Gln Gly Ala
            180                 185                 190

Arg Val Leu Asn His Thr Leu Pro Lys Val Val Ala Gln Leu Ala Asp
            195                 200                 205

Lys Leu Glu Phe Arg His Gln Val Gly Lys Gly Ala Val Glu Glu Val
            210                 215                 220

Ser Gln Leu Tyr Gly Glu Asn Leu Glu Gln Val Lys Ile Thr Glu Phe
225                 230                 235                 240

Ile Asp Asn Met Ala Glu Ala Tyr Ala Trp Ala Asp Val Val Ile Cys
            245                 250                 255

Arg Ser Gly Ala Leu Thr Val Cys Glu Ile Ala Ala Val Gly Ala Ala
            260                 265                 270

Ala Ile Phe Val Pro Phe Gln His Lys Asp Arg Gln Gln Tyr Leu Asn
            275                 280                 285

Ala Lys Tyr Leu Ser Asp Val Gly Ala Ala Lys Ile Ile Glu Gln Ala
            290                 295                 300

Asp Leu Thr Pro Glu Ile Leu Val Asn Tyr Leu Lys Asn Leu Thr Arg
305                 310                 315                 320

Glu Asn Leu Leu Gln Met Ala Leu Lys Ala Lys Thr Met Ser Met Pro
            325                 330                 335

Asn Ala Ala Gln Arg Val Ala Glu Val Ile Lys Gln Tyr Ser Asn
            340                 345                 350

<210> SEQ ID NO 3
<211> LENGTH: 362
<212> TYPE: PRT
<213> ORGANISM: Enterococcus faecalis

<400> SEQUENCE: 3

Met Lys Ile Leu Val Thr Gly Gly Thr Gly Gly His Ile Tyr Pro
1               5                   10                  15

Ala Leu Ser Phe Val Glu His Val Lys Lys Glu Ala Pro Ala Thr Glu
            20                  25                  30

Phe Leu Tyr Val Gly Thr Glu Asn Gly Leu Glu Ser Gln Ile Val Pro
        35                  40                  45
```

```
Lys Ala Lys Ile Pro Phe Lys Thr Ile Lys Ile Gln Gly Phe Lys Arg
 50                  55                  60

Ser Leu Ser Pro Gln Asn Phe Lys Thr Ile Tyr Leu Phe Leu Thr Ser
 65                  70                  75                  80

Ile Asn Lys Ala Lys Lys Ile Ile Arg Glu Phe Gln Pro Asp Val Val
                 85                  90                  95

Ile Gly Thr Gly Gly Tyr Val Ser Gly Val Val Tyr Ala Ala His
                100                 105                 110

Gln Leu Lys Ile Pro Thr Ile Ile His Glu Gln Asn Ser Ile Pro Gly
            115                 120                 125

Met Thr Asn Lys Phe Leu Ser Arg Tyr Val Asp Lys Ile Ala Ile Cys
130                 135                 140

Phe Pro Asp Val Ala Ser Phe Pro Lys Glu Lys Thr Ile Leu Thr
145                 150                 155                 160

Gly Asn Pro Arg Gly Gln Glu Val Val Thr Val Glu Lys Ser Ala Ile
                165                 170                 175

Leu Ser Glu Phe Gly Leu Asp Pro Ala Lys Lys Thr Val Val Leu Phe
            180                 185                 190

Gly Gly Ser Arg Gly Ala Leu Lys Ile Asn Gln Ala Phe Glu Gln Ala
            195                 200                 205

Phe Pro Leu Phe Glu Glu Arg Glu Tyr Gln Val Leu Tyr Ala Ser Gly
210                 215                 220

Glu Arg Tyr Tyr Gln Glu Leu Gln Glu Ser Leu Lys Leu Ser Glu Lys
225                 230                 235                 240

Lys Leu Thr Asn Ile Ser Val Gln Pro Tyr Ile Asp Lys Met Val Glu
                245                 250                 255

Val Met Ala Asn Thr Asp Leu Met Val Gly Arg Ala Gly Ala Thr Ser
            260                 265                 270

Ile Ala Glu Phe Thr Ala Leu Gly Leu Pro Ala Ile Leu Ile Pro Ser
            275                 280                 285

Pro Tyr Val Thr Asn Asp His Gln Thr Lys Asn Ala Gln Ser Leu Val
290                 295                 300

Lys Val Gly Ala Val Glu Met Ile Pro Asp Ala Glu Leu Thr Gly Ala
305                 310                 315                 320

Arg Leu Val Ala Ala Ile Asp Asp Ile Leu Leu Asn Asn Glu Lys Arg
                325                 330                 335

Gln Gln Met Ala Thr Ala Ser Lys Gly Glu Arg Ile Pro Asp Ala Ser
            340                 345                 350

Asp Arg Leu Tyr Gln Trp Lys Thr Leu Val
            355                 360

<210> SEQ ID NO 4
<211> LENGTH: 360
<212> TYPE: PRT
<213> ORGANISM: Enterococcus hirae

<400> SEQUENCE: 4

Met Lys Ile Leu Val Thr Gly Gly Thr Gly His Ile Tyr Pro
 1               5                  10                  15

Ala Leu Ala Phe Val Asn Tyr Val Lys Thr Lys Glu Pro Asn Thr Glu
                20                  25                  30

Phe Met Tyr Val Gly Ala Gln Arg Gly Leu Glu Asn Lys Ile Val Pro
            35                  40                  45

Glu Thr Gly Met Pro Phe Arg Thr Leu Glu Ile Gln Gly Phe Gln Arg
```

```
                50                  55                  60
Lys Leu Ser Leu His Asn Leu Lys Thr Ile Gln Leu Phe Leu Lys Ser
 65                  70                  75                  80

Ile Arg Glu Ala Lys Lys Ile Leu Lys Glu Phe Lys Pro Asp Val Val
                85                  90                  95

Ile Gly Thr Gly Gly Tyr Val Ser Gly Ala Val Tyr Ala Ala Ser
               100                 105                 110

Lys Leu Ala Ile Pro Thr Ile His Glu Gln Asn Ser Val Pro Gly
               115                 120                 125

Ile Thr Asn Lys Phe Leu Ser Arg Tyr Val Asp Arg Ile Ala Leu Ser
130                 135                 140

Phe Glu Asp Ala Ala Pro Phe Phe Pro Ala Glu Lys Ser Ser Leu Ile
145                 150                 155                 160

Gly Asn Pro Arg Ala Gln Glu Val Ala Asp Met Asp Lys Ser Lys Ile
                165                 170                 175

Leu Ala Thr Tyr Gly Leu Asp Pro Glu Lys Lys Thr Val Leu Ile Phe
               180                 185                 190

Gly Gly Ser Gln Gly Ala Leu Lys Ile Asn Gln Ala Val Thr Glu Phe
               195                 200                 205

Leu Met Ser Phe Asp Gln Glu Tyr Gln Val Leu Tyr Ala Ser Gly Glu
   210                 215                 220

Arg Tyr Tyr Lys Asp Ile Gln Thr Lys Val Pro Ala Cys Ala Asn Val
225                 230                 235                 240

Ser Ile Gln Pro Tyr Ile Asn Lys Met Ala Glu Val Met Ala Ser Ser
                245                 250                 255

Asp Leu Leu Val Gly Arg Ala Gly Ala Thr Ser Ile Ala Glu Leu Thr
               260                 265                 270

Ala Leu Gly Leu Pro Ala Ile Leu Ile Pro Ser Pro Tyr Val Thr Asn
               275                 280                 285

Asp His Gln Thr Lys Asn Ala Met Ser Leu Val Lys Asn Asn Ala Ala
   290                 295                 300

Lys Met Ile Lys Asp Asp Glu Leu Asp Gly Arg Ser Leu Lys Gln Ala
305                 310                 315                 320

Ile Glu Glu Ile Met Thr Asn Asp Gln Leu Gln Lys Gln Met Ser Leu
                325                 330                 335

Ala Ser Lys Gln Gln Gly Ile Pro Asp Ala Ser Glu Arg Met Tyr Glu
               340                 345                 350

Leu Val Lys Ser Leu Ile Gln Lys
               355                 360

<210> SEQ ID NO 5
<211> LENGTH: 352
<212> TYPE: PRT
<213> ORGANISM: Streptococcus pneumoniae

<400> SEQUENCE: 5

Met Lys Lys Ile Val Phe Thr Gly Gly Gly Thr Val Gly His Val Thr
 1               5                  10                  15

Leu Asn Leu Leu Leu Met Pro Lys Phe Ile Glu Asp Gly Trp Glu Val
                20                  25                  30

His Tyr Ile Gly Asp Lys Arg Gly Ile Glu His Gln Glu Ile Leu Lys
            35                  40                  45

Ser Gly Leu Asp Val Thr Phe His Ser Ile Ala Thr Gly Lys Leu Arg
  50                  55                  60
```

-continued

```
Arg Tyr Phe Ser Trp Gln Asn Met Leu Asp Val Phe Lys Val Cys Trp
 65                  70                  75                  80

Gly Ile Val Gln Ser Leu Phe Ile Met Leu Arg Leu Arg Pro Gln Thr
                 85                  90                  95

Leu Phe Ser Lys Gly Gly Phe Val Ser Val Pro Pro Val Ile Ala Ala
            100                 105                 110

Arg Val Ser Gly Val Pro Val Phe Ile His Glu Ser Asp Leu Ser Met
        115                 120                 125

Gly Leu Ala Asn Lys Ile Ala Tyr Lys Phe Ala Thr Lys Met Tyr Ser
    130                 135                 140

Thr Phe Glu Gln Ala Ser Ser Leu Ser Lys Val Glu His Val Gly Ala
145                 150                 155                 160

Val Thr Lys Val Ser Asp Gln Lys Asn Pro Glu Pro Asp Glu Leu Val
                165                 170                 175

Asp Ile Gln Ser His Phe Asn His Lys Leu Pro Thr Val Leu Phe Val
            180                 185                 190

Gly Gly Ser Ala Gly Ala Arg Val Phe Asn Gln Leu Val Thr Asp His
        195                 200                 205

Lys Lys Glu Leu Thr Glu Arg Tyr Asn Ile Ile Asn Leu Thr Gly Asp
    210                 215                 220

Ser Ser Leu Asn Glu Leu Ser Gln Asn Leu Phe Arg Val Asp Tyr Val
225                 230                 235                 240

Thr Asp Leu Tyr Gln Pro Leu Met Glu Leu Ala Asp Ile Val Val Thr
                245                 250                 255

Arg Gly Gly Ala Asn Thr Ile Phe Glu Leu Leu Ala Ile Ala Lys Leu
            260                 265                 270

His Val Ile Val Pro Leu Gly Arg Glu Ala Ser Arg Gly Asp Gln Leu
        275                 280                 285

Glu Asn Ala Ala Tyr Phe Val Lys Lys Gly Tyr Ala Glu Asp Leu Gln
    290                 295                 300

Glu Ser Asp Leu Thr Leu Asp Ser Leu Glu Glu Lys Leu Ser His Leu
305                 310                 315                 320

Leu Ser His Lys Glu Asp Tyr Gln Ala Lys Met Lys Ala Ser Lys Glu
                325                 330                 335

Leu Lys Ser Leu Ala Asp Phe Tyr Gln Leu Leu Lys Lys Asp Leu Ser
            340                 345                 350
```

<210> SEQ ID NO 6
<211> LENGTH: 385
<212> TYPE: PRT
<213> ORGANISM: Rickettsia prowazekii

<400> SEQUENCE: 6

```
Met Lys Lys Ile Ile Leu Val Ala Gly Gly Ile Gly Gly His Phe Phe
  1               5                  10                  15

Pro Ala Val Ala Leu Gly Glu Glu Leu Ile Lys Arg Gly Tyr Ile Val
             20                  25                  30

His Phe Ile Thr Asp Leu Arg Cys Lys Lys Tyr Ile Asn Lys Asp Met
         35                  40                  45

Lys Ile Ile Phe His Ile Leu Asn Leu Lys Arg Phe Ser Asn Ile Phe
     50                  55                  60

Leu Phe Leu Pro Ile Leu Ser Ile Thr Phe Leu Lys Ser Ile Arg Leu
 65                  70                  75                  80

Ile Tyr Asn Ile Lys Cys Cys Val Ile Ile Gly Phe Gly Gly Tyr Pro
                 85                  90                  95
```

```
Val Ile Ala Pro Met Phe Ala Ala Ile Phe Leu Arg Ile Pro Ile Ile
            100                 105                 110

Ile His Glu Gln Asn Ser Tyr Leu Gly Lys Val Asn Lys Phe Phe Ala
        115                 120                 125

Arg Phe Ala Lys Lys Ile Ala Thr Ser Tyr Glu Asp Ile Lys Asn Leu
    130                 135                 140

Pro Glu Phe Ala Lys Ser Lys Ile Val Leu Thr Gly Gly Ile Val Arg
145                 150                 155                 160

Lys Asn Ile Arg Glu Leu Asp Ser Phe Met Tyr Ser Val Ser Gln His
                165                 170                 175

Ser Leu Thr Lys Leu Thr Gln Thr Ala Leu Thr Asn Thr Phe Asn Pro
            180                 185                 190

Leu Val Lys Gly Arg Asn Asp Glu Phe Ala Asn Ser Asn Ile Phe Thr
        195                 200                 205

Ile Phe Ile Phe Gly Gly Ser Gln Gly Ala Lys Leu Phe Ser Glu Leu
    210                 215                 220

Ile Pro Ala Ser Ile Lys Ile Leu Met Lys Lys Gln Pro Ser Leu Glu
225                 230                 235                 240

Leu Asn Ile Ile Gln Gln Ala Ala Leu Asp His Gln Val Lys Ile Lys
                245                 250                 255

Asp Ile Tyr Ser Lys Leu Asn Ile Thr Tyr Glu Phe Ala Glu Phe Phe
            260                 265                 270

Asp Asn Ile Ala Leu Gln Tyr Lys Val Ala Asn Leu Val Ile Ser Arg
        275                 280                 285

Ala Gly Ala Ser Thr Ile Glu Glu Leu Thr Tyr Ile Gly Leu Pro Ala
    290                 295                 300

Ile Phe Ile Pro Leu Pro Ser Ala Ala Asp His Gln Tyr Tyr Asn
305                 310                 315                 320

Ala Lys Leu Leu Glu Asp Asn Lys Ala Gly Trp Cys Leu Glu Gln Asn
                325                 330                 335

Asn Ile Ser Ser Glu Lys Leu Ala Asp Lys Ile Leu Asp Leu Ile Ser
            340                 345                 350

Asn Arg Gln Leu Leu Glu Asp Ala Ser Gln Asn Leu Leu Asn Arg Lys
        355                 360                 365

Lys Glu Gly His Val Leu Leu Ser Asn Leu Ile Glu Asp Thr Val Phe
    370                 375                 380

Leu
385

<210> SEQ ID NO 7
<211> LENGTH: 363
<212> TYPE: PRT
<213> ORGANISM: Bacillus subtilis

<400> SEQUENCE: 7

Met Arg Ile Ala Ile Ser Gly Gly Thr Gly Gly His Thr Tyr Pro
  1               5                  10                  15

Ala Leu Ala Phe Ile Lys Glu Val Gln Arg Arg His Pro Asn Val Glu
                 20                  25                  30

Phe Leu Tyr Ile Gly Thr Glu Asn Gly Leu Glu Lys Lys Ile Val Glu
             35                  40                  45

Arg Glu Asn Ile Pro Phe Arg Ser Ile Glu Ile Thr Gly Phe Lys Arg
         50                  55                  60

Lys Leu Ser Phe Glu Asn Val Lys Ile Val Met Arg Phe Leu Lys Gly
```

-continued

```
                65                  70                  75                  80
Val Lys Lys Ser Lys Ser Tyr Leu Ala Glu Phe Lys Pro Asp Ala Val
                    85                  90                  95
Ile Gly Thr Gly Gly Tyr Val Cys Gly Pro Val Tyr Ala Ala Ala
                100                 105                 110
Lys Met Gly Ile Pro Thr Ile Val His Glu Gln Asn Ser Leu Pro Gly
            115                 120                 125
Ile Thr Asn Lys Phe Leu Ser Lys Tyr Val Asn Lys Val Ala Ile Cys
        130                 135                 140
Phe Glu Glu Ala Lys Ser His Phe Pro Ser Glu Lys Val Val Phe Thr
145                 150                 155                 160
Gly Asn Pro Arg Ala Ser Glu Val Val Ser Ile Lys Thr Gly Arg Ser
                165                 170                 175
Leu Ala Glu Phe Lys Leu Ser Glu Asp Lys Lys Thr Val Leu Ile Phe
                    180                 185                 190
Gly Gly Ser Arg Gly Ala Ala Pro Ile Asn Arg Ala Val Ile Asp Met
            195                 200                 205
Gln Asp Val Leu Lys Thr Arg Asp Tyr Gln Val Leu Tyr Ile Thr Gly
        210                 215                 220
Glu Val His Tyr Glu Lys Val Met Asn Glu Leu Lys Ser Lys Gly Ala
225                 230                 235                 240
Ala Asp Asn Met Val Thr Lys Pro Phe Leu His Gln Met Pro Glu Tyr
                245                 250                 255
Leu Lys Ala Ile Asp Val Ile Val Ala Arg Ala Gly Ala Ala Thr Ile
                    260                 265                 270
Ala Glu Ile Thr Ala Leu Gly Ile Pro Ser Val Leu Ile Pro Ser Pro
            275                 280                 285
Tyr Val Thr Ala Asn His Gln Glu Val Asn Ala Arg Ser Leu Gly Gln
        290                 295                 300
His Asp Ala Ala Ile Val Leu Lys Glu Thr Glu Leu Ser Gly Glu Lys
305                 310                 315                 320
Leu Ile Glu Ala Leu Asp Arg Ile Val Leu Asn Glu Gln Thr Leu Lys
                325                 330                 335
Glu Met Ser Glu Arg Thr Lys Ser Leu Gly Val Pro Asp Ala Ala Ala
                    340                 345                 350
Arg Leu Tyr Ser Val Leu Glu Glu Leu Lys Lys
                355                 360
```

<210> SEQ ID NO 8
<211> LENGTH: 410
<212> TYPE: PRT
<213> ORGANISM: Mycobacterium tuberculosis

<400> SEQUENCE: 8

```
Met Lys Asp Thr Val Ser Gln Pro Ala Gly Gly Arg Gly Ala Thr Ala
  1               5                  10                  15
Pro Arg Pro Ala Asp Ala Ala Ser Pro Ser Cys Gly Ser Ser Pro Ser
                 20                  25                  30
Ala Asp Ser Val Ser Val Val Leu Ala Gly Gly Thr Ala Gly His
             35                  40                  45
Val Glu Pro Ala Met Ala Val Ala Asp Ala Leu Val Ala Leu Asp Pro
         50                  55                  60
Arg Val Arg Ile Thr Ala Leu Gly Thr Leu Arg Gly Leu Glu Thr Arg
65                  70                  75                  80
```

-continued

```
Leu Val Pro Gln Arg Gly Tyr His Leu Glu Leu Ile Thr Ala Val Pro
                85                  90                  95

Met Pro Arg Lys Pro Gly Gly Asp Leu Ala Arg Leu Pro Ser Arg Val
                100                 105                 110

Trp Arg Ala Val Arg Glu Ala Arg Asp Val Leu Asp Asp Val Asp Ala
                115                 120                 125

Asp Val Val Gly Phe Gly Gly Tyr Val Ala Leu Pro Ala Tyr Leu
                130                 135                 140

Ala Ala Arg Gly Leu Pro Leu Pro Pro Arg Arg Arg Arg Ile Pro
145                 150                 155                 160

Val Val Ile His Glu Ala Asn Ala Arg Ala Gly Leu Ala Asn Arg Val
                165                 170                 175

Gly Ala His Thr Ala Asp Arg Val Leu Ser Ala Val Pro Asp Ser Gly
                180                 185                 190

Leu Arg Arg Ala Glu Val Val Gly Val Pro Val Arg Ala Ser Ile Ala
                195                 200                 205

Ala Leu Asp Arg Ala Val Leu Arg Ala Glu Ala Arg Ala His Phe Gly
                210                 215                 220

Phe Pro Asp Asp Ala Arg Val Leu Leu Val Phe Gly Gly Ser Gln Gly
225                 230                 235                 240

Ala Val Ser Leu Asn Arg Ala Val Ser Gly Ala Ala Ala Asp Leu Ala
                245                 250                 255

Ala Ala Gly Val Cys Val Leu His Ala His Gly Pro Gln Asn Val Leu
                260                 265                 270

Glu Leu Arg Arg Arg Ala Gln Gly Asp Pro Pro Tyr Val Ala Val Pro
                275                 280                 285

Tyr Leu Asp Arg Met Glu Leu Ala Tyr Ala Ala Ala Asp Leu Val Ile
                290                 295                 300

Cys Arg Ala Gly Ala Met Ile Val Ala Glu Val Ser Ala Val Gly Leu
305                 310                 315                 320

Pro Ala Ile Tyr Val Pro Leu Pro Ile Gly Asn Gly Glu Gln Arg Leu
                325                 330                 335

Asn Ala Leu Pro Val Val Asn Ala Gly Gly Gly Met Val Val Ala Asp
                340                 345                 350

Ala Ala Leu Thr Pro Glu Leu Val Ala Arg Gln Val Ala Gly Leu Leu
                355                 360                 365

Thr Asp Pro Ala Arg Leu Ala Ala Met Thr Ala Ala Ala Arg Val
    370                 375                 380

Gly His Arg Asp Ala Ala Gly Gln Val Ala Arg Ala Ala Leu Ala Val
385                 390                 395                 400

Ala Thr Gly Ala Gly Ala Arg Thr Thr Thr
                405                 410
```